(12) United States Patent
Brewis et al.

(10) Patent No.: US 9,028,822 B2
(45) Date of Patent: May 12, 2015

(54) ANTAGONISTS AGAINST TNFR1 AND METHODS OF USE THEREFOR

(75) Inventors: Neil D. Brewis, Hauxton (GB);
Benjamin P. Woolven, Bedford (GB);
Steve Holmes, Great Chishill (GB); Ian M. Tomlinson, Great Shelford (GB);
Jennifer Lee, Cambridge (GB); Carolyn Enever, Cambridge (GB); Amrik Basran, Cambridge (GB); Kate Jones, Cambridge (GB); Ruud de Wildt, Cambridge (GB); Stanislas Blein, Briancon (FR)

(73) Assignee: Domantis Limited, Brentford, Middlesex (GB)

( * ) Notice: Subject to any disclaimer, the term of this patent is extended or adjusted under 35 U.S.C. 154(b) by 643 days.

(21) Appl. No.: 13/181,834

(22) Filed: Jul. 13, 2011

(65) Prior Publication Data

US 2013/0022605 A1 Jan. 24, 2013

Related U.S. Application Data

(63) Continuation of application No. 11/664,542, filed on Sep. 6, 2007, now abandoned, which is a continuation-in-part of application No. 10/985,847, filed on Nov. 10, 2004, now abandoned, which is a continuation-in-part of application No. PCT/GB2004/004253, filed on Oct. 8, 2004, and a continuation-in-part of application No. PCT/GB03/05646, filed on Dec. 24, 2003, which is a continuation-in-part of application No. PCT/GB03/02804, filed on Jun. 30, 2003, which is a continuation-in-part of application No. PCT/GB02/03014, filed on Jun. 28, 2002.

(30) Foreign Application Priority Data

Dec. 27, 2002 (GB) .................................. 0230202.4
Nov. 28, 2003 (GB) .................................. 0327706.8

(51) Int. Cl.
| | | |
|---|---|---|
| *A61K 39/395* | (2006.01) | |
| *C07K 16/24* | (2006.01) | |
| *A61K 47/48* | (2006.01) | |
| *C07K 16/18* | (2006.01) | |
| *C07K 16/28* | (2006.01) | |
| *C07K 16/40* | (2006.01) | |
| *A61K 39/00* | (2006.01) | |

(52) U.S. Cl.
CPC ......... *C07K 16/241* (2013.01); *A61K 47/48215* (2013.01); *A61K 2039/505* (2013.01); *C07K 16/18* (2013.01); *C07K 16/2866* (2013.01); *C07K 16/2878* (2013.01); *C07K 16/40* (2013.01); *C07K 2317/21* (2013.01); *C07K 2317/31* (2013.01); *C07K 2317/569* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,677,063 A | 6/1987 | Mark et al. |
| 4,770,995 A | 9/1988 | Rubin et al. |
| 5,055,289 A | 10/1991 | Frincke et al. |
| 5,359,037 A | 10/1994 | Wallach et al. |
| 5,395,760 A | 3/1995 | Smith et al. |
| 5,582,998 A | 12/1996 | Adolf |
| 5,610,279 A | 3/1997 | Brockhaus et al. |
| 5,672,347 A | 9/1997 | Aggarwal et al. |
| 5,776,895 A | 7/1998 | Alber et al. |
| 5,795,975 A | 8/1998 | Wallach et al. |
| 5,888,511 A | 3/1999 | Skurkovich et al. |
| 6,017,718 A | 1/2000 | Taheri |
| RE36,755 E | 6/2000 | Smith et al. |
| 6,232,446 B1 | 5/2001 | Wallach et al. |
| 6,262,239 B1 | 7/2001 | Wallach et al. |
| 6,395,267 B1 | 5/2002 | Wallach et al. |
| 6,814,966 B1 | 11/2004 | Wax et al. |
| 2001/0021380 A1 | 9/2001 | Pluenneke |
| 2002/0004041 A1 | 1/2002 | Albert et al. |
| 2002/0006391 A1 | 1/2002 | Smith et al. |
| 2002/0142357 A1 | 10/2002 | Wallach et al. |
| 2002/0150582 A1 | 10/2002 | Friedrichs et al. |
| 2003/0108992 A1 | 6/2003 | Lenardo et al. |
| 2003/0157061 A1 | 8/2003 | Bennett |
| 2003/0165459 A1 | 9/2003 | Smith et al. |
| 2004/0009166 A1 | 1/2004 | Filpula et al. |

(Continued)

FOREIGN PATENT DOCUMENTS

| | | |
|---|---|---|
| DE | 40 06 269 A1 | 8/1991 |
| DE | 41 20 213 C2 | 12/1992 |

(Continued)

OTHER PUBLICATIONS

Chan, Ann Rheum Dis 2000;59(suppl I):i50-i53.*

(Continued)

*Primary Examiner* — Zachary Skelding
(74) *Attorney, Agent, or Firm* — Robert H. Brink

(57) ABSTRACT

The invention provides methods for treating inflammatory diseases (e.g., chronic inflammatory diseases) comprising administering an antagonist of Tumor Necrosis Factor Receptor 1. The invention also provides ligands that contain an immunoglobulin single variable domain (domain antibody, dAb) monomer that binds Tumor Necrosis Factor Receptor 1, and methods of using the ligands. Also provided are nucleic acids encoding the ligands, recombinant host cells and methods for preparing the ligands.

12 Claims, 92 Drawing Sheets

(56) References Cited

U.S. PATENT DOCUMENTS

| | | |
|---|---|---|
| 2004/0013646 A1 | 1/2004 | Wallach et al. |
| 2004/0057954 A1 | 3/2004 | Borrelli et al. |
| 2004/0170975 A1 | 9/2004 | Savitzky et al. |
| 2004/0235047 A1 | 11/2004 | Siber |
| 2005/0002900 A1 | 1/2005 | Wong et al. |
| 2005/0025765 A1 | 2/2005 | DiMauro et al. |
| 2005/0053973 A1 | 3/2005 | Kolkman et al. |
| 2005/0095246 A1 | 5/2005 | Shafer |
| 2005/0142539 A1 | 6/2005 | Herman |
| 2005/0164301 A1 | 7/2005 | Kolkman et al. |
| 2005/0180974 A1 | 8/2005 | Shafer |
| 2011/0301335 A1* | 12/2011 | Duffield et al. ............ 530/387.3 |

FOREIGN PATENT DOCUMENTS

| | | |
|---|---|---|
| DE | 199 22 444 A1 | 11/2000 |
| EP | 0 393 438 A2 | 10/1990 |
| EP | 0 417 563 B1 | 3/1991 |
| EP | 0 453 082 A1 | 10/1991 |
| EP | 0 525 570 A2 | 2/1993 |
| EP | 0 568 925 A2 | 11/1993 |
| EP | 0 575 545 B1 | 12/1993 |
| EP | 0 368 684 B2 | 3/1994 |
| EP | 0 585 939 B1 | 3/1994 |
| EP | 0 412 486 B1 | 11/1994 |
| EP | 0 398 327 B1 | 3/1995 |
| EP | 0 648 783 B1 | 4/1995 |
| EP | 0 433 900 B1 | 9/1995 |
| EP | 0 334 165 B1 | 12/1995 |
| EP | 0 418 014 B1 | 12/1995 |
| EP | 0 729 750 B1 | 9/1996 |
| EP | 0 936 923 B1 | 8/1999 |
| EP | 0 512 528 B1 | 9/1999 |
| EP | 0 939 121 A2 | 9/1999 |
| EP | 1 022 027 M | 7/2000 |
| EP | 1 026 239 A2 | 8/2000 |
| EP | 0 672 142 B1 | 2/2001 |
| EP | 1 325 932 B9 | 7/2003 |
| EP | 1 378 520 A1 | 1/2004 |
| EP | 0 308 378 B2 | 9/2004 |
| EP | 1 512 697 A1 | 3/2005 |
| GB | 2 218 101 A | 11/1989 |
| GB | 2 246 569 A | 2/1992 |
| WO | WO 89/07142 A1 | 8/1989 |
| WO | WO 90/05144 A1 | 5/1990 |
| WO | WO 90/14430 A1 | 11/1990 |
| WO | WO 91/03553 A1 | 3/1991 |
| WO | WO 92/01047 A1 | 1/1992 |
| WO | WO 92/01472 A1 | 2/1992 |
| WO | WO 92/13095 A1 | 8/1992 |
| WO | WO 92/20791 A1 | 11/1992 |
| WO | WO 92/22666 A1 | 12/1992 |
| WO | WO 93/11236 A1 | 6/1993 |
| WO | WO 93/21946 A1 | 11/1993 |
| WO | WO 94/08609 A1 | 4/1994 |
| WO | WO 94/26924 A2 | 11/1994 |
| WO | WO 95/03827 A1 | 2/1995 |
| WO | WO 95/15179 A1 | 6/1995 |
| WO | WO 97/02345 A1 | 1/1997 |
| WO | WO 97/06251 A1 | 2/1997 |
| WO | WO 97/30088 A2 | 8/1997 |
| WO | WO 97/34616 A1 | 9/1997 |
| WO | WO 98/22137 A1 | 5/1998 |
| WO | WO 98/51344 A1 | 11/1998 |
| WO | WO 00/29004 | 5/2000 |
| WO | WO 01/00229 A1 | 1/2001 |
| WO | WO 01/58473 A1 | 8/2001 |
| WO | WO 01/58953 A2 | 8/2001 |
| WO | WO 01/62272 A2 | 8/2001 |
| WO | WO 01/72298 A1 | 10/2001 |
| WO | WO 01/77342 A1 | 10/2001 |
| WO | WO 02/002773 A2 | 1/2002 |
| WO | WO 02/43660 A2 | 6/2002 |
| WO | WO 02/080891 A1 | 10/2002 |
| WO | WO 03/002609 A3 | 1/2003 |
| WO | WO 03/012072 A2 | 2/2003 |
| WO | WO 03/035694 | 5/2003 |
| WO | WO 03/045430 A1 | 6/2003 |
| WO | WO 03/070274 A1 | 8/2003 |
| WO | WO 2004/003019 A3 | 1/2004 |
| WO | WO 2004/009776 A2 | 1/2004 |
| WO | WO 2004/020608 A2 | 3/2004 |
| WO | WO 2004/022096 A1 | 3/2004 |
| WO | WO 2004/022718 A2 | 3/2004 |
| WO | WO 2004/041862 A2 | 5/2004 |
| WO | WO 2004/041867 A2 | 5/2004 |
| WO | WO 2004/058821 A2 | 7/2004 |
| WO | WO 2004/081026 A2 | 9/2004 |
| WO | WO 2004/101790 A1 | 11/2004 |
| WO | WO 2005/021578 A2 | 3/2005 |
| WO | WO 2005/028664 A2 | 3/2005 |
| WO | WO 2005/035572 A2 | 4/2005 |
| WO | WO 2005/037865 A2 | 4/2005 |
| WO | WO 2005/038056 A1 | 4/2005 |
| WO | WO 2005/044858 A1 | 5/2005 |
| WO | WO 2005/097202 A2 | 10/2005 |
| WO | WO 2005/115456 A2 | 12/2005 |
| WO | WO 2005/117966 A1 | 12/2005 |
| WO | WO 2005/123772 A2 | 12/2005 |
| WO | WO 2006/038027 A2 | 4/2006 |
| WO | WO 2006/059108 A2 | 6/2006 |

OTHER PUBLICATIONS

Kontermann, Roland E., et al., "A Humanized Tumor Necrosis Factor Receptor 1 (TNFR1)-specific Antagonistic Antibody for Selective Inhibition of Tumor Necrosis Factor (TNF)Action," J Immunother, Apr. 2008, pp. 225-234, vol. 31.

Alfthan, K, et al., "Properties of a Single-chain Antibody Containing Different Linker Peptides," Prot. Eng., 8(7): 725-731 (1995).

Bendele, A., et al., "Combination Benefit of Treatment With the Cytokine Inhibitors Interleukin-1 Receptor Antagonist and PEGylated Soluble Tumor Necrosis Factor Receptor Type I in Animal Models of Rheumatoid Arthritis," Arthritis and Rheumatism, 43(12): 2648-2659 (2000).

Chan, F., et al., "A Domain in Tnf Receptors That Mediates Ligand-independent Receptor Assembly and Signaling," Science, 288(5475): 2351-2354 (2000).

Conrath, K., et al., "Camel Single-domain Antibodies as Modular Building Units in Bispecific and Bivalent Antibody Constructs," J. Biol. Chem., 276(10): 7346-7350 (2001).

Davies, J., et al., "Affinity Improvement of Single Antibody VH Domains: Residues in All Three Hypervariable Regions Affect Antigen Binding," Immunotechnology, 2: 169-179 (1996).

Davies, J., et al., "'Camelising' Human Antibody Fragments: NMR Studies on VH Domains," FEBS Letters, 339: 285-290 (1994).

Davies, J., et al., "Antibody VH Domains as Small Recognition Units," Biotechnol., 13: 475-479 (1995).

Desmyter, A., et al., "Antigen Specificity and High Affinity Binding Provided by One Single Loop of a Camel Single-domain Antibody," The Journal of Biological Chemistry, 276(28): 26285-26290 (2001).

Fuchs, P., et al., "Structure of the Human TNF Receptor 1 (p60) Gene (TNRF1) and Localization to Chromosome 12p13," Genomics, 13: 219-224 (1992).

Hamers-Casterman, C., et al., "Naturally Occuring Antibodies Devoid of Light Chains," Nature, 363: 446-448 (1993).

Holt, L., et al., "Domain Antibodies: Proteins for Therapy," Trends in Biotechnology, 21(11): 484-490 (2003).

Winter, G., et al., "Man-made Antibodies," Nature, 349: 293-299 (1991).

Nissim, A., et al., "Antibody Fragments From a 'Single Pot' Phage Display Library as Immunochemical Reagents," The Embo J., 13(3): 692-698 (1994).

Tang, Y., et al., "Selection of Linkers for a Catalytic Single-chain Antibody Using Phage Display Technology," J. Biol. Chem., 271(26): 15682-15686 (1996).

Chung, K., "New Asthma Treatments: Recent Advances and Current Objectives," Rev. Fr. Allergol., 38(7S): S214-S221 (1998).

(56) References Cited

OTHER PUBLICATIONS de Boer, W., "Perspectives for Cytokine Antagonist Therapy in COPD," *Drug Discovery Today*, 10(2): 93-106 (2005).

Domain Antibody Products Treat Respiratory Disease, (2004) [retrieved on Feb. 13, 2008]. Retrieved from the Internet URL: <http://www.laboratorytalk.com/news/arg/arg109.html>.

Neumann, D., et al., "The Membrane Form of the Type II IL-I Receptor Accounts for Inhibitory Function," *Journal of Immunology*, 165(6): 3350-3357 (2000).

Abu-Amer, Y., et al., "Tumor Necrosis Factor Receptors Types 1 and 2 Differentially Regulate Osteoclastogenesis," *The Journal of Biological Chemistry*, 275(35): 27307-27310 (2000).

Aggarwal, B., et al., "Characterization of Receptors for Human Tumor Necrosis Factor and Their Regulation by γ-Interferon," *Nature*, 318(19): 665-667 (1985).

Banner D., et al., "Crystal Structure of the Soluble Human 55 kd TNF Receptor-Human TNFβ Complex: Implications for TNF Receptor Activation," *Cell*, 73: 431-445 (1993).

Barnes, P., "Chronic Obstructive Pulmonary Disease," *New Eng. J. Med.*, 343(4): 269-280 (2000).

Chen, G., et al., "TNF-R1 Signaling: A Beautiful Pathway," *Science*, 296: 1634-1635 (2002).

Davies, J., et al., "Affinity Improvement of Single Antibody VH Domains: Residues in All three Hypervariable Regions Affect Antigen Binding," *Immunotechnology*, 2(3) 169-179 (1996).

Deng, G., et al., "Amelioration of Inflammatory Arthritis by Targeting the Pre-Ligand Assembly Domain of Tumor Necrosis Factor Receptors," *Nature Medicine*, 11: 1066-1072 (2005).

Desmyter, A., et al., "Antigen Specificity and High Affinity Binding Provided by One Single Loop of a Camel Single-domain Antibody," *Journal of Biological Chemistry*, 276(28): 26285-26290 (2001).

Engelmann, H., et al., "Two Tumor Necrosis Factor-Binding Proteins Purified From Human Urine," *The Journal of Biological Chemistry*, 265(3): 1531-1536 (1990).

Espevik, T., et al., "Characterization of Binding and Biological Effects of Monoclonal Antibodies Against a Human Tumor Necrosis Factor Receptor," *J. Exp. Med.*, 171: 415-426 (1990).

Feldmann, M., et al., "Anti-TNFα Therapy of Rheumatoid Arthritis: What Have We Learned?" *Annu. Rev. Immunol.*, 19: 163-196 (2001).

Gómez, M., "*Staphylococcus aureus* Protein a Induces Airway Epithelial Inflammatory Responses by Activating TNFR1," *Nature Medicine*, 10(8): 842-848 (2004).

Griffiths, A., et al., "Isolation of High Affinity Human Antibodies Directly From Large Synthetic Repertoires," *EMBO J.*, 13(14): 3245-3260 (1994).

Himmler, A., et al., "Molecular Cloning and Expression of Human and Rat Tumor Necrosis Factor Receptor Chain (p60) and its Soluble Derivative, Tumor Necrosis Factor-Binding Protein," *DNA and Cell Biol.*, 9(10): 705-715 (1990).

Jespers, L., et al., "Crystal Structure of HEL4, a Soluble, Refoldable Human VH Single Domain With a Germ-line Scaffold," *Journal of Molecular Biology*, 337(4): 893-903 (2004).

Kollias, G., et al., "Role of TNF/TNFR in Autoimmunity: Specific TNF Receptor Blockade May be Advantageous to Anti-TNF Treatments," *Cytokine Growth Factor Rev.*, 13: 315-321 (2002).

Kontoyiannis, D., et al., "Genetic Dissection of the Cellular Pathways and Signaling Mechanisms in Modeled Tumor Necrosis Factor-induced Crohn's-like Inflammatory Bowel Disease," *J. Exp. Med.*, 196(12): 1563-1574 (2002).

Lewis, M., et. al., "Cloning and Expression of cDNAs for Two Distinct Murine Tumor Necrosis Factor Receptors Demonstrate One Receptor is Species Specific," *Proc. Natl. Acad. Sci. U.S.A.*, 88(7): 2830-2834 (1991).

Li, P., et al., "The TNF-α Transgenic Mouse Model of Inflammatory Arthritis," *Springer Semin. Immunopathol*, 25: 19-33 (2003).

Loetscher, H., et al., "Molecular Cloning and Expression of the Human 55 kd Tumor Necrosis Factor Receptor," *Cell*, 61: 351-359 (1990).

Naismith, J., et al., "Structures of the Extracellular Domain of the Type I Tumor Necrosis Factor Receptor," *Structure*, 4(11): 1251-1262 (1996).

Neurath, M., et al., "Predominant Pathogenic Role of Tumor Necrosis Factor in Experimental Colitis in Mice," *Eur. J. Immunol.*, 27: 1743-1750 (1997).

Nophar, Y., et al., "Soluble Forms of Tumor Necrosis Factor Receptors (TNF-Rs). The cDNA for the Type I TNF-R, Cloned Using Amino Acid Sequence Data of its Soluble Form, Encodes Both the Cell Surface and a Soluble Form of the Receptor," *EMBO Journal*, 9(10): 3269-3278 (1990).

Pizarro, T., et al., "Mouse Models for the Study of Crohn's Disease," *Trends in Molecular Medicine*, 9(5): 218-222 (2003).

Podolsky, D., "The Future of IBD Treatment," *J. Gastroenterol*, 38 (Suppl XV): 63-66 (2003).

Riechmann, L., et al., "Single Domain Antibodies: Comparison of Camel VH and Camelised Human VH Domains," *Journal of Immunological Methods*, 231(1/2): 25-38 (1999).

Rothe, J., et al., "Phenotypic Analysis of TNFR1,-Deficient Mice and Characterization of TNFR1-Deficient Fibroblasts In Vitro," *Circulatory Shock*, 44(2): 51-56 (1995).

Sheehan, K., et al., "Monoclonal Antibodies Specific for Murin p55 and p75 Tumor Necrosis Factor Receptors: Identification of a Novel In Vivo Role for p75," *J. Exp. Med.*, 181: 607-617 (1995).

Silva, F., et al., "Camelized Rabbit-derived VH Single-domain Intrabodies Against Vif Strongly Neutralize HIV-1 Infectivity," *Journal of Molecular Biology*, 340(3): 525-542 (2004).

Van den Beucken, T., et al., "Building Novel Binding Ligands to B7.1 and B7.2 Based on Human Antibody Single Variable Light Chain Domains,"*Journal of Molecular Biology*, 310(3): 591-601 (2001).

Wright, J., et al., "Animal Models of Cigarette Smoke-Induced COPD," *Chest Journal*, 122(6): 301S-306S (2002).

Zwerina, J., et al., "Single and Combined Inhibition of Tumor Necrosis Factor, Interleukin-1, and RANKL Pathways in Tumor Necrosis Factor-Induced Arthritis," *Arthritis & Rheumatism*, 50(1): 277-290 (2004).

Moosmayer et al., Ther Immunol. Feb. 1995;2(1):31-40.

Thoma et al., J Exp Med. Oct. 1, 1990;172(4):1019-23.

\* cited by examiner

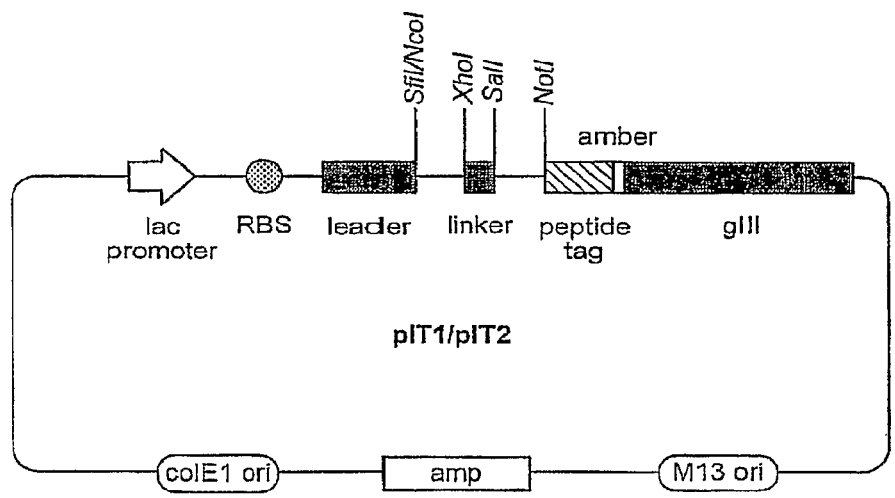

```
                                                                    RBS
CAGGAAACAGCTATGACCATGATTACGCCAAGCTTG CATGCAAATTCTATTTCAAGGAGACAGTCATA ATG AAA TAC CTA
------------------>                                                  M   K   Y   L
   LMB3
```

```
                                             SfiI      NcoI
TTG CCT ACG GCA GCC GCT GGA TTG TTA TTA CTC GCG GCC CAG CCG GCC ATG GCC GAG GTG TTT
 L   P   T   A   A   A   G   L   L   L   L   A   A   Q   P   A   M   A   E   V   F

XhoI                      linker
GAC TAC TGG GGC CAG GGA ACC CTG GTC ACC GTC TCG AGC GGT GGA GGC GGT TCA GGC GGA GGT
 D   Y   W   G   Q   G   T   L   V   T   V   S   S   G   G   G   G   S   G   G   G
```

```
                       SalI                                 NotI
GGC AGC GGC GGT GGC GGG TCG ACG GAC ATC CAG ATG ACC CAG GCG GCC GCA GAA CAA AAA CTC
 G   S   G   G   G   S   T   D   I   Q   M   T   Q   A   A   A   E   Q   K   L
    <--------------------------
         link seq new
```

```
                                                            HIS-tag
                                           CAT CAT CAT CAC CAT CAC GGG GCC GCA
                                            H   H   H   H   H   H   G   A   A
                                                      (insertion in pIT2 only)
```

```
   myc-tag                                                    Gene III
ATC TCA GAA GAG GAT CTG AAT GGG GCC GCA TAG ACT GTT GAA AGT TGT TTA GCA AAA CCT CAT
 I   S   E   E   D   L   N   G   A   A   *   T   V   E   S   C   L   A   K   P   H
                         <---------------------
                              pHEN seq
```

FIG. 3

VH chains

| | FR1 | | | CDR1 | FR2 | | CDR2 | | FR3 | | | CDR3 | | FR4 |
|---|---|---|---|---|---|---|---|---|---|---|---|---|---|---|
| | 1 | 2 | 3 | | 4 | 5 | | 6 | 7 | 8 | 9 | | 10 | 11 |
| | 1234567890123456789012345678 90 | | | 12345 | 6789012345678 9 | 012a3456789012345 | | | 6789012345678901 2abc345678 90 1234 | | | 567801 | | 23456789 0123 |
| VH dummy | EVQLLESGGGLVQPGGSLRLSCAASGFTFS | | | SYAMS | WVRQAPGKGLEWVS | AISGSGGSTYYADSVKG | | | RFTISRDNSKNTLYLQMNSLRAEDTAVYYCAK | | | SYGAFDY | | WGQGTLVTVSS |
| K8 | | | | | | H-SPY-AN-R--- | | | | | | GLRA--- | | |
| VH2 | | | | | | D-GAT-SK-G---P--- | | | | | | KVLT--- | | |
| VH4 | | | | | | R-NGP--*A-G--- | | | -I--- | | | HGAP--- | | |
| VHC11 | | | --N | | | S-PAS-LH-R--- | | | | | | PGLG--- | | |
| VHA10sd | | | | | | D-ERT-Y*-R--- | | | | | | KVLV--- | | |
| VHA1sd | | | | | | E-SAN-SK-Q--- | | | -L--- | | | KVLQ--- | | |
| VHA5sd | | | | | | T-PAN-*V-R--- | | | | | | SLLQ--- | | |
| VHC5sd | | | | | | D-AAT-SA-S--- | | | | | | KLLK--- | | |
| VHC11sd | | | --S--- | | | T-SSV-QS-R--- | | | | | | NLMS--- | | |

Vk chains

| | FR1 | | CDR1 | FR2 | CDR2 | FR3 | | CDR3 | FR4 |
|---|---|---|---|---|---|---|---|---|---|
| | 1 | 2 3 | | 4 5 | 6 | 7 | 8 | 9 10 | |
| | 123456789012345678901 23 | | 45678901234 | 56789012345678 9 | 0123456 | 78901234567890123456 78 | | 901234567 8901234567 8 | |
| Vk dummy | DIQMTQSPSSLSASVGDRVTITC | | RASQSISSYLN | WYQQKPGKAPKLLIY | AASSLQS | GVPSRFSGSGSGTDFTLTISSLQPEDFATYYC | | QQSYSTPNT | FGQGTKVEIKR |
| K8 | ---L--- | | | | R--H--- | | | --PWRS-G--- | |
| E5sd | | ---V--- | | | L--R--- | | | --NWWL-P--- | |
| C3 | | | | | *--L--- | | | --RVYD-L--- | |

FIG. 6

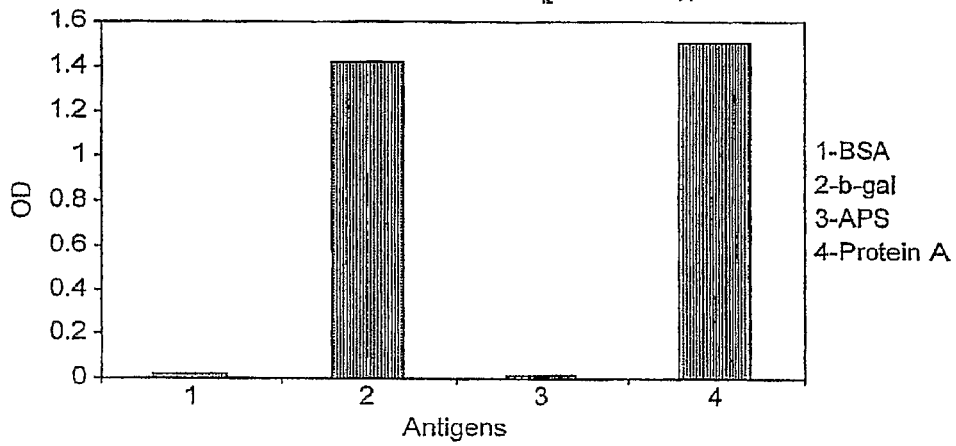

Soluble ScFv ELISA of K8V$_\kappa$/dummy V$_H$ clone

1-BSA
2-b-gal
3-APS
4-Protein A

FIG. 7

```
                                                                    RBS
CAGGAAACAGCTATGACCATGATTACGCCAAGCTTGCATGCAAATTCTATTTCAAGGAGACAGTCATA ATG AAA TAC CTA
------------------>                                                   M   K   Y   L
     LMB3

SfiI       NcoI
TTG CCT ACG GCA GCC GCT GGA TTG TTA TTA CTC GCG GCC CAG CCG GCC ATG GCC GAG GTG TTT
 L   P   T   A   A   A   G   L   L   L   L   A   A   Q   P   A   M   A   E   V   F

XhoI                         linker
GAC TAC TGG GGC CAG GGA ACC CTG GTC ACC GTC TCG AGC GGT GGA GGC GGT TCA GGC GGA GGT
 D   Y   W   G   Q   G   T   L   V   T   V   S   S   G   G   G   G   S   G   G   G SalI                           NotI
GGC AGC GGC GGT GGC GGG TCG ACG GAC ATC CAG ATG ACC CAG GCG GCC GCA GAA CAA AAA CTC
 G   S   G   G   G   G   S   T   D   I   Q   M   T   Q   A   A   A   E   Q   K   L
                    <-------------
                     link seq new HIS-tag
                                          CAT CAT CAT CAC CAT CAC GGG GCC GCA
                                           H   H   H   H   H   H   G   A   A
                                          (insertion in V domain vector 2 only myc-tag                                           Gene III
ATC TCA GAA GAG GAT CTG AAT GGG GCC GCA TAG ACT GTT GAA AGT TGT TTA GCA AAA CCT CAT
 I   S   E   E   D   L   N   G   A   A   *   T   V   E   S   C   L   A   K   P   H
                              <---------------------
                                     pHEN seq
```

TNF receptor assay

TNF receptor assay

FIG. 13

Dummy V$_H$ sequence for library 1

```
      E   V   Q   L   L   E   S   G   G   G   L   V   Q   P   G   G
  1   GAG GTG CAG CTG TTG GAG TCT GGG GGA GGC TTG GTA CAG CCT GGG GGG
      CTC CAC GTC GAC AAC CTC AGA CCC CCT CCG AAC CAT GTC GGA CCC CCC

S   L   R   L   S   C   A   A   S   G   F   T   F   S   S   Y
 49   TCC CTG CGT CTC TCC TGT GCA GCC TCC GGA TTC ACC TTT AGC AGC TAT
      AGG GAC GCA GAG AGG ACA CGT CGG AGG CCT AAG TGG AAA TCG TCG ATA

A   M   S   W   V   R   Q   A   P   G   K   G   L   E   W   V
 97   GCC ATG AGC TGG GTC CGC CAG GCT CCA GGG AAG GGT CTA GAG TGG GTC
      CGG TAC TCG ACC CAG GCG GTC CGA GGT CCC TTC CCA GAT CTC ACC CAG

S   A   I   S   G   S   G   G   S   T   Y   Y   A   D   S   V
145   TCA GCT ATT AGT GGT AGT GGT GGT AGC ACA TAC TAC GCA GAC TCC GTG
      AGT CGA TAA TCA CCA TCA CCA CCA TCG TGT ATG ATG CGT CTG AGG CAC

K   G   R   F   T   I   S   R   D   N   S   K   N   T   L   Y
193   AAG GGC CGG TTC ACC ATC TCC CGT GAC AAT TCC AAG AAC ACG CTG TAT
      TTC CCG GCC AAG TGG TAG AGG GCA CTG TTA AGG TTC TTG TGC GAC ATA

L   Q   M   N   S   L   R   A   E   D   T   A   V   Y   Y   C
241   CTG CAA ATG AAC AGC CTG CGT GCC GAG GAC ACC GCG GTA TAT TAC TGT
      GAC GTT TAC TTG TCG GAC GCA CGG CTC CTG TGG CGC CAT ATA ATG ACA

A   K   S   Y   G   A   F   D   Y   W   G   Q   G   T   L   V
289   GCG AAA AGT TAT GGT GCT TTT GAC TAC TGG GGC CAG GGA ACC CTG GTC
      CGC TTT TCA ATA CCA CGA AAA CTG ATG ACC CCG GTC CCT TGG GAC CAG

T   V   S   S
337   ACC GTC TCG AGC
      TGG CAG AGC TCG
```

FIG. 14

Dummy V<sub>H</sub> sequence for library 2

```
       E    V    Q    L    L    E    S    G    G    G    L    V    Q    P    G    G
  1   GAG  GTG  CAG  CTG  TTG  GAG  TCT  GGG  GGA  GGC  TTG  GTA  CAG  CCT  GGG  GGG
      CTC  CAC  GTC  GAC  AAC  CTC  AGA  CCC  CCT  CCG  AAC  CAT  GTC  GGA  CCC  CCC

S    L    R    L    S    C    A    A    S    G    F    T    F    S    S    Y
 49   TCC  CTG  CGT  CTC  TCC  TGT  GCA  GCC  TCC  GGA  TTC  ACC  TTT  AGC  AGC  TAT
      AGG  GAC  GCA  GAG  AGG  ACA  CGT  CGG  AGG  CCT  AAG  TGG  AAA  TCG  TCG  ATA

A    M    S    W    V    R    Q    A    P    G    K    G    L    E    W    V
 97   GCC  ATG  AGC  TGG  GTC  CGC  CAG  GCT  CCA  GGG  AAG  GGT  CTA  GAG  TGG  GTC
      CGG  TAC  TCG  ACC  CAG  GCG  GTC  CGA  GGT  CCC  TTC  CCA  GAT  CTC  ACC  CAG

S    A    I    S    G    S    G    S    T    Y    Y    A    D    S    V
145   TCA  GCT  ATT  AGT  GGT  AGT  GGT  AGC  ACA  TAC  TAC  GCA  GAC  TCC  GTG
      AGT  CGA  TAA  TCA  CCA  TCA  CCA  TCG  TGT  ATG  ATG  CGT  CTG  AGG  CAC

K    G    R    F    T    I    S    R    D    N    S    K    N    T    L    Y
193   AAG  GGC  CGG  TTC  ACC  ATC  TCC  CGT  GAC  AAT  TCC  AAG  AAC  ACG  CTG  TAT
      TTC  CCG  GCC  AAG  TGG  TAG  AGG  GCA  CTG  TTA  AGG  TTC  TTG  TGC  GAC  ATA

L    Q    M    N    S    L    R    A    E    D    T    A    V    Y    Y    C
241   CTG  CAA  ATG  AAC  AGC  CTG  CGT  GCC  GAG  GAC  ACC  GCG  GTA  TAT  TAC  TGT
      GAC  GTT  TAC  TTG  TCG  GAC  GCA  CGG  CTC  CTG  TGG  CGC  CAT  ATA  ATG  ACA

A    K    S    Y    G    A    X    X    X    X    F    D    Y    W    G    Q
289   GCG  AAA  AGT  TAT  GGT  GCT  NNK  NNK  NNK  NNK  TTT  GAC  TAC  TGG  GGC  CAG
      CGC  TTT  TCA  ATA  CCA  CGA  NNK  NNK  NNK  NNK  AAA  CTG  ATG  ACC  CCG  GTC

G    T    L    V    T    V    S    S
337   GGA  ACC  CTG  GTC  ACC  GTC  TCG  AGC
      CCT  TGG  GAC  CAG  TGG  CAG  AGC  TCG
```

FIG. 15

Dummy V$_K$ sequence for library 3

```
         D   I   Q   M   T   Q   S   P   S   S   L   S   A   S   V   G
  1     GAC ATC CAG ATG ACC CAG TCT CCA TCC TCC CTG TCT GCA TCT GTA GGA
        CTG TAG GTC TAC TGG GTC AGA GGT AGG AGG GAC AGA CGT AGA CAT CCT

D   R   V   T   I   T   C   R   A   S   Q   S   I   S   S   Y
 49     GAC CGT GTC ACC ATC ACT TGC CGG GCA AGT CAG AGC ATT AGC AGC TAT
        CTG GCA CAG TGG TAG TGA ACG GCC CGT TCA GTC TCG TAA TCG TCG ATA

L   N   W   Y   Q   Q   K   P   G   K   A   P   K   L   L   I
 97     TTA AAT TGG TAC CAG CAG AAA CCA GGG AAA GCC CCT AAG CTC CTG ATC
        AAT TTA ACC ATG GTC GTC TTT GGT CCC TTT CGG GGA TTC GAG GAC TAG

Y   A   A   S   S   L   Q   S   G   V   P   S   R   F   S   G
145     TAT GCT GCA TCC AGT TTG CAA AGT GGG GTC CCA TCA CGT TTC AGT GGC
        ATA CGA CGT AGG TCA AAC GTT TCA CCC CAG GGT AGT GCA AAG TCA CCG

S   G   S   G   T   D   F   T   L   T   I   S   S   L   Q   P
193     AGT GGA TCT GGG ACA GAT TTC ACT CTC ACC ATC AGC AGT CTG CAA CCT
        TCA CCT AGA CCC TGT CTA AAG TGA GAG TGG TAG TCG TCA GAC GTT GGA

E   D   F   A   T   Y   Y   C   Q   Q   S   Y   S   T   P   N
241     GAA GAT TTT GCT ACG TAC TAC TGT CAA CAG AGT TAC AGT ACC CCT AAT
        CTT CTA AAA CGA TGC ATG ATG ACA GTT GTC TCA ATG TCA TGG GGA TTA

T   F   G   Q   G   T   K   V   E   I   K   R
289     ACG TTC GGC CAA GGG ACC AAG GTG GAA ATC AAA CGG
        TGC AAG CCG GTT CCC TGG TTC CAC CTT TAG TTT GCC
```

FIG. 16

Nucleotide and amino acid sequence of anti MSA dAbs MSA 16 and MSA 26

A: MSA 16

```
GAC ATC CAG ATG ACC CAG TCT CCA TCC TCC CTG TCT GCA TCT
 D   I   Q   M   T   Q   S   P   S   S   L   S   A   S

GTA GGA GAC CGT GTC ACC ATC ACT TGC CGG GCA AGT CAG AGC
 V   G   D   R   V   T   I   T   C   R   A   S   Q   S

ATT ATT AAG CAT TTA AAG TGG TAC CAG CAG AAA CCA GGG AAA
 I   I   K   H   L   K   W   Y   Q   Q   K   P   G   K

GCC CCT AAG CTC CTG ATC TAT GGT GCA TCC CGG TTG CAA AGT
 A   P   K   L   L   I   Y   G   A   S   R   L   Q   S

GGG GTC CCA TCA CGT TTC AGT GGC AGT GGA TCT GGG ACA GAT
 G   V   P   S   R   F   S   G   S   G   S   G   T   D

TTC ACT CTC ACC ATC AGC AGT CTG CAA CCT GAA GAT TTT GCT
 F   T   L   T   I   S   S   L   Q   P   E   D   F   A

ACG TAC TAC TGT CAA CAG GGG GCT CGG TGG CCT CAG ACG TTC
 T   Y   Y   C   Q   Q   G   A   R   W   P   Q   T   F

GGC CAA GGG ACC AAG GTG GAA ATC AAA CGG
 G   Q   G   T   K   V   E   I   K   R
```

B: MSA 26

```
GAC ATC CAG ATG ACC CAG TCT CCA TCC TCC CTG TCT GCA TCT
 D   I   Q   M   T   Q   S   P   S   S   L   S   A   S

GTA GGA GAC CGT GTC ACC ATC ACT TGC CGG GCA AGT CAG AGC
 V   G   D   R   V   T   I   T   C   R   A   S   Q   S

ATT TAT TAT CAT TTA AAG TGG TAC CAG CAG AAA CCA GGG AAA
 I   Y   Y   H   L   K   W   Y   Q   Q   K   P   G   K

GCC CCT AAG CTC CTG ATC TAT AAG GCA TCC ACG TTG CAA AGT
 A   P   K   L   L   I   Y   K   A   S   T   L   Q   S

GGG GTC CCA TCA CGT TTC AGT GGC AGT GGA TCT GGG ACA GAT
 G   V   P   S   R   F   S   G   S   G   S   G   T   D

TTC ACT CTC ACC ATC AGC AGT CTG CAA CCT GAA GAT TTT GCT
 F   T   L   T   I   S   S   L   Q   P   E   D   F   A

ACG TAC TAC TGT CAA CAG GTT CGG AAG GTG CCT CGG ACG TTC
 T   Y   Y   C   Q   Q   V   R   K   V   P   R   T   F

GGC CAA GGG ACC AAG GTG GAA ATC AAA CGG
 G   Q   G   T   K   V   E   I   K   R
```

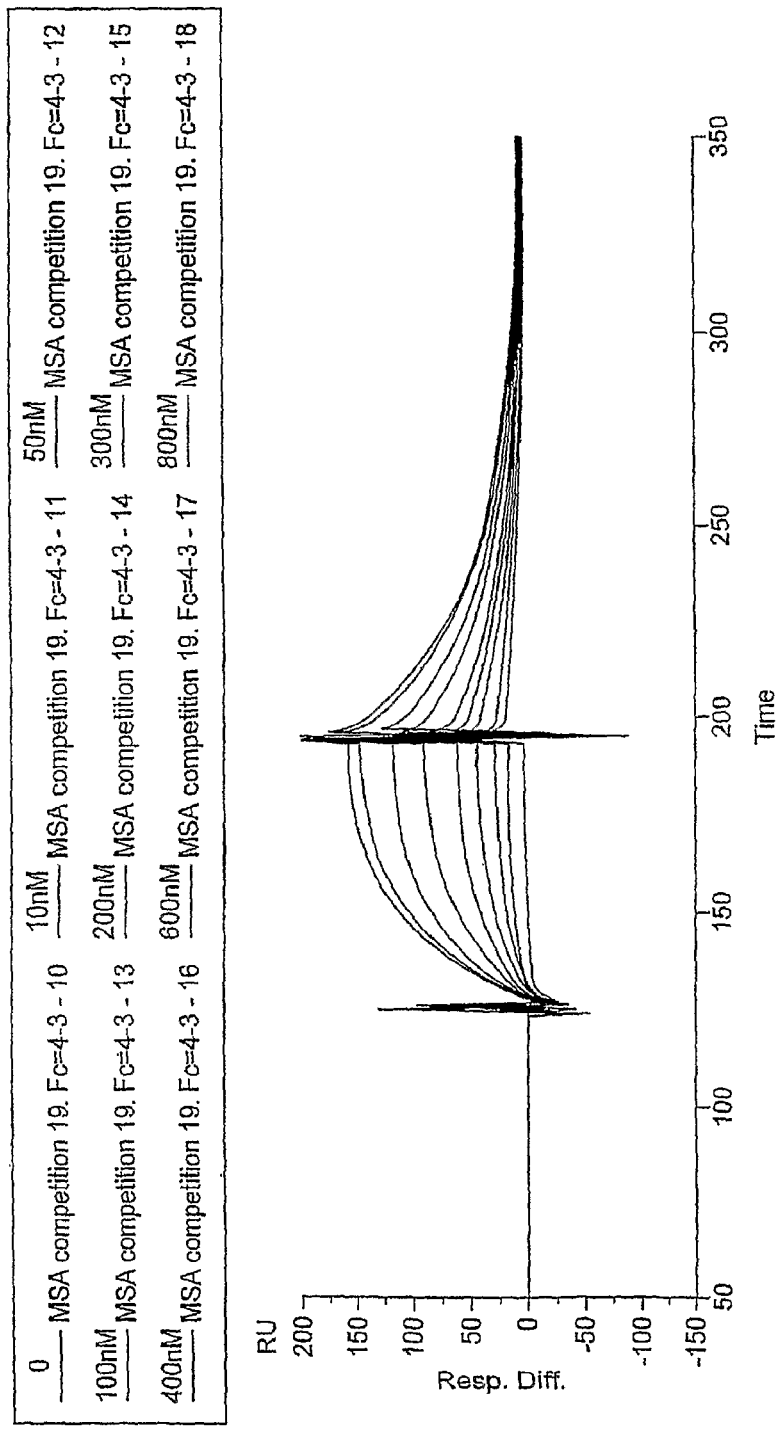

FIG. 19
(a)
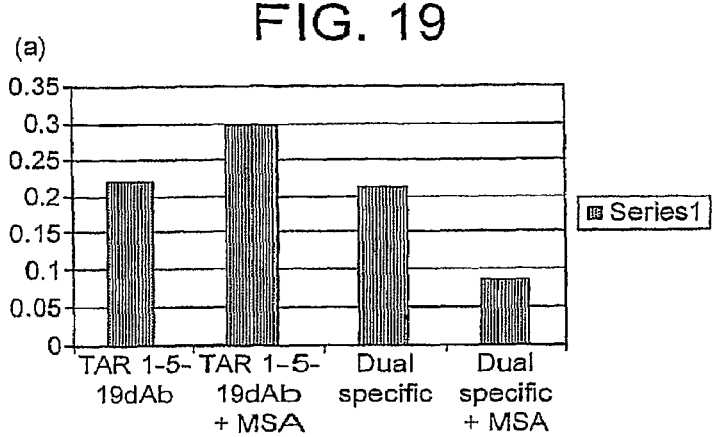
(b)
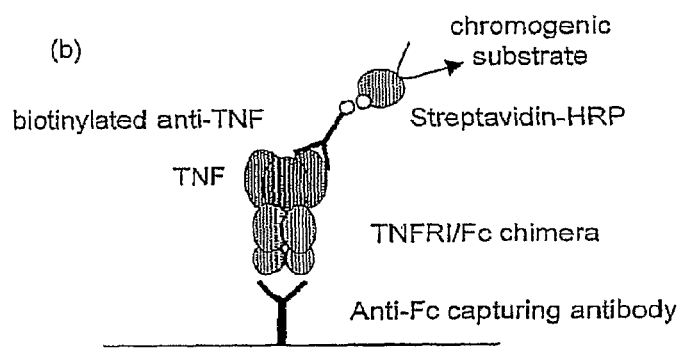
(c)
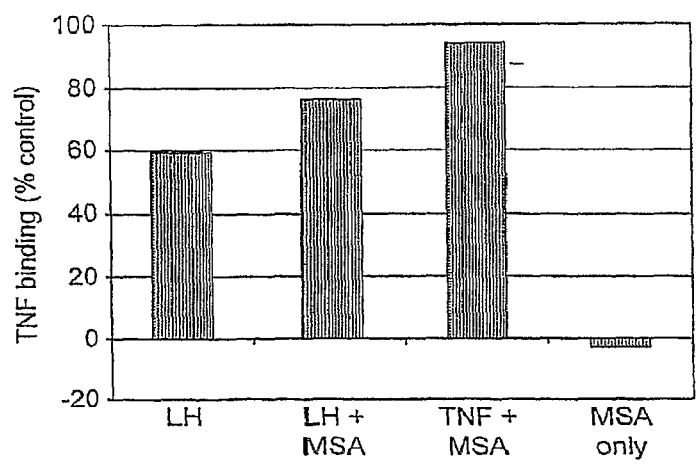

>TAR2h-10 (SEQ ID NO:31)
EVQLLESGGGLVQPGGSLRLSCAASGFTFE~WYWMG~WVRQAPGKGLEWVS~~AISGSGGSTYYADSVKG~~~RFTISRDNSKNTLYLQMNSLRAED
TAVYYCAK~~~VKLGGGPNFDY~~~WGQGTLVTVSS

>TAR2h-12 (SEQ ID NO:32)
EVQLLESGGGLVQPGGSLRLSCAASGFTFV~AYNMG~WVRQAPGKGLEWVS~~FIDMYGAKTYYADSVKG~~~RFTISRDNSKNTLYLQMNSLRAED
TAVYYCAK~~~LCLMDCSGDIFDY~~~WGQGTLVTVSS

>TAR2h-13 (SEQ ID NO:33)
EVQLLESGGGLVQPGGSLRLSCAASGFTFP~ADEMY~WVRQAPGKGLEWVS~~SIGWPGGATYYADSVKG~~~RFTISRDNSKNTLYLQMNSLRAED
TAVYYCAK~~~YGRNFDY~~~WGQGTLVTVSS

>TAR2h-14 (SEQ ID NO:34)
EVQLLESGGGLVQPGGSLRLSCAASGFTFD~QYDMS~WVRQAPGKGLEWVS~~LIDPSGGHTYYADSVKG~~~RFTISRNNSKNTLYLQMNSLRAED
TAVYYCAK~~~PVFSDWPAVEFDY~~~WGQGTLVTVSS

>TAR2h-16 (SEQ ID NO:35)
EVQLLESGGGLVQPGGSLRLSCAASGFTFG~NYDMQ~WVRQAPGKGLEWVS~~SIDGTGGTTYYADSVKG~~RFTISRDNSKNTLYLQMNSLRAED
TAVYYCAQ~~~ETNAFDY~~~WGQGTLVTVSS

>TAR2h-17 (SEQ ID NO:36)
EVQLLESGGGLVQPGGSLRLSCAASGFTFG~GYQMG~WVRQAPGKGLEWVS~~FIDFTGAHTYYADSVKG~~~RFTISRDNSKNTLYLQMNSLRAED
TAVYYCAK~~~LSDDLTLPERFPFDY~~~~WGQGTLVTVSS

>TAR2h-18 (SEQ ID NO:37)
EVQLLESGGGLVQPGGSLRLSCAASGFTFA~DYNMT~WVRQAPGKGLEWVS~~WIDQEGVFTYYADSVKG~~~RFTISRDNSKNTLYLQMNSLRAED
TAVYYCAK~~~DFSAAVMLRTSFDY~~~~WGQGTLVTVSS

>TAR2h-19 (SEQ ID NO:38)
EVQLLESGGGLVQPGGSLRLSCAVSGFTFH~DYGMV~WVRQAPGKGLEWVS~~QISIDGRTTYYADSVKG~~~RFTISRDNSKNTLYLQMNSLRAED
TAVYYCAK~~~RIFEFDY~~~~WGQGTLVTVSS

FIGURE 21A

>TAR2h-20 (SEQ ID NO:39)
EVQLLESGGGLVQPGGSLRLSCAASGFTFS~AYNMS~WVRQAPGKGLEWVS~~AISPSGNETYYADSVKG~~RFTISRDNSKNTLYLQMNSLRAED
TAVYYCAK~~~GAGEAFDY~~~WGQGTLVTVSS

>TAR2h-21 (SEQ ID NO:40)
EVQLLESGGGLVQPGGSLRLSCAASGFTFT~EYNMG~WVRQAPGKGLEWVS~~FIGHSGQHTYYADSVKG~~RFTISRDNSKNTLYLQMNSLRAED
TAVYYCAE~~~LNNLMFDY~~~WGQGTLVTVSS

>TAR2h-22 (SEQ ID NO:41)
EVQLLESGGGLVQPGGSLRLSCAASGFTFG~EYNMA~WVRQAPGKGQEWVS~~FISTGGHVTYYADSVKG~~RFTISRDNSKNTLYLQMNSLRAED
TAVYYCAK~~~FSVRFRSSIFDY~~~WGQGTLVTVSS

>TAR2h-23 (SEQ ID NO:42)
EVQLLESGGGLVQPGGSLRLSCAASGYTFT~EYTMG~WVRQAPGKGLEWVS~~WIAVDGIHTYYADSVKG~~RFTISRDNSKNTLYLQMNSLRAED
TAVYYCAK~~~LDWTATDFSIFDY~~~WGQGTLVTVSS

>TAR2h-24 (SEQ ID NO:43)
EVQLLESGGGLVQPGGSLRLSCAASGFTFA~NYTML~WVRQAPGKGLEWVS~~VISAEGRTTYYADSVKG~~RFTISRDNSKNTLYLQMNSLRAED
TAVYYCAK~~~LNMKATNFKDFDY~~~WGQGTLVTVSS

>TAR2h-25 (SEQ ID NO:44)
EVQLLESGGGLVQPGGSLRLSCAASGFTFS~EYAML~WVRQAPGKGLEWVS~~LIDRTGVITYYADSVKG~~RFTISRDNSKNTLYLQMNSLRAED
TAVYYCAK~~~RDYQYHLYQDFDY~~~RGQGTLVTVSS

>TAR2h-26 (SEQ ID NO:45)
EVQLLESGGGLVQPGGSLRLSCAASGFTFA~TYSMG~WVRQAPGKGLEWVS~~MIDPEGYHTYYADSVKG~~RFTISRDNSKNTLYLQMNSLRAED
TAVYYCAE~~~TNRPLTYKPWFDY~~~WGQGTLVTVSS

FIGURE 21B

>TAR2h-27   (SEQ ID NO:46)
EVQLLESGGGLVQPGGSLRLSCAASGFTFT~DYNMA~WVRQAPGKGLEWVS~~~FISQEGHHTYYADSVKG~~RFTISRDNSKNTLYLQMNSLRAED
TAVYYCAK~~~FSTIATLSLFDY~~~WGQGTLVTVSS

>TAR2h-29 (SEQ ID NO:47)
EVQLLESGGGLVQPGGSLRLSCAASGFTFA~TYNMG~WVRQAPGKGLEWVS~~~SIAWLGSETYYADSVKG~~RFTISRDNSKNTLYLQMNSLRAED
TAVYYCAK~~~HCKAECTGDLFDY~~~WGQGTLVTVSS

>TAR2h-30 (SEQ ID NO:48)
EVQLLESGGGLVQPGGALRLSCAASGFTFG~IYSMG~WVRQAPGKGLEWVS~~~SISGVGMETYYADSVKG~~RFTISRDNSENTLYLQMNSLRAED
TAVYYCAK~~~HSYPTRGRHLFDY~~~WGQGTLVTVSS

>TAR2h-32 (SEQ ID NO:49)
EVQLLESGGGLVQPGGSLRLSCAASGFTFE~WYWMG~WVRQAPGKGLEWVS~~~AISGSGGSTYYADSVKG~~RFTISRDNSKNTLYLQMNSLRAED
TAVYYCAK~~~VKLGGGPNFDY~~~RGQGTLVTVSS

>TAR2h-33 (SEQ ID NO:50)
EVQLLESGGGLVQPGGSLRLSCAASGFTFH~RYSMG~WVRQAPGKGLEWVS~~~AISSSGGITYYADSVKG~~RFTISRDNSKNTLYLQMNSLRAED
TAVYYCAK~~~STQAQGLELDY~~~WGQGTLVTVSS

>TAR2h-10-1(SEQ ID NO:51)
EVQLLESGGGLVQPGGSLRLSCAASGFTFE~WYWMG~WVRQAPGKGLEWVS~~~AISGSGGSTYYADSVKG~~RFTISRDNSKNTLYLQMNNLRAED
TAVYYCAK~~~VKLGGGPNFDY~~~RGQGTLVTVSS

>TAR2h-10-2   (SEQ ID NO:52)
EVQLLESGGGLVQPGGSLRLSCAASGFTFE~WYWMG~WVRQAPGKGLEWVS~~~AISGSGGSTYYADSVKG~~RFTISRDNSKNTLYLQMNNLRAED
TAVYYCAK~~~VKLGGGPNFDY~~~RGQGTLVTVSS

FIGURE 21C

>TAR2h-10-3 (SEQ ID NO:53)
EVQLLESGGGLVQPGGSLRLTCAASGFTFE-WYNMG-WVRQAPGKGLEWVS---AISGSGGSTYYADSVKG---RFTISRDNSKNTLYLQMNSLRAED
TAVYYCAK----VKLGGGPNFDY----WGQGTLVTVSS

>TAR2h-10-4 (SEQ ID NO:54)
EVQLLESGGGLVQPGGSLRLSCAASGFTFE-WYNMG-WIRQAPGKGLEWVS---AISGSGGSTYYADSVKG---RFTISRDNSKNTLYLQMNSLRAED
TAVYYCAK----VKLGGGPNFDY----WGQGTLVTVSS

>TAR2h-10-5 (SEQ ID NO:55)
EVQLLESGGGLVQPGGSLRLSCAASGFTFE-WYNMG-WVRQAPGKGLEWVS---AISGSGGSTYYADSVKG---RFTISRDNSKNTLYLQMNSLRAED
TAVYYCAK----VKLGGGPNFDY----RGQGTLVTVSS

>TAR2h-10-6 (SEQ ID NO:56)
EVQLLESGGGLVQPGGSLRLSCAASGFTFE-WYNMG-WVRQAPGKGPEWVS---AISGSGGSTYYADSVKG---RFTISRDNSKNTLYLQMNSLRAED
TAVYYCAK----VKLGGGPNFDY----RGQGTLVTVSS

>TAR2h-10-7 (SEQ ID NO:57)
EVQLLESGGGLVQPGGSLRLSCAASGFTFE-WYNMG-WVRQAPGKGLEWVS---AISGSGGSTYYADSVKG---RFTISRDNSKNTLYLQMNSLRAKD
TAVYYCAK----VKLGGGPNFDY----RGQGTLVTVSS

>TAR2h-10-8 (SEQ ID NO:58)
EVQLLESGGGLVQPGGSLRLSCAASGFTFE-WYNMG-WVRQAPGKGLEWVS---AISGSGGSTYYADSVKG---RFTISRDNSKNTLYLQMNSLRAGD
TAVYYCAK----VKLGGGPNFDY----RGQGTLVTVSS

>TAR2h-10-9 (SEQ ID NO:59)
EVQLLESGGGLVQPGGSLRLSCAASGFTFE-WYNMG-WVRQAPGKGLEWVS---AISGSGGRTYYADSVKG---RFTISRDNSKNTLYLQMNSLRAED
TAVYYCAK----VKLGGGPNFDY----WGQGTLVTVSS

FIGURE 21D

>TAR2h-10-10 (SEQ ID NO:60)
EVQLLESGGGLVQPGGSLRLSCAASGFTFE-WYWMG-WVRQAPGKGLEWVS---AISGSGGSTYYADSVKG---RFTISRDNSKNTLYLQMNSLRAED
TAVYYCAK----VKLGGGPNFDD---RGQGTLVTVSS

>TAR2h-10-11 (SEQ ID NO:61)
EVQLLESGGGLVQPGGSLRLSCAASGFTFE-WYWMG-WVRQAPGKGLEWVS---AISGSGGSKYYADSVKG---RFTISRDNSKNTLYLQMNSLRAED
TAVYYCAK----VKLGGGPNFDY---RGQGTLVTVSS

>TAR2h-10-12 (SEQ ID NO:62)
EVQLLESGGGLVQPGGSLRLSCAASGFTFG-WYWMG-WVRQAPGKGLEWAS---AISGSGGNTYYADSVKG---RFTISRDNSKNTLYLQMNSLRAED
TAVYYCAK----VKLGGGPNFDY---WGQGTLVTVSS

>TAR2h-10-13 (SEQ ID NO:63)
EVQLLESGGGLVQPGGSLRLSCAASGFTFE-WYWMG-WVRQAPGKGLGWVS---AISGSGGSTYYADSVRG---RFTISRDNSKNTLYLQMNSLRAED
TAVYYCAK----VKLGGGPNFDY---RGQGTLVTVSS

>TAR2h-10-14 (SEQ ID NO:64)
EVQLLESGGGLVQPGGSLRXSCAASGFTFE-WYWMG-WVRQAPGKGPEWVS---AISGSGGSTYYADSVKG---RFTISRDNSKNTLYLQMNSLRAED
TAVYYCAK----VKLGGGPNFDY---WGQGTLVTVSS

>TAR2h-10-15 (SEQ ID NO:65)
EVQLLESGGGLVQPGGSLRLSCAASGFTFE-WYWMG-WVRQAPGKGLEWVS---AISGSGGSTYYADSVKG---RFTISRDNSKNTLYLQMNSLRAED
TAVYYCAK----VKLGGGPNFDY---RGRGTLVTVSS

>TAR2h-10-16 (SEQ ID NO:66)
EVQLLESGGGLVQPGGSLRLSCAASGFTFE-WYWMG-WIRQAPGKGLEWVS---AISGSGGSTYYADSVKG---RFTISRDNSKNTLYLQMNSLRAKD
TAVYYCAK----VKLGGGPNFDY---RGQGTLVTVSS

>TAR2h-10-17 (SEQ ID NO:67)
EVQLLESGGGLVQPGGSLRLSCAASGFTFE-WYWMG-WIRQAPGKGLGWVS---AISGSGGSTYYADSVRG---RFTISRDNSKNTLYLQMNSLRAED
TAVYYCAK----VKLGGGPNFDY---RGQGTLVTVSS

FIGURE 21E

>TAR2h-10-18 (SEQ ID NO:68)
EVQLLESGGGLVQPGGSLRLSCAASGFTFG-WYWMG-WVRQAPGKGLEWAS--AISGSGGNTYYADSVKG--RFTISRDNSKNTLYLQMNSLRAED
TAVYYCAK---VKLGGGPNFDY---WGQGTLVTVSS

>TAR2h-10-19 (SEQ ID NO:69)
EVQLLESGGGLVQPGGSLRLSCAASGFTFE-WYWMG-WVRQAPGKGLGWVS--AISGSGGSTYYADSVRG--RFTISRDNSKNTLYLQMNSLRAKD
TAVYYCAK---VKLGGGPNFDY---RGQGTLVTVSS

>TAR2h-10-20 (SEQ ID NO:70)
EVQLLESGGGLVQPGGSLRLSCAASGFTFG-WYWMG-WVRQAPGKGLEWAS--AISGSGGNTYYADSVKG--RFTISRDNSKNTLYLQMNSLRAKD
TAVYYCAK---VKLGGGPNFDY---WGQGTLVTVSS

>TAR2h-10-21 (SEQ ID NO:71)
EVQLLESGGGLVQPGGSLRLSCAASGFTFG-WYWMG-WVRQAPGKGLEWVS--AISGSGGSTYYADSVKG--RFTISRDNSKNTLYLQMNSLRAKD
TAVYYCAK---VKLGGGPNFDY---RGQGTLVTVSS

>TAR2h-10-22 (SEQ ID NO:72)
EVQLLESGGGLVQPGGSLRLSCAASGFTFG-WYWMG-WVRQAPGKGLEWVS--AISGSGGSTYYADSVRG--RFTISRDNSKNTLYLQMNSLRAED
TAVYYCAK---VKLGGGPNFDY---RGQGTLVTVSS

>TAR2h-10-27 (SEQ ID NO:73)
EVQLLESGGGLVQPGGSLRLSCAASGFTFE-WYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-29 (SEQ ID NO:74)
EVQLLESGGGLVQPGGSLRLSCAASGFDFE-WYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-31 (SEQ ID NO:75)
EVQLLESGGGLVQPGGSLRLSCAASGFTFE-WYWMG-WVRQAPGKGLEWVS--AISGSGGSTYYADSVKG--RFTISRDNSKSTLYLQMNSLRAED
AAVYYCAK---VKLGGGPNFGY---RGQGTLVTVSS

FIGURE 21F

>TAR2h-10-35 (SEQ ID NO:76)
EVQLLESGGGLVQPGGSLRLSCAASGFDFE-WYWMG-WVRQAPGKGLEWVS--AISGSGGSTYYADSVKG--RFTISRDNSKNTLYLQMNSLHAED
AAVYYCAK---VKLGGGPNFGY---RGQGTLVTVSS

>TAR2h-10-36 (SEQ ID NO:77)
EVQLLESGGGLVQPGGSLRLSCAASGLTFE-WYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-37 (SEQ ID NO:78)
EVQLLGSGGGLVQPGGSLRLSCAASGFTFA-WYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-38 (SEQ ID NO:79)
EVQLLESGGGLVQPGGSLRLSCAASGFTFE-WYWMG-WVRQAPGKGLEWVS--AISGSGGSTYYADSVKG--RFTISRDNSKNTLYLQMNSLRAKD
AAVYYCAK---VKLGGGPNFGY---RGQGTLVTVSS

>TAR2h-10-45 (SEQ ID NO:80)
EVQLLESGGGLVQPGGSLRLSCAASGFTFE-PYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-47 (SEQ ID NO:81)
EVQLLESGGGFVQPGGSLRLSCAASGFTFE-WIWMS-WVRQAPGKGLEWVS--AISGSGGSTYYADSVKG--RFTISRDNSKNTLYLQMNSLRAED
ASVYYCAK---VKLGGGPNFGY---RGQGTLVTVSS

>TAR2h-10-48 (SEQ ID NO:82)
EVQLLESGGGLVQPGGSLRLPCAASGFTFE-WYWMT-WVRQAPGKGLEWVS--AISGSGGSTYYADSVKG--RFTISRDNSKNTLYLQMNSLRAED
AAVYYCAK---VKLGGGPNFGY---RGQGTLVTVSS

>TAR2h-10-57 (SEQ ID NO:83)
EVQLLESGGGLVQPGGSLRLSCAASGLTFE-WYWMG-WVRQAPGKGLEWVS--AISGSGGSTYYADSVKG--RFTISRDNSKNTLYLQMNSLRAED
AAVYYCAK---VKLGGGPNFGY---RGQGTLVTVSS

FIGURE 21G

>TAR2h-10-56 (SEQ ID NO:84)
EVQLLESGGGLVQPGGSLRLSCAASGLTFE~WYWMG~WVRQAPGKGLEWVS~~AVSGSGGSTYYADSVKG~~RFTISRDNSKNTLYLQMNSLRAED
AAVYYCAK~~~VKLGGGPNFGY~~~RGQGTLVTVSS

>TAR2h-10-58 (SEQ ID NO:85)
EVQLLESGGGLVQPGGSLRLSCAASGLTFE~WYWMG~WVRQAPGKGLEWVS~~AISGSGDSTYYADSVKG~~RFTISRDNSKNTLYLQMNSLRAED
AAVYYCAK~~~VKLGGGPNFGY~~~RGQGTLVTVSS

>TAR2h-10-66 (SEQ ID NO:86)
EVQLLESGGGLVQPGGSLRLSCAASGFTFE~WYWMG~WVRQAPGKGLEWVS~~AMSGSGGSTYYADSVKG~~RFTISRDNSKNTLYLQMNSLRAED
AAVYYCAK~~~VKLGGGPNFGN~~~RGLGTLVTVSS

>TAR2h-10-64 (SEQ ID NO:87)
EVQLLESGGGSVQPGGSLRLSCAASGFTFD~WYWMG~WVRQAPGKGLEWAS~~AISGSGGSTYYADSVKD~~RFTISRDNSKNTLYLQMNSLRAED
AAVYYCAK~~~VKLGGGPDFGY~~~RGQGTLVTVSS

>TAR2h-10-65 (SEQ ID NO:88)
EVQLLESGGGLVQPGGSLRLSCAASGFTFE~WYWMG~WVRQAPGKGLEWVS~~AISGSGGSTYYADSVKG~~RFTISRDNSKNTLYLQMNSLRAED
GAVYYCAK~~~VKLGGELNFGY~~~RGQGTLVTVSS

>TAR2h-10-68 (SEQ ID NO:89)
EVQLLESGGGLVQPGGSLRLSCAASGFTFE~WYWMG~WVRQAPGKGLEWVS~~AISGSGGSTYYADSVKG~~RFTISRDNSKNTLYLQMNSLRAED
AAVYYCAK~~~VKLGGGPNFGN~~~RGQGTPVTVSS

>TAR2h-10-69 (SEQ ID NO:90)
EVQLLESGGGLVQPGGSLRLSCAASGFTFE~WYWMG~WVRQAPGKGLEWVS~~AISGSGGSTYYADSVKG~~RFTISRDNSKNTLYLQMNSLRPED
AAVYYCAK~~~VKLGGGPNFGP~~~RGQGTLVTVSS

>TAR2h-10-67 (SEQ ID NO:91)
EVQLLESGGGLVQPGGSLRLSCAASGFTFE~WYWMG~WVRQAPGKGLEWVS~~AISGSGGSTYYADSVKG~~RFTISRDNSKNTLYLQMNSLRAED
AAVYYCAK~~~VKLGGGPNFGN~~~RGQGTLVTVSS

FIGURE 21H

>TAR2h-10-61 (SEQ ID NO:92)
EVQLLESGGGLVQPGGSLRLSCAASGFTIE~WYWMG~WVRQAPGKGLEWVS~~AISGSGGSTYYADSVKG~~RFTISRDNSKNTLYLQMNSLRAED
AAVYYCAK~~~VKLGGGPNFGY~~~RGQGTLVTVSS

>TAR2h-10-62 (SEQ ID NO:93)
EVQLLESGGGLVQPGGSLRLSCAASGFTFE~WYWMG~WVRQAPGKGLEWVS~~AISGSGGSTFYADSVKG~~RFTISRDNSKNTLYLQMNSLRAED
AAVYYCAK~~~VKLGGGPNFGY~~~RGQGTLVTVSS

>TAR2h-10-63 (SEQ ID NO:94)
EVQLLESGGGLVQPGGSLRLSCAASGFTFE~WYWMG~WVRQAPGKGLEWVT~~AISGSGGSTFYADSVKG~~RFTISRDNSKNTLYLQMNSLRAED
AAVYYCAK~~~VKLGGGPNFGY~~~RGQGTLVTVSS

>TAR2h-10-60 (SEQ ID NO:95)
EVQLLESGGGLVQPGGSLRLSCAASGFSFE~WYWMG~WVRQAPGKGLEWVS~~AISGSGDSTYYADSVKG~~RFTISRDNSKNTLYLQMNSLRAED
AAVYYCAK~~~VKLGGGPNFGY~~~RGQGTLVTVSS

>TAR2h-10-55 (SEQ ID NO:96)
EVQLLESGGGLVQPGGSLRLSCAASGFPFE~WYWMG~WVRQAPGKGLEWVS~~AISGSGGSTYYADSVKG~~RFTISRDNSKNTLYQQMNSLRAED
AAVYYCAK~~~VKLGGGPNFGY~~~RGQGTLVTVSS

>TAR2h-10-59 (SEQ ID NO:97)
EVQLLESGGGLVQPGGSLRLSCAASGFSFE~WYWMG~WVRQAPGKGLEWVS~~AISGSGGSTYYADSVKG~~RFTISRDNSKNTLYLQMNSLRAED
AAVYYCAK~~~VKLGGGPNFGY~~~RGQGTLVTVSS

>TAR2h-10-70 (SEQ ID NO:98)
EVQLLESGGGLVQPGGSLRLSCAASGFTFE~WYWMG~WVRQAPGKGLEWVS~~AISGSGGSTYYADSVKG~~RFTISRDNSKNTLYLQMNSLRAED
AAVYYCAK~~~VKLGGGPNYGY~~~RGQGTLVTVSS

FIGURE 21I

>TAR2h-34 (SEQ ID NO:373)
EVQLLESGGGLVQPGGSLRLSCAASGFTFP~EYGMA~WVRQAPGKGLEWVS~~~TISHGGEHTYADSVKG~~~RFTISRDNSKNTLYLQMNSLRAED
TAVYYCAQ~~~HPVSHPKFDY~~~~WGQGTLVTVSS

>TAR2h-35 (SEQ ID NO:374)
EVQLLESGGGLVQPGGSLRLSCAASGFTFD~AYNMF~WVRQAPGKGLEWVS~~~AISPSGRETYYADSVKG~~~RFTISRDNSKNTLYLQMNSLRAED
TAVYYCAK~~~RYPDFDY~~~WGQGTLVTVSS

>TAR2h-36 (SEQ ID NO:375)
EVQLLESGGGLVQPGGSLRLSCAASGFTFS~DYTMG~WVRQAPGKGLEWVS~~~LIDRPGNHTYYADSVKG~~~RFTISRDNSKNTLYLQMNSLRAED
TAVYYCAK~~~WGLNVEDFDY~~~~WGQGTLVTVSS

>TAR2h-37 (SEQ ID NO:376)
EVQLLESGGGLVQPGGSLRLSCAASGFTFI~EYDMG~WVRQAPGKGLEWVS~~~MISSDGRLTYYADSVKG~~~RFTISRDNSKNTLYLQMNSLRAED
TAVYYCAK~~~TWDGLNRNFDY~~~~WGQGTLVTVSS

>TAR2h-38 (SEQ ID NO:377)
EVQLLESGGGLVQPGGSLRLSCAASGFTFI~GYNMY~WVRQAPGKGLEWVS~~~FISPSGRETYYADSVKG~~~RFTISRDNSKNTLYLQMNSLRAED
TAVYYCAK~~~TLSADGRFDY~~~WGQGTLVTVSS

>TAR2h-39 (SEQ ID NO:378)
EVQLLESGGGLVQPGGSLRLSCAASGFTFG~SYDMG~WVRQAPGKGLEWVS~~~FIDVSGTLTYYADSVKG~~~RFTISRDNSKNTLYLQMNSLRAED
TAVYYCAK~~~TVELDGLDFDY~~~~WGQGTLVTVSS

>TAR2h-40 (SEQ ID NO:379)
EVQLLESGGGLVQPGGSLRLSCAASGFTFA~DYDMG~WVRQAPGKGLEWVS~~~FIDSSGSRTYYADSVKG~~~RFTISRDNSKNTLYLQMNSLRAED
TAVYYCAK~~~TAEIVNSRFDY~~~~WGQGTLVTVSS

FIGURE 21J

>TAR2h-41 (SEQ ID NO:380)
EVQLLESGGGLVQPGGSLRLSCAASGFTFD~KYQMG~WVRQAPGKGLEWVS~~FIDSNGHHTYYADSVKG~~RFTISRDNSKNTLYLQMNSLRAED
TAVYYCAE~~~LDNLSITPFDY~~~~WGQGTLVTVSS

>TAR2h-42 (SEQ ID NO:381)
EVQLLESGGGLVQPGGSLRLSCAASGFTFA~KYNMY~WVRQAPGKGLEWVS~~AISPKGQHTYYADSVKG~~RFTISRDNSKNTLYLQMNSLRAED
TAVYYCAE~~~GMGSDAITFDY~~~~WGQGTLVTVSS

>TAR2h-43 (SEQ ID NO:382)
EVQLLESGGGLVQPGGSLRLSCAASGFTFS~DYTMG~WARQAPGKGLEWVS~~FIDSDGLHTYYADSVKG~~RFTISRDNSKNTLYLQMNSLRAED
TAVYYCAQ~~~NPQYAYESSRFDY~~~WGQGTLVTVSS

>TAR2h-44 (SEQ ID NO:383)
EVQLLESGGGLVQPGGSLRLSCAASGFTFL~QYPMV~WVRQAPGKGLEWVS~~SILAPGPTYYADSVKG~~RFTISRDNSKNSLYLQMNSLRAED
TAVYYCAK~~~HPTHTPHPNFDY~~~~WGQGTLVTVSS

>TAR2h-45 (SEQ ID NO:384)
EVQLLESGGGLVQPGGSLRLSCAASGFTFG~GYRMA~WVRQAPGKGLEWVS~~FIDSEGVLTYYADSVKG~~RFTISRDNSKNTLYLQMNSLRAED
TAVYYCAK~~~LCSSNCNMRNFDY~~~WGQGTLVTVSS

>TAR2h-47 (SEQ ID NO:385)
EVQLLESGGGLVQPGGSLRLSCAASGFTFP~VYNMA~WVRQAPGKGLEWVS~~FIAGNGQQTYYADSVKG~~RFTISRDNSKNTLYLQMNSLRAED
TAVYYCAK~~~FASKVSPMSLITDFDY~~~WGQGTLVTVSS

>TAR2h-48 (SEQ ID NO:386)
EVQLLESGGGLVQPGGSLRLSCAASGFTFH~KYGMA~WVRQAPGKGLEWVS~~FIDLAGLHTYYADSVRG~~RFTISRDNSKNTLYLQMNSLRAED
TAVYYCAK~~~FATYSSGNEEQPFDY~~~~WGQGTLVTVSS

>TAR2h-50 (SEQ ID NO:387)
EVQLLESGGGLVQPGGSLRLSCAASGFTFS~AYNMA~WVRQAPGKGLEWVS~~FIAQSGGHTYYADSVKG~~RFTISRDNSKNTLYLQMNSLRAED
TAVYYCAK~~~FSHPDEEGTQMFDY~~~WGQGTLVTVSS

FIGURE 21K

>TAR2h-51 (SEQ ID NO:388)
EVQLLESGGGLVQPGGSLRLSCAASGFTFA-TYNMS-WVRQAPGKGLEWVS---AIDAGGMHTYYADSVKG~~~RFTISRDNSKNTLYLQMNSLRAED
TAVYYCAK----GTPFDY----WGQGTLVTVSS

>TAR2h-66 (SEQ ID NO:389)
EVQLLESGGGLVQPGGSLRLSCAASGFTFD-EYXMG-WVRQAPGKGLEWVS---LISPRGSKTYYADSVKG~~~RFTISRDNSKNTLYLQMNSLRAED
TAVYYCAK----YKPPFDY----WGQGTLVTVSS

>TAR2h-67 (SEQ ID NO:390)
EVQLLESGGGLVQPGGSLRLSCAASGFTFE-DYPMA-WVRQAPGKGLEWVS---FIGLKGIHTYYADSVKG~~~RFTISRDNSKNTLYLQMNSLRAED
TAVYYCAK----DLNNFDY----WGQGTLVTVSS

>TAR2h-68 (SEQ ID NO:391)
EVQLLESGGGLVQPGGSLRLSCAASGFTFG-NGNMV-WVRQAPGKGLEWVS---HIDEYGTNTYYADSVKG~~~RFTISRDNSKNTLYLQMNSLRAED
TAVYYCAK----PRNDRPGFDY---WGQGTLVTVSS

>TAR2h-70 (SEQ ID NO:392)
EVQLLESGGGLVQPGGSLRLSCAASGFTFP-TEHMY-WVRQAPGKGLEWVS---GIDTGGSHTYYADSVKG~~~RFTISRDNSKNTLYLQMNSLRAED
TAVYYCAK----GLHWSDSGPVHFDY---WGQGTLVTVSS

>TAR2h-71 (SEQ ID NO:393)
EVQLLESGGGLVQPGGSLRLSCAASGFTFG-NVDMH-WVRQAPGKGLEWVS---AISSAGGETYYADSVKG~~~RFTISRDNSKNTLYLQMNSLRAED
TAVYYCAK----RMLANSPLAFDY---WGQGTLVTVSS

>TAR2h-72 (SEQ ID NO:394)
EVQLLESGGGLVQPGGSLRLSCAASGFTFG-YEPMA-WVRQAPGKGLEWVS---TISHTGRDTYYADSVKG~~~RFTISRDNSKNTLYLQMNSLRAED
TAVYYCAK----RWSSFDY----WGQGTLVTVSS

>TAR2h-73 (SEQ ID NO:395)
EVQLLESGGGLVQPGGSLRLSCAASGFTFP-SEKMA-WVRQAPGKGLEWVS---SIDERGIMTYYADSVKG~~~RFTISRDNSKNTLYLQMNSLRAED
TAVYYCAK----RWTFNTAFDY---WGQGTLVTVSS

FIGURE 21L

>TAR2h-74 (SEQ ID NO:396)
EVQLLESGGGLVQPGGSLRLSCAASGFTFS~RENMH~WVRQAPGKGLEWVS~~GIGPRGMPTYYADSVKG~~RFTISRDNSKNTLYLQMNSLRAED
TAVYYCAK~~~GMNSHDGFDY~~~WGQGTLVTVSS

>TAR2h-75 (SEQ ID NO:397)
EVQLLESGGGLVQPGGSLRLSCAASGFTFN~AYTMI~WVRQAPGKGLEWVS~~YIDPHGTITYYADSVKG~~RFTISRDNSKNTLYLQMNSLRAED
TAVYYCAK~~~LPRAAPRFDY~~~WGQGTLVTVSS

>TAR2h-76 (SEQ ID NO:398)
EVQLLESGGGLVQPGGSLRLSCAASGFTFD~ASEMD~WVRQAPGKGLEWVS~~AISPSGSATYYADSVKG~~RFTISRDNSKNTLYLQMNSLRAED
TAVYYCAK~~~WTPGRTTFDY~~~WGQGTLVTVSS

>TAR2h-77 (SEQ ID NO:399)
EVQLLESGGGLVQPGGSLRLSCAASGFTFP~TEHMY~WVRQAPGKGLEWVS~~GIDTGGSHTYYADSVKG~~RFTISRDNSKNTLYLQMNSLRAED
TAVYYCAK~~~GLHWSSDSGPVHFDY~~~WGQGTLVTVSS

>TAR2h-78 (SEQ ID NO:400)
EVQLLESGGGLVQPGGSLRLSCAASGFTFK~LYNMA~WVRQAPGKGLEWVS~~FIAAAGPETYYADSVKG~~RFTISRDNSKNTLYLQMNSLRAED
TAVYYCAK~~~LGDISSIPQHPFDY~~~WGQGTLVTVSS

>TAR2h-79 (SEQ ID NO:401)
EVQLLESGGGLVQPGGSLRLSCAASGFTFG~NVDMH~WVRQAPGKGLEWVS~~AISSAGGETYYADSVKG~~RFTISRDNSKNTLYLQMNSLRAED
TAVYYCAK~~~SADITKGFDY~~~WGQGTLVTVSS

TAR2h-15 (SEQ ID NO:431)
EVRLLESGGGLVQPGGSLRLSCAASGFTF~GKYTMT~WVRQAPGKGLEWVS~~HISDDGNSTYYADSVKG~~RFTISRDNSKNTLYLQMNSLRAED
TAVYYCAK~~~VPILAPRNLFDY~~~WGQGTLVTVSS

FIGURE 21M

>TAR2h-10    (SEQ ID NO:99)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG-TGGTATTGGATGGGT-TGGGTCCGC
CAGGCTCCAGGGAAGGGTCTAGAGTGGGTCTCA--GCTATTAGTGGTAGTGGTGGTAGC
ACATACTACGCAGACTCCGTGAAGGGC--CGGTTCACCATCTCCCGCGACAATTCCAAG
AACACGCTGTATCTGCAAATGAACAGCCTGCGTGCCGAGGACACCGCGGTATATTACTGT
GCGAAA---GTTAAGTTGGGGGGGGGGCCTAATTTTGACTAC---TGGGGC
CAGGGAACCCTGGTCACCGTCTCGAGC

> TAR2h-12   (SEQ ID NO:100)
GAGGTGCAGCTGTTGGAGTCTGGGGGAGGCTTGGTACAGCCTGGGGGGTCCCTGCGTCTC
TCCTGTGCAGCCTCCGGATTCACCTTTGTT-GCTTATAATATGGGG-TGGGTCCGC
CAGGCTCCAGGGAAGGGTCTAGAGTGGGTCTCA--TTTATTGATATGTATGGTGCTAAG
ACATACTACGCAGACTCCGTGAAGGGC--CGGTTCACCATCTCCCGCGACAATTCCAAG
AACACGCTGTATCTGCAGATGAACAGCCTGCGTGCCGAGGATACCGCGGTATATTACTGT
GCGAAA---CTTTGTTTGATGGATTGTTCTGGGGATATTTTTGACTAC---TGGGGT
CAGGGAACCCTGGTCACCGTCTCGAGC

> TAR21h-13   (SEQ ID NO:101)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT-GCTGATGAGATGTAT-TGGGTCCGC
CAGGCTCCAGGGAAGGGTCTAGAGTGGGTCTCA--AGTATTGGTTGGCCGGGTGGTGCT
ACATACTACGCAGACTCCGTGAAGGGC--CGGTTCACCATCTCCCGCGACAATTCCAAG
AACACGCTGTATCTGCAAATGAACAGCCTGCGTGCCGAGGACACCGCGGTATATTACTGT
GCGAAA---TATGGTCGTAATTTTGACTAC---TGGGGTCAGGGAACCCTGGTCACCGTCTCGA
GC

> TAR2h-14   (SEQ ID NO:102)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT-CAGTATGATATGTCG-TGGGTCCGC
CAGGCTCCAGGGAAGGGTCTAGAGTGGGTCTCA--CTGATTGATCCGAGCGGTGGTCAT
ACATACTACGCAGACTCCGTGAAGGGC--CGGTTCACCATCTCCCGCAACAATTCCAAG
AACACGCTGTATCTGCAAATGAACAGCCTGCGTGCCGAGGACACCGCGGTATATTACTGT
GCGAAA---CCGGTTTTTTCTGATTGGCCTGCGGTGGAGTTTGACTAC---TGGGGT
CAGGGAACCCTGGTCACCGTCTCGAGC

> TAR2h-16   (SEQ ID NO:103)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG-AATTATGATATGCAG-TGGGTCCGC
CAGGCTCCAGGGAAGGGTCTAGAGTGGGTCTCA--TCTATTGATGGGACTGGTGGTACT
ACATACTACGCAGACTCCGTGAAGGGC--CGGTTCACCATCTCCCGCGACAATTCCAAG
AACACGCTGTATCTGCAAATGAACAGCCTGCGTGCCGAGGACACCGCGGTATATTACTGT
GCGCAA---GAGACTAATGCGTTTGACTAC---TGGGGTCAGGGAACCCTGGTCACCGTCTCGA
GC

Figure 22A

> TAR2h-17 (SEQ ID NO:104)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~GGTTATCAGATGGGT~TGGGTCCGC
CAGGCTCCAGGGAAGGGTCTTGAGTGGGTCTCA~~TTTATTGATTTTACTGGTGCGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGAGTGATGATCTTACTTTGCCTGAGCGGTTTCCGTTTGACTAC~~~TGGGGT
CAGGGAACCCTGGTCACCGTCTCGAGC

> TAR2h-18 (SEQ ID NO:105)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~GATTATAATATGACT~TGGGTCCGC
CAGGCTCCAGGGAAGGGTCTAGAGTGGGTCTCA~~TGGATTGATCAGGAGGGTGTTTTT
ACATACTACGCAGATTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~GATTTTTCGGCGGCTGTTATGCTTAGGACTAGTTTTGACTAC~~~TGGGGT
CAGGGAACCCTGGTCACCGTCTCGAGC

> TAR2h-19  (SEQ ID NO:106)
GAGGTGCAGCTGTTGGAGTCTGGGGGAGGCTTGGTACAGCCTGGGGGGTCCCTGCGTCTC
TCCTGTGCAGTCTCCGGATTCACCTTTCAT~GATTATGGGATGGTT~TGGGTCCGC
CAGGCTCCAGGGAAGGGTCTAGAGTGGGTCTCA~~CAGATTAGTATTGATGGTCGTACT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~AGGATTTTTGAGTTTGACTAC~~~TGGGGTCAGGGAACCCTGGTCACCGTCTCGAGC

> TAR2h-20 (SEQ ID NO:107)
GAGGTGCAGCTGTTGGAGTCTGGGGGAGGCTTGGTACAGCCTGGGGGGTCCCTGCGTCTC
TCCTGTGCAGCCTCCGGATTCACCTTTAGT~GCGTATAATATGTCT~TGGGTCCGC
CAGGCTCCAGGGAAGGGTCTAGAGTGGGTCTCA~~GCTATTTCGCCGTCTGGTAATGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGGGCTGGGGAGGCTTTTGACTAC~~~TGGGGTCAGGGAACCCTGGTCACCGTCT
CGAGC

> TAR2h-21 (SEQ ID NO:108)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~GAGTATAATATGGGT~TGGGTCCGC
CAGGCTCCAGGGAAGGGTCTAGAGTGGGTCTCA~~TTTATTGGGCATTCTGGTCAGCAT
ACATACTACGCAGACTCCGTGAAGGGC~~CGGTTCACCATCTCCCGCGACAATTCCAAG
AACACGCTGTATCTGCAAATGAATAGCCTGCGTGCCGAGGACACCGCGGTATATTACTGT
GCGGAA~~~CTGAATAATTTGATGTTTGACTAC~~~TGGGGTCAGGGAACCCTGGTCACCGTCT
CGAGC

Figure 22B

> TAR2h-22 (SEQ ID NO:109)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~GAGTATAATATGGCG~TGGGTCCGC
CAGGCTCCAGGGAAGGGTCAAGAGTGGGTCTCA~~TTTATTTCTACGGGTGGTCATGTT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTTCGGTGCGTTTTAGGTCGAGTATTTTTGACTAC~~~TGGGGTCAGGGAACCC
TGGTCACCGTCTCGAGC

> TAR2h-23 (SEQ ID NO:110)
GAGGTGCAGCTGTTGGAGTCTGGGGGAGGCTTGGTACAGCCTGGGGGGTCCCTGCGTCTC
TCCTGTGCAGCCTCCGGATACACCTTTACT~GAGTATACGATGGGT~TGGGTCCGC
CAGGCTCCAGGGAAGGGTCTAGAGTGGGTCTCA~~TGGATTGCTGTTGATGGTATTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGGATTGGACGGCTACTGATTTTTCTATTTTTGACTAC~~~TGGGGT
CAGGGAACCCTGGTCACCGTCTCGAGC

> TAR2h-24 (SEQ ID NO:111)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~AATTATACTATGCTG~TGGGTCCGC
CAGGCTCCAGGGAAGGGTCTAGAGTGGGTCTCA~~GTTATTAGTGCTGAGGGTCGGACT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CTTAATATGAAGGCTACTAATTTTAAGGATTTTGACTAC~~~TGGGGT
CAGGGAACCCTGGTCACCGTCTCGAGC

> TAR2h-25 (SEQ ID NO:112)
GAGGTGCAGCTGTTGGAGTCTGGGGGAGGCTTGGTACAGCCTGGGGGGTCCCTGCGTCTC
TCCTGCGCAGCCTCCGGATTCACCTTTTCG~GAGTATGCGATGCTT~TGGGTCCGC
CAGGCTCCAGGGAAGGGTCTAGAGTGGGTCTCA~~CTTATTGATCGGACGGGTGTTATT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CGGGATTATCAGTATCATCTGTATCAGGATTTTGACTAC~~~CGGGGT
CAGGGAACCCTGGTCACCGTCTCGAGC

> TAR2h-26 (SEQ ID NO:113)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~ACGTATAGTATGGGG~TGGGTCCGC
CAGGCTCCAGGGAAGGGTCTAGAGTGGGTCTCA~~ATGATTGATCCGGAGGGTTATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~ACGAATCGGCCTTTGACGTATAAGCCTTGGTTTGACTAC~~~TGGGGT
CAGGGAACCCTGGTCACCGTCTCGAGC

Figure 22C

> TAR2h-27 (SEQ ID NO:114)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~GATTATAATATGGCT~TGGGTCCGC
CAGGCTCCAGGGAAGGGTCTAGAGTGGGTCTCA~~TTTATTAGTCAGGAGGGTCATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTAGTACTATTGCTACGTTGTCTCTGTTTGACTAC~~~TGGGGTCAGGGAACCC
TGGTCACCGTCTCGAGC

> TAR2h-29 (SEQ ID NO:115)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~ACGTATAATATGGGT~TGGGTCCGC
CAGGCTCCAGGGAAGGGTCTAGAGTGGGTCTCA~~TCTATTGCGTGGCTTGGTTCTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CATTGTAAGGCGGAGTGTACTGGGGATCTTTTTGACTAC~~~TGGGGT
CAGGGAACCCTGGTCACCGTCTCGAGC

> TAR2h-30 (SEQ ID NO:116)
GAGGTGCAGCTGTTGGAGTCTGGGGGAGGCTTGGTACAGCCTGGGGGGGCCCTGCGTCTC
TCCTGTGCAGCCTCCGGATTCACCTTTGGT~ATTTATTCGATGGGT~TGGGTCCGC
CAGGCTCCAGGGAAGGGTCTAGAGTGGGTCTCA~~TCTATTTCGGGTGTTGGTATGGAG
ACATACTACGCAGACTCCGTGAAGGGC~~CGGTTCACCATCTCCCGCGACAATTCCGAG
AACACGCTGTATCTGCAAATGAACAGCCTGCGTGCCGAGGATACCGCGGTATATTACTGT
GCGAAA~~~CATTCTTATCCTACTCGGGGTCGTCATCTTTTTGACTAC~~~TGGGGT
CAGGGAACCCTGGTCACCGTCTCGAGC

> TAR2h-32 (SEQ ID NO:117)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGCAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGCCTAATTTTGACTAC~~~CGGGGC
CAGGGAACCCTGGTCACCGTCTCGAGC

> TAR2h-33 (SEQ ID NO:118)
GAGGTGCAGCTGTTGGAGTCTGGGGGAGGCTTGGTACAGCCTGGGGGGTCCCTGCGTCTC
TCCTGTGCAGCCTCCGGATTCACCTTTCAT~CGGTATTCTATGGGT~TGGGTCCGC
CAGGCTCCAGGGAAGGGTCTAGAGTGGGTCTCA~~GCTATTAGTTCTTCTGGTGGTATC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TCGACGCAGGCGCAGGGGCTGGAGTTAGACTAC~~~TGGGGT
CAGGGAACCCTGGTCACCGTCTCGAGC

Figure 22D

\> TAR2h-10-1 (SEQ ID NO:119)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAACCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGC

\> TAR2h-10-2 (SEQ ID NO:120)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGA~TGGGTCCGC
CAGGCTCCAGGCAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGC

\> TAR2h-10-3 (SEQ ID NO:121)
GAGGTGCAGCTGTTGGAGTCTGGGGGAGGCTTGGTACAGCCTGGGGGGTCCCTGCGTCTC
ACCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAACTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~TGGGGC
CAGGGAACCCTGGTCACCGTCTCGAGC

\> TAR2h-10-4 (SEQ ID NO:122)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGATCCGC
CAGGCTCCAGGGAAGGGTCTAGAGTGGGTCTCG~~GCTATCAGTGGTAGTGGTGGTAGT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~TGGGGC
CAGGGAACCCTGGTCACCGTCTCGAGC

\> TAR2h-10-5 (SEQ ID NO:123)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGc

Figure 22E

> TAR2h-10-6 (SEQ ID NO:124)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCCAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGCCCTAATTTTGACTAC~~~CGGGGC
CAGGGAACCCTGGTCACCGTCTCGAGc

> TAR2h-10-7 (SEQ ID NO:125)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCAAGGACACCGCGGTATATTACTGT
GCGAAA~~~GTGAAGTTGGGGGGGGGGCCTAATTTTGACTAC~~~AGGGGC
CAGGGAACCCTGGTCACCGTCTCGAGC

>TAR2h-10-8 (SEQ ID NO:126)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGGGGACACCGCGGTATATTACTGT
GCGAAA~~~GTTAAGTTGGGCGGGGGGCCTAATTTTGACTAC~~~AGGGGC
CAGGGAACCCTGGTCACCGTCTCGAgC

>TAR2h-10-9 (SEQ ID NO:127)
GAGGTGCAGCTGTTGGAGTCTGGGGGAGGCCTGGTACAGCCTGGGGGGTCCCTGCGTCTC
TCCTGTGCAGCCTCCGGATTCACCTTCGAG~TGGTATTGGATGGGT~TGGGTCCGC
CAGGCTCCAGGGAAGGGTCTAGAGTGGGTCTCA~~GCTATCAGTGGTAGTGGTGGTAGA
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGCCTAATTTTGACTAC~~~TGGGGC
CAGGGAACCCTGGTCACCGTCTCGAGC

>TAR2h-10-10 (SEQ ID NO:128)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGCGGGGGGCCTAATTTTGACGAC~~~CGGGGC
CAGGGAACCCTGGTCACCGTCTCGAGC

Figure 22F

>TAR2h-10-11 (SEQ ID NO:129)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
AAATACTACGCAGACTCCGTGAAGGGC~~CGGTTCACCATCTCCCGCGACAATTCCAAG
AACACACTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGC

>TAR2h-10-12 (SEQ ID NO:130)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~TGGTATTGGATGGGT~TGGGTCCGC
CAGGCTCCAGGGAAGGGTCTAGAGTGGGCCTCA~~GCTATCAGTGGTAGTGGTGGTAAC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~TGGGGC
CAGGGAACCCTGGTCACCGTCTCGAGC

>TAR2h-10-13 (SEQ ID NO:131)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGGGTGGGTCTCA~~GCTATCAGTGGTAGTGGTGGTAGC
ACATACTACGCAGACTCCGTGAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGC

>TAR2h-10-14 (SEQ ID NO:132)
GAGGTGCAGCTGTTGGAGTCTGGGGGAGGCTTGGTACAGCCTGGGGGGTCCCTGCGTCTN
TCCTGTGCAGCCTCCGGATTCACCTTTGAG~TGGTATTGGATGGGT~TGGGTCCGC
CAGGCTCCAGGCAAGGGTCCAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~TGGGGC
CAGGGAACCCTGGTCACCGTCTCGAGc

>TAR2h-10-15 (SEQ ID NO:133)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGCAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CGGGGAACCCTGGTCACCGTCTCGAGC

Figure 22G

\>TAR2h-10-16 (SEQ ID NO:134)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGATCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCAAGGACACCGCGGTATATTACTGT
GCGAAA~~~GTGAAGTTGGGGGGGGGGCCTAATTTTGACTAC~~~AGGGGC
CAGGGAACCCTGGTCACCGTCTCGAGc

\>TAR2h-10-17 (SEQ ID NO:135)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGATCCGC
CAGGCTCCAGGGAAGGGTCTAGGGTGGGTCTCA~~GCTATCAGTGGTAGTGGTGGTAGC
ACATACTACGCAGACTCCGTGAGGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGC

\>TAR2h-10-18 (SEQ ID NO:136)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~TGGTATTGGATGGGT~TGGGTCCGC
CAGGCTCCAGGGAAGGGTCTAGAGTGGGCCTCA~~GCTATCAGTGGTAGTGGTGGTAAC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGG GGGGGGCCTAATTTTGACTAC~~~TGGGGC
CAGGGAACCCTGGTCACCGT CTCGAGc

\>TAR2h-10-19 (SEQ ID NO:137)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGGGTGGGTCTCA~~GCTATCAGTGGTAGTGGTGGTAGC
ACATACTACGCAGACTCCGTGAGGGGC~~CGGTTCACCATCTCCCGCGACAATTCCAAG
AACACGCTGTATCTGCAAATGAACAGCCTGCGTGCCAAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGc

\>TAR2h-10-20 (SEQ ID NO:138)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~TGGTATTGGATGGGT~TGGGTCCGC
CAGGCTCCAGGGAAGGGTCTAGAGTGGGCCTCA~~GCTATCAGTGGTAGTGGTGGTAAC
ACATACTACGCAGACTCCGTGAAGGGC~~CGGTTCACCATCTCCCGCGACAATTCCAAG
AACACGCTGTATCTGCAAATGAACAGCCTGCGTGCCAAGGACACCGCGGTATATTACTGT
GCGAAA~~~GTTAAGTTGGGGGGGGGCCTAATTTTGACTAC~~~TGGGGC
CAGGGAACCCTGGTCACCGTCTCGAGc

Figure 22H

>TAR2h-10-21 (SEQ ID NO:139)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCAAGGACACCGCGGTATATTACTGT
GCGAAA~~~GTGAAGTTGGGGGGGGGGCCTAATTTTGACTAC~~~AGGGGC
CAGGGAACCCTGGTCACCGTCTCGAGc

>TAR2h-10-22 (SEQ ID NO:140)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~TGGTATTGGATGGGT~TGGGTCCGC
CAGGCTCCAGGGAAGGGTCTAGGGTGGGTCTCA~~GCTATCAGTGGTAGTGGTGGTAGC
ACATACTACGCAGACTCCGTGAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTAAGTTGGGGGGGGGGCCTAATTTTGACTAC~~~CGGGGC
CAGGGAACCCTGGTCACCGTCTCGAGc

>TAR2h-10-27 (SEQ ID NO:141)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

>TAR2h-10-29 (SEQ ID NO:142)
GAGGTGCAGCTGTTGGAGTCTGGGGGAGGCTTGGTACAGCCTGGGGGGTCCCTGCGTCTC
TCCTGTGCAGCCTCCGGATTCGACTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

>TAR2h-10-31 (SEQ ID NO:143)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AGCACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

Figure 22I

\>TAR2h-10-35 (SEQ ID NO:144)
GAGGTGCAGCTGTTGGAGTCTGGGGGAGGCTTGGTACAGCCTGGGGGGTCCCTGCGTCTc
TCCTGTGCAGCCTCCGGATTCGACTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCATGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

\>TAR2h-10-36 (SEQ ID NO:145)
GAGGTGCAGCTGTTGGAGTCTGGGGGAGGCTTGGTACAGCCTGGGGGGTCCCTGCGTCTC
TCCTGTGCAGTCTCCGGACTGACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

\>TAR2h-10-37 (SEQ ID NO:146)
GAGGTGCAGCTGTTGGGGTCTGGGGGAGGCTTGGTACAGCCTGGGGGGTCCCTGCGTCTC
TCCTGTGCAGCCTCCGGATTCACCTTTGCG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

\>TAR2h-10-38 (SEQ ID NO:147)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCAAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

\>TAR2h-10-45 (SEQ ID NO:148)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~CCGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

Figure 22J

>TAR2h-10-47 (SEQ ID NO:149)
GAGGTGCAGCTGTTGGAGTCTGGGGGAGGCTTTGTACAGCCTGGGGGGTCCCTGCGTCTC
TCCTGTGCAGCCTCCGGATTCACCTTTGAG~TGGTATTGGATGAGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCTCGGTATATTACTGT
GCGAAA~~~GTTAAGTTGGGGGGGGGGCCCAATTTTGGCTAC~~~CGGGGC
CAGGGAACCCTGGTCACCGTCTCGAGC

>TAR2h-10-48 (SEQ ID NO:150)
GAGGTGCAGCTGTTGGAGTCTGGGGGAGGCTTGGTACAGCCTGGGGGGTCCCTGCGTCTC
CCCTGTGCAGCCTCCGGATTCACCTTTGAG~TGGTATTGGATGACC~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGGCCTAATTTTGGCTAC~~~CGGGGC
CAGGGAACCCTGGTCACCGTCTCGAGC

>TAR2h-10-57 (SEQ ID NO:151)
GAGGTGCAGCTGTTGGAGTCTGGGGGAGGCTTGGTACAGCCTGGGGGGTCCCTGCGTCTC
TCCTGTGCAGCCTCCGGACTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-56 (SEQ ID NO:152)
GAGGTGCAGCTGTTGGAGTCTGGAGGAGGCTTGGTACAGCCTGGGGGGTCCCTGCGTCTC
TCCTGTGCAGCCTCCGGACTCACCTTTGAG~TGGTATTGGATGGGT~TGGGTCCGC
CAGGCTCCAGGGAAGGGTCTAGAGTGGGTCTCA~~GCTGTCAGTGGTAGTGGTGGTAGC
ACATACTACGCAGACTCCGTGAAGGGC~~CGGTTCACCATCTCCCGCGACAATTCCAAG
AACACGCTGTATTTGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-58 (SEQ ID NO:153)
GAGGTGCAGCTGTTGGAGTCTGGGGGAGGCTTGGTACAGCCTGGGGGGTCCCTGCGTCTC
TCCTGTGCAGCCTCCGGACTCACCTTTGAG~TGGTATTGGATGGGT~TGGGTCCGC
CAGGCTCCAGGGAAGGGTCTAGAGTGGGTCTCG~~GCTATTAGTGGTAGTGGTGATAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGgCCTAATTTTGGCTAC~~~CGGGGC
CAGGGAACCCTGGTCACCGTCTCGAGC

Figure 22K

>TAR2h-10-66 (SEQ ID NO:154)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATGAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCAAC~~~CGGGGC
CTGGGAACCCTGGTCACCGTCTCGAGC

>TAR2h-10-64 (SEQ ID NO:155)
GAGGTGCAGCTGTTGGAGTCTGGGGGAGGCTCGGTACAGCCTGGGGGGTCCCTGCGTCTC
TCCTGTGCAGCCTCCGGATTCACCTTTGAC~TGGTATTGGATGGGT~TGGGTCCGC
CAGGCTCCAGGGAAGGGTCTAGAGTGGGCCTCA~~GCTATCAGTGGTAGTGGTGGTAGC
ACATACTACGCAGACTCCGTGAAGGAC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTGATTTTGGCTAC~~~CGGGGC
CAGGGAACCCTGGTCACCGTCTCGAGC

>TAR2h-10-65 (SEQ ID NO:156)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTATATCTGCAAATGAACAGCCTGCGTGCCGAGGACGGCGCGGTATATTACTGT
GCGAAA~~~GTTAAGTTGGGGGGGGGAGCTTAACTTTGGCTAC~~~CGGGGC
CAGGGAACCCTGGTCACCGTCTCGAGC

>TAR2h-10-68 (SEQ ID NO:157)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCAAC~~~CGGGGC
CAGGGAACCCCGGTCACCGTCTCGAGC

>TAR2h-10-69 (SEQ ID NO:158)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAgACTCCGTGAAGGGC~~CGGTTCACCATCTCCCGCGACAATTCCAAG
AACACGCTGTATCTGCAAATGAACAGCCTGCGTCCCGAGGACGCCGCGGTATATTACTGT
GCGAAA~~~GTTAAGTTGGGGGGGGGgCCTAATTTTGGCCCC~~~CGGGGC
CAGGGAACCCTGGTCACCGTCTCGAGC

Figure 22L

>TAR2h-10-67 (SEQ ID NO:159)
GAGGTGCAGCTGTTGGAGTCTGGGGGAGGCTTGGTACAGCCTGGGGGGTCCCTGCGTCTC
TCCTGTGCAGCCTCCGGATTCACCTTTGAA~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCAAC~~~CGGGGC
CAGGGAACCCTGGTCACCGTCTCGAGC

>TAR2h-10-61 (SEQ ID NO:160)
GAGGTGCAGCTGTTGGAGTCTGGGGGAGGCTTGGTACAGCCTGGGGGGTCCCTGCGTCTC
TCCTGTGCAGCCTCCGGATTCACCATTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGTGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-62 (SEQ ID NO:161)
GAGGTGCAGCTGTTGGAGTCTGGGGGGGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATTCTACGCAGACTCCGTGAAGGGC~~CGGTTCACCATCTCCCGCGACAATTCCAAG
AACACGCTGTATCTGCAAATGAACAGCCTGCGCGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-63 (SEQ ID NO:162)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCACA~~GCTATCAGTGGTAGTGGTGGTAGC
ACTTTCTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-60 (SEQ ID NO:163)
GAGGTGCAGCTGTTGGAGTCTGGGGGAGGCTTGGTACAGCCTGGGGGGTCCCTGCGTCTC
TCCTGTGCAGCCTCCGGATTCAGCTTTGAG~TGGTATTGGATGGGT~TGGGTCCGC
CAGGCTCCAGGGAAGGGTCTAGAGTGGGTCTCA~~GCTATCAGTGGTAGTGGTGATAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCTAT~~~CGGGGC
CAGGGAACCCTGGTCACCGTCTCGAGC

Figure 22M

>TAR2h-10-55 (SEQ ID NO:164)
GAGGTGCAGCTGTTGGAGTCTGGGGGAGGCTTGGTACAGCCTGGGGGGTCCCTGCGTCTC
TCCTGTGCAGCCTCCGGATTCCCCTTTGAG~TGGTATTGGATGGGT~TGGGTCCGC
CAGGCTCCAGGGAAGGGTCTAGAGTGGGTCTCA~~GCTATCAGTGGTAGTGGTGATAGC
ACATACTACGCAGACTCCGTGAAGGGC~~CGGTTCACCATCTCCCGCGACAATTCCAAG
AACACGCTGTATCAGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAGC

>TAR2h-10-59 (SEQ ID NO:165)
GAGGTGCAGCTGTTGGAGTCTGGGGGAGGCTTGGTACAGCCTGGGGGGTCCCTGCGTCTC
TCCTGTGCAGCCTCCGGATTCAGCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTTTGGCTAC~~~CGGGGC
CAGGGAACCCTGGTCACCGTCTCGAG

>TAR2h-10-70 (SEQ ID NO:166)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGgCCTAATTATGGCTAC~~~CGGGGC
CAGGGAACCCTGGTCACCGTCTCGAGC

>TAR2h-34 (SEQ ID NO:402)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~GAGTATGGGATGGCG~TGGGTCCGC
CAGGCTCCAGGGAAGGGTCTAGAGTGGGTCTCA~~ACGATTTCTCATGGGGGTGAGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGCAA~~~CATCCGGTTAGTCATCCGAAGTTTGACTAC~~~TGGGGT
CAGGGAACCCTGGTCACCGTCTCGAGC

>TAR2h-35 (SEQ ID NO:403)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~GCTTATAATATGTTT~TGGGTCCGC
CAGGCTCCAGGGAAGGGTCTGGAGTGGGTCTCA~~GCTATTAGTCCGTCGGGTCGGGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~AGGTATCCTGATTTTGACTAC~~~TGGGGT
CAGGGAACCCTGGTCACCGTCTCGAGC

Figure 22N

>TAR2h-36 (SEQ ID NO:404)
GAGGTGCAGCTGTTGGAGTCTGGGGGAGGCTTGGTACAGCCTGGGGGGTCCCTGCGTCTC
TCCTGTGCAGCCTCCGGATTCACCTTTAGT~GATTATACTATGGGT~TGGGTCCGC
CAGGCTCCAGGGAAGGGTCTAGAGTGGGTCTCA~~TTGATTGATCGTCCTGGTAATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TGGGGGCTTAATGTGGAGGATTTTGACTAC~~~TGGGGT
CAGGGAACCCTGGTCACCGTCTCGAGC

>TAR2h-37 (SEQ ID NO:405)
GAGGTGCAGCTGTTGGAGTCTGGGGGAGGCTTGGTACAGCCTGGGGGGTCCCTGCGTCTC
TCCTGTGCAGCCTCCGGATTCACCTTTATT~GAGTATGATATGGGT~TGGGTCCGC
CAGGCTCCAGGGAAGGGTCTAGAGTGGGTCTCA~~ATGATTAGTTCGGATGGTAGGCTT
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~ACGTGGGATGGTTTGAATCGTAATTTTGACTAC~~~TGGGGT
CAGGGAACCCTGGTCACCGTCTCGAGC

>TAR2h-38 (SEQ ID NO:406)
GAGGTGCAGCTGTTGGAGTCTGGGGGAGGCTTGGTACAGCCTGGGGGGTC CCTGCGTCTC
TCCTGTGCAGCCTCCGGATTCACCTTTATT~GGGTATAATATGTAT~TGGGTCCGC
CAGGCTCCAGGGAAGGGTCTAGAGTGGGTCTCA~~TTTATTTCTCCTTCGGGTCGGGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~ACTTTGTCGGCGGATGGTAGGTTTGACTAC~~~TGGGGT
CAGGGAACCCTGGTCACCGTCTCGAGC

>TAR2h-39 (SEQ ID NO:407)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AGTTATGATATGGGT~TGGGTCCGC
CAGGCTCCAGGGAAGGGTCTAGAGTGGGTCTCA~~TTTATTGATGTGTCGGGTACTTTG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ACTGTTGAGCTGGATGGTCTGGATTTTGACTAC~~~TGGGGT
CAGGGAACCCTGGTCACCGTCTCGAGC

>TAR2h-40 (SEQ ID NO:408)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~GATTATGATATGGGG~TGGGTCCGC
CAGGCTCCAGGGAAGGGTCTAGAGTGGGTCTCA~~TTTATTGATAGTTCTGGTTCTCGT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ACGGCGGAGATTGTTAATAGTCGTTTTGACTAC~~~TGGGGT
CAGGGAACCCTGGTCACCGTCTCGAGC

Figure 220

>TAR2h-41 (SEQ ID NO:409)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~AAGTATCAGATGGGT~TGGGTCCGC
CAGGCTCCAGGGAAGGGTCTAGAGTGGGTCTCA~~TTTATTGATTCGAATGGTCATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~CTTGATAATCTTAGTATTACGCCGTTTGACTAC~~~TGGGGT
CAGGGAACCCTGGTCACCGTCTCGAGC

>TAR2h-42 (SEQ ID NO:410)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~AAGTATAATATGTAT~TGGGTCCGC
CAGGCTCCAGGGAAGGGTCTAGAGTGGGTCTCA~~GCGATTAGTCCTAAGGGTCAGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~GGGATGGGGTCGGATGCTATTACTTTTGACTAC~~~TGGGGT
CAGGGAACCCTGGTCACCGTCTCGAGC

>TAR2h-43 (SEQ ID NO:411)
GAGGTGCAGCTGTTGGAGTCTGGGGGAGGCTTGGTACAGCCTGGGGGGTCCCTGCGTCTC
TCCTGTGCAGCCTCCGGATTCACCTTTAGT~GATTATACTATGGGT~TGGGCCCGC
CAGGCTCCAGGGAAGGGTCTAGAGTGGGTCTCA~~TTTATTGATTCTGATGGTTTGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGCAA~~~AATCCGCAGTATGCGTATGAGAGTTCGAGGTTTGACTAC~~~TGGGGT
CAGGGAACCCTGGTCACCGTCTCGAGC

>TAR2h-44 (SEQ ID NO:412)
GAGGTGCAGCTGTTGGAGTCTGGGGGAGGCTTGGTACAGCCTGGGGGGTCCCTGCGTCTC
TCCTGTGCAGCCTCCGGATTCACCTTTTTG~CAGTATCCGATGGTT~TGGGTCCGC
CAGGCTCCAGGGAAGGGTCTGGAGTGGGTCTCA~~TCGATTTTGGCGCCGGGTGGGCCG
ACATACTACGCAGACTCCGTGAAGGGC~~CGGTTCACCATCTCCCGCGACAATTCCAAG
AACTCGCTGTATCTGCAAATGAACAGCCTGCGTGCCGAGGACACCGCGGTATATTACTGT
GCGAAA~~~CATCCTACTCATACTCCTCATCCGAATTTTGACTAC~~~TGGGGT
CAGGGAACCCTGGTCACCGTCTCGAGC

>TAR2h-45 (SEQ ID NO:413)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~GGTTATCGTATGGCT~TGGGTCCGC
CAGGCTCCAGGGAAGGGTCTAGAGTGGGTCTCA~~TTTATTGATAGTGAGGGTGTGTTG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~TTGTGTTCTTCTAATTGTAATATGCGGAATTTTGACTAC~~~TGGGGT
CAGGGAACCCTGGTCACCGTCTCGAGC

Figure 22P

>TAR2h-47 (SEQ ID NO:414)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~GTTTATAATATGGCG~TGGGTCCGC
CAGGCTCCAGGGAAGGGTCTAGAGTGGGTCTCA~~TTTATTGCGGGTAATGGTCAGCAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTGCGTCGAAGGTGTCGCCGATGTCGTTGACTGATTTTGACTAC~~~TGGGGT
CAGGGAACCCTGGTCACCGTCTCGAGC

>TAR2h-48 (SEQ ID NO:415)
GAGGTGCAGCTGTTGGAGTCTGGGGGAGGCTTGGTACAGCCTGGGGGGTCCCTGCGTCTC
TCCTGTGCAGCCTCCGGATTCACCTTTCAT~AAGTATGGGATGGCT~TGGGTCCGC
CAGGCTCCAGGGAAGGGTCTAGAGTGGGTCTCA~~TTTATTGATCTTGCGGGGTTACAT
ACATACTACGCAGACTCCGTGAGGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTGCTACTTATTCGTCGGGTAATGAGGAGCAGCCTTTTGACTAC~~~TGGGGT
CAGGGAACCCTGGTCACCGTCTCGAGC

>TAR2h-50 (SEQ ID NO:416)
GAGGTGCAGCTGTTGGAGTCTGGGGGAGGCTTGGTACAGCCTGGGGGGTCCCTGCGTCTC
TCCTGTGCAGCCTCCGGATTCACCTTTTCT~GCGTATAATATGGCT~TGGGTCCGC
CAGGCTCCAGGGAAGGGTCTAGAGTGGGTCTCA~~TTTATTGCTCAGTCGGGTGGTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTAGTCATCCTGATGAGGAGGGTACGCAGATGTTTGACTAC~~~TGGGGT
CAGGGAACCCTGGTCACCGTCTCGAGC

>TAR2h-51 (SEQ ID NO:417)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~ACTTATAATATGAGT~TGGGTCCGC
CAGGCTCCAGGGAAGGGTCTAGAGTGGGTCTCA~~GCGATTGATGCGGGGGGTATGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~GGTACGGAGCCTTTTGACTAC~~~TGGGGT
CAGGGAACCCTGGTCACCGTCTCGAGC

>TAR2h-66 (SEQ ID NO:418)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~GAGTATAANATGGGT~TGGGTCCGC
CAGGCTCCAGGGAAGGGTCTGGAGTGGGTCTCA~~CTGATTAGTCCTCGGGGTTCTAAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TATAAGCCGCCTTTTGACTAC~~~TGGGGT
CAGGGAACCCTGGTCACCGTCTCGAGC

Figure 22Q

>TAR2h-67 (SEQ ID NO:419)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~GATTATCCTATGGCG~TGGGTCCGC
CAGGCTCCAGGGAAGGGTCTAGAGTGGGTCTCA~~TTTATTGGTCTGAAGGGTATTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GATCTGAATAATTTTGACTAC~~~TGGGGT
CAGGGAACCCTGGTCACCGTCTCGAGC

>TAR2h-68 (SEQ ID NO:420)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGGTAATATGGTT~TGGGTCCGC
CAGGCTCCAGGGAAGGGTCTAGAGTGGGTCTCA~~CATATTGATGAGTATGGTACGAAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTCGTAATGATCGGCCTGGGTTTGACTAC~~~TGGGGT
CAGGGAACCCTGGTCACCGTCTCGAGC

>TAR2h-70 (SEQ ID NO:421)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~ACTGAGCATATGTAT~TGGGTCCGC
CAGGCTCCAGGGAAGGGTCTGGAGTGGGTCTCA~~GGTATTGATACGGGGGGTTCTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGTCTGCATTGGAGTAGTGATTCTGGGCCTGTTCATTTTGACTAC~~~TGGGGT
CAGGGAACCCTGGTCACCGTCTCGAGC

>TAR2h-71 (SEQ ID NO:422)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGTGGATATGCAT~TGGGTCCGC
CAGGCTCCAGGGAAGGGTCTAGAGTGGGTCTCA~~GCTATTAGTAGTGCGGGTGGTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CGTATGCTTGCGAATTCTCCTTTGGCTTTTGACTAC~~~TGGGGT
CAGGGAACCCTGGTCACCGTCTCGAGC

>TAR2h-72 (SEQ ID NO:423)
GAGGTGCAGCTGTTGGAGTCTGGGGGAGGCTTGGTACAGCCTGGGGGGTCCCTGCGTCTC
TCCTGCGCAGCCTCCGGATTCACCTTTGGG~TATGAGCCTATGGCT~TGGGTCCGC
CAGGCTCCAGGGAAGGGTCTAGAGTGGGTCTCA~~ACGATTTCTCATACGGGTCGTGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~CGTTGGTCTTCGTTTGACTAC~~~TGGGGT
CAGGGAACCCTGGTCACCGTCTCGAGC

Figure 22R

>TAR2h-73 (SEQ ID NO:424)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~AGTGAGAAGATGGCG~TGGGTCCGC
CAGGCTCCAGGGAAGGGTCTAGAGTGGGTCTCA~~TCGATTGATGAGAGGGGTATTATG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~AGGTGGACTTTTAATACTGCGTTTGACTAC~~~TGGGGT
CAGGGAACCCTGGTCACCGTCTCGAGC

>TAR2h-74 (SEQ ID NO:425)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG~CGGGAGAATATGCAT~TGGGTCCGC
CAGGCTCCAGGGAAGGGTCTGGAGTGGGTCTCA~~GGTATTGGGCCGAGGGGTATGCCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGTATGAATTCGCATGATGGGTTTGACTAC~~~TGGGGT
CAGGGAACCCTGGTCACCGTCTCGAGC

>TAR2h-75 (SEQ ID NO:426)
GAGGTGCAGCTGTTGGAGTCTGGGGGAGGCTTGGTACAGCCTGGGGGGTCCCTGCGTCTC
TCCTGTGCAGCCTCCGGATTCACCTTTAAT~GCGTATACTATGATT~TGGGTCCGC
CAGGCTCCAGGGAAGGGTCTAGAGTGGGTCTCA~~TATATTGATCCTCATGGTACGATT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGCCGCGTGCGGCGCCGCGGTTTGACTAC~~~TGGGGT
CAGGGAACCCTGGTCACCGTCTCGAGC

>TAR2h-76 (SEQ ID NO:427)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~GCGTCTGAGATGGAT~TGGGTCCGC
CAGGCTCCAGGGAAGGGTCTAGAGTGGGTCTCA~~GCGATTTCGCCTAGTGGTTCTGCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TGGACTCCGGGTCGTACTACTTTTGACTAC~~~TGGGGT
CAGGGAACCCTGGTCACCGTCTCGAGC

>TAR2h-77 (SEQ ID NO:428)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~ACTGAGCATATGTAT~TGGGTCCGC
CAGGCTCCAGGGAAGGGTCTGGAGTGGGTCTCA~~GGTATTGATACGGGGGGTTCTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGTCTGCATTGGAGTAGTGATTCTGGGCCTGTTCATTTTGACTAC~~~TGGGGT
CAGGGAACCCTGGTCACCGTCTCGAGC

Figure 22S

>TAR2h-78 (SEQ ID NO:429)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG~TTGTATAATATGGCG~TGGGTCCGC
CAGGCTCCAGGGAAGGGTCTAGAGTGGGTCTCA~~TTTATTGCTGCTGCTGGTCCTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGGGGGATATTAGTAGTATTCCTCAGCATCCGTTTGACTAC~~~TGGGGT
CAGGGAACCCTGGTCACCGTCTCGAGC

>TAR2h-79 (SEQ ID NO:430)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGTGGATATGCAT~TGGGTCCGC
CAGGCTCCAGGGAAGGGTCTAGAGTGGGTCTCA~~GCTATTAGTAGTGCGGGTGGTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TCTGCGGATATTACTAAGGGTTTTGACTAC~~~TGGGGT
CAGGGAACCCTGGTCACCGTCTCGAGC

TAR2h-15 (SEQ ID NO:432)
GAGGTGCGGCTGTTGGAGTCTGGGGGAGGCTTGGTACAGCCTGGGGGATCCCTGCGTCTCTCCT
GTGCAGCCTCCGGATTCACCTTT~GGTAAGTACACTATGACG~TGGGTCCGCCAGGCTCCAGGG
AAGGGTCTAGAGTGGGTCTCA~~CATATTTCGGATGATGGTAATTCTACATACTACGCAGACTC
CGTGAAGGGC~~CGGTTCACCATCTCCCGCGACAATTCCAAGAACACGCTGTATCTGCAAATGA
ACAGCCTGCGTGCCGAGGACACCGCGGTATATTACTGTGCGAAA~~~GTTCCGATTTTGGCTCC
TCGTAATCTTTTTGACTAC~~~TGGGGTCAGGGAACCCTGGTCACCGTCTCGAGC

Figure 22T

TAR2m-14 (SEQ ID NO:167)
DIQMTQSPSSLSASVGDRVTITC-RASQPIGVALN-WYQQKPGKAPKLLIY--GGSYLQS--GVPSRYSGSGSGTDFTLTISSLQPGDFATYYC----QQDWRYPGT----FGQGTKV
EIKR

TAR2m-15 (SEQ ID NO:168)
DIQMTQSPSSLSASVGDRVTITC-RASQYIHTSLQ-WYQQKPGKAPKLLIY--GSSRLQS--GVPSRFSGSGSGTDFTLTISSLQPEDFATYYC----QQNHHSPFT----FGQGTKV
EIKR

TAR2m-19 (SEQ ID NO:169)
EVQLLESGGGLVQPGGSLRLSCAASGFTFRKYDMHWVRQAPGKGLEWVSTISPSGRRTYYADSVKGRFTISRDNSKNTLYLQMNSLRAEDTAVYYCAENLDQVLSFDYWGQGTLVT
VSS

TAR2m-20 (SEQ ID NO:170)
EVQLLESGGGLVQPGGSLRLSCAASGFTFGSYSMSWVRQAPGKGLEWVSGIDNGGHSTYYADSVKGRFTISRDNSKNTLYLQMNSLRAEDTAVYYCAKRSSGLPFPFDYWGQGTLV
TVSS

TAR2m-21 (SEQ ID NO:171)
EVQLLESGGGLVQPGGSLRLSCAASGFTFTRYSMGWVRQAPGKGLEWVSRIDSYGRGTYYADSVKGRFTISRDNSKNTLYLQMNSLRAEDTAVYYCAKISQFGSNAFDYWGQGTLV
TVSS

TAR2m-24 (SEQ ID NO:172)
DIQMTQSPSLSASVGDRVTITCRASQYIHSSLQWYQQKPGKAPKLLIYSSSRLHSGVPPRFSGSGSGTDFTLTISSLQPEDFATYCQQNHFRPHTFGQGTKVEIKR

TAR2m-21-23 (SEQ ID NO:173)
EVQLLESGGGLVQPGGSLRLSCAASGFTFN--RYSMG-WLRQAPGKGLEWVS--RIDSYGRGTYYEDPVKG--RFSISRDNSKNTLYLQMNSLRAEDTAVYYCAK---ISQFGSNAF
DY---WGQGTQVTVSS

TAR2m-21-07 (SEQ ID NO:174)
EVQLLESGGGLVQPGGSLRLSCAASGFTFSRCSMGWLRQAPGKGLEWVSRIDSYGRGTYYADSVKGRFTISRDNSKNTLYLQMNSLRAEDTAVYYCAKISKFGSNAFDYWGQGTLV
TVSS

FIGURE 23A

TAR2m-21-43 (SEQ ID NO:175)
EVQLLESGGGLVQPGGSLRLSCAASGFTFTRYSMGWLRQAPGKGLEWVSRIDSYGRGTYDADSVKGRFTISRDNSKNTLYLQMNSLRAEDTAVYYCAKISQFGSNAFDYWGQGTLV
TVSS

TAR2m-21-48 (SEQ ID NO:176)
EVQLLESGGGLIQPGGSLRLSCAASGFTFTRYSMGWLRQAPGKGLEWVSRIDSYGRGTYDTDSVKGRFTISRDNSRNTLYLQMNSLRAEDTAVYYCAKISQFGSNAFDYWGQGTLV
TVSS

TAR2m-21-10 (SEQ ID NO:177)
EVQLLESGGGLVQPGGSLRLSCAASGFTFTRYSMGWLRQAPGKGLEWVSRIDSYGRGTYYADSVKGRFTISRDNSKNTLYLQMNSLRAEDTAVYYCAKISQFGSNAFDYWGQGTLV
TVSS

TAR2m-21-06 (SEQ ID NO:178)
EVQLLESGGGLVQPGGSLRLSCAASGFTFTRYSMGWIRQAPGKGLEWVSRIDSYGRGTYYADSVKGRFTISRDNSKNTLYLQMNSLRAEDTAVYYCAKISQFGSNAFDYWGQGTLV
TVSS

TAR2m-21-17 (SEQ ID NO:179)
EVQLLESGGGLVQPGGSLRLSCAASGFTFTRYSMGWVRQAPGKGLEWVSRIDSYGRGTYYADSVKGRFTISRDNSKNTLYLQMNSLRAEDTAVYYCAKISQFGSNAFDYWGQGTVV
TVSS

FIGURE 23B

TAR2m-14 (SEQ ID NO:180)
GATATTCAGatgaccCAGAGCCCGAGCAGCCTGAGCGTGGGCGATCGTGTGACCATTACCTGCCGTGCGAGCCAGCCGATTGGCTGTGGCGCTGAACTGTGGTATCAGCAGAA
ACCGGGCAAAGCGCCGAAACTGCTGATTTATGCGGCAGCTATCTGCAGAGCGCCGGTCCGAGCGTGCCAGCCGTTATAGCGGCAGCGGCACCGATTTACCCTGACCATTAGCAGCC
TGCAGCCGGGCGATTTGCGACCTATTATTGCCAGCAGGATTGGCGTTATCCGGGCACCTTTGGCCAGGGCACCAAAGTGAAATTAAACGT TAR2m-15 (SEQ ID NO:181)
GATATTCAGatgaccCAGAGCCCGAGCAGCCTGAGCGTGGGCGATCGTGTGACCATTACCTGCCGTGCGAGCCAGTATATTCATACCAGCCTGCAGTGGTATCAGCAGAA
ACCGGGCAAAGCGCCGAAACTGCTGATTTATGCAGCAGCCGTCTGCAGAGCGGCGTGCCGAGCCGTTTAGCGGCAGCGGCAGCGGCACCGATTTACCCTGACCATTAGCAGCC
TGCAGCCGGGAAGATTTGCGACCTATTATTGCCAGCAGAACCATCATAGCCCGTTTACCTTTGGCCAGGGCACCAAAGTGAAATTAAACGT TAR2m-19 (SEQ ID NO:182)
GAAGTGCAGCTGCTGGAAAGCGGCGGGCGGCCTGGTGCAGCCGGGCGGCAGCCTGCGTCTGAGCTGCGCCGGGCGAGCGGCTTTACCTTTCGTAAATATGAtatgCATTGGGTGCGTCA
GGCGCCCGGCAAAGGCCTGGAATGGGTGAGCACCATTATGCCCGAGCCGTCGTACCTATTATGCGGATATAGCGTGAAAGGCCGTTTACCATTAGCCGTGATAACAGCAAAACA
CCCTGTATCTGCAGatgaACAGCCTGCGTGCCGAAGATACCGCGGTGTATTATTGCGCGGAGATCAGGTGCGATCAGGTGCGAGCTTTGATTATTGGGGCCAGGGCACCCTGGTGACC
GTGAGCAGC TAR2m-20 (SEQ ID NO:183)
GAAGTGCAGCTGCTGGAAAGCGGCGGGCGGCCTGGTGCAGCCGGGCGGCAGCCTGCGTCTGAGCTGCGCCGGGCGAGCGGCTTTACCTTTGGCAGCTATAGCAtgAGCTGGGTGCGTCA
GGCGCCCGGCAAAGGCCTGGAATGGGTGAGCCGGCATTGATAACGGCGGTATTAGCCCTGGATAATGCGGATATAGCGTGAAAGGCCGTTTACCATTAGCCGTGATAACAGCAAAACA
CCCTGTATCTGCAGatgAACAGCCTGCGTGCCGAAGATACCGCGGTGTATTATTGCGCGGAAACGTAGCAGCGGCCTGCCTGCCGTTTCCGTTTGATTATTGGGGCCAGGGCACCCTGGTG
ACCGTGAGCAGC TAR2m-21 (SEQ ID NO:184)
GAAGTGCAGCTGCTGGAAAGCGGCGGGCGGCCTGGTGCAGCCGGGCGGCAGCCTGCGTCTGAGCTGCGCCGGGCGGCTTTACCTTTACCCGTTATAGCAtgGGCTGGGTGCGTCA
GGCGCCCGGCAAAGGCCTGGAATGGGTGAGCCGTATTGATAGCGGCGGTAGCACCTATTATGCGGATATAGCGTGAAAGGCCGTTTACCATTAGCCGTGATAACAGCAAAACA
CCCTGTATCTGCAGatgAACAGCCTGCGTGCCGAAGATACCGCGGTGTATTATTGCGCAGCAACCGTTTGATTATTGGCAGCAGCAGTTTGCAGCAACCGTTTGATTATTGGGGCCAGGGCACCCTGGTG
ACCGTGAGCAGC TAR2m-24 (SEQ ID NO:185)
GATATTCAGatgaccCAGAGCCCGAGCAGCCTGAGCGCGAGCGTGGGCGATCGTGTGACCATTACCTGCCGTGCGAGCCAGTATATTCATAGCAGCCTGCAGTGGTATCAGCAGAA
ACCGGGCAAAGCGCCGAAACTGCTGATTTATGCAGCAGCCCGTCTGCAGAGCGGCGTGCCGAGCCGTTTAGCGGCAGCGGCAGCGGCACCGATTTACCCTGACCATTAGCAGCC
TGCAGCCGGGAAGATTTGCGACCTATTATTGCGACCTATTATTGCCAGCAGAACCATTTTCGTCCAGCAACCTTTGCCAGGCACCAAAGTGAAATTAAACGT

FIGURE 24A

TAR2m-21-23 (SEQ ID NO:186)
GAAGTGCAGCTGCTGGAAAGCGGCGGCGGCCTGGTGCAGCCGGGCGGCAGCCTGCGCCTGAGCTGCGCGGCCAGCGGCTTTACCTTTAACCGTTATAGCatgGGCTGGCTGCGTCA
GGCGCCCGGGCAAAGGCCTGGAATGGGTGAGCCGTATTGATAGCTATGCCGGTGCACCTATTATGAAGATCCGTGAAAGGCCGTTTTAGCATTAGCCGTGATAACAGCAAAAACA
CCCTGTATCTGCAGatgAACAGCCTGCGTGCGGAAGATACCGCGGTGTATTATTGCGCGAAAATTAGCGCGTTGATTATTGGGGCCAGGGCCACCCAGGTG
ACCGTGAGCAGC TAR2m-21-07 (SEQ ID NO:187)
GAAGTGCAGCTGCTGGAAAGCGGCGGCGGCCTGGTGCAGCCGGGCGGCAGCCTGCGTCTGAGCTGCGCGGCCAGCGGCTTTACCTTTAGCCGTTGCAGCatgGGCTGGCTGCGTCA
GGCGCCCGGGCAAAGGCCTGGAATGGGTGAGCCGTATTGATAGCTATGCCGGTGCACCTATTATGCCGGTGCACCTATTAGCCGTGATAACAGCAAAAACA
CCCTGTATCTGCAGatgAACAGCCTGCGTGCGGAAGATACCGCGGTGTATTATTGCGCGAAAATTAGCGCAACGCGTTTGATTATTGGGGCCAGGGCACCCTGGTG
ACCGTGAGCAGC TAR2m-21-43 (SEQ ID NO:188)
GAAGTGCAGCTGCTGGAAAGCGGCGGCGGCCTGGTGCAGCCGGGCGGCAGCCTGCGTCTGAGCTGCGCGGCCAGCGGCTTTACCTTTACCGTTTATAGCatgGGCTGGCTGCGTCA
GGCGCCCGGGCAAAGGCCTGGAATGGGTGAGCCGTATTGATAGCTATGCCGGTGCACCTATCATGCCGTGCACCTATTAGCCGTGATAACAGCAAAAACA
CCCTGTATCTGCAGatgAACAGCCTGCGTGCGGAAGATACCGCGGTGTATTATTGCGCGAAAATTAGCCAGTTTGCAGCAACGCGTTTGATTATTGGGGCCAGGGCACCCTGGTG
ACCGTGAGCAGC TAR2m-21-48 (SEQ ID NO:189)
GAAGTGCAGCTGCTGGAAAGCGGCGGCGGCCTGGTGCAGCCGGGCGGCAGCCTGCGTCTGAGCTGCGCGGCCAGCGGCTTTACCTTTACCGTTTATAGCatgGGCTGGCTGCGTCA
GGCGCCCGGGCAAAGGCCTGGAATGGGTGAGCCGTATTGATAGCTATGCCGGTGCACCTATGATAGCCGTGCACCTATTAGCCGTGATAACAGCCGTAACA
CCCTGTATCTGCAGatgAACAGCCTGCGTGCGGAAGATACCGCGGTGTATTATTGCGCGAAAATTAGCCAGTTTGCCAGCAACGCGTTTGATTATTGGGCCAGGGCACCCTGGTG
ACCGTGAGCAGC TAR2m-21-10 (SEQ ID NO:190)
GAAGTGCAGCTGCTGGAAAGCGGCGGCGGCCTGGTGCAGCCGGGCGGCAGCCTGCGTCTGAGCTGCGCGGCCAGCGGCTTTACCTTTACCGTTTATAGCatgGGCTGGCTGCGTCA
GGCGCCCGGGCAAAGGCCTGGAATGGGTGAGCCGTATTGATAGCTATGCCGGTGCACCTATTATGCGGATAGCCGTGATAACAGCAAAAACA
CCCTGTATCTGCAGatgAACAGCCTGCGTGCGGAAGATACCGCGGTGTATTATTGCGAAAATTAGCCAGTTTGGCAGCAACGCGTTTGATTATTGGGCCAGGGCACCCTGGTG
ACCGTGAGCAGC

FIGURE 24B

TAR2m-21-06 (SEQ ID NO:191)
GAAGTGCAGCTGCTGGAAAGCGGCGGCGGCCTGGTGCAGCCGGGCGGCAGCCTGCGCCTGAGCTGCGCCGCCAGCGGCTTTACCTTTACCCGTTATAGCatgGGCTGGATTCGTCA
GGCGCCGGGCAAAGGCCTGGAATGGGTGAGCCGTATTGATAGCTATGGCCGTGAAAGGCCGTTTTACCATTAGCCGTGATAACAGCAAAAACA
CCCTGTATCTGCAGatgAACAGCCTGCGTGCCGAAGATACCGCGGTGTATTATTGCGCGAAAATTAGCCAGTTTGGCCAGCAACGCGTTTGATTATTGGGGCCAGGCACCCTGGTG
ACCGTGAGCAGC TAR2m-21-17 (SEQ ID NO:192)
GAAGTGCAGCTGCTGGAAAGCGGCGGCGGCCTGGTGCAGCCTGGCGGCAGCCTGCGCCTGAGCTGCGCCGCCAGCGGCTTTACCTTTACCCGTTATAGCatgGGCTGGGTGCGTCA
GGCGCCGGGCAAAGGCCTGGAATGGGTGAGCCGTATTGATAGCTATGGCCGTGATAGCGTGAAAGGCCGTTTTACCATTAGCCGTGATAACAGCAAAAACA
CCCTGTATCTGCAGatgAACAGCCTGCGTGCCGAAGATACCGCGGTGTATTATTGCGCGAAAATTAGCCAGTTTGGCCAGCAACGCGTTTGATTATTGGGGCCAGGGCACCGTGGTG
ACCGTGAGCAGC TAR2m-21-23a (SEQ ID NO:626)
GAGGTGCAGCTGTTGGAGTCTGGGGGAGGCTTGGTACAGCCTGGGGGGTCCCTGCGTCTCTCCTGTGCAGCCTCCGGATTCACCTTTAAT-AGGTATAGTATGGGG--TGGCTCCGC
CAGGCTCCAGGGAAGGGTCTAGAGTGGGTCTCA--CGGATTGATTCTTATGGTCGTGGTACATACGAAGACCCGTGAAGGGC--CGGTTCAGCATCTCCCGCGACAATTCCA
AgAACAGGCTGTATCTGCAAATGAACAGCCCGCGTGCCGAGGACACCGCGGTATATTACTGTGCGAAA---ATTTCTCAGTTTGGGTCAAATGCGTTTGACTAC---TGGGGTCAG
GGAACCCAGGTCACCGTCTCGAGC

FIGURE 24C

HEL4
E  V  Q  L  L  E  S  G  G  G  L  V  Q  P  G  G  S  L  R  L  S  C  A  A  S  G  F  R  I  S  D  E  D  M  ·
GAGGTGCAGC TGTTGGAGTC TGGGGGAGGC TTGGTACAGC CTGGGGGGTC CCTGCGTCTC TCCTGTGCAG CCTCCGGATT TAGGATTAGC GATGAGGATA

· G  W  V  R  Q  A  P  G  K  G  L  E  W  V  S  S  I  Y  G  P  S  G  S  T  Y  Y  A  D  S  V  K  G  R  ·
TGGGCTGGGT CCGCCAGGCT CCAGGGAAGG GTCTAGAGTG GTATCAAGC ATTTATGGCC CTAGCCGTAG CACATACTAC GCAGACTCCG TGAAGGGCCG

· F  T  I  S  R  D  N  S  K  N  T  L  Y  L  Q  M  N  S  L  R  A  E  D  T  A  V  Y  Y  C  A  S  A  L
GTTCACCATC TCCCGTGACA ATTCCAAGAA CACGCTGTAT CTGCAAATGA ACAGCCTGCG ACCCGGAGAC TGCCGAGGAC ACCCGGGTAT ATTAATTGCGC GAGTGCTTTG

E  P  L  S  E  P  L  G  F  W  G  Q  G  T  L  V  T  V  S  S          (SEQ ID NO:193)
GAGCCGCTTT CGGAGCCCCT GGGCTTTTGG GGTCAGGGAA CCCTGGTCAC CGTCTCGAGC  (SEQ ID NO:194)

TAR2-5
E  V  Q  L  L  E  S  G  G  G  L  V  Q  P  G  G  S  L  R  L  S  C  A  A  S  G  F  T  F  D  L  Y  N  M  ·
GAGGTGCAGC TGTTGGAGTC TGGGGGAGGC TTGGTACAGC CTGGGGGGTC CCTGCGTCTC TCCTGTGCAG CCTCCGGATT CACCTTTGAT CTTTATAATA

· F  W  V  R  Q  A  P  G  K  G  L  E  W  V  S  F  I  S  Q  T  G  R  L  T  W  Y  A  D  S  V  K  G  R  ·
TGTTTTGGGT CCGCCAGGCT CCAGGGAAGG GTCTAGAGTG GGTCTCATTT ATTAGTCAGA CTGGTAGGCT TACATGGTAC GCAGACTCCG TGAAGGGCCG

· F  T  I  S  R  D  N  S  K  N  T  L  Y  L  Q  M  N  S  L  R  A  E  D  T  A  V  Y  Y  C  A  K  T  L
GTTCACCATC TCCCGTGACA ATTCCAAGAA CACGCTGTAT CTGCAAATGA ACAGCCTGCG ACCCGGAGAC TGCCGAGGAC ACCGCGGTAT ATTACTGTGC GAAAACGCTG

E  D  F  D  Y  W  G  Q  G  T  L  V  T  V  S  S          (SEQ ID NO:195)
GAGGATTTTG ACTACTGGGG CCAGGGAACC CTGGTCACCG TCTCGAGC   (SEQ ID NO:196)

TAR1-5-19
D  I  Q  M  T  Q  S  P  S  S  L  S  A  S  V  G  D  R  V  T  I  T  C  R  A  S  Q  S  V  K  E  F  L  W  ·
GACATCCAGA TGACCCAGTC TCCATCCTCC CTGTCTGCAT CTGTAGGAGA CCGTGTCACC ATCACTTGCC GGGCAAGTCA GAGCGTTAAG GAGTTTTTAT

· W  Y  Q  Q  K  P  G  K  A  P  K  L  L  I  Y  M  A  S  N  L  Q  S  G  V  P  S  R  F  S  G  S  G  S  ·
GGTTGGTACCA GCAGAAACCA GGGAAAGCCC CTAAGCTCCT GATCTATATG GCATCCAATT TGCAAAGTGG GGTCCCATCA CGTTTCAGTG GCAGTGGATC

· G  T  D  F  T  L  T  I  S  S  L  Q  P  E  D  F  A  T  Y  Y  C  Q  Q  K  F  K  L  P  R  T  F  G  Q
TGGGACAGAT TTCACTCTCA CCATCAGCAG TCTGCAACCT GAAGATTTTG CTACCTACTA CTGTCAACAG AAGTTTAAGC TGCCCGTAC GTTCGGCCAA

G  T  K  V  E  I  K  R          (SEQ ID NO:197)
GGGACCAAGG TGGAAATCAA ACGG      (SEQ ID NO:198)

FIGURE 25A

TAR-1 dAb DNA and amino acid sequences.

dAbs 1, 2 and 3 are the partner sequences from TAR1-5 dimers 1-6. dAb1 is the partner dAb to dimers 1, 5 and 6 the second dAbs are the same but the linker lengths are different, likewise, dAb2 is the partner dAb to dimers 2 and 3, dAb3 is the partner dAb to dimer 4. * indicates the presence of an amber stop codon. Sequence homology between, TAR1-5,TAR1-5-19 and the unique second dAbs is 88%

TAR1-5-19

```
D  I  Q  M  T  Q  S  P  S  S  L  S  A  S  V  G  D  R  V  T  I  T  C  R  A  S  Q  S  I  D  S  Y  L  H
GACATCCAGA TGACCCAGTC TCCATCCTCT CTGTCTGCAT CTGTAGGAGA CCGTGTCACC ATCACTTGCC GGGCAAGTCA GAGCATTGAT AGTTATTTAC
 W  Y  Q  Q  K  P  G  K  A  P  K  L  L  I  Y  S  A  S  E  L  Q  S  G  V  P  S  R  F  S  G  S  G  S
ATTGGTACCA GCAGAAACCA GGGAAAGCCC CTAAGCTCCT GATCTATAGT GCATCCGAGT TGCAAAGTGG GGTCCCATCA CGTTTCAGTG GCAGTGGATC
 T  D  F  T  L  T  I  S  S  L  Q  P  E  D  F  A  T  Y  Y  C  Q  Q  V  V  W  R  P  F  T  F  G  Q
TGGGACAGAT TTCACTCTCA CCATCAGCAG TCTGCAACCT GAAGATTTTG CTACGTACTA CTGTCAACAG GTTGTGTGGC GTCCTTTTAC GTTCGGCCAA
 G  T  K  V  E  I  K  R
GGGACCAAGG TGGAAATCAA ACGC              (SEQ ID NO:200)
CCCTGGTTCC ACCTTTAGTT TGCG*             (SEQ ID NO:201)
                                        (SEQ ID NO:202)
```

TAR1-5

```
D  I  Q  M  T  Q  S  P  S  S  L  S  A  S  V  G  D  R  V  T  I  T  C  R  A  S  Q  S  I  F  M  N  L  L
GACATCCAGA TGACCCAGTC TCCATCCTCC CTGTCTGCAT CTGTAGGAGA CCGTGTCACC ATCACTTGCC GGGCAAGTCA GAGCATTTTT ATGAATTTAT
CTGTAGGTCT ACTGGGTCAG AGGTAGGAGG GACAGACGTA GACATCCTCT GGCACAGTGG TAGTGAACGG CCCGTTCAGT CTCGTAAAAA TACTTAAATA
 W  Y  Q  Q  K  P  G  K  A  P  K  L  L  I  Y  N  A  S  V  L  Q  S  G  V  P  S  R  F  S  G  S
TGTGTACCA GCAGAAACCA GGGAAAGCCC CCCTTTCGGG GATTCGAGGA CTAGATATTA CGTAGGCACA ACGTTTCACC CCAGGGTAGT GCAAAGTCAC CGTCACCTAG
 T  D  F  T  L  T  I  S  S  L  Q  P  E  D  F  A  T  Y  Y  C  Q  Q  V  V  W  R  P  F  T  F  G  Q
TGGGACAGAT TTCACTCTCA CCATCAGCAG TCTGCAACCT GAAGATTTTG CTACGTACTA CTGTCAACAG GTTGTGTGGC GTCCTTTTAC GTTCGGCCAA
 G  T  K  V  E  I  K  R
GGGACCAAGG TGGAAATCAA ACGG              (SEQ ID NO:203)
CCCTGGTTCC ACCTTTAGTT TGCC              (SEQ ID NO:204)
                                        (SEQ ID NO:205)
```

Monomer - dAb1: Partner dAb in TAR1-5d1 (3U linker), d5 (5U linker), d6 (7U linker)

```
D  I  Q  M  T  Q  S  P  S  S  L  S  A  S  V  G  D  R  V  T  I  T  C  R  A  S  Q  S  I  Y  D  A  L  E
GACATCCAGA TGACCCAGTC TCCATCCTCC CTGTCTGCAT CTGTAGGAGA CCGTGTCACC ATCACTTGCC GGGCAAGTCA GAGCATTTAT GATGCGTTAG
CTGTAGGTCT ACTGGGTCAG AGGTAGGAGG GACAGACGTA GACATCCTCT GGCACAGTGG TAGTGAACGG CCCGTTCAGT CTCGTAAATA CTACGCAATC
 W  Y  Q  Q  K  P  G  K  A  P  K  L  L  I  Y  T  A  S  R  L  Q  S  G  V  P  S  R  F  S  G  S  G  S
AGTGGTACCA GCAGAAACCA GGGAAAGCCC CTAAGCTCCT GATCTATACT GCATCCCGGT TGCAAAGTGG GGTCCCATCA CGTTTCAGTG GCAGTGGATC
TCACCATGGT CGTCTTTGGT CCCTTTCGGG GATTCGAGGA CTAGATATGA ACGTAGGGCA ACGTTTCACC CCAGGGTAGT CCAAAGTCAC CGTCACCTAG
```

FIGURE 25B

```
       G  T  D  F  T  L  T     I  S  S     L  Q  P     E  D  F  A     T  Y  Y     C  Q  Q     V  M  Q  R     P  V  T     F  G  Q
TGGGACAGAT TTCACTCTCA CCATCAGCAG TCTGCAACCT GAAGATTTTG CTACGTACTA CTGTCAACAG GTTATGCAGC GTCCTGTTAC GTTCGGCCAA
ACCCTGTCTA AAGTGAGAGT GGTAGTCGTC AGACGTTGGA CTTCTAAAAC GATGCATGAT GACAGTTGTC CAATACGTCG CAGGACAATG CAAGCCGGTT
   G  T  K  V     E  I  K     R                      (SEQ ID NO:206)
GGGACCAAGG TGAAATCAA ACGG                            (SEQ ID NO:207)
CCCTGGTTCC ACCTTTAGTT TGCC                           (SEQ ID NO:208)

Monomer - dAb2: Partner dAb in TAR1-5d2 (3U linker), d3 (5U linker)
   D  I  Q  M     T  Q  S     P  S  S     L  S  A  S     V  G  D     R  V  T     I  T  C  R     A  S  Q     S  I  Y     D  A  L *
GACATCCAGA TGACCCAGTC TCCATCCTCC CGTCTGCAT CTGTAGGAGA CCGTGTCACC ATCACTTGCC GGGCAAGTCA GAGCATTTAT GATGCTTTAC
CTGTAGGTCT ACTGGGTCAG AGGTAGGAGG GACAGACGTA GACATCCTCT GGCACAGTGG TAGTGAACGG CCCGTTCAGT CTCGTAAATA CTACGAAATG
   W  Y  Q     Q  K  P     G  K  A  P     K  L  L     I  Y  T     A  S  R  L     Q  S  G     V  P  S     R  F  S     G  S  G  S
AGTGGTACCA GCAGAAACCA GGGAAAGCCC CTAAGCTCCT GATCTATACT GCATCCCGGT TGCAAAGTGG GGTCCCATCA CGTTCAGTG GCAGTGGATC
TCACCATGGT CGTCTTTGGT CCCTTTCGGG GATTCGAGGA CTAGATATGA CGTAGGGCCA ACGTTTCACC CCAGGGTAGT GCAAAGTCAC CGTCACCTAG
   G  T  D  F  T  L  T     I  S  S     L  Q  P     E  D  F  A     T  Y  Y  H     C  Q  Q     V  M  Q  R     P  V  T     F  G  Q
TGGGACAGAT TTCACTCTCA CCATCAGCAG TCTGCAACCT GAAGATTTTG CTACGTACCA CTGTCAACAG GTTATGCAGC GTCCTGTTAC GTTCGGCCAA
ACCCTGTCTA AAGTGAGAGT GGTAGTCGTC AGACGTTGGA CTTCTAAAAC GATGCATGGT GACAGTTGTC CAATACGTCG CAGGACAATG CAAGCCGGTT
   G  T  K  V     E  I  K     R                      (SEQ ID NO:209)
GGGACCAAGG TGAAATCAA ACGG                            (SEQ ID NO:210)
CCCTGGTTCC ACCTTTAGTT TGCC                           (SEQ ID NO:211)

Monomer - dAb3: Partner dAb in TAR1-5d4 (5U linker)
   D  I  Q  M     T  Q  S     P  S  S     L  S  A  S     V  G  D     R  V  T     I  T  C  R     A  S  Q     S  V  K     E  F  L  W
GACATCCAGA TGACCCAGTC TCCATCCTCC CGTCTGCAT CTGTAGGAGA CCGTGTCACC ATCACTTGCC GGGCAAGTCA GAGCGTTAAG GAGTTTTTAT
CTGTAGGTCT ACTGGGTCAG AGGTAGGAGG GACAGACGTA GACATCCTCT GGCACAGTGG TAGTGAACGG CCCGTTCAGT CTCGCAATTC CTCAAAATA
   W  Y  Q     Q  K  P     G  K  A  P     K  L  L     I  Y  M     A  S  N  L     Q  S  G     V  P  S     R  F  S     G  S  G  S
GGTGGTACCA GCAGAAACCA GGGAAAGCCC CTAAGCTCCT GATCTATATG GCATCCAATT TGCAAAGTGG GGTCCCATCA CGTTCAGTG GCAGTGGATC
CCACCATGGT CGTCTTTGGT CCCTTTCGGG GATTCGAGGA CTAGATATAC CGTAGGTTAA ACGTTTCACC CCAGGGTAGT GCAAAGTCAC CGTCACCTAG
   G  T  D     F  T  L  T     I  S  S     L  Q  P     E  D  F  A     T  Y  Y     C  Q  Q     K  F  K  L     P  R  T     F  G  Q
TGGGACAGAT TTCACTCTCA CCATCAGCAG TCTGCAACCT GAAGATTTTG CTACGTACTA CTGTCAACAG AAGTTTAAGC TGCCTCGTAC GTTCGGCCAA
ACCCTGTCTA AAGTGAGAGT GGTAGTCGTC AGACGTTGGA CTTCTAAAAC GATGCATGAT GACAGTTGTC TTCAAATTCG ACGGAGCATG CAAGCCGGTT
   G  T  K  V     E  I  K     R                      (SEQ ID NO:212)
GGGACCAAGG TGAAATCAA ACGG                            (SEQ ID NO:213)
CCCTGGTTCC ACCTTTAGTT TGCC                           (SEQ ID NO:214)

TAR1-27 and related partner dAb amino acid and DNA sequences (* indicates the presences of an amber stop codon).
Sequence homology between TAR1-27 and the unique second dAbs is 90.4%.

TAR1-27
   D  I  Q  M     T  Q  S     P  S  S     L  S  A  S     V  G  D     R  V  T     I  T  C  R     A  S  Q     S  I  W     T  K  L  H
GACATCCAGA TGACCCAGTC TCCATCCTCC CGTCTGCAT CTGTAGGAGA CCGTGTCACC ATCACTTGCC GGGCAAGTCA GAGCATTTGG ACGAAGTTAC
CTGTAGGTCT ACTGGGTCAG AGGTAGGAGG GACACGACGTA GACATCCTCT GGCACAGTGG TAGTGAACGG CCCGTTCAGT CTCGTAAACC TGCTTCAATG
```

FIGURE 25C

```
                W  Y  Q    Q  K  P    G  K  A  P    K  L  L    I  Y  M    A  S  S  L    Q  S  G    V  P  S    R  F  S    G  S  G  S
ATTGGTACCA GCAGAAACCA GGGAAAGCCC CTAAGCTCCT GATCTATATG GCATCAGTT GGTCCCATCA CGTTTCAGTG GCAGTGGATC
TAACCATGGT CGTCTTTGGT CCCTTTCGGG GATTCGAGGA CTAGATATAC CGTAGGTCAA ACGTTTCACC CCAGGTAGT GCAAAGTCAC CGTCACCTAG
                G  T  D    F  T  L  T    I  S  S    L  Q  P    E  D  F  A    T  Y  Y    C  Q  Q    N  F  S  N    P  S  T    F  G  Q
GGGACAGAT TTCACTCTCA CCATCAGCAG TCTGCAACCT GAAGATTTTG CTACTTACTA CTGTCAACAG AATTCAACAT CCTACTACT GTTGGCCAA
ACCCTGTCTA AAGTGAGAGT GGTAGTCGTC AGACGTTGGA CTTCTAAAAC GATGAATGAT GACAGTTGTC ACCAAATCAT TAGGATCATG CAACCCGGTT
                G  T  K  V    E  I  K    R
GGGACCAAGG TGGAAATCAA ACGC                (SEQ ID NO:215)
CCCTGGTTCC ACCTTTAGTT TGCG                (SEQ ID NO:216)
                                          (SEQ ID NO:217)

Partner dAb monomer in TAR1-27d1 (3U linker)
                D  I  Q  M    T  Q  S    P  S  S    L  S  A  S    V  G  D    R  V  T    I  T  C  R    A  S  Q    S  I  *    P  I  L  C
GACATCCAGA TGACCCAGTC TCCATCCTCC CTGTCTGCAT CTGTAGGAGA CCGTGTCACC ATCACTTGCC GGGCAAGTCA GAGCATTTAT CCGATTTAT
CTGTAGGTCT ACTGGGTCAG AGGTAGGAGG GACAGACGTA GACATCCTCT GGCACAGTGG TAGTGAACGG CCCGTTCAGT CTCGTAAATC GGCTAAATA
                W  Y  Q    Q  K  P    G  K  A  P    K  L  L    I  Y  A    A  S  S  L    Q  S  G    V  P  S    R  F  S    G  S  G  S
GTTGGTACCA GCAGAAACCA GGGAAAGCCC CTAAGCTCC GATCTATGCT GCATCCAGTT GCAAAGTGG GGTCCCATCA CGTTTCAGTG GCAGTGGATC
CAACCATGGT CGTCTTTGGT CCCTTTCGGG GATTCGAGG CTAGATACGA CGTAGGTCAA ACGTTTCACC CCAGGTAGT GCAAAGTCAC CGTCACCTAG
                G  T  D    F  T  L  T    I  S  S    L  Q  P    E  D  F  A    T  Y  Y    C  Q  Q    I  Q  H  I    P  V  T    F  G  Q
TGGGACAGAT TTCACTCTCA CCATCAGCAG TCTGCAACCT GAAGATTTTG CTACTTACTA CTGTCAACAG ATTCAGCATA TTCCTGTGAC GTTCGGCCAA
ACCCTGTCTA AAGTGAGAGT GGTAGTCGTC AGACGTTGGA CTTCTAAAAC GATGAATGAT GACAGTTGTC TAAGTCGTAT AAGGACACTG CAAGCCCGTT
                G  T  K  V    E  I  K    R
GGGACCAAGG TGGAAATCAA ACGG                (SEQ ID NO:218)
CCCTGGTTCC ACCTTTAGTT TGCC                (SEQ ID NO:219)
                                          (SEQ ID NO:220)

Partner dAb monomer in TAR1-27d2 (3U linker)
                D  I  Q  M    T  Q  S    P  S  S    L  S  A  S    V  G  D    R  V  T    I  T  C  R    A  S  Q    S  I  G    *  D  L  H
GACATCCAGA TGACCCAGTC TCCATCCTCC CTGTCTGCAT CTGTAGGAGA CCGTGTCACC ATCACTTGCC GGGCAAGTCA GAGCATTGGG TAGGATTAC
CTGTAGGTCT ACTGGGTCAG AGGTAGGAGG GACAGACGTA GACATCCTCT GGCACAGTGG TAGTGAACGG CCGTTCAGT CTCGTAACCC ATCCTAAATG
                W  Y  Q    Q  K  P    G  K  A  P    K  L  L    I  Y  T    A  S  L  L    Q  S  G    V  P  S    R  F  S    G  S  G  S
ATTGGTACCA GCAGAAACCA GGGAAAGCCC CTAAGCTCCT GATCTATACG GCATCCTTT TGCAAAGTGG GGTCCCATCA CGTTTCAGTG GCAGTGGATC
TAACCATGGT CGTCTTTGGT CCCTTTCGGG GATTCGAGGA CTAGATATGC CGTAGGGAAA ACGTTTCACC CCAGGGTAGT GCAAAGTCAC CGTCACCTAG
                G  T  D    F  T  L  T    I  S  S    L  Q  P    E  D  F  A    T  Y  Y    C  Q  Q    Q  S  A  F    P  N  T    L  G  Q
TGGGACAGAT TTCACTCTCA CCATCAGCAG TCTGCAACCT GAAGATTTTG CTACTTACTA CTGTCAACAG CAGAGTGCTT TTCCTAATAC GCTCGGCCAA
ACCCTGTCTA AAGTGAGAGT GGTAGTCGTC AGACGTTGGA CTTCTAAAAC GATGAATGAT GACAGTTGTC GTCTCACGAA AAGGATTATG CGAGCCGGTT
                G  T  K  V    E  I  K    R
GGGACCAAGG TGGAAATCAA ACGG                (SEQ ID NO:221)
CCCTGGTTCC ACCTTTAGTT TGCC                (SEQ ID NO:222)
                                          (SEQ ID NO:223)

Partner dAb monomer in TAR1-27d7 (3U linker)
                D  I  Q  M    T  Q  S    P  S  S    L  S  A  S    V  G  D    R  V  T    I  T  C  R    A  S  Q    S  I  T    K  N  L  L
GACATCCAGA TGACCCAGTC TCCATCCTCC CTGTCTGCAT CTGTAGGAGA CCGTGTCACC ATCACTTGCC GGGCAAGTCA GAGCATAACG AAGAATTTAC
CTGTAGGTCT ACTGGGTCAG AGGTAGGAGG GACAGACGTA GGCACAGTGG TAGTGAACGG CCGTTCAGT CTCGTATTGC TTCTTAAATG
```

FIGURE 25D

```
                W  Y  Q  Q  K  P  G  K  A  P  K  L  L  I  Y  *  A  S  S  L  Q  S  G  V  P  S  R  F  S  G  S  G  S
TTTGGTACCA GCAGAAACCA GGGAAAGCCC CTAAGCTCCT GATCTATTAG GCATCCTCTT TGCAAAGTGG GGTCCCATCA CGTTTCAGTG GCAGTGGATC
AAACCATGGT CGTCTTTGGT CCCTTTCGGG GATTCGAGGA CTAGATAATC CGTAGGAGAA ACGTTTCACC CCAGGGTAGT GCAAAGTCAC CGTCACCTAG
 G  T  D  F  T  L  T  I  S  S  L  Q  P  E  D  F  A  T  Y  Y  C  Q  Q  L  R  H  K  P  P  T  F  G  Q
TGGGACAGAT TTCACTCTCA CCATCAGCAG TCTGCAACCT GAAGATTTTG CTACTACTA CTGTCAACAG CTTCGTCATA AGCCTCCGAC GTTCGGCCAA
ACCCTGTCTA AAGTGAGAGT GGTAGTCGTC AGACGTTGGA CTTCTAAAAC GATGATGATA GACAGTTGTC GAAGCAGTAT TCGGAGGCTG CAAGCCGGTT
 G  T  K  V  E  I  K  R
GGGACCAAGG TGGAAATCAA ACGG           (SEQ ID NO:224)
CCCTGGTTCC ACCTTTAGTT TGCC           (SEQ ID NO:225)
                                     (SEQ ID NO:226)

Partner dAb monomer in TAR1-27d8 (3Ulinker)
 D  I  Q  M  T  Q  S  P  S  S  L  S  A  S  V  G  D  R  V  T  I  T  C  R  A  S  Q  S  I  *  K  S  L  R
GACATCCAGA TGACCCAGTC TCCATCCTCC CTGTCTGCAT CTGTAGGAGA CCGTGTCACC ATCACTTGCC GGGCAAGTCA GAGCATTTAG AAGTCTTTAA
CTGTAGGTCT ACTGGGTCAG AGGTAGGAGG GACAGACGTA GACATCCTCT GGCACAGTGG TAGTGAACGG CCCGTTCAGT CTCGTAAATC TTCAGAAATT
 W  Y  Q  Q  K  P  G  K  A  P  K  L  L  I  Y  H  A  S  D  L  Q  S  G  V  P  S  R  F  S  G  S  G  S
GGTGGTACCA GCAGAAACCA GGGAAAGCCC CTAAGCTCC TGATCTATCAT GCATCCGATT TGCAAAGTGG GGTCCCATCA CGTTTCAGTG GCAGTGGATC
CCACCATGGT CGTCTTTGGT CCCTTTCGGG GATTCGAGGA CTAGATAGTA CGTAGGCTAA ACGTTTCACC CCAGGGTAGT GCAAAGTCAC CGTCACCTAG
 G  T  D  F  T  L  T  I  S  S  L  Q  P  E  D  F  A  T  Y  Y  C  Q  Q  M  V  N  S  P  V  T  F  G  Q
TGGGACAGAT TTCACTCTCA CCATCAGCAG TCTGCAACCT GAAGATTTTG CTACTACTA CTGTCAACAG ATGGTTAATA GTCCTGTTAC GTTCGGCCAA
ACCCTGTCTA AAGTGAGAGT GGTAGTCGTC AGACGTTGGA CTTCTAAAAC GATGATGAT GACAGTTGTC TACCAATTAT CAGGACAATG CAAGCCGGTT
 G  T  K  V  E  I  K  R
GGGACCAAGG TGGAAATCAA ACGG           (SEQ ID NO:227)
CCCTGGTTCC ACCTTTAGTT TGCC           (SEQ ID NO:228)
                                     (SEQ ID NO:229)

Partner dAb monomer in TAR1-27d12 (3Ulinker)
 D  I  Q  M  T  Q  S  P  S  S  L  S  A  S  V  G  D  R  V  T  I  T  C  R  A  S  Q  S  I  *  T  A  L  H
GACATCCAGA TGACCCAGTC TCCATCCTCC CTGTCTGCAT CTGTAGGAGA CCGTGTCACC ATCACTTGCC GGGCAAGTCA GAGCATTTAG ACGGCGTTAC
CTGTAGGTCT ACTGGGTCAG AGGTAGGAGG GACAGACGTA GACATCCTCT GGCACAGTGG TAGTGAACGG CCCGTTCAGT CTCGTAAATC TGCCGCAATG
 W  Y  Q  Q  K  P  G  K  A  P  K  L  L  I  Y  S  A  S  S  L  Q  S  G  V  P  S  R  F  S  G  S  G  S
ATTGGTACCA GCAGAAACCA GGGAAAGCCC CTAAGCTCCC TATCTATTCT GCATCCTCCT CTGCAAAGTG GGTCCCATCA CGTTTCAGTG GCAGTGGATC
TAACCATGGT CGTCTTTGGT CCCTTTCGGG GATTCGAGGA CTAGATAAGA CGTAGGAGGA GACGTTTCAC CCAGGGTAGT GCAAAGTCAC CGTCACCTAG
 G  T  D  F  T  L  T  I  S  S  L  Q  P  E  D  F  A  T  Y  Y  C  Q  Q  S  S  F  L  P  F  T  F  G  Q
TGGGACAGAT TTCACTCTCA CCATCAGCAG TCTGCAACCT GAAGATTTTG CTACTACTA CTGTCAACAG TCGAGTTTTT TGCCTTTTAC GTTCGGCCAA
ACCCTGTCTA AAGTGAGAGT GGTAGTCGTC AGACGTTGGA CTTCTAAAAC GATGATGAT GACAGTTGTC AGCTCAAAAA ACGGAAAATG CAAGCCGGTT
 G  T  K  V  E  I  K  R
GGGACCAAGG TGGAAATCAA ACGG           (SEQ ID NO:230)
CCCTGGTTCC ACCTTTAGTT TGCC           (SEQ ID NO:231)
                                     (SEQ ID NO:232)

Partner dAb monomer in TAR1-27d16 (3U linker)
 D  I  Q  M  T  Q  S  P  S  S  L  S  A  S  V  G  D  R  V  T  I  T  C  R  A  S  Q  S  I  G  P  N  L  E
GACATCCAGA TGACCCAGTC TCCATCCTCC CTGTCTGCAT CTGTAGGAGA CCGTGTCACC ATCACTTGCC GGGCAAGTCA GAGCATTGGG CCGAATTTAG
CTGTAGGTCT ACTGGGTCAG AGGTAGGAGG GACAGACGTA GACATCCTCT GGCACAGTGG TAGTGAACGG CCCGTTCAGT CTCGTAACCC GGCTTAAATC
```

```
                W Y Q  Q K P  G K A P  K L L  I Y *  A S L L  Q S G  V P S  R F S G  S G S
           GTTGTACCA GCAGAAACCA GGGAAAGCCC CTAAGCTCCT GATCTATTAG GCGTCCTTGT TGCAAAGTGG GGTCCCATCA CGTTTCAGTG GCAGTGGATC
           CAACCATGGT CGTCTTTGGT CCCTTTCGGG GATTCGAGGA CTAGATAATC CGCAGAACA ACGTTTCACC CCAGGGTAGT GCAAAGTCAC CGTCACCTAG
                G T D  F T L T  I S S  L Q P  E D F A  T Y Y  C Q Q  D S Y F  P R T  F G Q
           TGGGACAGAT TTCACTCTCA CCATCAGCAG TCTGCAACCT GAAGATTTTG CTACCTACTA CTGTCAACAG GATTCGTATT TTCCTCGTAC GTTCGGCCAA
           ACCCTGTCTA AAGTGAGAGT GGTAGTCGTC AGACGTTGGA CTTCTAAAAC GATGGATGAT GACAGTTGTC CTAAGCATAA AAGGAGCATG CAAGCCGGTT
                G T K V  E I K  R           (SEQ ID NO:242)
           GGGACCAAGG TGGAAATCAA ACGG
           CCCTGGTTCC ACCTTTAGTT TGCC        (SEQ ID NO:243)
                                             (SEQ ID NO:244)

Partner dAb monomer in TAR1-27d36 (7U linker)
                D I Q  M T Q S  P S S  L S A S  V G D  R V T  I T C R  A S Q  S I M  D K L K
           GACATCCAGA TGACCCAGTC TCCATCCTCC CTGTCTGCAT CTGTAGGAGA CCGTGTCACC ATCACTTGCC GGGCAAGTCA GAGCATTATG GATAAGTTAA
           CTGTAGGTCT ACTGGGTCAG AGGTAGGAGG GACAGACGTA GACATCCTCT GGCACAGTGG TAGTGAACGG CCCGTTCAGT CTCGTAATAC CTATTCAATT
                W Y Q  Q K P  G K A P  K L L  I Y *  A S I L  Q S G  V P S  R F S G  S G S
           AGTGGTACCA GCAGAAACCA GGGAAAGCCC CTAAGCTCCT GATCTATTAG GCATCCATTT TGCAAAGTGG GGTCCCATCA CGTTTCAGTG GCAGTGGATC
           TCACCATGGT CGTCTTTGGT CCCTTTCGGG GATTCGAGGA CTAGATAATC CGTAGGTAAA ACGTTTCACC CCAGGGTAGT GCAAAGTCAC CGTCACCTAG
                G T D  F T L T  I S S  L Q P  E D F A  T Y Y  C Q Q  D S G G  P N T  F G Q
           TGGGACAGAT TTCACTCTCA CCATCAGCAG TCTGCAACCT GAAGATTTTG CTACTACTA CTGTCAACAG GATAGTGGGG GTCCTAATAC GTTCGGCCAA
           ACCCTGTCTA AAGTGAGAGT GGTAGTCGTC AGACGTTGGA CTTCTAAAAC GATGGATGAT GACAGTTGTC CTATCACCCC CAGGATTATG CAAGCCGGTT
                G T K V  E I K  R           (SEQ ID NO:245)
           GGGACCAAGG TGGAAATCAA ACGG
           CCCTGGTTCC ACCTTTAGTT TGCC        (SEQ ID NO:246)
                                             (SEQ ID NO:247)

Partner dAb monomer in TAR1-27d37 (7U linker)
                D I Q  M T Q S  P S S  L S A S  V G D  R V T  I T C R  A S Q  S I G  R N L E
           GACATCCAGA TGACCCAGTC TCCATCCTCC CTGTCTGCAT CTGTAGGAGA CCGTGTCACC ATCACTTGCC GGGCAAGTCA GAGCATTGGG AGGAATTTAG
           CTGTAGGTCT ACTGGGTCAG AGGTAGGAGG GACAGACGTA GACATCCTCT GGCACAGTGG TAGTGAACGG CCCGTTCAGT CTCGTAACCC TCCTTAAATC
                W Y Q  Q K P  G K A P  K L L  I Y D  A S H L  Q S G  V P S  R F S G  S G S
           AGTGGTACCA GCAGAAACCA GGGAAAGCCC CTAAGCTCCT GATCTATGAT GCATCCCATT TGCAAAGTGG GGTCCCATCA CGTTTCAGTG GCAGTGGATC
           TCACCATGGT CGTCTTTGGT CCCTTTCGGG GATTCGAGGA CTAGATACTA CGTAGGGTAA ACGTTTCACC CCAGGGTAGT GCAAAGTCAC CGTCACCTAG
                G T D  F T L T  I S S  L Q P  E D F A  T Y Y  C Q Q  S R W L  P R T  F G Q
           TGGGACAGAT TTCACTCTCA CCATCAGCAG TCTGCAACCT GAAGATTTTG CTACTACTA CTGTCAACAG TCGGTTGGC TTCCTCGTAC GTTCGGCCAA
           ACCCTGTCTA AAGTGAGAGT GGTAGTCGTC AGACGTTGGA CTTCTAAAAC GATGGATGAT GACAGTTGTC AGCCGCACCG AAGGAGCATG CAAGCCGGTT
                G T K V  E I K  R           (SEQ ID NO:248)
           GGGACCAAGG TGGAAATCAA ACGG
           CCCTGGTTCC ACCTTTAGTT TGCC        (SEQ ID NO:249)
                                             (SEQ ID NO:250)

Partner dAb monomer in TAR1-27d39 (7U linker)
                D I Q  M T Q S  P S S  L S A S  V G D  R V T  I T C R  A S Q  S I R  K M L V
           GACATCCAGA TGACCCAGTC TCCATCCTCC CTGTCTGCAT CTGTAGGAGA CCGTGTCACC ATCACTTGCC GGGCAAGTCA GAGCATTAGG AAGATGTTAG
           CTGTAGGTCT ACTGGGTCAG AGGTAGGAGG GACAGACGTA GACATCCTCT GGCACAGTGG TAGTGAACGG CCCGTTCAGT CTCGTAATCC TTCTACAATC
```

FIGURE 25G

```
                W  Y  Q  Q  K  P  G  K  A  P  K  L  L  I  Y  R  A  S  Y  L  Q  S  G  V  P  S  R  F  S  G  S  G  S
TTTGGTACCA GCAGAAACCA GGGAAACCC CTAAGCTCCT GATCTATCGG GCATCCTATT TGCCAAGTGG GGTCCCATCA CGTTTCAGTG GCAGTGGATC
AAACCATGGT CGTCTTTGGT CCCTTTCGGG GATTCGAGGA CTAGATAGCC CGTAGGATAA ACGTTTCACC CCAGGTAGT GCAAAGTCAC CGTCACCTAG
                G  T  D  F  T  L  T  I  S  S  L  Q  P  E  D  F  A  T  Y  Y  C  Q  Q  A  F  R  R  P  R  T  F  G  Q
TGGGACAGAT TTCACTCTCA CCATCAGCAG TCTGCAACCT GAAGATTTTG CTACTTACTA CTGTCAACAG GCTTTTCGGC GGCCTAGGAC GTTCGGCCAA
ACCCTGTCTA AAGTGAGAGT GGTAGTCGTC AGACGTTGGA CTTCTAAAAC GATGAATGAT GACAGTTGTC CGAAAAGCCG CCGGATCCTG CAAGCCCGTT
                G  T  K  V  E  I  K  R              (SEQ ID NO:251)
GGGACCAAGG TGGAAATCAA ACGG                          (SEQ ID NO:252)
CCCTGGTTCC ACCTTTAGTT TGCC                          (SEQ ID NO:253)

TAR2 dAb amino acid and DNA sequences (* indicates the presences of an amber stop codon) sequence homology
between TAR2h-5 and the unique second dAbs is 83.5%

TAR2h-5

E  V  Q  L  L  E  S  G  G  G  L  V  Q  P  G  G  S  L  R  L  S  C  A  A  S  G  F  T  F  D  L  Y  N  M
GAGGTGCAGC TGTTGGAGTC TGGGGGAGGC TTGGTACAGC CTGGGGGGTC CCTGCGTCTC TCCTGTGCAG CCTCCGGATT CACCTTTGAT CTTTATAATA
CTCCACGTCG ACAACCTCAG ACCCCCTCCG AACCATGTCG GACCCCCCAG GGACGCAGAG AGGACACGTC GGAGGCCTAA GTGGAAACTA GAAATATTAT
                F  W  V  R  Q  A  P  G  K  G  L  E  W  V  S  F  I  S  Q  T  G  R  L  T  W  Y  A  D  S  V  K  G  R
TGTTTTGGGT CCGCCAGGCT CCAGGGAAGG GTCTAGAGTG GTCTCATTT ATTAGTCAGA CTGGTAGGCT TACATGGTAC GCAGACTCCG TGAAGGGCCG
ACAAAACCCA GGCGGTCCGA GGTCCCTTCC CAGATCTCAC CCAGACTAAA TAATCAGTCT GACCATCCGA ATGTACCATG CGTCTGAGGC ACTTCCGGC
                F  T  I  S  R  D  N  S  K  N  T  L  Y  L  Q  M  N  S  L  R  A  E  D  T  A  V  Y  Y  C  A  K  T  L
GTTCACCATC TCCCGCGACA ATTCCAAGAA CACCCTGTAT CTGCAAATGA ACAGCCTGCG TGCCGAGGAC ACCGCCGTTAT ATTACTGTGC GAAACGCTG
CAAGTGGTAG AGGGCGCTGT TAAGGTTCTT GTGGGACATA GACGTTTACT TGTCGGACGC ACGGCTCCTG TGGCCGCCATA TAATGACACG CTTTGCGAC
                E  D  F  D  Y  W  G  Q  G  T  L  V  T  V  S  S              (SEQ ID NO:254)
GAGGATTTTG ACTACTGGGG CCAGGGAACC CTGGTCACCG TCTCG                          (SEQ ID NO:255)
CTCCTAAAAC TGATGACCCC GGTCCCTTGG GACCAGTGGC AGAGC                          (SEQ ID NO:256)

Partner dAb monomer in TAR2h-5dL (3U linker)

E  V  Q  L  L  E  S  G  G  G  L  V  Q  P  G  G  S  L  R  L  S  C  A  A  S  G  F  T  F  P  V  Y  Y  M
GAGGTGCAGC TGTTGGAGTC TGGGGGAGGC TTGGTACAGC CTGGGGGGTC CCTGCGTCTC TCCTGTGCAG CCTCCGGATT CACCTTTCCG GTTATATGA
CTCCACGTCG ACAACCTCAG ACCCCCTCCG AACCATGTCG GACCCCCCAG GGACGCAGAG AGGACACGTC GGAGGCCTAA GTGGAAAGGC CAAATATACT
                G  W  V  R  Q  A  P  G  K  G  L  E  W  V  S  S  I  D  A  L  G  G  R  T  G  Y  A  D  S  V  K  G  R
TGGGTTTGGGT CCGCCAGGCT CCAGGGAAGG GTCTAGAGTG GTCTCATCG ATTGATGCTC TTGGTGGGCG GACAGGTTAC GCAGACTCCG TGAAGGGCCG
ACCCAACCCA GGCGGTCCGA GGTCCCTTCC CAGATCTCAC CCAGATAGC TAACTACGAG AACCACCCGC CTGTCCAATG CGTCTGAGGC ACTTCCCGGC
                F  T  I  S  R  D  N  S  K  N  T  L  Y  L  Q  M  N  S  L  R  A  E  D  T  A  V  Y  Y  C  A  K  T  M
GTTCACCATC TCCCGCGACA ATTCCAAGAA CACCCTGTAT CTGCAAATGA ACAGCCTGCG TGCCGAGGAC ACCGCCGTAT ATTACTGTGC GAAACTATG
CAAGTGGTAG AGGGCGCTGT TAAGGTTCTT GTGGGACATA GACGTTTACT TGTCGGACGC ACGGCTCCTG TGGCCCCATA TAATGACACG CTTTTGATAC
                S  N  K  T  H  T  F  D  Y  W  G  Q  G  T  L  V  T  V  S  S              (SEQ ID NO:257)
TCGAATAAGA CGCATACGTT TGACTACTGG GGCCAGGGAA CCCTGGTCAC CGTCTCG                          (SEQ ID NO:258)
AGCTTATTCT GCGTATGCAA ACTGATGACC CCGGTCCCTT GGGACCAGTG GCAGAGC                          (SEQ ID NO:259)
```

FIGURE 25H

Partner dAb monomer in TAR2h-5d2 (3U linker)
```
  E  V  Q  L  L  E  S  G  G  G  L  V  Q  P  G  G  S  L  R  L  S  C  A  A  S  G  F  T  F  V  A  Y  N  M
GAGGTGCAGC TGTTGGAGTC TGGGGGAGGC TTGGTACAGC CTGGGGGGTC CCTGCGTCTC TCCTGTGCAG CCTCCGGATT CACCTTTGTG GCTTATAATA
CTCCACGTCG ACAACCTCAG ACCCCCTCCG AACCCATGTCG GACCCCCCAG GGACGCAGAG AGGACACGTC GGAGGCCTAA GTGGAAACAC CGAATATTAT
  T  W  V  R  Q  A  P  G  K  G  L  E  W  V  S  S  I  N  T  F  G  N  *  T  R  Y  A  D  S  V  K  G  R
TGACTTGGGT CCGCCAGGCT CCAGGGAAGG GTCTAGAGTG GTCTCAAGTT ATTAATACTT TTGGTAATTA GACAAGGTAC GCAGACTCCG TGAAGGGCCG
ACTGAACCCA GGCGGTCCGA GGTCCCTTCC CAGATCTCAC CCAGATTCAA TAATTATGAA AACCATTAAT CTGTTCCATG CGTCTGAGGC ACTTCCCGGC
  F  T  I  S  R  D  N  S  K  N  T  L  Y  L  Q  M  N  S  L  R  A  E  D  T  A  V  Y  Y  C  A  K  G  S
GTTCACCATC TCCCGCGACA ATTCCAAGAA CACGCTGTAT CTGCAAATGA ACAGCCTGCG TGCCGAGGAC ACCGCGGTAT ATTACTGTGC GAAAGGTAGT
CAAGTGGTAG AGGGCGCTGT TAAGGTTCTT GTGCGACATA GACGTTTACT TGTCGGACGC ACGGCTCCTG TGGCGCCATA TAATGACACG CTTTCCATCA
  R  P  F  D  Y  W  G  Q  G  T  L  V  T  V  S
AGGCCTTTG ACTACTGGGG CCAGGGAACC CTGGTCACCG TCTCG                                         (SEQ ID NO:260)
TCCGGAAAAC TGATGACCCC GGTCCCTTGG GACCAGTGGC AGAGC                                        (SEQ ID NO:261)
                                                                                         (SEQ ID NO:262)
```

Partner dAb monomer in TAR2h-5d3 (3U linker)
```
  E  V  Q  L  L  E  S  G  G  G  L  V  Q  P  G  G  S  L  R  L  S  C  A  A  S  G  F  T  F  *  G  Y  R  M
GAGGTGCAGC TGTTGGAGTC TGGGGGAGGC TTGGTACAGC CTGGGGGGTC CCTGCGTCTC TCCTGTGCAG CCTCCGGATT CACCTTTTAG GGGTATCGTA
CTCCACGTCG ACAACCTCAG ACCCCCTCCG AACCATGTCG GACCCCCCAG GGACGCAGAG AGGACACGTC GGAGGCCTAA GTGGAAAATC CCCATAGCAT
  G  W  V  R  Q  A  P  G  K  G  L  E  W  V  S  W  I  T  R  T  G  G  T  T  Q  Y  A  D  S  V  K  G  R
TGGGTTGGGT CCGCCAGGCT CCAGGGAAGG GTCTAGAGTG GTCTCATGG ATTACGCGTA CTGGTGGGAC GACACAGTAC GCAGACTCCG TGAAGGGCCG
ACCCAACCCA GGCGGTCCGA GGTCCCTTCC CAGATCTCAC CCAGAGTACC TAATGCGCAT GACCACCCTG CTGTCTCATG CGTCTGAGGC ACTTCCCGGC
  F  T  I  S  R  D  N  S  K  N  T  L  Y  L  Q  M  N  S  L  R  A  E  D  T  A  V  Y  Y  C  A  K  P  A
GTTCACCATC TCCCGCGACA ATTCCAAGAA CACGCTGTAT CTGCAAATGA ACAGCCTGCG TGCCGAGGAC ACCGCGGTAT ATTACTGTGC GAAACCGGCG
CAAGTGGTAG AGGGCGCTGT TAAGGTTCTT GTGCGACATA GACGTTTACT TGTCGGACGC ACGGCTCCTG TGGCGCCATA TAATGACACG CTTTGGCCGC
  K  L  V  G  V  G  F  D  Y  W  G  Q  G  T  L  V  T  V  S
AAGCTTGTTG GGGTTGGGTT TGACTACTGG GGCCAGGGAA CCCTGGTCAC CGTCTCG                         (SEQ ID NO:263)
TTCGAACAAC CCCAACCCAA ACTGATGACC CCGGTCCCTT GGGACCAGTG GCAGAGC                         (SEQ ID NO:264)
                                                                                       (SEQ ID NO:265)
```

Partner dAb monomer in TAR2h-5d4 (3U linker)
```
  E  V  Q  L  L  E  S  G  G  G  L  V  Q  P  G  G  S  L  R  L  S  C  A  A  S  G  F  T  F  R  K  Y  *  M
GAGGTGCAGC TGTTGGAGTC TGGGGGAGGC TTGGTACAGC CTGGGGGGTC CCTGCGTCTC TCCTGTGCAG CCTCCGGATT CACCTTTCGG AAGTATTAGA
CTCCACGTCG ACAACCTCAG ACCCCCTCCG AACCATGTCG GACCCCCCAG GGACGCAGAG AGGACACGTC GGAGGCCTAA GTGGAAAGCC TTCATAATCT
  G  W  V  R  Q  A  P  G  K  G  L  E  W  V  S  Q  I  G  A  K  G  Q  S  T  D  Y  A  D  S  V  K  G  R
TGGGTCGGT CCGCCAGGCT CCAGGGAAGG GTCTAGAGTG GTCTCACAG ATTGGTGCGA AGGGTCAGTC TACAGATTAC GCAGACTCCG TGAAGGGCCG
ACCCCAGCCA GGCGGTCCGA GGTCCCTTCC CAGATCTCAC CCAGAGTGTC TAACCACGCT TCCCAGTCAG ATGTCTAATG CGTCTGAGGC ACTTCCCGGC
  F  T  I  S  R  D  N  S  K  N  T  L  Y  L  Q  M  N  S  L  R  A  E  D  T  A  V  Y  Y  C  A  K  K  K
GTTCACCATC TCCCGCGACA ATTCCAAGAA CACGCTGTAT CTGCAAATGA ACAGCCTGCG TGCCGAGGAC ACCGCGGTAT ATTACTGTGC GAAAAAGAAG
CAAGTGGTAG AGGGCGCTGT TAAGGTTCTT GTGCGACATA GACGTTTACT TGTCGGACGC ACGGCTCCTG TGGCGCCATA TAATGACACG CTTTTTCTTC
  R  G  E  N  Y  F  F  D  Y  W  G  Q  G  T  L  V  T  V  S
AGGGGGGAGA ATTATTTTTT TGACTACTGG GGCCAGGGAA CCCTGGTCAC CGTCTCG                          (SEQ ID NO:266)
TCCCCCCTCT TAATAAAAAA ACTGATGACC CCGGTCCCTT GGGACCAGTG GCAGAGC                          (SEQ ID NO:267)
                                                                                        (SEQ ID NO:268)
```

FIGURE 25I

Partner dAb monomer in TAR2h-5d5 (3U linker)

```
E V Q L L E S G G G L V Q P G G S L R L S C A A S G F T F R R Y S M
GAGGTGCAGC TGTTGGAGTC TGGGGGAGGC TTGGTACAGC CTGGGGGGTC CCTGCGTCTC TCCTGTGCAG CCTCCGGATT CACCTTTCGG CGGTATAGTA
  W V R Q A P G K G L E W V S D I S R S G R Y T H Y A D S V K G R
CTCCACGTCG ACAACCTCAG ACCCCCTCCG AACCCTCTCG GAGTGGGTCT CAGATCTCAC CCAGAGTCTA TAAAGAGCAA GACACGCTAT ATGTGTAATG CGTCTGAGGC ACTTCCCGGC
  F T I S R D N S K N T L Y L Q M N S L R A E D T A V Y Y C A K R I
GTTCACCATC TCCCGCGACA ATTCCAAGAA CACGCTGTAT CTGCAAATGA ACAGCCTGCG TGCCGAGGAC ACAGGCTGTC ATTACTGTGC GAAACGTATT
  D S S Q N G F D Y W G Q G T L V T V S              (SEQ ID NO:269)
GATTCTTCTC AGAATGGGTT TGACTACTGG GGCCAGGGAA CCCTGGTCAC CGTCTCG    (SEQ ID NO:270)
CTAAGAAGAG TCTTACCCAA ACTGATGACC CCGGTCCCTT GGGACCAGTG GCAGAGC    (SEQ ID NO:271)
```

Partner dAb monomer in TAR2h-5d6 (3U linker)

```
E V Q L L E S G G G L V Q P G G S L R L S C A A S G F T F * G Y K M
GAGGTGCAGC TGTTGGAGTC TGGGGGAGGC TTGGTACAGC CTGGGGGGTC CCTGCGTCTC TCCTGTGCAG CCTCCGGATT CACCTTTTAG GGGTATAAGA
  F W V R Q A P G K G L E W V S A I S G S G G S T Y Y A D S V K G R
CTCCAGTCG ACAACCTCAG ACCCCCTCCG GACCCCCCAG GGACGCAGAG AGGACAGTC GGAGGCAGAG GACCTGGAG TACATACTAC GCAGACTCCG TGAAGGGCCG
  F T I S R D N S K N T L Y L Q M N S L R A E D T A V Y Y C A K Q K
GTTCACCATC TCCCGCGACA ATTCCAAGAA CACGCTGTAT CTGCAAATGA ACAGCCTGCG TGCCGAGGAC ACCGGGTAT ATTACTGTGC GAAACAGAAG
  E N F D Y W G Q G T L V T V S                       (SEQ ID NO:272)
GAGAATTTTG ACTACTGGGG CCAGGGAACC CTGGTCACCG TCTCG              (SEQ ID NO:273)
CTCTTAAAAC TGATGACCCC GGTCCCTTGG GACCAGTGGC AGAGC              (SEQ ID NO:274)
```

Partner dAb monomer in TAR2h-5d7 (3U linker)

```
E V Q L L E S G G G L V Q P G G S L R L S C A A S G F T F G D Y A M
GAGGTGCAGC TGTTGGAGTC TGGGGGAGGC TTGGTACAGC CTGGGGGGTC CCTGCGTCTC TCCTGTGCAG CCTCCGGATT CACCTTTGGG GATTATGCTA
  W V R Q A P G K G L E W V S V I S S N G G S T F Y A D S V K G R
CTCCACGTCG ACAACCTCAG ACCCCCTCCG GACCCCCAG GGACGCAGAG AGGACAGCTC CAGAGTCAG ATTAGTTCGA ATGGTGGGAG TACATTTAC GCAGACTCCG TGAAGGGCCG
  F T I S R D N S K N T L Y L Q M N S L R A E D T A V Y Y C A K R V
GTTCACCATC TCCCGCGACA ATTCCAAGAA CACGCTGTAT CTGCAAATGA ACAGCCTGCG TGCCGAGGAC ACCGGGTAT ATTACTGTGC GAAACGTGTT
  R R T P E F D Y W G Q G T L V T V S                 (SEQ ID NO:275)
CGTAAGAGGA CTCCTGAGTT TGACTACTGG GGCCAGGGAA CCCTGGTCAC CGTCTCG  (SEQ ID NO:276)
GCATTCTCCT GAGGACTCAA ACTGATGACC CCGGTCCCTT GGGACCAGTG GCAGAGC  (SEQ ID NO:277)
```

FIGURE 25J

Partner dAb monomer in TAR2h-5d8 (3U linker)

```
E  V  Q  L  L  E  S  G  G  G  L  V  Q  P  G  G  S  L  R  L  S  C  A  A  S  G  F  T  F  R  R  Y  K  M
GAGGTGCAGC TGTTGGAGTC TGGGGGAGGC TTGGTACAGC CTGGGGGGTC CCTGCGTCTC TCCTGTGCAG CCTCCGGATT CACCTTTAGG AGGTATAAGA
CTCCACGTCG ACAACCTCAG ACCCCCTCCG AACCATGTCG GACCCCCCAG GGACGCAGAG AGGACACGTC GGAGGCCTAA GTGGAAATCC TCCATATTCT
 G  W  V  R  Q  A  P  G  K  G  L  E  W  V  S  A  I  G  R  N  T  N  Y  A  D  S  V  K  G  R
TGGGTTGGGT CCGGCAGGCT CCAGGGAAGG GTCTAGAGTG GTCTCAGCG ATTGGAAGGA ATGGTACGAA GACAAATTAC GCAGACTCCG TGAAGGCCCG
ACCCACCCA GGCGGTCCGA GGTCCCTTCC CAGATCTCAC CCAGAGTGC TAACCCTCCT TACCATGCTT CTGTTTAATG CGTCTGAGGC ACTTCCGGC
 F  T  I  S  R  D  N  S  K  N  T  L  Y  L  Q  M  N  S  L  R  A  E  D  T  A  V  Y  Y  C  A  K  I  Y
GTTCACCATC TCCCGCGACA ATTCCAAGAA CACGCTGTAT CTGCAAATGA ACAGCCTGCG TGCCGAGGAC ACCGGGTAT ATTACTGTGC GAAAATTTAT
CAAGTGGTAG AGGGCGCTGT TAAGGTTCTT GTGCGACATA GACGTTTACT TGTCGGACGC ACGGCTCCTG TGGCGCCATA TAATGACACG CTTTTAAATA
 T  G  K  P  A  A  F  D  Y  W  G  Q  G  T  L  V  T  V  S                              (SEQ ID NO:278)
ACGGGGAAGC CTGCTGCGTT TGACTACTGG GGCCAGGGAA CCCTGGTCAC CGTCTCG                         (SEQ ID NO:279)
TGCCCCCTTCG GACGACGCAA ACTGATGACC CCGGTCCCTT GGGACCAGTG GCAGAGC                        (SEQ ID NO:280)
```

Partner dAb monomer in TAR2h-5d9 (3U linker)

```
E  V  Q  L  L  E  S  G  G  G  L  V  Q  P  G  G  S  L  R  L  S  C  A  A  S  G  F  T  F  K  K  Y  * M
GAGGTGCAGC TGTTGGAGTC TGGGGGAGGC TTGGTACAGC CTGGGGGGTC CCTGCGTCTC TCCTGTGCAG CCTCCGGATT CACCTTTAAG AAGTATTAGA
CTCCACGTCG ACAACCTCAG ACCCCCTCCG AACCATGTCG GACCCCCCAG GGACGCAGAG AGGACACGTC GGAGGCCTAA GTGGAAATTC TTCATAATCT
 S  W  V  R  Q  A  P  G  K  G  L  E  W  V  S  A  I  S  G  S  G  G  S  T  Y  Y  A  D  S  V  K  G  R
TGTCTTGGGT CCGGCAGGCT CCAGGGAAGG GTCTAGAGTG GTCTCAGCT ATTAGTGGTA GTGGTGGTAG CACATACTAC GCAGACTCCG TGAAGGCCCG
ACAGAACCCA GGCGGTCCGA GGTCCCTTCC CAGATCTCAC CGAGATCGA TAATCACCAT CACCACCATC GTGTATGATG CGTCTGAGGC ACTTCCGGC
 F  T  I  S  R  D  N  S  K  N  T  L  Y  L  Q  M  N  S  L  R  A  E  D  T  A  V  Y  Y  C  A  K  M  L
GTTCACCATC TCCCGCGACA ATTCCAAGAA CACGCTGTAT CTGCAAATGA ACAGCCTGCG TGCCGAGGAC ACCGGGTAT ATTACTGTGC GAAAATGCTG
CAAGTGGTAG AGGGCGCTGT TAAGGTTCTT GTGCGACATA GACGTTTACT TGTCGGACGC ACGGCTCCTG TGGCGCCATA TAATGACACG
 R  T  K  N  K  V  F  D  Y  W  G  Q  G  T  L  V  T  V  S                              (SEQ ID NO:281)
AGGACTAAGA ATAAGGTGTT TGACTACTGG GGCCAGGGAA CCCTGGTCAC CGTCTCG                         (SEQ ID NO:282)
TCCTGATTCT TATTCCACAA ACTGATGACC CCGGTCCCTT GGGACCAGTG GCAGAGC                         (SEQ ID NO:283)
```

Partner dAb monomer in TAR2h-5d10 (5U linker)

```
E  V  Q  L  L  E  S  G  G  G  L  V  Q  P  G  G  S  L  R  L  S  C  A  A  S  G  F  T  F  R  R  Y  K  M
GAGGTGCAGC TGTTGGAGTC TGGGGGAGGC TTGGTACAGC CTGGGGGGTC CCTGCGTCTC TCCTGTGCAG CCTCCGGATT CACCTTTAGG AGGTATAAGA
CTCCACGTCG ACAACCTCAG ACCCCCTCCG AACCATGTCG GACCCCCCAG GGACGCAGAG AGGACACGTC GGAGGCCTAA GTGGAAATCC TCCATATTCT
 G  W  V  R  Q  A  P  G  K  G  L  E  W  V  S  A  I  G  R  N  T  N  Y  A  D  S  V  K  G  R
TGGGTTGGGT CCGGCAGGCT CCAGGGAAGG GTCTAGAGTG GTCTCAGCG ATTGGAAGGA ATGGTACGAA GACAAATTAC GCAGACTCCG TGAAGGCCCG
ACCCACCCA GGCGGTCCGA GGTCCCTTCC CAGATCTCAC CCAGAGTGC TAACCCTCCT TACCATGCTT CTGTTTAATG CGTCTGAGGC ACTTCCGGC
 F  T  I  S  R  D  N  S  K  N  T  L  Y  L  Q  M  N  S  L  R  A  E  D  T  A  V  Y  Y  C  A  K  I  Y
GTTCACCATC TCCCGCGACA ATTCCAAGAA CACGCTGTAT CTGCAAATGA ACAGCCTGCG TGCCGAGGAC ACCGGGTAT ATTACTGTGC GAAAATTTAT
CAAGTGGTAG AGGGCGCTGT TAAGGTTCTT GTGCGACATA GACGTTTACT TGTCGGACGC ACGGCTCCTG TGGCGCCATA TAATGACACG CTTTTAAATA
 T  G  K  P  A  A  F  D  Y  W  G  Q  G  T  L  V  T  V  S                              (SEQ ID NO:284)
ACGGGGAAGC CTGCTGCGTT TGACTACTGG GGCCAGGGAA CCCTGGTCAC CGTCTCG                         (SEQ ID NO:285)
TGCCCCCTTCG GACGACGCAA ACTGATGACC CCGGTCCCTT GGGACCAGTG GCAGAGC                        (SEQ ID NO:286)
```

FIGURE 25K

Partner dAb monomer in TAR2h-5dl1 (5U linker)

```
  E   V   Q   L   L   E   S   G   G   G   L   V   Q   P   G   G   S   L   R   L   S   C   A   A   S   G   F   T   F   *   S   Y   R   M
GAGGTGCAGC TGTTGGAGTC TGGGGGAGGC TTGGTACAGC CCTGCGTCTC TCCTGTGCAG CCTCCGGATT CACCTTTTAG AGTTATCGGA
CTCCACGTCG ACAACCTCAG ACCCCCTCCG AACCATGTCG GACGCAGAG AGGACACGTC GGAGGCCTAA GTGGAAAATC TCAATAGCCT
  G   W   V   R   Q   A   P   G   K   G   L   E   W   V   S   S   I   S   S   R   R   H   T   S   Y   A   D   S   V   K   G   R
TGGGTTGGGT CCGCCAGGCT CCAGGGAAGG GTCTAGAGTG CAGATCTCAC CCAGAGTTCA CCAGATCTCA TAACATCTTAC GCAGACTCCG TGAAGGGCCG
ACCCAACCCA GGCGGTCCGA GGTCCCTTCC CAGATCTCAC CCAGAGTTCA CCAGAGCTCA TAAAGCAGCT CCCCATCCGT ATGTAGAATG CGTCTGAGGC ACTTCCCGGC
  F   T   I   S   R   D   N   S   K   N   T   L   Y   L   Q   M   N   S   L   R   A   E   D   T   A   V   Y   Y   C   A   K   R   V
GTTCACCATC TCCCGCGACA ATTCCAAGAA CACGCTGTAT CTGCAAATGA ACAGCCTGCG TGCCGAGGAC ACCGCGGTAT ATTACTGTGC GAAAAGGGTT
CAAGTGGTAG AGGGCGCTGT TAAGGTTCTT GTGCGACATA GACGTTTACT TGTCGGACGC ACGGCTCCTG TGGCGCCATA TAATGACACG CTTTTCCCAA
  P   G   R   S   F   D   Y   W   G   Q   G   T   L   V   T   V   S                   (SEQ ID NO:287)
CCGGGTCGGG GGCGTTCTTT TGACTACTGG GGCCAGGGAA CCCTGGTCAC CGTCTCG                        (SEQ ID NO:288)
GGCCCAGCCC CCGCAAGAAA ACTGATGACC CCGGTCCCTT GGGACCAGTG GCAGAGC                        (SEQ ID NO:289)
```

Partner dAb monomer in TAR2h-5dl2 (5U linker)

```
  E   V   Q   L   L   E   S   G   G   G   L   V   Q   P   G   G   S   L   R   L   S   C   A   A   S   G   F   P   F   R   R   Y   R   M
GAGGTGCAGC TGTTGGAGTC TGGGGGAGGC TTGGTACAGC CCTGGGGGTC CCTGCGTCTC TCCTGTGCAG CCTCCGGATT CCCCTTTCGT CGGTATCGGA
CTCCACGTCG ACAACCTCAG ACCCCCTCCG AACCATGTCG GGACCCCCAG GGACGCAGAG AGGACACGTC GGAGGCCTAA GGGGAAAGCA GCCATAGCCT
  R   W   V   R   Q   A   P   G   K   G   L   E   W   V   S   G   I   S   P   G   K   H   T   T   Y   A   D   S   V   K   G   R
TGAGTGGGT CCGCCAGGCT CCAGGGAAGG GTCTAGAGTG GGTCTCAGGT ATTTCTCCGG GTGTAAGCA TACAACGTAC CAGACTCCG TGAAGGGCCG
ACTCCACCCA GGCGGTCCGA GGTCCCTTCC CAGATCTCAC CCAGAGTCCA CCAGATTCGT ATGTTGCATG CGTCTGAGGC ACTTCCCGGC
  F   T   I   S   R   D   N   S   K   N   T   L   Y   L   Q   M   N   S   L   R   A   E   D   T   A   V   Y   Y   C   A   K   G   E
GTTCACCATC TCCCGCGACA ATTCCAAGAA CACGCTGTAT CTGCAAATGA ACAGCCTGCG TGCCGAGGAC ACCGCGGTAT ATTACTGTGC GAAAGGTGAG
CAAGTGGTAG AGGGCGCTGT TAAGGTTCTT GTGCGACATA GACGTTTACT TGTCGGACGC ACGGCTCCTG TGGCGCCATA TAATGACACG CTTTCCACTC
  G   G   A   S   S   A   F   D   Y   W   G   Q   G   T   L   V   T   V   S                  (SEQ ID NO:290)
GGGGGGCGA GTCTCGCGTT TGACTACTGG GGCCAGGGAA CCCTGGTCAC CGTCTCG                           (SEQ ID NO:291)
CCCCCCGCT CAAGAGCGCAA ACTGATGACC CCGGTCCCTT GGGACCAGTG GCAGAGC                          (SEQ ID NO:292)
```

Partner dAb monomer in TAR2h-5dl3 (5U linker)

```
  E   V   Q   L   L   E   S   G   G   G   L   V   Q   P   G   G   S   L   R   L   S   C   A   A   S   G   F   T   F   *   R   Y   G   M
GAGGTGCAGC TGTTGGACTC TGGGGCAGGC TTGGTACAGC CCTGGCGTCTC CCTCGTCAG GGACGCAGAG AGGACACGTC GGAGGCCTAA GTGGAAAATC GCCATACCCT
CTCCACGTCG ACAACCTCAG ACCCCCTCCG AACCATGTCG GTCTCGAGTG CCTCGTCAGC TATTAGTGTA GTGGTGGTAG CACATACTAC GCAGACTCCG TGAAGGGCCG
  V   N   V   R   Q   A   P   G   K   G   L   E   W   V   S   A   I   S   G   S   G   G   S   T   Y   Y   A   D   S   V   K   G   R
TGGTTTGGT CCGCCAGGCT CCAGGAAGG GTCTAGAGTG GTCTCAGCT ATTAGTGGTA GTGGTGGTAG CACATACTAC GCAGACTCCG TGAAGGGCCG
ACCAAACCCA GGCGGTCCGA GGTCCCTTCC CAGATCTCAC CCAGAGTCGA TAATCACCAT CACCACCATC GTGTATGATG CGTCTGAGGC ACTTCCCGGC
  F   T   I   S   R   D   N   S   K   N   T   L   Y   L   Q   M   N   S   L   R   A   E   D   T   A   V   Y   Y   C   A   K   R   H
GTTCACCATC TCCCGCGACA ATTCCAAGAA CACGCTGTAT CTGCAAATGA ACAGCCTGCG TGCCGAGGAC ACCGCGGTAT ATTACTGTGC GAAACGGCAT
CAAGTGGTAG AGGGCGCTGT TAAGGTTCTT GTGCGACATA GACGTTTACT TGTCGGACGC ACGGCTCCTG TGGCGCCATA TAATGACACG CTTTGCCGTA
  S   S   E   A   R   Q   F   D   Y   W   G   Q   G   T   L   V   T   V   S                   (SEQ ID NO:293)
AGTTCTGAGG CTAGACAGTT TGACTACTGG GGCCAGGGAA CCCTGGTCAC CGTCTCG                          (SEQ ID NO:294)
TCAAGACTCC GATCCGTCAA ACTGATGACC CCGGTCCCTT GGGACCAGTG GCAGAGC                          (SEQ ID NO:295)
```

FIGURE 25L

TAR2h-131-8      (SEQ ID NO:433)
EVQLLESGGGLIQPGGSLRLSCAASGFTFA~HETMV~WVRQAPGKGLEWVS~~HIDRVGQD
TYYADSVKG~~RFTISRDNSKNTLYLQMNSLRAEDTAVYYCAK~~~LPKRGPWFDY~~~RG
QGTLVTVSS

TAR2h-131-24     (SEQ ID NO:434)
EVQLLESGGGLIQPGGSLRLSCAASGFTFA~HETMV~WVRQAPGKGLEWVS~~HIDRVGQD
TYYADSVKG~~RFTISRDNSKNTLYLQMNSLRAEDTAVYYCAR~~~LPKRGPWFDY~~~RG
QGTLVTVSS

TAR2h-15-8 (SEQ ID NO:435)
EVRLLESGGGLVQPGGSLRLSCVASGFTFG~KSTMT~WVRQAPGKGLEWVS~~HISDDGNS
TYYADSVKG~~RFTISRDNSKNTLYLQMNSLRAEDTAVYYCAK~~~VPILAPRNLFDY~~~WG
QGTLVTVSS

TAR2h-15-8-1     (SEQ ID NO:436)
EVRLLESGGGLVQPGGSLRLSCVASGFNFG~KSTMT~WVRQAPGKGLEWVS~HISDDGNS
TYYADSVKG~RFTISRDNSKNTLYLQMNSLRAEDTAVYYCAK~VPILAPRNLFDY
~~~WGQGTLVTVSS

TAR2h-15-8-2     (SEQ ID NO:437)
EVRLLESGGGLVQPGGSLRLSCVASGFTFG~KGTMT~WVRQAPGKGLEWVS~~HISDDGNS
TYYADSVKG~~RFTISRDNSKNTLYLQMNSLRAEDTAVYYCAK~~~VPILAPRNLFDY~~~WG
QGTLVTVSS

TAR2h-185-23     (SEQ ID NO:438)
EVQLLESGGGLVQPGGSLRLSCAASGFTFA~RYNMG~WVRQAPGKGLEWVS~~LIDPSGGH
TYYAXSVKG~~RSTISRNNSKNTLYLQMNSLRAEDTAVYYCGK~~~PVFSDWPAVEFDY~~~WG
QGTLVTVSS

TAR2h-154-10-5   (SEQ ID NO:439)
EVQLLESGGGMVQPGGSLRLSCAAPGFTFE~HEGMV~WVRQAPGKGLEWVS~~HIGEDGQS
TYYADSVKG~~RFTISRDNSKNTLYLQMNSLRAEDTAVYYCAS~~~IPKAGPSFDY~~~WG
QGTLVTVSS

TAR2h-14-2 (SEQ ID NO:440)
EVQLLESGGGLVQPGGSLRLSCAASGSTFD~QYDMS~WVRRAPGKGLEWVS~~LIDPSGGH
TYYADSVKG~~RFTISRNNTKNTLYLQMNSLRAEDTAVYYCAK~~~PVFSDWPAVEFDY~~~WG
QGTLVTVSS

TAR2h-151-8      (SEQ ID NO:441)
EVQLLESGGGLVQPGGSLRLSCAASGFTFD~YGNMF~WVRQAPGKGLEWIS~~AISGSGGS
TYYADSVKG~~RFTISRDNSKNTLYLQMNSLRAEDTAVYYCAK~~~DMTTDSPPGFDY~~~WG
QGTLVTVSS

TAR2h-152-7      (SEQ ID NO:442)
EVQLLESGGGLVQPGGSLRLSCAASGFTFA~KETMS~WVRQAPGKGLEWVS~~WISPHGAH
TFYADSVKG~~RFTISRDNSKNTLYLQMNSLRAEDTAVYYCAK~~~PRFSYYPRVSFDY~~~RG
QGTLVTVSS

FIGURE 27A

TAR2h-35-4 (SEQ ID NO:443)
EVQLLESGGGLVQPGGSLRLSCAASGFTFD~AYNMF~WFRQAPGKGPEWVS~~AIGPSGRE
TYYADSVKG~~RFTITRDNSKNTLYLQMNSLRAEDTAVYYCAK~~~RYPDFDY~~~WG
QGTLVTVSS

TAR2h-154-7 (SEQ ID NO:444)
EVQLLESGGGLVQPGGSLRLSCAASGFTFE~HEGMV~WVRQAPGKGLEWVS~~HIGEDGQS
TYYADSVKG~~RFTISRDNSRNTLYLQMNSLRAEDTAVYYCAN~~~IPKAGPSFDY~~~WG
QGTLVTVSS

TAR2h-80 (SEQ ID NO:445)
EVQLLESGGGLVQPGGSLRLSCAASGFTFK~LYNMA~WVRQAPGKGLEWVS~~FIAAAGPE
TYYADSVKG~~RFTISRDNSKNTLYLQMNSLRAEDTAVYYCAK~~~LGDISSIPQHPFDY~~~WG
QGTLVTVSS

TAR2h-81 (SEQ ID NO:446)
EVQLLESGGGLVQPGGSLRLSCAASGFTFS~RENMH~WVRQAPGKGLEWVS~~GIGPRGMP
TYYADSVKG~~RFTISRDNSKNTLYLQMNSLRAEDTAVYYCAK~~~GMNSHDGFDY~~~WG
QGTLVTVSS

TAR2h-82 (SEQ ID NO:447)
EVQLLESGGGLVQPGGSLRLSCAASGFTFD~ASEMD~WVRQAPGKGLEWVS~~AISPSGSA
TYYADSVKG~~RFTISRDNSKNTLYLQMNSLRAEDTAVYYCAK~~~RMLANSPLAFDY~~~WG
QGTLVTVSS

TAR2h-83 (SEQ ID NO:448)
EVQLLESGGGLVQPGGSLRLSCAASGFTFS~AYNMA~WVRQAPGKGLEWVS~~FIAQSGGH
TYYADSVKG~~RFTISRDNSKNTLYLQMNSLRAEDTAVYYCAK~~~FSHPDEEGTQMFDY~~~WG
QGTLVTVSS

TAR2h-84 (SEQ ID NO:449)
EVQLLESGGGLVQPGGSLRLSCAASGFTFA~DYQMA~WVRQAPGKGLEWVS~~RIDRGGFH
TYYADSVKG~~RFTISRDNSKNTLYLQMNSLRAEDTAVYYCAK~~~PSWHADQYFDY~~~WG
QGTLVTVSS

TAR2h-85 (SEQ ID NO:450)
EVQLLESGGGLVQPGGSLRLSCAASGFTPK~DYNMM~WVRQAPGKGLEWVS~~AIATSGRE
TYYADSVKG~~RFTISRDNSKNTLYLQMNSLRAEDTAVYYCAK~~~FTFGGNQDFDY~~~WG
QGTLVTVSS

TAR2h-86 (SEQ ID NO:451)
EVQLLESGGGLVQPGGSLRLSCAASGFTFA~KYNMY~WVRQAPGKGLEWVS~~AISPKGQH
TYYADSVKG~~RFTISRDNSKNTLYLQMNSLRAEDTAVYYCAE~~~GMGSDAITFDY~~~WG
QGTLVTVSS

TAR2h-87 (SEQ ID NO:452)
EVQLLESGGGLVQPGGSLRLSCAASGFTFS~AYNMA~WVRQAPGKGLEWVS~~FIAQSGGH
TYYADSVKG~~RFTISRDNSKNTLYLQMNSLRAEDTAVYYCAK~~~FSHPDEEGTQMFDY~~~WG
QGTLVTVSS

FIGURE 27B

TAR2h-88    (SEQ ID NO:453)
EVQLLESGGGLVQPGGSLRLSCAASGFTFE~RYDMF~WVRQAPGKGLEWVS~~GISPRGRE
TYYADSVKG~~RFTISRDNSKNTLYLQMNSLRAEDTAVYYCAK~~~DMINYHGTPSFDY~~~WG
QGTLVTVSS

TAR2h-89    (SEQ ID NO:454)
EVQLLESGGGLVQPGGSLRLSCAASGFTFX~NYNMV~WVRQAPGKGLEWVS~~WISGAGHS
TYYADSVKG~~RFTISRDNSKNTLYLQMNSLRAEDTAVYYCAK~~~DVDMAGKLNVFDY~~~WG
QGTLVTVSS

TAR2h-90    (SEQ ID NO:455)
EVQLLESGGGLVQPGGSLRLSCAASGFTFK~QYNMY~WVRQAPGKGLEWVS~~FISPSGGE
TYYADSVKG~~RFTTSRDNSKNTLYLQMNSLRAEDTAVYYCAK~~~DVDMAGKLNVFDY~~~WG
QGTLVTVSS

TAR2h-91    (SEQ ID NO:456)
EVQLLESGGGLVQPGGSLRLSCAASGFTFA~DYQMA~WVRQAPGKGLEWVS~~RIDRGGFH
TYYADSVKG~~RFTISRDNSKNTLYLQMNSLRAEDTAVYYCAK~~~PSWHADQYFDY~~~WG
QGTLVTVSS

TAR2h-92    (SEQ ID NO:457)
EVQLLESGGGLVQPGGSLRLTCAASGFTFD~DVNMT~WVRQAPGKGLEWVS~~AIGPSGTE
TYYADSVKG~~RFTISRDNSKNTLYLQMNSLRAEDTAVYYCAK~~~HSKTGSAMFDY~~~WG
QGTLVTVSS

TAR2h-93    (SEQ ID NO:458)
EVQLLESGGGLVQPGGSLRLSCAASGFTFG~NGNMV~WVRQAPGKGLEWVS~~HIDEYGTN
TYYADSVKG~~RFTISRDNSKNTLYLQMNSLRAEDTAVYYCAK~~~PRNDRPGFDY~~~WG
QGTLVTVSS

TAR2h-94    (SEQ ID NO:459)
EVQLLESGGGLVQPGGSLRLSCAASGFTFS~RENMH~WVRQAPGKGLEWVS~~GIGPRGMP
TYYADSVKG~~RFTISRDNSKNTLYLQMNSLRAEDTAVYYCAK~~~GMNSHDGFDY~~~WG
QGTLVTVSS

TAR2h-95    (SEQ ID NO:460)
EVQLLESGGGLVQPGGSLRLSCAASGFTFK~GSNMG~WVRQAPGKGLEWVS~~LIDGRGQH
TYYADSVKG~~RFTISRDNSKNTLYLQMNSLRAEDTAVYYCAK~~~PSVREFDY~~~RG
QGTLVTVSS

TAR2h-96    (SEQ ID NO:461)
EVQLLESGGGLVQPGGSLRLSCAASGFTFS~RENMH~WVRQAPGKGLEWVS~~GIGPRGMP
TYYADSVKG~~RFTISRDNSKNTLYLQMNSLRAEDTAVYYCAK~~~RMLANSPLAFDY~~~WG
QGTLVTVSS

TAR2h-97    (SEQ ID NO:462)
EVQLLESGGGLVQPGGSLRLSCTASGFTFS~ESTMN~WVRQAPGKGLEWVS~~VITAQGGD
TYYADSVKG~~RFTISRDNSKNTLYLQMNSLRAEDTAVYYCAK~~~PDVLFDY~~~WG
QGTLVTVSS

FIGURE 27C

TAR2h-99   (SEQ ID NO:463)
EVQLLESGGGLVQPGGSLRLSCAASGFTFE~EYNML~WVRQAPGKGLEWVS~~GIGPSGRE
TYYADSVKG~~RFTISRDNSKNTLYLQMNSLRAEDTAVYYCAK~~~GSITLFDY~~~WG
QGTLVTVSS

TAR2h-100  (SEQ ID NO:464)
EVQLLESGGGLVQPGGSLRLSCAASGFTFS~GYNMY~WVRQAPGKGLEWVS~~AIDAYGTH
TYYADSVKG~~RFTISRDNSKNTLYLQMNSLRAEDTAVYYCAE~~~GLQTSDHGERISFDY~~~W
GQGTLVTVSS

TAR2h-101  (SEQ ID NO:465)
EVQLLESGGGLVQPGGSLRLSCAASGFTFD~QYDMS~WVRQAPGKGLEWVS~~LIDPSGGH
TYYADSVKG~~RFTISRNNSKNTLYLQMNSLRAEDTAVYYCAK~~~PVFSDWPAVEFDY~~~WG
QGTLVTVSS

TAR2h-102  (SEQ ID NO:466)
EVQLLESGGGLVQPGGSLRLSCAASGFTFD~QYDMS~WVRQAPGKGLEWVS~~LIDPSGGH
TYYADSVKG~~RFTISRNNSKNTLYLQMNSLRAEDTAVYYCAK~~~PVFSDWPAVEFDY~~~WG
QGTLVTVSS

TAR2h-103  (SEQ ID NO:467)
EVQLLESGGGLVQPGGSLRLSCAASGFTFT~RYSMG~WVRQAPGKGLEWVS~~MIDVPGLH
TYYADSVKG~~RFTISRDNSKNTLYLQMNSLRAEDTAVYYCAK~~~ISQFGSNAFDY~~~WG
QGTLVTVSS

TAR2h-104  (SEQ ID NO:468)
EVQLLESGGGLVQPGGSLRLSCAASGFTFE~WYWMG~WVRQAPGKGLEWVS~~AISGSGGS
TYYAXSVKG~~RFTISRDNSKNTLYLQMNSLRAEDAAVYYCAK~~~VKLGGXPNFGY~~~RG
QGTLVTVSS

TAR2h-105  (SEQ ID NO:469)
EVQLLESGGGLVQPGGSLRLSCAASGFTFT~RYSMG~WVRQAPGKGLEWVS~~FIDPPSVH
TYYADSVKG~~RFTISRDNSKNTLYLQMNSLRAEDTAVYYCAK~~~ISQFGSNAFDY~~~WG
QGTLVTVSS

TAR2h-106  (SEQ ID NO:470)
EVQLLESGGGLVQPGGSLRLSCAASGFTFT~RYSMG~WVRQAPGKGLEWVS~~MIDVGGSH
TYYAXSVKG~~RFTISRDNSKNTLYLQMNSLRAEDTAVYYCAK~~~ISQFGSNAFDY~~~WG
QGTLVTVSS

TAR2h-107  (SEQ ID NO:471)
EVQLLESGGGLVQPGGSLRLSCAASGFTFT~RYSMG~WVRQAPGKGLEWVS~~MIDTGGVH
TYYAXSVKG~~RFTISRDNSKNTLYLQMNSLRAEDTAVYYCAK~~~ISQFGSNAFDY~~~WG
QGTLVTVSS

FIGURE 27D

TAR2h-108  (SEQ ID NO:472)
EVQLLESGGGLVQPGGSLRLSCAASGFTFT~RYSMG~WVRQAPGKGLEWVS~~MIDVPGRH
TYYADSVKG~~RFTISRDNSKNTLYLQMNSLRAEDTAVYYCAK~~~ISQFGSNAFDY~~~WG
QGTLVTVSS

TAR2h-109  (SEQ ID NO:473)
EVQLLESGGGLVQPGGSLRLSCAASGFTFT~RYSMG~WVRQAPGKGLEWVS~~MIAHAGPE
TYYADSVKG~~RFTISRDNSKNTLYLQMNSLRAEDTAVYYCAK~~~ISQFGSNAFDY~~~WG
QGTLVTVSS

TAR2h-110  (SEQ ID NO:474)
EVQLLESGGGLVQPGGSLRLSCAASGFTFT~RYSMG~WVRQAPGKGLEWVS~~MIDTRGVR
TYYADSVKG~~RFTISRDNSKNTLYLQMNSLRAEDTAVYYCAK~~~ISQFGSNAFDY~~~WG
QGTLVTVSS

TAR2h-111  (SEQ ID NO:475)
EVQLLESGGGLVQPGGSLRLSCAASGFTFT~RYSMG~WVRQAPGKGLEWVS~~MIDVPGNH
TYYADSVKG~~RFTISRDNSKNTLYLQMNSLRAEDTAVYYCAK~~~ISQFGSNAFDY~~~WG
QGTLVTVSS

TAR2h-112  (SEQ ID NO:476)
EVQLLESGGGLVQPGGSLRLSCAASGFTFT~RYSMG~WVRQAPGKGLEWVS~~MIDVGGRH
TYYADSVKG~~RFTISRDNSKNTLYLQMNSLRAEDTAVYYCAK~~~ISQFGPNAFDY~~~WG
QGTLVTVSS

TAR2h-113  (SEQ ID NO:477)
EVQLLESGGGSVQPGGSLRLSCAASGFTFT~RYSMG~WVRQAPGKGLEWVS~~RIDSYGRG
TYYADSVKG~~RFTISRDNSKNTLYLQMNSLRAEDTAVYYCAK~~~VRSPYTFDY~~~WG
QGTLVTVSS

TAR2h-114  (SEQ ID NO:478)
EVQLLESGGGLVQPGGSLRLSCAASGFTFS~GYNMG~WVRQAPGKGLEWVS~~TISTQGYH
TYYADSVKG~~RFTISRDNSKNTLYLQMNSLRAEDTAVYYCAK~~~AFTSDFDY~~~WG
QGTLVTVSS

TAR2h-115  (SEQ ID NO:479)
EVQLLESGGGLVQPGGSLRLSCAASGFTFS~GYNMY~WVRQAPGKGLEWVS~~GISGPGLE
TYYADSVKG~~RFTISRDNSKNTLYLQMNSLRAEDTAVYYCAQ~~~GMSKTSTFDY~~~WG
QGTLVTVSS

TAR2h-116  (SEQ ID NO:480)
EVQLLESGGGLVQPGGSLRLSCAASGFTFT~EYYME~WVRQAPGKGLEWVS~~SIDPDGSL
TYYADSVKG~~RFTISRDNSKNTLYLQMNSLRAEDTAVYYCAK~~~YPREKFDY~~~WG
QGTLVTVSS

TAR2h-117  (SEQ ID NO:481)
EVQLLESGGGLVQPGGSLRLSCAASGFTFD~KYQMG~WVRQAPGKGLEWVS~~FIDSNGHH
TYYADSVKG~~RFTISRDNSKNTLYLQMNSLRAEDTAVYYCAQ~~~LSVQGSNLFDY~~~WG
QGTLVTVSS

FIGURE 27E

TAR2h-118 (SEQ ID NO:482)
EVQLLESGGGLVQPGGSLRLSCAASGFTFV~HYTMG~WVRQAPGKGLEWVS~~WIHSDGVH
TYYADSVKG~~RFTISRDNSKNTLYLQMNSLRAEDTAVYYCAK~~~FTWGEKKTFDY~~~WG
QGTLVTVSS

TAR2h-119 (SEQ ID NO:483)
EVQLLESGGGLVQPGGSLRLSCAASGFTFM~GYDMH~WVRQAPGKGLEWVS~~GISAKGTE
TYYADSVKG~~RFTISRDNSKNTLYLQMNSLRAEDTAVYYCAK~~~GSSGSDGLFDY~~~WG
QGTLVTVSS

TAR2h-120 (SEQ ID NO:484)
EVQLLESGGGLVQPGGSLRLSCAASGFTFP~VYNMA~WVRQAPGKGLEWVS~~FIAGNGQQ
TYYADSVKG~~RFTISRDNSKNTLYLQMNSLRAEDTAVYYCAK~~~FASKVSPMSLTDFDY~~~W
GQGTLVTVSS

TAR2h-121 (SEQ ID NO:485)
EVQLLESGGGLVQPGGSLRLSCAASGFTFV~QYNMH~WVRQAPGKGLEWVS~~GISSGGMR
TYYADSVKG~~RFTISRDNSKNTLYLQMNSLRAEDTAVYYCAK~~~GIRDSTLPRGTLFDY~~~W
GQGTLVTVSS

TAR2h-122 (SEQ ID NO:486)
EVQLLESGGGLVQPGGSLRLSCAASGFTFE~TYSMH~WVRQAPGKGLEWVS~~SISLPGSR
TYYADSVKG~~RFTISRDNSKNTLYLQMNSLRAEDTAVYYCAK~~~HSKSSHRQSFDY~~~WG
QGTLVTVSS

TAR2h-123 (SEQ ID NO:487)
EVQLLESGGGLVQPGGSLRLSCAASGFTFN~QYDMH~WVRQAPGKGLEWVS~~GISFSGYE
TYYADSVKG~~RFTISRDNSKNTLYLQMNSLRAEDTAVYYCAK~~~GRGPAPMRSLFDY~~~WG
QGTLVTVSS

TAR2h-124 (SEQ ID NO:488)
EVQLLESGGGLVQPGGSLRLSCAASGFTFV~DYPMV~WVRQAPGKGLEWVS~~HITSMGES
TYYADSVKG~~RFTISRDNSKNMLYLQMNSLRAEDTAVYYCAK~~~LPTHFPIRFDY~~~WG
QGTLVTVSS

TAR2h-125 (SEQ ID NO:489)
EVQLLESGGGLVQPGGSLRLSCAASGFTFK~QYNMY~WVRQAPGKGLEWVS~~FISPSGGE
TYYADSVKG~~RFTISRDNSKNTLYLQMNSLRAEDTAVYYCAK~~~SIKPFDY~~~WG
QGTLVTVSS

TAR2h-126 (SEQ ID NO:490)
EVQLLESGGGLVQPGGSLRLSCAASGFTFS~MYSMA~WVRQAPGKGLEWVS~~FIDFDGLH
TYYADSVKG~~RFTISRDNSKNTLYLQMNSLRAEDTAVYYCAK~~~FSTSTMALFDY~~~WG
QGTLVTVSS

TAR2h-127 (SEQ ID NO:491)
EVQLLESGGGLVRPGGSLRLSCAASGFTFP~EYNMH~WVRQAPGKGLEWVS~~AIGTAGGS
TYYADSVKG~~RFTISRDNSKNMLYLQMNSLRAEDTAVYYCAK~~~GYRPRTGSMLFDY~~~WG
QGTLVTVSS

FIGURE 27F

TAR2h-128 (SEQ ID NO:492)
EVQLLESGGGLVQPGGSLRLSCAASGFTFA~KYNMY~WVRQAPGKGLEWVS~~AISPKGQQ
TYYADSVKG~~RFTISRDNSKNTLYLQMNSLRAEDTAVYYCAE~~~GMGSDAITFDY~~~WG
QGTLVTVSS

TAR2h-129 (SEQ ID NO:493)
EVQLLESGGGLVQPGGSLRLSCAASGFTFA~DYDMA~WVRQAPGKGLEWVS~~FIDRKGHH
TYYADSVKG~~RFTISRDNSKNTLYLQMNSLRAEDTAVYYCAK~~~TTDIQRLNSAFDY~~~WG
QGTLVTVSS

TAR2h-130 (SEQ ID NO:494)
EVQLLESGGGLVQPGGSLRLSCAASGFTFG~NGVMA~WVRQAPGKGLEWVS~~HINENGGA
TYYADSVKG~~RFTISRDNSKNTLYLQMNSLRAEDTAVYYCAK~~~PSIESPIFDY~~~WG
QGTLVTVSS

TAR2h-131 (SEQ ID NO:495)
EVQLLESGGGLVQPGGSLRLSCAASGFTFA~HEPMV~WVRQAPGKGLEWVS~~HIDRVGQD
TYYADSVKG~~RFTISRDNSKNTLYLQMNSLRAEDTAVYYCAK~~~LPKRGPRFDY~~~WG
QGTLVTVSS

TAR2h-132 (SEQ ID NO:496)
EVQLLESGGGLVQPGGSLRLSCAASGFTFE~ESVMG~WVRQAPGKGLEWVS~~AISPGGSE
TYYADSVKG~~RFTISRDNSKNTLYLQMNSLRAEDAAVYYCAK~~~RTGPPGSTVFDY~~~WG
QGTLVTVSS

TAR2h-133 (SEQ ID NO:497)
EVQLLESGGGLVQPGGSLRLSCAASGFTFG~DEPMH~WVRQAPGKGLEWVS~~GIGKEGQP
TYYADSVKG~~RFTISRDNSKNTLYLQMNSLRAEDTAVYYCAK~~~LGGPFDY~~~WG
QGTLVTVSS

TAR2h-151 (SEQ ID NO:498)
EVQLLESGGGLVQPGGSLRLSCAASGFTFD~YGNMF~WVRQAPGKGLEWVS~~AISGSGGS
TYYADSVKG~~RFTISRDNSKNTLYLQMNSLRAEDTAVYYCAK~~~DMTTDSPPGFDY~~~WG
QGTLVTVSS

TAR2h-152 (SEQ ID NO:499)
EVQLLESGGGLVQPGGSLRLSCAASGFTFA~KETMS~WVRQAPGKGLEWVS~~WISPHGAL
TYYADSVKG~~RFTISRDNSKNTLYLQMNSLRAEDTAVYYCAK~~~PRFSYYPRVSFDY~~~WG
QGTLVTVSS

TAR2h-153 (SEQ ID NO:500)
EVQLLESGGGLVQPGGSLRLSCAASGFTFG~NGMV~WVRQAPGKGLEWVS~~HIDEYGTN
TYYADSVKG~~RFTISRDNSKNTLYLQMNSLRAEDTAVYYCAK~~~PRNDRPGFDY~~~WG
QGTLVTVSS

TAR2h-154 (SEQ ID NO:501)
EVQLLESGGGLVQPGGSLRLSCAASGFTFG~NGMV~WVRQAPGKGLEWVS~~HIDXYGTN
TYYADSVKG~~RFTISRDNSKNTLYLQMNSLRAGDTAVYYCAK~~~PRNDRPGFDY~~~WG
QGTLVTVSS

FIGURE 27G

TAR2h-159    (SEQ ID NO:502)
EVQLLESGGGLVQPGGSLRLSCAASGFTFA~GQDMR~WVRQAPGKGLEWVS~~SIPSSGFN
TYYADSVKG~~RFTISRDNSKNTLYLQMNSLRAEDTAVYYCAK~~~RAKDRSVSQMPYFDY~~~W
GQGTLVTVSS

TAR2h-165    (SEQ ID NO:503)
EVQLLESGGGLVQPGGSLRLSCAASGFTFM~RPDMV~WVRQAPGKGLEWVS~~TIKDWGDQ
TYYADSVKG~~RFTISRDNSKNTLYLQMNSLRAEDAAVYYCAK~~~ADSRAQLDFDY~~~WG
QGTLVTVSS

TAR2h-166    (SEQ ID NO:504)
EVQLLESGGGLVQPGGSLRLSCAASGFTFS~SYAMS~WVRQAPGKGLEWVS~~AISGSGGS
TYYADSVKG~~RFTISRDNSKNTLYLQMNSLRAEDTAVYYCAK~~~PYFLFRATSFDY~~~WG
QGTLVTVSS

TAR2h-168    (SEQ ID NO:505)
EVQLLESGGGLVQPGGSLRLSCAASGFTFH~DDDMV~WVRQAPGKGLEWVS~~SIPGNGYV
TYYADSVKG~~RFTISRDNSKNTLYLQMNSLRAEDTAVYYCAK~~~RPDPTSVFFDY~~~WG
QGTLVTVSS

TAR2h-171    (SEQ ID NO:506)
EVQLLESGGGLVQPGGSLRLSCAASGFTFG-DDWMT~WVRQAPGKGLEWVS~~GIAAYGIS
TYYADSVKG~~RFTISRDNSKNTLYLQMNSLRAEDAAVYYCAE~~~SGKVFDY~~~WG
QGTLVTVSS

TAR2h-172    (SEQ ID NO:507)
EVQLLESGGGLVQPGGSLRLSCAASGFTFV~ERPMD~WVRQAPGKGLEWVS~~LIGADGLS
TYYADSVKG~~RFTISRDNSKNTLYLQMNSLRAEDTAVYYCAK~~~LFRPGLLWFDY~~~WG
QGTLVTVSS

TAR2h-173    (SEQ ID NO:508)
EVQLLESGGGLVQPGGSLRLSCAASGFTFT~GQDMQ~WVRQAPGKGLEWVS~~GINADGMA
TYYADSVKG~~RFTISRDNSKNTLYLQMNSLRAEDTAVYYCAK~~~TSPTMRSFDY~~~WG
QGTLVTVSS

TAR2h-174    (SEQ ID NO:509)
EVQLLESGGGLVQPGGSLRLSCAASGFTFG~EEYMQ~WVRQAPGKGLEWVS~~LIPHTGNP
TYYADSVKG~~RFTISRDNSKNTLYLQMNSLRAEDTAVYYCAK~~~LANSLLFDY~~~WG
QGTLVTVSS

TAR2h-176    (SEQ ID NO:510)
EVQLLESGGGLVQPGGSLRLSCAASGFTFH~RCKMG~WVRQAPGKGLEWVS~~FIEYDGRD
TYYADSVKG~~RFTISRDNSKNTLYLQMNSLRAEDTAVYYCAK~~~ECTRPYGMFDY~~~WG
QGTLVTVSS

TAR2h-178    (SEQ ID NO:511)
EVQLLESGGGLVQPGGSLRLSCAASGFTFN~RYSMG~WLRQAPGKGLEWVS~~FIDKVGHH
TWYEDPVKG~~RFTISRDNSKNTLYLQMNSLRAEDTAVYYCAK~~~ISQFGPNAFDY~~~WG
QGTQVTVSS

FIGURE 27H

TAR2h-201   (SEQ ID NO:512)
EVQLLESGGGLVQPGGSLRLSCAASGFTFT-RYSMG-WVRQAPGKGLEWVS--MIAHAGPE
RYYADSVKG--RFTISRDNSKNTLYLQMNSLRAEDTAVYYCAK---ISXFGSNAFDY---WG
QGTLVTVSS

TAR2h-202   (SEQ ID NO:513)
EVQLLESGGGLVQPGGSLRLSCAASGFTFT-RYNMG-WVRQAPGKGLEWVS--FIDPPSVH
TYYADSVKG--RFTISRDNSKNTLYLQMNSLRAEDTAVYYCAN---ISQFGSNAFDY---WG
QGTLVTVSS

TAR2h-203   (SEQ ID NO:514)
EVQLLESGGGLVQPGGSLRLSCAASGFTFT-RYSMG-WVRQAPGKGLEWVS--FIDPPSVH
TYYADSVKG--RFTISRDNSKNTLYLQMNSLRAEDTAVYYXAE---ISQFGSNAFDY---WG
QGTLVTVSS

TAR2h-204   (SEQ ID NO:515)
EVQLFESGGGLVQPGGSLRLSCAASGFTFT-RYSMG-WVRQAPGKGLEWVS--MIAHAGPE
TYYADSVKG--RFTISRDNSKNTLYLQMNSLRAEDTAVYYCAK---ISQFGSNALDY---WG
RGTLVTVSS

TAR2h-185-25 (SEQ ID NO:516)
EVQLLESGGGLVQPGGSLRLSCAASGFTFA-RYNMG-WVRQAPGKGLEWVS--LIDPSGGHT
YYADSVKG--RFTISRNNSKNTLYLQMNSLRAEDTAVYYCGK---PVFSDWPAVEFDY---W
GQGTVVTVSS

TAR2h-154-10 (SEQ ID NO:517)
EVQLLESGGGMVQPGGSLRLSCAASGFTFE-HEGMV-WVRQAPGKGLEWVS--HIGEDGQST
YYADSVKG--RFTISRDNSKNTLYLQMNSLRAEDTAVYYCAN---IPKAGPSFDY---WGQG
TLVTVSS

TAR2h-205   (SEQ ID NO:627)
EVQLLESGGGLVQPGGSLRLSCAASGFTFV-KYSMG-WVRQAPGKGLEWVS--QISNTGGHT
YYADSVKG--RFTISRDNSKNTLYLQMNSLRAEDTAVYYCAK---YTGRWEPFDY---WGQG
TLVTVSS

FIGURE 27I

TAR2h-131-8      (SEQ ID NO: 518)
GAGGTGCAGCTGTTGGAGTCTGGGGGAGGCTTGATACAGCCTGGGGGGTCCCTGCGTCTC
TCCTGTGCAGCCTCCGGATTCACCTTTGCG~CATGAGACGATGGTG~TGGGTCCGC
CAGGCTCCAGGGAAGGGTCTAGAGTGGGTCTCA~~CATATTGATCGTGTTGGTCAGGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACAGCGGTATATTACTGT
GCGAAA~~~CTTCCTAAGAGGGGCCTTGGTTTGACTAC~~~CGGGGT
CAGGGAACCCTGGTCACCGTCTCGAGC

TAR2h-131-24     (SEQ ID NO: 519)
GAGGTGCAGCTGTTGGAGTCTGGGGGAGGCTTGATACAGCCTGGGGGGTCCCTGCGTCTC
TCCTGTGCAGCCTCCGGATTCACCTTTGCG~CATGAGACGATGGTG~TGGGTCCGC
CAGGCTCCAGGGAAGGGTCTAGAGTGGGTCTCA~~CATATTGATCGTGTTGGTCAGGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACAGCGGTATATTACTGT
GCGCGC~~~CTTCCTAAGAGGGGCCTTGGTTTGACTAC~~~CGGGGT
CAGGGAACCCTGGTCACCGTCTCGAGC

TAR2h-15-8 (SEQ ID NO:520)
GAGGTGCGGCTGTTGGAGTCTGGGGGAGGCTTGGTACAGCCTGGGGGATCCCTGCGTCTC
TCCTGTGTAGCCTCCGGATTCACCTTTGGT~AAGTCCACTATGACG~TGGGTCCGC
CAGGCTCCAGGGAAGGGTCTAGAGTGGGTCTCA~~CATATTTCGGATGATGGTAATTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTCCGATTCTGGCTCCTCGTAATCTTTTTGACTAC~~~TGGGGT
CAGGGAACCCTGGTCACCGTCTCGAGC

TAR2h-15-8-1     (SEQ ID NO: 521)
GAGGTGCGGCTGTTGGAGTCTGGGGGAGGCTTGGTACAGCCTGGGGGATCCCTGCGTCTC
TCCTGTGTAGCCTCCGGATTCAACTTTGGT~AAGTCCACTATGACG~TGGGTCCGC
CAGGCTCCAGGGAAGGGTCTAGAGTGGGTCTCA~~CATATTTCGGATGATGGTAATTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTCCGATTCTGGCTCCTCGTAATCTTTTTGACTAC~~~TGGGGT
CAGGGAACCCTGGTCACCGTCTCGAGC

TAR2h-15-8-2     (SEQ ID NO: 522)
GAGGTGCGGCTGTTGGAGTCTGGGGGAGGCTTGGTACAGCCTGGGGGATCCCTGCGTCTC
TCCTGTGTAGCCTCCGGATTCACCTTTGGT~AAGGGGACTATGACG~TGGGTCCGC
CAGGCTCCAGGGAAGGGTCTAGAGTGGGTCTCA~~CATATTTCGGATGATGGTAATTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTTCCGATTCTGGCTCCTCGTAATCTTTTTGACTAC~~~TGGGGT
CAGGGAACCCTGGTCACCGTCTCGAGC

TAR2h-185-23     (SEQ ID NO: 523)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~CGGTATAATATGGGT~TGGGTCCGC
CAGGCTCCAGGGAAGGGTCTAGAGTGGGTCTCA~~CTGATTGATCCGAGCGGTGGTCAT
ACATACTACGCANACTCCGTGAAGGGC~~CGGTCCACCATCTCCCGCAACAATTCCAAG
AACACGCTGTATCTGCAAATGAACAGCCTGCGTGCCGAGGACACCGCGGTATATTACTGT
GGGAAA~~~CCGGTTTTTTCTGATTGGCCTGCGGTGGAGTTTGACTAC~~~TGGGGT
CAGGGAACCCTGGTCACCGTCTCGAGC

Figure 28A

TAR2h-154-10-5    (SEQ ID NO:524)
GAGGTGCAGCTGTTGGAGTCTGGGGGAGGCATGGTACAGCCTGGGGGGTCACTGCGTCTC
TCCTGTGCAGCCCCCGGATTCACCTTTGAG~CATGAGGGGATGGTG~TGGGTCCGC
CAGGCTCCAGGGAAGGGTCTAGAGTGGGTCTCA~~CATATTGGTGAGGATGGTCAGTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGTCC~~~ATTCCGAAGGCGGGGCCTTCGTTTGACTAC~~~TGGGGT
CAGGGAACCCTGGTCACCGTCTCGAGC

TAR2h-14-2 (SEQ ID NO:525)
GAGGTGCAGCTGTTGGAGTCTGGGGGAGGCTTGGTACAGCCTGGGGGGTCCCTGCGTCTC
TCCTGTGCAGCCTCCGGATCCACCTTTGAT~CAGTATGATATGTCG~TGGGTCCGC
CGGGCTCCAGGGAAGGGTCTAGAGTGGGTCTCA~~CTGATTGATCCGAGCGGTGGTCAT
ACATACTACGCAGACTCCGTGAAGGGC~~CGGTTCACCATCTCCCGCAACAATACCAAG
AACACGCTGTATCTGCAAATGAACAGCCTGCGTGCCGAGGACACCGCGGTATATTACTGT
GCGAAA~~~CCGGTTTTTTCTGATTGGCCTGCGGTGGAGTTTGACTAC~~~TGGGGT
CAGGGAACCCTGGTCACCGTCTCGAGCC

TAR2h-151-8      (SEQ ID NO:526)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~TATGGGAATATGTTT~TGGGTCCGC
CAGGCTCCAGGGAAGGGTCTAGAGTGGATCTCA~~GCTATTAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GATATGACGACGGATTCGCCTCCTGGGTTTGACTAC~~~TGGGGT
CAGGGAACCCTGGTCACCGTCTCGAGCG

TAR2h-152-7      (SEQ ID NO:527)
GAGGTGCAGCTGTTGGAGTCTGGGGGAGGCTTGGTACAGCCGGGGGGGTCCCTGCGTCTC
TCCTGTGCAGCCTCCGGATTCACCTTTGCG~AAGGAGACGATGAGT~TGGGTCCGC
CAGGCTCCAGGGAAGGGTCTAGAGTGGGTCTCA~~TGGATTAGTCCTCATGGTGCTCAT
ACATTCTACGCAGACTCCGTGAAGGGC~~AGGTTCACCATCTCCCGCGACAATTCCAAG
AACACGCTGTATCTGCAAATGAACAGCCTGCGTGCCGAGGACACCGCGGTATATTACTGC
GCGAAA~~~CCTCGGTTTTCGTATTATCCTCGGGTTTCATTTGACTAC~~~CGGGGT
CAGGGAACCCTGGTCACAGTCTCGAGCN

TAR2h-35-4 (SEQ ID NO:528)
GAGGTGCAGCTGTTGGAGTCTGGGGGAGGCTTGGTGCAGCCTGGGGGGTCCCTGCGTCTC
TCCTGTGCAGCCTCCGGATTCACCTTTGAT~GCTTATAATATGTTT~TGGTTCCGC
CAGGCTCCAGGGAAGGGTCCGGAGTGGGTCTCA~~GCTATTGGTCCGTCGGGTCGGGAG
ACATACTACGCAGACTCCGTGAAGGGC~~CGGTTCACCATCACCCGCGACAATTCCAAG
AACACGCTGTATCTGCAAATGAACAGCCTGCGTGCCGAGGACACCGCGGTATATTACTGT
GCGAAA~~~AGGTATCCTGATTTTGACTAC~~~TGGGGTCAGGGAACCCTGGTCACCGTCTC
GAGC

TAR2h-154-7      (SEQ ID NO:529)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~CATGAGGGGATGGTG~TGGGTTCGC
CAGGCTCCAGGGAAGGGTCTAGAGTGGGTCTCA~~CATATTGGTGAGGATGGTCAGTCT
ACATACTACGCAGACTCCGTGAAGGGC~~CGGTTCACTATCTCCCGCGACAATTCCAGG
AACACGCTGTATCTGCAAATGAACAGCCTGCGTGCCGAGGACACCGCGGTATATTACTGT
GCGAAC~~~ATTCCGAAGGCGGGGCCTTCGTTTGACTAC~~~TGGGGT
CAGGGAACCCTGGTCACCGTCTCGAGC

Figure 28B

TAR2h-80    (SEQ ID NO:530)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG-TTGTATAATATGCCG-TGGGTCCGC
CAGGCTCCAGGGAAGGGTCTAGAGTGGGTCTCA~~TTTATTGCTGCTGCTGGTCCTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGGGGGATATTAGTAGTATTCCTCAGCATCCGTTTGACTAC~~~TGGGGT
CAGGGAACCCTGGTCACCGTCTCGAGC

TAR2h-81    (SEQ ID NO:531)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG-CGGGAGAATATGCAT-TGGGTCCGC
CAGGCTCCAGGGAAGGGTCTGGAGTGGGTCTCA~~GGTATTGGGCCGAGGGGTATGCCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGTATGAATTCGCATGATGGGTTTGACTAC~~~TGGGGT
CAGGGAACCCTGGTCACCGTCTCGAGC

TAR2h-82    (SEQ ID NO:532)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT-GCGTCTGAGATGGAT-TGGGTCCGC
CAGGCTCCAGGGAAGGGTCTAGAGTGGGTCTCA~~GCGATTTCGCCTAGTGGTTCTGCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CGTATGCTTGCGAATTCTCCTTTGGCTTTTGACTAC~~~TGGGGT
CAGGGAACCCTGGTCACCGTCTCGAGC

TAR2h-83    (SEQ ID NO:533)
GAGGTGCAGCTGTTGGAGTCTGGGGGAGGCTTGGTACAGCCTGGGGGGTCCCTGCGTCTC
TCCTGTGCAGCCTCCGGATTCACCTTTTCT-GCGTATAATATGGCT-TGGGTCCGC
CAGGCTCCAGGGAAGGGTCTAGAGTGGGTCTCA~~TTTATTGCTCAGTCGGGTGGTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTAGTCATCCTGATGAGGAGGGTACGCAGATGTTTGACTAC~~~TGGGGT
CAGGGAACCCTGGTCACCGTCTCGAGC

TAR2h-84    (SEQ ID NO:534)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG-GATTATCAGATGGCT-TGGGTCCGC
CAGGCTCCAGGGAAGGGTCTAGAGTGGGTCTCA~~CGTATTGATCGTGGGGGTTTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCGTCTTGGCATGCTGATCAGTATTTTGACTAC~~~TGGGGT
CAGGGAACCCTGGTCACCGTCTCGAGC

TAR2h-85    (SEQ ID NO:535)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG-GATTATAATATGATG-TGGGTCCGC
CAGGCTCCAGGGAAGGGTCTAGAGTGGGTCTCA~~GCTATTGCTACGAGTGGTAGGGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~TTTACTTTTGGGGGGAATCAGGATTTTGACTAC~~~TGGGGT
CAGGGAACCCTGGTCACCGTCTCGAGC

Figure 28C

TAR2h-86    (SEQ ID NO:536)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~AAGTATAATATGTAT~TGGGTCCGC
CAGGCTCCAGGGAAGGGTCTAGAGTGGGTCTCA~~GCGATTAGTCCTAAGGGTCAGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~GGGATGGGGTCGGATGCTATTACTTTTGACTAC~~~TGGGGT
CAGGGAACCCTGGTCACCGTCTCGAGC

TAR2h-87    (SEQ ID NO:537)
GAGGTGCAGCTGTTGGAGTCTGGGGGAGGCTTGGTACAGCCTGGGGGGTCCCTGCGTCTC
TCCTGTGCAGCCTCCGGATTCACCTTTTCT~GCGTATAATATGGCT~TGGGTCCGC
CAGGCTCCAGGGAAGGGTCTAGAGTGGGTCTCA~~TTTATTGCTCAGTCGGGTGGTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTAGTCATCCTGATGAGGAGGGTACGCAGATGTTTGACTAC~~~TGGGGT
CAGGGAACCCTGGTCACCGTCTCGAGC

TAR2h-88    (SEQ ID NO:538)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~AGGTATGATATGTTT~TGGGTCCGC
CAGGCTCCAGGGAAGGGTCTAGAGTGGGTCTCA~~GGTATTTCTCCTAGGGGTAGGGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~GATATGATTAATTATCATGGTACTCCTTCGTTTGACTAC~~~TGGGGT
CAGGGAACCCTGGTCACCGTCTCGAGC

TAR2h-89    (SEQ ID NO:539)
GAGGTGCAGCTGTTGGAGTCTGGGGGAGGCTTGGTACAGCCTGGGGGGTCCCTGCGTCTC
TCCTGTGCAGCCTCCGGATTCACCTTTTCN~AATTATAATATGGTT~TGGGTCCGC
CAGGCTCCAGGGAAGGGTCTGGAGTGGGTCTCA~~TGGATTAGTGGGGCGGGTCATTCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GATGTGGATATGGCGGGTAAGCTTAATGTTTTTGACTAC~~~TGGGGT
CAGGGAACCCTGGTCACCGTCTCGAGC

TAR2h-90    (SEQ ID NO:540)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG~CAGTATAATATGTAT~TGGGTCCGC
CAGGCTCCAGGGAAGGGTCTAGAGTGGGTCTCA~~TTTATTAGTCCGTCTGGTGGTGAG
ACATACTACGCAGACTCCGTGAAGGGC~~CGGTTCACCACCTCCCGCGACAATTCCAAG
AACACGCTGTATCTGCAAATGAACAGCCTGCGTGCCGAGGACACCGCGGTATATTACTGT
GCGAAA~~~GATGTGGATATGGCGGGTAAGCTTAATGTTTTTGACTAC~~~TGGGGT
CAGGGAACCCTGGTCACCGTCTCGAGC

TAR2h-91    (SEQ ID NO:541)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~GATTATCAGATGGCT~TGGGTCCGC
CAGGCTCCAGGGAAGGGTCTAGAGTGGGTCTCA~~CGTATTGATCGTGGGGGTTTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCGTCTTGGCATGCTGATCAGTATTTTGACTAC~~~TGGGGT
CAGGGAACCCTGGTCACCGTCTCGAGC

Figure 28D

TAR2h-92    (SEQ ID NO:542)
GAGGTGCAGCTGTTGGAGTCTGGGGGAGGCTTGGTACAGCCTGGGGGGTCCCTGCGTCTC
ACCTGTGCAGCCTCCGGATTCACCTTTGAT~GATGTGAATATGACT~TGGGTCCGC
CAGGCTCCAGGGAAGGGTCTAGAGTGGGTCTCA~~GCGATTGGTCCTTCGGGTACTGAG
ACATACTACGCAGACTCCGTGAAGGGC~~CGGTTCACCATCTCCCGTGACAATTCCAAG
AACACGCTGTATCTGCAAATGAACAGCCTGCGTGCCGAGGACACCGCGGTATATTACTGT
GCGAAA~~~CATAGTAAGACTGGTAGTGCTATGTTTGACTAC~~~TGGGGT
CAGGGAACCCTGGTCACCGTCTCGAGC

TAR2h-93    (SEQ ID NO:543)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGGTAATATGGTT~TGGGTCCGC
CAGGCTCCAGGGAAGGGTCTAGAGTGGGTCTCA~~CATATTGATGAGTATGGTACGAAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTCGTAATGATCGGCCTGGGTTTGACTAC~~~TGGGGT
CAGGGAACCCTGGTCACCGTCTCGAGC

TAR2h-94    (SEQ ID NO:544)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG~CGGGAGAATATGCAT~TGGGTCCGC
CAGGCTCCAGGGAAGGGTCTGGAGTGGGTCTCA~~GGTATTGGGCCGAGGGGTATGCCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGTATGAATTCGCATGATGGGTTTGACTAC~~~TGGGGT
CAGGGAACCCTGGTCACCGTCTCGAGC

TAR2h-95    (SEQ ID NO:545)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG~GGGAGTAATATGGGT~TGGGTCCGC
CAGGCTCCAGGGAAGGGTCTAGAGTGGGTCTCA~~CTGATTGATGGGCGTGGTCAGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTAGTGTGAGGGAGTTTGACTAC~~~AGGGGT
CAGGGAACCCTGGTCACCGTCTCGAGC

TAR2h-96    (SEQ ID NO:546)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG~CGGGAGAATATGCAT~TGGGTCCGC
CAGGCTCCAGGGAAGGGTCTGGAGTGGGTCTCA~~GGTATTGGGCCGAGGGGTATGCCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CGTATGCTTGCGAATTCTCCTTTGGCTTTTGACTAC~~~TGGGGT
CAGGGAACCCTGGTCACCGTCTCGAGC

TAR2h-97    (SEQ ID NO:547)
GAGGTGCAGCTGTTGGAGTCTGGGGGAGGCTTGGTACAGCCTGGGGGGTCCCTGCGTCTC
TCCTGTACAGCCTCCGGATTCACCTTTTCG~GAGAGTACTATGAAT~TGGGTCCGC
CAGGCTCCAGGGAAGGGTCTAGAGTGGGTCTCA~~GTTATTACGGCGCAGGGTGGGGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTGATGTTTTGTTTGACTAC~~~TGGGGT
CAGGGAACCCTGGTCACCGTCTCGAGC

Figure 28E

TAR2h-99    (SEQ ID NO:548)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~GAGTATAATATGTTG~TGGGTCCGC
CAGGCTCCAGGGAAGGGTCTGGAGTGGGTCTCA~~GGGATTGGGCCTTCGGGTAGGGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~GGTTCTATTACGCTGTTTGACTAC~~~TGGGGT
CAGGGAACCCTGGTCACCGTCTCGAGC

TAR2h-100   (SEQ ID NO:549)
GAGGTGCAGCTGTTGGAGTCTGGGGGAGGCTTGGTACAGCCTGGGGGGTCCCTGCGTCTC
TCCTGTGCAGCCTCCGGATTCACCTTTAGT~GGTTATAATATGTAT~TGGGTCCGC
CAGGCTCCAGGGAAGGGTCTAGAGTGGGTCTCA~~GCGATTGATGCGTATGGTACGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~GGGTTGCAGACGTCTGATCATGGTGAGAGGATTTCTTTTGACTAC~~~TGG
GGTCAGGGAACCCTGGTCACCGTCTCGAGC

TAR2h-101   (SEQ ID NO:550)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~CAGTATGATATGTCG~TGGGTCCGC
CAGGCTCCAGGGAAGGGTCTAGAGTGGGTCTCA~~CTGATTGATCCGAGCGGTGGTCAT
ACATACTACGCAGACTCCGTGAAGGGC~~CGGTTCACCATCTCCCGCAACAATTCCAAG
AACACGCTGTATCTGCAAATGAACAGCCTGCGTGCCGAGGACACCGCGGTATATTACTGT
GCGAAA~~~CCGGTTTTTTCTGATTGGCCTGCGGTGGAGTTTGACTAC~~~TGGGGT
CAGGGAACCCTGGTCACCGTCTCGAGC

TAR2h-102   (SEQ ID NO:551)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~CAGTATGATATGTCG~TGGGTCCGC
CAGGCTCCAGGGAAGGGTCTAGAGTGGGTCTCA~~CTGATTGATCCGAGCGGTGGTCAT
ACATACTACGCGGACTCCGTGAAGGGC~~CGGTTCACCATCTCCCGCAACAATTCCAAG
AACACGCTGTATCTGCAAATGAACAGCCTGCGTGCCGAGGACACCGCGGTATATTACTGT
GCGAAA~~~CCGGTTTTTTCTGATTGGCCTGCGGTGGAGTTTGACTAC~~~TGGGGT
CAGGGAACCCTGGTCACCGTCTCGAGC

TAR2h-103   (SEQ ID NO:552)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGATGTTCCTGGTCTGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

Figure 28F

TAR2h-104 (SEQ ID NO:553)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~TGGTATTGGATGGGT~TGGGTCCGC
CAGGCTCCAGGGAAGGGTCTAGAGTGGGTCTCA~~GCTATCAGTGGTAGTGGTGGTAGC
ACATACTACGCANACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GTTAAGTTGGGGGGGGGNCCTAATTTTGGCTAC~~~CGGGGC
CAGGGAACCCTGGTCACCGTCTCGAGC

TAR2h-105 (SEQ ID NO:554)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~TTTATTGATCCTCCGAGTGTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

TAR2h-106 (SEQ ID NO:555)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGATGTTGGTGGTTCTCAT
ACATACTACGCANACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCAAGC

TAR2h-107 (SEQ ID NO:556)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGATACTGGGGGTGTTCAT
ACATACTACGCANACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

TAR2h-108 (SEQ ID NO:557)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGATGTTCCTGGTCGTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

TAR2h-109 (SEQ ID NO:558)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGCGCATGCTGGTCCTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

Figure 28G

TAR2h-110   (SEQ ID NO:559)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTGGAGTGGGTCTCA~~ATGATTGATACTCGGGGTGTTCGT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

TAR2h-111   (SEQ ID NO:560)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTGGAGTGGGTCTCA~~ATGATTGATGTGCCTGGTAATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTTGACTAC~~~TGGGGT
CAGGGAACCCTGGTCACCGTCTCGAGC

TAR2h-112   (SEQ ID NO:561)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGATGTTGGTGGTCGGCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGCCAAATGCGTTTGACTAC~~~TGGGGT
CAGGGAACCCTGGTCACCGTCTCGAGC

TAR2h-113   (SEQ ID NO:562)
GAGGTGCAGCTGTTGGAGTCTGGGGGAGGCTCGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~CGGATTGATTCTTATGGTCGTGGT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GTGCGTTCTCCTTATACGTTTGACTAC~~~TGGGGT
CAGGGAACCCTGGTCACCGTCTCGAGC

TAR2h-114   (SEQ ID NO:563)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG~GGTTATAATATGGGT~TGGGTCCGC
CAGGCTCCAGGGAAGGGTCTAGAGTGGGTCTCA~~ACTATTTCGACTCAGGGTTATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GCGTTTACTAGTGATTTTGACTAC~~~TGGGGT
CAGGGAACCCTGGTCACCGTCTCGAGC

TAR2h-115   (SEQ ID NO:564)
GAGGTGCAGCTGTTGGAGTCTGGGGGAGGCTTGGTACAGCCTGGGGGGTCCCTGCGTCTC
TCCTGTGCAGCCTCCGGATTCACCTTTTCG~GGTTATAATATGTAT~TGGGTCCGC
CAGGCTCCAGGGAAGGGTCTAGAGTGGGTCTCA~~GGGATTTCTGGTCCGGGTCTTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGCAA~~~GGTATGTCGAAGACGTCTACGTTTGACTAC~~~TGGGGT
CAGGGAACCCTGGTCACCGTCTCGAGC

Figure 28H

TAR2h-116  (SEQ ID NO:565)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~GAGTATTATATGGAG~TGGGTCCGC
CAGGCTCCAGGGAAGGGTCTAGAGTGGGTCTCA~~AGTATTGATCCGGATGGTTCTCTT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TATCCGCGTGAGAAGTTTGACTAC~~~TGGGGT
CAGGGAACCCTGGTCACCGTCTCGAGC

TAR2h-117  (SEQ ID NO:566)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~AAGTATCAGATGGGT~TGGGTCCGC
CAGGCTCCAGGGAAGGGTCTAGAGTGGGTCTCA~~TTTATTGATTCGAATGGTCATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGCAA~~~CTGTCGGTTCAGGGGTCGAATCTGTTTGACTAC~~~TGGGGT
CAGGGAACCCTGGTCACCGTCTCGAGC

TAR2h-118  (SEQ ID NO:567)
GAGGTGCAGCTGTTGGAGTCTGGGGGAGGCTTGGTACAGCCTGGGGGGTCCCTGCGTCTC
TCCTGTGCAGCCTCCGGATTCACCTTTGTG~CATTATACGATGGGT~TGGGTCCGC
CAGGCTCCAGGGAAGGGTCTAGAGTGGGTCTCA~~TGGATTCATTCTGATGGTGTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~TTTACTTGGGGTGAGAAGAAGACTTTTGACTAC~~~TGGGGT
CAGGGAACCCTGGTCACCGTCTCGAGC

TAR2h-119  (SEQ ID NO:568)
GAGGTGCAGCTGTTGGAGTCTGGGGGAGGCTTGGTACAGCCTGGGGGGTCCCTGCGTCTC
TCCTGTGCAGCCTCCGGATTCACCTTTATG~GGGTATGATATGCAT~TGGGTCCGC
CAGGCTCCAGGGAAGGGTCTAGAGTGGGTCTCA~~GGTATTTCTGCTAAGGGTACTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGGAGTTCTGGTTCTGATGGGCTGTTTGACTAC~~~TGGGGT
CAGGGAACCCTGGTCACCGTCTCGAGC

TAR2h-120  (SEQ ID NO:569)
GAGGTGCAGCTGTTGGAGTCTGGGGGAGGCTTGGTACAGCCTGGGGGGTCCCTGCGTCTC
TCCTGTGCAGCCTCCGGATTCACCTTTCCT~GTTTATAATATGCGC~TGGGTCCGC
CAGGCTCCAGGGAAGGGTCTAGAGTGGGTCTCA~~TTTATTGCGGGTAATGGTCAGCAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTGCGTCGAAGGTGTCGCCGATGTCGTTGACTGATTTTGACTAC~~~TGG
GGTCAGGGAACCCTGGTCACCGTCTCGAGC

TAR2h-121  (SEQ ID NO:570)
GAGGTGCAGCTGTTGGAGTCTGGGGGAGGCTTGGTACAGCCTGGGGGGTCCCTGCGTCTC
TCCTGTGCAGCCTCCGGATTCACCTTTGTG~CAGTATAATATGCAC~TGGGTCCGC
CAGGCTCCAGGGAAGGGTCTTGAGTGGGTCTCA~~GGGATTTCTTCGGGTGGTATGCGT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GGGATTCGGGATAGTACGCTTCCGAGGGGTACTTTGTTTGACTAC~~~TGG
GGTCAGGGAACCCTGGTCACCGTCTCGAGC

Figure 28I

TAR2h-122 (SEQ ID NO:571)
GAGGTGCAGCTGTTGGAGTCTGGGGGAGGCTTGGTACAGCCTGGGGGGTCCCTGCGTCTC
TCCTGTGCAGCCTCCGGGTTCACCTTTGAG~ACTTATAGTATGCAT~TGGGTCCGC
CAGGCTCCAGGGAAGGGTCTAGAGTGGGTCTCA~~TCGATTTCTTTGCCTGGTTCGCGG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CATTCGAAGAGTTCTCATCGTCAGTCTTTTGACTAC~~~TGGGGT
CAGGGAACCCTGGTCACCGTCTCGAGC

TAR2h-123 (SEQ ID NO:572)
GAGGTGCAGCTGTTGGAGTCTGGGGGAGGCTTGGTACAGCCTGGGGGGTCCCTGCGTCTC
TCCTGTGCAGCCTCCGGATTCACCTTTAAT~CAGTATGATATGCAT~TGGGTCCGC
CAGGCTCCAGGGAAGGGTCTAGAGTGGGTCTCA~~GGGATTTCTTTTAGTGGTTATGAG
ACATACTACGCAGACTCCGTGAAGGGC~~CGGTTTACCATCTCCCGCGACAATTCCAAG
AACACGCTGTATCTGCAAATGAACAGCCTGCGTGCCGAGGACACCGCGGTATATTACTGT
GCGAAA~~~GGTAGGGGGCCTGCGCCGATGCGTTCGCTTTTTGACTAC~~~TGGGGT
CAGGGAACCCTGGTCACCGTCTCGAGC

TAR2h-124 (SEQ ID NO:573)
GAGGTGCAGCTGTTGGAGTCTGGGGGAGGCTTGGTACAGCCTGGGGGGTCCCTGCGTCTC
TCCTGTGCAGCCTCCGGATTCACCTTTGTG~GATTATCCGATGGTG~TGGGTCCGC
CAGGCTCCAGGGAAGGGTCTAGAGTGGGTCTCA~~CATATTACTAGTATGGGTGAGTCT
ACATACTACGCAGACTCCGTGAAGGGC~~CGGTTCACCATCTCCCGCGACAATTCCAAG
AACATGCTGTATCTGCAAATGAACAGCCTGCGTGCCGAGGACACCGCGGTATATTACTGT
GCGAAA~~~TTGCCGACGCATTTTCCGATTAGGTTTGACTAC~~~TGGGGT
CAGGGAACCCTGGTCACCGTCTCGAGC

TAR2h-125 (SEQ ID NO:574)
GAGGTGCAGCTGTTGGAGTCTGGGGGAGGCTTGGTACAGCCTGGGGGGTCCCTGCGTCTC
TCCTGTGCAGCCTCCGGATTCACCTTTAAG~CAGTATAATATGTAT~TGGGTCCGC
CAGGCTCCAGGGAAGGGTCTAGAGTGGGTCTCA~~TTTATTAGTCCGTCTGGTGGTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TCGATTAAGCCTTTTGACTAC~~~TGGGGT
CAGGGAACCCTGGTCACCGTCTCGAGC

TAR2h-126 (SEQ ID NO:575)
GAGGTGCAGCTGTTGGAGTCTGGGGGAGGCTTGGTACAGCCTGGGGGGTCCCTGCGTCTC
TCCTGTGCAGCCTCCGGATTCACCTTTAGT~ATGTATTCGATGGCT~TGGGTCCGC
CAGGCTCCAGGGAAGGGTCTAGAGTGGGTCTCA~~TTTATTGATTTTGATGGTCTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTTTCTACGTCTACGATGGCTCTGTTTGACTAC~~~TGGGGT
CAGGGAACCCTGGTCACCGTCTCGAGC

TAR2h-127 (SEQ ID NO:576)
GAGGTGCAGCTGTTGGAGTCTGGGGGAGGCTTGGTACGGCCTGGGGGGTCCCTGCGTCTC
TCCTGTGCAGCCTCCGGATTCACCTTTCCT~GAGTATAATATGCAT~TGGGTCCGC
CAGGCTCCAGGGAAGGGCCTGGAGTGGGTCTCA~~GCGATTGGTACTGCTGGTGGTAGT
ACATACTACGCAGACTCCGTGAAGGGC~~CGGTTCACCATCTCCCGCGACAATTCCAAG
AACATGCTGTATCTGCAAATGAACAGCCTGCGTGCCGAGGACACCGCGGTATATTACTGT
GCGAAA~~~GGGTATCGTCCTCGGACTGGTAGTATGTTGTTTGACTAC~~~TGGGGT
CAGGGAACCCTGGTCACCGTCTCGAGC

Figure 28J

TAR2h-128   (SEQ ID NO:577)
GAGGTGCAGCTGTTGGAGTCTGGGGGAGGCTTGGTACAGCCTGGGGGGTCCCTGCGTCTC
TCCTGTGCAGCCTCCGGATTCACCTTTGCT~AAGTATAATATGTAT~TGGGTCCGC
CAGGCTCCAGGGAAGGGTCTAGAGTGGGTCTCA~~GCGATTAGTCCTAAGGGTCAGCAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGGAA~~~GGGATGGGGTCGGATGCTATTACTTTTGACTAC~~~TGGGGT
CAGGGAACCCTGGTCACCGTCTCGAGC

TAR2h-129   (SEQ ID NO:578)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~GATTATGATATGGCT~TGGGTCCGC
CAGGCTCCAGGGAAGGGTCTAGAGTGGGTCTCA~~TTTATTGATCGTAAGGGTCATCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ACGACTGATATTCAGCGTTTGAATTCTGCGTTTGACTAC~~~TGGGGT
CAGGGAACCCTGGTCACCGTCTCGAGC

TAR2h-130   (SEQ ID NO:579)
GAGGTGCAGCTGTTGGAGTCTGGGGGAGGCTTGGTACAGCCTGGGGGGTCCCTACGTCTC
TCCTGTGCAGCCTCCGGATTCACCTTTGGG~AATGGGGTGATGGCG~TGGGTCCGC
CAGGCTCCAGGGAAGGGTCTAGAGTGGGTCTCA~~CATATTAATGAGAATGGTGGTGCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTTCTATTGAGTCGCCTATTTTTGACTAC~~~TGGGGT
CAGGGAACCCTGGTCACCGTCTCGAGC

TAR2h-131   (SEQ ID NO:580)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~CATGAGCCGATGGTG~TGGGTCCGC
CAGGCTCCAGGGAAGGGTCTAGAGTGGGTCTCA~~CATATTGATCGTGTTGGTCAGGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CTTCCTAAGAGGGGCCTAGGTTTGACTAC~~~TGGGGT
CAGGGAACCCTGGTCACCGTCTCGAGC

TAR2h-132   (SEQ ID NO:581)
GAGGTGCAGCTGTTGGAGTCTGGGGGAGGCTTGGTACAGCCTGGGGGGTCCCTGCGTCTC
TCCTGTGCAGCCTCCGGATTCACCTTTGAG~GAGTCGGTTATGGGG~TGGGTCCGC
CAGGCTCCAGGGAAGGGTCTGGAGTGGGTCTCA~~GCGATTAGTCCTGGGGGTAGTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~CGTACGGGGCCTCCTGGGTCTACGGTTTTGACTAC~~~TGGGGT
CAGGGAACCCTGGTCACCGTCTCGAGC

TAR2h-133   (SEQ ID NO:582)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~GATGAGCCGATGCAT~TGGGTCCGC
CAGGCTCCAGGGAAGGGTCTAGAGTGGGTCTCA~~GGTATTGGTAAGGAGGGTCAGCCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~TTGGGGGGGCCTTTTGACTAC~~~TGGGGT
CAGGGAACCCTGGTCACCGTCTCGAGC

Figure 28K

TAR2h-151  (SEQ ID NO:583)
GAGGTGCAGCTGTTGGAGTCTGGGGGAGGCTTGGTACAGCCTGGGGGGTCCCTGCGTCTC
TCCTGTGCAGCCTCCGGATTCACCTTTGAT~TATGGGAATATGTTT~TGGGTCCGC
CAGGCTCCAGGGAAGGGTCTAGAGTGGGTCTCA~~GCTATTAGTGGTAGTGGTGGTAGC
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GATATGACGACGGATTCGCCTCCTGGGTTTGACTAC~~~TGGGGT
CAGGGAACCCTGGTCACCGTCTCGAGC

TAR2h-152  (SEQ ID NO:584)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~AAGGAGACGATGAGT~TGGGTCCGC
CAGGCTCCAGGGAAGGGTCTAGAGTGGGTCTCA~~TGGATTAGTCCTCATGGTGCTCTT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTCGGTTTTCGTATTATCCTCGGGTTTCGTTTGACTAC~~~TGGGGT
CAGGGAACCCTGGTCACCGTCTCGAGC

TAR2h-153  (SEQ ID NO:585)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGGTAATATGGTT~TGGGTCCGC
CAGGCTCCAGGGAAGGGTCTAGAGTGGGTCTCA~~CATATTGATGAGTATGGTACGAAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCTCGTAATGATCGGCCTGGGTTTGACTAC~~~TGGGGT
CAGGGAACCCTGGTCACCGTCTCGAGC

TAR2h-154  (SEQ ID NO:586)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~AATGGTAATATGGTT~TGGGTCCGC
CAGGCTCCAGGGAAGGGTCTAGAGTGGGTCTCA~~CATATTGATGANTATGGTACGAAT
ACATACTACGCAGACTCCGTGAAGGGC~~CGGTTCACCATCTCCCGCGACAATTCCAAG
AACACGCTGTATCTGCAAATGAACAGCCTGCGTGCCGGGGACACCGCGGTATATTACTGT
GCGAAA~~~CCTCGTAATGATCGGCCTGGGTTTGACTAC~~~TGGGGT
CAGGGAACCCTGGTCACCGTCTCGAGC

TAR2h-159  (SEQ ID NO:587)
GAGGTGCAGCTGTTGGAGTCTGGGGGAGGCTTGGTACAGCCTGGGGGGTCCCTGCGTCTC
TCCTGTGCAGCCTCCGGATTCACCTTTGCG~GGTCAGGATATGCGT~TGGGTCCGC
CAGGCTCCAGGGAAGGGTCTAGAGTGGGTCTCA~~TCGATTCCGTCGTCTGGTTTTAAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~CGTGCTAAGGATCGTAGTGTGTCGCAGATGCCGTATTTTGACTAC~~~TGG
GGTCAGGGAACCCTGGTCACCGTCTCGAGC

TAR2h-165  (SEQ ID NO:588)
GAGGTGCAGCTGTTGGAGTCTGGGGGAGGCTTGGTACAGCCTGGGGGGTCCCTGCGTCTC
TCCTGTGCAGCCTCCGGATTCACCTTTATG~AGGCCTGATATGGTT~TGGGTCCGC
CAGGCTCCAGGGAAGGGTCTGGAGTGGGTCTCA~~ACTATTAAGGATTGGGGTGATCAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGAAA~~~GCTGATAGTCGTGCGCAGCTGGATTTTGACTAC---TGGGGT
CAGGGAACCCTGGTCACCGTCTCGAGC

Figure 28L

TAR2h-166  (SEQ ID NO:589)
GAGGTGCAGCTGTTGGAGTCTGGGGGAGGCTTGGTACAGCCTGGGGGGTCCCTGCGTCTC
TCCTGTGCAGCCTCCGGATTCACCTTTAGC~AGCTATGCCATGAGC~TGGGTCCGC
CAGGCTCCAGGGAAGGGTCTAGAGTGGGTCTCA~~GCTATTAGTGGTAGTGGTGGTAGC
ACATACTACGCAGATTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CCGTATTTTCTGTTTAGGGCTACTAGTTTTGACTAC~~~TGGGGT
CAGGGAACCCTGGTCACCGTCTCGAGC

TAR2h-168  (SEQ ID NO:590)
GAGGTGCAGCTGTTGGAGTCTGGGGGAGGCTTGGTACAGCCTGGGGGGTCCCTGCGTCTC
TCCTGTGCAGCCTCCGGATTCACCTTTCAT~GATGATGATATGGTT~TGGGTCCGC
CAGGCTCCAGGGAAGGGTCTAGAGTGGGTCTCA~~TCGATTCCGGGGAATGGTTATGTG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CGTCCTGATCCGACTTCGGTGTTTTTTGACTAC~~~TGGGGT
CAGGGAACCCTGGTCACCGTCTCGAGC

TAR2h-171  (SEQ ID NO:591)
GAGGTGCAGCTGTTGGAGTCTGGGGGAGGCTTGGTACAGCCTGGGGGGTCCCTGCGTCTC
TCCTGTGCAGCCTCCGGATTCACCTTTGGT~GATGATTGGATGACT~TGGGTCCGC
CAGGCTCCAGGGAAGGGTCTAGAGTGGGTCTCA~~GGTATTGCGGCTTATGGTATTTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACGCCGCGGTATATTACTGT
GCGGAA~~~TCTGGGAAGGTGTTTGACTAC~~~TGGGGT
CAGGGAACCCTGGTCACCGTCTCGAGC

TAR2h-172  (SEQ ID NO:592)
GAGGTGCAGCTGTTGGAGTCTGGGGGAGGCTTGGTACAGCCTGGGGGGTCCCTGCGTCTC
TCCTGTGCAGCCTCCGGATTCACCTTTGTT~GAGCGTCCTATGGAT~TGGGTCCGC
CAGGCTCCAGGGAAGGGTCTAGAGTGGGTCTCA~~TTGATTGGTGCGGATGGTTTGTCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CTTTTTCGTCCTGGTCTTCTTTGGTTTGACTAC~~~TGGGGT
CAGGGAACCCTGGTCACCGTCTCGAGC

TAR2h-173  (SEQ ID NO:593)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~GGGCAGGATATGCAG~TGGGTCCGC
CAGGCTCCAGGGAAGGGTCTAGAGTGGGTCTCA~~GGGATTAATGCTGATGGTATGGCG
ACATACTACGCAGACTCCGTGAAGGGC~~CGGTTCACCATCTCCCGCGACAATTCCAAG
AACACGCTGTATCTGCAAATGAACAGCCTGCGTGCCGAGGATACCGCGGTATATTACTGT
GCGAAA~~~ACGTCGCCGACTATGAGGTCGTTTGACTAC~~~TGGGGT
CAGGGAACCCTGGTCACCGTCTCGAGC

TAR2h-174  (SEQ ID NO:594)
GAGGTGCAGCTGTTGGAGTCTGGGGGAGGCTTGGTACAGCCTGGGGGGTCCCTGCGTCTC
TCCTGTGCAGCCTCCGGATTCACCTTTGGG~GAGGAGTATATGCAG~TGGGTCCGC
CAGGCTCCAGGGAAGGGTCTAGAGTGGGTCTCA~~TTGATTCCGCATACTGGTAATCCT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~CTTGCGAATAGTTTGCTGTTTGACTAC~~~TGGGGT
CAGGGAACCCTGGTCACCGTCTCGAGC

Figure 28M

TAR2h-176 (SEQ ID NO:595)
GAGGTGCAGCTGTTGGAGTCTGGGGGAGGCTTGGTACAGCCTGGGGGGTCCCTGCGTCTC
TCCTGTGCAGCCTCCGGATTCACCTTTCAT~AGGTGTAAGATGGGG~TGGGTCCGC
CAGGCTCCAGGGAAGGGTCTAGAGTGGGTCTCA~~TTTATTGAGTATGATGGTAGGGAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~GAGTGTACGAGGCCGTATGGTATGTTTGACTAC~~~TGGGGT
CAGGGAACCCTGGTCACCGTCTCGAGC

TAR2h-178 (SEQ ID NO:596)
GAGGTGCAGCTGTTGGAGTCTGGGGGAGGCTTGGTACAGCCTGGGGGGTCCCTGCGTCTC
TCCTGTGCAGCCTCCGGATTCACCTTTAAT~AGGTATAGTATGGGG~TGGCTCCGC
CAGGCTCCAGGGAAGGGTCTAGAGTGGGTCTCA~~TTCATTGACAAGGTCGGTCATCAC
ACATGGTACGAAGACCCCGTGAAGGGC~~CGGTTCACCATCTCCCGCGACAATTCCAAG
AACACGCTGTATCTGCAAATGAACAGCCTGCGTGCCGAGGACACCGCCGTGTATTACTGT
GCGAAA~~~ATTTCTCAGTTTGGGCCAAATGCGTTTGACTAC~~~TGGGGT
CAGGGAACCCAGGTCACCGTCTCGAGC

TAR2h-201 (SEQ ID NO:597)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGCGCATGCTGGTCCTGAG
AGATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCANTTTGGGTCAAATGCGTTTGACTAC~~~TGGGGT
CAGGGAACCCTGGTCACCGTCTCGAGC

TAR2h-202 (SEQ ID NO:598)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAATATGGGG~TGGGTCCGC
CAGGCTCCAGGGAAGGGTCTAGAGTGGGTCTCA~~TTTATTGATCCTCCGAGTGTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAT~~~ATTTCTCAGTTTGGGTCAAACGCGTTTGACTAC~~~TGGGGT
CAGGGAACCCTGGTCACCGTCTCGAGC

TAR2h-203 (SEQ ID NO:599)
GAGGTGCAGCTGTTGGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~TTTATTGATCCTCCGAGTGTTCAT
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGN
GCGGAA~~~ATTTCTCAGTTTGGGTCAAATGCGTTTGACTAC~~~TGGGGT
CAGGGAACCCTGGTCACCGTCTCGAGC

TAR2h-204 (SEQ ID NO:600)
GAGGTGCAGTTGTTTGAGTCTGGGGGAGGCTTGGTACAGCCTGGGGGGTCCCTGCGTCTC
TCCTGTGCAGCCTCCGGATTCACCTTTACT~AGGTATAGTATGGGG~TGGGTCCGC
CAGGCTCCAGGGAAGGGTCTAGAGTGGGTCTCA~~ATGATTGCGCATGCTGGTCCTGAG
ACATACTACGCAGACTCCGTGAAGGGC~~CGGTTCACCATCTCCCGCGACAATTCCAAG
AACACGCTGTATCTGCAAATGAACAGCCTGCGTGCCGAGGACACCGCGGTATATTACTGT
GCGAAA~~~ATTTCTCAGTTTGGGTCAAATGCGTTAGACTAC~~~TGGGGC
CGGGGAACCCTGGTCACCGTCTCGAGC

Figure 28N

TAR2h-185-25 (SEQ ID NO:601)
GAGGTGCAGCTGTTGGAGTCTGGGGGAGGCTTGGTACAGCCTGGGGGGTCCCTGCGTCTCTC
CTGTGCAGCCTCCGGATTCACCTTTGCG~CGGTATAATATGGGT~TGGGTCCGCCAGGCTCC
AGGGAAGGGTCTAGAGTGGGTCTCA~~CTGATTGATCCGAGCGGTGGTCATACATACTACGC
AGACTCCGTGAAGGGC~~CGGTTCACCATCTCCCGCAACAATTCCAAGAACACGCTGTATCT
GCAAATGAACAGCCTGCGTGCCGAGGACACCGCGGTATATTACTGTGGGAAA~~~CCGGTTT
TTTCTGATTGGCCTGCGGTGGAGTTTGACTAC~~~TGGGGTCAGGGAACCGTGGTCACCGTC
TCGAGC

TAR2h-154-10 (SEQ ID NO:602)
GAGGTGCAGCTGTTGGAGTCTGGGGGAGGCATGGTACAGCCTGGGGGGTCACTGCGTCTCTC
CTGTGCAGCCTCCGGATTCACCTTTGAG~CATGAGGGGATGGTG~TGGGTCCGCCAGGCTCC
AGGGAAGGGTCTAGAGTGGGTCTCA~~CATATTGGTGAGGATGGTCAGTCTACATACTACGC
AGACTCCGTGAAGGGC~~CGGTTCACCATCTCCCGCGACAATTCCAAGAACACGCTGTATCT
GCAAATGAACAGCCTGCGTGCCGAGGACACCGCGGTATATTACTGTGCGAAT~~~ATTCCGA
AGGCGGGGCCTTCGTTTGACTAC~~~TGGGGTCAGGGAACCCTGGTCACCGTCTCGAGC

TAR2h-205 (SEQ ID NO:628)
GAGGTGCAGCTGTTGGAGTCTGGGGGAGGCTTGGTACAGCCTGGGGGGTCCCTGCGTCTCTC
CTGTGCAGCCTCCGGATTCACCTTTGTT~AAGTATTCGATGGGG~TGGGTCCGCCAGGCTCC
AGGGAAGGGTCTAGAGTGGGTCTCA~~CAGATTTCGAATACGGGTGGTCATACATACTACGC
AGACTCCGTGAAGGGC~~CGGTTCACCATCTCCCGCGACAATTCCAAGAACACGCTGTATCT
GCAAATGAACAGCCTGCGTGCCGAGGACACCGCGGTATATTACTGTGCGAAA~~~TATACGG
GTCGTTGGGAGCCTTTTGACTAC~~~TGGGGTCAGGGAACCCTGGTCACCGTCTCGAGC

Figure 280 ns or canonical structures (Chothia and Lesk (1987) *J. Mol.*

SEQUENCE LISTING

<160> NUMBER OF SEQ ID NOS: 639

<210> SEQ ID NO 1
<211> LENGTH: 720
<212> TYPE: DNA
<213> ORGANISM: Homo sapiens

<400> SEQUENCE: 1

```
gaggtgcagc tgttggagtc tgggggaggc ttggtacagc ctgggggtc cctgagactc        60 tcctgtgcag cctctggatt caccttagc agctatgcca tgagctgggt ccgccaggct       120
ccagggaagg ggctggagtg ggtctcagct attagtggta gtggtggtag cacatactac      180
gcagactccg tgaagggccg gttcaccatc tccagagaca attccaagaa cacgctgtat      240
ctgcaaatga acagcctgag agccgaggac acggccgtat attactgtgc gaaaagttat      300
ggtgcttttg actactgggg ccagggaacc ctggtcaccg tctcgagcgg tggaggcggt      360
tcaggcggag gtggcagcgg cggtggcggg tcgacggaca tccagatgac ccagtctcca      420
```

```
tcctccctgt ctgcatctgt aggagacaga gtcaccatca cttgccgggc aagtcagagc    480
attagcagct atttaaattg gtatcagcag aaaccaggga aagcccctaa gctcctgatc    540
tatgctgcat ccagtttgca aagtggggtc ccatcaaggt tcagtggcag tggatctggg    600
acagatttca ctctcaccat cagcagtctg caacctgaag attttgcaac ttactactgt    660
caacagagtt acagtacccc taatacgttc ggccaaggga ccaaggtgga aatcaaacgg    720
```

<210> SEQ ID NO 2
<211> LENGTH: 240
<212> TYPE: PRT
<213> ORGANISM: Homo sapiens

<400> SEQUENCE: 2

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Tyr
    210                 215                 220

Ser Thr Pro Asn Thr Phe Gly Gln Gly Thr Lys Val Glu Ile Lys Arg
225                 230                 235                 240
```

<210> SEQ ID NO 3
<211> LENGTH: 359
<212> TYPE: DNA
<213> ORGANISM: Artificial Sequence
<220> FEATURE:
<223> OTHER INFORMATION: Phagemide pIP1/pIT2

<400> SEQUENCE: 3

```
caggaaacag ctatgaccat gattacgcca agcttgcatg caaattctat ttcaaggaga     60
cagtcataat gaaataccta ttgcctacgg cagccgctgg attgttatta ctcgcggccc    120
agccggccat ggccgaggtg tttgactact ggggccaggg aaccctggtc accgtctcga    180
```

```
gcggtggagg cggttcaggc ggaggtggca gcggcggtgg cgggtcgacg gacatccaga    240
tgacccaggc ggccgcagaa caaaaactcc atcatcatca ccatcacggg gccgcaatct    300
cagaagagga tctgaatggg gccgcataga ctgttgaaag ttgtttagca aaacctcat     359
```

<210> SEQ ID NO 4
<211> LENGTH: 96
<212> TYPE: PRT
<213> ORGANISM: Homo sapiens
<220> FEATURE:
<223> OTHER INFORMATION: phagemide pIP1/pIT2

<400> SEQUENCE: 4

```
Met Lys Tyr Leu Leu Pro Thr Ala Ala Ala Gly Leu Leu Leu Leu Ala
1               5                   10                  15

Ala Gln Pro Ala Met Ala Glu Val Phe Asp Tyr Trp Gly Gln Gly Thr
            20                  25                  30

Leu Val Thr Val Ser Ser Gly Gly Gly Gly Ser Gly Gly Gly Gly Ser
        35                  40                  45

Gly Gly Gly Gly Ser Thr Asp Ile Gln Met Thr Gln Ala Ala Ala Glu
    50                  55                  60

Gln Lys Leu His His His His His Gly Ala Ala Ile Ser Glu Glu
65                  70                  75                  80

Asp Leu Asn Gly Ala Ala Thr Val Glu Ser Cys Leu Ala Lys Pro His
                85                  90                  95
```

<210> SEQ ID NO 5
<211> LENGTH: 116
<212> TYPE: PRT
<213> ORGANISM: Homo sapiens

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Tyr Gly Ala Phe Asp Tyr Trp Gly Gln Gly Thr Leu Val
            100                 105                 110

Thr Val Ser Ser
        115
```

<210> SEQ ID NO 6
<211> LENGTH: 116
<212> TYPE: PRT
<213> ORGANISM: Homo sapiens

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30
```

Ala Met Ser Trp Val Arg Gln Ala Pro Gly Lys Gly Leu Glu Trp Val
            35                  40                  45

Ser His Ile Ser Pro Tyr Gly Ala Asn Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu Arg Ala Phe Asp Tyr Trp Gly Gln Gly Thr Leu Val
            100                 105                 110

Thr Val Ser Ser
            115

<210> SEQ ID NO 7
<211> LENGTH: 116
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Asp Ile Gly Ala Thr Gly Ser Lys Thr Gly Tyr Ala Asp Pro Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Val Leu Thr Phe Asp Tyr Trp Gln Gly Thr Leu Val
            100                 105                 110

Thr Val Ser Ser
            115

<210> SEQ ID NO 8
<211> LENGTH: 115
<212> TYPE: PRT
<213> ORGANISM: Homo sapiens

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Arg Ile Asn Gly Pro Gly Ala Thr Gly Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Ile Asn Ser Leu Arg Ala Glu Asp Thr Ala Val Tyr Tyr Cys Ala
                85                  90                  95

Lys His Gly Ala Pro Phe Asp Tyr Trp Gly Gln Gly Thr Leu Val Thr
            100                 105                 110

```
Val Ser Ser
        115

<210> SEQ ID NO 9
<211> LENGTH: 116
<212> TYPE: PRT
<213> ORGANISM: Homo sapiens

<400> SEQUENCE: 9

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Asn Trp Val Arg Gln Ala Pro Gly Lys Gly Leu Glu Trp Val
         35                  40                  45

Ser Ser Ile Pro Ala Ser Gly Leu His Thr Arg Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Gly Leu Gly Phe Asp Tyr Trp Gly Gln Gly Thr Leu Val
            100                 105                 110

Thr Val Ser Ser
        115

<210> SEQ ID NO 10
<211> LENGTH: 115
<212> TYPE: PRT
<213> ORGANISM: Homo sapiens

<400> SEQUENCE: 10

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Asp Ile Glu Arg Thr Gly Tyr Thr Arg Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Lys Val Leu Val Phe Asp Tyr Trp Gly Gln Gly Thr Leu Val Thr
            100                 105                 110

Val Ser Ser
        115

<210> SEQ ID NO 11
<211> LENGTH: 116
<212> TYPE: PRT
<213> ORGANISM: Homo sapiens

<400> SEQUENCE: 11

Glu Val Gln Leu Leu Glu Ser Gly Gly Gly Leu Val Gln Pro Gly Gly
  1               5                  10                  15
```

```
Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Glu Ile Ser Ala Asn Gly Ser Lys Thr Gln Tyr Ala Asp Ser Val
 50                      55                  60

Lys Gly Arg Leu Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Lys Val Leu Gln Phe Asp Tyr Trp Gly Gln Gly Thr Leu Val
            100                 105                 110

Thr Val Ser Ser
            115

<210> SEQ ID NO 12
<211> LENGTH: 115
<212> TYPE: PRT
<213> ORGANISM: Homo sapiens

<400> SEQUENCE: 12

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Thr Ile Pro Ala Asn Gly Val Thr Arg Tyr Ala Asp Ser Val Lys
 50                      55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Ser Leu Leu Gln Phe Asp Tyr Trp Gly Gln Gly Thr Leu Val Thr
            100                 105                 110

Val Ser Ser
     115

<210> SEQ ID NO 13
<211> LENGTH: 116
<212> TYPE: PRT
<213> ORGANISM: Homo sapiens

<400> SEQUENCE: 13

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Asp Ile Ala Ala Thr Gly Ser Ala Thr Ser Tyr Ala Asp Ser Val
 50                      55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

```
Ala Lys Lys Ile Leu Lys Phe Asp Tyr Trp Gly Gln Gly Thr Leu Val
            100                 105                 110

Thr Val Ser Ser
        115

<210> SEQ ID NO 14
<211> LENGTH: 116
<212> TYPE: PRT
<213> ORGANISM: Homo sapiens

<400> SEQUENCE: 14

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Ser Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Ser Val Gly Gln Ser Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Leu Met Ser Phe Asp Tyr Trp Gly Gln Gly Thr Leu Val
            100                 105                 110

Thr Val Ser Ser
        115

<210> SEQ ID NO 15
<211> LENGTH: 15
<212> TYPE: PRT
<213> ORGANISM: Artificial Sequence
<220> FEATURE:
<223> OTHER INFORMATION: Modified IgGC1 hinge

<400> SEQUENCE: 15

Glu Pro Lys Ser Gly Asp Lys Thr His Thr Cys Pro Pro Cys Pro
 1               5                  10                  15

<210> SEQ ID NO 16
<211> LENGTH: 108
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Asn
                85                  90                  95

Thr Phe Gly Gln Gly Thr Lys Val Glu Ile Lys Arg
            100                 105
```

<210> SEQ ID NO 17
<211> LENGTH: 108
<212> TYPE: PRT
<213> ORGANISM: Homo sapiens

<400> SEQUENCE: 17

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Arg Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Pro Trp Arg Ser Pro Gly
                85                  90                  95

Thr Phe Gly Gln Gly Thr Lys Val Glu Ile Lys Arg
            100                 105
```

<210> SEQ ID NO 18
<211> LENGTH: 108
<212> TYPE: PRT
<213> ORGANISM: Homo sapiens

<400> SEQUENCE: 18

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Tyr
            20                  25                  30

Leu Asn Trp Tyr Gln Gln Lys Pro Gly Lys Ala Pro Lys Leu Leu Ile
        35                  40                  45

Tyr Leu Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Trp Trp Leu Pro Pro
                85                  90                  95

Thr Phe Gly Gln Gly Thr Lys Val Glu Ile Lys Arg
            100                 105
```

<210> SEQ ID NO 19
<211> LENGTH: 107
<212> TYPE: PRT
<213> ORGANISM: Homo sapiens

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ser Leu Leu Gln Ser Gly Val Pro Ser Arg Phe Ser Gly Ser
    50                  55                  60
```

```
Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Arg Val Tyr Asp Pro Leu Thr
                 85                  90                  95

Phe Gly Gln Gly Thr Lys Val Glu Ile Lys Arg
                100                 105
```

<210> SEQ ID NO 20
<211> LENGTH: 348
<212> TYPE: DNA
<213> ORGANISM: Homo sapiens

<400> SEQUENCE: 20

```
gaggtgcagc tgttggagtc tgggggaggc ttggtacagc ctggggggtc cctgcgtctc     60
tcctgtgcag cctccggatt cacctttagc agctatgcca tgagctgggt ccgccaggct    120
ccagggaagg gtctagagtg ggtctcagct attagtggta gtggtggtag cacatactac    180
gcagactccg tgaagggccg gttcaccatc tcccgtgaca attccaagaa cacgctgtat    240
ctgcaaatga acagcctgcg tgccgaggac accgcggtat attactgtgc gaaaagttat    300
ggtgcttttg actactgggg ccagggaacc ctggtcaccg tctcgagc                 348
```

<210> SEQ ID NO 21
<211> LENGTH: 348
<212> TYPE: DNA
<213> ORGANISM: Homo sapiens

<400> SEQUENCE: 21

```
gctcgagacg gtgaccaggg ttccctggcc ccagtagtca aaagcaccat aactttcgc     60
acagtaatat accgcggtgt cctcggcacg caggctgttc atttgcagat acagcgtgtt   120
cttggaattg tcacgggaga tggtgaaccg gcccttcacg gagtctgcgt agtatgtgct   180
accaccacta ccactaatag ctgagaccca ctctagaccc ttccctggag cctggcggac   240
ccagctcatg gcatagctgc taaaggtgaa tccggaggct gcacaggaga gacgcaggga   300
ccccccaggc tgtaccaagc ctcccccaga ctccaacagc tgcacctc                 348
```

<210> SEQ ID NO 22
<211> LENGTH: 120
<212> TYPE: PRT
<213> ORGANISM: Homo sapiens
<220> FEATURE:
<221> NAME/KEY: VARIANT
<222> LOCATION: 103, 104, 105, 106
<223> OTHER INFORMATION: Xaa = Any Amino Acid

<400> SEQUENCE: 22

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ser Ala Ile Ser Gly Ser Gly Gly Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95
```

Ala Lys Ser Tyr Gly Ala Xaa Xaa Xaa Xaa Phe Asp Tyr Trp Gly Gln
            100                 105                 110

Gly Thr Leu Val Thr Val Ser Ser
        115                 120

<210> SEQ ID NO 23
<211> LENGTH: 360
<212> TYPE: DNA
<213> ORGANISM: Homo sapiens
<220> FEATURE:
<221> NAME/KEY: misc_feature
<222> LOCATION: 309, 312, 315, 318
<223> OTHER INFORMATION: K = G or T
<220> FEATURE:
<221> NAME/KEY: misc_feature
<222> LOCATION: 307, 308, 310, 311, 313, 314, 316, 317
<223> OTHER INFORMATION: n = A,T,C or G

<400> SEQUENCE: 23
gaggtgcagc tgttggagtc tgggggaggc ttggtacagc ctgggggtc cctgcgtctc      60 tcctgtgcag cctccggatt cacctttagc agctatgcca tgagctgggt ccgccaggct     120
ccagggaagg gtctagagtg ggtctcagct attagtggta gtggtggtag cacatactac    180
gcagactccg tgaagggccg gttcaccatc tcccgtgaca attccaagaa cacgctgtat    240
ctgcaaatga acagcctgcg tgccgaggac accgcggtat attactgtgc gaaaagttat    300
ggtgctnnkn nknnknnktt tgactactgg ggccaggaa ccctggtcac cgtctcgagc    360

<210> SEQ ID NO 24
<211> LENGTH: 360
<212> TYPE: DNA
<213> ORGANISM: Homo sapiens
<220> FEATURE:
<221> NAME/KEY: misc_feature
<222> LOCATION: 43, 46, 49, 52
<223> OTHER INFORMATION: K = G or T
<220> FEATURE:
<221> NAME/KEY: misc_feature
<222> LOCATION: 44, 45, 47, 48, 50, 51, 53, 54
<223> OTHER INFORMATION: n = A,T,C or G

<400> SEQUENCE: 24
gctcgagacg gtgaccaggg ttccctggcc ccagtagtca aaknnknnkn nknnagcacc     60
ataacttttc gcacagtaat ataccgcggt gtcctcggca cgcaggctgt tcatttgcag    120
atacagcgtg ttcttggaat tgtcacggga gatggtgaac cggcccttca cggagtctgc    180
gtagtatgtg ctaccaccac taccactaat agctgagacc cactctagac ccttccctgg    240
agcctggcgg acccagctca tggcatagct gctaaaggtg aatccggagg ctgcacagga    300
gagacgcagg gaccccccag gctgtaccaa gcctccccca gactccaaca gctgcacctc    360

<210> SEQ ID NO 25
<211> LENGTH: 324
<212> TYPE: DNA
<213> ORGANISM: Homo sapiens

<400> SEQUENCE: 25
gacatccaga tgacccagtc tccatcctcc ctgtctgcat ctgtaggaga ccgtgtcacc     60
atcacttgcc gggcaagtca gagcattagc agctatttaa attggtacca gcagaaacca    120
gggaaagccc ctaagctcct gatctatgct gcatccagtt tgcaaagtgg ggtcccatca    180
cgtttcagtg gcagtggatc tgggacagat ttcactctca ccatcagcag tctgcaacct    240
gaagattttg ctacgtacta ctgtcaacag agttacagta cccctaatac gttcggccaa    300

```
gggaccaagg tggaaatcaa acgg                                          324
```

<210> SEQ ID NO 26
<211> LENGTH: 324
<212> TYPE: DNA
<213> ORGANISM: Homo sapiens

<400> SEQUENCE: 26

```
ccgtttgatt tccaccttgg tcccttggcc gaacgtatta ggggtactgt aactctgttg     60
acagtagtac gtagcaaaat cttcaggttg cagactgctg atggtgagag tgaaatctgt    120
cccagatcca ctgccactga aacgtgatgg gaccccactt tgcaaactgg atgcagcata    180
gatcaggagc ttaggggctt tccctggttt ctgctggtac caatttaaat agctgctaat    240
gctctgactt gcccggcaag tgatggtgac acggtctcct acagatgcag acagggagga    300
tggagactgg gtcatctgga tgtc                                          324
```

<210> SEQ ID NO 27
<211> LENGTH: 324
<212> TYPE: DNA
<213> ORGANISM: Homo sapiens

<400> SEQUENCE: 27

```
gacatccaga tgacccagtc tccatcctcc ctgtctgcat ctgtaggaga ccgtgtcacc     60
atcacttgcc gggcaagtca gagcattatt aagcatttaa gtggtacca gcagaaacca    120 gggaaagccc ctaagctcct gatctatggt gcatcccgt tgcaaagtgg ggtcccatca    180
cgtttcagtg gcagtggatc tgggacagat ttcactctca ccatcagcag tctgcaacct    240
gaagattttg ctacgtacta ctgtcaacag ggggctcggt ggcctcagac gttcggccaa    300
gggaccaagg tggaaatcaa acgg                                          324
```

<210> SEQ ID NO 28
<211> LENGTH: 108
<212> TYPE: PRT
<213> ORGANISM: Homo sapiens

<400> SEQUENCE: 28

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Ile Lys His
             20                  25                  30

Leu Lys Trp Tyr Gln Gln Lys Pro Gly Lys Ala Pro Lys Leu Leu Ile
         35                  40                  45

Tyr Gly Ala Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Ala Arg Trp Pro Gln
                 85                  90                  95

Thr Phe Gly Gln Gly Thr Lys Val Glu Ile Lys Arg
            100                 105
```

<210> SEQ ID NO 29
<211> LENGTH: 324
<212> TYPE: DNA
<213> ORGANISM: Homo sapiens

<400> SEQUENCE: 29

```
gacatccaga tgacccagtc tccatcctcc ctgtctgcat ctgtaggaga ccgtgtcacc    60
atcacttgcc gggcaagtca gagcatttat tatcatttaa agtggtacca gcagaaacca   120
gggaaagccc ctaagctcct gatctataag gcatccacgt tgcaaagtgg ggtcccatca   180
cgtttcagtg gcagtggatc tgggacagat ttcactctca ccatcagcag tctgcaacct   240
gaagattttg ctacgtacta ctgtcaacag gttcggaagg tgcctcggac gttcggccaa   300
gggaccaagg tggaaatcaa acgg                                          324
```

<210> SEQ ID NO 30
<211> LENGTH: 108
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Tyr His
            20                  25                  30

Leu Lys Trp Tyr Gln Gln Lys Pro Gly Lys Ala Pro Lys Leu Leu Ile
        35                  40                  45

Tyr Lys Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Arg Lys Val Pro Arg
                85                  90                  95

Thr Phe Gly Gln Gly Thr Lys Val Glu Ile Lys Arg
            100                 105

<210> SEQ ID NO 31
<211> LENGTH: 120
<212> TYPE: PRT
<213> ORGANISM: Mus musculus

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Pro Asn Phe Asp Tyr Trp Gly Gln
            100                 105                 110

Gly Thr Leu Val Thr Val Ser Ser
        115                 120

<210> SEQ ID NO 32
<211> LENGTH: 122
<212> TYPE: PRT
<213> ORGANISM: Homo sapiens

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Ala Tyr
            20                  25                  30

Asn Met Gly Trp Val Arg Gln Ala Pro Gly Lys Gly Leu Glu Trp Val
        35                  40                  45

Ser Phe Ile Asp Met Tyr Gly Ala Lys Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Cys Leu Met Asp Cys Ser Gly Asp Ile Phe Asp Tyr Trp
            100                 105                 110

Gly Gln Gly Thr Leu Val Thr Val Ser Ser
        115                 120

<210> SEQ ID NO 33
<211> LENGTH: 116
<212> TYPE: PRT
<213> ORGANISM: Homo sapiens

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ala Asp
            20                  25                  30

Glu Met Tyr Trp Val Arg Gln Ala Pro Gly Lys Gly Leu Glu Trp Val
        35                  40                  45

Ser Ser Ile Gly Trp Pro Gly Gly Ala Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Gly Arg Asn Phe Asp Tyr Trp Gly Gln Gly Thr Leu Val
            100                 105                 110

Thr Val Ser Ser
        115

<210> SEQ ID NO 34
<211> LENGTH: 122
<212> TYPE: PRT
<213> ORGANISM: Homo sapiens

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
50                  55                  60

```
Lys Gly Arg Phe Thr Ile Ser Arg Asn Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
            115                 120

<210> SEQ ID NO 35
<211> LENGTH: 116
<212> TYPE: PRT
<213> ORGANISM: Homo sapiens

<400> SEQUENCE: 35

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Tyr
             20                  25                  30

Asp Met Gln Trp Val Arg Gln Ala Pro Gly Lys Gly Leu Glu Trp Val
         35                  40                  45

Ser Ser Ile Asp Gly Thr Gly Gly Thr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Gln Glu Thr Asn Ala Phe Asp Tyr Trp Gly Gln Gly Thr Leu Val
            100                 105                 110

Thr Val Ser Ser
        115

<210> SEQ ID NO 36
<211> LENGTH: 124
<212> TYPE: PRT
<213> ORGANISM: Homo sapiens

<400> SEQUENCE: 36

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Gly Tyr
             20                  25                  30

Gln Met Gly Trp Val Arg Gln Ala Pro Gly Lys Gly Leu Glu Trp Val
         35                  40                  45

Ser Phe Ile Asp Phe Thr Gly His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Ser Asp Asp Leu Thr Leu Pro Glu Arg Phe Pro Phe Asp
            100                 105                 110

Tyr Trp Gly Gln Gly Thr Leu Val Thr Val Ser Ser
        115                 120

<210> SEQ ID NO 37
<211> LENGTH: 123
```

```
<212> TYPE: PRT
<213> ORGANISM: Homo sapiens

<400> SEQUENCE: 37

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asp Tyr
            20                  25                  30

Asn Met Thr Trp Val Arg Gln Ala Pro Gly Lys Gly Leu Glu Trp Val
        35                  40                  45

Ser Trp Ile Asp Gln Glu Gly Val Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Phe Ser Ala Ala Val Met Leu Arg Thr Ser Phe Asp Tyr
            100                 105                 110

Trp Gly Gln Gly Thr Leu Val Thr Val Ser Ser
            115                 120

<210> SEQ ID NO 38
<211> LENGTH: 116
<212> TYPE: PRT
<213> ORGANISM: Homo sapiens

<400> SEQUENCE: 38

Glu Val Gln Leu Leu Glu Ser Gly Gly Gly Leu Val Gln Pro Gly Gly
 1               5                  10                  15

Ser Leu Arg Leu Ser Cys Ala Val Ser Gly Phe Thr Phe His Asp Tyr
            20                  25                  30

Gly Met Val Trp Val Arg Gln Ala Pro Gly Lys Gly Leu Glu Trp Val
        35                  40                  45

Ser Gln Ile Ser Ile Asp Gly Arg Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ile Phe Glu Phe Asp Tyr Trp Gly Gln Gly Thr Leu Val
            100                 105                 110

Thr Val Ser Ser
            115

<210> SEQ ID NO 39
<211> LENGTH: 117
<212> TYPE: PRT
<213> ORGANISM: Homo sapiens

<400> SEQUENCE: 39

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ala Tyr
            20                  25                  30

Asn Met Ser Trp Val Arg Gln Ala Pro Gly Lys Gly Leu Glu Trp Val
        35                  40                  45

Ser Ala Ile Ser Pro Ser Gly Asn Glu Thr Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ala Gly Glu Ala Phe Asp Tyr Trp Gly Gln Gly Thr Leu
            100                 105                 110

Val Thr Val Ser Ser
        115

<210> SEQ ID NO 40
<211> LENGTH: 117
<212> TYPE: PRT
<213> ORGANISM: Homo sapiens

<400> SEQUENCE: 40

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Glu Tyr
                 20                  25                  30

Asn Met Gly Trp Val Arg Gln Ala Pro Gly Lys Gly Leu Glu Trp Val
             35                  40                  45

Ser Phe Ile Gly His Ser Gly Gln His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Leu Asn Asn Leu Met Phe Asp Tyr Trp Gly Gln Gly Thr Leu
            100                 105                 110

Val Thr Val Ser Ser
        115

<210> SEQ ID NO 41
<211> LENGTH: 121
<212> TYPE: PRT
<213> ORGANISM: Homo sapiens

<400> SEQUENCE: 41

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Glu Tyr
                 20                  25                  30

Asn Met Ala Trp Val Arg Gln Ala Pro Gly Lys Gly Gln Glu Trp Val
             35                  40                  45

Ser Phe Ile Ser Thr Gly Gly His Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ser Val Arg Phe Arg Ser Ser Ile Phe Asp Tyr Trp Gly
            100                 105                 110

Gln Gly Thr Leu Val Thr Val Ser Ser
            115                 120
```

```
<210> SEQ ID NO 42
<211> LENGTH: 122
<212> TYPE: PRT
<213> ORGANISM: Homo sapiens

<400> SEQUENCE: 42

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Tyr Thr Phe Thr Glu Tyr
            20                  25                  30

Thr Met Gly Trp Val Arg Gln Ala Pro Gly Lys Gly Leu Glu Trp Val
        35                  40                  45

Ser Trp Ile Ala Val Asp Gly Ile His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asp Trp Thr Ala Thr Asp Phe Ser Ile Phe Asp Tyr Trp
            100                 105                 110

Gly Gln Gly Thr Leu Val Thr Val Ser Ser
        115                 120

<210> SEQ ID NO 43
<211> LENGTH: 122
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asn Tyr
            20                  25                  30

Thr Met Leu Trp Val Arg Gln Ala Pro Gly Lys Gly Leu Glu Trp Val
        35                  40                  45

Ser Val Ile Ser Ala Glu Gly Arg Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Asn Met Lys Ala Thr Asn Phe Lys Asp Phe Asp Tyr Trp
            100                 105                 110

Gly Gln Gly Thr Leu Val Thr Val Ser Ser
        115                 120

<210> SEQ ID NO 44
<211> LENGTH: 122
<212> TYPE: PRT
<213> ORGANISM: Homo sapiens

<400> SEQUENCE: 44

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Glu Tyr
            20                  25                  30

Ala Met Leu Trp Val Arg Gln Ala Pro Gly Lys Gly Leu Glu Trp Val
        35                  40                  45
```

Ser Leu Ile Asp Arg Thr Gly Val Ile Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Arg Asp Tyr Gln Tyr His Leu Tyr Gln Asp Phe Asp Tyr Arg
                100                 105                 110

Gly Gln Gly Thr Leu Val Thr Val Ser Ser
                115                 120

<210> SEQ ID NO 45
<211> LENGTH: 122
<212> TYPE: PRT
<213> ORGANISM: Homo sapiens

<400> SEQUENCE: 45

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Thr Tyr
                20                  25                  30

Ser Met Gly Trp Val Arg Gln Ala Pro Gly Lys Gly Leu Glu Trp Val
                35                  40                  45

Ser Met Ile Asp Pro Glu Gly Tyr His Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Glu Thr Asn Arg Pro Leu Thr Tyr Lys Pro Trp Phe Asp Tyr Trp
                100                 105                 110

Gly Gln Gly Thr Leu Val Thr Val Ser Ser
                115                 120

<210> SEQ ID NO 46
<211> LENGTH: 121
<212> TYPE: PRT
<213> ORGANISM: Homo sapiens

<400> SEQUENCE: 46

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
                20                  25                  30

Asn Met Ala Trp Val Arg Gln Ala Pro Gly Lys Gly Leu Glu Trp Val
                35                  40                  45

Ser Phe Ile Ser Gln Glu Gly His His Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Phe Ser Thr Ile Ala Thr Leu Ser Leu Phe Asp Tyr Trp Gly
                100                 105                 110

Gln Gly Thr Leu Val Thr Val Ser Ser
                115                 120

<210> SEQ ID NO 47
<211> LENGTH: 122
<212> TYPE: PRT
<213> ORGANISM: Homo sapiens

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Thr Tyr
            20                  25                  30

Asn Met Gly Trp Val Arg Gln Ala Pro Gly Lys Gly Leu Glu Trp Val
        35                  40                  45

Ser Ser Ile Ala Trp Leu Gly Ser Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Cys Lys Ala Glu Cys Thr Gly Asp Leu Phe Asp Tyr Trp
            100                 105                 110

Gly Gln Gly Thr Leu Val Thr Val Ser Ser
        115                 120

<210> SEQ ID NO 48
<211> LENGTH: 122
<212> TYPE: PRT
<213> ORGANISM: Homo sapiens

<400> SEQUENCE: 48

Glu Val Gln Leu Leu Glu Ser Gly Gly Gly Leu Val Gln Pro Gly Gly
1               5                   10                  15

Ala Leu Arg Leu Ser Cys Ala Ala Ser Gly Phe Thr Phe Gly Ile Tyr
            20                  25                  30

Ser Met Gly Trp Val Arg Gln Ala Pro Gly Lys Gly Leu Glu Trp Val
        35                  40                  45

Ser Ser Ile Ser Gly Val Gly Met Glu Thr Tyr Tyr Ala Asp Ser Val
    50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Ser Tyr Pro Thr Arg Gly Arg His Leu Phe Asp Tyr Trp
            100                 105                 110

Gly Gln Gly Thr Leu Val Thr Val Ser Ser
        115                 120

<210> SEQ ID NO 49
<211> LENGTH: 120
<212> TYPE: PRT
<213> ORGANISM: Homo sapiens

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

```
Trp Met Gly Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Pro Asn Phe Asp Tyr Arg Gly Gln
                100                 105                 110

Gly Thr Leu Val Thr Val Ser Ser
            115                 120
```

<210> SEQ ID NO 50
<211> LENGTH: 120
<212> TYPE: PRT
<213> ORGANISM: Homo sapiens

<400> SEQUENCE: 50

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe His Arg Tyr
            20                  25                  30

Ser Met Gly Trp Val Arg Gln Ala Pro Gly Lys Gly Leu Glu Trp Val
            35                  40                  45

Ser Ala Ile Ser Ser Ser Gly Gly Ile Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Thr Gln Ala Gln Gly Leu Glu Leu Asp Tyr Trp Gly Gln
                100                 105                 110

Gly Thr Leu Val Thr Val Ser Ser
            115                 120
```

<210> SEQ ID NO 51
<211> LENGTH: 120
<212> TYPE: PRT
<213> ORGANISM: Homo sapiens

<400> SEQUENCE: 51

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
            35                  40                  45

Ser Ala Ile Ser Gly Ser Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Asn Leu Arg Ala Glu Asp Thr Ala Val Tyr Tyr Cys
                 85                  90                  95

Ala Lys Val Lys Leu Gly Gly Pro Asn Phe Asp Tyr Arg Gly Gln
                100                 105                 110
```

```
Gly Thr Leu Val Thr Val Ser Ser
        115                 120

<210> SEQ ID NO 52
<211> LENGTH: 120
<212> TYPE: PRT
<213> ORGANISM: Homo sapiens

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Pro Asn Phe Asp Tyr Arg Gly Gln
            100                 105                 110

Gly Thr Leu Val Thr Val Ser Ser
        115                 120

<210> SEQ ID NO 53
<211> LENGTH: 120
<212> TYPE: PRT
<213> ORGANISM: Homo sapiens

<400> SEQUENCE: 53

Glu Val Gln Leu Leu Glu Ser Gly Gly Gly Leu Val Gln Pro Gly Gly
1               5                   10                  15

Ser Leu Arg Leu Thr Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Pro Asn Phe Asp Tyr Trp Gly Gln
            100                 105                 110

Gly Thr Leu Val Thr Val Ser Ser
        115                 120

<210> SEQ ID NO 54
<211> LENGTH: 120
<212> TYPE: PRT
<213> ORGANISM: Homo sapiens

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
```

```
                 20                  25                  30

Trp Met Gly Trp Ile Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Trp Gly Gln
            100                 105                 110

Gly Thr Leu Val Thr Val Ser Ser
            115                 120

<210> SEQ ID NO 55
<211> LENGTH: 120
<212> TYPE: PRT
<213> ORGANISM: Homo sapiens

<400> SEQUENCE: 55

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
            100                 105                 110

Gly Thr Leu Val Thr Val Ser Ser
            115                 120

<210> SEQ ID NO 56
<211> LENGTH: 120
<212> TYPE: PRT
<213> ORGANISM: Homo sapiens

<400> SEQUENCE: 56

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Pro Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Gly Pro Asn Phe Asp Tyr Arg Gly Gln
```

Gly Thr Leu Val Thr Val Ser Ser
        115                 120

<210> SEQ ID NO 57
<211> LENGTH: 120
<212> TYPE: PRT
<213> ORGANISM: Homo sapiens

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 58
<211> LENGTH: 120
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 59
<211> LENGTH: 120
<212> TYPE: PRT
<213> ORGANISM: Homo sapiens

<400> SEQUENCE: 59

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
            115                 120

<210> SEQ ID NO 60
<211> LENGTH: 120
<212> TYPE: PRT
<213> ORGANISM: Homo sapiens

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Asp Arg Gly Gln
            100                 105                 110

Gly Thr Leu Val Thr Val Ser Ser
            115                 120

<210> SEQ ID NO 61
<211> LENGTH: 120
<212> TYPE: PRT
<213> ORGANISM: Homo sapiens

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 62
<211> LENGTH: 120
<212> TYPE: PRT
<213> ORGANISM: Homo sapiens

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Ala
        35                  40                  45

Ser Ala Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
        115                 120

<210> SEQ ID NO 63
<211> LENGTH: 120
<212> TYPE: PRT
<213> ORGANISM: Homo sapiens

<400> SEQUENCE: 63

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Gly Trp Val
        35                  40                  45

Ser Ala Ile Ser Gly Ser Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 64
<211> LENGTH: 120
<212> TYPE: PRT
<213> ORGANISM: Homo sapiens
<220> FEATURE:
<221> NAME/KEY: VARIANT
<222> LOCATION: 20

<223> OTHER INFORMATION: Xaa = Any Amino Acid

<400> SEQUENCE: 64

```
Glu Val Gln Leu Leu Glu Ser Gly Gly Gly Leu Val Gln Pro Gly Gly
1               5                   10                  15

Ser Leu Arg Xaa Ser Cys Ala Ala Ser Gly Phe Thr Phe Glu Trp Tyr
            20                  25                  30

Trp Met Gly Trp Val Arg Gln Ala Pro Gly Lys Gly Pro Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
        115                 120
```

<210> SEQ ID NO 65
<211> LENGTH: 120
<212> TYPE: PRT
<213> ORGANISM: Homo sapiens

<400> SEQUENCE: 65

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Lys Leu Gly Gly Gly Pro Asn Phe Asp Tyr Arg Gly Arg
            100                 105                 110

Gly Thr Leu Val Thr Val Ser Ser
        115                 120
```

<210> SEQ ID NO 66
<211> LENGTH: 120
<212> TYPE: PRT
<213> ORGANISM: Homo sapiens

<400> SEQUENCE: 66

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Ile Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
            85                  90                  95

Ala Lys Val Lys Leu Gly Gly Pro Asn Phe Asp Tyr Arg Gly Gln
        100                 105                 110

Gly Thr Leu Val Thr Val Ser Ser
        115                 120

<210> SEQ ID NO 67
<211> LENGTH: 120
<212> TYPE: PRT
<213> ORGANISM: Homo sapiens

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Ile Arg Gln Ala Pro Gly Lys Gly Leu Gly Trp Val
        35                  40                  45

Ser Ala Ile Ser Gly Ser Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Val Lys Leu Gly Gly Pro Asn Phe Asp Tyr Arg Gly Gln
        100                 105                 110

Gly Thr Leu Val Thr Val Ser Ser
        115                 120

<210> SEQ ID NO 68
<211> LENGTH: 120
<212> TYPE: PRT
<213> ORGANISM: Homo sapiens

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Ala
        35                  40                  45

Ser Ala Ile Ser Gly Ser Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Val Lys Leu Gly Gly Pro Asn Phe Asp Tyr Trp Gly Gln
        100                 105                 110

Gly Thr Leu Val Thr Val Ser Ser
        115                 120

<210> SEQ ID NO 69

<211> LENGTH: 120
<212> TYPE: PRT
<213> ORGANISM: Homo sapiens

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Gly Trp Val
        35                  40                  45

Ser Ala Ile Ser Gly Ser Gly Gly Ser Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Lys Val Lys Leu Gly Gly Gly Pro Asn Phe Asp Tyr Arg Gly Gln
            100                 105                 110

Gly Thr Leu Val Thr Val Ser Ser
        115                 120

<210> SEQ ID NO 70
<211> LENGTH: 120
<212> TYPE: PRT
<213> ORGANISM: Homo sapiens

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Ala
        35                  40                  45

Ser Ala Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Thr Ala Val Tyr Tyr Cys
                85                  90                  95

Ala Lys Val Lys Leu Gly Gly Gly Pro Asn Phe Asp Tyr Trp Gly Gln
            100                 105                 110

Gly Thr Leu Val Thr Val Ser Ser
        115                 120

<210> SEQ ID NO 71
<211> LENGTH: 120
<212> TYPE: PRT
<213> ORGANISM: Homo sapiens

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Trp Tyr
            20                  25                  30

Trp Met Gly Trp Val Arg Gln Ala Pro Gly Lys Gly Leu Glu Trp Val
        35                  40                  45

```
Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Lys Asp Thr Ala Val Tyr Tyr Cys
                 85                  90                  95

Ala Lys Val Lys Leu Gly Gly Pro Asn Phe Asp Tyr Arg Gly Gln
             100                 105                 110

Gly Thr Leu Val Thr Val Ser Ser
             115                 120

<210> SEQ ID NO 72
<211> LENGTH: 120
<212> TYPE: PRT
<213> ORGANISM: Homo sapiens

<400> SEQUENCE: 72

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Gly Trp Tyr
             20                  25                  30

Trp Met Gly Trp Val Arg Gln Ala Pro Gly Lys Gly Leu Gly Trp Val
             35                  40                  45

Ser Ala Ile Ser Gly Ser Gly Gly Ser Thr Tyr Tyr Ala Asp Ser Val
 50                  55                  60

Arg Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Val Lys Leu Gly Gly Pro Asn Phe Asp Tyr Arg Gly Gln
             100                 105                 110

Gly Thr Leu Val Thr Val Ser Ser
             115                 120

<210> SEQ ID NO 73
<211> LENGTH: 120
<212> TYPE: PRT
<213> ORGANISM: Homo sapiens

<400> SEQUENCE: 73

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Pro Asn Phe Gly Tyr Arg Gly Gln
             100                 105                 110

Gly Thr Leu Val Thr Val Ser Ser
             115                 120
```

<210> SEQ ID NO 74
<211> LENGTH: 120
<212> TYPE: PRT
<213> ORGANISM: Homo sapiens

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 75
<211> LENGTH: 120
<212> TYPE: PRT
<213> ORGANISM: Homo sapiens

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Ser Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 76
<211> LENGTH: 120
<212> TYPE: PRT
<213> ORGANISM: Homo sapiens

<400> SEQUENCE: 76

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Trp Tyr
            20                  25                  30

Trp Met Gly Trp Val Arg Gln Ala Pro Gly Lys Gly Leu Glu Trp Val

```
                35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu His Ala Glu Asp Ala Ala Val Tyr Tyr Cys
                 85                  90                  95
Ala Lys Val Lys Leu Gly Gly Gly Pro Asn Phe Gly Tyr Arg Gly Gln
            100                 105                 110
Gly Thr Leu Val Thr Val Ser Ser
        115                 120

<210> SEQ ID NO 77
<211> LENGTH: 120
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
  1               5                  10                  15
Ser Leu Arg Leu Ser Cys Ala Val Ser Gly Leu Thr Phe Glu Trp Tyr
             20                  25                  30
Trp Met Gly Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Val Lys Leu Gly Gly Gly Pro Asn Phe Gly Tyr Arg Gly Gln
            100                 105                 110
Gly Thr Leu Val Thr Val Ser Ser
        115                 120

<210> SEQ ID NO 78
<211> LENGTH: 120
<212> TYPE: PRT
<213> ORGANISM: Homo sapiens

<400> SEQUENCE: 78

Glu Val Gln Leu Leu Gly Ser Gly Gly Gly Leu Val Gln Pro Gly Gly
  1               5                  10                  15
Ser Leu Arg Leu Ser Cys Ala Ala Ser Gly Phe Thr Phe Ala Trp Tyr
             20                  25                  30
Trp Met Gly Trp Val Arg Gln Ala Pro Gly Lys Gly Leu Glu Trp Val
         35                  40                  45
Ser Ala Ile Ser Gly Ser Gly Gly Ser Thr Tyr Tyr Ala Asp Ser Val
         50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Val Lys Leu Gly Gly Gly Pro Asn Phe Gly Tyr Arg Gly Gln
            100                 105                 110
Gly Thr Leu Val Thr Val Ser Ser
```

<210> SEQ ID NO 79
<211> LENGTH: 120
<212> TYPE: PRT
<213> ORGANISM: Homo sapiens

<400> SEQUENCE: 79

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Lys Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 80
<211> LENGTH: 120
<212> TYPE: PRT
<213> ORGANISM: Homo sapiens

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Pro Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
        115                 120

<210> SEQ ID NO 81
<211> LENGTH: 120
<212> TYPE: PRT
<213> ORGANISM: Homo sapiens

<400> SEQUENCE: 81

Glu Val Gln Leu Leu Glu Ser Gly Gly Gly Phe Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ser Val Tyr Tyr Cys
                85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 82
<211> LENGTH: 120
<212> TYPE: PRT
<213> ORGANISM: Homo sapiens

<400> SEQUENCE: 82

Glu Val Gln Leu Leu Glu Ser Gly Gly Gly Leu Val Gln Pro Gly Gly
1               5                   10                  15

Ser Leu Arg Leu Pro Cys Ala Ala Ser Gly Phe Thr Phe Glu Trp Tyr
            20                  25                  30

Trp Met Thr Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 83
<211> LENGTH: 120
<212> TYPE: PRT
<213> ORGANISM: Homo sapiens

<400> SEQUENCE: 83

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Glu Trp Tyr
            20                  25                  30

Trp Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
                100                 105                 110

Gly Thr Leu Val Thr Val Ser Ser
        115                 120

<210> SEQ ID NO 84
<211> LENGTH: 120
<212> TYPE: PRT
<213> ORGANISM: Homo sapiens

<400> SEQUENCE: 84

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Glu Trp Tyr
            20                  25                  30

Trp Met Gly Trp Val Arg Gln Ala Pro Gly Lys Gly Leu Glu Trp Val
        35                  40                  45

Ser Ala Val Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Pro Asn Phe Gly Tyr Arg Gly Gln
            100                 105                 110

Gly Thr Leu Val Thr Val Ser Ser
        115                 120

<210> SEQ ID NO 85
<211> LENGTH: 120
<212> TYPE: PRT
<213> ORGANISM: Homo sapiens

<400> SEQUENCE: 85

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Pro Asn Phe Gly Tyr Arg Gly Gln
            100                 105                 110

Gly Thr Leu Val Thr Val Ser Ser
        115                 120

<210> SEQ ID NO 86
<211> LENGTH: 120
<212> TYPE: PRT
<213> ORGANISM: Homo sapiens

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
            35                  40                  45

Ser Ala Met Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Asn Arg Gly Leu
            100                 105                 110

Gly Thr Leu Val Thr Val Ser Ser
            115                 120

<210> SEQ ID NO 87
<211> LENGTH: 120
<212> TYPE: PRT
<213> ORGANISM: Homo sapiens

<400> SEQUENCE: 87

Glu Val Gln Leu Leu Glu Ser Gly Gly Gly Ser Val Gln Pro Gly Gly
1               5                   10                  15

Ser Leu Arg Leu Ser Cys Ala Ala Ser Gly Phe Thr Phe Asp Trp Tyr
            20                  25                  30

Trp Met Gly Trp Val Arg Gln Ala Pro Gly Lys Gly Leu Glu Trp Ala
            35                  40                  45

Ser Ala Ile Ser Gly Ser Gly Gly Ser Thr Tyr Tyr Ala Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asp Phe Gly Tyr Arg Gly Gln
            100                 105                 110

Gly Thr Leu Val Thr Val Ser Ser
            115                 120

<210> SEQ ID NO 88
<211> LENGTH: 120
<212> TYPE: PRT
<213> ORGANISM: Homo sapiens

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Gly Ala Val Tyr Tyr Cys
                85                  90                  95

Ala Lys Val Lys Leu Gly Gly Glu Leu Asn Phe Gly Tyr Arg Gly Gln
              100                 105                 110

Gly Thr Leu Val Thr Val Ser Ser
            115                 120

<210> SEQ ID NO 89
<211> LENGTH: 120
<212> TYPE: PRT
<213> ORGANISM: Homo sapiens

<400> SEQUENCE: 89

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Gly Pro Asn Phe Gly Asn Arg Gly Gln
              100                 105                 110

Gly Thr Pro Val Thr Val Ser Ser
            115                 120

<210> SEQ ID NO 90
<211> LENGTH: 120
<212> TYPE: PRT
<213> ORGANISM: Homo sapiens

<400> SEQUENCE: 90

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
             20                  25                  30

Trp Met Gly Trp Val Arg Gln Ala Pro Gly Lys Gly Leu Glu Trp Val
             35                  40                  45

Ser Ala Ile Ser Gly Ser Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Pro Glu Asp Ala Ala Val Tyr Tyr Cys
                 85                  90                  95

Ala Lys Val Lys Leu Gly Gly Gly Pro Asn Phe Gly Pro Arg Gly Gln
              100                 105                 110

Gly Thr Leu Val Thr Val Ser Ser
            115                 120

<210> SEQ ID NO 91
<211> LENGTH: 120
<212> TYPE: PRT
<213> ORGANISM: Homo sapiens

<400> SEQUENCE: 91

Glu Val Gln Leu Leu Glu Ser Gly Gly Gly Leu Val Gln Pro Gly Gly

-continued

```
                1               5                  10                 15
Ser Leu Arg Leu Ser Cys Ala Ala Ser Gly Phe Thr Phe Glu Trp Tyr
                20                 25                 30

Trp Met Gly Trp Val Arg Gln Ala Pro Gly Lys Gly Leu Glu Trp Val
            35                 40                 45

Ser Ala Ile Ser Gly Ser Gly Ser Thr Tyr Tyr Ala Asp Ser Val
        50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Ala Ala Val Tyr Tyr Cys
                85                 90                 95

Ala Lys Val Lys Leu Gly Gly Pro Asn Phe Gly Asn Arg Gly Gln
                100                105                110

Gly Thr Leu Val Thr Val Ser Ser
            115                120
```

<210> SEQ ID NO 92
<211> LENGTH: 120
<212> TYPE: PRT
<213> ORGANISM: Homo sapiens

<400> SEQUENCE: 92

```
                1               5                  10                 15
Glu Val Gln Leu Leu Glu Ser Gly Gly Gly Leu Val Gln Pro Gly Gly

Ser Leu Arg Leu Ser Cys Ala Ala Ser Gly Phe Thr Ile Glu Trp Tyr
                20                 25                 30

Trp Met Gly Trp Val Arg Gln Ala Pro Gly Lys Gly Leu Glu Trp Val
            35                 40                 45

Ser Ala Ile Ser Gly Ser Gly Ser Thr Tyr Tyr Ala Asp Ser Val
        50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Ala Ala Val Tyr Tyr Cys
                85                 90                 95

Ala Lys Val Lys Leu Gly Gly Pro Asn Phe Gly Tyr Arg Gly Gln
                100                105                110

Gly Thr Leu Val Thr Val Ser Ser
            115                120
```

<210> SEQ ID NO 93
<211> LENGTH: 120
<212> TYPE: PRT
<213> ORGANISM: Homo sapiens

<400> SEQUENCE: 93

```
                1               5                  10                 15
Glu Val Gln Leu Leu Glu Ser Gly Gly Gly Leu Val Gln Pro Gly Gly

Ser Leu Arg Leu Ser Cys Ala Ala Ser Gly Phe Thr Phe Glu Trp Tyr
                20                 25                 30

Trp Met Gly Trp Val Arg Gln Ala Pro Gly Lys Gly Leu Glu Trp Val
            35                 40                 45

Ser Ala Ile Ser Gly Ser Gly Ser Thr Phe Tyr Ala Asp Ser Val
        50                 55                 60

Lys Gly Arg Phe Thr Ile Ser Arg Asp Asn Ser Lys Asn Thr Leu Tyr
65                  70                 75                 80

Leu Gln Met Asn Ser Leu Arg Ala Glu Asp Ala Ala Val Tyr Tyr Cys
```

```
                    85                  90                  95
Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 94
<211> LENGTH: 120
<212> TYPE: PRT
<213> ORGANISM: Homo sapiens

<400> SEQUENCE: 94

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Trp Tyr
                 20                  25                  30

Trp Met Gly Trp Val Arg Gln Ala Pro Gly Lys Gly Leu Glu Trp Val
                 35                  40                  45

Thr Ala Ile Ser Gly Ser Gly Ser Thr Phe Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 95
<211> LENGTH: 120
<212> TYPE: PRT
<213> ORGANISM: Homo sapiens

<400> SEQUENCE: 95

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Ser Phe Glu Trp Tyr
                 20                  25                  30

Trp Met Gly Trp Val Arg Gln Ala Pro Gly Lys Gly Leu Glu Trp Val
                 35                  40                  45

Ser Ala Ile Ser Gly Ser Gly Asp Ser Thr Tyr Tyr Ala Asp Ser Val
             50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Val Lys Leu Gly Gly Gly Pro Asn Phe Gly Tyr Arg Gly Gln
                100                 105                 110

Gly Thr Leu Val Thr Val Ser Ser
            115                 120

<210> SEQ ID NO 96
<211> LENGTH: 120
<212> TYPE: PRT
<213> ORGANISM: Homo sapiens

<400> SEQUENCE: 96
```

-continued

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Pro Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Gln Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
            115                 120

<210> SEQ ID NO 97
<211> LENGTH: 120
<212> TYPE: PRT
<213> ORGANISM: Homo sapiens

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Gly Pro Asn Phe Gly Tyr Arg Gly Gln
            100                 105                 110

Gly Thr Leu Val Thr Val Ser Ser
            115                 120

<210> SEQ ID NO 98
<211> LENGTH: 120
<212> TYPE: PRT
<213> ORGANISM: Homo sapiens

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Ala Ala Val Tyr Tyr Cys
                85                  90                  95

Ala Lys Val Lys Leu Gly Gly Gly Pro Asn Tyr Gly Tyr Arg Gly Gln
            100                 105                 110

Gly Thr Leu Val Thr Val Ser Ser
            115             120
```

<210> SEQ ID NO 99
<211> LENGTH: 360
<212> TYPE: DNA
<213> ORGANISM: Homo sapiens

<400> SEQUENCE: 99

```
gaggtgcagc tgttggagtc tgggggaggc ttggtacagc ctgggggtc cctgcgtctc      60
tcctgtgcag cctccggatt cacctttgag tggtattgga tgggttgggt ccgccaggct    120
ccagggaagg gtctagagtg ggtctcagct attagtggta gtggtggtag cacatactac    180
gcagactccg tgaagggccg gttcaccatc tcccgcgaca attccaagaa cacgctgtat    240
ctgcaaatga acagcctgcg tgccgaggac accgcggtat attactgtgc gaaagttaag    300
ttggggggggg ggcctaatttt tgactactgg ggccaggaa ccctggtcac cgtctcgagc    360
```

<210> SEQ ID NO 100
<211> LENGTH: 366
<212> TYPE: DNA
<213> ORGANISM: Homo sapiens

<400> SEQUENCE: 100

```
gaggtgcagc tgttggagtc tgggggaggc ttggtacagc ctgggggtc cctgcgtctc      60
tcctgtgcag cctccggatt cacctttgtt gcttataata tggggtgggt ccgccaggct    120
ccagggaagg gtctagagtg ggtctcattt attgatatgt atggtgctaa gacatactac    180
gcagactccg tgaagggccg gttcaccatc tcccgcgaca attccaagaa cacgctgtat    240
ctgcagatga acagcctgcg tgccgaggat accgcggtat attactgtgc gaaactttgt    300
ttgatggatt gttctgggga tattttttgac tactggggtc agggaaccct ggtcaccgtc    360
tcgagc                                                                366
```

<210> SEQ ID NO 101
<211> LENGTH: 348
<212> TYPE: DNA
<213> ORGANISM: Homo sapiens

<400> SEQUENCE: 101

```
gaggtgcagc tgttggagtc tgggggaggc ttggtacagc ctgggggtc cctgcgtctc      60
tcctgtgcag cctccggatt cacctttcct gctgatgaga tgtattgggt ccgccaggct    120
ccagggaagg gtctagagtg ggtctcaagt attggttggc cggtggtgc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatggt    300
cgtaattttg actactgggg tcagggaacc ctggtcaccg tctcgagc                 348
```

<210> SEQ ID NO 102
<211> LENGTH: 366
<212> TYPE: DNA
<213> ORGANISM: Homo sapiens

<400> SEQUENCE: 102

```
gaggtgcagc tgttggagtc tgggggaggc ttggtacagc ctggggggtc cctgcgtctc      60
tcctgtgcag cctccggatt cacctttgat cagtatgata tgtcgtgggt ccgccaggct     120
ccagggaagg gtctagagtg ggtctcactg attgatccga gcggtggtca tacatactac     180
gcagactccg tgaagggccg gttcaccatc tcccgcaaca attccaagaa cacgctgtat     240
ctgcaaatga acagcctgcg tgccgaggac accgcggtat attactgtgc gaaaccggtt     300
ttttctgatt ggcctgcggt ggagtttgac tactggggtc agggaaccct ggtcaccgtc     360
tcgagc                                                                366
```

<210> SEQ ID NO 103
<211> LENGTH: 348
<212> TYPE: DNA
<213> ORGANISM: Homo sapiens

<400> SEQUENCE: 103

```
gaggtgcagc tgttggagtc tgggggaggc ttggtacagc ctggggggtc cctgcgtctc      60
tcctgtgcag cctccggatt cacctttggg aattatgata tgcagtgggt ccgccaggct     120
ccagggaagg gtctagagtg ggtctcatct attgatggga ctggtggtac tacatactac     180
gcagactccg tgaagggccg gttcaccatc tcccgcgaca attccaagaa cacgctgtat     240
ctgcaaatga acagcctgcg tgccgaggac accgcggtat attactgtgc gcaagagact     300
aatgcgtttg actactgggg tcagggaacc ctggtcaccg tctcgagc                  348
```

<210> SEQ ID NO 104
<211> LENGTH: 372
<212> TYPE: DNA
<213> ORGANISM: Homo sapiens

<400> SEQUENCE: 104

```
gaggtgcagc tgttggagtc tgggggaggc ttggtacagc ctggggggtc cctgcgtctc      60
tcctgtgcag cctccggatt cacctttggt ggttatcaga tgggttgggt ccgccaggct     120
ccagggaagg gtcttgagtg ggtctcatttt attgatttta ctggtgcgca tacatactac    180
gcagactccg tgaagggccg gttcaccatc tcccgcgaca attccaagaa cacgctgtat     240
ctgcaaatga acagcctgcg tgccgaggac accgcggtat attactgtgc gaaattgagt     300
gatgatctta ctttgcctga gcggtttccg tttgactact ggggtcaggg aaccctggtc     360
accgtctcga gc                                                         372
```

<210> SEQ ID NO 105
<211> LENGTH: 369
<212> TYPE: DNA
<213> ORGANISM: Homo sapiens

<400> SEQUENCE: 105

```
gaggtgcagc tgttggagtc tgggggaggc ttggtacagc ctggggggtc cctgcgtctc      60
tcctgtgcag cctccggatt cacctttgct gattataata tgacttgggt ccgccaggct     120
ccagggaagg gtctagagtg ggtctcatgg attgatcagg agggtgtttt tacatactac     180
gcagattccg tgaagggccg gttcaccatc tcccgcgaca attccaagaa cacgctgtat     240
ctgcaaatga acagcctgcg tgccgaggat accgcggtat attactgtgc gaaagatttt     300
tcggcggctg ttatgcttag gactagtttt gactactggg gtcagggaac cctggtcacc     360
gtctcgagc                                                             369
```

<210> SEQ ID NO 106
<211> LENGTH: 348
<212> TYPE: DNA
<213> ORGANISM: Homo sapiens

<400> SEQUENCE: 106

| | | | | | | |
|---|---|---|---|---|---|---|
| gaggtgcagc | tgttggagtc | tgggggaggc | ttggtacagc | ctgggggtc | cctgcgtctc | 60 |
| tcctgtgcag | tctccggatt | cacctttcat | gattatggga | tggtttgggt | ccgccaggct | 120 |
| ccagggaagg | gtctagagtg | ggtctcacag | attagtattg | atggtcgtac | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaaaggatt | 300 |
| tttgagtttg | actactgggg | tcagggaacc | ctggtcaccg | tctcgagc | | 348 |

<210> SEQ ID NO 107
<211> LENGTH: 351
<212> TYPE: DNA
<213> ORGANISM: Homo sapiens

<400> SEQUENCE: 107

| | | | | | | |
|---|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttagt | gcgtataata | tgtcttgggt | ccgccaggct | 120 |
| ccagggaagg | gtctagagtg | ggtctcagct | atttcgccgt | ctggtaatga | dacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaaggggct | 300 |
| ggggaggctt | ttgactactg | gggtcaggga | accctggtca | ccgtctcgag | c | 351 |

<210> SEQ ID NO 108
<211> LENGTH: 351
<212> TYPE: DNA
<213> ORGANISM: Homo sapiens

<400> SEQUENCE: 108

| | | | | | | |
|---|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttact | gagtataata | tgggttgggt | ccgccaggct | 120 |
| ccagggaagg | gtctagagtg | ggtctcattt | attgggcatt | ctggtcagca | tacatactac | 180 |
| gcagactccg | tgaagggccg | gttcaccatc | tcccgcgaca | attccaagaa | cacgctgtat | 240 |
| ctgcaaatga | atagcctgcg | tgccgaggac | accgcggtat | attactgtgc | ggaactgaat | 300 |
| aatttgatgt | ttgactactg | gggtcaggga | accctggtca | ccgtctcgag | c | 351 |

<210> SEQ ID NO 109
<211> LENGTH: 363
<212> TYPE: DNA
<213> ORGANISM: Homo sapiens

<400> SEQUENCE: 109

| | | | | | | |
|---|---|---|---|---|---|---|
| gaggtgcagc | tgttggagtc | tgggggaggc | ttggtacagc | ctgggggtc | cctgcgtctc | 60 |
| tcctgtgcag | cctccggatt | cacctttggt | gagtataata | tggcgtgggt | ccgccaggct | 120 |
| ccagggaagg | gtcaagagtg | ggtctcattt | atttctacgg | gtggtcatgt | tacatactac | 180 |
| gcagactccg | tgaagggccg | gttcaccatc | tcccgcgaca | attccaagaa | cacgctgtat | 240 |
| ctgcaaatga | acagcctgcg | tgccgaggac | accgcggtat | attactgtgc | gaaattttcg | 300 |
| gtgcgttttta | ggtcgagtat | ttttgactac | tggggtcagg | gaaccctggt | caccgtctcg | 360 | agc                                                                  363

<210> SEQ ID NO 110
<211> LENGTH: 366
<212> TYPE: DNA
<213> ORGANISM: Homo sapiens

<400> SEQUENCE: 110
gaggtgcagc tgttggagtc tgggggaggc ttggtacagc ctgggggtc cctgcgtctc     60 tcctgtgcag cctccggata cacctttact gagtatacga tgggttgggt ccgccaggct   120
ccagggaagg gtctagagtg ggtctcatgg attgctgttg atggtattca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaattggat   300
tggacggcta ctgattttc tattttgac tactggggtc agggaaccct ggtcaccgtc     360
tcgagc                                                               366

<210> SEQ ID NO 111
<211> LENGTH: 366
<212> TYPE: DNA
<213> ORGANISM: Homo sapiens

<400> SEQUENCE: 111
gaggtgcagc tgttggagtc tgggggaggc ttggtacagc ctgggggtc cctgcgtctc     60 tcctgtgcag cctccggatt cacctttgcg aattatacta tgctgtgggt ccgccaggct   120
ccagggaagg gtctagagtg ggtctcagtt attagtgctg aggtcggac tacatactac   180 gcagactccg tgaagggccg gttcaccatc tcccgcgaca attccaagaa cacgctgtat   240
ctgcaaatga acagcctgcg tgccgaggac accgcggtat attactgtgc gaaacttaat   300
atgaaggcta ctaattttaa ggattttgac tactggggtc agggaaccct ggtcaccgtc   360
tcgagc                                                               366

<210> SEQ ID NO 112
<211> LENGTH: 366
<212> TYPE: DNA
<213> ORGANISM: Homo sapiens

<400> SEQUENCE: 112
gaggtgcagc tgttggagtc tgggggaggc ttggtacagc ctgggggtc cctgcgtctc     60 tcctgcgcag cctccggatt cacctttcg gagtatgcga tgctttgggt ccgccaggct   120
ccagggaagg gtctagagtg ggtctcactt attgatcgga cgggtgttat tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacgggat   300
tatcagtatc atctgtatca ggattttgac taccggggtc agggaaccct ggtcaccgtc   360
tcgagc                                                               366

<210> SEQ ID NO 113
<211> LENGTH: 366
<212> TYPE: DNA
<213> ORGANISM: Homo sapiens

<400> SEQUENCE: 113
gaggtgcagc tgttggagtc tgggggaggc ttggtacagc ctgggggtc cctgcgtctc     60

```
tcctgtgcag cctccggatt cacctttgcg acgtatagta tggggtgggt ccgccaggct      120
ccagggaagg gtctagagtg ggtctcaatg attgatccgg agggttatca tacatactac      180
gcagactccg tgaagggccg gttcaccatc tcccgcgaca attccaagaa cacgctgtat      240
ctgcaaatga acagcctgcg tgccgaggac accgcggtat attactgtgc ggaaacgaat      300
cggcctttga cgtataagcc ttggtttgac tactggggtc agggaaccct ggtcaccgtc      360
tcgagc                                                                 366
```

<210> SEQ ID NO 114
<211> LENGTH: 363
<212> TYPE: DNA
<213> ORGANISM: Homo sapiens

<400> SEQUENCE: 114

```
gaggtgcagc tgttggagtc tgggggaggc ttggtacagc ctggggggtc cctgcgtctc       60
tcctgtgcag cctccggatt cacctttact gattataata tggcttgggt ccgccaggct      120
ccagggaagg gtctagagtg ggtctcattt attagtcagg agggtcatca tacatactac      180
gcagactccg tgaagggccg gttcaccatc tcccgcgaca attccaagaa cacgctgtat      240
ctgcaaatga acagcctgcg tgccgaggac accgcggtat attactgtgc gaaatttagt      300
actattgcta cgttgtctct gtttgactac tggggtcagg gaaccctggt caccgtctcg      360
agc                                                                    363
```

<210> SEQ ID NO 115
<211> LENGTH: 366
<212> TYPE: DNA
<213> ORGANISM: Homo sapiens

<400> SEQUENCE: 115

```
gaggtgcagc tgttggagtc tgggggaggc ttggtacagc ctggggggtc cctgcgtctc       60
tcctgtgcag cctccggatt cacctttgct acgtataata tgggttgggt ccgccaggct      120
ccagggaagg gtctagagtg ggtctcatct attgcgtggc ttggttctga catatactac      180
gcagactccg tgaagggccg gttcaccatc tcccgcgaca attccaagaa cacgctgtat      240
ctgcaaatga acagcctgcg tgccgaggac accgcggtat attactgtgc gaaacattgt      300
aaggcggagt gtactgggga tcttttttgac tactggggtc agggaaccct ggtcaccgtc      360
tcgagc                                                                 366
```

<210> SEQ ID NO 116
<211> LENGTH: 366
<212> TYPE: DNA
<213> ORGANISM: Homo sapiens

<400> SEQUENCE: 116

```
gaggtgcagc tgttggagtc tgggggaggc ttggtacagc ctgggggggc cctgcgtctc       60
tcctgtgcag cctccggatt cacctttggt atttattcga tgggttgggt ccgccaggct      120
ccagggaagg gtctagagtg ggtctcatct atttcgggtg ttggtatgga gacatactac      180
gcagactccg tgaagggccg gttcaccatc tcccgcgaca attccagaa cacgctgtat       240 ctgcaaatga acagcctgcg tgccgaggat accgcggtat attactgtgc gaaacattct      300
tatcctactc ggggtcgtca tcttttttgac tactggggtc agggaaccct ggtcaccgtc      360
tcgagc                                                                 366
```

```
<210> SEQ ID NO 117
<211> LENGTH: 360
<212> TYPE: DNA
<213> ORGANISM: Homo sapiens

<400> SEQUENCE: 117
gaggtgcagc tgttggagtc tgggggaggc ttggtacagc ctggggggtc cctgcgtctc    60
tcctgtgcag cctccggatt cacctttgag tggtattgga tgggttgggt ccgccaggct   120
ccaggcaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccgaggac accgcggtat attactgtgc gaaagttaag   300 ttggggggg ggcctaattt tgactaccgg ggccagggaa ccctggtcac cgtctcgagc    360

<210> SEQ ID NO 118
<211> LENGTH: 360
<212> TYPE: DNA
<213> ORGANISM: Homo sapiens

<400> SEQUENCE: 118
gaggtgcagc tgttggagtc tgggggaggc ttggtacagc ctggggggtc cctgcgtctc    60
tcctgtgcag cctccggatt cacctttcat cggtattcta tgggttgggt ccgccaggct   120
ccagggaagg gtctagagtg gtctcagct attagttctt ctggtggtat cacatactac    180
gcagactccg tgaagggccg gttcaccatc tcccgcgaca attccaagaa cacgctgtat   240
ctgcaaatga acagcctgcg tgccgaggac accgcggtat attactgtgc gaaatcgacg   300
caggcgcagg ggctggagtt agactactgg ggtcagggaa ccctggtcac cgtctcgagc   360

<210> SEQ ID NO 119
<211> LENGTH: 360
<212> TYPE: DNA
<213> ORGANISM: Homo sapiens

<400> SEQUENCE: 119
gaggtgcagc tgttggagtc tgggggaggc ttggtacagc ctggggggtc cctgcgtctc    60
tcctgtgcag cctccggatt cacctttgag tggtattgga tgggttgggt ccgccaggct   120
ccagggaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acaacctgcg tgccgaggac accgcggtat attactgtgc gaaagttaag   300 ttggggggg ggcctaattt tgactaccgg ggccagggaa ccctggtcac cgtctcgagc    360

<210> SEQ ID NO 120
<211> LENGTH: 360
<212> TYPE: DNA
<213> ORGANISM: Homo sapiens

<400> SEQUENCE: 120
gaggtgcagc tgttggagtc tgggggaggc ttggtacagc ctggggggtc cctgcgtctc    60
tcctgtgcag cctccggatt cacctttgag tggtattgga tgggatgggt ccgccaggct   120
ccaggcaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccgaggac accgcggtat attactgtgc gaaagttaag   300 ttggggggg ggcctaattt tgactaccgg ggccagggaa ccctggtcac cgtctcgagc    360
```

<210> SEQ ID NO 121
<211> LENGTH: 360
<212> TYPE: DNA
<213> ORGANISM: Homo sapiens

<400> SEQUENCE: 121
gaggtgcagc tgttggagtc tgggggaggc ttggtacagc ctgggggtc cctgcgtctc    60 acctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca actccaagaa cacgctgtat   240
ctgcaaatga acagcctgcg tgccgaggac accgcggtat attactgtgc gaaagttaag   300
ttgggggggg ggcctaattt tgactactgg ggccagggaa ccctggtcac cgtctcgagc   360

<210> SEQ ID NO 122
<211> LENGTH: 360
<212> TYPE: DNA
<213> ORGANISM: Homo sapiens

<400> SEQUENCE: 122
gaggtgcagc tgttggagtc tgggggaggc ttggtacagc ctgggggtc cctgcgtctc    60 tcctgtgcag cctccggatt cacctttgag tggtattgga tgggttggat ccgccaggct   120
ccagggaagg gtctagagtg ggtctcggct atcagtggta gtggtggtag tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg ggcctaattt tgactactgg ggccagggaa ccctggtcac cgtctcgagc   360

<210> SEQ ID NO 123
<211> LENGTH: 360
<212> TYPE: DNA
<213> ORGANISM: Homo sapiens

<400> SEQUENCE: 123
gaggtgcagc tgttggagtc tgggggaggc ttggtacagc ctgggggtc cctgcgtctc    60 tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg ggcctaattt tgactaccgg ggccagggaa ccctggtcac cgtctcgagc   360

<210> SEQ ID NO 124
<211> LENGTH: 360
<212> TYPE: DNA
<213> ORGANISM: Homo sapiens

<400> SEQUENCE: 124
gaggtgcagc tgttggagtc tgggggaggc ttggtacagc ctgggggtc cctgcgtctc    60 tcctgtgcag cctccggatt cacctttgag tggtattgga tgggttgggt ccgccaggct   120
ccagggaagg gtccagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg gccctaattt tgactaccgg ggccagggaa ccctggtcac cgtctcgagc   360

<210> SEQ ID NO 125
<211> LENGTH: 360
<212> TYPE: DNA
<213> ORGANISM: Homo sapiens

<400> SEQUENCE: 125

```
gaggtgcagc tgttggagtc tgggggaggc ttggtacagc ctgggggctc cctgcgtctc      60
tcctgtgcag cctccggatt cacctttgag tggtattgga tgggttgggt ccgccaggct    120
ccagggaagg gtctagagtg ggtctcagct atcagtggta gtggtggtag cacatactac    180
gcagactccg tgaagggccg gttcaccatc tcccgcgaca attccaagaa cacgctgtat    240
ctgcaaatga acagcctgcg tgccaaggac accgcggtat attactgtgc gaaagtgaag    300
ttggggggg ggcctaattt tgactacagg ggccagggaa ccctggtcac cgtctcgagc    360
```

<210> SEQ ID NO 126
<211> LENGTH: 360
<212> TYPE: DNA
<213> ORGANISM: Homo sapiens

<400> SEQUENCE: 126

```
gaggtgcagc tgttggagtc tgggggaggc ttggtacagc ctgggggctc cctgcgtctc     60
tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccggggac accgcggtat attactgtgc gaaagttaag   300
ttgggcgggg ggcctaattt tgactacagg ggccagggaa ccctggtcac cgtctcgagc   360
```

<210> SEQ ID NO 127
<211> LENGTH: 360
<212> TYPE: DNA
<213> ORGANISM: Homo sapiens

<400> SEQUENCE: 127

```
gaggtgcagc tgttggagtc tgggggaggc ctggtacagc ctgggggctc cctgcgtctc     60
tcctgtgcag cctccggatt caccttcgag tggtattgga tgggttgggt ccgccaggct   120
ccagggaagg gtctagagtg ggtctcagct atcagtggta gtggtggtag aacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
ttgggggggg ggcctaattt tgactactgg ggccagggaa ccctggtcac cgtctcgagc   360
```

<210> SEQ ID NO 128
<211> LENGTH: 360
<212> TYPE: DNA
<213> ORGANISM: Homo sapiens

<400> SEQUENCE: 128

```
gaggtgcagc tgttggagtc tgggggaggc ttggtacagc ctgggggctc cctgcgtctc     60
tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttaag   300
```
ttgggcgggg ggcctaattt tgacgaccgg ggccagggaa ccctggtcac cgtctcgagc    360

<210> SEQ ID NO 129
<211> LENGTH: 360
<212> TYPE: DNA
<213> ORGANISM: Homo sapiens

<400> SEQUENCE: 129
gaggtgcagc tgttggagtc tgggggaggc ttggtacagc ctgggggtc cctgcgtctc     60 tcctgtgcag cctccggatt cacctttgag tggtattgga tgggttgggt ccgccaggct    120
ccagggaagg gtctagagtg ggtctcagct atcagtggta gtggtggtag caaatactac    180
gcagactccg tgaagggccg gttcaccatc tcccgcgaca attccaagaa cacactgtat    240
ctgcaaatga acagcctgcg tgccgaggac accgcggtat attactgtgc gaaagttaag    300
ttgggggggg ggcctaattt tgactaccgg ggccagggaa ccctggtcac cgtctcgagc    360

<210> SEQ ID NO 130
<211> LENGTH: 360
<212> TYPE: DNA
<213> ORGANISM: Homo sapiens

<400> SEQUENCE: 130
gaggtgcagc tgttggagtc tgggggaggc ttggtacagc ctgggggtc cctgcgtctc     60 tcctgtgcag cctccggatt cacctttggg tggtattgga tgggttgggt ccgccaggct    120
ccagggaagg gtctagagtg ggcctcagct atcagtggta gtggtggtaa cacatactac    180
gcagactccg tgaagggccg gttcaccatc tcccgcgaca attccaagaa cacgctgtat    240
ctgcaaatga acagcctgcg tgccgaggac accgcggtat attactgtgc gaaagttaag    300
ttgggggggg ggcctaattt tgactactgg ggccagggaa ccctggtcac cgtctcgagc    360

<210> SEQ ID NO 131
<211> LENGTH: 360
<212> TYPE: DNA
<213> ORGANISM: Homo sapiens

<400> SEQUENCE: 131
gaggtgcagc tgttggagtc tgggggaggc ttggtacagc ctgggggtc cctgcgtctc     60 tcctgtgcag cctccggatt cacctttgag tggtattgga tgggttgggt ccgccaggct    120
ccagggaagg gtctagggtg ggtctcagct atcagtggta gtggtggtag cacatactac    180
gcagactccg tgaggggccg gttcaccatc tcccgcgaca attccaagaa cacgctgtat    240
ctgcaaatga acagcctgcg tgccgaggac accgcggtat attactgtgc gaaagttaag    300
ttgggggggg ggcctaattt tgactaccgg ggccagggaa ccctggtcac cgtctcgagc    360

<210> SEQ ID NO 132
<211> LENGTH: 360
<212> TYPE: DNA
<213> ORGANISM: Homo sapiens
<220> FEATURE:
<221> NAME/KEY: misc_feature
<222> LOCATION: 60
<223> OTHER INFORMATION: n = A,T,C or G

<400> SEQUENCE: 132
gaggtgcagc tgttggagtc tgggggaggc ttggtacagc ctgggggtc cctgcgtctn     60 tcctgtgcag cctccggatt cacctttgag tggtattgga tgggttgggt ccgccaggct    120
ccaggcaagg gtccagagtg ggtctcagct atcagtggta gtggtggtag cacatactac    180

```
gcagactccg tgaagggccg gttcaccatc tcccgcgaca attccaagaa cacgctgtat    240
ctgcaaatga acagcctgcg tgccgaggac accgcggtat attactgtgc gaaagttaag    300 ttggggggggg ggcctaattt tgactactgg ggccagggaa ccctggtcac cgtctcgagc   360
```

```
<210> SEQ ID NO 133
<211> LENGTH: 360
<212> TYPE: DNA
<213> ORGANISM: Homo sapiens

<400> SEQUENCE: 133
gaggtgcagc tgttggagtc tgggggaggc ttggtacagc ctgggggtc cctgcgtctc     60 tcctgtgcag cctccggatt cacctttgag tggtattgga tgggttgggt ccgccaggct   120
ccaggcaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccgaggac accgcggtat attactgtgc gaaagttaag   300 ttggggggggg ggcctaattt tgactaccgg ggccggggaa ccctggtcac cgtctcgagc  360
```

```
<210> SEQ ID NO 134
<211> LENGTH: 360
<212> TYPE: DNA
<213> ORGANISM: Homo sapiens

<400> SEQUENCE: 134
gaggtgcagc tgttggagtc tgggggaggc ttggtacagc ctgggggtc cctgcgtctc     60 tcctgtgcag cctccggatt cacctttgag tggtattgga tgggttggat ccgccaggct   120
ccagggaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccaaggac accgcggtat attactgtgc gaaagtgaag   300 ttggggggggg ggcctaattt tgactacagg ggccagggaa ccctggtcac cgtctcgagc  360
```

```
<210> SEQ ID NO 135
<211> LENGTH: 360
<212> TYPE: DNA
<213> ORGANISM: Homo sapiens

<400> SEQUENCE: 135
gaggtgcagc tgttggagtc tgggggaggc ttggtacagc ctgggggtc cctgcgtctc     60 tcctgtgcag cctccggatt caccctttgag tggtattgga tgggttggat ccgccaggct  120
ccagggaagg gtctagggtg gtctcagct atcagtggta gtggtggtag cacatactac    180
gcagactccg tgagggcccg gttcaccatc tcccgcgaca attccaagaa cacgctgtat   240
ctgcaaatga acagcctgcg tgccgaggac accgcggtat attactgtgc gaaagttaag   300 ttggggggggg ggcctaattt tgactaccgg ggccagggaa ccctggtcac cgtctcgagc  360
```

```
<210> SEQ ID NO 136
<211> LENGTH: 360
<212> TYPE: DNA
<213> ORGANISM: Homo sapiens

<400> SEQUENCE: 136
gaggtgcagc tgttggagtc tgggggaggc ttggtacagc ctgggggtc cctgcgtctc     60 tcctgtgcag cctccggatt cacctttggg tggtattgga tgggttgggt ccgccaggct   120
```

```
ccagggaagg gtctagagtg ggcctcagct atcagtggta gtggtggtaa cacatactac    180
gcagactccg tgaagggccg gttcaccatc tcccgcgaca attccaagaa cacgctgtat    240
ctgcaaatga acagcctgcg tgccgaggac accgcggtat attactgtgc gaaagttaag    300 ttggggggggg ggcctaattt tgactactgg ggccagggaa ccctggtcac cgtctcgagc   360
```

<210> SEQ ID NO 137
<211> LENGTH: 360
<212> TYPE: DNA
<213> ORGANISM: Homo sapiens

<400> SEQUENCE: 137

```
gaggtgcagc tgttggagtc tgggggaggc ttggtacagc ctgggggggtc cctgcgtctc    60 tcctgtgcag cctccggatt cacctttgag tggtattgga tgggttgggt ccgccaggct   120
ccagggaagg gtctaggggtg ggtctcagct atcagtggta gtggtggtag cacatactac   180
gcagactccg tgagggggccg gttcaccatc tcccgcgaca attccaagaa cacgctgtat   240
ctgcaaatga acagcctgcg tgccaaggac accgcggtat attactgtgc gaaagttaag   300 ttggggggggg ggcctaattt tgactaccgg ggccagggaa ccctggtcac cgtctcgagc   360
```

<210> SEQ ID NO 138
<211> LENGTH: 360
<212> TYPE: DNA
<213> ORGANISM: Homo sapiens

<400> SEQUENCE: 138

```
gaggtgcagc tgttggagtc tgggggaggc ttggtacagc ctgggggggtc cctgcgtctc    60 tcctgtgcag cctccggatt cacctttggg tggtattgga tgggttgggt ccgccaggct   120
ccagggaagg gtctagagtg ggcctcagct atcagtggta gtggtggtaa cacatactac   180
gcagactccg tgaagggccg gttcaccatc tcccgcgaca attccaagaa cacgctgtat   240
ctgcaaatga acagcctgcg tgccaaggac accgcggtat attactgtgc gaaagttaag   300 ttggggggggg ggcctaattt tgactactgg ggccagggaa ccctggtcac cgtctcgagc   360
```

<210> SEQ ID NO 139
<211> LENGTH: 360
<212> TYPE: DNA
<213> ORGANISM: Homo sapiens

<400> SEQUENCE: 139

```
gaggtgcagc tgttggagtc tgggggaggc ttggtacagc ctgggggggtc cctgcgtctc    60 tcctgtgcag cctccggatt cacctttggg tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccaaggac accgcggtat attactgtgc gaaagtgaag   300 ttggggggggg ggcctaattt tgactacagg ggccagggaa ccctggtcac cgtctcgagc   360
```

<210> SEQ ID NO 140
<211> LENGTH: 360
<212> TYPE: DNA
<213> ORGANISM: Homo sapiens

<400> SEQUENCE: 140

```
gaggtgcagc tgttggagtc tgggggaggc ttggtacagc ctgggggggtc cctgcgtctc    60 tcctgtgcag cctccggatt cacctttggg tggtattgga tgggttgggt ccgccaggct   120
```

```
ccagggaagg gtctagggtg ggtctcagct atcagtggta gtggtggtag cacatactac    180
gcagactccg tgaggggccg gttcaccatc tcccgcgaca attccaagaa cacgctgtat    240
ctgcaaatga acagcctgcg tgccgaggac accgcggtat attactgtgc gaaagttaag    300 ttggggggggg ggcctaattt tgactaccgg ggccagggaa ccctggtcac cgtctcgagc   360
```

<210> SEQ ID NO 141
<211> LENGTH: 360
<212> TYPE: DNA
<213> ORGANISM: Homo sapiens

<400> SEQUENCE: 141

```
gaggtgcagc tgttggagtc tgggggaggc ttggtacagc ctggggggtc cctgcgtctc     60
tcctgtgcag cctccggatt cacctttgag tggtattgga tgggttgggt ccgccaggct    120
ccagggaagg gtctagagtg ggtctcagct atcagtggta gtggtggtag cacatactac    180
gcagactccg tgaagggccg gttcaccatc tcccgcgaca attccaagaa cacgctgtat    240
ctgcaaatga acagcctgcg tgccgaggac gccgcggtat attactgtgc gaaagttaag    300 ttggggggggg ggcctaattt tggctaccgg ggccagggaa ccctggtcac cgtctcgagc   360
```

<210> SEQ ID NO 142
<211> LENGTH: 360
<212> TYPE: DNA
<213> ORGANISM: Homo sapiens

<400> SEQUENCE: 142

```
gaggtgcagc tgttggagtc tgggggaggc ttggtacagc ctggggggtc cctgcgtctc     60
tcctgtgcag cctccggatt cgactttgag tggtattgga tgggttgggt ccgccaggct    120
ccagggaagg gtctagagtg ggtctcagct atcagtggta gtggtggtag cacatactac    180
gcagactccg tgaagggccg gttcaccatc tcccgcgaca attccaagaa cacgctgtat    240
ctgcaaatga acagcctgcg tgccgaggac gccgcggtat attactgtgc gaaagttaag    300 ttggggggggg ggcctaattt tggctaccgg ggccagggaa ccctggtcac cgtctcgagc   360
```

<210> SEQ ID NO 143
<211> LENGTH: 360
<212> TYPE: DNA
<213> ORGANISM: Homo sapiens

<400> SEQUENCE: 143

```
gaggtgcagc tgttggagtc tgggggaggc ttggtacagc ctggggggtc cctgcgtctc     60
tcctgtgcag cctccggatt cacctttgag tggtattgga tgggttgggt ccgccaggct    120
ccagggaagg gtctagagtg ggtctcagct atcagtggta gtggtggtag cacatactac    180
gcagactccg tgaagggccg gttcaccatc tcccgcgaca attccaagag cacgctgtat    240
ctgcaaatga acagcctgcg tgccgaggac gccgcggtat attactgtgc gaaagttaag    300 ttggggggggg ggcctaattt tggctaccgg ggccagggaa ccctggtcac cgtctcgagc   360
```

<210> SEQ ID NO 144
<211> LENGTH: 360
<212> TYPE: DNA
<213> ORGANISM: Homo sapiens

<400> SEQUENCE: 144

```
gaggtgcagc tgttggagtc tgggggaggc ttggtacagc ctggggggtc cctgcgtctc     60
```

```
tcctgtgcag cctccggatt cgactttgag tggtattgga tgggttgggt ccgccaggct    120
ccagggaagg gtctagagtg gtctcagct atcagtggta gtggtggtag cacatactac     180
gcagactccg tgaagggccg gttcaccatc tcccgcgaca attccaagaa cacgctgtat    240
ctgcaaatga acagcctgca tgccgaggac gccgcggtat attactgtgc gaaagttaag    300
ttgggggggg ggcctaattt tggctaccgg ggccagggaa ccctggtcac cgtctcgagc    360

<210> SEQ ID NO 145
<211> LENGTH: 360
<212> TYPE: DNA
<213> ORGANISM: Homo sapiens

<400> SEQUENCE: 145
gaggtgcagc tgttggagtc tgggggaggc ttggtacagc ctgggggtc  cctgcgtctc     60 tcctgtgcag tctccggact gacctttgag tggtattgga tgggttgggt ccgccaggct   120
ccagggaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttgggggggg ggcctaattt tggctaccgg ggccagggaa ccctggtcac cgtctcgagc   360

<210> SEQ ID NO 146
<211> LENGTH: 360
<212> TYPE: DNA
<213> ORGANISM: Homo sapiens

<400> SEQUENCE: 146
gaggtgcagc tgttggggtc tgggggaggc ttggtacagc ctgggggtc  cctgcgtctc     60 tcctgtgcag cctccggatt cacctttgcg tggtattgga tgggttgggt ccgccaggct   120
ccagggaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttgggggggg ggcctaattt tggctaccgg ggccagggaa ccctggtcac cgtctcgagc   360

<210> SEQ ID NO 147
<211> LENGTH: 360
<212> TYPE: DNA
<213> ORGANISM: Homo sapiens

<400> SEQUENCE: 147
gaggtgcagc tgttggagtc tgggggaggc ttggtacagc ctgggggtc  cctgcgtctc     60 tcctgtgcag cctccggatt cacctttgag tggtattgga tgggttgggt ccgccaggct   120
ccagggaagg gtctagagtg gtctcagct atcagtggta gtggtggtag cacatactac    180
gcagactccg tgaagggccg gttcaccatc tcccgcgaca attccaagaa cacgctgtat   240
ctgcaaatga acagcctgcg tgccaaggac gccgcggtat attactgtgc gaaagttaag   300
ttgggggggg ggcctaattt tggctaccgg ggccagggaa ccctggtcac cgtctcgagc   360

<210> SEQ ID NO 148
<211> LENGTH: 360
<212> TYPE: DNA
<213> ORGANISM: Homo sapiens

<400> SEQUENCE: 148
gaggtgcagc tgttggagtc tgggggaggc ttggtacagc ctgggggtc  cctgcgtctc     60
```

```
tcctgtgcag cctccggatt cacctttgag ccgtattgga tgggttgggt ccgccaggct    120
ccagggaagg gtctagagtg gtctcagct atcagtggta gtggtggtag cacatactac    180
gcagactccg tgaagggccg gttcaccatc tcccgcgaca attccaagaa cacgctgtat    240
ctgcaaatga acagcctgcg tgccgaggac gccgcggtat attactgtgc gaaagttaag    300 ttggggggg ggcctaattt tggctaccgg ggccagggaa ccctggtcac cgtctcgagc    360
```

<210> SEQ ID NO 149
<211> LENGTH: 360
<212> TYPE: DNA
<213> ORGANISM: Homo sapiens

<400> SEQUENCE: 149

```
gaggtgcagc tgttggagtc tgggggaggc tttgtacagc ctgggggtc cctgcgtctc    60 tcctgtgcag cctccggatt cacctttgag tggtattgga tgagttgggt ccgccaggct   120
ccagggaagg gtctagagtg gtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gcctcggtat attactgtgc gaaagttaag   300
ttgggggggg ggcccaattt tggctaccgg ggccagggaa ccctggtcac cgtctcgagc   360
```

<210> SEQ ID NO 150
<211> LENGTH: 360
<212> TYPE: DNA
<213> ORGANISM: Homo sapiens

<400> SEQUENCE: 150

```
gaggtgcagc tgttggagtc tgggggaggc ttggtacagc ctgggggtc cctgcgtctc    60 ccctgtgcag cctccggatt cacctttgag tggtattgga tgacctgggt ccgccaggct   120
ccagggaagg gtctagagtg gtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttgggggggg ggcctaattt tggctaccgg ggccagggaa ccctggtcac cgtctcgagc   360
```

<210> SEQ ID NO 151
<211> LENGTH: 360
<212> TYPE: DNA
<213> ORGANISM: Homo sapiens

<400> SEQUENCE: 151

```
gaggtgcagc tgttggagtc tgggggaggc ttggtacagc ctgggggtc cctgcgtctc    60 tcctgtgcag cctccggact cacctttgag tggtattgga tgggttgggt ccgccaggct   120
ccagggaagg gtctagagtg gtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttgggggggg ggcctaattt tggctaccgg ggccagggaa ccctggtcac cgtctcgagc   360
```

<210> SEQ ID NO 152
<211> LENGTH: 360
<212> TYPE: DNA
<213> ORGANISM: Homo sapiens

<400> SEQUENCE: 152

```
gaggtgcagc tgttggagtc tggaggaggc ttggtacagc ctggggggtc cctgcgtctc    60
tcctgtgcag cctccggact cacctttgag tggtattgga tgggttgggt ccgccaggct   120
ccagggaagg gtctagagtg ggtctcagct gtcagtggta gtggtggtag cacatactac   180
gcagactccg tgaagggccg gttcaccatc tcccgcgaca attccaagaa cacgctgtat   240
ttgcaaatga acagcctgcg tgccgaggac gccgcggtat attactgtgc gaaagttaag   300 ttggggggggg ggcctaatttt tggctaccgg ggccagggaa ccctggtcac cgtctcgagc   360
```

<210> SEQ ID NO 153
<211> LENGTH: 360
<212> TYPE: DNA
<213> ORGANISM: Homo sapiens

<400> SEQUENCE: 153

```
gaggtgcagc tgttggagtc tgggggaggc ttggtacagc ctggggggtc cctgcgtctc    60
tcctgtgcag cctccggact cacctttgag tggtattgga tgggttgggt ccgccaggct   120
ccagggaagg gtctagagtg ggtctcggct attagtggta gtggtgatag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300 ttggggggggg ggcctaatttt tggctaccgg ggccagggaa ccctggtcac cgtctcgagc   360
```

<210> SEQ ID NO 154
<211> LENGTH: 360
<212> TYPE: DNA
<213> ORGANISM: Homo sapiens

<400> SEQUENCE: 154

```
gaggtgcagc tgttggagtc tgggggaggc ttggtacagc ctggggggtc cctgcgtctc    60
tcctgtgcag cctccggatt cacctttgag tggtattgga tgggttgggt ccgccaggct   120
ccagggaagg gtctagagtg ggtctcagct atgagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300 ttggggggggg ggcctaatttt tggcaaccgg ggcctgggaa ccctggtcac cgtctcgagc   360
```

<210> SEQ ID NO 155
<211> LENGTH: 360
<212> TYPE: DNA
<213> ORGANISM: Homo sapiens

<400> SEQUENCE: 155

```
gaggtgcagc tgttggagtc tgggggaggc tcggtacagc ctggggggtc cctgcgtctc    60
tcctgtgcag cctccggatt cacctttgac tggtattgga tgggttgggt ccgccaggct   120
ccagggaagg gtctagagtg ggcctcagct atcagtggta gtggtggtag cacatactac   180
gcagactccg tgaaggaccg gttcaccatc tcccgcgaca attccaagaa cacgctgtat   240
ctgcaaatga acagcctgcg tgccgaggac gccgcggtat attactgtgc gaaagttaag   300 ttggggggggg ggcctgatttt tggctaccgg ggccagggaa ccctggtcac cgtctcgagc   360
```

<210> SEQ ID NO 156
<211> LENGTH: 360
<212> TYPE: DNA
<213> ORGANISM: Homo sapiens

<400> SEQUENCE: 156

```
gaggtgcagc tgttggagtc tggggggaggc ttggtacagc ctggggggtc cctgcgtctc    60
tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctatat   240
ctgcaaatga acagcctgcg tgccgaggac ggcgcggtat attactgtgc gaaagttaag   300 ttggggggg agcttaactt tggctaccgg ggccagggaa ccctggtcac cgtctcgagc    360
```

<210> SEQ ID NO 157
<211> LENGTH: 360
<212> TYPE: DNA
<213> ORGANISM: Homo sapiens

<400> SEQUENCE: 157

```
gaggtgcagc tgttggagtc tggggggaggc ttggtacagc ctggggggtc cctgcgtctc    60
tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300 ttggggggg ggcctaattt tggcaaccgg ggccagggaa ccccggtcac cgtctcgagc    360
```

<210> SEQ ID NO 158
<211> LENGTH: 360
<212> TYPE: DNA
<213> ORGANISM: Homo sapiens

<400> SEQUENCE: 158

```
gaggtgcagc tgttggagtc tggggggaggc ttggtacagc ctggggggtc cctgcgtctc    60
tcctgtgcag cctccggatt cacctttgag tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tcccgaggac gccgcggtat attactgtgc gaaagttaag   300 ttggggggg ggcctaattt tggcccccgg ggccagggaa ccctggtcac cgtctcgagc    360
```

<210> SEQ ID NO 159
<211> LENGTH: 360
<212> TYPE: DNA
<213> ORGANISM: Homo sapiens

<400> SEQUENCE: 159

```
gaggtgcagc tgttggagtc tggggggaggc ttggtacagc ctggggggtc cctgcgtctc    60
tcctgtgcag cctccggatt cacctttgaa tggtattgga tgggttgggt ccgccaggct   120
ccagggaagg gtctagagtg ggtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300 ttggggggg ggcctaattt tggcaaccgg ggccagggaa ccctggtcac cgtctcgagc    360
```

<210> SEQ ID NO 160
<211> LENGTH: 360
<212> TYPE: DNA
<213> ORGANISM: Homo sapiens

<400> SEQUENCE: 160

```
gaggtgcagc tgttggagtc tgggggaggc ttggtacagc ctgggggtc cctgcgtctc        60
tcctgtgcag cctccggatt caccattgag tggtattgga tgggttgggt ccgccaggct      120
ccagggaagg gtctagagtg ggtctcagct atcagtggta gtggtggtag cacatactac      180
gcagactccg tgaagggccg gttcaccatc tcccgtgaca attccaagaa cacgctgtat      240
ctgcaaatga acagcctgcg tgccgaggac gccgcggtat attactgtgc gaaagttaag      300
ttggggggggg ggcctaattt tggctaccgg ggccagggaa ccctggtcac cgtctcgagc    360
```

<210> SEQ ID NO 161
<211> LENGTH: 360
<212> TYPE: DNA
<213> ORGANISM: Homo sapiens

<400> SEQUENCE: 161

```
gaggtgcagc tgttggagtc tggggggggc ttggtacagc ctgggggtc cctgcgtctc        60
tcctgtgcag cctccggatt caccttgag tggtattgga tgggttgggt ccgccaggct      120
ccagggaagg gtctagagtg ggtctcagct atcagtggta gtggtggtag cacattctac      180
gcagactccg tgaagggccg gttcaccatc tcccgcgaca attccaagaa cacgctgtat      240
ctgcaaatga acagcctgcg cgccgaggac gccgcggtat attactgtgc gaaagttaag      300
ttggggggggg ggcctaattt tggctaccgg ggccagggaa ccctggtcac cgtctcgagc    360
```

<210> SEQ ID NO 162
<211> LENGTH: 360
<212> TYPE: DNA
<213> ORGANISM: Homo sapiens

<400> SEQUENCE: 162

```
gaggtgcagc tgttggagtc tgggggaggc ttggtacagc ctgggggtc cctgcgtctc         60
tcctgtgcag cctccggatt caccttgag tggtattgga tgggttgggt ccgccaggct      120
ccagggaagg gtctagagtg ggtcacagct atcagtggta gtggtggtag cactttctac      180
gcagactccg tgaagggccg gttcaccatc tcccgcgaca attccaagaa cacgctgtat      240
ctgcaaatga acagcctgcg tgccgaggac gccgcggtat attactgtgc gaaagttaag      300
ttggggggggg ggcctaattt tggctaccgg ggccagggaa ccctggtcac cgtctcgagc    360
```

<210> SEQ ID NO 163
<211> LENGTH: 360
<212> TYPE: DNA
<213> ORGANISM: Homo sapiens

<400> SEQUENCE: 163

```
gaggtgcagc tgttggagtc tgggggaggc ttggtacagc ctgggggtc cctgcgtctc         60
tcctgtgcag cctccggatt cagctttgag tggtattgga tgggttgggt ccgccaggct      120
ccagggaagg gtctagagtg ggtctcagct atcagtggta gtggtgatag cacatactac      180
gcagactccg tgaagggccg gttcaccatc tcccgcgaca attccaagaa cacgctgtat      240
ctgcaaatga acagcctgcg tgccgaggac gccgcggtat attactgtgc gaaagttaag      300
ttggggggggg ggcctaattt tggctatcgg ggccagggaa ccctggtcac cgtctcgagc    360
```

<210> SEQ ID NO 164
<211> LENGTH: 360
<212> TYPE: DNA
<213> ORGANISM: Homo sapiens

<400> SEQUENCE: 164

```
gaggtgcagc tgttggagtc tgggggaggc ttggtacagc ctggggggtc cctgcgtctc    60
tcctgtgcag cctccggatt ccccttgag tggtattgga tgggttgggt ccgccaggct   120
ccagggaagg gtctagagtg gtctcagct atcagtggta gtggtgatag cacatactac   180
gcagactccg tgaagggccg gttcaccatc tcccgcgaca attccaagaa cacgctgtat   240
cagcaaatga acagcctgcg tgccgaggac gccgcggtat attactgtgc gaaagttaag   300
ttggggggg ggcctaattt tggctaccgg ggccagggaa ccctggtcac cgtctcgagc   360
```

<210> SEQ ID NO 165
<211> LENGTH: 359
<212> TYPE: DNA
<213> ORGANISM: Homo sapiens

<400> SEQUENCE: 165

```
gaggtgcagc tgttggagtc tgggggaggc ttggtacagc ctggggggtc cctgcgtctc    60
tcctgtgcag cctccggatt cagctttgag tggtattgga tgggttgggt ccgccaggct   120
ccagggaagg gtctagagtg gtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttggggggg ggcctaattt tggctaccgg ggccagggaa ccctggtcac cgtctcgag   359
```

<210> SEQ ID NO 166
<211> LENGTH: 360
<212> TYPE: DNA
<213> ORGANISM: Homo sapiens

<400> SEQUENCE: 166

```
gaggtgcagc tgttggagtc tgggggaggc ttggtacagc ctggggggtc cctgcgtctc    60
tcctgtgcag cctccggatt caccttgag tggtattgga tgggttgggt ccgccaggct   120
ccagggaagg gtctagagtg gtctcagct atcagtggta gtggtggtag cacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagttaag   300
ttggggggg ggcctaatta tggctaccgg ggccagggaa ccctggtcac cgtctcgagc   360
```

<210> SEQ ID NO 167
<211> LENGTH: 108
<212> TYPE: PRT
<213> ORGANISM: Homo sapiens

<400> SEQUENCE: 167

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Pro Ile Gly Val Ala
            20                  25                  30

Leu Asn Trp Tyr Gln Gln Lys Pro Gly Lys Ala Pro Lys Leu Leu Ile
        35                  40                  45

Tyr Gly Gly Ser Tyr Leu Gln Ser Gly Val Pro Ser Arg Tyr Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Asp Trp Arg Tyr Pro Gly

```
                        85                  90                  95

Thr Phe Gly Gln Gly Thr Lys Val Glu Ile Lys Arg
                100                 105

<210> SEQ ID NO 168
<211> LENGTH: 108
<212> TYPE: PRT
<213> ORGANISM: Homo sapiens

<400> SEQUENCE: 168

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Tyr Ile His Thr Ser
             20                  25                  30

Leu Gln Trp Tyr Gln Gln Lys Pro Gly Lys Ala Pro Lys Leu Leu Ile
         35                  40                  45

Tyr Gly Ser Ser Arg Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Asn His His Ser Pro Phe
                 85                  90                  95

Thr Phe Gly Gln Gly Thr Lys Val Glu Ile Lys Arg
                100                 105

<210> SEQ ID NO 169
<211> LENGTH: 119
<212> TYPE: PRT
<213> ORGANISM: Homo sapiens

<400> SEQUENCE: 169

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Lys Tyr
             20                  25                  30

Asp Met His Trp Val Arg Gln Ala Pro Gly Lys Gly Leu Glu Trp Val
         35                  40                  45

Ser Thr Ile Ser Pro Ser Gly Arg Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Asn Leu Asp Gln Val Leu Ser Phe Asp Tyr Trp Gly Gln Gly
                100                 105                 110

Thr Leu Val Thr Val Ser Ser
        115

<210> SEQ ID NO 170
<211> LENGTH: 120
<212> TYPE: PRT
<213> ORGANISM: Homo sapiens

<400> SEQUENCE: 170

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Ser Tyr
             20                  25                  30
```

Ser Met Ser Trp Val Arg Gln Ala Pro Gly Lys Gly Leu Glu Trp Val
            35                  40                  45

Ser Gly Ile Asp Asn Gly Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ser Ser Gly Leu Pro Phe Pro Phe Asp Tyr Trp Gly Gln
            100                 105                 110

Gly Thr Leu Val Thr Val Ser Ser
            115                 120

<210> SEQ ID NO 171
<211> LENGTH: 120
<212> TYPE: PRT
<213> ORGANISM: Homo sapiens

<400> SEQUENCE: 171

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
            35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120

<210> SEQ ID NO 172
<211> LENGTH: 108
<212> TYPE: PRT
<213> ORGANISM: Homo sapiens

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Ile His Ser Ser
            20                  25                  30

Leu Gln Trp Tyr Gln Gln Lys Pro Gly Lys Ala Pro Lys Leu Leu Ile
            35                  40                  45

Tyr Ser Ser Ser Arg Leu His Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His Phe Arg Pro His
                85                  90                  95

Thr Phe Gly Gln Gly Thr Lys Val Glu Ile Lys Arg
            100                 105

<210> SEQ ID NO 173
<211> LENGTH: 120
<212> TYPE: PRT
<213> ORGANISM: Homo sapiens

<400> SEQUENCE: 173

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser
        115                 120

<210> SEQ ID NO 174
<211> LENGTH: 120
<212> TYPE: PRT
<213> ORGANISM: Homo sapiens

<400> SEQUENCE: 174

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Cys
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Lys Phe Gly Ser Asn Ala Phe Asp Tyr Trp Gly Gln
            100                 105                 110

Gly Thr Leu Val Thr Val Ser Ser
        115                 120

<210> SEQ ID NO 175
<211> LENGTH: 120
<212> TYPE: PRT
<213> ORGANISM: Homo sapiens

<400> SEQUENCE: 175

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Asp Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
             100                 105                 110

Gly Thr Leu Val Thr Val Ser Ser
         115                 120

<210> SEQ ID NO 176
<211> LENGTH: 120
<212> TYPE: PRT
<213> ORGANISM: Homo sapiens

<400> SEQUENCE: 176

Glu Val Gln Leu Leu Glu Ser Gly Gly Gly Leu Ile Gln Pro Gly Gly
 1               5                  10                  15

Ser Leu Arg Leu Ser Cys Ala Ala Ser Gly Phe Thr Phe Thr Arg Tyr
             20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Asp Thr Asp Ser Val
 50                  55                  60

Lys Gly Arg Phe Thr Ile Ser Arg Asp Asn Ser Arg Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
             100                 105                 110

Gly Thr Leu Val Thr Val Ser Ser
         115                 120

<210> SEQ ID NO 177
<211> LENGTH: 120
<212> TYPE: PRT
<213> ORGANISM: Homo sapiens

<400> SEQUENCE: 177

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
             20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
             100                 105                 110

```
Gly Thr Leu Val Thr Val Ser Ser
        115                 120

<210> SEQ ID NO 178
<211> LENGTH: 120
<212> TYPE: PRT
<213> ORGANISM: Homo sapiens

<400> SEQUENCE: 178

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Ile Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 179
<211> LENGTH: 120
<212> TYPE: PRT
<213> ORGANISM: Homo sapiens

<400> SEQUENCE: 179

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Val Val Thr Val Ser Ser
        115                 120

<210> SEQ ID NO 180
<211> LENGTH: 324
<212> TYPE: DNA
<213> ORGANISM: Homo sapiens

<400> SEQUENCE: 180
gatattcaga tgacccagag cccgagcagc ctgagcgcga gcgtgggcga tcgtgtgacc      60
attacctgcc gtgcgagcca gccgattggc gtggcgctga ctggtatca gcagaaaccg     120
```

```
ggcaaagcgc cgaaactgct gatttatggc ggcagctatc tgcagagcgg cgtgccgagc    180
cgttatagcg gcagcggcag cggcaccgat tttaccctga ccattagcag cctgcagccg    240
ggcgattttg cgacctatta ttgccagcag gattggcgtt atccgggcac ctttggccag    300
ggcaccaaag tggaaattaa acgt                                           324
```

<210> SEQ ID NO 181
<211> LENGTH: 324
<212> TYPE: DNA
<213> ORGANISM: Homo sapiens

<400> SEQUENCE: 181

```
gatattcaga tgacccagag cccgagcagc ctgagcgcga gcgtgggcga tcgtgtgacc     60
attacctgcc gtgcgagcca gtatattcat accagcctgc agtggtatca gcagaaaccg    120
ggcaaagcgc cgaaactgct gatttatggc agcagccgtc tgcagagcgg cgtgccgagc    180
cgttttagcg gcagcggcag cggcaccgat tttaccctga ccattagcag cctgcagccg    240
gaagattttg cgacctatta ttgccagcag aaccatcata gcccgtttac ctttggccag    300
ggcaccaaag tggaaattaa acgt                                           324
```

<210> SEQ ID NO 182
<211> LENGTH: 357
<212> TYPE: DNA
<213> ORGANISM: Homo sapiens

<400> SEQUENCE: 182

```
gaagtgcagc tgctggaaag cggcggcggc ctggtgcagc cgggcggcag cctgcgtctg     60
agctgcgcgg cgagcggctt tacctttcgt aaatatgata tgcattgggt gcgtcaggcg    120
ccgggcaaag cctggaatgg gtgagcacc attagcccga gcggccgtcg tacctattat    180
gcggatagcg tgaaaggccg ttttaccatt agccgtgata cagcaaaaaa caccctgtat    240
ctgcagatga acagcctgcg tgcggaagat accgcggtgt attattgcgc ggaaaacctg    300
gatcaggtgc tgagctttga ttattgggc cagggcaccc tggtgaccgt gagcagc       357
```

<210> SEQ ID NO 183
<211> LENGTH: 360
<212> TYPE: DNA
<213> ORGANISM: Homo sapiens

<400> SEQUENCE: 183

```
gaagtgcagc tgctggaaag cggcggcggc ctggtgcagc cgggcggcag cctgcgtctg     60
agctgcgcgg cgagcggctt tacctttggc agctatagca tgagctgggt gcgtcaggcg    120
ccgggcaaag cctggaatgg ggtgagcggc attgataacg gcggccatag cacctattat    180
gcggatagcg tgaaaggccg ttttaccatt agccgtgata cagcaaaaaa caccctgtat    240
ctgcagatga acagcctgcg tgcggaagat accgcggtgt attattgcgc gaaacgtagc    300
agcggcctgc cgtttccgtt tgattattgg ggccagggca ccctggtgac cgtgagcagc    360
```

<210> SEQ ID NO 184
<211> LENGTH: 360
<212> TYPE: DNA
<213> ORGANISM: Homo sapiens

<400> SEQUENCE: 184

```
gaagtgcagc tgctggaaag cggcggcggc ctggtgcagc cgggcggcag cctgcgtctg     60
agctgcgcgg cgagcggctt tacctttacc cgttatagca tgggctgggt gcgtcaggcg    120
```

```
ccgggcaaag gcctggaatg ggtgagccgt attgatagct atggccgtgg cacctattat    180
gcggatagcg tgaaaggccg ttttaccatt agccgtgata acagcaaaaa cacccctgtat   240 ctgcagatga acagcctgcg tgcggaagat accgcggtgt attattgcgc gaaaattagc    300
cagtttggca gcaacgcgtt tgattattgg ggccagggca ccctggtgac cgtgagcagc    360
```

<210> SEQ ID NO 185
<211> LENGTH: 324
<212> TYPE: DNA
<213> ORGANISM: Homo sapiens

<400> SEQUENCE: 185

```
gatattcaga tgacccagag cccgagcagc ctgagcgcga gcgtgggcga tcgtgtgacc    60
attacctgcc gtgcgagcca gtatattcat agcagcctgc agtggtatca gcagaaaccg    120
ggcaaagcgc cgaaactgct gatttatagc agcagccgtc tgcatagcgg cgtgccgccg    180
cgttttagcg gcagcggcag cggcaccgat tttaccctga ccattagcag cctgcagccg    240
gaagattttg cgacctatta ttgccagcag aaccattttc gtccgcatac ctttggccag    300
ggcaccaaag tggaaattaa acgt                                           324
```

<210> SEQ ID NO 186
<211> LENGTH: 360
<212> TYPE: DNA
<213> ORGANISM: Homo sapiens

<400> SEQUENCE: 186

```
gaagtgcagc tgctggaaag cggcggcggc ctggtgcagc cgggcggcag cctgcgtctg    60
agctgcgcgg cgagcggctt tacctttaac cgttatagca tgggctggct cgtcaggcg    120 ccgggcaaag gcctggaatg ggtgagccgt attgatagct atggccgtgg cacctattat    180
gaagatccgg tgaaaggccg ttttagcatt agccgtgata acagcaaaaa cacccctgtat   240 ctgcagatga acagcctgcg tgcggaagat accgcggtgt attattgcgc gaaaattagc    300
cagtttggca gcaacgcgtt tgattattgg ggccagggca cccaggtgac cgtgagcagc    360
```

<210> SEQ ID NO 187
<211> LENGTH: 360
<212> TYPE: DNA
<213> ORGANISM: Homo sapiens

<400> SEQUENCE: 187

```
gaagtgcagc tgctggaaag cggcggcggc ctggtgcagc cgggcggcag cctgcgtctg    60
agctgcgcgg cgagcggctt taccttagc cgttgcagca tgggctggct cgtcaggcg     120 ccgggcaaag gcctggaatg ggtgagccgt attgatagct atggccgtgg cacctattat    180
gcggatagcg tgaaaggccg ttttaccatt agccgtgata acagcaaaaa cacccctgtat   240 ctgcagatga acagcctgcg tgcggaagat accgcggtgt attattgcgc gaaaattagc    300
aaatttggca gcaacgcgtt tgattattgg ggccagggca ccctggtgac cgtgagcagc    360
```

<210> SEQ ID NO 188
<211> LENGTH: 360
<212> TYPE: DNA
<213> ORGANISM: Homo sapiens

<400> SEQUENCE: 188

```
gaagtgcagc tgctggaaag cggcggcggc ctggtgcagc cgggcggcag cctgcgtctg    60
```

| | | |
|---|---|---|
| agctgcgcgg cgagcggctt taccttt acc cgttatagca tgggctggct gcgtcaggcg | 120 | |
| ccgggcaaag gcctggaatg ggtgagccgt attgatagct atggccgtgg cacctatgat | 180 | |
| gcggatagcg tgaaaggccg ttttaccatt agccgtgata acagcaaaaa caccctgtat | 240 | |
| ctgcagatga acagcctgcg tgcggaagat accgcggtgt attattgcgc gaaaattagc | 300 | |
| cagtttggca gcaacgcgtt tgattattgg ggccagggca ccctggtgac cgtgagcagc | 360 | |

<210> SEQ ID NO 189
<211> LENGTH: 360
<212> TYPE: DNA
<213> ORGANISM: Homo sapiens

<400> SEQUENCE: 189

| | | |
|---|---|---|
| gaagtgcagc tgctggaaag cggcggcggc ctgattcagc cgggcggcag cctgcgtctg | 60 | |
| agctgcgcgg cgagcggctt taccttt acc cgttatagca tgggctggct gcgtcaggcg | 120 | |
| ccgggcaaag gcctggaatg ggtgagccgt attgatagct atggccgtgg cacctatgat | 180 | |
| accgatagcg tgaaaggccg ttttaccatt agccgtgata acagccgtaa caccctgtat | 240 | |
| ctgcagatga acagcctgcg tgcggaagat accgcggtgt attattgcgc gaaaattagc | 300 | |
| cagtttggca gcaacgcgtt tgattattgg ggccagggca ccctggtgac cgtgagcagc | 360 | |

<210> SEQ ID NO 190
<211> LENGTH: 360
<212> TYPE: DNA
<213> ORGANISM: Homo sapiens

<400> SEQUENCE: 190

| | | |
|---|---|---|
| gaagtgcagc tgctggaaag cggcggcggc ctggtgcagc cgggcggcag cctgcgtctg | 60 | |
| agctgcgcgg cgagcggctt taccttt acc cgttatagca tgggctggct gcgtcaggcg | 120 | |
| ccgggcaaag gcctggaatg ggtgagccgt attgatagct atggccgtgg cacctattat | 180 | |
| gcggatagcg tgaaaggccg ttttaccatt agccgtgata acagcaaaaa caccctgtat | 240 | |
| ctgcagatga acagcctgcg tgcggaagat accgcggtgt attattgcgc gaaaattagc | 300 | |
| cagtttggca gcaacgcgtt tgattattgg ggccagggca ccctggtgac cgtgagcagc | 360 | |

<210> SEQ ID NO 191
<211> LENGTH: 360
<212> TYPE: DNA
<213> ORGANISM: Homo sapiens

<400> SEQUENCE: 191

| | | |
|---|---|---|
| gaagtgcagc tgctggaaag cggcggcggc ctggtgcagc cgggcggcag cctgcgtctg | 60 | |
| agctgcgcgg cgagcggctt taccttt acc cgttatagca tgggctggat tcgtcaggcg | 120 | |
| ccgggcaaag gcctggaatg ggtgagccgt attgatagct atggccgtgg cacctattat | 180 | |
| gcggatagcg tgaaaggccg ttttaccatt agccgtgata acagcaaaaa caccctgtat | 240 | |
| ctgcagatga acagcctgcg tgcggaagat accgcggtgt attattgcgc gaaaattagc | 300 | |
| cagtttggca gcaacgcgtt tgattattgg ggccagggca ccctggtgac cgtgagcagc | 360 | |

<210> SEQ ID NO 192
<211> LENGTH: 360
<212> TYPE: DNA
<213> ORGANISM: Homo sapiens

<400> SEQUENCE: 192

| | | |
|---|---|---|
| gaagtgcagc tgctggaaag cggcggcggc ctggtgcagc cgggcggcag cctgcgtctg | 60 | |

```
agctgcgcgg cgagcggctt tacctttacc cgttatagca tgggctgggt gcgtcaggcg    120
ccgggcaaag gcctggaatg ggtgagccgt attgatagct atggccgtgg cacctattat    180
gcggatagcg tgaaaggccg ttttaccatt agccgtgata acagcaaaaa cacccctgtat   240 ctgcagatga acagcctgcg tgcggaagat accgcggtgt attattgcgc gaaaattagc    300
cagtttggca gcaacgcgtt tgattattgg ggccagggca ccgtggtgac cgtgagcagc    360
```

<210> SEQ ID NO 193
<211> LENGTH: 120
<212> TYPE: PRT
<213> ORGANISM: Homo sapiens

<400> SEQUENCE: 193

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Arg Ile Ser Asp Glu
            20                  25                  30

Asp Met Gly Trp Val Arg Gln Ala Pro Gly Lys Gly Leu Glu Trp Val
        35                  40                  45

Ser Ser Ile Tyr Gly Pro Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ala Leu Glu Pro Leu Ser Glu Pro Leu Gly Phe Trp Gly Gln
            100                 105                 110

Gly Thr Leu Val Thr Val Ser Ser
        115                 120
```

<210> SEQ ID NO 194
<211> LENGTH: 360
<212> TYPE: DNA
<213> ORGANISM: Homo sapiens

<400> SEQUENCE: 194

```
gaggtgcagc tgttggagtc tgggggaggc ttggtacagc ctggggggtc cctgcgtctc     60
tcctgtgcag cctccggatt taggattagc gatgaggata tgggctgggt ccgccaggct    120
ccagggaagg gtctagagtg ggtatcaagc atttatggcc ctagcggtag cacatactac    180
gcagactccg tgaagggccg gttcaccatc tcccgtgaca attccaagaa cacgctgtat    240
ctgcaaatga acagcctgcg tgccgaggac accgcggtat attattgcgc gagtgctttg    300
gagccgcttt cggagcccct gggcttttgg ggtcagggaa ccctggtcac cgtctcgagc    360
```

<210> SEQ ID NO 195
<211> LENGTH: 116
<212> TYPE: PRT
<213> ORGANISM: Homo sapiens

<400> SEQUENCE: 195

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Leu Tyr
            20                  25                  30

Asn Met Phe Trp Val Arg Gln Ala Pro Gly Lys Gly Leu Glu Trp Val
        35                  40                  45
```

Ser Phe Ile Ser Gln Thr Gly Arg Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Glu Asp Phe Asp Tyr Trp Gly Gln Gly Thr Leu Val
            100                 105                 110

Thr Val Ser Ser
        115

<210> SEQ ID NO 196
<211> LENGTH: 348
<212> TYPE: DNA
<213> ORGANISM: Homo sapiens

<400> SEQUENCE: 196
gaggtgcagc tgttggagtc tgggggaggc ttggtacagc ctggggggtc cctgcgtctc      60
tcctgtgcag cctccggatt cacctttgat ctttataata tgttttgggt ccgccaggct     120
ccagggaagg gtctagagtg ggtctcattt attagtcaga ctggtaggct tacatggtac     180
gcagactccg tgaagggccg gttcaccatc tcccgcgaca attccaagaa cacgctgtat     240
ctgcaaatga acagcctgcg tgccgaggac accgcggtat attactgtgc gaaaacgctg     300
gaggattttg actactgggg ccagggaacc ctggtcaccg tctcgagc                  348

<210> SEQ ID NO 197
<211> LENGTH: 108
<212> TYPE: PRT
<213> ORGANISM: Homo sapiens

<400> SEQUENCE: 197

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Lys Glu Phe
            20                  25                  30

Leu Trp Trp Tyr Gln Gln Lys Pro Gly Lys Ala Pro Lys Leu Leu Ile
        35                  40                  45

Tyr Met Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Lys Phe Lys Leu Pro Arg
                85                  90                  95

Thr Phe Gly Gln Gly Thr Lys Val Glu Ile Lys Arg
            100                 105

<210> SEQ ID NO 198
<211> LENGTH: 324
<212> TYPE: DNA
<213> ORGANISM: Homo sapiens

<400> SEQUENCE: 198
gacatccaga tgacccagtc tccatcctcc ctgtctgcat ctgtaggaga ccgtgtcacc      60
atcacttgcc gggcaagtca gagcgttaag gagtttttat ggtggtacca gcagaaacca     120
gggaaagccc ctaagctcct gatctatatg gcatccaatt tgcaaagtgg ggtcccatca     180

```
cgtttcagtg gcagtggatc tgggacagat ttcactctca ccatcagcag tctgcaacct    240
gaagattttg ctacgtacta ctgtcaacag aagtttaagc tgcctcgtac gttcggccaa    300
gggaccaagg tggaaatcaa acgg                                           324
```

<210> SEQ ID NO 199
<211> LENGTH: 15
<212> TYPE: PRT
<213> ORGANISM: Artificial Sequence
<220> FEATURE:
<223> OTHER INFORMATION: 3U Linker

<400> SEQUENCE: 199

Gly Gly Gly Gly Ser Gly Gly Gly Gly Ser Gly Gly Gly Gly Ser
 1               5                  10                  15

<210> SEQ ID NO 200
<211> LENGTH: 108
<212> TYPE: PRT
<213> ORGANISM: Homo sapiens

<400> SEQUENCE: 200

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Asp Ser Tyr
             20                  25                  30

Leu His Trp Tyr Gln Gln Lys Pro Gly Lys Ala Pro Lys Leu Leu Ile
         35                  40                  45

Tyr Ser Ala Ser Glu Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Val Val Trp Arg Pro Phe
                 85                  90                  95

Thr Phe Gly Gln Gly Thr Lys Val Glu Ile Lys Arg
            100                 105

<210> SEQ ID NO 201
<211> LENGTH: 324
<212> TYPE: DNA
<213> ORGANISM: Homo sapiens

<400> SEQUENCE: 201

```
gacatccaga tgacccagtc tccatcctct ctgtctgcat ctgtaggaga ccgtgtcacc    60
atcacttgcc gggcaagtca gagcattgat agttatttac attggtacca gcagaaacca    120
gggaaagccc ctaagctcct gatctatagt gcatccgagt tgcaaagtgg ggtcccatca    180
cgtttcagtg gcagtggatc tgggacagat ttcactctca ccatcagcag tctgcaacct    240
gaagattttg ctacgtacta ctgtcaacag gttgtgtggc gtccttttac gttcggccaa    300
gggaccaagg tggaaatcaa acgc                                           324
```

<210> SEQ ID NO 202
<211> LENGTH: 324
<212> TYPE: DNA
<213> ORGANISM: Homo sapiens

<400> SEQUENCE: 202

```
gcgtttgatt tccaccttgg tcccttggcc gaacgtaaaa ggacgccaca caacctgttg    60
acagtagtac gtagcaaaat cttcaggttg cagactgctg atggtgagag tgaaatctgt    120
```

```
cccagatcca ctgccactga aacgtgatgg gacccccactt tgcaactcgg atgcactata    180
gatcaggagc ttaggggctt tccctggttt ctgctggtac caatgtaaat aactatcaat    240
gctctgactt gcccggcaag tgatggtgac acggtctcct acagatgcag acagagagga    300
tggagactgg gtcatctgga tgtc                                           324
```

<210> SEQ ID NO 203
<211> LENGTH: 108
<212> TYPE: PRT
<213> ORGANISM: Homo sapiens

<400> SEQUENCE: 203

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Phe Met Asn
                20                  25                  30

Leu Leu Trp Tyr Gln Gln Lys Pro Gly Lys Ala Pro Lys Leu Leu Ile
            35                  40                  45

Tyr Asn Ala Ser Val Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Val Trp Arg Pro Phe
                85                  90                  95

Thr Phe Gly Gln Gly Thr Lys Val Glu Ile Lys Arg
            100                 105
```

<210> SEQ ID NO 204
<211> LENGTH: 324
<212> TYPE: DNA
<213> ORGANISM: Homo sapiens

<400> SEQUENCE: 204

```
gacatccaga tgacccagtc tccatcctcc ctgtctgcat ctgtaggaga ccgtgtcacc     60
atcacttgcc gggcaagtca gagcattttt atgaatttat tgtggtacca gcagaaacca    120
gggaaagccc ctaagctcct gatctataat gcatccgtgt tgcaaagtgg ggtcccatca    180
cgtttcagtg gcagtggatc tgggacagat ttcactctca ccatcagcag tctgcaacct    240
gaagattttg ctacgtacta ctgtcaacag gttgtgtggc gtccttttac gttcggccaa    300
gggaccaagg tggaaatcaa acgg                                           324
```

<210> SEQ ID NO 205
<211> LENGTH: 324
<212> TYPE: DNA
<213> ORGANISM: Homo sapiens

<400> SEQUENCE: 205

```
ccgtttgatt tccaccttgg tcccttggcc gaacgtaaaa ggacgccaca caacctgttg     60
acagtagtac gtagcaaaat cttcaggttg cagactgctg atggtgagag tgaaatctgt    120
cccagatcca ctgccactga aacgtgatgg gacccccactt tgcaacacgg atgcattata    180
gatcaggagc ttaggggctt tccctggttt ctgctggtac cacaataaat tcataaaaat    240
gctctgactt gcccggcaag tgatggtgac acggtctcct acagatgcag acagggagga    300
tggagactgg gtcatctgga tgtc                                           324
```

<210> SEQ ID NO 206
<211> LENGTH: 108
<212> TYPE: PRT
<213> ORGANISM: Homo sapiens

<400> SEQUENCE: 206

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Asp Ala
            20                  25                  30

Leu Glu Trp Tyr Gln Gln Lys Pro Gly Lys Ala Pro Lys Leu Leu Ile
        35                  40                  45

Tyr Thr Ala Ser Arg Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Val Met Gln Arg Pro Val
                85                  90                  95

Thr Phe Gly Gln Gly Thr Lys Val Glu Ile Lys Arg
            100                 105

<210> SEQ ID NO 207
<211> LENGTH: 324
<212> TYPE: DNA
<213> ORGANISM: Homo sapiens

<400> SEQUENCE: 207
gacatccaga tgacccagtc tccatcctcc ctgtctgcat ctgtaggaga ccgtgtcacc    60
atcacttgcc gggcaagtca gagcatttat gatgcgttag agtggtacca gcagaaacca   120
gggaaagccc ctaagctcct gatctatact gcatcccggt tgcaaagtgg ggtcccatca   180
cgtttcagtg gcagtggatc tgggacagat ttcactctca ccatcagcag tctgcaacct   240
gaagattttg ctacgtacta ctgtcaacag gttatgcagc gtcctgttac gttcggccaa   300
gggaccaagg tggaaatcaa acgg                                          324

<210> SEQ ID NO 208
<211> LENGTH: 324
<212> TYPE: DNA
<213> ORGANISM: Homo sapiens

<400> SEQUENCE: 208
ccgtttgatt tccaccttgg tcccttggcc gaacgtaaca ggacgctgca taacctgttg    60
acagtagtac gtagcaaaat cttcaggttg cagactgctg atggtgagag tgaaatctgt   120
cccagatcca ctgccactga acgtgatggg acccacttt gcaaccggg atgcagtata    180
gatcaggagc ttaggggctt tccctggttt ctgctggtac cactctaacg catcataaat   240
gctctgactt gcccggcaag tgatggtgac acggtctcct acagatgcag acaggagga    300
tggagactgg gtcatctgga tgtc                                          324

<210> SEQ ID NO 209
<211> LENGTH: 107
<212> TYPE: PRT
<213> ORGANISM: Homo sapiens

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Tyr Asp Ala
            20                  25                  30

Leu Trp Tyr Gln Gln Lys Pro Gly Lys Ala Pro Lys Leu Leu Ile Tyr
        35                  40                  45

Thr Ala Ser Arg Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr His Cys Gln Gln Val Met Gln Arg Pro Val Thr
                85                  90                  95

Phe Gly Gln Gly Thr Lys Val Glu Ile Lys Arg
            100                 105

<210> SEQ ID NO 210
<211> LENGTH: 324
<212> TYPE: DNA
<213> ORGANISM: Homo sapiens

<400> SEQUENCE: 210
gacatccaga tgacccagtc tccatcctcc ctgtctgcat ctgtaggaga ccgtgtcacc    60
atcacttgcc gggcaagtca gagcatttat gatgctttac agtggtacca gcagaaacca   120
gggaaagccc ctaagctcct gatctatact gcatcccggt tgcaaagtgg ggtcccatca   180
cgtttcagtg gcagtggatc tgggacagat ttcactctca ccatcagcag tctgcaacct   240
gaagattttg ctacgtacca ctgtcaacag gttatgcagc gtcctgttac gttcggccaa   300
gggaccaagg tggaaatcaa acgg                                          324

<210> SEQ ID NO 211
<211> LENGTH: 324
<212> TYPE: DNA
<213> ORGANISM: Homo sapiens

<400> SEQUENCE: 211
ccgtttgatt ccaccttggt cccttggccg aacgtaacag gacgctgcat aacctgttg    60 acagtggtac gtagcaaaat cttcaggttg cagactgctg atggtgagag tgaaatctgt   120
cccagatcca ctgccactga acgtgatgg accccactt tgcaaccggg atgcagtata    180
gatcaggagc ttaggggctt tccctggttt ctgctggtac cactgtaaag catcataaat   240
gctctgactt gcccggcaag tgatggtgac acggtctcct acagatgcag acagggagga   300
tggagactgg gtcatctgga tgtc                                          324

<210> SEQ ID NO 212
<211> LENGTH: 108
<212> TYPE: PRT
<213> ORGANISM: Homo sapiens

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Lys Glu Phe
            20                  25                  30

Leu Trp Trp Tyr Gln Gln Lys Pro Gly Lys Ala Pro Lys Leu Leu Ile
        35                  40                  45

Tyr Met Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro

```
                    65                  70                  75                  80
Glu Asp Phe Ala Thr Tyr Tyr Cys Gln Gln Lys Phe Lys Leu Pro Arg
                    85                  90                  95

Thr Phe Gly Gln Gly Thr Lys Val Glu Ile Lys Arg
                   100                 105

<210> SEQ ID NO 213
<211> LENGTH: 324
<212> TYPE: DNA
<213> ORGANISM: Homo sapiens

<400> SEQUENCE: 213
gacatccaga tgacccagtc tccatcctcc ctgtctgcat ctgtaggaga ccgtgtcacc      60
atcacttgcc gggcaagtca gagcgttaag gagtttttat ggtggtacca gcagaaacca     120
gggaaagccc ctaagctcct gatctatatg catccaatt tgcaaagtgg ggtcccatca      180
cgtttcagtg gcagtggatc tgggacagat ttcactctca ccatcagcag tctgcaacct     240
gaagattttg ctacgtacta ctgtcaacag aagtttaagc tgcctcgtac gttcggccaa     300
gggaccaagg tggaaatcaa acgg                                            324

<210> SEQ ID NO 214
<211> LENGTH: 324
<212> TYPE: DNA
<213> ORGANISM: Homo sapiens

<400> SEQUENCE: 214
ccgtttgatt tccaccttgg tcccttggcc gaacgtacga ggcagcttaa acttctgttg      60
acagtagtac gtagcaaaat cttcaggttg cagactgctg atggtgagag tgaaatctgt    120
cccagatcca ctgccactga aacgtgatgg acccccactt tgcaaattgg atgccatata    180
gatcaggagc ttaggggctt tccctggttt ctgctggtac caccataaaa actccttaac    240
gctctgactt gcccggcaag tgatggtgac acggtctcct acagatgcag acagggagga    300
tggagactgg gtcatctgga tgtc                                           324

<210> SEQ ID NO 215
<211> LENGTH: 108
<212> TYPE: PRT
<213> ORGANISM: Homo sapiens

<400> SEQUENCE: 215

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Trp Thr Lys
                20                  25                  30

Leu His Trp Tyr Gln Gln Lys Pro Gly Lys Ala Pro Lys Leu Leu Ile
            35                  40                  45

Tyr Met Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Trp Phe Ser Asn Pro Ser
                    85                  90                  95

Thr Phe Gly Gln Gly Thr Lys Val Glu Ile Lys Arg
                   100                 105

<210> SEQ ID NO 216
```

<210> SEQ ID NO 216
<211> LENGTH: 324
<212> TYPE: DNA
<213> ORGANISM: Homo sapiens

<400> SEQUENCE: 216

```
gacatccaga tgacccagtc tccatcctcc ctgtctgcat ctgtaggaga ccgtgtcacc    60
atcacttgcc gggcaagtca gagcatttgg acgaagttac attggtacca gcagaaacca   120
gggaaagccc ctaagctcct gatctatatg catccagtt tgcaaagtgg ggtcccatca    180
cgtttcagtg gcagtggatc tgggacagat ttcactctca ccatcagcag tctgcaacct   240
gaagattttg ctacgtacta ctgtcaacag tggtttagta atcctagtac gttcggccaa   300
gggaccaagg tggaaatcaa acgc                                          324
```

<210> SEQ ID NO 217
<211> LENGTH: 324
<212> TYPE: DNA
<213> ORGANISM: Homo sapiens

<400> SEQUENCE: 217

```
gcgtttgatt tccaccttgg tcccttggcc gaacgtacta ggattactaa accactgttg    60
acagtagtac gtagcaaaat cttcaggttg cagactgctg atggtgagag tgaaatctgt   120
cccagatcca ctgccactga aacgtgatgg acccccactt tgcaaactgg atgccatata   180
gatcaggagc ttaggggctt tcccctggttt ctgctggtac caatgtaact tcgtccaaat  240
gctctgactt gcccggcaag tgatggtgac acggtctcct acagatgcag acagggagga   300
tggagactgg gtcatctgga tgtc                                          324
```

<210> SEQ ID NO 218
<211> LENGTH: 107
<212> TYPE: PRT
<213> ORGANISM: Homo sapiens

<400> SEQUENCE: 218

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Pro Ile Leu
             20                  25                  30

Cys Trp Tyr Gln Gln Lys Pro Gly Lys Ala Pro Lys Leu Leu Ile Tyr
         35                  40                  45

Ala Ala Ser Ser Leu Gln Ser Gly Val Pro Ser Arg Phe Ser Gly Ser
     50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Ile Gln His Ile Pro Val Thr
                 85                  90                  95

Phe Gly Gln Gly Thr Lys Val Glu Ile Lys Arg
            100                 105
```

<210> SEQ ID NO 219
<211> LENGTH: 324
<212> TYPE: DNA
<213> ORGANISM: Homo sapiens

<400> SEQUENCE: 219

```
gacatccaga tgacccagtc tccatcctcc ctgtctgcat ctgtaggaga ccgtgtcacc    60
atcacttgcc gggcaagtca gagcatttag ccgattttat gttggtacca gcagaaacca   120
```

```
gggaaagccc ctaagctcct gatctatgct gcatccagtt tgcaaagtgg ggtcccatca      180
cgtttcagtg gcagtggatc tgggacagat ttcactctca ccatcagcag tctgcaacct      240
gaagattttg ctacgtacta ctgtcaacag attcagcata ttcctgtgac gttcggccaa      300
gggaccaagg tggaaatcaa acgg                                             324
```

<210> SEQ ID NO 220
<211> LENGTH: 324
<212> TYPE: DNA
<213> ORGANISM: Homo sapiens

<400> SEQUENCE: 220

```
ccgtttgatt tccaccttgg tcccttggcc gaacgtcaca ggaatatgct gaatctgttg      60
acagtagtac gtagcaaaat cttcaggttg cagactgctg atggtgagag tgaaatctgt      120
cccagatcca ctgccactga aacgtgatgg gaccccactt tgcaaactgg atgcagcata      180
gatcaggagc ttaggggctt tccctggttt ctgctggtac caacataaaa tcggctaaat      240
gctctgactt gcccggcaag tgatggtgac acggtctcct acagatgcag acagggagga      300
tggagactgg gtcatctgga tgtc                                             324
```

<210> SEQ ID NO 221
<211> LENGTH: 107
<212> TYPE: PRT
<213> ORGANISM: Homo sapiens

<400> SEQUENCE: 221

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Asp Leu
            20                  25                  30

His Trp Tyr Gln Gln Lys Pro Gly Lys Ala Pro Lys Leu Leu Ile Tyr
        35                  40                  45

Thr Ala Ser Leu Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Gln Ser Ala Phe Pro Asn Thr
                85                  90                  95

Leu Gly Gln Gly Thr Lys Val Glu Ile Lys Arg
            100                 105

<210> SEQ ID NO 222
<211> LENGTH: 324
<212> TYPE: DNA
<213> ORGANISM: Homo sapiens

<400> SEQUENCE: 222

```
gacatccaga tgacccagtc tccatcctcc ctgtctgcat ctgtaggaga ccgtgtcacc      60
atcacttgcc gggcaagtca gagcattggg taggatttac attggtacca gcagaaacca      120
gggaaagccc ctaagctcct gatctatacg gcatccctt tgcaaagtgg ggtcccatca      180
cgtttcagtg gcagtggatc tgggacagat ttcactctca ccatcagcag tctgcaacct      240
gaagattttg ctacgtacta ctgtcaacag cagagtgctt ttcctaatac gctcggccaa      300
gggaccaagg tggaaatcaa acgg                                             324
```

<210> SEQ ID NO 223

<211> LENGTH: 324
<212> TYPE: DNA
<213> ORGANISM: Homo sapiens

<400> SEQUENCE: 223

```
ccgtttgatt tccaccttgg tcccttggcc gagcgtatta ggaaaagcac tctgctgttg      60
acagtagtac gtagcaaaat cttcaggttg cagactgctg atggtgagag tgaaatctgt     120
cccagatcca ctgccactga aacgtgatgg acccccactt tgcaaaaggg atgccgtata    180
gatcaggagc ttaggggctt tccctggttt ctgctggtac caatgtaaat cctacccaat    240
gctctgactt gcccggcaag tgatggtgac acggtctcct acagatgcag acagggagga    300
tggagactgg gtcatctgga tgtc                                           324
```

<210> SEQ ID NO 224
<211> LENGTH: 107
<212> TYPE: PRT
<213> ORGANISM: Homo sapiens

<400> SEQUENCE: 224

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Thr Lys Asn
            20                  25                  30

Leu Leu Trp Tyr Gln Lys Pro Gly Lys Ala Pro Lys Leu Leu Ile
        35                  40                  45

Tyr Ala Ser Ser Leu Gln Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Leu Arg His Lys Pro Pro Thr
                85                  90                  95

Phe Gly Gln Gly Thr Lys Val Glu Ile Lys Arg
            100                 105
```

<210> SEQ ID NO 225
<211> LENGTH: 324
<212> TYPE: DNA
<213> ORGANISM: Homo sapiens

<400> SEQUENCE: 225

```
gacatccaga tgacccagtc tccatcctcc ctgtctgcat ccgtaggaga ccgtgtcacc      60
atcacttgcc gggcaagtca gagcataacg aagaatttac tttggtacca gcagaaacca    120
gggaaagccc ctaagctcct gatctattag gcatcctctt tgcaaagtgg ggtcccatca    180
cgtttcagtg gcagtggatc tgggacagat ttcactctca ccatcagcag tctgcaacct    240
gaagattttg ctacgtacta ctgtcaacag cttcgtcata agcctccgac gttcggccaa    300
gggaccaagg tggaaatcaa acgg                                           324
```

<210> SEQ ID NO 226
<211> LENGTH: 324
<212> TYPE: DNA
<213> ORGANISM: Homo sapiens

<400> SEQUENCE: 226

```
ccgtttgatt tccaccttgg tcccttggcc gaacgtcgga ggcttatgac gaagctgttg      60
acagtagtac gtagcaaaat cttcaggttg cagactgctg atggtgagag tgaaatctgt     120
```

```
cccagatcca ctgccactga aacgtgatgg acccccactt tgcaaagagg atgcctaata    180
gatcaggagc ttagggggctt tccctggttt ctgctggtac caaagtaaat tcttcgttat   240
gctctgactt gcccggcaag tgatggtgac acggtctcct acggatgcag acagggagga   300
tggagactgg gtcatctgga tgtc                                           324
```

<210> SEQ ID NO 227
<211> LENGTH: 107
<212> TYPE: PRT
<213> ORGANISM: Homo sapiens

<400> SEQUENCE: 227

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Lys Ser Leu
            20                  25                  30

Arg Trp Tyr Gln Gln Lys Pro Gly Lys Ala Pro Lys Leu Leu Ile Tyr
        35                  40                  45

His Ala Ser Asp Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Met Val Asn Ser Pro Val Thr
                85                  90                  95

Phe Gly Gln Gly Thr Lys Val Glu Ile Lys Arg
            100                 105

<210> SEQ ID NO 228
<211> LENGTH: 324
<212> TYPE: DNA
<213> ORGANISM: Homo sapiens

<400> SEQUENCE: 228

```
gacatccaga tgacccagtc tccatcctcc ctgtctgcat ctgtaggaga ccgtgtcacc    60
atcacttgcc gggcaagtca gagcatttag aagtctttaa ggtggtacca gcagaaacca   120
gggaaagccc ctaagctcct gatctatcat gcatccgatt tgcaaagtgg ggtcccatca   180
cgtttcagtg gcagtggatc tgggacagat ttcactctca ccatcagcag tctgcaacct   240
gaagattttg ctacgtacta ctgtcaacag atggttaata gtcctgttac gttcggccaa   300
gggaccaagg tggaaatcaa acgg                                          324
```

<210> SEQ ID NO 229
<211> LENGTH: 324
<212> TYPE: DNA
<213> ORGANISM: Homo sapiens

<400> SEQUENCE: 229

```
ccgtttgatt tccaccttgg tcccttggcc gaacgtaaca ggactattaa ccatctgttg    60
acagtagtac gtagcaaaat cttcaggttg cagactgctg atggtgagag tgaaatctgt   120
cccagatcca ctgccactga aacgtgatgg acccccactt tgcaaatcgg atgcatgata   180
gatcaggagc ttagggggctt tccctggttt ctgctggtac cacccttaaag acttctaaat  240 gctctgactt gcccggcaag tgatggtgac acggtctcct acagatgcag acagggagga   300
tggagactgg gtcatctgga tgtc                                           324
```

<210> SEQ ID NO 230

<211> LENGTH: 107
<212> TYPE: PRT
<213> ORGANISM: Homo sapiens

<400> SEQUENCE: 230

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Ala Leu
            20                  25                  30

His Trp Tyr Gln Gln Lys Pro Gly Lys Ala Pro Lys Leu Leu Ile Tyr
        35                  40                  45

Ser Ala Ser Ser Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Ser Ser Phe Leu Pro Phe Thr
                85                  90                  95

Phe Gly Gln Gly Thr Lys Val Glu Ile Lys Arg
            100                 105

<210> SEQ ID NO 231
<211> LENGTH: 324
<212> TYPE: DNA
<213> ORGANISM: Homo sapiens

<400> SEQUENCE: 231
gacatccaga tgacccagtc tccatcctcc ctgtctgcat ctgtaggaga ccgtgtcacc    60
atcacttgcc gggcaagtca gagcatttag acggcgttac attggtacca gcagaaacca   120
gggaaagccc ctaagctcct gatctattct gcatccagtt tgcaaagtgg ggtcccatca   180
cgtttcagtg gcagtggatc tgggacagat ttcactctca ccatcagcag tctgcaacct   240
gaagattttg ctacgtacta ctgtcaacag tcgagttttt tgccttttac gttcggccaa   300
gggaccaagg tggaaatcaa acgg                                          324

<210> SEQ ID NO 232
<211> LENGTH: 324
<212> TYPE: DNA
<213> ORGANISM: Homo sapiens

<400> SEQUENCE: 232
ccgtttgatt tccaccttgg tcccttggcc gaacgtaaaa ggcaaaaaac tcgactgttg    60
acagtagtac gtagcaaaat cttcaggttg cagactgctg atggtgagag tgaaatctgt   120
cccagatcca ctgccactga acgtgatggg acccccactt tgcaaactgg atgcagaata   180
gatcaggagc ttagggcctt ccctggtttt ctgctggtac caatgtaacg ccgtctaaat   240
gctctgactt gcccggcaag tgatggtgac acggtctcct acagatgcag acagggagga   300
tggagactgg gtcatctgga tgtc                                          324

<210> SEQ ID NO 233
<211> LENGTH: 108
<212> TYPE: PRT
<213> ORGANISM: Homo sapiens

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Pro Asn

```
            20                  25                  30
Leu Glu Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
            50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Gln Met Gly Arg Pro Arg
                85                  90                  95

Thr Phe Gly Gln Gly Thr Lys Val Glu Ile Lys Arg
            100                 105
```

```
<210> SEQ ID NO 234
<211> LENGTH: 324
<212> TYPE: DNA
<213> ORGANISM: Homo sapiens

<400> SEQUENCE: 234
gacatccaga tgacccagtc tccatcctcc ctgtctgcat ctgtaggaga ccgtgtcacc    60
atcacttgcc gggcaagtca gagcattggg ccgaatttag agtggtacca gcagaaacca   120
gggaaagccc ctaagctcct gatctatgct gcatccagtt tgcaaagtgg ggtcccatca   180
cgtttcagtg gcagtggatc tgggacagat ttcactctca ccatcagcag tctgcaacct   240
gaagattttg ctacgtacta ctgtcaacag cagatggggc gtcctcggac gttcggccaa   300
gggaccaagg tggaaatcaa acgg                                          324

<210> SEQ ID NO 235
<211> LENGTH: 324
<212> TYPE: DNA
<213> ORGANISM: Homo sapiens

<400> SEQUENCE: 235
ccgtttgatt tccaccttgg tccctttggcc gaacgtccga ggacgcccca tctgctgttg   60
acagtagtac gtagcaaaat cttcaggttg cagactgctg atggtgagag tgaaatctgt   120
cccagatcca ctgccactga acgtgatggg acccccactt tgcaaactgg atgcagcata   180
gatcaggagc ttaggggctt tccctggttt ctgctggtac cactctaaat tcggcccaat   240
gctctgactt gcccggcaag tgatggtgac acggtctcct acagatgcag acagggagga   300
tggagactgg gtcatctgga tgtc                                          324

<210> SEQ ID NO 236
<211> LENGTH: 107
<212> TYPE: PRT
<213> ORGANISM: Homo sapiens

<400> SEQUENCE: 236

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Lys His Leu
            20                  25                  30

Ala Trp Tyr Gln Gln Lys Pro Gly Lys Ala Pro Lys Leu Leu Ile Tyr
            35                  40                  45

Lys Ala Ser Val Leu Gln Ser Gly Val Pro Ser Arg Phe Ser Gly Ser
            50                  55                  60

Gly Ser Gly Thr Asp Phe Thr Leu Thr Ile Ser Ser Leu Gln Pro Glu
 65                 70                  75                  80
```

Asp Phe Ala Thr Tyr Tyr Cys Gln Gln Leu Arg Arg Pro Thr Thr
                85                  90                  95

Phe Gly Gln Gly Thr Lys Val Glu Ile Lys Arg
            100                 105

<210> SEQ ID NO 237
<211> LENGTH: 324
<212> TYPE: DNA
<213> ORGANISM: Homo sapiens

<400> SEQUENCE: 237
gacatccaga tgacccagtc tccatcctcc ctgtctgcat ctgtaggaga ccgtgtcacc    60
atcacttgcc gggcaagtca gagcattaag cattagttag cttggtacca gcagaaacca   120
gggaaagccc ctaagctcct gatctataag gcatccgtgt tgcaaagtgg ggtcccatca   180
cgtttcagtg gcagtggatc tgggacagat ttcactctca ccatcagcag tctgcaacct   240
gaagattttg ctacgtacta ctgtcaacag cttaggcgtc gtcctactac gttcggccaa   300
gggaccaagg tggaaatcaa acgg                                           324

<210> SEQ ID NO 238
<211> LENGTH: 324
<212> TYPE: DNA
<213> ORGANISM: Homo sapiens

<400> SEQUENCE: 238
ccgtttgatt tccaccttgg tcccttggcc gaacgtagta ggacgacgcc taagctgttg    60
acagtagtac gtagcaaaat cttcaggttg cagactgctg atggtgagag tgaaatctgt   120
cccagatcca ctgccactga acgtgatgg gacccacctt tgcaacacgg atgccttata    180
gatcaggagc ttaggggctt tccctggttt ctgctggtac caagctaact aatgcttaat   240
gctctgactt gcccggcaag tgatggtgac acggtctcct acagatgcag acagggagga   300
tggagactgg gtcatctgga tgtc                                           324

<210> SEQ ID NO 239
<211> LENGTH: 107
<212> TYPE: PRT
<213> ORGANISM: Homo sapiens

<400> SEQUENCE: 239

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Lys Ala Leu
            20                  25                  30

Thr Trp Tyr Gln Gln Lys Pro Gly Lys Ala Pro Lys Leu Leu Ile Tyr
        35                  40                  45

Lys Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln His Ser Ser Arg Pro Tyr Thr
                85                  90                  95

Phe Gly Gln Gly Thr Lys Val Glu Ile Lys Arg
            100                 105

<210> SEQ ID NO 240
<211> LENGTH: 324

<212> TYPE: DNA
<213> ORGANISM: Homo sapiens

<400> SEQUENCE: 240

```
gacatccaga tgacccagtc tccatcctcc ctgtctgcat ctgtaggaga ccgtgtcacc      60
atcacttgcc gggcaagtca gagcgttaag gcttagttaa cttggtacca gcagaaacca     120
gggaaagccc ctaagctcct gatctataag gcatccactt tgcaaagtgg ggtcccatca     180
cgtttcagtg gcagtggatc tgggacagat ttcactctca ccatcagcag tctgcaacct     240
gaagattttg ctacgtacta ctgtcaacag catagttcta ggccttatac gttcggccaa     300
gggaccaagg tggaaatcaa acgg                                            324
```

<210> SEQ ID NO 241
<211> LENGTH: 324
<212> TYPE: DNA
<213> ORGANISM: Homo sapiens

<400> SEQUENCE: 241

```
ccgtttgatt tccaccttgg tcccttggcc gaacgtataa ggcctagaac tatgctgttg      60
acagtagtac gtagcaaaat cttcaggttg cagactgctg atggtgagag tgaaatctgt     120
cccagatcca ctgccactga acgtgatgg gacccacctt tgcaaagtgg atgccttata      180
gatcaggagc ttaggggctt tccctggttt ctgctggtac caagttaact aagcctaac      240
gctctgactt gcccggcaag tgatggtgac acggtctcct acagatgcag acagggagga     300
tggagactgg gtcatctgga tgtc                                            324
```

<210> SEQ ID NO 242
<211> LENGTH: 107
<212> TYPE: PRT
<213> ORGANISM: Homo sapiens

<400> SEQUENCE: 242

```
Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ser Ile Glu Asn Arg
             20                  25                  30
Leu Gly Trp Tyr Gln Gln Lys Pro Gly Lys Ala Pro Lys Leu Leu Ile
         35                  40                  45
Tyr Ala Ser Leu Leu Gln Ser Gly Val Pro Ser Arg Phe Ser Gly Ser
     50                  55                  60
Gly Ser Gly Thr Asp Phe Thr Leu Thr Ile Ser Ser Leu Gln Pro Glu
 65                  70                  75                  80
Asp Phe Ala Thr Tyr Tyr Cys Gln Gln Asp Ser Tyr Phe Pro Arg Thr
                 85                  90                  95
Phe Gly Gln Gly Thr Lys Val Glu Ile Lys Arg
                100                 105
```

<210> SEQ ID NO 243
<211> LENGTH: 324
<212> TYPE: DNA
<213> ORGANISM: Homo sapiens

<400> SEQUENCE: 243

```
gacatccaga tgacccagtc tccatcctcc ctgtctgcat ctgtaggaga ccgtgtcacc      60
atcacttgcc gggcaagtca gagcattgag aatcggttag gttggtacca gcagaaacca     120
gggaaagccc ctaagctcct gatctattag gcgtccttgt tgcaaagtgg ggtcccatca     180
```

```
cgtttcagtg gcagtggatc tgggacagat ttcactctca ccatcagcag tctgcaacct    240
gaagattttg ctacgtacta ctgtcaacag gattcgtatt ttcctcgtac gttcggccaa    300
gggaccaagg tggaaatcaa acgg                                           324
```

<210> SEQ ID NO 244
<211> LENGTH: 324
<212> TYPE: DNA
<213> ORGANISM: Homo sapiens

<400> SEQUENCE: 244

```
ccgtttgatt tccaccttgg tcccttggcc gaacgtacga ggaaaatacg aatcctgttg    60
acagtagtac gtagcaaaat cttcaggttg cagactgctg atggtgagag tgaaatctgt    120
cccagatcca ctgccactga aacgtgatgg acccccactt tgcaacaagg acgcctaata    180
gatcaggagc ttagggggctt tccctggttt ctgctggtac caacctaacc gattctcaat    240
gctctgactt gcccggcaag tgatggtgac acggtctcct acagatgcag acagggagga    300
tggagactgg gtcatctgga tgtc                                           324
```

<210> SEQ ID NO 245
<211> LENGTH: 107
<212> TYPE: PRT
<213> ORGANISM: Homo sapiens

<400> SEQUENCE: 245

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Met Asp Lys
            20                  25                  30

Leu Lys Trp Tyr Gln Gln Lys Pro Gly Lys Ala Pro Lys Leu Leu Ile
        35                  40                  45

Tyr Ala Ser Ile Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Asp Ser Gly Gly Pro Asn Thr
                85                  90                  95

Phe Gly Gln Gly Thr Lys Val Glu Ile Lys Arg
            100                 105
```

<210> SEQ ID NO 246
<211> LENGTH: 324
<212> TYPE: DNA
<213> ORGANISM: Homo sapiens

<400> SEQUENCE: 246

```
gacatccaga tgacccagtc tccatcctcc ctgtctgcat ctgtaggaga ccgtgtcacc    60
atcacttgcc gggcaagtca gagcattatg gataagttaa agtggtacca gcagaaacca    120
gggaaagccc ctaagctcct gatctattag catccatttt gcaaagtggg gtcccatca    180 cgtttcagtg gcagtggatc tgggacagat ttcactctca ccatcagcag tctgcaacct    240
gaagattttg ctacgtacta ctgtcaacag gatagtgggg gtcctaatac gttcggccaa    300
gggaccaagg tggaaatcaa acgg                                           324
```

<210> SEQ ID NO 247
<211> LENGTH: 324

<212> TYPE: DNA
<213> ORGANISM: Homo sapiens

<400> SEQUENCE: 247

```
ccgtttgatt tccaccttgg tcccttggcc gaacgtatta ggaccccac tatcctgttg      60
acagtagtac gtagcaaaat cttcaggttg cagactgctg atggtgagag tgaaatctgt    120
cccagatcca ctgccactga acgtgatgg gaccccactt tgcaaaatgg atgcctaata    180
gatcaggagc ttaggggctt tccctggttt ctgctggtac cactttaact tatccataat    240
gctctgactt gcccggcaag tgatggtgac acggtctcct acagatgcag acagggagga    300
tggagactgg gtcatctgga tgtc                                            324
```

<210> SEQ ID NO 248
<211> LENGTH: 108
<212> TYPE: PRT
<213> ORGANISM: Homo sapiens

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Arg Asn
            20                  25                  30

Leu Glu Trp Tyr Gln Gln Lys Pro Gly Lys Ala Pro Lys Leu Leu Ile
        35                  40                  45

Tyr Asp Ala Ser His Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Arg Trp Leu Pro Arg
                85                  90                  95

Thr Phe Gly Gln Gly Thr Lys Val Glu Ile Lys Arg
            100                 105

<210> SEQ ID NO 249
<211> LENGTH: 324
<212> TYPE: DNA
<213> ORGANISM: Homo sapiens

<400> SEQUENCE: 249

```
gacatccaga tgacccagtc tccatcctcc ctgtctgcat ctgtaggaga ccgtgtcacc      60
atcacttgcc gggcaagtca gagcattggg aggaatttag agtggtacca gcagaaacca    120
gggaaagccc ctaagctcct gatctatgat gcatcccatt tgcaaagtgg ggtcccatca    180
cgtttcagtg gcagtggatc tgggacagat ttcactctca ccatcagcag tctgcaacct    240
gaagattttg ctacgtacta ctgtcaacag tcgcgttggc ttcctcgtac gttcggccaa    300
gggaccaagg tggaaatcaa acgg                                            324
```

<210> SEQ ID NO 250
<211> LENGTH: 324
<212> TYPE: DNA
<213> ORGANISM: Homo sapiens

<400> SEQUENCE: 250

```
ccgtttgatt tccaccttgg tcccttggcc gaacgtacga ggaagccaac gcgactgttg      60
acagtagtac gtagcaaaat cttcaggttg cagactgctg atggtgagag tgaaatctgt    120
cccagatcca ctgccactga acgtgatgg gaccccactt tgcaaatggg atgcatcata    180
```

```
gatcaggagc ttagggctt tccctggttt ctgctggtac cactctaaat tcctcccaat    240
gctctgactt gcccggcaag tgatggtgac acggtctcct acagatgcag acagggagga    300
tggagactgg gtcatctgga tgtc                                            324
```

<210> SEQ ID NO 251
<211> LENGTH: 108
<212> TYPE: PRT
<213> ORGANISM: Homo sapiens

<400> SEQUENCE: 251

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Ser Ile Arg Lys Met
             20                  25                  30

Leu Val Trp Tyr Gln Gln Lys Pro Gly Lys Ala Pro Lys Leu Leu Ile
         35                  40                  45

Tyr Arg Ala Ser Tyr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Phe Arg Arg Pro Arg
                 85                  90                  95

Thr Phe Gly Gln Gly Thr Lys Val Glu Ile Lys Arg
            100                 105
```

<210> SEQ ID NO 252
<211> LENGTH: 324
<212> TYPE: DNA
<213> ORGANISM: Homo sapiens

<400> SEQUENCE: 252

```
gacatccaga tgacccagtc tccatcctcc ctgtctgcat ctgtaggaga ccgtgtcacc     60
atcacttgcc gggcaagtca gagcattagg aagatgttag tttggtacca gcagaaacca    120
gggaaagccc ctaagctcct gatctatcgg gcatcctatt tgcaaagtgg ggtcccatca    180
cgtttcagtg gcagtggatc tgggacagat ttcactctca ccatcagcag tctgcaacct    240
gaagattttg ctacgtacta ctgtcaacag gcttttcggc ggcctaggac gttcggccaa    300
gggaccaagg tggaaatcaa acgg                                            324
```

<210> SEQ ID NO 253
<211> LENGTH: 324
<212> TYPE: DNA
<213> ORGANISM: Homo sapiens

<400> SEQUENCE: 253

```
ccgtttgatt tccaccttgg tcccttggcc gaacgtccta ggccgccgaa aagcctgttg     60
acagtagtac gtagcaaaat cttcaggttg cagactgctg atggtgagag tgaaatctgt    120
cccagatcca ctgccactga acgtgatggg acccccactt tgcaaatagg atgcccgata    180
gatcaggagc ttaggggctt tccctggttt ctgctggtac caaactaaca tcttcctaat    240
gctctgactt gcccggcaag tgatggtgac acggtctcct acagatgcag acagggagga    300
tggagactgg gtcatctgga tgtc                                            324
```

<210> SEQ ID NO 254
<211> LENGTH: 115

-continued

<212> TYPE: PRT
<213> ORGANISM: Homo sapiens

<400> SEQUENCE: 254

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Thr | Phe | Asp | Leu | Tyr |
|---|---|---|---|---|---|---|---|---|---|---|---|---|---|---|---|
| | | | 20 | | | | | 25 | | | | | 30 | | |

| Asn | Met | Phe | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ser | Phe | Ile | Ser | Gln | Thr | Gly | Arg | Leu | Thr | Trp | Tyr | Ala | Asp | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Ile | Ser | Arg | Asp | Asn | Ser | Lys | Asn | Thr | Leu | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Lys | Thr | Leu | Glu | Asp | Phe | Asp | Tyr | Trp | Gly | Gln | Gly | Thr | Leu | Val |
|---|---|---|---|---|---|---|---|---|---|---|---|---|---|---|---|
| | | | 100 | | | | | 105 | | | | | 110 | | |

Thr Val Ser
115

<210> SEQ ID NO 255
<211> LENGTH: 345
<212> TYPE: DNA
<213> ORGANISM: Homo sapiens

<400> SEQUENCE: 255
gaggtgcagc tgttggagtc tgggggaggc ttggtacagc ctggggggtc cctgcgtctc     60
tcctgtgcag cctccggatt cacctttgat ctttataata tgttttgggt ccgccaggct    120
ccagggaagg gtctagagtg ggtctcattt attagtcaga ctggtaggct acatggtac    180 gcagactccg tgaagggccg gttcaccatc tcccgcgaca attccaagaa cacgctgtat    240
ctgcaaatga acagcctgcg tgccgaggac accgcggtat attactgtgc gaaaacgctg    300
gaggattttg actactgggg ccagggaacc ctggtcaccg tctcg                    345

<210> SEQ ID NO 256
<211> LENGTH: 345
<212> TYPE: DNA
<213> ORGANISM: Homo sapiens

<400> SEQUENCE: 256
cgagacggtg accagggttc cctggcccca gtagtcaaaa tcctccagcg ttttcgcaca     60
gtaatatacc gcggtgtcct cggcacgcag gctgttcatt tgcagataca gcgtgttctt    120
ggaattgtcg cgggagatgg tgaaccggcc cttcacggag tctgcgtacc atgtaagcct    180
accagtctga ctaataaatg agacccactc tagacccttc cctggagcct ggcggaccca    240
aaacatatta taaagatcaa aggtgaatcc ggaggctgca caggagagac gcagggaccc    300
cccaggctgt accaagcctc ccccagactc aacagctgc acctc                     345

<210> SEQ ID NO 257
<211> LENGTH: 119
<212> TYPE: PRT
<213> ORGANISM: Homo sapiens

<400> SEQUENCE: 257

| Glu | Val | Gln | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

Ser Leu Arg Leu Ser Cys Ala Ala Ser Gly Phe Thr Phe Pro Val Tyr
        20                  25                  30

Met Met Gly Trp Val Arg Gln Ala Pro Gly Lys Gly Leu Glu Trp Val
        35                  40                  45

Ser Ser Ile Asp Ala Leu Gly Gly Arg Thr Gly Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Met Ser Asn Lys Thr His Thr Phe Asp Tyr Trp Gly Gln
            100                 105                 110

Gly Thr Leu Val Thr Val Ser
        115

<210> SEQ ID NO 258
<211> LENGTH: 357
<212> TYPE: DNA
<213> ORGANISM: Homo sapiens

<400> SEQUENCE: 258
gaggtgcagc tgttggagtc tgggggaggc ttggtacagc ctggggggtc cctgcgtctc     60
tcctgtgcag cctccggatt cacctttccg gtttatatga tgggttgggt ccgccaggct    120
ccagggaagg gtctagagtg gtctcatcg attgatgctc ttggtgggcg acaggttac     180 gcagactccg tgaagggccg gttcaccatc tcccgcgaca attccaagaa cacgctgtat    240
ctgcaaatga acagcctgcg tgccgaggac accgcggtat attactgtgc gaaaactatg    300
tcgaataaga cgcatacgtt tgactactgg ggccagggaa ccctggtcac cgtctcg      357

<210> SEQ ID NO 259
<211> LENGTH: 357
<212> TYPE: DNA
<213> ORGANISM: Homo sapiens

<400> SEQUENCE: 259
cgagacggtg accagggttc cctggcccca gtagtcaaac gtatgcgtct tattcgacat     60
agttttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
acctgtccgc ccaccaagag catcaatcga tgagacccac tctagaccct tccctggagc    240
ctggcggacc caacccatca tataaaccgg aaaggtgaat ccggaggctg cacaggagag    300
acgcagggac cccccaggct gtaccaagcc tccccagac tccaacagct gcacctc       357

<210> SEQ ID NO 260
<211> LENGTH: 114
<212> TYPE: PRT
<213> ORGANISM: Homo sapiens

<400> SEQUENCE: 260

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Ala Tyr
        20                  25                  30

Asn Met Thr Trp Val Arg Gln Ala Pro Gly Lys Gly Leu Glu Trp Val
        35                  40                  45

Ser Ser Ile Asn Thr Phe Gly Asn Thr Arg Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Lys Gly Ser Arg Pro Phe Asp Tyr Trp Gly Gln Gly Thr Leu Val Thr
            100                 105                 110

Val Ser

<210> SEQ ID NO 261
<211> LENGTH: 345
<212> TYPE: DNA
<213> ORGANISM: Homo sapiens

<400> SEQUENCE: 261
gaggtgcagc tgttggagtc tgggggaggc ttggtacagc ctggggggtc cctgcgtctc    60
tcctgtgcag cctccggatt cacctttgtg cttataata tgacttgggt ccgccaggct   120
ccagggaagg gtctagagtg ggtctcaagt attaatactt ttggtaatta caaggtac    180 gcagactccg tgaagggccg gttcaccatc tcccgcgaca attccaagaa cacgctgtat   240
ctgcaaatga acagcctgcg tgccgaggac accgcggtat attactgtgc gaaaggtagt   300
aggccttttg actactgggg ccagggaacc ctggtcaccg tctcg                  345

<210> SEQ ID NO 262
<211> LENGTH: 345
<212> TYPE: DNA
<213> ORGANISM: Homo sapiens

<400> SEQUENCE: 262
cgagacggtg accagggttc cctggcccca gtagtcaaaa ggcctactac ctttcgcaca    60
gtaatatacc gcggtgtcct cggcacgcag gctgttcatt tgcagataca gcgtgttctt   120
ggaattgtcg cgggagatgg tgaaccggcc cttcacggag tctgcgtacc ttgtctaatt   180
accaaaagta ttaatacttg agacccactc tagacccttc cctggagcct ggcggaccca   240
agtcatatta aagccacaa aggtgaatcc ggaggctgca caggagagac gcagggaccc    300
cccaggctgt accaagcctc ccccagactc aacagctgc acctc                   345

<210> SEQ ID NO 263
<211> LENGTH: 118
<212> TYPE: PRT
<213> ORGANISM: Homo sapiens

<400> SEQUENCE: 263

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Tyr Arg
             20                  25                  30

Met Gly Trp Val Arg Gln Ala Pro Gly Lys Gly Leu Glu Trp Val Ser
         35                  40                  45

Trp Ile Thr Arg Thr Gly Gly Thr Gln Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                85                  90                  95

Lys Pro Ala Lys Leu Val Gly Val Gly Phe Asp Tyr Trp Gly Gln Gly
                100                 105                 110

Thr Leu Val Thr Val Ser
        115

<210> SEQ ID NO 264
<211> LENGTH: 357
<212> TYPE: DNA
<213> ORGANISM: Homo sapiens

<400> SEQUENCE: 264
gaggtgcagc tgttggagtc tgggggaggc ttggtacagc ctggggggtc cctgcgtctc    60
tcctgtgcag cctccggatt cacctttag gggtatcgta tgggttgggt ccgccaggct    120
ccagggaagg gtctagagtg gtctcatgg attacgcgta ctggtgggac gacacagtac    180
gcagactccg tgaagggccg gttcaccatc tcccgcgaca attccaagaa cacgctgtat    240
ctgcaaatga acagcctgcg tgccgaggac accgcggtat attactgtgc gaaaccggcg    300
aagcttgttg gggttgggtt tgactactgg ggccagggaa ccctggtcac cgtctcg      357

<210> SEQ ID NO 265
<211> LENGTH: 357
<212> TYPE: DNA
<213> ORGANISM: Homo sapiens

<400> SEQUENCE: 265
cgagacggtg accagggttc cctggcccca gtagtcaaac ccaaccccaa caagcttcgc    60
cggtttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
ctgtgtcgtc ccaccagtac gcgtaatcca tgagacccac tctagaccct ccctggagc    240 ctggcggacc caacccatac gatacccta aaaggtgaat ccggaggctg cacaggagag    300
acgcagggac cccccaggct gtaccaagcc tcccccagac tccaacagct gcacctc      357

<210> SEQ ID NO 266
<211> LENGTH: 118
<212> TYPE: PRT
<213> ORGANISM: Homo sapiens

<400> SEQUENCE: 266

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Arg Lys Tyr
            20                  25                  30

Met Gly Trp Val Arg Gln Ala Pro Gly Lys Gly Leu Glu Trp Val Ser
        35                  40                  45

Gln Ile Gly Ala Lys Gly Gln Ser Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Lys Lys Arg Gly Glu Asn Tyr Phe Phe Asp Tyr Trp Gly Gln Gly
                100                 105                 110

Thr Leu Val Thr Val Ser
        115

<210> SEQ ID NO 267
<211> LENGTH: 357
<212> TYPE: DNA
<213> ORGANISM: Homo sapiens

<400> SEQUENCE: 267

```
gaggtgcagc tgttggagtc tgggggaggc ttggtacagc ctggggggtc cctgcgtctc      60
tcctgtgcag cctccggatt cacctttcgg aagtattaga tggggtgggt ccgccaggct     120
ccagggaagg gtctagagtg ggtctcacag attggtgcga agggtcagtc tacagattac     180
gcagactccg tgaagggccg gttcaccatc tcccgcgaca attccaagaa cacgctgtat     240
ctgcaaatga acagcctgcg tgccgaggac accgcggtat attactgtgc gaaaaagaag     300
agggggggaga attatttttt tgactactgg ggccagggaa ccctggtcac cgtctcg      357
```

<210> SEQ ID NO 268
<211> LENGTH: 357
<212> TYPE: DNA
<213> ORGANISM: Homo sapiens

<400> SEQUENCE: 268

```
cgagacggtg accagggttc cctggcccca gtagtcaaaa aaataattct ccccccctctt    60
cttttttcgca cagtaatata ccgcggtgtc ctcggcacgc aggctgttca tttgcagata   120
cagcgtgttc ttggaattgt cgcgggagat ggtgaaccgg cccttcacgg agtctgcgta   180
atctgtagac tgacccttcg caccaatctg tgagacccac tctagaccct ccctggagc    240
ctggcggacc caccccatct aatacttccg aaaggtgaat ccggaggctg cacaggagag   300
acgcagggac cccccaggct gtaccaagcc tcccccagac tccaacagct gcacctc       357
```

<210> SEQ ID NO 269
<211> LENGTH: 119
<212> TYPE: PRT
<213> ORGANISM: Homo sapiens

<400> SEQUENCE: 269

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Arg Tyr
            20                  25                  30

Ser Met Ser Trp Val Arg Gln Ala Pro Gly Lys Gly Leu Glu Trp Val
        35                  40                  45

Ser Asp Ile Ser Arg Ser Gly Arg Tyr Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ile Asp Ser Ser Gln Asn Gly Phe Asp Tyr Trp Gly Gln
            100                 105                 110

Gly Thr Leu Val Thr Val Ser
        115

<210> SEQ ID NO 270
<211> LENGTH: 357
<212> TYPE: DNA
<213> ORGANISM: Homo sapiens

<400> SEQUENCE: 270

```
gaggtgcagc tgttggagtc tgggggaggc ttggtacagc ctgggggggtc cctgcgtctc      60 tcctgtgcag cctccggatt cacctttcgg cggtatagta tgtcgtgggt ccgccaggct     120
ccagggaagg gtctagagtg ggtctcagat atttctcgtt ctggtcggta tacacattac     180
gcagactccg tgaagggccg gttcaccatc tcccgcgaca attccaagaa cacgctgtat     240
ctgcaaatga acagcctgcg tgccgaggac accgcggtat attactgtgc gaaacgtatt     300
gattcttctc agaatgggtt tgactactgg ggccagggaa ccctggtcac cgtctcg        357
```

<210> SEQ ID NO 271
<211> LENGTH: 357
<212> TYPE: DNA
<213> ORGANISM: Homo sapiens

<400> SEQUENCE: 271

```
cgagacggtg accagggttc cctggcccca gtagtcaaac ccattctgag aagaatcaat      60
acgtttcgca cagtaatata ccgcggtgtc ctcggcacgc aggctgttca tttgcagata     120
cagcgtgttc ttggaattgt cgcgggagat ggtgaaccgg cccttcacgg agtctgcgta     180
atgtgtatac cgaccagaac gagaaatatc tgagacccac tctagaccct tccctggagc     240
ctggcggacc cacgacatac tataccgccg aaaggtgaat ccggaggctg cacaggagag     300
acgcagggac cccccaggct gtaccaagcc tccccagac tccaacagct gcacctc          357
```

<210> SEQ ID NO 272
<211> LENGTH: 114
<212> TYPE: PRT
<213> ORGANISM: Homo sapiens

<400> SEQUENCE: 272

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Gly Tyr Lys
             20                  25                  30

Met Phe Trp Val Arg Gln Ala Pro Gly Lys Gly Leu Glu Trp Val Ser
         35                  40                  45

Ala Ile Ser Gly Ser Gly Gly Ser Thr Tyr Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Lys Gln Lys Glu Asn Phe Asp Tyr Trp Gly Gln Gly Thr Leu Val Thr
            100                 105                 110

Val Ser
```

<210> SEQ ID NO 273
<211> LENGTH: 345
<212> TYPE: DNA
<213> ORGANISM: Homo sapiens

<400> SEQUENCE: 273

```
gaggtgcagc tgttggagtc tgggggaggc ttggtacagc ctgggggggtc cctgcgtctc      60 tcctgtgcag cctccggatt cacctttag gggtataaga tgttttgggt ccgccaggct      120
ccagggaagg gtctagagtg ggtctcagct attagtggta gtggtggtag cacatactac     180
gcagactccg tgaagggccg gttcaccatc tcccgcgaca attccaagaa cacgctgtat     240
```
ctgcaaatga acagcctgcg tgccgaggac accgcggtat attactgtgc gaaacagaag    300
gagaattttg actactgggg ccagggaacc ctggtcaccg tctcg                    345

<210> SEQ ID NO 274
<211> LENGTH: 345
<212> TYPE: DNA
<213> ORGANISM: Homo sapiens

<400> SEQUENCE: 274
cgagacggtg accagggttc cctggcccca gtagtcaaaa ttctccttct gtttcgcaca     60
gtaatatacc gcggtgtcct cggcacgcag gctgttcatt tgcagataca gcgtgttctt   120
ggaattgtcg cgggagatgg tgaaccggcc cttcacggag tctgcgtagt atgtgctacc   180
accactacca ctaatagctg agacccactc tagacccttc cctggagcct ggcggaccca   240
aaacatctta taccctaaaa aggtgaatcc ggaggctgca caggagagac gcagggaccc   300
cccaggctgt accaagcctc ccccagactc aacagctgc acctc                    345

<210> SEQ ID NO 275
<211> LENGTH: 119
<212> TYPE: PRT
<213> ORGANISM: Homo sapiens

<400> SEQUENCE: 275

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Tyr
            20                  25                  30

Ala Met Trp Trp Val Arg Gln Ala Pro Gly Lys Gly Leu Glu Trp Val
        35                  40                  45

Ser Val Ile Ser Ser Asn Gly Gly Ser Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Val Arg Lys Arg Thr Pro Glu Phe Asp Tyr Trp Gly Gln
            100                 105                 110

Gly Thr Leu Val Thr Val Ser
        115

<210> SEQ ID NO 276
<211> LENGTH: 357
<212> TYPE: DNA
<213> ORGANISM: Homo sapiens

<400> SEQUENCE: 276
gaggtgcagc tgttggagtc tgggggaggc ttggtacagc ctgggggtc cctgcgtctc     60 tcctgtgcag cctccggatt cacctttggg gattatgcta tgtggtgggt ccgccaggct   120
ccagggaagg gtctagagtg gtctcagtg attagttcga atggtgggag tacattttac    180
gcagactccg tgaagggccg gttcaccatc tcccgcgaca attccaagaa cacgctgtat   240
ctgcaaatga acagcctgcg tgccgaggac accgcggtat attactgtgc gaaacgtgtt   300
cgtaagagga ctcctgagtt tgactactgg ggccaggaa ccctggtcac cgtctcg       357

<210> SEQ ID NO 277

<211> LENGTH: 357
<212> TYPE: DNA
<213> ORGANISM: Homo sapiens

<400> SEQUENCE: 277

```
cgagacggtg accagggttc cctggcccca gtagtcaaac tcaggagtcc tcttacgaac    60
acgtttcgca cagtaatata ccgcggtgtc ctcggcacgc aggctgttca tttgcagata   120
cagcgtgttc ttggaattgt cgcgggagat ggtgaaccgg cccttcacgg agtctgcgta   180
aaatgtactc ccaccattcg aactaatcac tgagacccac tctagaccct ccctggagc    240
ctggcggacc caccacatag cataatcccc aaaggtgaat ccggaggctg cacaggagag   300
acgcagggac cccccaggct gtaccaagcc tcccccagac tccaacagct gcacctc      357
```

<210> SEQ ID NO 278
<211> LENGTH: 119
<212> TYPE: PRT
<213> ORGANISM: Homo sapiens

<400> SEQUENCE: 278

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Arg Tyr
             20                  25                  30

Lys Met Gly Trp Val Arg Gln Ala Pro Gly Lys Gly Leu Glu Trp Val
         35                  40                  45

Ser Ala Ile Gly Arg Asn Gly Thr Lys Thr Asn Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Tyr Thr Gly Lys Pro Ala Ala Phe Asp Tyr Trp Gly Gln
            100                 105                 110

Gly Thr Leu Val Thr Val Ser
        115
```

<210> SEQ ID NO 279
<211> LENGTH: 357
<212> TYPE: DNA
<213> ORGANISM: Homo sapiens

<400> SEQUENCE: 279

```
gaggtgcagc tgttggagtc tgggggaggc ttggtacagc ctggggggtc cctgcgtctc    60
tcctgtgcag cctccggatt cacctttagg aggtataaga tgggttgggt ccgccaggct   120
ccagggaagg gtctagagtg ggtctcagcg attggggagga atggtacgaa gacaaattac   180
gcagactccg tgaagggccg gttcaccatc tcccgcgaca attccaagaa cacgctgtat   240
ctgcaaatga acagcctgcg tgccgaggac accgcggtat attactgtgc gaaaatttat   300
acggggaagc ctgctgcgtt tgactactgg ggccagggaa ccctggtcac cgtctcg      357
```

<210> SEQ ID NO 280
<211> LENGTH: 357
<212> TYPE: DNA
<213> ORGANISM: Homo sapiens

<400> SEQUENCE: 280

```
cgagacggtg accagggttc cctggcccca gtagtcaaac gcagcaggct tccccgtata    60
```

```
aattttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
atttgtcttc gtaccattcc tcccaatcgc tgagacccac tctagaccct tccctggagc    240
ctggcggacc caacccatct tatacctcct aaaggtgaat ccggaggctg cacaggagag    300
acgcagggac cccccaggct gtaccaagcc tcccccagac tccaacagct gcacctc       357
```

<210> SEQ ID NO 281
<211> LENGTH: 118
<212> TYPE: PRT
<213> ORGANISM: Homo sapiens

<400> SEQUENCE: 281

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Lys Tyr
            20                  25                  30

Met Ser Trp Val Arg Gln Ala Pro Gly Lys Gly Leu Glu Trp Val Ser
        35                  40                  45

Ala Ile Ser Gly Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Met Leu Arg Thr Lys Asn Lys Val Phe Asp Tyr Trp Gly Gln Gly
            100                 105                 110

Thr Leu Val Thr Val Ser
        115

<210> SEQ ID NO 282
<211> LENGTH: 357
<212> TYPE: DNA
<213> ORGANISM: Homo sapiens

<400> SEQUENCE: 282

```
gaggtgcagc tgttggagtc tgggggaggc ttggtacagc ctgggggtc cctgcgtctc     60 tcctgtgcag cctccggatt cacctttaag aagtattaga tgtcttgggt ccgccaggct    120
ccagggaagg gtctagagtg ggtctcagct attagtggta gtggtggtag cacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatgctg    300
aggactaaga ataaggtgtt tgactactgg ggccaggaa ccctggtcac cgtctcg        357
```

<210> SEQ ID NO 283
<211> LENGTH: 357
<212> TYPE: DNA
<213> ORGANISM: Homo sapiens

<400> SEQUENCE: 283

```
cgagacggtg accagggttc cctggcccca gtagtcaaac accttattct tagtcctcag     60
cattttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
gtatgtgcta ccaccactac cactaatagc tgagacccac tctagaccct tccctggagc    240
```
ctggcggacc aagacatct aatacttctt aaaggtgaat ccggaggctg cacaggagag   300
acgcagggac cccccaggct gtaccaagcc tcccccagac tccaacagct gcacctc   357

<210> SEQ ID NO 284
<211> LENGTH: 119
<212> TYPE: PRT
<213> ORGANISM: Homo sapiens

<400> SEQUENCE: 284

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Arg Arg Tyr
            20                  25                  30

Lys Met Gly Trp Val Arg Gln Ala Pro Gly Lys Gly Leu Glu Trp Val
        35                  40                  45

Ser Ala Ile Gly Arg Asn Gly Thr Lys Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Tyr Thr Gly Lys Pro Ala Ala Phe Asp Tyr Trp Gly Gln
            100                 105                 110

Gly Thr Leu Val Thr Val Ser
        115

<210> SEQ ID NO 285
<211> LENGTH: 357
<212> TYPE: DNA
<213> ORGANISM: Homo sapiens

<400> SEQUENCE: 285
gaggtgcagc tgttggagtc tgggggaggc ttggtacagc ctgggggtc cctgcgtctc   60 tcctgtgcag cctccggatt cacctttagg aggtataaga tgggttgggt ccgccaggct   120
ccagggaagg gtctagagtg gtctcagcg attgggagga atggtacgaa gacaaattac   180
gcagactccg tgaagggccg gttcaccatc tcccgcgaca attccaagaa cacgctgtat   240
ctgcaaatga acagcctgcg tgccgaggac ccgcggtat attactgtgc gaaaatttat   300
acggggaagc tgctgcgtt tgactactgg ggccagggaa ccctggtcac cgtctcg   357

<210> SEQ ID NO 286
<211> LENGTH: 357
<212> TYPE: DNA
<213> ORGANISM: Homo sapiens

<400> SEQUENCE: 286
cgagacggtg accagggttc cctggcccca gtagtcaaac gcagcaggct tccccgtata   60
aattttcgca cagtaatata ccgcggtgtc ctcggcacgc aggctgttca tttgcagata   120
cagcgtgttc ttggaattgt cgcgggagat ggtgaaccgg cccttcacgg agtctgcgta   180
atttgtcttc gtaccattcc tcccaatcgc tgagacccac tctagaccct tcctggagc   240 ctggcggacc aacccatct tataccctct aaaggtgaat ccggaggctg cacaggagag   300
acgcagggac cccccaggct gtaccaagcc tcccccagac tccaacagct gcacctc   357

<210> SEQ ID NO 287
<211> LENGTH: 118

```
<212> TYPE: PRT
<213> ORGANISM: Homo sapiens

<400> SEQUENCE: 287

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Tyr Arg
            20                  25                  30

Met Gly Trp Val Arg Gln Ala Pro Gly Lys Gly Leu Glu Trp Val Ser
        35                  40                  45

Ser Ile Ser Ser Arg Gly Arg His Thr Ser Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Arg Val Pro Gly Arg Gly Ser Phe Asp Tyr Trp Gly Gln Gly
            100                 105                 110

Thr Leu Val Thr Val Ser
        115

<210> SEQ ID NO 288
<211> LENGTH: 357
<212> TYPE: DNA
<213> ORGANISM: Homo sapiens

<400> SEQUENCE: 288
gaggtgcagc tgttggagtc tgggggaggc ttggtacagc ctgggggtc  cctgcgtctc      60 tcctgtgcag cctccggatt cacctttag  agttatcgga tgggttgggt ccgccaggct     120
ccagggaagg gtctagagtg gtctcaagt  atttcgtcga ggggtaggca tacatcttac     180
gcagactccg tgaagggccg gttcaccatc tcccgcgaca attccaagaa cacgctgtat     240
ctgcaaatga acagcctgcg tgccgaggac accgcggtat attactgtgc gaaagggtt      300 ccgggtcggg ggcgttcttt tgactactgg ggccagggaa ccctggtcac cgtctcg       357

<210> SEQ ID NO 289
<211> LENGTH: 357
<212> TYPE: DNA
<213> ORGANISM: Homo sapiens

<400> SEQUENCE: 289
cgagacggtg accagggttc cctggcccca gtagtcaaaa gaacgccccc gacccggaac      60
ccttttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
agatgtatgc ctacccctcg acgaaatact tgagacccac tctagaccct tccctggagc    240
ctggcggacc caaccatcc  gataactcta aaaggtgaat ccggaggctg cacaggagag    300
acgcagggac cccccaggct gtaccaagcc tcccccagac tccaacagct gcacctc       357

<210> SEQ ID NO 290
<211> LENGTH: 119
<212> TYPE: PRT
<213> ORGANISM: Homo sapiens

<400> SEQUENCE: 290

Glu Val Gln Leu Leu Glu Ser Gly Gly Gly Leu Val Gln Pro Gly Gly
 1               5                  10                  15
```

```
Ser Leu Arg Leu Ser Cys Ala Ala Ser Gly Phe Pro Phe Arg Arg Tyr
            20                  25                  30

Arg Met Arg Trp Val Arg Gln Ala Pro Gly Lys Gly Leu Glu Trp Val
            35                  40                  45

Ser Gly Ile Ser Pro Gly Gly Lys His Thr Thr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Glu Gly Gly Ala Ser Ala Phe Asp Tyr Trp Gly Gln
            100                 105                 110

Gly Thr Leu Val Thr Val Ser
            115

<210> SEQ ID NO 291
<211> LENGTH: 357
<212> TYPE: DNA
<213> ORGANISM: Homo sapiens

<400> SEQUENCE: 291
gaggtgcagc tgttggagtc tgggggaggc ttggtacagc ctggggggtc cctgcgtctc    60
tcctgtgcag cctccggatt ccccttcgt cggtatcgga tgaggtgggt ccgccaggct    120
ccagggaagg gtctagagtg ggtctcaggt atttctccgg tggtaagca tacaacgtac     180 gcagactccg tgaagggccg gttcaccatc tcccgcgaca attccaagaa cacgctgtat    240
ctgcaaatga acagcctgcg tgccgaggac accgcggtat attactgtgc gaaaggtgag    300 ggggggggcga gttctgcgtt tgactactgg ggccaggaa ccctggtcac cgtctcg      357

<210> SEQ ID NO 292
<211> LENGTH: 357
<212> TYPE: DNA
<213> ORGANISM: Homo sapiens

<400> SEQUENCE: 292
cgagacggtg accagggttc cctggcccca gtagtcaaac gcagaactcg ccccccctc     60 acctttcgca cagtaatata ccgcggtgtc ctcggcacgc aggctgttca tttgcagata    120
cagcgtgttc ttggaattgt cgcgggagat ggtgaaccgg cccttcacgg agtctgcgta    180
cgttgtatgc ttaccacccg gagaaatacc tgagacccac tctagaccct tccctggagc    240
ctggcggacc cacctcatcc gataccgacg aaagggggaat ccggaggctg cacaggagag   300
acgcagggac cccccaggct gtaccaagcc tccccagac tccaacagct gcacctc        357

<210> SEQ ID NO 293
<211> LENGTH: 118
<212> TYPE: PRT
<213> ORGANISM: Homo sapiens

<400> SEQUENCE: 293

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Tyr Gly
            20                  25                  30

Met Val Trp Val Arg Gln Ala Pro Gly Lys Gly Leu Glu Trp Val Ser
            35                  40                  45
```

```
Ala Ile Ser Gly Ser Gly Gly Ser Thr Tyr Tyr Ala Asp Ser Val Lys
     50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Lys Arg His Ser Ser Glu Ala Arg Gln Phe Asp Tyr Trp Gly Gln Gly
             100                 105                 110
Thr Leu Val Thr Val Ser
            115
```

<210> SEQ ID NO 294
<211> LENGTH: 357
<212> TYPE: DNA
<213> ORGANISM: Homo sapiens

<400> SEQUENCE: 294

```
gaggtgcagc tgttggagtc tgggggaggc ttggtacagc ctgggggtc cctgcgtctc    60
tcctgtgcag cctccggatt cacctttag cggtatggga tggtttgggt ccgccaggct   120
ccagggaagg gtctagagtg ggtctcagct attagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaacggcat   300
agttctgagg ctaggcagtt tgactactgg ggccagggaa ccctggtcac cgtctcg    357
```

<210> SEQ ID NO 295
<211> LENGTH: 357
<212> TYPE: DNA
<213> ORGANISM: Homo sapiens

<400> SEQUENCE: 295

```
cgagacggtg accagggttc cctggcccca gtagtcaaac tgcctagcct cagaactatg    60
ccgtttcgca cagtaatata ccgcggtgtc ctcggcacgc aggctgttca tttgcagata   120
cagcgtgttc ttggaattgt cgcgggagat ggtgaaccgg cccttcacgg agtctgcgta   180
gtatgtgcta ccaccactac cactaatagc tgagaccac  tctagaccct tccctggagc   240
ctggcggacc caaccatcc cataccgcta aaaggtgaat ccggaggctg cacaggagag   300
acgcagggac cccccaggct gtaccaagcc tccccagac tccaacagct gcacctc      357
```

<210> SEQ ID NO 296
<211> LENGTH: 39
<212> TYPE: DNA
<213> ORGANISM: Artificial Sequence
<220> FEATURE:
<223> OTHER INFORMATION: primer

<400> SEQUENCE: 296

```
tggagcgcgt cgacggacat ccagatgacc cagtctcca                           39
```

<210> SEQ ID NO 297
<211> LENGTH: 39
<212> TYPE: DNA
<213> ORGANISM: Artificial Sequence
<220> FEATURE:
<223> OTHER INFORMATION: primer

<400> SEQUENCE: 297

```
ttagcagccg gatccttatt agcaccgttt gatttccac                           39
```

<210> SEQ ID NO 298
<211> LENGTH: 5
<212> TYPE: PRT
<213> ORGANISM: Artificial Sequence
<220> FEATURE:
<223> OTHER INFORMATION: CDR1
<220> FEATURE:
<221> NAME/KEY: VARIANT
<222> LOCATION: 1, 2, 3, 5
<223> OTHER INFORMATION: Xaa = Any Amino Acid

<400> SEQUENCE: 298

Xaa Xaa Xaa Leu Xaa
1               5

<210> SEQ ID NO 299
<211> LENGTH: 7
<212> TYPE: PRT
<213> ORGANISM: Artificial Sequence
<220> FEATURE:
<223> OTHER INFORMATION: CDR2
<220> FEATURE:
<221> NAME/KEY: VARIANT
<222> LOCATION: 1, 4
<223> OTHER INFORMATION: Xaa = Any Amino Acid

<400> SEQUENCE: 299

Xaa Ala Ser Xaa Leu Gln Ser
1               5

<210> SEQ ID NO 300
<211> LENGTH: 9
<212> TYPE: PRT
<213> ORGANISM: Artificial Sequence
<220> FEATURE:
<223> OTHER INFORMATION: CDR3
<220> FEATURE:
<221> NAME/KEY: VARIANT
<222> LOCATION: 3, 4, 5, 6, 8
<223> OTHER INFORMATION: Xaa = Any Amino Acid

<400> SEQUENCE: 300

Gln Gln Xaa Xaa Xaa Xaa Pro Xaa Thr
1               5

<210> SEQ ID NO 301
<211> LENGTH: 5
<212> TYPE: PRT
<213> ORGANISM: Artificial Sequence
<220> FEATURE:
<223> OTHER INFORMATION: CDR1

<400> SEQUENCE: 301

Ser Ser Tyr Leu Asn
1               5

<210> SEQ ID NO 302
<211> LENGTH: 7
<212> TYPE: PRT
<213> ORGANISM: Artificial Sequence
<220> FEATURE:
<223> OTHER INFORMATION: CDR2

<400> SEQUENCE: 302

Arg Ala Ser Pro Leu Gln Ser
1               5

<210> SEQ ID NO 303

```
<211> LENGTH: 9
<212> TYPE: PRT
<213> ORGANISM: Artificial Sequence
<220> FEATURE:
<223> OTHER INFORMATION: CDR3

<400> SEQUENCE: 303

Gln Gln Thr Tyr Ser Val Pro Pro Thr
  1               5

<210> SEQ ID NO 304
<211> LENGTH: 5
<212> TYPE: PRT
<213> ORGANISM: Artificial Sequence
<220> FEATURE:
<223> OTHER INFORMATION: CDR1

<400> SEQUENCE: 304

Ser Ser Tyr Leu Asn
  1               5

<210> SEQ ID NO 305
<211> LENGTH: 7
<212> TYPE: PRT
<213> ORGANISM: Artificial Sequence
<220> FEATURE:
<223> OTHER INFORMATION: CDR2

<400> SEQUENCE: 305

Arg Ala Ser Pro Leu Gln Ser
  1               5

<210> SEQ ID NO 306
<211> LENGTH: 9
<212> TYPE: PRT
<213> ORGANISM: Artificial Sequence
<220> FEATURE:
<223> OTHER INFORMATION: CDR3

<400> SEQUENCE: 306

Gln Gln Thr Tyr Arg Ile Pro Pro Thr
  1               5

<210> SEQ ID NO 307
<211> LENGTH: 5
<212> TYPE: PRT
<213> ORGANISM: Artificial Sequence
<220> FEATURE:
<223> OTHER INFORMATION: CDR1

<400> SEQUENCE: 307

Phe Lys Ser Leu Lys
  1               5

<210> SEQ ID NO 308
<211> LENGTH: 7
<212> TYPE: PRT
<213> ORGANISM: Artificial Sequence
<220> FEATURE:
<223> OTHER INFORMATION: CDR2

<400> SEQUENCE: 308

Asn Ala Ser Tyr Leu Gln Ser
  1               5

<210> SEQ ID NO 309
<211> LENGTH: 9
```

```
<212> TYPE: PRT
<213> ORGANISM: Artificial Sequence
<220> FEATURE:
<223> OTHER INFORMATION: CDR3

<400> SEQUENCE: 309

Gln Gln Val Val Tyr Trp Pro Val Thr
 1               5

<210> SEQ ID NO 310
<211> LENGTH: 5
<212> TYPE: PRT
<213> ORGANISM: Artificial Sequence
<220> FEATURE:
<223> OTHER INFORMATION: CDR1

<400> SEQUENCE: 310

Tyr Tyr His Leu Lys
 1               5

<210> SEQ ID NO 311
<211> LENGTH: 7
<212> TYPE: PRT
<213> ORGANISM: Artificial Sequence
<220> FEATURE:
<223> OTHER INFORMATION: CDR2

<400> SEQUENCE: 311

Lys Ala Ser Thr Leu Gln Ser
 1               5

<210> SEQ ID NO 312
<211> LENGTH: 9
<212> TYPE: PRT
<213> ORGANISM: Artificial Sequence
<220> FEATURE:
<223> OTHER INFORMATION: CDR3

<400> SEQUENCE: 312

Gln Gln Val Arg Lys Val Pro Arg Thr
 1               5

<210> SEQ ID NO 313
<211> LENGTH: 5
<212> TYPE: PRT
<213> ORGANISM: Artificial Sequence
<220> FEATURE:
<223> OTHER INFORMATION: CDR1

<400> SEQUENCE: 313

Arg Arg Tyr Leu Lys
 1               5

<210> SEQ ID NO 314
<211> LENGTH: 7
<212> TYPE: PRT
<213> ORGANISM: Artificial Sequence
<220> FEATURE:
<223> OTHER INFORMATION: CDR2

<400> SEQUENCE: 314

Gln Ala Ser Val Leu Gln Ser
 1               5

<210> SEQ ID NO 315
<211> LENGTH: 9
<212> TYPE: PRT
```

```
<213> ORGANISM: Artificial Sequence
<220> FEATURE:
<223> OTHER INFORMATION: CDR3

<400> SEQUENCE: 315

Gln Gln Gly Leu Tyr Pro Pro Ile Thr
 1               5

<210> SEQ ID NO 316
<211> LENGTH: 5
<212> TYPE: PRT
<213> ORGANISM: Artificial Sequence
<220> FEATURE:
<223> OTHER INFORMATION: CDR1

<400> SEQUENCE: 316

Tyr Asn Trp Leu Lys
 1               5

<210> SEQ ID NO 317
<211> LENGTH: 7
<212> TYPE: PRT
<213> ORGANISM: Artificial Sequence
<220> FEATURE:
<223> OTHER INFORMATION: CDR2

<400> SEQUENCE: 317

Arg Ala Ser Ser Leu Gln Ser
 1               5

<210> SEQ ID NO 318
<211> LENGTH: 9
<212> TYPE: PRT
<213> ORGANISM: Artificial Sequence
<220> FEATURE:
<223> OTHER INFORMATION: CDR3

<400> SEQUENCE: 318

Gln Gln Asn Val Val Ile Pro Arg Thr
 1               5

<210> SEQ ID NO 319
<211> LENGTH: 5
<212> TYPE: PRT
<213> ORGANISM: Artificial Sequence
<220> FEATURE:
<223> OTHER INFORMATION: CDR1

<400> SEQUENCE: 319

Leu Trp His Leu Arg
 1               5

<210> SEQ ID NO 320
<211> LENGTH: 7
<212> TYPE: PRT
<213> ORGANISM: Artificial Sequence
<220> FEATURE:
<223> OTHER INFORMATION: CDR2

<400> SEQUENCE: 320

His Ala Ser Leu Leu Gln Ser
 1               5

<210> SEQ ID NO 321
<211> LENGTH: 9
<212> TYPE: PRT
<213> ORGANISM: Artificial Sequence
```

```
<220> FEATURE:
<223> OTHER INFORMATION: CDR3

<400> SEQUENCE: 321

Gln Gln Ser Ala Val Tyr Pro Lys Thr
 1               5

<210> SEQ ID NO 322
<211> LENGTH: 5
<212> TYPE: PRT
<213> ORGANISM: Artificial Sequence
<220> FEATURE:
<223> OTHER INFORMATION: CDR1

<400> SEQUENCE: 322

Phe Arg Tyr Leu Ala
 1               5

<210> SEQ ID NO 323
<211> LENGTH: 7
<212> TYPE: PRT
<213> ORGANISM: Artificial Sequence
<220> FEATURE:
<223> OTHER INFORMATION: CDR2

<400> SEQUENCE: 323

His Ala Ser His Leu Gln Ser
 1               5

<210> SEQ ID NO 324
<211> LENGTH: 9
<212> TYPE: PRT
<213> ORGANISM: Artificial Sequence
<220> FEATURE:
<223> OTHER INFORMATION: CDR3

<400> SEQUENCE: 324

Gln Gln Arg Leu Leu Tyr Pro Lys Thr
 1               5

<210> SEQ ID NO 325
<211> LENGTH: 5
<212> TYPE: PRT
<213> ORGANISM: Artificial Sequence
<220> FEATURE:
<223> OTHER INFORMATION: CDR1

<400> SEQUENCE: 325

Phe Tyr His Leu Ala
 1               5

<210> SEQ ID NO 326
<211> LENGTH: 7
<212> TYPE: PRT
<213> ORGANISM: Artificial Sequence
<220> FEATURE:
<223> OTHER INFORMATION: CDR2

<400> SEQUENCE: 326

Pro Ala Ser Lys Leu Gln Ser
 1               5

<210> SEQ ID NO 327
<211> LENGTH: 9
<212> TYPE: PRT
<213> ORGANISM: Artificial Sequence
<220> FEATURE:
```

<223> OTHER INFORMATION: CDR3

<400> SEQUENCE: 327

Gln Gln Arg Ala Arg Trp Pro Arg Thr
1               5

<210> SEQ ID NO 328
<211> LENGTH: 5
<212> TYPE: PRT
<213> ORGANISM: Artificial Sequence
<220> FEATURE:
<223> OTHER INFORMATION: CDR1

<400> SEQUENCE: 328

Ile Trp His Leu Asn
1               5

<210> SEQ ID NO 329
<211> LENGTH: 7
<212> TYPE: PRT
<213> ORGANISM: Artificial Sequence
<220> FEATURE:
<223> OTHER INFORMATION: CDR2

<400> SEQUENCE: 329

Arg Ala Ser Arg Leu Gln Ser
1               5

<210> SEQ ID NO 330
<211> LENGTH: 9
<212> TYPE: PRT
<213> ORGANISM: Artificial Sequence
<220> FEATURE:
<223> OTHER INFORMATION: CDR3

<400> SEQUENCE: 330

Gln Gln Val Ala Arg Val Pro Arg Thr
1               5

<210> SEQ ID NO 331
<211> LENGTH: 5
<212> TYPE: PRT
<213> ORGANISM: Artificial Sequence
<220> FEATURE:
<223> OTHER INFORMATION: CDR1

<400> SEQUENCE: 331

Tyr Arg Tyr Leu Arg
1               5

<210> SEQ ID NO 332
<211> LENGTH: 7
<212> TYPE: PRT
<213> ORGANISM: Artificial Sequence
<220> FEATURE:
<223> OTHER INFORMATION: CDR2

<400> SEQUENCE: 332

Lys Ala Ser Ser Leu Gln Ser
1               5

<210> SEQ ID NO 333
<211> LENGTH: 9
<212> TYPE: PRT
<213> ORGANISM: Artificial Sequence
<220> FEATURE:
<223> OTHER INFORMATION: CDR3

<400> SEQUENCE: 333

Gln Gln Tyr Val Gly Tyr Pro Arg Thr
1               5

<210> SEQ ID NO 334
<211> LENGTH: 5
<212> TYPE: PRT
<213> ORGANISM: Artificial Sequence
<220> FEATURE:
<223> OTHER INFORMATION: CDR1

<400> SEQUENCE: 334

Leu Lys Tyr Leu Lys
1               5

<210> SEQ ID NO 335
<211> LENGTH: 7
<212> TYPE: PRT
<213> ORGANISM: Artificial Sequence
<220> FEATURE:
<223> OTHER INFORMATION: CDR2

<400> SEQUENCE: 335

Asn Ala Ser His Leu Gln Ser
1               5

<210> SEQ ID NO 336
<211> LENGTH: 9
<212> TYPE: PRT
<213> ORGANISM: Artificial Sequence
<220> FEATURE:
<223> OTHER INFORMATION: CDR3

<400> SEQUENCE: 336

Gln Gln Thr Thr Tyr Tyr Pro Ile Thr
1               5

<210> SEQ ID NO 337
<211> LENGTH: 5
<212> TYPE: PRT
<213> ORGANISM: Artificial Sequence
<220> FEATURE:
<223> OTHER INFORMATION: CDR1

<400> SEQUENCE: 337

Leu Arg Tyr Leu Arg
1               5

<210> SEQ ID NO 338
<211> LENGTH: 7
<212> TYPE: PRT
<213> ORGANISM: Artificial Sequence
<220> FEATURE:
<223> OTHER INFORMATION: CDR2

<400> SEQUENCE: 338

Lys Ala Ser Trp Leu Gln Ser
1               5

<210> SEQ ID NO 339
<211> LENGTH: 9
<212> TYPE: PRT
<213> ORGANISM: Artificial Sequence
<220> FEATURE:
<223> OTHER INFORMATION: CDR3

```
<400> SEQUENCE: 339

Gln Gln Val Leu Tyr Tyr Pro Gln Thr
 1               5

<210> SEQ ID NO 340
<211> LENGTH: 5
<212> TYPE: PRT
<213> ORGANISM: Artificial Sequence
<220> FEATURE:
<223> OTHER INFORMATION: CDR1

<400> SEQUENCE: 340

Leu Arg Ser Leu Lys
 1               5

<210> SEQ ID NO 341
<211> LENGTH: 7
<212> TYPE: PRT
<213> ORGANISM: Artificial Sequence
<220> FEATURE:
<223> OTHER INFORMATION: CDR2

<400> SEQUENCE: 341

Ala Ala Ser Arg Leu Gln Ser
 1               5

<210> SEQ ID NO 342
<211> LENGTH: 9
<212> TYPE: PRT
<213> ORGANISM: Artificial Sequence
<220> FEATURE:
<223> OTHER INFORMATION: CDR3

<400> SEQUENCE: 342

Gln Gln Val Val Tyr Trp Pro Ala Thr
 1               5

<210> SEQ ID NO 343
<211> LENGTH: 5
<212> TYPE: PRT
<213> ORGANISM: Artificial Sequence
<220> FEATURE:
<223> OTHER INFORMATION: CDR1

<400> SEQUENCE: 343

Phe Arg His Leu Lys
 1               5

<210> SEQ ID NO 344
<211> LENGTH: 7
<212> TYPE: PRT
<213> ORGANISM: Artificial Sequence
<220> FEATURE:
<223> OTHER INFORMATION: CDR2

<400> SEQUENCE: 344

Ala Ala Ser Arg Leu Gln Ser
 1               5

<210> SEQ ID NO 345
<211> LENGTH: 9
<212> TYPE: PRT
<213> ORGANISM: Artificial Sequence
<220> FEATURE:
<223> OTHER INFORMATION: CDR3

<400> SEQUENCE: 345
```

```
Gln Gln Val Ala Leu Tyr Pro Lys Thr
 1               5
```

<210> SEQ ID NO 346
<211> LENGTH: 5
<212> TYPE: PRT
<213> ORGANISM: Artificial Sequence
<220> FEATURE:
<223> OTHER INFORMATION: CDR1

<400> SEQUENCE: 346

```
Arg Lys Tyr Leu Arg
 1               5
```

<210> SEQ ID NO 347
<211> LENGTH: 7
<212> TYPE: PRT
<213> ORGANISM: Artificial Sequence
<220> FEATURE:
<223> OTHER INFORMATION: CDR2

<400> SEQUENCE: 347

```
Thr Ala Ser Ser Leu Gln Ser
 1               5
```

<210> SEQ ID NO 348
<211> LENGTH: 9
<212> TYPE: PRT
<213> ORGANISM: Artificial Sequence
<220> FEATURE:
<223> OTHER INFORMATION: CDR3

<400> SEQUENCE: 348

```
Gln Gln Asn Leu Phe Trp Pro Arg Thr
 1               5
```

<210> SEQ ID NO 349
<211> LENGTH: 5
<212> TYPE: PRT
<213> ORGANISM: Artificial Sequence
<220> FEATURE:
<223> OTHER INFORMATION: CDR1

<400> SEQUENCE: 349

```
Arg Arg Tyr Leu Asn
 1               5
```

<210> SEQ ID NO 350
<211> LENGTH: 7
<212> TYPE: PRT
<213> ORGANISM: Artificial Sequence
<220> FEATURE:
<223> OTHER INFORMATION: CDR2

<400> SEQUENCE: 350

```
Ala Ala Ser Ser Leu Gln Ser
 1               5
```

<210> SEQ ID NO 351
<211> LENGTH: 9
<212> TYPE: PRT
<213> ORGANISM: Artificial Sequence
<220> FEATURE:
<223> OTHER INFORMATION: CDR3

<400> SEQUENCE: 351

```
Gln Gln Met Leu Phe Tyr Pro Lys Thr
1               5

<210> SEQ ID NO 352
<211> LENGTH: 5
<212> TYPE: PRT
<213> ORGANISM: Artificial Sequence
<220> FEATURE:
<223> OTHER INFORMATION: CDR1

<400> SEQUENCE: 352

Ile Lys His Leu Lys
1               5

<210> SEQ ID NO 353
<211> LENGTH: 7
<212> TYPE: PRT
<213> ORGANISM: Artificial Sequence
<220> FEATURE:
<223> OTHER INFORMATION: CDR2

<400> SEQUENCE: 353

Gly Ala Ser Arg Leu Gln Ser
1               5

<210> SEQ ID NO 354
<211> LENGTH: 9
<212> TYPE: PRT
<213> ORGANISM: Artificial Sequence
<220> FEATURE:
<223> OTHER INFORMATION: CDR3

<400> SEQUENCE: 354

Gln Gln Gly Ala Arg Trp Pro Gln Thr
1               5

<210> SEQ ID NO 355
<211> LENGTH: 5
<212> TYPE: PRT
<213> ORGANISM: Artificial Sequence
<220> FEATURE:
<223> OTHER INFORMATION: CDR1

<400> SEQUENCE: 355

Tyr Tyr His Leu Lys
1               5

<210> SEQ ID NO 356
<211> LENGTH: 7
<212> TYPE: PRT
<213> ORGANISM: Artificial Sequence
<220> FEATURE:
<223> OTHER INFORMATION: CDR2

<400> SEQUENCE: 356

Lys Ala Ser Thr Leu Gln Ser
1               5

<210> SEQ ID NO 357
<211> LENGTH: 9
<212> TYPE: PRT
<213> ORGANISM: Artificial Sequence
<220> FEATURE:
<223> OTHER INFORMATION: CDR3

<400> SEQUENCE: 357

Gln Gln Val Arg Lys Val Pro Arg Thr
```

```
<210> SEQ ID NO 358
<211> LENGTH: 5
<212> TYPE: PRT
<213> ORGANISM: Artificial Sequence
<220> FEATURE:
<223> OTHER INFORMATION: CDR1

<400> SEQUENCE: 358

Tyr Lys His Leu Lys
1               5

<210> SEQ ID NO 359
<211> LENGTH: 7
<212> TYPE: PRT
<213> ORGANISM: Artificial Sequence
<220> FEATURE:
<223> OTHER INFORMATION: CDR2

<400> SEQUENCE: 359

Asn Ala Ser His Leu Gln Ser
1               5

<210> SEQ ID NO 360
<211> LENGTH: 9
<212> TYPE: PRT
<213> ORGANISM: Artificial Sequence
<220> FEATURE:
<223> OTHER INFORMATION: CDR3

<400> SEQUENCE: 360

Gln Gln Val Gly Arg Tyr Pro Lys Thr
1               5

<210> SEQ ID NO 361
<211> LENGTH: 5
<212> TYPE: PRT
<213> ORGANISM: Artificial Sequence
<220> FEATURE:
<223> OTHER INFORMATION: CDR1

<400> SEQUENCE: 361

Phe Lys Ser Leu Lys
1               5

<210> SEQ ID NO 362
<211> LENGTH: 7
<212> TYPE: PRT
<213> ORGANISM: Artificial Sequence
<220> FEATURE:
<223> OTHER INFORMATION: CDR2

<400> SEQUENCE: 362

Asn Ala Ser Tyr Leu Gln Ser
1               5

<210> SEQ ID NO 363
<211> LENGTH: 9
<212> TYPE: PRT
<213> ORGANISM: Artificial Sequence
<220> FEATURE:
<223> OTHER INFORMATION: CDR3

<400> SEQUENCE: 363

Gln Gln Val Val Tyr Trp Pro Val Thr
1               5
```

<210> SEQ ID NO 364
<211> LENGTH: 6
<212> TYPE: PRT
<213> ORGANISM: Artificial Sequence
<220> FEATURE:
<223> OTHER INFORMATION: CDR1
<220> FEATURE:
<221> NAME/KEY: VARIANT
<222> LOCATION: 1, 2, 4, 5, 6
<223> OTHER INFORMATION: Xaa = Any Amino Acid

<400> SEQUENCE: 364

Xaa Xaa Tyr Xaa Xaa Xaa
 1               5

<210> SEQ ID NO 365
<211> LENGTH: 17
<212> TYPE: PRT
<213> ORGANISM: Artificial Sequence
<220> FEATURE:
<223> OTHER INFORMATION: CDR2
<220> FEATURE:
<221> NAME/KEY: VARIANT
<222> LOCATION: 1, 3, 4, 5, 7, 8, 10
<223> OTHER INFORMATION: Xaa = Any Amino Acid

<400> SEQUENCE: 365

Xaa Ile Xaa Xaa Xaa Gly Xaa Xaa Thr Xaa Tyr Ala Asp Ser Val Lys
 1               5                  10                  15

Gly

<210> SEQ ID NO 366
<211> LENGTH: 11
<212> TYPE: PRT
<213> ORGANISM: Artificial Sequence
<220> FEATURE:
<223> OTHER INFORMATION: CDR3
<220> FEATURE:
<221> NAME/KEY: VARIANT
<222> LOCATION: 1, 2, 3, 4, 5, 6, 7, 8
<223> OTHER INFORMATION: Xaa = Any Amino Acid

<400> SEQUENCE: 366

Xaa Xaa Xaa Xaa Xaa Xaa Xaa Xaa Phe Asp Tyr
 1               5                  10

<210> SEQ ID NO 367
<211> LENGTH: 6
<212> TYPE: PRT
<213> ORGANISM: Artificial Sequence
<220> FEATURE:
<223> OTHER INFORMATION: CDR1

<400> SEQUENCE: 367

Trp Val Tyr Gln Met Asp
 1               5

<210> SEQ ID NO 368
<211> LENGTH: 17
<212> TYPE: PRT
<213> ORGANISM: Artificial Sequence
<220> FEATURE:
<223> OTHER INFORMATION: CDR2

<400> SEQUENCE: 368

Ser Ile Ser Ala Phe Gly Ala Lys Thr Leu Tyr Ala Asp Ser Val Lys
 1               5                  10                  15

Gly

<210> SEQ ID NO 369
<211> LENGTH: 7
<212> TYPE: PRT
<213> ORGANISM: Artificial Sequence
<220> FEATURE:
<223> OTHER INFORMATION: CDR3

<400> SEQUENCE: 369

Leu Ser Gly Lys Phe Asp Tyr
1               5

<210> SEQ ID NO 370
<211> LENGTH: 6
<212> TYPE: PRT
<213> ORGANISM: Artificial Sequence
<220> FEATURE:
<223> OTHER INFORMATION: CDR1

<400> SEQUENCE: 370

Trp Ser Tyr Gln Met Thr
1               5

<210> SEQ ID NO 371
<211> LENGTH: 17
<212> TYPE: PRT
<213> ORGANISM: Artificial Sequence
<220> FEATURE:
<223> OTHER INFORMATION: CDR2

<400> SEQUENCE: 371

Ser Ile Ser Ser Phe Gly Ser Ser Thr Leu Tyr Ala Asp Ser Val Lys
1               5                   10                  15
Gly

<210> SEQ ID NO 372
<211> LENGTH: 11
<212> TYPE: PRT
<213> ORGANISM: Artificial Sequence
<220> FEATURE:
<223> OTHER INFORMATION: CDR3

<400> SEQUENCE: 372

Gly Arg Asp His Asn Tyr Ser Leu Phe Asp Tyr
1               5                   10

<210> SEQ ID NO 373
<211> LENGTH: 119
<212> TYPE: PRT
<213> ORGANISM: Homo sapiens

<400> SEQUENCE: 373

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Pro Glu Tyr
            20                  25                  30

Gly Met Ala Trp Val Arg Gln Ala Pro Gly Lys Gly Leu Glu Trp Val
        35                  40                  45

Ser Thr Ile Ser His Gly Gly Glu His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Gln His Pro Val Ser His Pro Lys Phe Asp Tyr Trp Gly Gln Gly
            100                 105                 110

Thr Leu Val Thr Val Ser Ser
        115

<210> SEQ ID NO 374
<211> LENGTH: 116
<212> TYPE: PRT
<213> ORGANISM: Homo sapiens

<400> SEQUENCE: 374

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Ala Tyr
             20                  25                  30

Asn Met Phe Trp Val Arg Gln Ala Pro Gly Lys Gly Leu Glu Trp Val
         35                  40                  45

Ser Ala Ile Ser Pro Ser Gly Arg Glu Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Tyr Pro Asp Phe Asp Tyr Trp Gly Gln Gly Thr Leu Val
            100                 105                 110

Thr Val Ser Ser
        115

<210> SEQ ID NO 375
<211> LENGTH: 119
<212> TYPE: PRT
<213> ORGANISM: Homo sapiens

<400> SEQUENCE: 375

Glu Val Gln Leu Leu Glu Ser Gly Gly Gly Leu Val Gln Pro Gly Gly
  1               5                  10                  15

Ser Leu Arg Leu Ser Cys Ala Ser Gly Phe Thr Phe Ser Asp Tyr
             20                  25                  30

Thr Met Gly Trp Val Arg Gln Ala Pro Gly Lys Gly Leu Glu Trp Val
         35                  40                  45

Ser Leu Ile Asp Arg Pro Gly Asn His Thr Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Leu Asn Val Glu Asp Phe Asp Tyr Trp Gly Gln Gly
            100                 105                 110

Thr Leu Val Thr Val Ser Ser
        115

<210> SEQ ID NO 376
<211> LENGTH: 120
<212> TYPE: PRT
<213> ORGANISM: Homo sapiens
```

<400> SEQUENCE: 376

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Glu Tyr
            20                  25                  30

Asp Met Gly Trp Val Arg Gln Ala Pro Gly Lys Gly Leu Glu Trp Val
        35                  40                  45

Ser Met Ile Ser Ser Asp Gly Arg Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Trp Asp Gly Leu Asn Arg Asn Phe Asp Tyr Trp Gly Gln
            100                 105                 110

Gly Thr Leu Val Thr Val Ser Ser
            115                 120

<210> SEQ ID NO 377
<211> LENGTH: 119
<212> TYPE: PRT
<213> ORGANISM: Homo sapiens

<400> SEQUENCE: 377

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ile Gly Tyr
            20                  25                  30

Asn Met Tyr Trp Val Arg Gln Ala Pro Gly Lys Gly Leu Glu Trp Val
        35                  40                  45

Ser Phe Ile Ser Pro Ser Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Leu Ser Ala Asp Gly Arg Phe Asp Tyr Trp Gly Gln Gly
            100                 105                 110

Thr Leu Val Thr Val Ser Ser
            115

<210> SEQ ID NO 378
<211> LENGTH: 120
<212> TYPE: PRT
<213> ORGANISM: Homo sapiens

<400> SEQUENCE: 378

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Asp Met Gly Trp Val Arg Gln Ala Pro Gly Lys Gly Leu Glu Trp Val
        35                  40                  45

Ser Phe Ile Asp Val Ser Gly Thr Leu Thr Tyr Tyr Ala Asp Ser Val
    50                  55                  60

-continued

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Val Glu Leu Asp Gly Leu Asp Phe Asp Tyr Trp Gly Gln
            100                 105                 110

Gly Thr Leu Val Thr Val Ser Ser
        115                 120

<210> SEQ ID NO 379
<211> LENGTH: 120
<212> TYPE: PRT
<213> ORGANISM: Homo sapiens

<400> SEQUENCE: 379

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Asp Met Gly Trp Val Arg Gln Ala Pro Gly Lys Gly Leu Glu Trp Val
        35                  40                  45

Ser Phe Ile Asp Ser Ser Gly Ser Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ala Glu Ile Val Asn Ser Arg Phe Asp Tyr Trp Gly Gln
            100                 105                 110

Gly Thr Leu Val Thr Val Ser Ser
        115                 120

<210> SEQ ID NO 380
<211> LENGTH: 120
<212> TYPE: PRT
<213> ORGANISM: Homo sapiens

<400> SEQUENCE: 380

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Lys Tyr
            20                  25                  30

Gln Met Gly Trp Val Arg Gln Ala Pro Gly Lys Gly Leu Glu Trp Val
        35                  40                  45

Ser Phe Ile Asp Ser Asn Gly His His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Leu Asp Asn Leu Ser Ile Thr Pro Phe Asp Tyr Trp Gly Gln
            100                 105                 110

Gly Thr Leu Val Thr Val Ser Ser
        115                 120

<210> SEQ ID NO 381
<211> LENGTH: 120

<212> TYPE: PRT
<213> ORGANISM: Homo sapiens

<400> SEQUENCE: 381

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Lys Tyr
            20                  25                  30

Asn Met Tyr Trp Val Arg Gln Ala Pro Gly Lys Gly Leu Glu Trp Val
        35                  40                  45

Ser Ala Ile Ser Pro Lys Gly Gln His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gly Met Gly Ser Asp Ala Ile Thr Phe Asp Tyr Trp Gly Gln
            100                 105                 110

Gly Thr Leu Val Thr Val Ser Ser
        115                 120

<210> SEQ ID NO 382
<211> LENGTH: 122
<212> TYPE: PRT
<213> ORGANISM: Homo sapiens

<400> SEQUENCE: 382

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Thr Met Gly Trp Ala Arg Gln Ala Pro Gly Lys Gly Leu Glu Trp Val
        35                  40                  45

Ser Phe Ile Asp Ser Asp Gly Leu His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Asn Pro Gln Tyr Ala Tyr Glu Ser Ser Arg Phe Asp Tyr Trp
            100                 105                 110

Gly Gln Gly Thr Leu Val Thr Val Ser Ser
        115                 120

<210> SEQ ID NO 383
<211> LENGTH: 121
<212> TYPE: PRT
<213> ORGANISM: Homo sapiens

<400> SEQUENCE: 383

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Leu Gln Tyr
            20                  25                  30

Pro Met Val Trp Val Arg Gln Ala Pro Gly Lys Gly Leu Glu Trp Val
        35                  40                  45

Ser Ser Ile Leu Ala Pro Gly Gly Pro Thr Tyr Tyr Ala Asp Ser Val

```
                  50                   55                   60
Lys Gly Arg Phe Thr Ile Ser Arg Asp Asn Ser Lys Asn Ser Leu Tyr
 65                   70                   75                   80

Leu Gln Met Asn Ser Leu Arg Ala Glu Asp Thr Ala Val Tyr Tyr Cys
                     85                   90                   95

Ala Lys His Pro Thr His Thr Pro His Pro Asn Phe Asp Tyr Trp Gly
                    100                  105                  110

Gln Gly Thr Leu Val Thr Val Ser Ser
            115                  120

<210> SEQ ID NO 384
<211> LENGTH: 122
<212> TYPE: PRT
<213> ORGANISM: Homo sapiens

<400> SEQUENCE: 384

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Gly Gly Tyr
                20                  25                  30

Arg Met Ala Trp Val Arg Gln Ala Pro Gly Lys Gly Leu Glu Trp Val
             35                  40                  45

Ser Phe Ile Asp Ser Glu Gly Val Leu Thr Tyr Tyr Ala Asp Ser Val
 50                  55                  60

Lys Gly Arg Phe Thr Ile Ser Arg Asp Asn Ser Lys Asn Thr Leu Tyr
 65                  70                   75                  80

Leu Gln Met Asn Ser Leu Arg Ala Glu Asp Thr Ala Val Tyr Tyr Cys
                 85                  90                   95

Ala Lys Leu Cys Ser Ser Asn Cys Asn Met Arg Asn Phe Asp Tyr Trp
             100                 105                  110

Gly Gln Gly Thr Leu Val Thr Val Ser Ser
            115                 120

<210> SEQ ID NO 385
<211> LENGTH: 124
<212> TYPE: PRT
<213> ORGANISM: Homo sapiens

<400> SEQUENCE: 385

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Pro Val Tyr
                20                  25                  30

Asn Met Ala Trp Val Arg Gln Ala Pro Gly Lys Gly Leu Glu Trp Val
             35                  40                  45

Ser Phe Ile Ala Gly Asn Gly Gln Gln Thr Tyr Tyr Ala Asp Ser Val
 50                  55                  60

Lys Gly Arg Phe Thr Ile Ser Arg Asp Asn Ser Lys Asn Thr Leu Tyr
 65                  70                   75                  80

Leu Gln Met Asn Ser Leu Arg Ala Glu Asp Thr Ala Val Tyr Tyr Cys
                 85                  90                   95

Ala Lys Phe Ala Ser Lys Val Ser Pro Met Ser Leu Thr Asp Phe Asp
             100                 105                  110

Tyr Trp Gly Gln Gly Thr Leu Val Thr Val Ser Ser
            115                 120
```

<210> SEQ ID NO 386
<211> LENGTH: 124
<212> TYPE: PRT
<213> ORGANISM: Homo sapiens

<400> SEQUENCE: 386

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Lys Tyr
            20                  25                  30

Gly Met Ala Trp Val Arg Gln Ala Pro Gly Lys Gly Leu Glu Trp Val
        35                  40                  45

Ser Phe Ile Asp Leu Ala Gly Leu His Thr Tyr Tyr Ala Asp Ser Val
    50                  55                  60

Arg Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ala Thr Tyr Ser Ser Gly Asn Glu Glu Gln Pro Phe Asp
            100                 105                 110

Tyr Trp Gly Gln Gly Thr Leu Val Thr Val Ser Ser
        115                 120

<210> SEQ ID NO 387
<211> LENGTH: 123
<212> TYPE: PRT
<213> ORGANISM: Homo sapiens

<400> SEQUENCE: 387

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Ala Trp Val Arg Gln Ala Pro Gly Lys Gly Leu Glu Trp Val
        35                  40                  45

Ser Phe Ile Ala Gln Ser Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser His Pro Asp Glu Glu Gly Thr Gln Met Phe Asp Tyr
            100                 105                 110

Trp Gly Gln Gly Thr Leu Val Thr Val Ser Ser
        115                 120

<210> SEQ ID NO 388
<211> LENGTH: 116
<212> TYPE: PRT
<213> ORGANISM: Homo sapiens

<400> SEQUENCE: 388

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Thr Tyr
            20                  25                  30

Asn Met Ser Trp Val Arg Gln Ala Pro Gly Lys Gly Leu Glu Trp Val
        35                  40                  45

```
Ser Ala Ile Asp Ala Gly Gly Met His Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Thr Glu Pro Phe Asp Tyr Trp Gly Gln Gly Thr Leu Val
                100                 105                 110

Thr Val Ser Ser
            115

<210> SEQ ID NO 389
<211> LENGTH: 116
<212> TYPE: PRT
<213> ORGANISM: Homo sapiens
<220> FEATURE:
<221> NAME/KEY: VARIANT
<222> LOCATION: 33
<223> OTHER INFORMATION: Xaa = Any Amino Acid

<400> SEQUENCE: 389

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asp Glu Tyr
                 20                  25                  30

Xaa Met Gly Trp Val Arg Gln Ala Pro Gly Lys Gly Leu Glu Trp Val
             35                  40                  45

Ser Leu Ile Ser Pro Arg Gly Ser Lys Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Tyr Lys Pro Pro Phe Asp Tyr Trp Gly Gln Gly Thr Leu Val
                100                 105                 110

Thr Val Ser Ser
            115

<210> SEQ ID NO 390
<211> LENGTH: 116
<212> TYPE: PRT
<213> ORGANISM: Homo sapiens

<400> SEQUENCE: 390

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Asp Tyr
                 20                  25                  30

Pro Met Ala Trp Val Arg Gln Ala Pro Gly Lys Gly Leu Glu Trp Val
             35                  40                  45

Ser Phe Ile Gly Leu Lys Gly Ile His Thr Tyr Tyr Ala Asp Ser Val
            50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Leu Asn Asn Phe Asp Tyr Trp Gly Gln Gly Thr Leu Val
```

Thr Val Ser Ser
    115

<210> SEQ ID NO 391
<211> LENGTH: 119
<212> TYPE: PRT
<213> ORGANISM: Homo sapiens

<400> SEQUENCE: 391

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Gly
            20                  25                  30

Asn Met Val Trp Val Arg Gln Ala Pro Gly Lys Gly Leu Glu Trp Val
        35                  40                  45

Ser His Ile Asp Glu Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Asn Asp Arg Pro Gly Phe Asp Tyr Trp Gly Gln Gly
            100                 105                 110

Thr Leu Val Thr Val Ser Ser
        115

<210> SEQ ID NO 392
<211> LENGTH: 124
<212> TYPE: PRT
<213> ORGANISM: Homo sapiens

<400> SEQUENCE: 392

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Thr Glu
            20                  25                  30

His Met Tyr Trp Val Arg Gln Ala Pro Gly Lys Gly Leu Glu Trp Val
        35                  40                  45

Ser Gly Ile Asp Thr Gly Gly Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu His Trp Ser Ser Asp Ser Gly Pro Val His Phe Asp
            100                 105                 110

Tyr Trp Gly Gln Gly Thr Leu Val Thr Val Ser Ser
        115                 120

<210> SEQ ID NO 393
<211> LENGTH: 121
<212> TYPE: PRT
<213> ORGANISM: Homo sapiens

<400> SEQUENCE: 393

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Val
            20                  25                  30

Asp Met His Trp Val Arg Gln Ala Pro Gly Lys Gly Leu Glu Trp Val
        35                  40                  45

Ser Ala Ile Ser Ser Ala Gly Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Met Leu Ala Asn Ser Pro Leu Ala Phe Asp Tyr Trp Gly
            100                 105                 110

Gln Gly Thr Leu Val Thr Val Ser Ser
            115                 120

<210> SEQ ID NO 394
<211> LENGTH: 116
<212> TYPE: PRT
<213> ORGANISM: Homo sapiens

<400> SEQUENCE: 394

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Tyr Glu
            20                  25                  30

Pro Met Ala Trp Val Arg Gln Ala Pro Gly Lys Gly Leu Glu Trp Val
        35                  40                  45

Ser Thr Ile Ser His Thr Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Trp Ser Ser Phe Asp Tyr Trp Gly Gln Gly Thr Leu Val
            100                 105                 110

Thr Val Ser Ser
            115

<210> SEQ ID NO 395
<211> LENGTH: 119
<212> TYPE: PRT
<213> ORGANISM: Homo sapiens

<400> SEQUENCE: 395

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Ser Glu
            20                  25                  30

Lys Met Ala Trp Val Arg Gln Ala Pro Gly Lys Gly Leu Glu Trp Val
        35                  40                  45

Ser Ser Ile Asp Glu Arg Gly Ile Met Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Arg Trp Thr Phe Asn Thr Ala Phe Asp Tyr Trp Gly Gln Gly
            100                 105                 110

Thr Leu Val Thr Val Ser Ser
        115

<210> SEQ ID NO 396
<211> LENGTH: 119
<212> TYPE: PRT
<213> ORGANISM: Homo sapiens

<400> SEQUENCE: 396

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Arg Glu
             20                  25                  30

Asn Met His Trp Val Arg Gln Ala Pro Gly Lys Gly Leu Glu Trp Val
         35                  40                  45

Ser Gly Ile Gly Pro Arg Gly Met Pro Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Met Asn Ser His Asp Gly Phe Asp Tyr Trp Gly Gln Gly
            100                 105                 110

Thr Leu Val Thr Val Ser Ser
        115

<210> SEQ ID NO 397
<211> LENGTH: 119
<212> TYPE: PRT
<213> ORGANISM: Homo sapiens

<400> SEQUENCE: 397

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Ala Tyr
             20                  25                  30

Thr Met Ile Trp Val Arg Gln Ala Pro Gly Lys Gly Leu Glu Trp Val
         35                  40                  45

Ser Tyr Ile Asp Pro His Gly Thr Ile Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Pro Arg Ala Ala Pro Arg Phe Asp Tyr Trp Gly Gln Gly
            100                 105                 110

Thr Leu Val Thr Val Ser Ser
        115

<210> SEQ ID NO 398
<211> LENGTH: 119
<212> TYPE: PRT
<213> ORGANISM: Homo sapiens

<400> SEQUENCE: 398
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ala Ser
            20                  25                  30

Glu Met Asp Trp Val Arg Gln Ala Pro Gly Lys Gly Leu Glu Trp Val
        35                  40                  45

Ser Ala Ile Ser Pro Ser Gly Ser Ala Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Thr Pro Gly Arg Thr Thr Phe Asp Tyr Trp Gly Gln Gly
            100                 105                 110

Thr Leu Val Thr Val Ser Ser
            115

<210> SEQ ID NO 399
<211> LENGTH: 124
<212> TYPE: PRT
<213> ORGANISM: Homo sapiens

<400> SEQUENCE: 399

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Pro Thr Glu
            20                  25                  30

His Met Tyr Trp Val Arg Gln Ala Pro Gly Lys Gly Leu Glu Trp Val
        35                  40                  45

Ser Gly Ile Asp Thr Gly Ser His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Leu His Trp Ser Ser Asp Ser Gly Pro Val His Phe Asp
            100                 105                 110

Tyr Trp Gly Gln Gly Thr Leu Val Thr Val Ser Ser
            115                 120

<210> SEQ ID NO 400
<211> LENGTH: 123
<212> TYPE: PRT
<213> ORGANISM: Homo sapiens

<400> SEQUENCE: 400

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Leu Tyr
            20                  25                  30

Asn Met Ala Trp Val Arg Gln Ala Pro Gly Lys Gly Leu Glu Trp Val
        35                  40                  45

Ser Phe Ile Ala Ala Ala Gly Pro Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Lys Leu Gly Asp Ile Ser Ser Ile Pro Gln His Pro Phe Asp Tyr
            100                 105                 110

Trp Gly Gln Gly Thr Leu Val Thr Val Ser Ser
        115                 120

<210> SEQ ID NO 401
<211> LENGTH: 119
<212> TYPE: PRT
<213> ORGANISM: Homo sapiens

<400> SEQUENCE: 401

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Val
            20                  25                  30

Asp Met His Trp Val Arg Gln Ala Pro Gly Lys Gly Leu Glu Trp Val
        35                  40                  45

Ser Ala Ile Ser Ser Ala Gly Gly Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Asp Ile Thr Lys Gly Phe Asp Tyr Trp Gly Gln Gly
            100                 105                 110

Thr Leu Val Thr Val Ser Ser
        115

<210> SEQ ID NO 402
<211> LENGTH: 357
<212> TYPE: DNA
<213> ORGANISM: Homo sapiens

<400> SEQUENCE: 402
gaggtgcagc tgttggagtc tgggggaggc ttggtacagc ctggggggtc cctgcgtctc      60
tcctgtgcag cctccggatt cacctttcct gagtatggga tggcgtgggt ccgccaggct     120
ccagggaagg gtctagagtg ggtctcaacg atttctcatg ggggtgagca tacatactac     180
gcagactccg tgaagggccg gttcaccatc tcccgcgaca attccaagaa cacgctgtat     240
ctgcaaatga acagcctgcg tgccgaggac accgcggtat attactgtgc gcaacatccg     300
gttagtcatc cgaagtttga ctactggggt cagggaaccc tggtcaccgt ctcgagc       357

<210> SEQ ID NO 403
<211> LENGTH: 348
<212> TYPE: DNA
<213> ORGANISM: Homo sapiens

<400> SEQUENCE: 403
gaggtgcagc tgttggagtc tgggggaggc ttggtacagc ctggggggtc cctgcgtctc      60
tcctgtgcag cctccggatt caccttttgat gcttataata tgttttgggt ccgccaggct    120
ccagggaagg gtctggagtg ggtctcagct attagtccgt cgggtcggga gacatactac     180
gcagactccg tgaagggccg gttcaccatc tcccgcgaca attccaagaa cacgctgtat     240
ctgcaaatga acagcctgcg tgccgaggac accgcggtat attactgtgc gaaaaggtat     300
```

```
cctgattttg actactgggg tcagggaacc ctggtcaccg tctcgagc              348
```

<210> SEQ ID NO 404
<211> LENGTH: 357
<212> TYPE: DNA
<213> ORGANISM: Homo sapiens

<400> SEQUENCE: 404

```
gaggtgcagc tgttggagtc tggggaggc ttggtacagc ctgggggtc cctgcgtctc    60 tcctgtgcag cctccggatt cacctttagt gattatacta tgggttgggt ccgccaggct  120
ccagggaagg gtctagagtg gtctcattg attgatcgtc tggtaatca tacatactac    180 gcagactccg tgaagggccg gttcaccatc tcccgcgaca attccaagaa cacgctgtat  240
ctgcaaatga acagcctgcg tgccgaggac accgcggtat attactgtgc gaaatggggg  300
cttaatgtgg aggattttga ctactgggt cagggaaccc tggtcaccgt ctcgagc      357
```

<210> SEQ ID NO 405
<211> LENGTH: 360
<212> TYPE: DNA
<213> ORGANISM: Homo sapiens

<400> SEQUENCE: 405

```
gaggtgcagc tgttggagtc tggggaggc ttggtacagc ctgggggtc cctgcgtctc    60 tcctgtgcag cctccggatt cacctttatt gagtatgata tgggttgggt ccgccaggct  120
ccagggaagg gtctagagtg gtctcaatg attagttcgg atggtaggct tacatactac   180
gcagactccg tgaagggccg gttcaccatc tcccgcgaca attccaagaa cacgctgtat  240
ctgcaaatga acagcctgcg tgccgaggat accgcggtat attactgtgc gaaaacgtgg  300
gatggtttga atcgtaattt tgactactgg ggtcaggaa ccctggtcac cgtctcgagc   360
```

<210> SEQ ID NO 406
<211> LENGTH: 357
<212> TYPE: DNA
<213> ORGANISM: Homo sapiens

<400> SEQUENCE: 406

```
gaggtgcagc tgttggagtc tggggaggc ttggtacagc ctgggggtc cctgcgtctc    60 tcctgtgcag cctccggatt cacctttatt gggtataata tgtattgggt ccgccaggct  120
ccagggaagg gtctagagtg gtctcattt atttctcctt cgggtcggga gacatactac   180
gcagactccg tgaagggccg gttcaccatc tcccgcgaca attccaagaa cacgctgtat  240
ctgcaaatga acagcctgcg tgccgaggat accgcggtat attactgtgc gaaaactttg  300
tcggcggatg gtaggtttga ctactgggt cagggaaccc tggtcaccgt ctcgagc      357
```

<210> SEQ ID NO 407
<211> LENGTH: 360
<212> TYPE: DNA
<213> ORGANISM: Homo sapiens

<400> SEQUENCE: 407

```
gaggtgcagc tgttggagtc tggggaggc ttggtacagc ctgggggtc cctgcgtctc    60 tcctgtgcag cctccggatt cacctttggt agttatgata tgggttgggt ccgccaggct  120
ccagggaagg gtctagagtg gtctcattt attgatgtgt cgggtacttt gacatactac   180
gcagactccg tgaagggccg gttcaccatc tcccgcgaca attccaagaa cacgctgtat  240
ctgcaaatga acagcctgcg tgccgaggac accgcggtat attactgtgc gaaaactgtt  300
```
gagctggatg gtctggattt tgactactgg ggtcagggaa ccctggtcac cgtctcgagc    360

<210> SEQ ID NO 408
<211> LENGTH: 360
<212> TYPE: DNA
<213> ORGANISM: Homo sapiens

<400> SEQUENCE: 408
gaggtgcagc tgttggagtc tgggggaggc ttggtacagc ctgggggggtc cctgcgtctc    60
tcctgtgcag cctccggatt cacctttgct gattatgata tggggtgggt ccgccaggct   120
ccagggaagg gtctagagtg gtctcatttt attgatagtt ctggttctcg tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaacggcg   300
gagattgtta atagtcgttt tgactactgg ggtcagggaa ccctggtcac cgtctcgagc   360

<210> SEQ ID NO 409
<211> LENGTH: 360
<212> TYPE: DNA
<213> ORGANISM: Homo sapiens

<400> SEQUENCE: 409
gaggtgcagc tgttggagtc tgggggaggc ttggtacagc ctgggggggtc cctgcgtctc    60
tcctgtgcag cctccggatt cacctttgat aagtatcaga tgggttgggt ccgccaggct   120
ccagggaagg gtctagagtg gtctcatttt attgattcga atggtcatca tacatactac   180
gcagactccg tgaagggccg gttcaccatc tcccgcgaca attccaagaa cacgctgtat   240
ctgcaaatga acagcctgcg tgccgaggac accgcggtat attactgtgc ggaacttgat   300
aatcttagta ttacgccgtt tgactactgg ggtcagggaa ccctggtcac cgtctcgagc   360

<210> SEQ ID NO 410
<211> LENGTH: 360
<212> TYPE: DNA
<213> ORGANISM: Homo sapiens

<400> SEQUENCE: 410
gaggtgcagc tgttggagtc tgggggaggc ttggtacagc ctgggggggtc cctgcgtctc    60
tcctgtgcag cctccggatt cacctttgct aagtataata tgtattgggt ccgccaggct   120
ccagggaagg gtctagagtg gtctcagcg attagtccta agggtcagca tacatactac   180
gcagactccg tgaagggccg gttcaccatc tcccgcgaca attccaagaa cacgctgtat   240
ctgcaaatga acagcctgcg tgccgaggac accgcggtat attactgtgc ggaagggatg   300
gggtcgatg ctattacttt tgactactgg ggtcagggaa ccctggtcac cgtctcgagc   360

<210> SEQ ID NO 411
<211> LENGTH: 366
<212> TYPE: DNA
<213> ORGANISM: Homo sapiens

<400> SEQUENCE: 411
gaggtgcagc tgttggagtc tgggggaggc ttggtacagc ctgggggggtc cctgcgtctc    60
tcctgtgcag cctccggatt cacctttagt gattatacta tgggttgggc ccgccaggct   120
ccagggaagg gtctagagtg gtctcatttt attgattctg atggtttgca tacatactac   180
gcagactccg tgaagggccg gttcaccatc tcccgcgaca attccaagaa cacgctgtat   240

```
ctgcaaatga acagcctgcg tgccgaggac accgcggtat attactgtgc gcaaaatccg    300
cagtatgcgt atgagagttc gaggtttgac tactggggtc agggaaccct ggtcaccgtc    360
tcgagc                                                              366
```

```
<210> SEQ ID NO 412
<211> LENGTH: 363
<212> TYPE: DNA
<213> ORGANISM: Homo sapiens

<400> SEQUENCE: 412
gaggtgcagc tgttggagtc tgggggaggc ttggtacagc ctgggggtc cctgcgtctc    60 tcctgtgcag cctccggatt cacctttttg cagtatccga tggtttgggt ccgccaggct   120
ccagggaagg gtctggagtg gtctcatcg attttggcgc cggtgggcc gacatactac     180 gcagactccg tgaagggccg gttcaccatc tcccgcgaca attccaagaa ctcgctgtat   240
ctgcaaatga acagcctgcg tgccgaggac accgcggtat attactgtgc gaaacatcct   300
actcatactc tcatccgaa ttttgactac tggggtcagg aaccctggt caccgtctcg    360 agc                                                                363
```

```
<210> SEQ ID NO 413
<211> LENGTH: 366
<212> TYPE: DNA
<213> ORGANISM: Homo sapiens

<400> SEQUENCE: 413
gaggtgcagc tgttggagtc tgggggaggc ttggtacagc ctgggggtc cctgcgtctc    60 tcctgtgcag cctccggatt cacctttggg ggttatcgta tggcttgggt ccgccaggct   120
ccagggaagg gtctagagtg gtctcatttt attgatagtg aggtgtgtt gacatactac    180 gcagactccg tgaagggccg gttcaccatc tcccgcgaca attccaagaa cacgctgtat   240
ctgcaaatga acagcctgcg tgccgaggat accgcggtat attactgtgc gaaattgtgt   300
tcttctaatt gtaatatgcg gaattttgac tactggggtc agggaaccct ggtcaccgtc   360
tcgagc                                                              366
```

```
<210> SEQ ID NO 414
<211> LENGTH: 372
<212> TYPE: DNA
<213> ORGANISM: Homo sapiens

<400> SEQUENCE: 414
gaggtgcagc tgttggagtc tgggggaggc ttggtacagc ctgggggtc cctgcgtctc    60 tcctgtgcag cctccggatt cacctttcct gtttataata tggcgtgggt ccgccaggct   120
ccagggaagg gtctagagtg gtctcatttt attgcgggta atggtcagca gacatactac    180
gcagactccg tgaagggccg gttcaccatc tcccgcgaca attccaagaa cacgctgtat   240
ctgcaaatga acagcctgcg tgccgaggac accgcggtat attactgtgc gaaatttgcg   300
tcgaaggtgt cgccgatgtc gttgactgat tttgactact ggggtcaggg aaccctggtc   360
accgtctcga gc                                                        372
```

```
<210> SEQ ID NO 415
<211> LENGTH: 372
<212> TYPE: DNA
<213> ORGANISM: Homo sapiens

<400> SEQUENCE: 415
```

```
gaggtgcagc tgttggagtc tgggggaggc ttggtacagc ctgggggtc cctgcgtctc    60 tcctgtgcag cctccggatt cacctttcat aagtatggga tggcttgggt ccgccaggct   120
ccagggaagg gtctagagtg ggtctcattt attgatcttg cggggttaca tacatactac   180
gcagactccg tgaggggccg gttcaccatc tcccgcgaca attccaagaa cacgctgtat   240
ctgcaaatga acagcctgcg tgccgaggac accgcggtat attactgtgc gaaatttgct   300
acttattcgt cgggtaatga ggagcagcct tttgactact ggggtcaggg aaccctggtc   360
accgtctcga gc                                                       372
```

<210> SEQ ID NO 416
<211> LENGTH: 369
<212> TYPE: DNA
<213> ORGANISM: Homo sapiens

<400> SEQUENCE: 416

```
gaggtgcagc tgttggagtc tgggggaggc ttggtacagc ctgggggtc cctgcgtctc    60 tcctgtgcag cctccggatt cacctttct gcgtataata tggcttgggt ccgccaggct   120
ccagggaagg gtctagagtg ggtctcattt attgctcagt cgggtggtca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaatttagt   300
catcctgatg aggagggtac gcagatgttt gactactggg gtcagggaac cctggtcacc   360
gtctcgagc                                                           369
```

<210> SEQ ID NO 417
<211> LENGTH: 348
<212> TYPE: DNA
<213> ORGANISM: Homo sapiens

<400> SEQUENCE: 417

```
gaggtgcagc tgttggagtc tgggggaggc ttggtacagc ctgggggtc cctgcgtctc    60 tcctgtgcag cctccggatt cacctttgcg acttataata tgagttgggt ccgccaggct   120
ccagggaagg gtctagagtg ggtctcagcg attgatgcgg ggggtatgca tacatactac   180
gcagactccg tgaagggccg gttcaccatc tcccgcgaca attccaagaa cacgctgtat   240
ctgcaaatga acagcctgcg tgccgaggat accgcggtat attactgtgc gaaaggtacg   300
gagccttttg actactgggg tcagggaacc ctggtcaccg tctcgagc               348
```

<210> SEQ ID NO 418
<211> LENGTH: 348
<212> TYPE: DNA
<213> ORGANISM: Homo sapiens
<220> FEATURE:
<221> NAME/KEY: misc_feature
<222> LOCATION: 99
<223> OTHER INFORMATION: n = A,T,C or G

<400> SEQUENCE: 418

```
gaggtgcagc tgttggagtc tgggggaggc ttggtacagc ctgggggtc cctgcgtctc    60 tcctgtgcag cctccggatt cacctttgat gagtataana tggttggt ccgccaggct   120 ccagggaagg gtctggagtg ggtctcactg attagtcctc ggggttctaa gacatactac   180
gcagactccg tgaagggccg gttcaccatc tcccgcgaca attccaagaa cacgctgtat   240
ctgcaaatga acagcctgcg tgccgaggac accgcggtat attactgtgc gaaatataag   300
```

```
ccgccttttg actactgggg tcagggaacc ctggtcaccg tctcgagc              348
```

<210> SEQ ID NO 419
<211> LENGTH: 348
<212> TYPE: DNA
<213> ORGANISM: Homo sapiens

<400> SEQUENCE: 419

```
gaggtgcagc tgttggagtc tggggaggc ttggtacagc ctggggggtc cctgcgtctc    60
tcctgtgcag cctccggatt cacctttgag gattatccta tggcgtgggt ccgccaggct   120
ccagggaagg gtctagagtg gtctcatttt attggtctga agggtattca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatctg   300
aataattttg actactgggg tcagggaacc ctggtcaccg tctcgagc              348
```

<210> SEQ ID NO 420
<211> LENGTH: 357
<212> TYPE: DNA
<213> ORGANISM: Homo sapiens

<400> SEQUENCE: 420

```
gaggtgcagc tgttggagtc tggggaggc ttggtacagc ctggggggtc cctgcgtctc    60
tcctgtgcag cctccggatt cacctttggt aatgtaata tggtttgggt ccgccaggct   120
ccagggaagg gtctagagtg gtctcacat attgatgagt atggtacgaa tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacctcgt   300
aatgatcggc tgggtttga ctactggggt caggaaccc tggtcaccgt ctcgagc      357
```

<210> SEQ ID NO 421
<211> LENGTH: 372
<212> TYPE: DNA
<213> ORGANISM: Homo sapiens

<400> SEQUENCE: 421

```
gaggtgcagc tgttggagtc tggggaggc ttggtacagc ctggggggtc cctgcgtctc    60
tcctgtgcag cctccggatt cacctttcct actgagcata tgtattgggt ccgccaggct   120
ccagggaagg gtctggagtg gtctcaggt attgatacgg ggggttctca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaggtctg   300
cattggagta gtgattctgg gcctgttcat tttgactact ggggtcaggg aaccctggtc   360
accgtctcga gc                                                      372
```

<210> SEQ ID NO 422
<211> LENGTH: 363
<212> TYPE: DNA
<213> ORGANISM: Homo sapiens

<400> SEQUENCE: 422

```
gaggtgcagc tgttggagtc tggggaggc ttggtacagc ctggggggtc cctgcgtctc    60
tcctgtgcag cctccggatt cacctttggt aatgtggata tgcattgggt ccgccaggct   120
ccagggaagg gtctagagtg gtctcagct attagtagtg cggtggtga gacatactac   180
gcagactccg tgaagggccg gttcaccatc tcccgcgaca attccaagaa cacgctgtat   240
```

```
ctgcaaatga acagcctgcg tgccgaggac accgcggtat attactgtgc gaaacgtatg      300
cttgcgaatt ctcctttggc ttttgactac tggggtcagg gaaccctggt caccgtctcg      360
agc                                                                   363
```

<210> SEQ ID NO 423
<211> LENGTH: 348
<212> TYPE: DNA
<213> ORGANISM: Homo sapiens

<400> SEQUENCE: 423

```
gaggtgcagc tgttggagtc tgggggaggc ttggtacagc ctgggggtc cctgcgtctc       60 tcctgcgcag cctccggatt cacctttggg tatgagccta tggcttgggt ccgccaggct     120
ccagggaagg gtctagagtg ggtctcaacg atttctcata cgggtcgtga tacatactac     180
gcagactccg tgaagggccg gttcaccatc tcccgcgaca attccaagaa cacgctgtat     240
ctgcaaatga acagcctgcg tgccgaggat accgcggtat attactgtgc gaaacgttgg     300
tcttcgtttg actactgggg tcagggaacc ctggtcaccg tctcgagc                  348
```

<210> SEQ ID NO 424
<211> LENGTH: 357
<212> TYPE: DNA
<213> ORGANISM: Homo sapiens

<400> SEQUENCE: 424

```
gaggtgcagc tgttggagtc tgggggaggc ttggtacagc ctgggggtc cctgcgtctc       60 tcctgtgcag cctccggatt cacctttcct agtgagaaga tggcgtgggt ccgccaggct     120
ccagggaagg gtctagagtg ggtctcatcg attgatgaga ggggtattat gacatactac     180
gcagactccg tgaagggccg gttcaccatc tcccgcgaca attccaagaa cacgctgtat     240
ctgcaaatga acagcctgcg tgccgaggat accgcggtat attactgtgc gaaaggtgg     300 acttttaata ctgcgtttga ctactggggt caggaaccc tggtcaccgt ctcgagc         357
```

<210> SEQ ID NO 425
<211> LENGTH: 357
<212> TYPE: DNA
<213> ORGANISM: Homo sapiens

<400> SEQUENCE: 425

```
gaggtgcagc tgttggagtc tgggggaggc ttggtacagc ctgggggtc cctgcgtctc       60 tcctgtgcag cctccggatt cacctttccg cgggagaata tgcattgggt ccgccaggct     120
ccagggaagg gtctggagtg gtctcaggt attgggccga ggggtatgcc gacatactac      180
gcagactccg tgaagggccg gttcaccatc tcccgcgaca attccaagaa cacgctgtat     240
ctgcaaatga acagcctgcg tgccgaggac accgcggtat attactgtgc gaaaggtatg     300
aattcgcatg atgggtttga ctactggggt caggaaccc tggtcaccgt ctcgagc         357
```

<210> SEQ ID NO 426
<211> LENGTH: 357
<212> TYPE: DNA
<213> ORGANISM: Homo sapiens

<400> SEQUENCE: 426

```
gaggtgcagc tgttggagtc tgggggaggc ttggtacagc ctgggggtc cctgcgtctc       60 tcctgtgcag cctccggatt cacctttaat gcgtatacta tgatttgggt ccgccaggct     120
```

```
ccagggaagg gtctagagtg ggtctcatat attgatcctc atggtacgat tacatactac    180
gcagactccg tgaagggccg gttcaccatc tcccgcgaca attccaagaa cacgctgtat    240
ctgcaaatga acagcctgcg tgccgaggac accgcggtat attactgtgc gaaattgccg    300
cgtgcggcgc gcggtttga ctactgggt cagggaaccc tggtcaccgt ctcgagc         357
```

<210> SEQ ID NO 427
<211> LENGTH: 357
<212> TYPE: DNA
<213> ORGANISM: Homo sapiens

<400> SEQUENCE: 427

```
gaggtgcagc tgttggagtc tgggggaggc ttggtacagc ctgggggtc cctgcgtctc     60 tcctgtgcag cctccggatt cacctttgat gcgtctgaga tggattgggt ccgccaggct   120
ccagggaagg gtctagagtg gtctcagcg atttcgccta gtggttctgc tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatggact    300
ccgggtcgta ctacttttga ctactgggt cagggaaccc tggtcaccgt ctcgagc       357
```

<210> SEQ ID NO 428
<211> LENGTH: 372
<212> TYPE: DNA
<213> ORGANISM: Homo sapiens

<400> SEQUENCE: 428

```
gaggtgcagc tgttggagtc tgggggaggc ttggtacagc ctgggggtc cctgcgtctc     60 tcctgtgcag cctccggatt cacctttcct actgagcata tgtattgggt ccgccaggct   120
ccagggaagg gtctggagtg gtctcaggt attgatacgg ggggttctca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggtctg    300
cattggagta gtgattctgg gcctgttcat tttgactact ggggtcaggg aaccctggtc   360
accgtctcga gc                                                        372
```

<210> SEQ ID NO 429
<211> LENGTH: 369
<212> TYPE: DNA
<213> ORGANISM: Homo sapiens

<400> SEQUENCE: 429

```
gaggtgcagc tgttggagtc tgggggaggc ttggtacagc ctgggggtc cctgcgtctc     60 tcctgtgcag cctccggatt cacctttaag ttgtataata tggcgtgggt ccgccaggct   120
ccagggaagg gtctagagtg gtctcatttt attgctgctg ctggtcctga cacatactac    180
gcagactccg tgaagggccg gttcaccatc tcccgcgaca attccaagaa cacgctgtat    240
ctgcaaatga acagcctgcg tgccgaggac accgcggtat attactgtgc gaaattgggg    300
gatattagta gtattcctca gcatccgttt gactactggg gtcagggaac cctggtcacc   360
gtctcgagc                                                            369
```

<210> SEQ ID NO 430
<211> LENGTH: 357
<212> TYPE: DNA
<213> ORGANISM: Homo sapiens

<400> SEQUENCE: 430

```
gaggtgcagc tgttggagtc tggggggaggc ttggtacagc ctgggggggtc cctgcgtctc    60 tcctgtgcag cctccggatt cacctttggt aatgtggata tgcattgggt ccgccaggct   120
ccagggaagg gtctagagtg ggtctcagct attagtagtg cgggtggtga cacatactac   180
gcagactccg tgaagggccg gttcaccatc tcccgcgaca attccaagaa cacgctgtat   240
ctgcaaatga acagcctgcg tgccgaggac accgcggtat attactgtgc gaaatctgcg   300
gatattacta agggttttga ctactggggt cagggaaccc tggtcaccgt ctcgagc      357
```

```
<210> SEQ ID NO 431
<211> LENGTH: 121
<212> TYPE: PRT
<213> ORGANISM: Homo sapiens

<400> SEQUENCE: 431
```

Glu Val Arg Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Lys Tyr
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
        115                 120

```
<210> SEQ ID NO 432
<211> LENGTH: 363
<212> TYPE: DNA
<213> ORGANISM: Homo sapiens

<400> SEQUENCE: 432
gaggtgcggc tgttggagtc tggggggaggc ttggtacagc ctgggggatc cctgcgtctc    60
tcctgtgcag cctccggatt cacctttggt aagtacacta tgacgtgggt ccgccaggct   120
ccagggaagg gtctagagtg ggtctcacat atttcggatg atggtaattc tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagttccg   300
attttggctc ctcgtaatct ttttgactac tggggtcagg gaaccctggt caccgtctcg   360
agc                                                                  363
```

```
<210> SEQ ID NO 433
<211> LENGTH: 119
<212> TYPE: PRT
<213> ORGANISM: Homo sapiens

<400> SEQUENCE: 433
```

Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu

```
            20                  25                  30
Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 434
<211> LENGTH: 119
<212> TYPE: PRT
<213> ORGANISM: Homo sapiens

<400> SEQUENCE: 434

```
Glu Val Gln Leu Leu Glu Ser Gly Gly Gly Leu Ile Gln Pro Gly Gly
1               5                   10                  15

Ser Leu Arg Leu Ser Cys Ala Ala Ser Gly Phe Thr Phe Ala His Glu
            20                  25                  30

Thr Met Val Trp Val Arg Gln Ala Pro Gly Lys Gly Leu Glu Trp Val
        35                  40                  45

Ser His Ile Asp Arg Val Gly Gln Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Pro Lys Arg Gly Pro Trp Phe Asp Tyr Arg Gly Gln Gly
            100                 105                 110

Thr Leu Val Thr Val Ser Ser
            115
```

<210> SEQ ID NO 435
<211> LENGTH: 121
<212> TYPE: PRT
<213> ORGANISM: Homo sapiens

<400> SEQUENCE: 435

```
Glu Val Arg Leu Leu Glu Ser Gly Gly Gly Leu Val Gln Pro Gly Gly
1               5                   10                  15

Ser Leu Arg Leu Ser Cys Val Ala Ser Gly Phe Thr Phe Gly Lys Ser
            20                  25                  30

Thr Met Thr Trp Val Arg Gln Ala Pro Gly Lys Gly Leu Glu Trp Val
        35                  40                  45

Ser His Ile Ser Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
```

Gln Gly Thr Leu Val Thr Val Ser Ser
        115                 120

<210> SEQ ID NO 436
<211> LENGTH: 121
<212> TYPE: PRT
<213> ORGANISM: Homo sapiens

<400> SEQUENCE: 436

Glu Val Arg Leu Leu Glu Ser Gly Gly Gly Leu Val Gln Pro Gly Gly
1               5                   10                  15

Ser Leu Arg Leu Ser Cys Val Ala Ser Gly Phe Asn Phe Gly Lys Ser
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
        115                 120

<210> SEQ ID NO 437
<211> LENGTH: 121
<212> TYPE: PRT
<213> ORGANISM: Homo sapiens

<400> SEQUENCE: 437

Glu Val Arg Leu Leu Glu Ser Gly Gly Gly Leu Val Gln Pro Gly Gly
1               5                   10                  15

Ser Leu Arg Leu Ser Cys Val Ala Ser Gly Phe Thr Phe Gly Lys Gly
            20                  25                  30

Thr Met Thr Trp Val Arg Gln Ala Pro Gly Lys Gly Leu Glu Trp Val
        35                  40                  45

Ser His Ile Ser Asp Asp Gly Asn Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Pro Ile Leu Ala Pro Arg Asn Leu Phe Asp Tyr Trp Gly
            100                 105                 110

Gln Gly Thr Leu Val Thr Val Ser Ser
        115                 120

<210> SEQ ID NO 438
<211> LENGTH: 122
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid -continued

<400> SEQUENCE: 438

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Arg Tyr
            20                  25                  30

Asn Met Gly Trp Val Arg Gln Ala Pro Gly Lys Gly Leu Glu Trp Val
        35                  40                  45

Ser Leu Ile Asp Pro Ser Gly Gly His Thr Tyr Tyr Ala Xaa Ser Val
    50                  55                  60

Lys Gly Arg Ser Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Pro Val Phe Ser Asp Trp Pro Ala Val Glu Phe Asp Tyr Trp
            100                 105                 110

Gly Gln Gly Thr Leu Val Thr Val Ser Ser
        115                 120

<210> SEQ ID NO 439
<211> LENGTH: 119
<212> TYPE: PRT
<213> ORGANISM: Homo sapiens

<400> SEQUENCE: 439

Glu Val Gln Leu Leu Glu Ser Gly Gly Gly Met Val Gln Pro Gly Gly
1               5                   10                  15

Ser Leu Arg Leu Ser Cys Ala Ala Pro Gly Phe Thr Phe Glu His Glu
            20                  25                  30

Gly Met Val Trp Val Arg Gln Ala Pro Gly Lys Gly Leu Glu Trp Val
        35                  40                  45

Ser His Ile Gly Glu Asp Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Ile Pro Lys Ala Gly Pro Ser Phe Asp Tyr Trp Gly Gln Gly
            100                 105                 110

Thr Leu Val Thr Val Ser Ser
        115

<210> SEQ ID NO 440
<211> LENGTH: 122
<212> TYPE: PRT
<213> ORGANISM: Homo sapiens

<400> SEQUENCE: 440

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ser Thr Phe Asp Gln Tyr
            20                  25                  30

Asp Met Ser Trp Val Arg Arg Ala Pro Gly Lys Gly Leu Glu Trp Val
        35                  40                  45

Ser Leu Ile Asp Pro Ser Gly Gly His Thr Tyr Tyr Ala Asp Ser Val
    50                  55                  60

Lys Gly Arg Phe Thr Ile Ser Arg Asn Asn Thr Lys Asn Thr Leu Tyr

```
              65                  70                  75                  80
Leu Gln Met Asn Ser Leu Arg Ala Glu Asp Thr Ala Val Tyr Tyr Cys
                    85                  90                  95
Ala Lys Pro Val Phe Ser Asp Trp Pro Ala Val Glu Phe Asp Tyr Trp
                100                 105                 110
Gly Gln Gly Thr Leu Val Thr Val Ser Ser
                115                 120

<210> SEQ ID NO 441
<211> LENGTH: 121
<212> TYPE: PRT
<213> ORGANISM: Homo sapiens

<400> SEQUENCE: 441

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Asp Tyr Gly
                20                  25                  30
Asn Met Phe Trp Val Arg Gln Ala Pro Gly Lys Gly Leu Glu Trp Ile
                35                  40                  45
Ser Ala Ile Ser Gly Ser Gly Ser Thr Tyr Tyr Ala Asp Ser Val
                50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                    85                  90                  95
Ala Lys Asp Met Thr Thr Asp Ser Pro Pro Gly Phe Tyr Trp Gly
                100                 105                 110
Gln Gly Thr Leu Val Thr Val Ser Ser
                115                 120

<210> SEQ ID NO 442
<211> LENGTH: 122
<212> TYPE: PRT
<213> ORGANISM: Homo sapiens

<400> SEQUENCE: 442

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ala Lys Glu
                20                  25                  30
Thr Met Ser Trp Val Arg Gln Ala Pro Gly Lys Gly Leu Glu Trp Val
                35                  40                  45
Ser Trp Ile Ser Pro His Gly Ala His Thr Phe Tyr Ala Asp Ser Val
                50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                    85                  90                  95
Ala Lys Pro Arg Phe Ser Tyr Tyr Pro Arg Val Ser Phe Asp Tyr Arg
                100                 105                 110
Gly Gln Gly Thr Leu Val Thr Val Ser Ser
                115                 120

<210> SEQ ID NO 443
<211> LENGTH: 116
<212> TYPE: PRT
```

-continued

<213> ORGANISM: Homo sapiens

<400> SEQUENCE: 443

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ala Tyr
            20                  25                  30

Asn Met Phe Trp Phe Arg Gln Ala Pro Gly Lys Gly Pro Glu Trp Val
        35                  40                  45

Ser Ala Ile Gly Pro Ser Gly Arg Glu Thr Tyr Tyr Ala Asp Ser Val
    50                  55                  60

Lys Gly Arg Phe Thr Ile Thr Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Tyr Pro Asp Phe Asp Tyr Trp Gly Gln Gly Thr Leu Val
            100                 105                 110

Thr Val Ser Ser
            115

<210> SEQ ID NO 444
<211> LENGTH: 119
<212> TYPE: PRT
<213> ORGANISM: Homo sapiens

<400> SEQUENCE: 444

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu His Glu
            20                  25                  30

Gly Met Val Trp Val Arg Gln Ala Pro Gly Lys Gly Leu Glu Trp Val
        35                  40                  45

Ser His Ile Gly Glu Asp Gly Gln Ser Thr Tyr Tyr Ala Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Pro Lys Ala Gly Pro Ser Phe Asp Tyr Trp Gly Gln Gly
            100                 105                 110

Thr Leu Val Thr Val Ser Ser
            115

<210> SEQ ID NO 445
<211> LENGTH: 123
<212> TYPE: PRT
<213> ORGANISM: Homo sapiens

<400> SEQUENCE: 445

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Leu Tyr
            20                  25                  30

Asn Met Ala Trp Val Arg Gln Ala Pro Gly Lys Gly Leu Glu Trp Val
        35                  40                  45

Ser Phe Ile Ala Ala Ala Gly Pro Glu Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Leu Gly Asp Ile Ser Ser Ile Pro Gln His Pro Phe Asp Tyr
            100                 105                 110

Trp Gly Gln Gly Thr Leu Val Thr Val Ser Ser
        115                 120

<210> SEQ ID NO 446
<211> LENGTH: 119
<212> TYPE: PRT
<213> ORGANISM: Homo sapiens

<400> SEQUENCE: 446

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Arg Glu
             20                  25                  30

Asn Met His Trp Val Arg Gln Ala Pro Gly Lys Gly Leu Glu Trp Val
         35                  40                  45

Ser Gly Ile Gly Pro Arg Gly Met Pro Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Met Asn Ser His Asp Gly Phe Asp Tyr Trp Gly Gln Gly
            100                 105                 110

Thr Leu Val Thr Val Ser Ser
        115

<210> SEQ ID NO 447
<211> LENGTH: 121
<212> TYPE: PRT
<213> ORGANISM: Homo sapiens

<400> SEQUENCE: 447

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Ala Ser
             20                  25                  30

Glu Met Asp Trp Val Arg Gln Ala Pro Gly Lys Gly Leu Glu Trp Val
         35                  40                  45

Ser Ala Ile Ser Pro Ser Gly Ser Ala Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Met Leu Ala Asn Ser Pro Leu Ala Phe Asp Tyr Trp Gly
            100                 105                 110

Gln Gly Thr Leu Val Thr Val Ser Ser
        115                 120

<210> SEQ ID NO 448
```

<211> LENGTH: 123
<212> TYPE: PRT
<213> ORGANISM: Homo sapiens

<400> SEQUENCE: 448

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Ala Trp Val Arg Gln Ala Pro Gly Lys Gly Leu Glu Trp Val
        35                  40                  45

Ser Phe Ile Ala Gln Ser Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Ser His Pro Asp Glu Glu Gly Thr Gln Met Phe Asp Tyr
            100                 105                 110

Trp Gly Gln Gly Thr Leu Val Thr Val Ser Ser
        115                 120

<210> SEQ ID NO 449
<211> LENGTH: 120
<212> TYPE: PRT
<213> ORGANISM: Homo sapiens

<400> SEQUENCE: 449

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Gln Met Ala Trp Val Arg Gln Ala Pro Gly Lys Gly Leu Glu Trp Val
        35                  40                  45

Ser Arg Ile Asp Arg Gly Gly Phe His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Ser Trp His Ala Asp Gln Tyr Phe Asp Tyr Trp Gly Gln
            100                 105                 110

Gly Thr Leu Val Thr Val Ser Ser
        115                 120

<210> SEQ ID NO 450
<211> LENGTH: 120
<212> TYPE: PRT
<213> ORGANISM: Homo sapiens

<400> SEQUENCE: 450

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Asp Tyr
            20                  25                  30

Asn Met Met Trp Val Arg Gln Ala Pro Gly Lys Gly Leu Glu Trp Val
        35                  40                  45

```
Ser Ala Ile Ala Thr Ser Gly Arg Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Thr Phe Gly Gly Asn Gln Asp Phe Asp Tyr Trp Gly Gln
                100                 105                 110

Gly Thr Leu Val Thr Val Ser Ser
                115                 120

<210> SEQ ID NO 451
<211> LENGTH: 120
<212> TYPE: PRT
<213> ORGANISM: Homo sapiens

<400> SEQUENCE: 451

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Lys Tyr
                 20                  25                  30

Asn Met Tyr Trp Val Arg Gln Ala Pro Gly Lys Gly Leu Glu Trp Val
             35                  40                  45

Ser Ala Ile Ser Pro Lys Gly Gln His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Gly Met Gly Ser Asp Ala Ile Thr Phe Asp Tyr Trp Gly Gln
                100                 105                 110

Gly Thr Leu Val Thr Val Ser Ser
                115                 120

<210> SEQ ID NO 452
<211> LENGTH: 123
<212> TYPE: PRT
<213> ORGANISM: Homo sapiens

<400> SEQUENCE: 452

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Ala Tyr
                 20                  25                  30

Asn Met Ala Trp Val Arg Gln Ala Pro Gly Lys Gly Leu Glu Trp Val
             35                  40                  45

Ser Phe Ile Ala Gln Ser Gly Gly His Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ser His Pro Asp Glu Glu Gly Thr Gln Met Phe Asp Tyr
                100                 105                 110

Trp Gly Gln Gly Thr Leu Val Thr Val Ser Ser
                115                 120
```

-continued

```
<210> SEQ ID NO 453
<211> LENGTH: 122
<212> TYPE: PRT
<213> ORGANISM: Homo sapiens

<400> SEQUENCE: 453
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Glu Arg Tyr
            20                  25                  30

Asp Met Phe Trp Val Arg Gln Ala Pro Gly Lys Gly Leu Glu Trp Val
        35                  40                  45

Ser Gly Ile Ser Pro Arg Gly Arg Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Ile Asn Tyr His Gly Thr Pro Ser Phe Asp Tyr Trp
            100                 105                 110

Gly Gln Gly Thr Leu Val Thr Val Ser Ser
        115                 120

```
<210> SEQ ID NO 454
<211> LENGTH: 122
<212> TYPE: PRT
<213> ORGANISM: Homo sapiens
<220> FEATURE:
<221> NAME/KEY: VARIANT
<222> LOCATION: 30
<223> OTHER INFORMATION: Xaa = Any Amino Acid

<400> SEQUENCE: 454
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Xaa Asn Tyr
            20                  25                  30

Asn Met Val Trp Val Arg Gln Ala Pro Gly Lys Gly Leu Glu Trp Val
        35                  40                  45

Ser Trp Ile Ser Gly Ala Gly His Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Val Asp Met Ala Gly Lys Leu Asn Val Phe Asp Tyr Trp
            100                 105                 110

Gly Gln Gly Thr Leu Val Thr Val Ser Ser
        115                 120

```
<210> SEQ ID NO 455
<211> LENGTH: 122
<212> TYPE: PRT
<213> ORGANISM: Homo sapiens

<400> SEQUENCE: 455
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Lys Gln Tyr
            20                  25                  30

Asn Met Tyr Trp Val Arg Gln Ala Pro Gly Lys Gly Leu Glu Trp Val
            35                  40                  45

Ser Phe Ile Ser Pro Ser Gly Gly Glu Thr Tyr Tyr Ala Asp Ser Val
50                  55                  60

Lys Gly Arg Phe Thr Thr Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Asp Val Asp Met Ala Gly Lys Leu Asn Val Phe Asp Tyr Trp
            100                 105                 110

Gly Gln Gly Thr Leu Val Thr Val Ser Ser
            115                 120

<210> SEQ ID NO 456
<211> LENGTH: 120
<212> TYPE: PRT
<213> ORGANISM: Homo sapiens

<400> SEQUENCE: 456

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ala Asp Tyr
            20                  25                  30

Gln Met Ala Trp Val Arg Gln Ala Pro Gly Lys Gly Leu Glu Trp Val
            35                  40                  45

Ser Arg Ile Asp Arg Gly Gly Phe His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys Pro Ser Trp His Ala Asp Gln Tyr Phe Asp Tyr Trp Gly Gln
            100                 105                 110

Gly Thr Leu Val Thr Val Ser Ser
            115                 120

<210> SEQ ID NO 457
<211> LENGTH: 120
<212> TYPE: PRT
<213> ORGANISM: Homo sapiens

<400> SEQUENCE: 457

Glu Val Gln Leu Leu Glu Ser Gly Gly Gly Leu Val Gln Pro Gly Gly
1               5                   10                  15

Ser Leu Arg Leu Thr Cys Ala Ala Ser Gly Phe Thr Phe Asp Asp Val
            20                  25                  30

Asn Met Thr Trp Val Arg Gln Ala Pro Gly Lys Gly Leu Glu Trp Val
            35                  40                  45

Ser Ala Ile Gly Pro Ser Gly Thr Glu Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Lys His Ser Lys Thr Gly Ser Ala Met Phe Asp Tyr Trp Gly Gln
            100                 105                 110

Gly Thr Leu Val Thr Val Ser Ser
        115                 120

<210> SEQ ID NO 458
<211> LENGTH: 119
<212> TYPE: PRT
<213> ORGANISM: Homo sapiens

<400> SEQUENCE: 458

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Gly
            20                  25                  30

Asn Met Val Trp Val Arg Gln Ala Pro Gly Lys Gly Leu Glu Trp Val
        35                  40                  45

Ser His Ile Asp Glu Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Asn Asp Arg Pro Gly Phe Asp Tyr Trp Gly Gln Gly
            100                 105                 110

Thr Leu Val Thr Val Ser Ser
        115

<210> SEQ ID NO 459
<211> LENGTH: 119
<212> TYPE: PRT
<213> ORGANISM: Homo sapiens

<400> SEQUENCE: 459

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Glu
            20                  25                  30

Asn Met His Trp Val Arg Gln Ala Pro Gly Lys Gly Leu Glu Trp Val
        35                  40                  45

Ser Gly Ile Gly Pro Arg Gly Met Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Met Asn Ser His Asp Gly Phe Asp Tyr Trp Gly Gln Gly
            100                 105                 110

Thr Leu Val Thr Val Ser Ser
        115

<210> SEQ ID NO 460
<211> LENGTH: 117
<212> TYPE: PRT
<213> ORGANISM: Homo sapiens

<400> SEQUENCE: 460

Glu Val Gln Leu Leu Glu Ser Gly Gly Gly Leu Val Gln Pro Gly Gly

```
                1               5                  10                 15
Ser Leu Arg Leu Ser Cys Ala Ala Ser Gly Phe Thr Phe Lys Gly Ser
                        20                  25                 30

Asn Met Gly Trp Val Arg Gln Ala Pro Gly Lys Gly Leu Glu Trp Val
            35                      40                  45

Ser Leu Ile Asp Gly Arg Gly Gln His Thr Tyr Tyr Ala Asp Ser Val
        50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Lys Pro Ser Val Arg Glu Phe Asp Tyr Arg Gly Gln Gly Thr Leu
                100                 105                 110

Val Thr Val Ser Ser
                115
```

<210> SEQ ID NO 461
<211> LENGTH: 121
<212> TYPE: PRT
<213> ORGANISM: Homo sapiens

<400> SEQUENCE: 461

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Glu
                    20                  25                  30

Asn Met His Trp Val Arg Gln Ala Pro Gly Lys Gly Leu Glu Trp Val
            35                      40                  45

Ser Gly Ile Gly Pro Arg Gly Met Pro Thr Tyr Tyr Ala Asp Ser Val
        50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
                    85                  90                  95

Ala Lys Arg Met Leu Ala Asn Ser Pro Leu Ala Phe Asp Tyr Trp Gly
                100                 105                 110

Gln Gly Thr Leu Val Thr Val Ser Ser
                115                 120
```

<210> SEQ ID NO 462
<211> LENGTH: 116
<212> TYPE: PRT
<213> ORGANISM: Homo sapiens

<400> SEQUENCE: 462

```
Glu Val Gln Leu Leu Glu Ser Gly Gly Gly Leu Val Gln Pro Gly Gly
1               5                   10                  15

Ser Leu Arg Leu Ser Cys Thr Ala Ser Gly Phe Thr Phe Ser Glu Ser
                    20                  25                  30

Thr Met Asn Trp Val Arg Gln Ala Pro Gly Lys Gly Leu Glu Trp Val
            35                      40                  45

Ser Val Ile Thr Ala Gln Gly Gly Asp Thr Tyr Tyr Ala Asp Ser Val
        50                      55                  60

Lys Gly Arg Phe Thr Ile Ser Arg Asp Asn Ser Lys Asn Thr Leu Tyr
65                      70                  75                  80

Leu Gln Met Asn Ser Leu Arg Ala Glu Asp Thr Ala Val Tyr Tyr Cys
```

85                  90                  95
Ala Lys Pro Asp Val Leu Phe Asp Tyr Trp Gly Gln Gly Thr Leu Val
                100                 105                 110

Thr Val Ser Ser
        115

<210> SEQ ID NO 463
<211> LENGTH: 117
<212> TYPE: PRT
<213> ORGANISM: Homo sapiens

<400> SEQUENCE: 463

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Glu Tyr
             20                  25                  30

Asn Met Leu Trp Val Arg Gln Ala Pro Gly Lys Gly Leu Glu Trp Val
         35                  40                  45

Ser Gly Ile Gly Pro Ser Gly Arg Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ser Ile Thr Leu Phe Asp Tyr Trp Gly Gln Gly Thr Leu
                100                 105                 110

Val Thr Val Ser Ser
        115

<210> SEQ ID NO 464
<211> LENGTH: 124
<212> TYPE: PRT
<213> ORGANISM: Homo sapiens

<400> SEQUENCE: 464

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ser Gly Tyr
             20                  25                  30

Asn Met Tyr Trp Val Arg Gln Ala Pro Gly Lys Gly Leu Glu Trp Val
         35                  40                  45

Ser Ala Ile Asp Ala Tyr Gly Thr His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Glu Gly Leu Gln Thr Ser Asp His Gly Glu Arg Ile Ser Phe Asp
                100                 105                 110

Tyr Trp Gly Gln Gly Thr Leu Val Thr Val Ser Ser
        115                 120

<210> SEQ ID NO 465
<211> LENGTH: 122
<212> TYPE: PRT
<213> ORGANISM: Homo sapiens

<400> SEQUENCE: 465

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
50                      55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
            115                 120

<210> SEQ ID NO 466
<211> LENGTH: 122
<212> TYPE: PRT
<213> ORGANISM: Homo sapiens

<400> SEQUENCE: 466

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Gln Tyr
            20                  25                  30

Asp Met Ser Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
50                      55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Val Phe Ser Asp Trp Pro Ala Val Glu Phe Asp Tyr Trp
            100                 105                 110

Gly Gln Gly Thr Leu Val Thr Val Ser Ser
            115                 120

<210> SEQ ID NO 467
<211> LENGTH: 120
<212> TYPE: PRT
<213> ORGANISM: Homo sapiens

<400> SEQUENCE: 467

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Pro Gly Leu His Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 468
<211> LENGTH: 120
<212> TYPE: PRT
<213> ORGANISM: Homo sapiens
<220> FEATURE:
<221> NAME/KEY: VARIANT
<222> LOCATION: 62, 104
<223> OTHER INFORMATION: Xaa = Any Amino Acid

<400> SEQUENCE: 468

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Glu Trp Tyr
            20                  25                  30

Trp Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Xaa Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys Val Lys Leu Gly Gly Xaa Pro Asn Phe Gly Tyr Arg Gly Gln
            100                 105                 110

Gly Thr Leu Val Thr Val Ser Ser
        115                 120

<210> SEQ ID NO 469
<211> LENGTH: 120
<212> TYPE: PRT
<213> ORGANISM: Homo sapiens

<400> SEQUENCE: 469

Glu Val Gln Leu Leu Glu Ser Gly Gly Gly Leu Val Gln Pro Gly Gly
1               5                   10                  15

Ser Leu Arg Leu Ser Cys Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Phe Ile Asp Pro Pro Ser Val His Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

-continued

```
<210> SEQ ID NO 470
<211> LENGTH: 120
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid

<400> SEQUENCE: 470

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Val Gly Gly Ser His Thr Tyr Tyr Ala Xaa Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 471
<211> LENGTH: 120
<212> TYPE: PRT
<213> ORGANISM: Homo sapiens
<220> FEATURE:
<221> NAME/KEY: VARIANT
<222> LOCATION: 62
<223> OTHER INFORMATION: Xaa = Any Amino Acid

<400> SEQUENCE: 471

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Asp Thr Gly Gly Val His Thr Tyr Tyr Ala Xaa Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120

<210> SEQ ID NO 472
<211> LENGTH: 120
<212> TYPE: PRT
<213> ORGANISM: Homo sapiens

<400> SEQUENCE: 472
```

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Asp Val Pro Gly Arg His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120
```

<210> SEQ ID NO 473
<211> LENGTH: 120
<212> TYPE: PRT
<213> ORGANISM: Homo sapiens

<400> SEQUENCE: 473

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Ala His Ala Gly Pro Glu Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
            115                 120
```

<210> SEQ ID NO 474
<211> LENGTH: 120
<212> TYPE: PRT
<213> ORGANISM: Homo sapiens

<400> SEQUENCE: 474

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Asp Thr Arg Gly Val Arg Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120
```

<210> SEQ ID NO 475
<211> LENGTH: 120
<212> TYPE: PRT
<213> ORGANISM: Homo sapiens

<400> SEQUENCE: 475

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Asp Val Pro Gly Asn His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Leu Val Thr Val Ser Ser
        115                 120
```

<210> SEQ ID NO 476
<211> LENGTH: 120
<212> TYPE: PRT
<213> ORGANISM: Homo sapiens

<400> SEQUENCE: 476

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Asp Val Gly Gly Arg His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Pro Asn Ala Phe Asp Tyr Trp Gly Gln
            100                 105                 110

Gly Thr Leu Val Thr Val Ser Ser
        115                 120
```

<210> SEQ ID NO 477
<211> LENGTH: 118
<212> TYPE: PRT
<213> ORGANISM: Homo sapiens -continued

```
<400> SEQUENCE: 477

Glu Val Gln Leu Leu Glu Ser Gly Gly Gly Ser Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Arg Ile Asp Ser Tyr Gly Arg Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Arg Ser Pro Tyr Thr Phe Asp Tyr Trp Gly Gln Gly Thr
            100                 105                 110

Leu Val Thr Val Ser Ser
        115

<210> SEQ ID NO 478
<211> LENGTH: 117
<212> TYPE: PRT
<213> ORGANISM: Homo sapiens

<400> SEQUENCE: 478

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Asn Met Gly Trp Val Arg Gln Ala Pro Gly Lys Gly Leu Glu Trp Val
        35                  40                  45

Ser Thr Ile Ser Thr Gln Gly Tyr His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Phe Thr Ser Asp Phe Asp Tyr Trp Gly Gln Gly Thr Leu
            100                 105                 110

Val Thr Val Ser Ser
        115

<210> SEQ ID NO 479
<211> LENGTH: 119
<212> TYPE: PRT
<213> ORGANISM: Homo sapiens

<400> SEQUENCE: 479

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Gly Tyr
            20                  25                  30

Asn Met Tyr Trp Val Arg Gln Ala Pro Gly Lys Gly Leu Glu Trp Val
        35                  40                  45

Ser Gly Ile Ser Gly Pro Gly Leu Glu Thr Tyr Tyr Ala Asp Ser Val
    50                  55                  60

Lys Gly Arg Phe Thr Ile Ser Arg Asp Asn Ser Lys Asn Thr Leu Tyr
```

```
                65                  70                  75                  80
Leu Gln Met Asn Ser Leu Arg Ala Glu Asp Thr Ala Val Tyr Tyr Cys
                    85                  90                  95

Ala Gln Gly Met Ser Lys Thr Ser Thr Phe Asp Tyr Trp Gly Gln Gly
                100                 105                 110

Thr Leu Val Thr Val Ser Ser
        115

<210> SEQ ID NO 480
<211> LENGTH: 117
<212> TYPE: PRT
<213> ORGANISM: Homo sapiens

<400> SEQUENCE: 480

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Glu Tyr
                20                  25                  30

Tyr Met Glu Trp Val Arg Gln Ala Pro Gly Lys Gly Leu Glu Trp Val
            35                  40                  45

Ser Ser Ile Asp Pro Asp Gly Ser Leu Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys Tyr Pro Arg Glu Lys Phe Asp Tyr Trp Gly Gln Gly Thr Leu
                100                 105                 110

Val Thr Val Ser Ser
        115

<210> SEQ ID NO 481
<211> LENGTH: 120
<212> TYPE: PRT
<213> ORGANISM: Homo sapiens

<400> SEQUENCE: 481

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Lys Tyr
                20                  25                  30

Gln Met Gly Trp Val Arg Gln Ala Pro Gly Lys Gly Leu Glu Trp Val
            35                  40                  45

Ser Phe Ile Asp Ser Asn Gly His His Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Gln Leu Ser Val Gln Gly Ser Asn Leu Phe Asp Tyr Trp Gly Gln
                100                 105                 110

Gly Thr Leu Val Thr Val Ser Ser
        115                 120

<210> SEQ ID NO 482
<211> LENGTH: 120
<212> TYPE: PRT
```

<213> ORGANISM: Homo sapiens

<400> SEQUENCE: 482

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val His Tyr
            20                  25                  30

Thr Met Gly Trp Val Arg Gln Ala Pro Gly Lys Gly Leu Glu Trp Val
        35                  40                  45

Ser Trp Ile His Ser Asp Gly Val His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Thr Trp Gly Glu Lys Lys Thr Phe Asp Tyr Trp Gly Gln
            100                 105                 110

Gly Thr Leu Val Thr Val Ser Ser
            115                 120

<210> SEQ ID NO 483
<211> LENGTH: 120
<212> TYPE: PRT
<213> ORGANISM: Homo sapiens

<400> SEQUENCE: 483

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Met Gly Tyr
            20                  25                  30

Asp Met His Trp Val Arg Gln Ala Pro Gly Lys Gly Leu Glu Trp Val
        35                  40                  45

Ser Gly Ile Ser Ala Lys Gly Thr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Ser Gly Ser Asp Gly Leu Phe Asp Tyr Trp Gly Gln
            100                 105                 110

Gly Thr Leu Val Thr Val Ser Ser
            115                 120

<210> SEQ ID NO 484
<211> LENGTH: 124
<212> TYPE: PRT
<213> ORGANISM: Homo sapiens

<400> SEQUENCE: 484

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Pro Val Tyr
            20                  25                  30

Asn Met Ala Trp Val Arg Gln Ala Pro Gly Lys Gly Leu Glu Trp Val
        35                  40                  45

Ser Phe Ile Ala Gly Asn Gly Gln Gln Thr Tyr Tyr Ala Asp Ser Val
    50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ala Ser Lys Val Ser Pro Met Ser Leu Thr Asp Phe Asp
            100                 105                 110

Tyr Trp Gly Gln Gly Thr Leu Val Thr Val Ser Ser
            115                 120
```

<210> SEQ ID NO 485
<211> LENGTH: 124
<212> TYPE: PRT
<213> ORGANISM: Homo sapiens

<400> SEQUENCE: 485

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Val Gln Tyr
                 20                  25                  30

Asn Met His Trp Val Arg Gln Ala Pro Gly Lys Gly Leu Glu Trp Val
             35                  40                  45

Ser Gly Ile Ser Ser Gly Gly Met Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Ile Arg Asp Ser Thr Leu Pro Arg Gly Thr Leu Phe Asp
            100                 105                 110

Tyr Trp Gly Gln Gly Thr Leu Val Thr Val Ser Ser
            115                 120
```

<210> SEQ ID NO 486
<211> LENGTH: 121
<212> TYPE: PRT
<213> ORGANISM: Homo sapiens

<400> SEQUENCE: 486

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Glu Thr Tyr
                 20                  25                  30

Ser Met His Trp Val Arg Gln Ala Pro Gly Lys Gly Leu Glu Trp Val
             35                  40                  45

Ser Ser Ile Ser Leu Pro Gly Ser Arg Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys His Ser Lys Ser Ser His Arg Gln Ser Phe Tyr Trp Gly
            100                 105                 110

Gln Gly Thr Leu Val Thr Val Ser Ser
            115                 120
```

<210> SEQ ID NO 487

<211> LENGTH: 122
<212> TYPE: PRT
<213> ORGANISM: Homo sapiens

<400> SEQUENCE: 487

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Gln Tyr
            20                  25                  30

Asp Met His Trp Val Arg Gln Ala Pro Gly Lys Gly Leu Glu Trp Val
        35                  40                  45

Ser Gly Ile Ser Phe Ser Gly Tyr Glu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Arg Gly Pro Ala Pro Met Arg Ser Leu Phe Asp Tyr Trp
            100                 105                 110

Gly Gln Gly Thr Leu Val Thr Val Ser Ser
        115                 120

<210> SEQ ID NO 488
<211> LENGTH: 120
<212> TYPE: PRT
<213> ORGANISM: Homo sapiens

<400> SEQUENCE: 488

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Val Asp Tyr
            20                  25                  30

Pro Met Val Trp Val Arg Gln Ala Pro Gly Lys Gly Leu Glu Trp Val
        35                  40                  45

Ser His Ile Thr Ser Met Gly Glu Ser Thr Tyr Tyr Ala Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Val Tyr Tyr Cys
                85                  90                  95

Ala Lys Leu Pro Thr His Phe Pro Ile Arg Phe Asp Tyr Trp Gly Gln
            100                 105                 110

Gly Thr Leu Val Thr Val Ser Ser
        115                 120

<210> SEQ ID NO 489
<211> LENGTH: 116
<212> TYPE: PRT
<213> ORGANISM: Homo sapiens

<400> SEQUENCE: 489

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Lys Gln Tyr
            20                  25                  30

Asn Met Tyr Trp Val Arg Gln Ala Pro Gly Lys Gly Leu Glu Trp Val
        35                  40                  45

Ser Phe Ile Ser Pro Ser Gly Gly Glu Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Ile Lys Pro Phe Asp Tyr Trp Gly Gln Gly Thr Leu Val
                100                 105                 110

Thr Val Ser Ser
        115

<210> SEQ ID NO 490
<211> LENGTH: 120
<212> TYPE: PRT
<213> ORGANISM: Homo sapiens

<400> SEQUENCE: 490

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Met Tyr
                20                  25                  30

Ser Met Ala Trp Val Arg Gln Ala Pro Gly Lys Gly Leu Glu Trp Val
             35                  40                  45

Ser Phe Ile Asp Phe Asp Gly Leu His Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Ser Thr Ser Thr Met Ala Leu Phe Asp Tyr Trp Gly Gln
                100                 105                 110

Gly Thr Leu Val Thr Val Ser Ser
            115                 120

<210> SEQ ID NO 491
<211> LENGTH: 122
<212> TYPE: PRT
<213> ORGANISM: Homo sapiens

<400> SEQUENCE: 491

Glu Val Gln Leu Leu Glu Ser Gly Gly Gly Leu Val Arg Pro Gly Gly
 1               5                  10                  15

Ser Leu Arg Leu Ser Cys Ala Ala Ser Gly Phe Thr Phe Pro Glu Tyr
                20                  25                  30

Asn Met His Trp Val Arg Gln Ala Pro Gly Lys Gly Leu Glu Trp Val
             35                  40                  45

Ser Ala Ile Gly Thr Ala Gly Gly Ser Thr Tyr Tyr Ala Asp Ser Val
    50                  55                  60

Lys Gly Arg Phe Thr Ile Ser Arg Asp Asn Ser Lys Asn Met Leu Tyr
 65                  70                  75                  80

Leu Gln Met Asn Ser Leu Arg Ala Glu Asp Thr Ala Val Tyr Tyr Cys
                 85                  90                  95

Ala Lys Gly Tyr Arg Pro Arg Thr Gly Ser Met Leu Phe Asp Tyr Trp
                100                 105                 110

Gly Gln Gly Thr Leu Val Thr Val Ser Ser
            115                 120

<210> SEQ ID NO 492
<211> LENGTH: 120
<212> TYPE: PRT
<213> ORGANISM: Homo sapiens

<400> SEQUENCE: 492

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Lys Tyr
            20                  25                  30

Asn Met Tyr Trp Val Arg Gln Ala Pro Gly Lys Gly Leu Glu Trp Val
        35                  40                  45

Ser Ala Ile Ser Pro Lys Gly Gln Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Glu Gly Met Gly Ser Asp Ala Ile Thr Phe Asp Tyr Trp Gly Gln
            100                 105                 110

Gly Thr Leu Val Thr Val Ser Ser
        115                 120

<210> SEQ ID NO 493
<211> LENGTH: 122
<212> TYPE: PRT
<213> ORGANISM: Homo sapiens

<400> SEQUENCE: 493

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Asp Tyr
            20                  25                  30

Asp Met Ala Trp Val Arg Gln Ala Pro Gly Lys Gly Leu Glu Trp Val
        35                  40                  45

Ser Phe Ile Asp Arg Lys Gly His His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Thr Asp Ile Gln Arg Leu Asn Ser Ala Phe Asp Tyr Trp
            100                 105                 110

Gly Gln Gly Thr Leu Val Thr Val Ser Ser
        115                 120

<210> SEQ ID NO 494
<211> LENGTH: 119
<212> TYPE: PRT
<213> ORGANISM: Homo sapiens

<400> SEQUENCE: 494

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asn Gly
            20                  25                  30

Val Met Ala Trp Val Arg Gln Ala Pro Gly Lys Gly Leu Glu Trp Val

```
                35                  40                  45
Ser His Ile Asn Glu Asn Gly Gly Ala Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Pro Ser Ile Glu Ser Pro Ile Phe Asp Tyr Trp Gly Gln Gly
                100                 105                 110
Thr Leu Val Thr Val Ser Ser
            115

<210> SEQ ID NO 495
<211> LENGTH: 119
<212> TYPE: PRT
<213> ORGANISM: Homo sapiens

<400> SEQUENCE: 495

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ala His Glu
                20                  25                  30
Pro Met Val Trp Val Arg Gln Ala Pro Gly Lys Gly Leu Glu Trp Val
                35                  40                  45
Ser His Ile Asp Arg Val Gly Gln Asp Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                 85                  90                  95
Ala Lys Leu Pro Lys Arg Gly Pro Arg Phe Asp Tyr Trp Gly Gln Gly
                100                 105                 110
Thr Leu Val Thr Val Ser Ser
            115

<210> SEQ ID NO 496
<211> LENGTH: 121
<212> TYPE: PRT
<213> ORGANISM: Homo sapiens

<400> SEQUENCE: 496

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Glu Glu Ser
                20                  25                  30
Val Met Gly Trp Val Arg Gln Ala Pro Gly Lys Gly Leu Glu Trp Val
                35                  40                  45
Ser Ala Ile Ser Pro Gly Gly Ser Glu Thr Tyr Tyr Ala Asp Ser Val
 50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Ala Ala Val Tyr Tyr Cys
                 85                  90                  95
Ala Lys Arg Thr Gly Pro Pro Gly Ser Thr Val Phe Asp Tyr Trp Gly
                100                 105                 110
Gln Gly Thr Leu Val Thr Val Ser Ser
```

```
                    115                 120
```

<210> SEQ ID NO 497
<211> LENGTH: 116
<212> TYPE: PRT
<213> ORGANISM: Homo sapiens

<400> SEQUENCE: 497

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Gly Asp Glu
            20                  25                  30

Pro Met His Trp Val Arg Gln Ala Pro Gly Lys Gly Leu Glu Trp Val
        35                  40                  45

Ser Gly Ile Gly Lys Glu Gly Gln Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Gly Gly Pro Phe Asp Tyr Trp Gly Gln Gly Thr Leu Val
            100                 105                 110

Thr Val Ser Ser
        115
```

<210> SEQ ID NO 498
<211> LENGTH: 121
<212> TYPE: PRT
<213> ORGANISM: Homo sapiens

<400> SEQUENCE: 498

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Tyr Gly
            20                  25                  30

Asn Met Phe Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Met Thr Thr Asp Ser Pro Pro Gly Phe Asp Tyr Trp Gly
            100                 105                 110

Gln Gly Thr Leu Val Thr Val Ser Ser
        115                 120
```

<210> SEQ ID NO 499
<211> LENGTH: 122
<212> TYPE: PRT
<213> ORGANISM: Homo sapiens

<400> SEQUENCE: 499

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Lys Glu
            20                  25                  30
```

```
Thr Met Ser Trp Val Arg Gln Ala Pro Gly Lys Gly Leu Glu Trp Val
        35                  40                  45

Ser Trp Ile Ser Pro His Gly Ala Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Phe Ser Tyr Tyr Pro Arg Val Ser Phe Asp Tyr Trp
                100                 105                 110

Gly Gln Gly Thr Leu Val Thr Val Ser Ser
                115                 120

<210> SEQ ID NO 500
<211> LENGTH: 119
<212> TYPE: PRT
<213> ORGANISM: Homo sapiens

<400> SEQUENCE: 500

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Gly
                20                  25                  30

Asn Met Val Trp Val Arg Gln Ala Pro Gly Lys Gly Leu Glu Trp Val
            35                  40                  45

Ser His Ile Asp Glu Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Asn Asp Arg Pro Gly Phe Asp Tyr Trp Gly Gln Gly
                100                 105                 110

Thr Leu Val Thr Val Ser Ser
            115

<210> SEQ ID NO 501
<211> LENGTH: 119
<212> TYPE: PRT
<213> ORGANISM: Homo sapiens
<220> FEATURE:
<221> NAME/KEY: VARIANT
<222> LOCATION: 53
<223> OTHER INFORMATION: Xaa = Any Amino Acid

<400> SEQUENCE: 501

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asn Gly
                20                  25                  30

Asn Met Val Trp Val Arg Gln Ala Pro Gly Lys Gly Leu Glu Trp Val
            35                  40                  45

Ser His Ile Asp Xaa Tyr Gly Thr Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Gly Asp Thr Ala Val Tyr Tyr Cys
```

```
                    85                  90                  95

Ala Lys Pro Arg Asn Asp Arg Pro Gly Phe Asp Tyr Trp Gln Gly
                100                 105                 110

Thr Leu Val Thr Val Ser Ser
            115

<210> SEQ ID NO 502
<211> LENGTH: 124
<212> TYPE: PRT
<213> ORGANISM: Homo sapiens

<400> SEQUENCE: 502

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Ala Gly Gln
                 20                  25                  30

Asp Met Arg Trp Val Arg Gln Ala Pro Gly Lys Gly Leu Glu Trp Val
             35                  40                  45

Ser Ser Ile Pro Ser Ser Gly Phe Asn Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Arg Ala Lys Asp Arg Ser Val Ser Gln Met Pro Tyr Phe Asp
                100                 105                 110

Tyr Trp Gly Gln Gly Thr Leu Val Thr Val Ser Ser
            115                 120

<210> SEQ ID NO 503
<211> LENGTH: 120
<212> TYPE: PRT
<213> ORGANISM: Homo sapiens

<400> SEQUENCE: 503

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Met Arg Pro
                 20                  25                  30

Asp Met Val Trp Val Arg Gln Ala Pro Gly Lys Gly Leu Glu Trp Val
             35                  40                  45

Ser Thr Ile Lys Asp Trp Gly Asp Gln Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Ala Ala Val Tyr Tyr Cys
                 85                  90                  95

Ala Lys Ala Asp Ser Arg Ala Gln Leu Asp Phe Asp Tyr Trp Gly Gln
                100                 105                 110

Gly Thr Leu Val Thr Val Ser Ser
            115                 120

<210> SEQ ID NO 504
<211> LENGTH: 121
<212> TYPE: PRT
<213> ORGANISM: Homo sapiens

<400> SEQUENCE: 504
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Tyr Phe Leu Phe Arg Ala Thr Ser Phe Asp Tyr Trp Gly
            100                 105                 110

Gln Gly Thr Leu Val Thr Val Ser Ser
            115                 120

<210> SEQ ID NO 505
<211> LENGTH: 120
<212> TYPE: PRT
<213> ORGANISM: Homo sapiens

<400> SEQUENCE: 505

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Asp Asp
            20                  25                  30

Asp Met Val Trp Val Arg Gln Ala Pro Gly Lys Gly Leu Glu Trp Val
        35                  40                  45

Ser Ser Ile Pro Gly Asn Gly Tyr Val Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Pro Asp Pro Thr Ser Val Phe Phe Asp Tyr Trp Gly Gln
            100                 105                 110

Gly Thr Leu Val Thr Val Ser Ser
            115             120

<210> SEQ ID NO 506
<211> LENGTH: 116
<212> TYPE: PRT
<213> ORGANISM: Homo sapiens

<400> SEQUENCE: 506

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Asp Asp
            20                  25                  30

Trp Met Thr Trp Val Arg Gln Ala Pro Gly Lys Gly Leu Glu Trp Val
        35                  40                  45

Ser Gly Ile Ala Ala Tyr Gly Ile Ser Thr Tyr Tyr Ala Asp Ser Val
50                      55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Ala Ala Val Tyr Tyr Cys
                85                  90                  95
Ala Glu Ser Gly Lys Val Phe Asp Tyr Trp Gly Gln Gly Thr Leu Val
            100                 105                 110
Thr Val Ser Ser
        115

<210> SEQ ID NO 507
<211> LENGTH: 120
<212> TYPE: PRT
<213> ORGANISM: Homo sapiens

<400> SEQUENCE: 507

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Val Glu Arg
             20                  25                  30
Pro Met Asp Trp Val Arg Gln Ala Pro Gly Lys Gly Leu Glu Trp Val
         35                  40                  45
Ser Leu Ile Gly Ala Asp Gly Leu Ser Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Leu Phe Arg Pro Gly Leu Leu Trp Phe Asp Tyr Trp Gly Gln
            100                 105                 110
Gly Thr Leu Val Thr Val Ser Ser
        115                 120

<210> SEQ ID NO 508
<211> LENGTH: 119
<212> TYPE: PRT
<213> ORGANISM: Homo sapiens

<400> SEQUENCE: 508

Glu Val Gln Leu Leu Glu Ser Gly Gly Gly Leu Val Gln Pro Gly Gly
  1               5                  10                  15
Ser Leu Arg Leu Ser Cys Ala Ala Ser Gly Phe Thr Phe Thr Gly Gln
             20                  25                  30
Asp Met Gln Trp Val Arg Gln Ala Pro Gly Lys Gly Leu Glu Trp Val
         35                  40                  45
Ser Gly Ile Asn Ala Asp Gly Met Ala Thr Tyr Tyr Ala Asp Ser Val
     50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Val Tyr Tyr Cys
                85                  90                  95
Ala Lys Thr Ser Pro Thr Met Arg Ser Phe Asp Tyr Trp Gly Gln Gly
            100                 105                 110
Thr Leu Val Thr Val Ser Ser
        115

<210> SEQ ID NO 509
<211> LENGTH: 118
<212> TYPE: PRT
<213> ORGANISM: Homo sapiens
```

<400> SEQUENCE: 509

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Glu Glu
            20                  25                  30

Tyr Met Gln Trp Val Arg Gln Ala Pro Gly Lys Gly Leu Glu Trp Val
        35                  40                  45

Ser Leu Ile Pro His Thr Gly Asn Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ala Asn Ser Leu Leu Phe Asp Tyr Trp Gly Gln Gly Thr
            100                 105                 110

Leu Val Thr Val Ser Ser
            115

<210> SEQ ID NO 510
<211> LENGTH: 120
<212> TYPE: PRT
<213> ORGANISM: Homo sapiens

<400> SEQUENCE: 510

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe His Arg Cys
            20                  25                  30

Lys Met Gly Trp Val Arg Gln Ala Pro Gly Lys Gly Leu Glu Trp Val
        35                  40                  45

Ser Phe Ile Glu Tyr Asp Gly Arg Asp Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Cys Thr Arg Pro Tyr Gly Met Phe Asp Tyr Trp Gly Gln
            100                 105                 110

Gly Thr Leu Val Thr Val Ser Ser
        115                 120

<210> SEQ ID NO 511
<211> LENGTH: 120
<212> TYPE: PRT
<213> ORGANISM: Homo sapiens

<400> SEQUENCE: 511

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Phe Ile Asp Lys Val Gly His His Thr Trp Tyr Glu Asp Pro Val
    50                  55                  60

-continued

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Gln Phe Gly Pro Asn Ala Phe Asp Tyr Trp Gly Gln
            100                 105                 110

Gly Thr Gln Val Thr Val Ser Ser
            115                 120

<210> SEQ ID NO 512
<211> LENGTH: 120
<212> TYPE: PRT
<213> ORGANISM: Homo sapiens
<220> FEATURE:
<221> NAME/KEY: VARIANT
<222> LOCATION: 101
<223> OTHER INFORMATION: Xaa = Any Amino Acid

<400> SEQUENCE: 512

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Ser Met Gly Trp Val Arg Gln Ala Pro Gly Lys Gly Leu Glu Trp Val
         35                  40                  45

Ser Met Ile Ala His Ala Gly Pro Glu Arg Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Xaa Phe Gly Ser Asn Ala Phe Asp Tyr Trp Gly Gln
            100                 105                 110

Gly Thr Leu Val Thr Val Ser Ser
            115                 120

<210> SEQ ID NO 513
<211> LENGTH: 120
<212> TYPE: PRT
<213> ORGANISM: Homo sapiens

<400> SEQUENCE: 513

Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Thr Arg Tyr
             20                  25                  30

Asn Met Gly Trp Val Arg Gln Ala Pro Gly Lys Gly Leu Glu Trp Val
         35                  40                  45

Ser Phe Ile Asp Pro Pro Ser Val His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Asn Ile Ser Gln Phe Gly Ser Asn Ala Phe Asp Tyr Trp Gly Gln
            100                 105                 110

Gly Thr Leu Val Thr Val Ser Ser
            115                 120
```

<210> SEQ ID NO 514
<211> LENGTH: 120
<212> TYPE: PRT
<213> ORGANISM: Homo sapiens
<220> FEATURE:
<221> NAME/KEY: VARIANT
<222> LOCATION: 96
<223> OTHER INFORMATION: Xaa = Any Amino Acid

<400> SEQUENCE: 514

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Phe Ile Asp Pro Pro Ser Val His Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Xaa
            85                  90                  95

Ala Glu Ile Ser Gln Phe Gly Ser Asn Ala Phe Asp Tyr Trp Gly Gln
        100                 105                 110

Gly Thr Leu Val Thr Val Ser Ser
    115                 120

<210> SEQ ID NO 515
<211> LENGTH: 120
<212> TYPE: PRT
<213> ORGANISM: Homo sapiens

<400> SEQUENCE: 515

Glu Val Gln Leu Phe Glu Ser Gly Gly Gly Leu Val Gln Pro Gly Gly
 1               5                  10                  15

Ser Leu Arg Leu Ser Cys Ala Ala Ser Gly Phe Thr Phe Thr Arg Tyr
            20                  25                  30

Ser Met Gly Trp Val Arg Gln Ala Pro Gly Lys Gly Leu Glu Trp Val
        35                  40                  45

Ser Met Ile Ala His Ala Gly Pro Glu Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
            85                  90                  95

Ala Lys Ile Ser Gln Phe Gly Ser Asn Ala Leu Asp Tyr Trp Gly Arg
        100                 105                 110

Gly Thr Leu Val Thr Val Ser Ser
    115                 120

<210> SEQ ID NO 516
<211> LENGTH: 122
<212> TYPE: PRT
<213> ORGANISM: Homo sapiens

<400> SEQUENCE: 516

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ala Arg Tyr
            20                  25                  30

Asn Met Gly Trp Val Arg Gln Ala Pro Gly Lys Gly Leu Glu Trp Val
        35                  40                  45

Ser Leu Ile Asp Pro Ser Gly Gly His Thr Tyr Tyr Ala Asp Ser Val
    50                  55                  60

Lys Gly Arg Phe Thr Ile Ser Arg Asn Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Lys Pro Val Phe Ser Asp Trp Pro Ala Val Glu Asp Tyr Trp
            100                 105                 110

Gly Gln Gly Thr Val Val Thr Val Ser Ser
        115                 120

<210> SEQ ID NO 517
<211> LENGTH: 119
<212> TYPE: PRT
<213> ORGANISM: Homo sapiens

<400> SEQUENCE: 517

Glu Val Gln Leu Leu Glu Ser Gly Gly Gly Met Val Gln Pro Gly Gly
1               5                   10                  15

Ser Leu Arg Leu Ser Cys Ala Ala Ser Gly Phe Thr Phe Glu His Glu
            20                  25                  30

Gly Met Val Trp Val Arg Gln Ala Pro Gly Lys Gly Leu Glu Trp Val
        35                  40                  45

Ser His Ile Gly Glu Asp Gly Gln Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Asn Ile Pro Lys Ala Gly Pro Ser Phe Asp Tyr Trp Gly Gln Gly
            100                 105                 110

Thr Leu Val Thr Val Ser Ser
        115

<210> SEQ ID NO 518
<211> LENGTH: 357
<212> TYPE: DNA
<213> ORGANISM: Homo sapiens

<400> SEQUENCE: 518
gaggtgcagc tgttggagtc tgggggaggc ttgatacagc ctggggggtc cctgcgtctc      60
tcctgtgcag cctccggatt caccttttgcg catgagacga tggtgtgggt ccgccaggct    120
ccagggaagg gtctagagtg gtctcacat attgatcgtg ttggtcagga tacatactac    180
gcagactccg tgaagggccg gttcaccatc tcccgcgaca attccaagaa cacgctgtat    240
ctgcaaatga acagcctgcg tgccgaggac acagcgtat attactgtgc gaaacttcct    300
aagagggggc cttggtttga ctaccgggt cagggaaccc tggtcaccgt ctcgagc       357

<210> SEQ ID NO 519
<211> LENGTH: 357
<212> TYPE: DNA
<213> ORGANISM: Homo sapiens

<400> SEQUENCE: 519

```
gaggtgcagc tgttggagtc tgggggaggc ttgatacagc ctgggggtc cctgcgtctc      60
tcctgtgcag cctccggatt cacctttgcg catgagacga tggtgtgggt ccgccaggct     120
ccagggaagg gtctagagtg gtctcacat attgatcgtg ttggtcagga tacatactac     180
gcagactccg tgaagggccg gttcaccatc tcccgcgaca attccaagaa cacgctgtat    240
ctgcaaatga acagcctgcg tgccgaggac acagcggtat attactgtgc gcgcttcct    300
aagagggggc cttggtttga ctaccggggt cagggaaccc tggtcaccgt ctcgagc       357
```

<210> SEQ ID NO 520
<211> LENGTH: 363
<212> TYPE: DNA
<213> ORGANISM: Homo sapiens

<400> SEQUENCE: 520

```
gaggtgcggc tgttggagtc tgggggaggc ttggtacagc ctgggggatc cctgcgtctc     60
tcctgtgtag cctccggatt cacctttggt aagtccacta tgacgtgggt ccgccaggct   120
ccagggaagg gtctagagtg gtctcacat atttcggatg atggtaattc tacatactac   180
gcagactccg tgaagggccg gttcaccatc tcccgcgaca attccaagaa cacgctgtat  240
ctgcaaatga acagcctgcg tgccgaggac accgcggtat attactgtgc gaaagttccg  300
attctggctc ctcgtaatct ttttgactac tggggtcagg aaccctggt caccgtctcg   360
agc                                                                363
```

<210> SEQ ID NO 521
<211> LENGTH: 363
<212> TYPE: DNA
<213> ORGANISM: Homo sapiens

<400> SEQUENCE: 521

```
gaggtgcggc tgttggagtc tgggggaggc ttggtacagc ctgggggatc cctgcgtctc     60
tcctgtgtag cctccggatt caactttggt aagtccacta tgacgtgggt ccgccaggct  120
ccagggaagg gtctagagtg gtctcacat atttcggatg atggtaattc tacatactac   180
gcagactccg tgaagggccg gttcaccatc tcccgcgaca attccaagaa cacgctgtat  240
ctgcaaatga acagcctgcg tgccgaggac accgcggtat attactgtgc gaaagttccg  300
attctggctc ctcgtaatct ttttgactac tggggtcagg aaccctggt caccgtctcg   360
agc                                                                363
```

<210> SEQ ID NO 522
<211> LENGTH: 363
<212> TYPE: DNA
<213> ORGANISM: Homo sapiens

<400> SEQUENCE: 522

```
gaggtgcggc tgttggagtc tgggggaggc ttggtacagc ctgggggatc cctgcgtctc     60
tcctgtgtag cctccggatt cacctttggt aagggggacta tgacgtgggt ccgccaggct 120
ccagggaagg gtctagagtg gtctcacat atttcggatg atggtaattc tacatactac   180
gcagactccg tgaagggccg gttcaccatc tcccgcgaca attccaagaa cacgctgtat  240
ctgcaaatga acagcctgcg tgccgaggac accgcggtat attactgtgc gaaagttccg  300
attctggctc ctcgtaatct ttttgactac tggggtcagg aaccctggt caccgtctcg   360
```

```
agc                                                                   363
```

<210> SEQ ID NO 523
<211> LENGTH: 366
<212> TYPE: DNA
<213> ORGANISM: Homo sapiens
<220> FEATURE:
<221> NAME/KEY: misc_feature
<222> LOCATION: 184
<223> OTHER INFORMATION: n = A,T,C or G

<400> SEQUENCE: 523

```
gaggtgcagc tgttggagtc tgggggaggc ttggtacagc ctgggggtc cctgcgtctc      60
tcctgtgcag cctccggatt cacctttgcg cggtataata tgggttgggt ccgccaggct    120
ccagggaagg gtctagagtg gtctcactg attgatccga gcggtggtca tacatactac     180
gcanactccg tgaagggccg gtccaccatc tcccgcaaca attccaagaa cacgctgtat    240
ctgcaaatga acagcctgcg tgccgaggac accgcggtat attactgtgg gaaaccggtt    300
ttttctgatt ggcctgcggt ggagtttgac tactggggtc agggaaccct ggtcaccgtc    360
tcgagc                                                              366
```

<210> SEQ ID NO 524
<211> LENGTH: 357
<212> TYPE: DNA
<213> ORGANISM: Homo sapiens

<400> SEQUENCE: 524

```
gaggtgcagc tgttggagtc tgggggaggc atggtacagc ctgggggtc actgcgtctc      60
tcctgtgcag ccccggatt cacctttgag catgagggga tggtgtgggt ccgccaggct    120
ccagggaagg gtctagagtg gtctcacat attggtgagg atggtcagtc tacatactac     180
gcagactccg tgaagggccg gttcaccatc tcccgcgaca attccaagaa cacgctgtat    240
ctgcaaatga acagcctgcg tgccgaggac accgcggtat attactgtgc gtccattccg    300
aaggcgggc cttcgtttga ctactgggt cagggaaccc tggtcaccgt ctcgagc        357
```

<210> SEQ ID NO 525
<211> LENGTH: 367
<212> TYPE: DNA
<213> ORGANISM: Homo sapiens

<400> SEQUENCE: 525

```
gaggtgcagc tgttggagtc tgggggaggc ttggtacagc ctgggggtc cctgcgtctc      60
tcctgtgcag cctccggatc cacctttgat cagtatgata tgtcgtgggt ccgccgggct    120
ccagggaagg gtctagagtg gtctcactg attgatccga gcggtggtca tacatactac     180
gcagactccg tgaagggccg gttcaccatc tcccgcaaca ataccaagaa cacgctgtat    240
ctgcaaatga acagcctgcg tgccgaggac accgcggtat attactgtgc gaaaccggtt    300
ttttctgatt ggcctgcggt ggagtttgac tactggggtc agggaaccct ggtcaccgtc    360
tcgagcc                                                             367
```

<210> SEQ ID NO 526
<211> LENGTH: 364
<212> TYPE: DNA
<213> ORGANISM: Homo sapiens

<400> SEQUENCE: 526

```
gaggtgcagc tgttggagtc tgggggaggc ttggtacagc ctgggggtc cctgcgtctc      60
```

```
tcctgtgcag cctccggatt cacctttgat tatgggaata tgttttgggt ccgccaggct      120
ccagggaagg gtctagagtg gatctcagct attagtggta gtggtggtag cacatactac      180
gcagactccg tgaagggccg gttcaccatc tcccgcgaca attccaagaa cacgctgtat      240
ctgcaaatga acagcctgcg tgccgaggac accgcggtat attactgtgc gaaagatatg      300
acgacggatt cgcctcctgg gtttgactac tggggtcagg gaaccctggt caccgtctcg      360
agcg                                                                   364
```

<210> SEQ ID NO 527
<211> LENGTH: 367
<212> TYPE: DNA
<213> ORGANISM: Homo sapiens
<220> FEATURE:
<221> NAME/KEY: misc_feature
<222> LOCATION: 367
<223> OTHER INFORMATION: n = A,T,C or G

<400> SEQUENCE: 527

```
gaggtgcagc tgttggagtc tgggggaggc ttggtacagc cggggggggtc cctgcgtctc      60 tcctgtgcag cctccggatt cacctttgcg aaggagacga tgagttgggt ccgccaggct      120
ccagggaagg gtctagagtg ggtctcatgg attagtcctc atggtgctca tacattctac      180
gcagactccg tgaagggcag gttcaccatc tcccgcgaca attccaagaa cacgctgtat      240
ctgcaaatga acagcctgcg tgccgaggac accgcggtat attactgcgc gaaacctcgg      300
ttttcgtatt atcctcgggt ttcatttgac taccggggtc agggaaccct ggtcacagtc      360 tcgagcn                                                                367
```

<210> SEQ ID NO 528
<211> LENGTH: 348
<212> TYPE: DNA
<213> ORGANISM: Homo sapiens

<400> SEQUENCE: 528

```
gaggtgcagc tgttggagtc tgggggaggc ttggtgcagc ctgggggtc cctgcgtctc        60 tcctgtgcag cctccggatt cacctttgat gcttataata tgttttggtt ccgccaggct      120
ccagggaagg gtccggagtg ggtctcagct attggtccgt cgggtcggga gacatactac      180
gcagactccg tgaagggccg gttcaccatc acccgcgaca attccaagaa cacgctgtat      240
ctgcaaatga acagcctgcg tgccgaggac accgcggtat attactgtgc gaaaaggtat      300
cctgattttg actactgggg tcagggaacc ctggtcaccg tctcgagc                    348
```

<210> SEQ ID NO 529
<211> LENGTH: 357
<212> TYPE: DNA
<213> ORGANISM: Homo sapiens

<400> SEQUENCE: 529

```
gaggtgcagc tgttggagtc tgggggaggc ttggtacagc ctggggggtc cctgcgtctc        60
tcctgtgcag cctccggatt cacctttgag catgagggga tggtgtgggt tcgccaggct      120
ccagggaagg gtctagagtg ggtctcacat attggtgagg atggtcagtc tacatactac      180
gcagactccg tgaagggccg gttcactatc tcccgcgaca attccaggaa cacgctgtat      240
ctgcaaatga acagcctgcg tgccgaggac accgcggtat attactgtgc gaacattccg      300 aaggcgggc cttcgtttga ctactggggt caggggaccc tggtcaccgt ctcgagc          357
```

<210> SEQ ID NO 530
<211> LENGTH: 369
<212> TYPE: DNA
<213> ORGANISM: Homo sapiens

<400> SEQUENCE: 530

```
gaggtgcagc tgttggagtc tgggggaggc ttggtacagc ctggggggtc cctgcgtctc      60
tcctgtgcag cctccggatt cacctttaag ttgtataata tggcgtgggt ccgccaggct     120
ccagggaagg gtctagagtg ggtctcattt attgctgctg ctggtcctga dacatactac     180
gcagactccg tgaagggccg gttcaccatc tcccgcgaca attccaagaa cacgctgtat     240
ctgcaaatga acagcctgcg tgccgaggac accgcggtat attactgtgc gaaattgggg     300
gatattagta gtattcctca gcatccgttt gactactggg gtcagggaac cctggtcacc     360
gtctcgagc                                                             369
```

<210> SEQ ID NO 531
<211> LENGTH: 357
<212> TYPE: DNA
<213> ORGANISM: Homo sapiens

<400> SEQUENCE: 531

```
gaggtgcagc tgttggagtc tgggggaggc ttggtacagc ctggggggtc cctgcgtctc      60
tcctgtgcag cctccggatt cacctttcg cgggagaata tgcattgggt ccgccaggct     120
ccagggaagg gtctggagtg ggtctcaggt attgggccga ggggtatgcc gacatactac     180
gcagactccg tgaagggccg gttcaccatc tcccgcgaca attccaagaa cacgctgtat     240
ctgcaaatga acagcctgcg tgccgaggac accgcggtat attactgtgc gaaaggtatg     300
aattcgcatg atgggttga ctactggggt cagggaaccc tggtcaccgt ctcgagc         357
```

<210> SEQ ID NO 532
<211> LENGTH: 363
<212> TYPE: DNA
<213> ORGANISM: Homo sapiens

<400> SEQUENCE: 532

```
gaggtgcagc tgttggagtc tgggggaggc ttggtacagc ctggggggtc cctgcgtctc      60
tcctgtgcag cctccggatt cacctttgat gcgtctgaga tggattgggt ccgccaggct     120
ccagggaagg gtctagagtg ggtctcagcg atttcgccta gtggttctgc tacatactac     180
gcagactccg tgaagggccg gttcaccatc tcccgcgaca attccaagaa cacgctgtat     240
ctgcaaatga acagcctgcg tgccgaggac accgcggtat attactgtgc gaaacgtatg     300
cttgcgaatt ctccttttggc ttttgactac tggggtcagg gaaccctggt caccgtctcg    360
agc                                                                   363
```

<210> SEQ ID NO 533
<211> LENGTH: 369
<212> TYPE: DNA
<213> ORGANISM: Homo sapiens

<400> SEQUENCE: 533

```
gaggtgcagc tgttggagtc tgggggaggc ttggtacagc ctggggggtc cctgcgtctc      60
tcctgtgcag cctccggatt caccttttct gcgtataata tggcttgggt ccgccaggct     120
ccagggaagg gtctagagtg ggtctcattt attgctcagt cgggtggtca tacatactac     180
gcagactccg tgaagggccg gttcaccatc tcccgcgaca attccaagaa cacgctgtat     240
```

```
ctgcaaatga acagcctgcg tgccgaggac accgcggtat attactgtgc gaaatttagt    300
catcctgatg aggagggtac gcagatgttt gactactggg gtcagggaac cctggtcacc    360
gtctcgagc                                                            369
```

<210> SEQ ID NO 534
<211> LENGTH: 360
<212> TYPE: DNA
<213> ORGANISM: Homo sapiens

<400> SEQUENCE: 534

```
gaggtgcagc tgttggagtc tgggggaggc ttggtacagc ctgggggtc cctgcgtctc     60 tcctgtgcag cctccggatt cacctttgcg gattatcaga tggcttgggt ccgccaggct   120
ccagggaagg gtctagagtg gtctcacgt attgatcgtg ggggttttca tacatactac    180
gcagactccg tgaagggccg gttcaccatc tcccgcgaca attccaagaa cacgctgtat   240
ctgcaaatga acagcctgcg tgccgaggac accgcggtat attactgtgc gaaaccgtct   300
tggcatgctg atcagtattt tgactactgg ggtcagggaa ccctggtcac cgtctcgagc   360
```

<210> SEQ ID NO 535
<211> LENGTH: 360
<212> TYPE: DNA
<213> ORGANISM: Homo sapiens

<400> SEQUENCE: 535

```
gaggtgcagc tgttggagtc tgggggaggc ttggtacagc ctgggggtc cctgcgtctc     60 tcctgtgcag cctccggatt cacctttaag gattataata tgatgtgggt ccgccaggct   120
ccagggaagg gtctagagtg gtctcagct attgctacga gtggtaggga gacatactac    180
gcagactccg tgaagggccg gttcaccatc tcccgcgaca attccaagaa cacgctgtat   240
ctgcaaatga acagcctgcg tgccgaggat accgcggtat attactgtgc gaaatttact   300
tttgggggga atcaggattt tgactactgg ggtcagggaa ccctggtcac cgtctcgagc   360
```

<210> SEQ ID NO 536
<211> LENGTH: 360
<212> TYPE: DNA
<213> ORGANISM: Homo sapiens

<400> SEQUENCE: 536

```
gaggtgcagc tgttggagtc tgggggaggc ttggtacagc ctgggggtc cctgcgtctc     60 tcctgtgcag cctccggatt caccttgct aagtataata tgtattgggt ccgccaggct    120
ccagggaagg gtctagagtg gtctcagcg attagtccta agggtcagca tacatactac    180
gcagactccg tgaagggccg gttcaccatc tcccgcgaca attccaagaa cacgctgtat   240
ctgcaaatga acagcctgcg tgccgaggac accgcggtat attactgtgc ggaagggatg   300
gggtcggatg ctattacttt tgactactgg ggtcagggaa ccctggtcac cgtctcgagc   360
```

<210> SEQ ID NO 537
<211> LENGTH: 369
<212> TYPE: DNA
<213> ORGANISM: Homo sapiens

<400> SEQUENCE: 537

```
gaggtgcagc tgttggagtc tgggggaggc ttggtacagc ctgggggtc cctgcgtctc     60 tcctgtgcag cctccggatt cacctttct gcgtataata tggcttgggt ccgccaggct    120
```

```
ccagggaagg gtctagagtg gtctccattt attgctcagt cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatttagt    300
catcctgatg aggagggtac gcagatgttt gactactggg gtcagggaac cctggtcacc    360
gtctcgagc                                                             369

<210> SEQ ID NO 538
<211> LENGTH: 366
<212> TYPE: DNA
<213> ORGANISM: Homo sapiens

<400> SEQUENCE: 538
gaggtgcagc tgttggagtc tgggggaggc ttggtacagc ctgggggtc cctgcgtctc       60 tcctgtgcag cctccggatt caccttgag aggtatgata tgttttgggt ccgccaggct     120
ccagggaagg gtctagagtg gtctcaggt atttctccta gggtaggga gacatactac      180 gcagactccg tgaagggccg gttcaccatc tcccgcgaca attccaagaa cacgctgtat    240
ctgcaaatga acagcctgcg tgccgaggat accgcggtat attactgtgc gaaagatatg    300
attaattatc atggtactcc ttcgtttgac tactggggtc agggaaccct ggtcaccgtc    360
tcgagc                                                               366

<210> SEQ ID NO 539
<211> LENGTH: 366
<212> TYPE: DNA
<213> ORGANISM: Homo sapiens
<220> FEATURE:
<221> NAME/KEY: misc_feature
<222> LOCATION: 90
<223> OTHER INFORMATION: n = A,T,C or G

<400> SEQUENCE: 539
gaggtgcagc tgttggagtc tgggggaggc ttggtacagc ctgggggtc cctgcgtctc       60 tcctgtgcag cctccggatt cacctttcn aattataata tggtttgggt ccgccaggct     120
ccagggaagg gtctggagtg gtctcatgg attagtgggg cgggtcattc gacatactac    180
gcagactccg tgaagggccg gttcaccatc tcccgcgaca attccaagaa cacgctgtat    240
ctgcaaatga acagcctgcg tgccgaggac accgcggtat attactgtgc gaaagatgtg    300
gatatggcgg gtaagcttaa tgttttgac tactggggtc agggaaccct ggtcaccgtc    360
tcgagc                                                               366

<210> SEQ ID NO 540
<211> LENGTH: 366
<212> TYPE: DNA
<213> ORGANISM: Homo sapiens

<400> SEQUENCE: 540
gaggtgcagc tgttggagtc tgggggaggc ttggtacagc ctgggggtc cctgcgtctc       60 tcctgtgcag cctccggatt cacctttaag cagtataata tgtattgggt ccgccaggct    120
ccagggaagg gtctagagtg gtctcattt attagtccgt ctggtggtga gacatactac     180
gcagactccg tgaagggccg gttcaccacc tcccgcgaca attccaagaa cacgctgtat    240
ctgcaaatga acagcctgcg tgccgaggac accgcggtat attactgtgc gaaagatgtg    300
gatatggcgg gtaagcttaa tgttttgac tactggggtc agggaaccct ggtcaccgtc    360
tcgagc                                                               366
```

<210> SEQ ID NO 541
<211> LENGTH: 360
<212> TYPE: DNA
<213> ORGANISM: Homo sapiens

<400> SEQUENCE: 541

```
gaggtgcagc tgttggagtc tgggggaggc ttggtacagc ctgggggtc cctgcgtctc      60
tcctgtgcag cctccggatt cacctttgcg gattatcaga tggcttgggt ccgccaggct    120
ccagggaagg gtctagagtg ggtctcacgt attgatcgtg ggggttttca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaccgtct    300
tggcatgctg atcagtattt tgactactgg ggtcaggaa ccctggtcac cgtctcgagc    360
```

<210> SEQ ID NO 542
<211> LENGTH: 360
<212> TYPE: DNA
<213> ORGANISM: Homo sapiens

<400> SEQUENCE: 542

```
gaggtgcagc tgttggagtc tgggggaggc ttggtacagc ctgggggtc cctgcgtctc      60
acctgtgcag cctccggatt cacctttgat gatgtgaata tgacttgggt ccgccaggct    120
ccagggaagg gtctagagtg ggtctcagcg attggtcctt cgggtactga gacatactac    180
gcagactccg tgaagggccg gttcaccatc tcccgtgaca attccaagaa cacgctgtat    240
ctgcaaatga acagcctgcg tgccgaggac accgcggtat attactgtgc gaaacatagt    300
aagactggta gtgctatgtt tgactactgg ggtcaggaa ccctggtcac cgtctcgagc    360
```

<210> SEQ ID NO 543
<211> LENGTH: 357
<212> TYPE: DNA
<213> ORGANISM: Homo sapiens

<400> SEQUENCE: 543

```
gaggtgcagc tgttggagtc tgggggaggc ttggtacagc ctgggggtc cctgcgtctc      60
tcctgtgcag cctccggatt cacctttggt aatggtaata tggtttgggt ccgccaggct    120
ccagggaagg gtctagagtg ggtctcacat attgatgagt atggtacgaa tacatactac    180
gcagactccg tgaagggccg gttcaccatc tcccgcgaca attccaagaa cacgctgtat    240
ctgcaaatga acagcctgcg tgccgaggac accgcggtat attactgtgc gaaacctcgt    300
aatgatcggc tgggtttga ctactggggt cagggaaccc tggtcaccgt ctcgagc       357
```

<210> SEQ ID NO 544
<211> LENGTH: 357
<212> TYPE: DNA
<213> ORGANISM: Homo sapiens

<400> SEQUENCE: 544

```
gaggtgcagc tgttggagtc tgggggaggc ttggtacagc ctgggggtc cctgcgtctc      60
tcctgtgcag cctccggatt cacctttcg cgggagaata tgcattgggt ccgccaggct    120
ccagggaagg gtctggagtg ggtctcaggt attgggccga ggggtatgcc gacatactac    180
gcagactccg tgaagggccg gttcaccatc tcccgcgaca attccaagaa cacgctgtat    240
ctgcaaatga acagcctgcg tgccgaggac accgcggtat attactgtgc gaaaggtatg    300
```

```
aattcgcatg atgggtttga ctactgggt  cagggaaccc  tggtcaccgt  ctcgagc      357
```

<210> SEQ ID NO 545
<211> LENGTH: 351
<212> TYPE: DNA
<213> ORGANISM: Homo sapiens

<400> SEQUENCE: 545

```
gaggtgcagc tgttggagtc tgggggaggc ttggtacagc ctgggggtc  cctgcgtctc   60
tcctgtgcag cctccggatt cacctttaag gggagtaata tgggttgggt ccgccaggct  120
ccagggaagg gtctagagtg gtctcactg  attgatgggc gtggtcagca tacatactac  180
gcagactccg tgaagggccg gttcaccatc tcccgcgaca attccaagaa cacgctgtat  240
ctgcaaatga acagcctgcg tgccgaggac accgcggtat attactgtgc gaaacctagt  300
gtgagggagt ttgactacag gggtcaggga accctggtca ccgtctcgag c            351
```

<210> SEQ ID NO 546
<211> LENGTH: 363
<212> TYPE: DNA
<213> ORGANISM: Homo sapiens

<400> SEQUENCE: 546

```
gaggtgcagc tgttggagtc tgggggaggc ttggtacagc ctgggggtc  cctgcgtctc   60
tcctgtgcag cctccggatt cacctttcg  cgggagaata tgcattgggt ccgccaggct  120
ccagggaagg gtctggagtg gtctcaggt  attgggccga ggggtatgcc gacatactac  180
gcagactccg tgaagggccg gttcaccatc tcccgcgaca attccaagaa cacgctgtat  240
ctgcaaatga acagcctgcg tgccgaggac accgcggtat attactgtgc gaaacgtatg  300
cttgcgaatt tcctttggc  ttttgactac tggggtcagg gaaccctggt caccgtctcg  360
agc                                                                  363
```

<210> SEQ ID NO 547
<211> LENGTH: 348
<212> TYPE: DNA
<213> ORGANISM: Homo sapiens

<400> SEQUENCE: 547

```
gaggtgcagc tgttggagtc tgggggaggc ttggtacagc ctgggggtc  cctgcgtctc   60
tcctgtacag cctccggatt cacctttcg  gagagtacta tgaattgggt ccgccaggct  120
ccagggaagg gtctagagtg gtctcagtt  attacgcgc  agggtgggga tacatactac  180
gcagactccg tgaagggccg gttcaccatc tcccgcgaca attccaagaa cacgctgtat  240
ctgcaaatga acagcctgcg tgccgaggac accgcggtat attactgtgc gaaacctgat  300
gttttgtttg actactgggg tcaggaacc  ctggtcaccg tctcgagc                348
```

<210> SEQ ID NO 548
<211> LENGTH: 351
<212> TYPE: DNA
<213> ORGANISM: Homo sapiens

<400> SEQUENCE: 548

```
gaggtgcagc tgttggagtc tgggggaggc ttggtacagc ctgggggtc  cctgcgtctc   60
tcctgtgcag cctccggatt cacctttgag gagtataata tgttgtgggt ccgccaggct  120
ccagggaagg gtctggagtg gtctcaggg  attgggcctt cgggtaggga gacatactac  180
gcagactccg tgaagggccg gttcaccatc tcccgcgaca attccaagaa cacgctgtat  240
```

```
ctgcaaatga acagcctgcg tgccgaggat accgcggtat attactgtgc gaaaggttct    300
attacgctgt tgactactg gggtcaggga accctggtca ccgtctcgag c              351
```

<210> SEQ ID NO 549
<211> LENGTH: 372
<212> TYPE: DNA
<213> ORGANISM: Homo sapiens

<400> SEQUENCE: 549

```
gaggtgcagc tgttggagtc tgggggaggc ttggtacagc ctgggggtc cctgcgtctc     60 tcctgtgcag cctccggatt cacctttagt ggttataata tgtattgggt ccgccaggct   120
ccagggaagg gtctagagtg ggtctcagcg attgatgcgt atggtacgca tacatactac   180
gcagactccg tgaagggccg gttcaccatc tcccgcgaca attccaagaa cacgctgtat   240
ctgcaaatga acagcctgcg tgccgaggac accgcggtat attactgtgc ggaagggttg   300
cagacgtctg atcatggtga gaggatttct tttgactact ggggtcaggg aaccctggtc   360
accgtctcga gc                                                        372
```

<210> SEQ ID NO 550
<211> LENGTH: 366
<212> TYPE: DNA
<213> ORGANISM: Homo sapiens

<400> SEQUENCE: 550

```
gaggtgcagc tgttggagtc tgggggaggc ttggtacagc ctgggggtc cctgcgtctc     60 tcctgtgcag cctccggatt cacctttgat cagtatgata tgtcgtgggt ccgccaggct   120
ccagggaagg gtctagagtg ggtctcactg attgatccga gcggtggtca tacatactac   180
gcagactccg tgaagggccg gttcaccatc tcccgcaaca attccaagaa cacgctgtat   240
ctgcaaatga acagcctgcg tgccgaggac accgcggtat attactgtgc gaaaccggtt   300
ttttctgatt ggcctgcggt ggagtttgac tactggggtc agggaaccct ggtcaccgtc   360
tcgagc                                                               366
```

<210> SEQ ID NO 551
<211> LENGTH: 366
<212> TYPE: DNA
<213> ORGANISM: Homo sapiens

<400> SEQUENCE: 551

```
gaggtgcagc tgttggagtc tgggggaggc ttggtacagc ctgggggtc cctgcgtctc     60 tcctgtgcag cctccggatt cacctttgat cagtatgata tgtcgtgggt ccgccaggct   120
ccagggaagg gtctagagtg ggtctcactg attgatccga gcggtggtca tacatactac   180
gcggactccg tgaagggccg gttcaccatc tcccgcaaca attccaagaa cacgctgtat   240
ctgcaaatga acagcctgcg tgccgaggac accgcggtat attactgtgc gaaaccggtt   300
ttttctgatt ggcctgcggt ggagtttgac tactggggtc agggaaccct ggtcaccgtc   360
tcgagc                                                               366
```

<210> SEQ ID NO 552
<211> LENGTH: 360
<212> TYPE: DNA
<213> ORGANISM: Homo sapiens

<400> SEQUENCE: 552

```
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcaatg attgatgttc ctggtctgca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcgagc   360
```

<210> SEQ ID NO 553
<211> LENGTH: 360
<212> TYPE: DNA
<213> ORGANISM: Homo sapiens
<220> FEATURE:
<221> NAME/KEY: misc_feature
<222> LOCATION: 184, 312
<223> OTHER INFORMATION: n = A,T,C or G

<400> SEQUENCE: 553

```
gaggtgcagc tgttggagtc tgggggaggc ttggtacagc ctggggggtc cctgcgtctc    60
tcctgtgcag cctccggatt cacctttgag tggtattgga tgggttgggt ccgccaggct   120
ccagggaagg gtctagagtg ggtctcagct atcagtggta gtggtggtag cacatactac   180
gcanactccg tgaagggccg gttcaccatc tcccgcgaca attccaagaa cacgctgtat   240
ctgcaaatga acagcctgcg tgccgaggac gccgcggtat attactgtgc gaaagttaag   300 ttggggggg gncctaattt tggctaccgg ggccagggaa ccctggtcac cgtctcgagc   360
```

<210> SEQ ID NO 554
<211> LENGTH: 360
<212> TYPE: DNA
<213> ORGANISM: Homo sapiens

<400> SEQUENCE: 554

```
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcattt attgatcctc cgagtgttca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcgagc   360
```

<210> SEQ ID NO 555
<211> LENGTH: 360
<212> TYPE: DNA
<213> ORGANISM: Homo sapiens
<220> FEATURE:
<221> NAME/KEY: misc_feature
<222> LOCATION: 184
<223> OTHER INFORMATION: n = A,T,C or G

<400> SEQUENCE: 555

```
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcaatg attgatgttg gtggttctca tacatactac   180
gcanactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcaagc   360
```

<210> SEQ ID NO 556
<211> LENGTH: 360
<212> TYPE: DNA
<213> ORGANISM: Homo sapiens
<220> FEATURE:
<221> NAME/KEY: misc_feature
<222> LOCATION: 184
<223> OTHER INFORMATION: n = A,T,C or G

<400> SEQUENCE: 556
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcaatg attgatactg ggggtgttca tacatactac   180
gcanactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcgagc   360

<210> SEQ ID NO 557
<211> LENGTH: 360
<212> TYPE: DNA
<213> ORGANISM: Homo sapiens

<400> SEQUENCE: 557
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcaatg attgatgttc ctggtcgtca tacatactac   180
gcagactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcgagc   360

<210> SEQ ID NO 558
<211> LENGTH: 360
<212> TYPE: DNA
<213> ORGANISM: Homo sapiens

<400> SEQUENCE: 558
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctagagtg ggtctcaatg attgcgcatg ctggtcctga catactac   180 gcagactccg tgaagggccg gttcaccatc tcccgcgaca attccaagaa cacgctgtat   240
ctgcaaatga acagcctgcg tgccgaggac accgcggtat attactgtgc gaaaatttct   300
cagtttgggt caaatgcgtt tgactactgg ggtcagggaa ccctggtcac cgtctcgagc   360

<210> SEQ ID NO 559
<211> LENGTH: 360
<212> TYPE: DNA
<213> ORGANISM: Homo sapiens

<400> SEQUENCE: 559
gaggtgcagc tgttggagtc tgggggaggc ttggtacagc ctggggggtc cctgcgtctc    60
tcctgtgcag cctccggatt cacctttact aggtatagta tggggtgggt ccgccaggct   120
ccagggaagg gtctggagtg ggtctcaatg attgatactc ggggtgttcg tacatactac   180

```
gcagactccg tgaagggccg gttcaccatc tcccgcgaca attccaagaa cacgctgtat    240
ctgcaaatga acagcctgcg tgccgaggac accgcggtat attactgtgc gaaaatttct    300
cagtttgggt caaatgcgtt tgactactgg ggtcagggaa ccctggtcac cgtctcgagc    360
```

<210> SEQ ID NO 560
<211> LENGTH: 360
<212> TYPE: DNA
<213> ORGANISM: Homo sapiens

<400> SEQUENCE: 560

```
gaggtgcagc tgttggagtc tggggggaggc ttggtacagc ctgggggggtc cctgcgtctc    60 tcctgtgcag cctccggatt cacctttact aggtatagta tggggtgggt ccgccaggct   120
ccagggaagg gtctggagtg ggtctcaatg attgatgtgc tggtaatca tacatactac    180 gcagactccg tgaagggccg gttcaccatc tcccgcgaca attccaagaa cacgctgtat    240
ctgcaaatga acagcctgcg tgccgaggac accgcggtat attactgtgc gaaaatttct    300
cagtttgggt caaatgcgtt tgactactgg ggtcagggaa ccctggtcac cgtctcgagc    360
```

<210> SEQ ID NO 561
<211> LENGTH: 360
<212> TYPE: DNA
<213> ORGANISM: Homo sapiens

<400> SEQUENCE: 561

```
gaggtgcagc tgttggagtc tggggggaggc ttggtacagc ctgggggggtc cctgcgtctc    60 tcctgtgcag cctccggatt cacctttact aggtatagta tggggtgggt ccgccaggct   120
ccagggaagg gtctagagtg ggtctcaatg attgatgttg gtggtcggca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatttct    300
cagtttgggc caaatgcgtt tgactactgg ggtcagggaa ccctggtcac cgtctcgagc    360
```

<210> SEQ ID NO 562
<211> LENGTH: 354
<212> TYPE: DNA
<213> ORGANISM: Homo sapiens

<400> SEQUENCE: 562

```
gaggtgcagc tgttggagtc tggggggaggc tcggtacagc ctgggggggtc cctgcgtctc    60 tcctgtgcag cctccggatt cacctttact aggtatagta tggggtgggt ccgccaggct   120
ccagggaagg gtctagagtg ggtctcacgg attgattctt atggtcgtgg tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagtgcgt    300
tctccttata cgtttgacta ctggggtcag ggaaccctgg tcaccgtctc gagc          354
```

<210> SEQ ID NO 563
<211> LENGTH: 351
<212> TYPE: DNA
<213> ORGANISM: Homo sapiens

<400> SEQUENCE: 563

```
gaggtgcagc tgttggagtc tggggggaggc ttggtacagc ctgggggggtc cctgcgtctc    60 tcctgtgcag cctccggatt caccttttcg ggttataata tgggttgggt ccgccaggct   120
ccagggaagg gtctagagtg ggtctcaact atttcgactc agggttatca tacatactac    180
```

```
gcagactccg tgaagggccg gttcaccatc tcccgcgaca attccaagaa cacgctgtat    240
ctgcaaatga acagcctgcg tgccgaggac accgcggtat attactgtgc gaaagcgttt    300
actagtgatt ttgactactg gggtcaggga accctggtca ccgtctcgag c             351
```

<210> SEQ ID NO 564
<211> LENGTH: 357
<212> TYPE: DNA
<213> ORGANISM: Homo sapiens

<400> SEQUENCE: 564

```
gaggtgcagc tgttggagtc tgggggaggc ttggtacagc ctgggggtc cctgcgtctc     60 tcctgtgcag cctccggatt caccttttcg ggttataata tgtattgggt ccgccaggct   120
ccagggaagg gtctagagtg gtctcaggg atttctggtc cggtcttga gacatactac    180 gcagactccg tgaagggccg gttcaccatc tcccgcgaca attccaagaa cacgctgtat    240
ctgcaaatga acagcctgcg tgccgaggac accgcggtat attactgtgc gcaaggtatg    300
tcgaagacgt ctacgtttga ctactggggt cagggaaccc tggtcaccgt ctcgagc      357
```

<210> SEQ ID NO 565
<211> LENGTH: 351
<212> TYPE: DNA
<213> ORGANISM: Homo sapiens

<400> SEQUENCE: 565

```
gaggtgcagc tgttggagtc tgggggaggc ttggtacagc ctgggggtc cctgcgtctc     60 tcctgtgcag cctccggatt cacctttact gagtattata tggagtgggt ccgccaggct   120
ccagggaagg gtctagagtg gtctcaagt attgatccgg atggttctct tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatccg    300
cgtgagaagt ttgactactg gggtcaggga accctggtca ccgtctcgag c             351
```

<210> SEQ ID NO 566
<211> LENGTH: 360
<212> TYPE: DNA
<213> ORGANISM: Homo sapiens

<400> SEQUENCE: 566

```
gaggtgcagc tgttggagtc tgggggaggc ttggtacagc ctgggggtc cctgcgtctc     60 tcctgtgcag cctccggatt cacctttgat aagtatcaga tgggttgggt ccgccaggct   120
ccagggaagg gtctagagtg gtctcatttt attgattcga atggtcatca tacatactac    180
gcagactccg tgaagggccg gttcaccatc tcccgcgaca attccaagaa cacgctgtat    240
ctgcaaatga acagcctgcg tgccgaggac accgcggtat attactgtgc gaactgtcg     300 gttcaggggt cgaatctgtt tgactactgg ggtcaggaa ccctggtcac cgtctcgagc   360
```

<210> SEQ ID NO 567
<211> LENGTH: 360
<212> TYPE: DNA
<213> ORGANISM: Homo sapiens

<400> SEQUENCE: 567

```
gaggtgcagc tgttggagtc tgggggaggc ttggtacagc ctgggggtc cctgcgtctc     60 tcctgtgcag cctccggatt cacctttgtg cattatacga tgggttgggt ccgccaggct   120
```

```
ccagggaagg gtctagagtg ggtctcatgg attcattctg atggtgttca tacatactac    180
gcagactccg tgaagggccg gttcaccatc tcccgcgaca attccaagaa cacgctgtat    240
ctgcaaatga acagcctgcg tgccgaggat accgcggtat attactgtgc gaaatttact    300
tggggtgaga agaagacttt tgactactgg ggtcagggaa ccctggtcac cgtctcgagc    360
```

<210> SEQ ID NO 568
<211> LENGTH: 360
<212> TYPE: DNA
<213> ORGANISM: Homo sapiens

<400> SEQUENCE: 568

```
gaggtgcagc tgttggagtc tgggggaggc ttggtacagc ctggggggtc cctgcgtctc     60
tcctgtgcag cctccggatt cacctttatg gggtatgata tgcattgggt ccgccaggct    120
ccagggaagg gtctagagtg gtctcaggt atttctgcta agggtactga  gacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggagt    300
tctggttctg atgggctgtt tgactactgg ggtcagggaa ccctggtcac cgtctcgagc    360
```

<210> SEQ ID NO 569
<211> LENGTH: 372
<212> TYPE: DNA
<213> ORGANISM: Homo sapiens

<400> SEQUENCE: 569

```
gaggtgcagc tgttggagtc tgggggaggc ttggtacagc ctggggggtc cctgcgtctc     60
tcctgtgcag cctccggatt cacctttcct gtttataata tggcgtgggt ccgccaggct    120
ccagggaagg gtctagagtg gtctcatttt attgcggta atggtcagca gacatactac    180
gcagactccg tgaagggccg gttcaccatc tcccgcgaca attccaagaa cacgctgtat    240
ctgcaaatga acagcctgcg tgccgaggac accgcggtat attactgtgc gaaatttgcg    300
tcgaaggtgt cgccgatgtc gttgactgat tttgactact ggggtcaggg aaccctggtc    360
accgtctcga gc                                                         372
```

<210> SEQ ID NO 570
<211> LENGTH: 372
<212> TYPE: DNA
<213> ORGANISM: Homo sapiens

<400> SEQUENCE: 570

```
gaggtgcagc tgttggagtc tgggggaggc ttggtacagc ctggggggtc cctgcgtctc     60
tcctgtgcag cctccggatt cacctttgtg cagtataata tgcactgggt ccgccaggct    120
ccagggaagg gtcttgagtg gtctcaggg atttcttcgg gtggtatgcg tacatactac    180
gcagactccg tgaagggccg gttcaccatc tcccgcgaca attccaagaa cacgctgtat    240
ctgcaaatga acagcctgcg tgccgaggac accgcggtat attactgtgc gaaagggatt    300
cgggatagta cgcttccgag gggtactttg tttgactact ggggtcaggg aaccctggtc    360
accgtctcga gc                                                         372
```

<210> SEQ ID NO 571
<211> LENGTH: 363
<212> TYPE: DNA
<213> ORGANISM: Homo sapiens

<400> SEQUENCE: 571

```
gaggtgcagc tgttggagtc tgggggaggc ttggtacagc ctgggggtc cctgcgtctc      60 tcctgtgcag cctccgggtt cacctttgag acttatagta tgcattgggt ccgccaggct    120
ccagggaagg gtctagagtg ggtctcatcg atttctttgc ctggttcgcg gacatactac    180
gcagactccg tgaagggccg gttcaccatc tcccgcgaca attccaagaa cacgctgtat    240
ctgcaaatga acagcctgcg tgccgaggac accgcggtat attactgtgc gaaacattcg    300
aagagttctc atcgtcagtc ttttgactac tggggtcagg gaaccctggt caccgtctcg    360
agc                                                                   363

<210> SEQ ID NO 572
<211> LENGTH: 366
<212> TYPE: DNA
<213> ORGANISM: Homo sapiens

<400> SEQUENCE: 572
gaggtgcagc tgttggagtc tgggggaggc ttggtacagc ctgggggtc cctgcgtctc      60 tcctgtgcag cctccggatt cacctttaat cagtatgata tgcattgggt ccgccaggct    120
ccagggaagg gtctagagtg ggtctcaggg atttctttta gtggttatga gacatactac    180
gcagactccg tgaagggccg gtttaccatc tcccgcgaca attccaagaa cacgctgtat    240
ctgcaaatga acagcctgcg tgccgaggac accgcggtat attactgtgc gaaaggtagg    300
gggcctgcgc cgatgcgttc gcttttttgac tactggggtc agggaaccct ggtcaccgtc    360
tcgagc                                                                366

<210> SEQ ID NO 573
<211> LENGTH: 360
<212> TYPE: DNA
<213> ORGANISM: Homo sapiens

<400> SEQUENCE: 573
gaggtgcagc tgttggagtc tgggggaggc ttggtacagc ctgggggtc cctgcgtctc      60 tcctgtgcag cctccggatt cacctttgtg gattatccga tggtgtgggt ccgccaggct    120
ccagggaagg gtctagagtg ggtctcacat attactagta tgggtgagtc tacatactac    180
gcagactccg tgaagggccg gttcaccatc tcccgcgaca attccaagaa catgctgtat    240
ctgcaaatga acagcctgcg tgccgaggac accgcggtat attactgtgc gaaattgccg    300
acgcattttc cgattaggtt tgactactgg ggtcagggaa ccctggtcac cgtctcgagc    360

<210> SEQ ID NO 574
<211> LENGTH: 348
<212> TYPE: DNA
<213> ORGANISM: Homo sapiens

<400> SEQUENCE: 574
gaggtgcagc tgttggagtc tgggggaggc ttggtacagc ctgggggtc cctgcgtctc      60 tcctgtgcag cctccggatt cacctttaag cagtataata tgtattgggt ccgccaggct    120
ccagggaagg gtctagagtg ggtctcattt attagtccgt ctggtggtga gacatactac    180
gcagactccg tgaagggccg gttcaccatc tcccgcgaca attccaagaa cacgctgtat    240
ctgcaaatga acagcctgcg tgccgaggac accgcggtat attactgtgc gaaatcgatt    300 aagcctttg actactgggg tcagggaacc ctggtcaccg tctcgagc                  348

<210> SEQ ID NO 575
```

```
<211> LENGTH: 360
<212> TYPE: DNA
<213> ORGANISM: Homo sapiens

<400> SEQUENCE: 575
gaggtgcagc tgttggagtc tgggggaggc ttggtacagc ctgggggtc cctgcgtctc      60 tcctgtgcag cctccggatt cacctttagt atgtattcga tggcttgggt ccgccaggct     120
ccagggaagg gtctagagtg gtctcatttt attgattttg atggtcttca tacatactac    180
gcagactccg tgaagggccg gttcaccatc tcccgcgaca attccaagaa cacgctgtat     240
ctgcaaatga acagcctgcg tgccgaggac accgcggtat attactgtgc gaaattttct    300
acgtctacga tggctctgtt tgactactgg ggtcaggaa ccctggtcac cgtctcgagc     360

<210> SEQ ID NO 576
<211> LENGTH: 366
<212> TYPE: DNA
<213> ORGANISM: Homo sapiens

<400> SEQUENCE: 576
gaggtgcagc tgttggagtc tgggggaggc ttggtacggc ctgggggtc cctgcgtctc      60 tcctgtgcag cctccggatt cacctttcct gagtataata tgcattgggt ccgccaggct     120
ccagggaagg gcctgagtg gtctcagcg attggtactg ctggtggtag tacatactac    180
gcagactccg tgaagggccg gttcaccatc tcccgcgaca attccaagaa catgctgtat     240
ctgcaaatga acagcctgcg tgccgaggac accgcggtat attactgtgc gaaagggtat    300
cgtcctcgga ctggtagtat gttgtttgac tactggggtc agggaaccct ggtcaccgtc    360
tcgagc                                                                366

<210> SEQ ID NO 577
<211> LENGTH: 360
<212> TYPE: DNA
<213> ORGANISM: Homo sapiens

<400> SEQUENCE: 577
gaggtgcagc tgttggagtc tgggggaggc ttggtacagc ctgggggtc cctgcgtctc      60 tcctgtgcag cctccggatt cacctttgct aagtataata tgtattgggt ccgccaggct     120
ccagggaagg gtctagagtg gtctcagcg attagtccta aggtcagca gacatactac    180 gcagactccg tgaagggccg gttcaccatc tcccgcgaca attccaagaa cacgctgtat     240
ctgcaaatga acagcctgcg tgccgaggac accgcggtat attactgtgc ggaagggatg    300
gggtcggatg ctattacttt tgactactgg ggtcagggaa ccctggtcac cgtctcgagc    360

<210> SEQ ID NO 578
<211> LENGTH: 366
<212> TYPE: DNA
<213> ORGANISM: Homo sapiens

<400> SEQUENCE: 578
gaggtgcagc tgttggagtc tgggggaggc ttggtacagc ctgggggtc cctgcgtctc      60 tcctgtgcag cctccggatt cacctttgcg gattatgata tggcttgggt ccgccaggct     120
ccagggaagg gtctagagtg gtctcatttt attgatcgta aggtcatca tacatactac    180 gcagactccg tgaagggccg gttcaccatc tcccgcgaca attccaagaa cacgctgtat     240
ctgcaaatga acagcctgcg tgccgaggac accgcggtat attactgtgc gaaaacgact    300
gatattcagc gtttgaattc tgcgtttgac tactggggtc agggaaccct ggtcaccgtc    360
```

```
<210> SEQ ID NO 579
<211> LENGTH: 357
<212> TYPE: DNA
<213> ORGANISM: Homo sapiens

<400> SEQUENCE: 579
gaggtgcagc tgttggagtc tgggggaggc ttggtacagc ctgggggtc cctacgtctc    60 tcctgtgcag cctccggatt cacctttggg aatggggtga tggcgtgggt ccgccaggct   120
ccagggaagg gtctagagtg gtctcacat attaatgaga atggtggtgc tacatactac    180
gcagactccg tgaagggccg gttcaccatc tcccgcgaca attccaagaa cacgctgtat   240
ctgcaaatga acagcctgcg tgccgaggac accgcggtat attactgtgc gaaaccttct   300
attgagtcgc tattttttga ctactgggt cagggaaccc tggtcaccgt ctcgagc      357

<210> SEQ ID NO 580
<211> LENGTH: 357
<212> TYPE: DNA
<213> ORGANISM: Homo sapiens

<400> SEQUENCE: 580
gaggtgcagc tgttggagtc tgggggaggc ttggtacagc ctgggggtc cctgcgtctc    60 tcctgtgcag cctccggatt cacctttgcg catgagccga tggtgtgggt ccgccaggct   120
ccagggaagg gtctagagtg gtctcacat attgatcgtg ttggtcagga tacatactac    180
gcagactccg tgaagggccg gttcaccatc tcccgcgaca attccaagaa cacgctgtat   240
ctgcaaatga acagcctgcg tgccgaggac accgcggtat attactgtgc gaaacttcct   300 aagaggggc ctaggtttga ctactgggt cagggaaccc tggtcaccgt ctcgagc       357

<210> SEQ ID NO 581
<211> LENGTH: 363
<212> TYPE: DNA
<213> ORGANISM: Homo sapiens

<400> SEQUENCE: 581
gaggtgcagc tgttggagtc tgggggaggc ttggtacagc ctgggggtc cctgcgtctc    60 tcctgtgcag cctccggatt cacctttgag gagtcggtta tggggtgggt ccgccaggct   120
ccagggaagg gtctggagtg gtctcagcg attagtcctg ggggtagtga gacatactac    180
gcagactccg tgaagggccg gttcaccatc tcccgcgaca attccaagaa cacgctgtat   240
ctgcaaatga acagcctgcg tgccgaggac gccgcggtat attactgtgc gaaacgtacg   300
gggcctcctg ggtctacggt ttttgactac tggggtcagg gaaccctggt caccgtctcg   360
agc                                                                 363

<210> SEQ ID NO 582
<211> LENGTH: 348
<212> TYPE: DNA
<213> ORGANISM: Homo sapiens

<400> SEQUENCE: 582
gaggtgcagc tgttggagtc tgggggaggc ttggtacagc ctgggggtc cctgcgtctc    60 tcctgtgcag cctccggatt cacctttggt gatgagccga tgcattgggt ccgccaggct   120
ccagggaagg gtctagagtg gtctcaggt attggtaagg agggtcagcc gacatactac   180
```

```
gcagactccg tgaagggccg gttcaccatc tcccgcgaca attccaagaa cacgctgtat    240
ctgcaaatga acagcctgcg tgccgaggac accgcggtat attactgtgc gaaattgggg    300
gggccttttg actactgggg tcagggaacc ctggtcaccg tctcgagc                 348
```

<210> SEQ ID NO 583
<211> LENGTH: 363
<212> TYPE: DNA
<213> ORGANISM: Homo sapiens

<400> SEQUENCE: 583

```
gaggtgcagc tgttggagtc tgggggaggc ttggtacagc ctgggggggtc cctgcgtctc    60 tcctgtgcag cctccggatt cacctttgat tatgggaata tgttttgggt ccgccaggct   120
ccagggaagg gtctagagtg ggtctcagct attagtggta gtggtggtag cacatactac   180
gcagactccg tgaagggccg gttcaccatc tcccgcgaca attccaagaa cacgctgtat   240
ctgcaaatga acagcctgcg tgccgaggac accgcggtat attactgtgc gaaagatatg   300
acgacggatt cgcctcctgg gtttgactac tggggtcagg gaaccctggt caccgtctcg   360
agc                                                                 363
```

<210> SEQ ID NO 584
<211> LENGTH: 366
<212> TYPE: DNA
<213> ORGANISM: Homo sapiens

<400> SEQUENCE: 584

```
gaggtgcagc tgttggagtc tgggggaggc ttggtacagc ctgggggggtc cctgcgtctc    60 tcctgtgcag cctccggatt cacctttgcg aaggagacga tgagttgggt ccgccaggct   120
ccagggaagg gtctagagtg ggtctcatgg attagtcctc atggtgctct tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacctcgg   300
ttttcgtatt atcctcgggt ttcgtttgac tactggggtc agggaaccct ggtcaccgtc   360
tcgagc                                                              366
```

<210> SEQ ID NO 585
<211> LENGTH: 357
<212> TYPE: DNA
<213> ORGANISM: Homo sapiens

<400> SEQUENCE: 585

```
gaggtgcagc tgttggagtc tgggggaggc ttggtacagc ctgggggggtc cctgcgtctc    60 tcctgtgcag cctccggatt cacctttggt aatggtaata tggtttgggt ccgccaggct   120
ccagggaagg gtctagagtg gtctcacat attgatgagt atggtacgaa tacatactac    180
gcagactccg tgaagggccg gttcaccatc tcccgcgaca attccaagaa cacgctgtat   240
ctgcaaatga acagcctgcg tgccgaggac accgcggtat attactgtgc gaaacctcgt   300
aatgatcggc tgggtttga ctactggggt cagggaaccc tggtcaccgt ctcgagc       357
```

<210> SEQ ID NO 586
<211> LENGTH: 357
<212> TYPE: DNA
<213> ORGANISM: Homo sapiens
<220> FEATURE:
<221> NAME/KEY: misc_feature
<222> LOCATION: 159
<223> OTHER INFORMATION: n = A,T,C or G

<400> SEQUENCE: 586

```
gaggtgcagc tgttggagtc tgggggaggc ttggtacagc ctggggggtc cctgcgtctc    60
tcctgtgcag cctccggatt cacctttggt aatggtaata tggtttgggt ccgccaggct   120
ccagggaagg gtctagagtg ggtctcacat attgatgant atggtacgaa tacatactac   180
gcagactccg tgaagggccg gttcaccatc tcccgcgaca attccaagaa cacgctgtat   240
ctgcaaatga acagcctgcg tgccggggac accgcggtat attactgtgc gaaacctcgt   300
aatgatcggc tgggtttga ctactgggt cagggaaccc tggtcaccgt ctcgagc        357
```

<210> SEQ ID NO 587
<211> LENGTH: 372
<212> TYPE: DNA
<213> ORGANISM: Homo sapiens

<400> SEQUENCE: 587

```
gaggtgcagc tgttggagtc tgggggaggc ttggtacagc ctggggggtc cctgcgtctc    60
tcctgtgcag cctccggatt cacctttgcg ggtcaggata tgcgttgggt ccgccaggct   120
ccagggaagg gtctagagtg ggtctcatcg attccgtcgt ctggttttaa tacatactac   180
gcagactccg tgaagggccg gttcaccatc tcccgcgaca attccaagaa cacgctgtat   240
ctgcaaatga acagcctgcg tgccgaggat accgcggtat attactgtgc gaaacgtgct   300
aaggatcgta gtgtgtcgca gatgccgtat tttgactact ggggtcaggg aaccctggtc   360
accgtctcga gc                                                        372
```

<210> SEQ ID NO 588
<211> LENGTH: 360
<212> TYPE: DNA
<213> ORGANISM: Homo sapiens

<400> SEQUENCE: 588

```
gaggtgcagc tgttggagtc tgggggaggc ttggtacagc ctggggggtc cctgcgtctc    60
tcctgtgcag cctccggatt cacctttatg aggcctgata tggtttgggt ccgccaggct   120
ccagggaagg gtctggagtg ggtctcaact attaaggatt ggggtgatca gacatactac   180
gcagactccg tgaagggccg gttcaccatc tcccgcgaca attccaagaa cacgctgtat   240
ctgcaaatga acagcctgcg tgccgaggac gccgcggtat attactgtgc gaaagctgat   300
agtcgtgcgc agctggattt tgactactgg ggtcagggaa ccctggtcac cgtctcgagc   360
```

<210> SEQ ID NO 589
<211> LENGTH: 363
<212> TYPE: DNA
<213> ORGANISM: Homo sapiens

<400> SEQUENCE: 589

```
gaggtgcagc tgttggagtc tgggggaggc ttggtacagc ctggggggtc cctgcgtctc    60
tcctgtgcag cctccggatt cacctttagc agctatgcca tgagctgggt ccgccaggct   120
ccagggaagg gtctagagtg ggtctcagct attagtggta gtggtggtag cacatactac   180
gcagattccg tgaagggccg gttcaccatc tcccgcgaca attccaagaa cacgctgtat   240
ctgcaaatga acagcctgcg tgccgaggac accgcggtat attactgtgc gaaaccgtat   300
tttctgttta gggctactag ttttgactac tggggtcagg gaaccctggt caccgtctcg   360
agc                                                                  363
```

<210> SEQ ID NO 590
<211> LENGTH: 360
<212> TYPE: DNA
<213> ORGANISM: Homo sapiens

<400> SEQUENCE: 590
gaggtgcagc tgttggagtc tgggggaggc ttggtacagc ctgggggtc cctgcgtctc      60 tcctgtgcag cctccggatt cacctttcat gatgatgata tggtttgggt ccgccaggct     120
ccagggaagg gtctagagtg gtctcatcg attccgggga atggttatgt gacatactac     180
gcagactccg tgaagggccg gttcaccatc tcccgcgaca attccaagaa cacgctgtat     240
ctgcaaatga acagcctgcg tgccgaggac accgcggtat attactgtgc gaaacgtcct     300
gatccgactt cggtgttttt tgactactgg ggtcagggaa ccctggtcac cgtctcgagc     360

<210> SEQ ID NO 591
<211> LENGTH: 348
<212> TYPE: DNA
<213> ORGANISM: Homo sapiens

<400> SEQUENCE: 591
gaggtgcagc tgttggagtc tgggggaggc ttggtacagc ctgggggtc cctgcgtctc      60 tcctgtgcag cctccggatt cacctttggt gatgattgga tgacttgggt ccgccaggct     120
ccagggaagg gtctagagtg gtctcaggt attgcggctt atggtatttc tacatactac     180
gcagactccg tgaagggccg gttcaccatc tcccgcgaca attccaagaa cacgctgtat     240
ctgcaaatga acagcctgcg tgccgaggac gccgcggtat attactgtgc ggaatctggg     300
aaggtgtttg actactgggg tcagggaacc ctggtcaccg tctcgagc                  348

<210> SEQ ID NO 592
<211> LENGTH: 360
<212> TYPE: DNA
<213> ORGANISM: Homo sapiens

<400> SEQUENCE: 592
gaggtgcagc tgttggagtc tgggggaggc ttggtacagc ctgggggtc cctgcgtctc      60 tcctgtgcag cctccggatt cacctttgtt gagcgtccta tggattgggt ccgccaggct     120
ccagggaagg gtctagagtg gtctcattg attggtgcgg atggtttgtc tacatactac     180
gcagactccg tgaagggccg gttcaccatc tcccgcgaca attccaagaa cacgctgtat     240
ctgcaaatga acagcctgcg tgccgaggac accgcggtat attactgtgc gaaactttt     300 cgtcctggtc ttctttggtt tgactactgg ggtcagggaa ccctggtcac cgtctcgagc     360

<210> SEQ ID NO 593
<211> LENGTH: 357
<212> TYPE: DNA
<213> ORGANISM: Homo sapiens

<400> SEQUENCE: 593
gaggtgcagc tgttggagtc tgggggaggc ttggtacagc ctgggggtc cctgcgtctc      60 tcctgtgcag cctccggatt cacctttact gggcaggata tgcagtgggt ccgccaggct     120
ccagggaagg gtctagagtg gtctcaggg attaatgctg atggtatggc gacatactac     180
gcagactccg tgaagggccg gttcaccatc tcccgcgaca attccaagaa cacgctgtat     240
ctgcaaatga acagcctgcg tgccgaggat accgcggtat attactgtgc gaaacgtcg     300 ccgactatga ggtcgtttga ctactggggt cagggaaccc tggtcaccgt ctcgagc       357

<210> SEQ ID NO 594
<211> LENGTH: 354
<212> TYPE: DNA
<213> ORGANISM: Homo sapiens

<400> SEQUENCE: 594
gaggtgcagc tgttggagtc tgggggaggc ttggtacagc ctgggggggtc cctgcgtctc    60 tcctgtgcag cctccggatt cacctttggg gaggagtata tgcagtgggt ccgccaggct   120
ccagggaagg gtctagagtg ggtctcattg attccgcata ctggtaatcc tacatactac   180
gcagactccg tgaagggccg gttcaccatc tcccgcgaca attccaagaa cacgctgtat   240
ctgcaaatga acagcctgcg tgccgaggac accgcggtat attactgtgc gaaacttgcg   300 aatagttttgc tgtttgacta ctggggtcag ggaaccctgg tcaccgtctc gagc         354

<210> SEQ ID NO 595
<211> LENGTH: 360
<212> TYPE: DNA
<213> ORGANISM: Homo sapiens

<400> SEQUENCE: 595
gaggtgcagc tgttggagtc tgggggaggc ttggtacagc ctgggggggtc cctgcgtctc    60 tcctgtgcag cctccggatt cacctttcat aggtgtaaga tggggtgggt ccgccaggct   120
ccagggaagg gtctagagtg ggtctcattt attgagtatg atggtaggga tacatactac   180
gcagactccg tgaagggccg gttcaccatc tcccgcgaca attccaagaa cacgctgtat   240
ctgcaaatga acagcctgcg tgccgaggac accgcggtat attactgtgc gaaagagtgt   300
acgaggccgt atggtatgtt tgactactgg ggtcagggaa ccctggtcac cgtctcgagc   360

<210> SEQ ID NO 596
<211> LENGTH: 360
<212> TYPE: DNA
<213> ORGANISM: Homo sapiens

<400> SEQUENCE: 596
gaggtgcagc tgttggagtc tgggggaggc ttggtacagc ctgggggggtc cctgcgtctc    60 tcctgtgcag cctccggatt cacctttaat aggtatagta tggggtggct ccgccaggct   120
ccagggaagg gtctagagtg ggtctcattc attgacaagg tcggtcatca cacatggtac   180
gaagaccccg tgaagggccg gttcaccatc tcccgcgaca attccaagaa cacgctgtat   240
ctgcaaatga acagcctgcg tgccgaggac accgccgtgt attactgtgc gaaaatttct   300
cagtttgggc caaatgcgtt tgactactgg ggtcagggaa cccaggtcac cgtctcgagc   360

<210> SEQ ID NO 597
<211> LENGTH: 360
<212> TYPE: DNA
<213> ORGANISM: Homo sapiens
<220> FEATURE:
<221> NAME/KEY: misc_feature
<222> LOCATION: 303
<223> OTHER INFORMATION: n = A,T,C or G

<400> SEQUENCE: 597
gaggtgcagc tgttggagtc tgggggaggc ttggtacagc ctgggggggtc cctgcgtctc    60 tcctgtgcag cctccggatt cacctttact aggtatagta tggggtgggt ccgccaggct   120
ccagggaagg gtctagagtg ggtctcaatg attgcgcatg ctggtcctga gagatactac   180

```
gcagactccg tgaagggccg gttcaccatc tcccgcgaca attccaagaa cacgctgtat     240
ctgcaaatga acagcctgcg tgccgaggac accgcggtat attactgtgc gaaaatttct     300 cantttggt  caaatgcgtt tgactactgg ggtcaggaa  ccctggtcac cgtctcgagc     360

<210> SEQ ID NO 598
<211> LENGTH: 360
<212> TYPE: DNA
<213> ORGANISM: Homo sapiens

<400> SEQUENCE: 598
gaggtgcagc tgttggagtc tggggggaggc ttggtacagc ctgggggtc  cctgcgtctc     60 tcctgtgcag cctccggatt cacctttact aggtataata tggggtgggt ccgccaggct    120
ccagggaagg gtctagagtg gtctcatttt attgatcctc cgagtgttca tacatactac    180
gcagactccg tgaagggccg gttcaccatc tcccgcgaca attccaagaa cacgctgtat    240
ctgcaaatga acagcctgcg tgccgaggac accgcggtat attactgtgc gaatatttct    300
cagtttgggt caaacgcgtt tgactactgg ggtcaggaa  ccctggtcac cgtctcgagc    360

<210> SEQ ID NO 599
<211> LENGTH: 360
<212> TYPE: DNA
<213> ORGANISM: Homo sapiens
<220> FEATURE:
<221> NAME/KEY: misc_feature
<222> LOCATION: 288
<223> OTHER INFORMATION: n = A,T,C or G

<400> SEQUENCE: 599
gaggtgcagc tgttggagtc tggggggaggc ttggtacagc ctgggggtc  cctgcgtctc     60 tcctgtgcag cctccggatt cacctttact aggtatagta tggggtgggt ccgccaggct    120
ccagggaagg gtctagagtg gtctcatttt attgatcctc cgagtgttca tacatactac    180
gcagactccg tgaagggccg gttcaccatc tcccgcgaca attccaagaa cacgctgtat    240
ctgcaaatga acagcctgcg tgccgaggac accgcggtat attactgngc ggaaatttct    300
cagtttgggt caaatgcgtt tgactactgg ggtcaggaa  ccctggtcac cgtctcgagc    360

<210> SEQ ID NO 600
<211> LENGTH: 360
<212> TYPE: DNA
<213> ORGANISM: Homo sapiens

<400> SEQUENCE: 600
gaggtgcagt tgtttgagtc tggggggaggc ttggtacagc ctgggggtc  cctgcgtctc     60 tcctgtgcag cctccggatt cacctttact aggtatagta tggggtgggt ccgccaggct    120
ccagggaagg gtctagagtg gtctcaatg  attgcgcatg ctggtcctga gacatactac    180
gcagactccg tgaagggccg gttcaccatc tcccgcgaca attccaagaa cacgctgtat    240
ctgcaaatga acagcctgcg tgccgaggac accgcggtat attactgtgc gaaaatttct    300
cagtttgggt caaatgcgtt agactactgg ggccggggaa ccctggtcac cgtctcgagc    360

<210> SEQ ID NO 601
<211> LENGTH: 366
<212> TYPE: DNA
<213> ORGANISM: Homo sapiens

<400> SEQUENCE: 601
gaggtgcagc tgttggagtc tggggggaggc ttggtacagc ctgggggtc  cctgcgtctc     60
```

```
tcctgtgcag cctccggatt cacctttgcg cggtataata tgggttgggt ccgccaggct    120
ccagggaagg gtctagagtg ggtctcactg attgatccga gcggtggtca tacatactac    180
gcagactccg tgaagggccg gttcaccatc tcccgcaaca attccaagaa cacgctgtat    240
ctgcaaatga acagcctgcg tgccgaggac accgcggtat attactgtgg gaaaccggtt    300 tttctgatt ggcctgcggt ggagtttgac tactggggtc agggaaccgt ggtcaccgtc    360
tcgagc                                                              366
```

<210> SEQ ID NO 602
<211> LENGTH: 357
<212> TYPE: DNA
<213> ORGANISM: Homo sapiens

<400> SEQUENCE: 602

```
gaggtgcagc tgttggagtc tgggggaggc atggtacagc ctgggggtc actgcgtctc     60 tcctgtgcag cctccggatt cacctttgag catgagggga tggtgtgggt ccgccaggct    120
ccagggaagg gtctagagtg ggtctcacat attggtgagg atggtcagtc tacatactac    180
gcagactccg tgaagggccg gttcaccatc tcccgcgaca attccaagaa cacgctgtat    240
ctgcaaatga acagcctgcg tgccgaggac accgcggtat attactgtgc gaatattccg    300
aaggcggggc cttcgtttga ctactggggt cagggaaccc tggtcaccgt ctcgagc      357
```

<210> SEQ ID NO 603
<211> LENGTH: 182
<212> TYPE: PRT
<213> ORGANISM: Homo sapiens

<400> SEQUENCE: 603

Leu Val Pro His Leu Gly Asp Arg Glu Lys Arg Asp Ser Val Cys Pro
1               5                   10                  15

Gln Gly Lys Tyr Ile His Pro Gln Asn Asn Ser Ile Cys Cys Thr Lys
            20                  25                  30

Cys His Lys Gly Thr Tyr Leu Tyr Asn Asp Cys Pro Gly Pro Gly Gln
        35                  40                  45

Asp Thr Asp Cys Arg Glu Cys Glu Ser Gly Ser Phe Thr Ala Ser Glu
    50                  55                  60

Asn His Leu Arg His Cys Leu Ser Cys Ser Lys Cys Arg Lys Glu Met
65                  70                  75                  80

Gly Gln Val Glu Ile Ser Ser Cys Thr Val Asp Arg Asp Thr Val Cys
                85                  90                  95

Gly Cys Arg Lys Asn Gln Tyr Arg His Tyr Trp Ser Glu Asn Leu Phe
            100                 105                 110

Gln Cys Phe Asn Cys Ser Leu Cys Leu Asn Gly Thr Val His Leu Ser
        115                 120                 125

Cys Gln Glu Lys Gln Asn Thr Val Cys Thr Cys His Ala Gly Phe Phe
    130                 135                 140

Leu Arg Glu Asn Glu Cys Val Ser Cys Ser Asn Cys Lys Lys Ser Leu
145                 150                 155                 160

Glu Cys Thr Lys Leu Cys Leu Pro Gln Ile Glu Asn Val Lys Gly Thr
                165                 170                 175

Glu Asp Ser Gly Thr Thr
            180

<210> SEQ ID NO 604

```
<211> LENGTH: 183
<212> TYPE: PRT
<213> ORGANISM: Mus musculus

<400> SEQUENCE: 604

Leu Val Pro Ser Leu Gly Asp Arg Glu Lys Arg Asp Ser Leu Cys Pro
1               5                   10                  15
Gln Gly Lys Tyr Val His Ser Lys Asn Asn Ser Ile Cys Cys Thr Lys
            20                  25                  30
Cys His Lys Gly Thr Tyr Leu Val Ser Asp Cys Pro Ser Pro Gly Arg
        35                  40                  45
Asp Thr Val Cys Arg Glu Cys Glu Lys Gly Thr Phe Thr Ala Ser Gln
    50                  55                  60
Asn Tyr Leu Arg Gln Cys Leu Ser Cys Lys Thr Cys Arg Lys Glu Met
65                  70                  75                  80
Ser Gln Val Glu Ile Ser Pro Cys Gln Ala Asp Lys Asp Thr Val Cys
                85                  90                  95
Gly Cys Lys Glu Asn Gln Phe Gln Arg Tyr Leu Ser Glu Thr His Phe
            100                 105                 110
Gln Cys Val Asp Cys Ser Pro Cys Phe Asn Gly Thr Val Thr Ile Pro
        115                 120                 125
Cys Lys Glu Thr Gln Asn Thr Val Cys Asn Cys His Ala Gly Phe Phe
    130                 135                 140
Leu Arg Glu Ser Glu Cys Val Pro Cys Ser His Cys Lys Lys Asn Glu
145                 150                 155                 160
Glu Cys Met Lys Leu Cys Leu Pro Pro Leu Ala Asn Val Thr Asn
                165                 170                 175
Pro Gln Asp Ser Gly Thr Ala
            180

<210> SEQ ID NO 605
<211> LENGTH: 21
<212> TYPE: DNA
<213> ORGANISM: Artificial Sequence
<220> FEATURE:
<223> OTHER INFORMATION: Primer 1

<400> SEQUENCE: 605
gccagcattg ctgctaaaga a                                           21

<210> SEQ ID NO 606
<211> LENGTH: 19
<212> TYPE: DNA
<213> ORGANISM: Artificial Sequence
<220> FEATURE:
<223> OTHER INFORMATION: Primer 2

<400> SEQUENCE: 606
ggtcgacggc gctattcag                                              19

<210> SEQ ID NO 607
<211> LENGTH: 22
<212> TYPE: DNA
<213> ORGANISM: Artificial Sequence
<220> FEATURE:
<223> OTHER INFORMATION: Primer 3

<400> SEQUENCE: 607
ctgcagggag tgtgagagcg gc                                          22
```

```
<210> SEQ ID NO 608
<211> LENGTH: 21
<212> TYPE: DNA
<213> ORGANISM: Artificial Sequence
<220> FEATURE:
<223> OTHER INFORMATION: Primer 4

<400> SEQUENCE: 608
gtgtgtggct gcaggaagaa c                                              21

<210> SEQ ID NO 609
<211> LENGTH: 20
<212> TYPE: DNA
<213> ORGANISM: Artificial Sequence
<220> FEATURE:
<223> OTHER INFORMATION: Primer 5

<400> SEQUENCE: 609
ctgccatgca ggtttctttc                                                20

<210> SEQ ID NO 610
<211> LENGTH: 21
<212> TYPE: DNA
<213> ORGANISM: Artificial Sequence
<220> FEATURE:
<223> OTHER INFORMATION: Primer 6

<400> SEQUENCE: 610
ctgcagggag tgtgaaaagg g                                              21

<210> SEQ ID NO 611
<211> LENGTH: 22
<212> TYPE: DNA
<213> ORGANISM: Artificial Sequence
<220> FEATURE:
<223> OTHER INFORMATION: Primer 7

<400> SEQUENCE: 611
gtgtgtggct gtaaggagaa cc                                             22

<210> SEQ ID NO 612
<211> LENGTH: 20
<212> TYPE: DNA
<213> ORGANISM: Artificial Sequence
<220> FEATURE:
<223> OTHER INFORMATION: Primer 8

<400> SEQUENCE: 612
ctgccatgca gggttctttc                                                20

<210> SEQ ID NO 613
<211> LENGTH: 19
<212> TYPE: DNA
<213> ORGANISM: Artificial Sequence
<220> FEATURE:
<223> OTHER INFORMATION: Primer 9

<400> SEQUENCE: 613
tcacactccc tgcagtccg                                                 19

<210> SEQ ID NO 614
<211> LENGTH: 21
<212> TYPE: DNA
<213> ORGANISM: Artificial Sequence
<220> FEATURE:
<223> OTHER INFORMATION: Primer 10
```

-continued

```
<400> SEQUENCE: 614
cagccacaca cggtgtcccg g                                              21

<210> SEQ ID NO 615
<211> LENGTH: 22
<212> TYPE: DNA
<213> ORGANISM: Artificial Sequence
<220> FEATURE:
<223> OTHER INFORMATION: Primer 11

<400> SEQUENCE: 615
cctgcatggc aggtgcacac gg                                             22

<210> SEQ ID NO 616
<211> LENGTH: 19
<212> TYPE: DNA
<213> ORGANISM: Artificial Sequence
<220> FEATURE:
<223> OTHER INFORMATION: Primer 12

<400> SEQUENCE: 616
tcacactccc tgcagactg                                                 19

<210> SEQ ID NO 617
<211> LENGTH: 21
<212> TYPE: DNA
<213> ORGANISM: Artificial Sequence
<220> FEATURE:
<223> OTHER INFORMATION: Primer 13

<400> SEQUENCE: 617
cagccacaca ccgtgtcctt g                                              21

<210> SEQ ID NO 618
<211> LENGTH: 22
<212> TYPE: DNA
<213> ORGANISM: Artificial Sequence
<220> FEATURE:
<223> OTHER INFORMATION: Primer 14

<400> SEQUENCE: 618
cctgcatggc agttacacac gg                                             22

<210> SEQ ID NO 619
<211> LENGTH: 495
<212> TYPE: DNA
<213> ORGANISM: Artificial Sequence
<220> FEATURE:
<223> OTHER INFORMATION: human/mouse chimeric construct

<400> SEQUENCE: 619
agtgtgtgtc cccaaggaaa atatatccac cctcaaaata attcgatttg ctgtaccaag    60
tgccacaaag gaacctactt gtacaatgac tgtccaggcc cggggcagga tacggactgc   120
agggagtgtg aaaagggcac ctttacggct tcccagaatt acctcaggca gtgcctcagt   180
tgcaagacat gtcggaaaga aatgtcccag gtggagatct ctccttgcca agctgacaag   240
gacacggtgt gtggctgtaa ggagaaccag ttccaacgct acctgagtga gacacacttc   300
cagtgcgtgg actgcagccc ctgcttcaac ggcaccgtga caatcccctg taaggagact   360
cagaacaccg tgtgtaactg ccatgcaggg ttctttctga gagaaagtga gtgcgtccct   420
tgcagccact gcaagaaaaa tgaggagtgt atgaagttgt gcctaagcgc tcatcatcat   480
catcatcatt aatga                                                    495
```

<210> SEQ ID NO 620
<211> LENGTH: 495
<212> TYPE: DNA
<213> ORGANISM: Artificial Sequence
<220> FEATURE:
<223> OTHER INFORMATION: human/mouse chimeric construct

<400> SEQUENCE: 620

```
agtgtgtgtc cccaaggaaa atatatccac cctcaaaata attcgatttg ctgtaccaag      60
tgccacaaag gaacctactt gtacaatgac tgtccaggcc cggggcagga tacggactgc     120
agggagtgtg agagcggctc cttcaccgct tcagaaaacc acctcagaca ctgcctcagc     180
tgctccaaat gccgaaagga atgggtcag gtggagatct cttcttgcac agtggaccgg     240
gacaccgtgt gtggctgcag gaagaaccag taccggcatt attggagtga aaacctttc     300
cagtgcttca attgcagcct ctgcctcaat gggaccgtgc acctctcctg ccaggagaaa     360
cagaacaccg tgtgcacctg ccatgcaggg ttctttctga gagaaagtga gtgcgtccct     420
tgcagccact gcaagaaaaa tgaggagtgt atgaagttgt gcctaagcgc tcatcatcat     480
catcatcatt aatga                                                     495
```

<210> SEQ ID NO 621
<211> LENGTH: 594
<212> TYPE: DNA
<213> ORGANISM: Artificial Sequence
<220> FEATURE:
<223> OTHER INFORMATION: human/mouse chimeric construct

<400> SEQUENCE: 621

```
agtgtgtgtc cccaaggaaa atatatccac cctcaaaata attcgatttg ctgtaccaag      60
tgccacaaag gaacctactt gtacaatgac tgtccaggcc cggggcagga tacggactgc     120
agggagtgtg agagcggctc cttcaccgct tcagaaaacc acctcagaca ctgcctcagc     180
tgctccaaat gccgaaagga atgggtcag gtggagatct cttcttgcac agtggaccgg     240
gacaccgtgt gtggctgtaa ggagaaccag ttcaacgct acctgagtga gacacacttc     300
cagtgcgtgg actgcagccc ctgcttcaac ggcaccgtga caatcccctg taaggagact     360
cagaacaccg tgtgtaactg ccatgcaggt ttctttctaa gagaaaacga gtgtgtctcc     420
tgtagtaact gtaagaaaag cctggagtgc acgaagttgt gcctacccca gattgagaat     480
gttaagggca ctgaggactc aggcaccaca gcggccgcca gctttctaga acaaaaactc     540
atctcagaag aggatctgaa tagcgccgtc gaccatcatc atcatcatca ttga           594
```

<210> SEQ ID NO 622
<211> LENGTH: 594
<212> TYPE: DNA
<213> ORGANISM: Artificial Sequence
<220> FEATURE:
<223> OTHER INFORMATION: human/mouse chimeric construct

<400> SEQUENCE: 622

```
agtgtgtgtc cccaaggaaa atatatccac cctcaaaata attcgatttg ctgtaccaag      60
tgccacaaag gaacctactt gtacaatgac tgtccaggcc cggggcagga tacggactgc     120
agggagtgtg aaaagggcac ctttacggct tcccagaatt acctcaggca gtgtctcagt     180
tgcaagacat gtcggaaaga aatgtccag gtggagatct ctccttgcca agctgacaag     240
gacacggtgt gtggctgcag gaagaaccag taccggcatt attggagtga aaacctttc     300
```

```
cagtgcttca attgcagcct ctgcctcaat gggaccgtgc acctctcctg ccaggagaaa      360
cagaacaccg tgtgcacctg ccatgcaggt ttctttctaa gagaaaacga gtgtgtctcc      420
tgtagtaact gtaagaaaag cctggagtgc acgaagttgt gcctacccca gattgagaat      480
gttaagggca ctgaggactc aggcaccaca gcggccgcca gctttctaga acaaaaactc      540
atctcagaag aggatctgaa tagcgccgtc gaccatcatc atcatcatca ttga            594

<210> SEQ ID NO 623
<211> LENGTH: 594
<212> TYPE: DNA
<213> ORGANISM: Artificial Sequence
<220> FEATURE:
<223> OTHER INFORMATION: human/mouse chimeric construct

<400> SEQUENCE: 623
agcttgtgtc cccaaggaaa gtatgtccat tctaagaaca attccatctg ctgcaccaag       60
tgccacaaag gaacctactt ggtgagtgac tgtccgagcc cagggcggga tacagtctgc      120
agggagtgtg agagcggctc cttcaccgct tcagaaaacc acctcagaca ctgcctcagc      180
tgctccaaat gccgaaagga aatgggtcag gtggagatct cttcttgcac agtggaccgg      240
gacaccgtgt gtgctgcag gaagaaccag taccggcatt attggagtga aaacctttc       300 cagtgcttca attgcagcct ctgcctcaat gggaccgtgc acctctcctg ccaggagaaa      360
cagaacaccg tgtgcacctg ccatgcaggt ttctttctaa gagaaaacga gtgtgtctcc      420
tgtagtaact gtaagaaaag cctggagtgc acgaagttgt gcctacccca gattgagaat      480
gttaagggca ctgaggactc aggcaccaca gcggccgcca gctttctaga acaaaaactc      540
atctcagaag aggatctgaa tagcgccgtc gaccatcatc atcatcatca ttga            594

<210> SEQ ID NO 624
<211> LENGTH: 546
<212> TYPE: DNA
<213> ORGANISM: Homo sapiens

<400> SEQUENCE: 624
ctggtccctc acctagggga cagggagaag agagatagtg tgtgtcccca aggaaaatat       60
atccaccctc aaaataattc gatttgctgt accaagtgcc acaaggaac ctacttgtac       120 aatgactgtc caggcccggg gcaggatacg gactgcaggg agtgtgagag cggctccttc      180
accgcttcag aaaaccacct cagacactgc ctcagctgct ccaaatgccg aaaggaaatg      240
ggtcaggtgg agatctcttc ttgcacagtg gaccgggaca ccgtgtgtgg ctgcaggaag      300
aaccagtacc ggcattattg gagtgaaaac cttttccagt gcttcaattg cagcctctgc      360
ctcaatggga ccgtgcacct ctcctgccag gagaaacaga caccgtgtg cacctgccat       420 gcaggttct ttctaagaga aaacgagtgt gtctcctgta gtaactgtaa gaaaagcctg       480
gagtgcacga gttgtgcct accccagatt gagaatgtta agggcactga ggactcaggc      540
accaca                                                                546

<210> SEQ ID NO 625
<211> LENGTH: 549
<212> TYPE: DNA
<213> ORGANISM: Mus musculus

<400> SEQUENCE: 625 ctagtcccctt ctcttggtga ccggagaag agggatagct tgtgtcccca aggaaagtat       60
gtccattcta agaacaattc catctgctgc accaagtgcc acaaggaac ctacttggtg       120
```

```
agtgactgtc cgagcccagg gcgggataca gtctgcaggg agtgtgaaaa gggcaccttt    180
acggcttccc agaattacct caggcagtgt ctcagttgca agacatgtcg gaaagaaatg    240
tcccaggtgg agatctctcc ttgccaagct gacaaggaca cggtgtgtgg ctgtaaggag    300
aaccagttcc aacgctacct gagtgagaca cacttccagt gcgtggactg cagccctgc     360 ttcaacggca ccgtgacaat cccctgtaag gagactcaga acaccgtgtg taactgccat    420
gcagggttct ttctgagaga aagtgagtgc gtcccttgca gccactgcaa gaaaaatgag    480
gagtgtatga agttgtgcct acctcctccg cttgcaaatg tcacaaaccc ccaggactca    540
ggtactgcg                                                            549
```

<210> SEQ ID NO 626
<211> LENGTH: 360
<212> TYPE: DNA
<213> ORGANISM: Homo sapiens

<400> SEQUENCE: 626

```
gaggtgcagc tgttggagtc tgggggaggc ttggtacagc ctggggggtc cctgcgtctc    60
tcctgtgcag cctccggatt cacctttaat aggtatagta tggggtggct ccgccaggct   120
ccagggaagg gtctagagtg ggtctcacgg attgattctt atggtcgtgg tacatactac   180 gaagacccg tgaagggccg gttcagcatc tcccgcgaca attccaagaa cacgctgtat    240
ctgcaaatga acagcctgcg tgccgaggac accgccgtat attactgtgc gaaaattict   300 cagtttgggt caaatgcgtt tgactactgg ggtcaggaa cccaggtcac cgtctcgagc    360
```

<210> SEQ ID NO 627
<211> LENGTH: 119
<212> TYPE: PRT
<213> ORGANISM: Homo sapiens

<400> SEQUENCE: 627

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Val Lys Tyr
            20                  25                  30

Ser Met Gly Trp Val Arg Gln Ala Pro Gly Lys Gly Leu Glu Trp Val
        35                  40                  45

Ser Gln Ile Ser Asn Thr Gly Gly His Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Gly Arg Trp Glu Pro Phe Asp Tyr Trp Gly Gln Gly
            100                 105                 110

Thr Leu Val Thr Val Ser Ser
        115

<210> SEQ ID NO 628
<211> LENGTH: 357
<212> TYPE: DNA
<213> ORGANISM: Homo sapiens

<400> SEQUENCE: 628

```
gaggtgcagc tgttggagtc tgggggaggc ttggtacagc ctggggggtc cctgcgtctc    60
```

```
tcctgtgcag cctccggatt caccttttgtt aagtattcga tggggtgggt ccgccaggct    120
ccagggaagg gtctagagtg ggtctcacag atttcgaata cgggtggtca tacatactac    180
gcagactccg tgaagggccg gttcaccatc tcccgcgaca attccaagaa cacgctgtat    240
ctgcaaatga acagcctgcg tgccgaggac accgcggtat attactgtgc gaaatatacg    300
ggtcgttggg agccttttga ctactggggt cagggaaccc tggtcaccgt ctcgagc       357
```

```
<210> SEQ ID NO 629
<211> LENGTH: 25
<212> TYPE: PRT
<213> ORGANISM: Artificial Sequence
<220> FEATURE:
<223> OTHER INFORMATION: 5U Linker

<400> SEQUENCE: 629

Gly Gly Gly Gly Ser Gly Gly Gly Gly Ser Gly Gly Gly Gly Ser Gly
 1               5                  10                  15

Gly Gly Gly Ser Gly Gly Gly Gly Ser
            20                  25
```

```
<210> SEQ ID NO 630
<211> LENGTH: 35
<212> TYPE: PRT
<213> ORGANISM: Artificial Sequence
<220> FEATURE:
<223> OTHER INFORMATION: 7U Linker

<400> SEQUENCE: 630

Gly Gly Gly Gly Ser Gly Gly Gly Gly Ser Gly Gly Gly Gly Ser Gly
 1               5                  10                  15

Gly Gly Gly Ser Gly Gly Gly Gly Ser Gly Gly Gly Gly Ser Gly Gly
            20                  25                  30

Gly Gly Ser
        35
```

```
<210> SEQ ID NO 631
<211> LENGTH: 27
<212> TYPE: DNA
<213> ORGANISM: Artificial Sequence
<220> FEATURE:
<223> OTHER INFORMATION: HA Tag

<400> SEQUENCE: 631
tatccttatg atgttcctga ttatgca                                         27
```

```
<210> SEQ ID NO 632
<211> LENGTH: 9
<212> TYPE: PRT
<213> ORGANISM: Artificial Sequence
<220> FEATURE:
<223> OTHER INFORMATION: HA Tag

<400> SEQUENCE: 632

Tyr Pro Tyr Asp Val Pro Asp Tyr Ala
 1               5
```

```
<210> SEQ ID NO 633
<211> LENGTH: 117
<212> TYPE: PRT
<213> ORGANISM: Homo sapiens

<400> SEQUENCE: 633

Trp Ser Ala Ser Thr Asp Ile Gln Met Thr Gln Ser Pro Ser Ser Leu
```

```
             1               5                  10                 15
Ser Ala Ser Val Gly Asp Arg Val Thr Ile Thr Cys Arg Ala Ser Gln
                    20                  25                  30
Ser Ile Asp Ser Tyr Leu His Trp Tyr Gln Gln Lys Pro Gly Lys Ala
                    35                  40                  45
Pro Lys Leu Leu Ile Tyr Ser Ala Ser Glu Leu Gln Ser Gly Val Pro
                    50                  55                  60
Ser Arg Phe Ser Gly Ser Gly Ser Gly Thr Asp Phe Thr Leu Thr Ile
65                  70                  75                  80
Ser Ser Leu Gln Pro Glu Asp Phe Ala Thr Tyr Tyr Cys Gln Gln Val
                    85                  90                  95
Val Trp Arg Pro Phe Thr Phe Gly Gln Gly Thr Lys Val Glu Ile Lys
                    100                 105                 110
Arg Cys Gly Ser Gly
            115

<210> SEQ ID NO 634
<211> LENGTH: 357
<212> TYPE: DNA
<213> ORGANISM: Homo sapiens

<400> SEQUENCE: 634
tggagcgcgt cgacggacat ccagatgacc cagtctccat cctctctgtc tgcatctgta      60
ggagaccgtg tcaccatcac ttgccgggca agtcagagca ttgatagtta tttacattgg     120
taccagcaga aaccagggaa agcccctaag ctcctgatct atagtgcatc cgagttgcaa     180
agtggggtcc catcacgttt cagtggcagt ggatctggga cagatttcac tctcaccatc     240
agcagtctgc aacctgaaga ttttgctacg tactactgtc aacaggttgt gtggcgtcct     300
tttacgttcg gccaagggac caaggtggaa atcaaacggt gctaataagg atccggc       357

<210> SEQ ID NO 635
<211> LENGTH: 357
<212> TYPE: DNA
<213> ORGANISM: Homo sapiens

<400> SEQUENCE: 635
gccggatcct tattagcacc gtttgatttc caccttggtc ccttggccga acgtaaaagg      60
acgccacaca acctgttgac agtagtacgt agcaaaatct tcaggttgca gactgctgat     120
ggtgagagtg aaatctgtcc cagatccact gccactgaaa cgtgatggga ccccactttg     180
caactcggat gcactataga tcaggagctt aggggctttc cctggtttct gctggtacca     240
atgtaaataa ctatcaatgc tctgacttgc ccggcaagtg atggtgacac ggtctcctac     300
agatgcagac agagaggatg gagactgggt catctggatg tccgtcgacg cgctcca       357

<210> SEQ ID NO 636
<211> LENGTH: 774
<212> TYPE: DNA
<213> ORGANISM: Mus musculus

<400> SEQUENCE: 636
gaggtgcagc tgttggagtc tgggggaggc ttggtacagc ctggggggtc cctgcgtctc      60
tcctgtgcag cctccggatt cacctttaat aggtatagta tggggtggct ccgccaggct     120
ccagggaagg gtctagagtg ggtctcacgg attgattctt atggtcgtgg tacatactac     180
gaagaccccg tgaagggccg gttcagcatc tcccgcgaca attccaagaa cacgctgtat     240
```

```
ctgcaaatga acagcctgcg tgccgaggac accgccgtat attactgtgc gaaaatttct      300
cagtttgggt caaatgcgtt tgactactgg ggtcagggaa cccaggtcac cgtctcgagc      360
ggtggaggcg gttcaggcgg aggtggcagc ggcggtggcg gtcgacgga catccagatg       420 acccagtctc catcctccct gtctgcatct gtaggagacc gtgtcaccat cacttgccgg      480
gcaagtcaga gcattattaa catttaaag tggtaccagc agaaaccagg aaagccccct       540
aagctcctga tctatggtgc atccggttg caaagtgggg tcccatcacg tttcagtggc       600
agtggatctg ggacagattt cactctcacc atcagcagtc tgcaacctga gattttgct       660 acgtactact gtcaacaggg ggctcggtgg cctcagacgt tcggccaagg gaccaaggtg      720
gaaatcaaac gggcggccgc agaacaaaaa ctcatctcag aagaggatct gaat            774
```

<210> SEQ ID NO 637
<211> LENGTH: 258
<212> TYPE: PRT
<213> ORGANISM: Mus musculus

<400> SEQUENCE: 637

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asn Arg Tyr
            20                  25                  30

Ser Met Gly Trp Leu Arg Gln Ala Pro Gly Lys Gly Leu Glu Trp Val
        35                  40                  45

Ser Arg Ile Asp Ser Tyr Gly Arg Gly Thr Tyr Tyr Glu Asp Pro Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Gln Phe Gly Ser Asn Ala Phe Asp Tyr Trp Gly Gln
            100                 105                 110

Gly Thr Gln Val Thr Val Ser Ser Gly Gly Gly Gly Ser Gly Gly Gly
        115                 120                 125

Gly Ser Gly Gly Gly Ser Thr Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Ser Ile Ile Lys His Leu Lys Trp Tyr Gln Gln Lys Pro
                165                 170                 175

Gly Lys Ala Pro Lys Leu Leu Ile Tyr Gly Ala Ser Arg Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Gly Ala Arg Trp Pro Gln Thr Phe Gly Gln Gly Thr Lys Val
225                 230                 235                 240

Glu Ile Lys Arg Ala Ala Ala Glu Gln Lys Leu Ile Ser Glu Glu Asp
                245                 250                 255

Leu Asn
```

<210> SEQ ID NO 638
<211> LENGTH: 22

```
<212> TYPE: DNA
<213> ORGANISM: Artificial Sequence
<220> FEATURE:
<223> OTHER INFORMATION: VK-DLIBF primer

<400> SEQUENCE: 638
cggccatggc gtcaacggac at                                              22

<210> SEQ ID NO 639
<211> LENGTH: 23
<212> TYPE: DNA
<213> ORGANISM: Artificial Sequence
<220> FEATURE:
<223> OTHER INFORMATION: VKXhO1R primer

<400> SEQUENCE: 639
atgtgcgctc gagcgtttga ttt                                             23
```

ANTAGONISTS AGAINST TNFR1 AND METHODS OF USE THEREFOR

RELATED APPLICATIONS

This application is a continuation of U.S. application Ser. No. 11/664,542, filed Sep. 6, 2007, now abandoned which is a continuation-in-part of U.S. patent application Ser. No. 10/985,847, filed Nov. 10, 2004, now abandoned which is a continuation-in-part of International Application No. PCT/GB2004/004253, filed Oct. 8, 2004; and a continuation-in-part of International Application No. PCT/GB2003/005646, filed Dec. 24, 2003, and claims priority to United Kingdom Application No. GB 0230202.4, filed, Dec. 27, 2002 and United Kingdom Application No. GB0327706.8 filed, Nov. 28, 2003, which is a continuation-in-part of International Application No. PCT/GB2003/002804, filed Jun. 30, 2003, and claims priority to United Kingdom Application No. GB0230202.4, filed Dec. 27, 2002, which is a continuation-in-part of International Application No. PCT/GB2002/003014, filed Jun. 28, 2002 which are incorporated herein in their entirety.

BACKGROUND OF THE INVENTION

The antigen binding domain of an antibody comprises two separate regions: a heavy chain variable domain ($V_H$) and a light chain variable domain ($V_L$: which can be either $V_\kappa$ or $V_\lambda$). The antigen binding site itself is formed by six polypeptide loops: three from $V_H$ domain (H1, H2 and H3) and three from $V_L$ domain (L1, L2 and L3). A diverse primary repertoire of V genes that encode the $V_H$ and $V_L$ domains is produced by the combinatorial rearrangement of gene segments. The $V_H$ gene is produced by the recombination of three gene segments, $V_H$, D and $J_H$. In humans, there are approximately 51 functional $V_H$ segments (Cook and Tomlinson (1995) *Immunol Today*, 16: 237), 25 functional D segments (Corbett et al. (1997) *J. Mol. Biol.*, 268: 69) and 6 functional $J_H$ segments (Ravetch et al. (1981) *Cell*, 27: 583), depending on the haplotype. The $V_H$ segment encodes the region of the polypeptide chain which forms the first and second antigen binding loops of the $V_H$ domain (H1 and H2), whilst the $V_H$, D and $J_H$ segments combine to form the third antigen binding loop of the $V_H$ domain (H3). The $V_L$ gene is produced by the recombination of only two gene segments, $V_L$ and $J_L$. In humans, there are approximately 40 functional $V_\kappa$ segments (Schäble and Zachau (1993) *Biol. Chem. Hoppe-Seyler*, 374: 1001), 31 functional $V_\lambda$ segments (Williams et al. (1996) *J. Mol. Biol.*, 264: 220; Kawasaki et al. (1997) *Genome Res.*, 7: 250), 5 functional $J_\kappa$ segments (Hieter et al. (1982) *J. Biol. Chem.*, 257: 1516) and 4 functional $J_\lambda$ segments (Vasicek and Leder (1990) *J. Exp. Med.*, 172: 609), depending on the haplotype. The $V_L$ segment encodes the region of the polypeptide chain which forms the first and second antigen binding loops of the $V_L$ domain (L1 and L2), whilst the $V_L$ and $J_L$ segments combine to form the third antigen binding loop of the $V_L$ domain (L3). Antibodies selected from this primary repertoire are believed to be sufficiently diverse to bind almost all antigens with at least moderate affinity. High affinity antibodies are produced by "affinity maturation" of the rearranged genes, in which point mutations are generated and selected by the immune system on the basis of improved binding.

Analysis of the structures and sequences of antibodies has shown that five of the six antigen binding loops (H1, H2, L1, L2, L3) possess a limited number of main-chain conformations or canonical structures (Chothia and Lesk (1987) *J. Mol. Biol.*, 196: 901; Chothia et al. (1989) *Nature*, 342: 877). The main-chain conformations are determined by (i) the length of the antigen binding loop, and (ii) particular residues, or types of residue, at certain key position in the antigen binding loop and the antibody framework. Analysis of the loop lengths and key residues has enabled us to the predict the main-chain conformations of H1, H2, L1, L2 and L3 encoded by the majority of human antibody sequences (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1.

Bispecific antibodies comprising complementary pairs of $V_H$ and $V_L$ regions are known in the art. These bispecific antibodies must comprise two pairs of $V_H$ and $V_L$s, each $V_H/V_L$ pair binding to a single antigen or epitope. Methods described involve hybrid hybridomas (Milstein & Cuello A C, Nature 305:537-40), minibodies (Hu et al., (1996) Cancer Res 56:3055-3061;), diabodies (Holliger et al., (1993) Proc. Natl. Acad. Sci. USA 90, 6444-6448; WO 94/13804), chelating recombinant antibodies (CRAbs; (Neri et al., (1995) J. Mol. Biol. 246, 367-373), biscFv (e.g. Atwell et al., (1996) Mol. Immunol. 33, 1301-1312), "knobs in holes" stabilised antibodies (Carter et al., (1997) Protein Sci. 6, 781-788). In each case each antibody species comprises two antigen-binding sites, each fashioned by a complementary pair of $V_H$ and $V_L$ domains. Each antibody is thereby able to bind to two different antigens or epitopes at the same time, with the binding to EACH antigen or epitope mediated by a $V_H$ and its complementary $V_L$ domain. Each of these techniques presents its particular disadvantages; for instance in the case of hybrid hybridomas, inactive $V_H/V_L$ pairs can greatly reduce the fraction of bispecific IgG. Furthermore, most bispecific approaches rely on the association of the different $V_H/V_L$ pairs or the association of $V_H$ and $V_L$ chains to recreate the two different $V_H/V_L$ binding sites. It is therefore impossible to control the ratio of binding sites to each antigen or epitope in the assembled molecule and thus many of the assembled molecules will bind to one antigen or epitope but not the other. In some cases it has been possible to engineer the heavy or light chains at the sub-unit interfaces (Carter et al., 1997) in order to improve the number of molecules which have binding sites to both antigens or epitopes but this never results in all molecules having binding to both antigens or epitopes.

There is some evidence that two different antibody binding specificities might be incorporated into the same binding site, but these generally represent two or more specificities that correspond to structurally related antigens or epitopes or to antibodies that are broadly cross-reactive. For example, cross-reactive antibodies have been described, usually where the two antigens are related in sequence and structure, such as hen egg white lysozyme and turkey lysozyme (McCafferty et al., WO 92/01047) or to free hapten and to hapten conjugated to carrier (Griffiths A D et al. *EMBO J* 1994 13:14 3245-60). In a further example, WO 02/02773 (Abbott Laboratories) describes antibody molecules with "dual specificity". The antibody molecules referred to are antibodies raised or selected against multiple antigens, such that their specificity spans more than a single antigen. Each complementary $V_H/V_L$ pair in the antibodies of WO 02/02773 specifies a single binding specificity for two or more structurally related antigens; the $V_H$ and $V_L$ domains in such complementary pairs do not each possess a separate specificity. The antibodies thus have a broad single specificity which encompasses two antigens, which are structurally related. Furthermore natural autoantibodies have been described that are polyreactive (Casali & Notkins, Ann. Rev. Immunol. 7, 515-531), reacting with at least two (usually more) different antigens or epitopes that are not structurally related. It has also been shown that selections of random peptide repertoires using phage display technology on a monoclonal antibody will identify a range of peptide sequences that fit the antigen binding site. Some of the sequences are highly related, fitting a consensus sequence, whereas others are very different and have been termed mimotopes (Lane & Stephen, Current Opinion in Immunology, 1993, 5, 268-271). It is therefore clear that a natural four-chain antibody, comprising associated and complementary $V_H$ and $V_L$ domains, has the potential to bind to many different antigens from a large universe of known antigens. It is less clear how to create a binding site to two given antigens in the same antibody, particularly those which are not necessarily structurally related.

Protein engineering methods have been suggested that may have a bearing on this. For example it has also been proposed that a catalytic antibody could be created with a binding activity to a metal ion through one variable domain, and to a hapten (substrate) through contacts with the metal ion and a complementary variable domain (Barbas et al., 1993 Proc. Natl. Acad. Sci. USA 90, 6385-6389). However in this case, the binding and catalysis of the substrate (first antigen) is proposed to require the binding of the metal ion (second antigen). Thus the binding to the $V_H/V_L$ pairing relates to a single but multi-component antigen.

Methods have been described for the creation of bispecific antibodies from camel antibody heavy chain single domains in which binding contacts for one antigen are created in one variable domain, and for a second antigen in a second variable domain. However the variable domains were not complementary. Thus a first heavy chain variable domain is selected against a first antigen, and a second heavy chain variable domain against a second antigen, and then both domains are linked together on the same chain to give a bispecific antibody fragment (Conrath et al., J. Biol. Chem. 270, 27589-27594). However the camel heavy chain single domains are unusual in that they are derived from natural camel antibodies which have no light chains, and indeed the heavy chain single domains are unable to associate with camel light chains to form complementary $V_H$ and $V_L$ pairs.

Single heavy chain variable domains have also been described, derived from natural antibodies which are normally associated with light chains (from monoclonal antibodies or from repertoires of domains; see EP-A-0368684). These heavy chain variable domains have been shown to interact specifically with one or more related antigens but have not been combined with other heavy or light chain variable domains to create a ligand with a specificity for two or more different antigens. Furthermore, these single domains have been shown to have a very short in vivo half-life. Therefore such domains are of limited therapeutic value.

It has been suggested to make bispecific antibody fragments by linking heavy chain variable domains of different specificity together (as described above). The disadvantage with this approach is that isolated antibody variable domains may have a hydrophobic interface that normally makes interactions with the light chain and is exposed to solvent and may be "sticky" allowing the single domain to bind to hydrophobic surfaces. Furthermore, in the absence of a partner light chain the combination of two or more different heavy chain variable domains and their association, possibly via their hydrophobic interfaces, may prevent them from binding to one in not both of the ligands they are able to bind in isolation. Moreover, in this case the heavy chain variable domains would not be associated with complementary light chain variable domains and thus may be less stable and readily unfold (Worn & Pluckthun, 1998 Biochemistry 37, 13120-7).

SUMMARY OF THE INVENTION

The invention relates to antagonists of Tumor Necrosis Factor 1 (TNFR1, p55, CD120a, P60, TNF receptor superfamily member 1A, TNFRSF1A) and methods of using the antagonists. Preferred antagonists have efficacy in treating, suppressing or preventing a chronic inflammatory disease and do not substantially antagonize Tumor Necrosis Factor 2 (TNFR2, P75, P80, CD120b, TNF receptor superfamily member 1B, TNFRSF1B). In some embodiments, the antagonist is monovalent.

In other embodiments, the antagonist is an antibody or antigen-binding fragment thereof, such as a monovalent antigen-binding fragment (e.g., scFv, Fab, Fab', dAb) that has binding specificity for TNFR1.

Other preferred antagonists are ligands described herein that bind TNFR1. The ligands comprise an immunoglobulin single variable domain or domain antibody (dAb) that has binding specificity for TNFR1, or the complementarity determining regions of such a dAb in a suitable format. In some embodiments, the ligand is a dAb monomer that consists essentially of, or consists of, an immunoglobulin single variable domain or dAb that has binding specificity for TNFR1. In other embodiments, the ligand is a polypeptide that comprises a dAb (or the CDRs of a dAb) in a suitable format, such as an antibody format.

In certain embodiments, the ligand is a dual-specific ligand that comprises a first dAb that binds TNFR1 and a second dAb that has a different binding specificity from the first dAb. In one example, the dual-specific ligand comprises a first dAb that binds a first epitope on TNFR1 and a second dAb that binds an epitope on a different target. In another example, the second dAb binds an epitope on serum albumin.

In other embodiments, the ligand is a multispecific ligand that comprises a first epitope binding domain that has binding specificity for TNFR1 and at least one other epitope binding domain that has binding specificity different from the first epitope binding domain. For example, the first epitope binding domain can be a dAb that binds TNFR1 or can be a domain that comprises the CDRs of a dAb that binds TNFR1 (e.g., CDRs grafted onto a suitable protein scaffold or skeleton, e.g., an affibody, an SpA scaffold, an LDL receptor class A domain or an EGF domain) or can be a domain that binds TNFR1, wherein the domain is selected from an affibody, an SpA domain, an LDL receptor class A domain or an EGF domain).

In certain embodiments, the ligand or dAb monomer is characterized by one or more of the following: 1) dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$; 2) inhibits binding of Tumor Necrosis Factor Alpha (TNFα) to TNFR1 with an IC50 of 500 nM to 50 pM; 3) neutralizes human TNFR1 in a standard L929 cell assay with an ND50 of 500 nM to 50 pM; 4) antagonizes the activity of the TNFR1 in a standard cell assay with an $ND_{50}$ of ≤100 nM, and at a concentration of ≤10 μM the dAb agonizes the activity of the TNFR1 by ≤5% in the assay; 5) inhibits lethality in the mouse LPS/D-galactosamine-induced septic shock model; 6) resists aggregation; 7) is secreted in a quantity of at least about 0.5 mg/L when expressed in *E. coli* or *Pichia* species (e.g., *P. pastoris*); 8) unfolds reversibly; 9) has efficacy in a model of chronic inflammatory disease selected from the group consisting of mouse collagen-induced arthritis model, mouse ΔARE model of arthritis, mouse ΔARE model of inflammatory bowel disease, mouse dextran sulfate sodium-induced model of inflammatory bowel disease, mouse tobacco smoke model of chronic obstructive pulmonary disease, and suitable primate models (e.g., primate collagen-induced arthritis model); and/or 10) has efficacy in treating, suppressing or preventing a chronic inflammatory disease.

In particular embodiments, the ligand or dAb monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$; inhibits binding of Tumor Necrosis Factor Alpha (TNFα) to TNFR1 with an IC50 of 500 nM to 50 pM; and neutralizes human TNFR1 in a standard L929 cell assay with an ND50 of 500 nM to 50 pM. In other particular embodiments, the ligand or dAb monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$; inhibits binding of Tumor Necrosis Factor Alpha (TNFα) to TNFR1 with an IC50 of 500 nM to 50 pM; and has efficacy in a model of chronic inflammatory disease selected from the group consisting of mouse collagen-induced arthritis model, mouse ΔARE model of arthritis, mouse ΔARE model of inflammatory bowel disease, mouse dextran sulfate sodium-induced model of inflammatory bowel disease, mouse tobacco smoke model of chronic obstructive pulmonary disease, and suitable primate models (e.g., primate collagen-induced arthritis model). In other particular embodiments, the ligand or dAb monomer dissociates from human TNFR1 with a dissociation constant ($K_d$) of 50 nM to 20 pM, and a $K_{off}$ rate constant of $5 \times 10^{-1}$ to $1 \times 10^{-7}$ s$^{-1}$; neutralizes human TNFR1 in a standard L929 cell assay with an ND50 of 500 nM to 50 pM; and antagonizes the activity of the TNFR1 in a standard cell assay with an $ND_{50}$ of ≤100 nM, and at a concentration of ≤10 μM the dAb agonizes the activity of the TNFR1 by ≤5% in the assay.

In more particular embodiment, the ligand or dAb monomer comprises an amino acid sequence that is at least about 90% homologous to an amino acid sequence of a dAb selected from the group consisting of TAR2h-12 (SEQ ID NO:32), TAR2h-13 (SEQ ID NO:33), TAR2h-14 (SEQ ID NO:34), TAR2h-16 (SEQ ID NO:35), TAR2h-17 (SEQ ID NO:36), TAR2h-18 (SEQ ID NO:37), TAR2h-19 (SEQ ID NO:38), TAR2h-20 (SEQ ID NO:39), TAR2h-21 (SEQ ID NO:40), TAR2h-22 (SEQ ID NO:41), TAR2h-23 (SEQ ID NO:42), TAR2h-24 (SEQ ID NO:43), TAR2h-25 (SEQ ID NO:44), TAR2h-26 (SEQ ID NO:45), TAR2h-27 (SEQ ID NO:46), TAR2h-29 (SEQ ID NO:47), TAR2h-30 (SEQ ID NO:48), TAR2h-32 (SEQ ID NO:49), TAR2h-33 (SEQ ID NO:50), TAR2h-10-1 (SEQ ID NO:51), TAR2h-10-2 (SEQ ID NO:52), TAR2h-10-3 (SEQ ID NO:53), TAR2h-10-4 (SEQ ID NO:54), TAR2h-10-5 (SEQ ID NO:55), TAR2h-10-6 (SEQ ID NO:56), TAR2h-10-7 (SEQ ID NO:57), TAR2h-10-8 (SEQ ID NO:58), TAR2h-10-9 (SEQ ID NO:59), TAR2h-10-10 (SEQ ID NO:60), TAR2h-10-11 (SEQ ID NO:61), TAR2h-10-12 (SEQ ID NO:62), TAR2h-10-13 (SEQ ID NO:63), TAR2h-10-14 (SEQ ID NO:64), TAR2h-10-15 (SEQ ID NO:65), TAR2h-10-16 (SEQ ID NO:66), TAR2h-10-17 (SEQ ID NO:67), TAR2h-10-18 (SEQ ID NO:68), TAR2h-10-19 (SEQ ID NO:69), TAR2h-10-20 (SEQ ID NO:70), TAR2h-10-21 (SEQ ID NO:71), TAR2h-10-22 (SEQ ID NO:72), TAR2h-10-27 (SEQ ID NO:73), TAR2h-10-29 (SEQ ID NO:74), TAR2h-10-31 (SEQ ID NO:75), TAR2h-10-35 (SEQ ID NO:76), TAR2h-10-36 (SEQ ID NO:77), TAR2h-10-37 (SEQ ID NO:78), TAR2h-10-38 (SEQ ID NO:79), TAR2h-10-45 (SEQ ID NO:80), TAR2h-10-47 (SEQ ID NO:81), TAR2h-10-48 (SEQ ID NO:82), TAR2h-10-57 (SEQ ID NO:83), TAR2h-10-56 (SEQ ID NO:84), TAR2h-10-58 (SEQ ID NO:85), TAR2h-10-66 (SEQ ID NO:86), TAR2h-10-64 (SEQ ID NO:87), TAR2h-10-65 (SEQ ID NO:88), TAR2h-10-68 (SEQ ID NO:89), TAR2h-10-69 (SEQ ID NO:90), TAR2h-10-67 (SEQ ID NO:91), TAR2h-10-61 (SEQ ID NO:92), TAR2h-10-62 (SEQ ID NO:93), TAR2h-10-63 (SEQ ID NO:94), TAR2h-10-60 (SEQ ID NO:95), TAR2h-10-55 (SEQ ID NO:96), TAR2h-10-59 (SEQ ID NO:97), TAR2h-10-70 (SEQ ID NO:98), TAR2h-34 (SEQ ID NO:373), TAR2h-35 (SEQ ID NO:374), TAR2h-36 (SEQ ID NO:375), TAR2h-37 (SEQ ID NO:376), TAR2h-38 (SEQ ID NO:377), TAR2h-39 (SEQ ID NO:378), TAR2h-40 (SEQ ID NO:379), TAR2h-41 (SEQ ID NO:380), TAR2h-42 (SEQ ID NO:381), TAR2h-43 (SEQ ID NO:382), TAR2h-44 (SEQ ID NO:383), TAR2h-45 (SEQ ID NO:384), TAR2h-47 (SEQ ID NO:385), TAR2h-48 (SEQ ID NO:386), TAR2h-50 (SEQ ID NO:387), TAR2h-51 (SEQ ID NO:388), TAR2h-66 (SEQ ID NO:389), TAR2h-67 (SEQ ID NO:390), TAR2h-68 (SEQ ID NO:391), TAR2h-70 (SEQ ID NO:392), TAR2h-71 (SEQ ID NO:393), TAR2h-72 (SEQ ID NO:394), TAR2h-73 (SEQ ID NO:395), TAR2h-74 (SEQ ID NO:396), TAR2h-75 (SEQ ID NO:397), TAR2h-76 (SEQ ID NO:398), TAR2h-77 (SEQ ID NO:399), TAR2h-78 (SEQ ID NO:400), TAR2h-79 (SEQ ID NO:401), and TAR2h-15 (SEQ ID NO:431).

In additional embodiments, the ligand or dAb monomer comprises an amino acid sequence that is at least about 90% homologous to an amino acid sequence of a dAb selected from the group consisting of TAR2h-131-8 (SEQ ID NO:433), TAR2h-131-24 (SEQ ID NO:434), TAR2h-15-8 (SEQ ID NO:435), TAR2h-15-8-1 SEQ ID NO:436), TAR2h-15-8-2 (SEQ ID NO:437), TAR2h-185-23 (SEQ ID NO:438), TAR2h-154-10-5 (SEQ ID NO:439), TAR2h-14-2 (SEQ ID NO:440), TAR2h-151-8 (SEQ ID NO:441), TAR2h-152-7 (SEQ ID NO:442), TAR2h-35-4 (SEQ ID NO:443), TAR2h-154-7 (SEQ ID NO:444), TAR2h-80 (SEQ ID NO:445), TAR2h-81 (SEQ ID NO:446), TAR2h-82 (SEQ ID NO:447), TAR2h-83 (SEQ ID NO:448), TAR2h-84 (SEQ ID NO:449), TAR2h-85 (SEQ ID NO:450), TAR2h-86 (SEQ ID NO:451), TAR2h-87 (SEQ ID NO:452), TAR2h-88 (SEQ ID NO:453), TAR2h-89 (SEQ ID NO:454), TAR2h-90 (SEQ ID NO:455), TAR2h-91 (SEQ ID NO:456), TAR2h-92 (SEQ ID NO:457), TAR2h-93 (SEQ ID NO:458), TAR2h-94 (SEQ ID NO:459), TAR2h-95 (SEQ ID NO:460), TAR2h-96 (SEQ ID NO:461), TAR2h-97 (SEQ ID NO:462), TAR2h-99 (SEQ ID NO:463), TAR2h-100 (SEQ ID NO:464), TAR2h-101 (SEQ ID NO:465), TAR2h-102 (SEQ ID NO:466), TAR21'-103 (SEQ ID NO:467), TAR2h-104 (SEQ ID NO:468), TAR2h-105 (SEQ ID NO:469), TAR2h-106 (SEQ ID NO:470), TAR2h-107 (SEQ ID NO:471), TAR2h-108 (SEQ ID NO:472), TAR2h-109 (SEQ ID NO:473), TAR2h-110 (SEQ ID NO:474), TAR2h-111 (SEQ ID NO:475), TAR2h-112 (SEQ ID NO:476), TAR2h-113 (SEQ ID NO:477), TAR2h-114 (SEQ ID NO:478), TAR2h-115 (SEQ ID NO:479), TAR2h-116 (SEQ ID NO:480), TAR2h-117 (SEQ ID NO:481), TAR2h-118 (SEQ ID NO:482), TAR2h-119 (SEQ ID NO:483), TAR2h-120 (SEQ ID NO:484), TAR2h-121 (SEQ ID NO:485), TAR2h-122 (SEQ ID NO:486), TAR2h-123 (SEQ ID NO:487), TAR2h-124 (SEQ ID NO:488), TAR2h-125 (SEQ ID NO:489), TAR2h-126 (SEQ ID NO:490), TAR2h-127 (SEQ ID NO:490), TAR2h-128 (SEQ ID NO:492), TAR2h-129 (SEQ ID NO:493), TAR2h-130 (SEQ ID NO:494), TAR2h-131 (SEQ ID NO:495), TAR2h-132 (SEQ ID NO:496), TAR2h-133 (SEQ ID NO:497), TAR2h-

151 (SEQ ID NO:498), TAR2h-152 (SEQ ID NO:499), TAR2h-153 (SEQ ID NO:500), TAR2h-154 (SEQ ID NO:501), TAR2h-159 (SEQ ID NO:502), TAR2h-165 (SEQ ID NO:503), TAR2h-166 (SEQ ID NO:504), TAR2h-168 (SEQ ID NO:505), TAR2h-171 (SEQ ID NO:506), TAR2h-172 (SEQ ID NO:507), TAR2h-173 (SEQ ID NO:508), TAR2h-174 (SEQ ID NO:509), TAR2h-176 (SEQ ID NO:510), TAR2h-178 (SEQ ID NO:511), TAR2h-201 (SEQ ID NO:512), TAR2h-202 (SEQ ID NO:513), TAR2h-203 (SEQ ID NO:514), TAR2h-204 (SEQ ID NO:515), TAR2h-185-25 (SEQ ID NO:516), TAR2h-154-10 (SEQ ID NO:517), and TAR2h-205 (SEQ ID NO:627).

The invention relates to an antagonist of Tumor Necrosis Factor I (TNFR1) that binds Tumor Necrosis Factor 1 (TNFR1) and inhibits signal transduction through TNFR1, wherein said antagonist does not inhibit binding of TNFα to TNFR1. In some embodiments, the antagonist comprises a first domain antibody (dAb) monomer and a second dAb monomer, wherein said first dAb monomer binds a domain of TNFR1 selected from the group consisting of Domain 1, Domain 2, Domain 3 and Domain 4, and said second dAb monomer binds a domain of TNFR1 selected from the group consisting of Domain 1, Domain 2, Domain 3 and Domain 4, wherein said antagonist does not agonize TNFR1 when present at a concentration of about 1 µM in a standard L929 cytotoxicity assay or a standard HeLa IL-8 assay.

In some embodiments, the invention is a domain antibody (dAb) monomer or ligand comprising a dAb that binds Tumor Necrosis Factor 1 (TNFR1) and inhibits signal transduction through TNFR1, wherein said dAb monomer does not inhibit binding of TNFα to TNFR1.

In other embodiments, the invention is a domain antibody (dAb) monomer or ligand comprising a dAb that binds Tumor Necrosis Factor I (TNFR1), wherein said dAb binds Domain 1 of TNFR1 and competes with TAR2m-21-23 for binding to mouse TNFR1 or competes with TAR2h-205 for binding to human TNFR1.

In other embodiments, the invention is a domain antibody (dAb) monomer or ligand comprising a dAb that binds Tumor Necrosis Factor I (TNFR1), wherein said dAb binds Domain 3 of TNFR1 and competes with TAR2h-131-8, TAR2h-15-8, TAR2h-35-4, TAR2h-154-7, TAR2h-154-10 or TAR2h-185-25 for binding to human TNFR1.

The invention also relates to an antibody or antigen-binding fragment thereof that has binding specificity for TNFR1 and has efficacy in treating, suppressing or preventing a chronic inflammatory disease. In some embodiments, the antibody or antigen-binding fragment is a monovalent antigen-binding fragment.

The invention also provides a dAb monomer, and ligands comprising the dAb monomer, that has binding specificity for TNFR1 and inhibits TNFR-1-mediated signaling, but does not substantially inhibit binding of TNFα to TNFR1. In some embodiments the dAb monomer inhibits TNFα-induced crosslinking or clustering of TNFR1 on the surface of a cell.

The invention also provides isolated and/or recombinant nucleic acid molecules that encode the ligands of the invention, and vectors that comprise the recombinant nucleic acid molecules. Also provided are host cells comprising the recombinant nucleic acid molecules or vectors of the invention and methods for producing the ligands.

The invention also relates to pharmaceutical compositions comprising an antagonist or ligand of the invention and a pharmacologically, physiologically or pharmaceutically acceptable carrier.

The invention also relates to methods for treating, suppressing or preventing a disease or disorder (e.g., a chronic inflammatory disease, an autoimmune disorder, inflammatory disease, arthritis, multiple sclerosis, inflammatory bowel disease, chronic obstructive pulmonary disease, pneumonia, septic shock), comprising administering to a mammal in need thereof a therapeutically effective amount or dose of an antagonist or ligand of the invention.

The invention also relates to an antagonist or ligand of the invention for use in therapy or diagnosis, and to the use of an antagonist or ligand of the invention for the manufacture of a medicament for treating, suppressing or preventing a disease or disorder as described herein (e.g., a chronic inflammatory disease, an autoimmune disorder, inflammatory disease, arthritis, multiple sclerosis, inflammatory bowel disease, chronic obstructive pulmonary disease, pneumonia or septic shock. In other embodiments, the disease may be cystic fibrosis or severe steroid-resistant asthma).

The invention further relates to a pharmaceutical composition for treating, suppressing or preventing a disease or disorder described herein (e.g., a chronic inflammatory disease, an autoimmune disorder, inflammatory disease, arthritis, multiple sclerosis, inflammatory bowel disease, chronic obstructive pulmonary disease, pneumonia or septic shock. In other embodiments, the disease may be cystic fibrosis or severe steroid-resistant asthma) comprising an antagonist or ligand of the invention as an active ingredient.

The single variable domains or domain antibodies (dAb) that have binding specificity for TNFR1 and ligands comprising these single variable domains or dAbs have several advantages. For example, the single variable domains or dAbs that have binding specificity for TNFR1 described herein antagonize TNFR1. Accordingly therapeutic agents that comprise an anti-TNFR1 immunoglobulin single variable domain or dAb of the invention can be administered (e.g., for therapeutic, diagnostic or prophylactic purposes) with substantially reduced risk of side effects caused by binding and/or antagonizing TNFR2 (e.g., immunosuppression). Therapeutic agents that target TNF alpha, such as ENBREL® (entarecept; Immunex Corporation) antagonize TNFR1 and TNFR2, and administering such agents can produce immunosuppression and related side effects (e.g., serious infections). These side effects can limit the use of such agents, particularly for chronic diseases where the agent is administered over a long period. (Kollias G. and Kontoyiannis D., *Cytokine Growth Factor Rev.*, 13(4-5):315-321 (2002).) In contrast, because the ligands of the invention specifically antagonize TNFR1, they can be administered over long periods, on a chronic basis, with reduced risk of side effects and provide advantages for treating inflammatory conditions and chronic inflammatory conditions (including long duration diseases characterized by periods of quiescence and periods of active inflammation, such as inflammatory bowel disease and arthritis).

BRIEF DESCRIPTION OF THE DRAWINGS

FIG. 1 shows the diversification of $V_H$/HSA at positions H50, H52, H52a, H53, H55, H56, H58, H95, H96, H97, H98 (DVT or NNK encoded respectively) which are in the antigen binding site of $V_H$HSA. (SEQ ID NO:1, nucleotide sequence; SEQ ID NO:2, amino acid sequence.) The sequence of $V_K$ is diversified at positions L50, L53.

FIG. 2 is a schematic showing the structure of the plasmid pIT1/pIT2 used to prepare single chain Fv (scFv) libraries, and shows the nucleotide sequence of the plasmid across the expression control and cloning regions (SEQ ID NO:3) and the encoded amino acid sequence (SEQ ID NO:4). The plasmid was used to prepare Library 1: Germline V$_K$/DVT V$_H$,
Library 2: Germline V$_K$/NNK V$_H$,
Library 3: Germline V$_H$/DVT V$_K$, and
Library 4: Germline V$_H$/NNK V$_K$ in phage display/ScFv format.

These libraries were pre-selected for binding to generic ligands protein A and protein L so that the majority of the clones and selected libraries are functional. Libraries were selected on HSA (first round) and β-gal (second round) or HSA β-gal selection or on β-gal (first round) and HSA (second round) β-gal HSA selection. Soluble scFv from these clones of PCR are amplified in the sequence. One clone encoding a dual specific antibody K8 was chosen for further work.

FIG. 3 shows an alignment of V$_H$ chains (V$_H$ dummy (SEQ ID NO:5), K8 (SEQ ID NO:6), VH2 (SEQ ID NO:7), VH4 (SEQ ID NO:8), VHC11 (SEQ ID NO:9), VHA10d (SEQ ID NO:10), VHA1sd (SEQ ID NO:11), VHA5sd (SEQ ID NO:12), VHC5sd (SEQ ID NO:13), VHC11sd (SEQ ID NO:14), VHC11 sd (SEQ ID NO:15)) and V$_K$ chains (Vk dummy (SEQ ID NO:16), K8 (SEQ ID NO:17), E5sc (SEQ ID NO:18), C3 (SEQ ID NO:19)).

Figure 4:
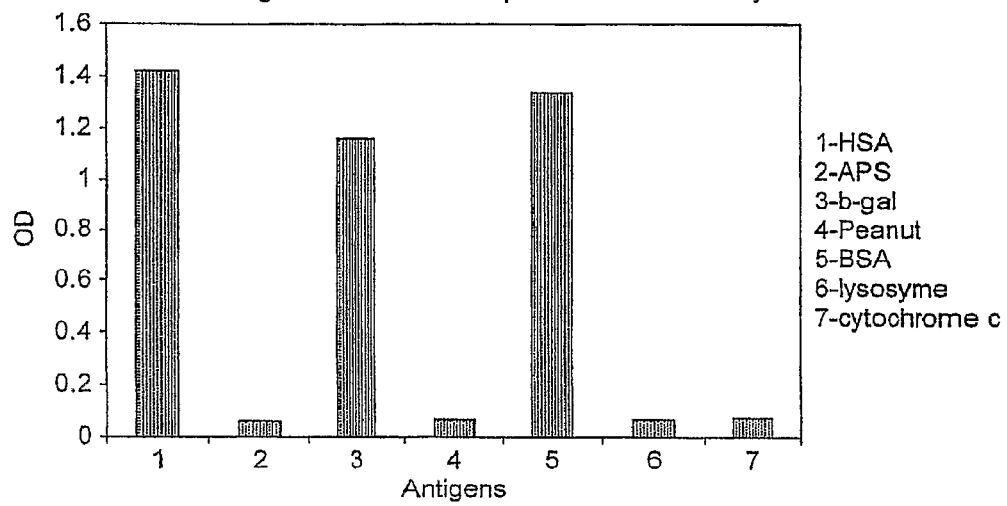

FIG. 4 shows the characterisation of the binding properties of the K8 antibody, the binding properties of the K8 antibody characterised by monoclonal phage ELISA, the dual specific K8 antibody was found to bind HSA and β-gal and displayed on the surface of the phage with absorbent signals greater than 1.0. No cross reactivity with other proteins was detected.

Figure 5:
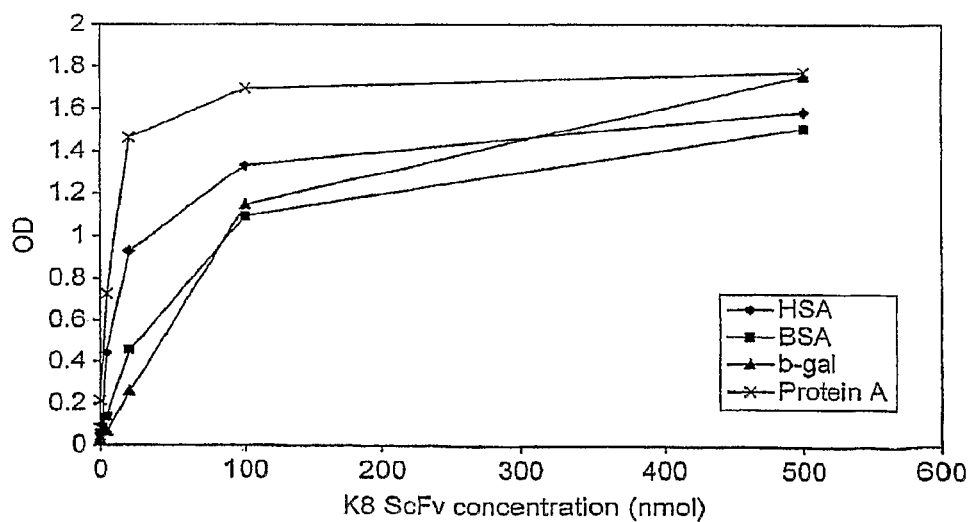

FIG. 5 shows soluble scFv ELISA performed using known concentrations of the K8 antibody fragment. A 96-well plate was coated with 100 μg of HSA, BSA and β-gal at 10 μg/ml and 100 μg/ml of Protein A at 1 μg/ml concentration. 50 μg of the serial dilutions of the K8 scFv was applied and the bound antibody fragments were detected with Protein L-HRP. ELISA results confirm the dual specific nature of the K8 antibody.

FIG. 6 shows the binding characteristics of the clone K8V$_K$/dummy V$_H$ analysed using soluble scFv ELISA. Production of the soluble scFv fragments was induced by IPTG as described by Harrison et al, Methods Enzymol. 1996; 267:83-109 and the supernatant containing scFv assayed directly. Soluble scFv ELISA is performed as described in example 1 and the bound scFvs were detected with Protein L-HRP. The ELISA results revealed that this clone was still able to bind β-gal, whereas binding BSA was abolished.

FIG. 7 shows the sequence (SEQ ID NO:2 and SEQ ID NO:3) of variable domain vectors 1 and 2.

Figure 8:
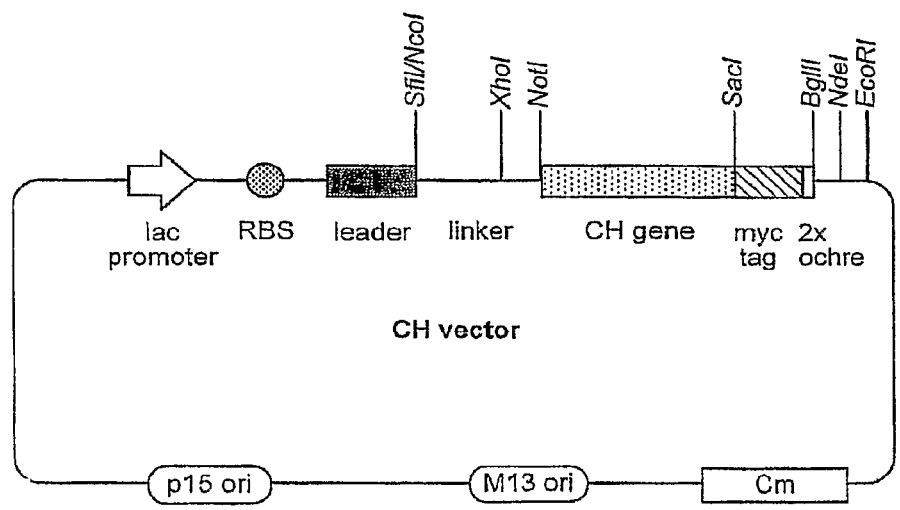

FIG. 8 is a map of the C$_H$ vector used to construct a V$_H$1/V$_H$2 multipsecific ligand.

Figure 9:
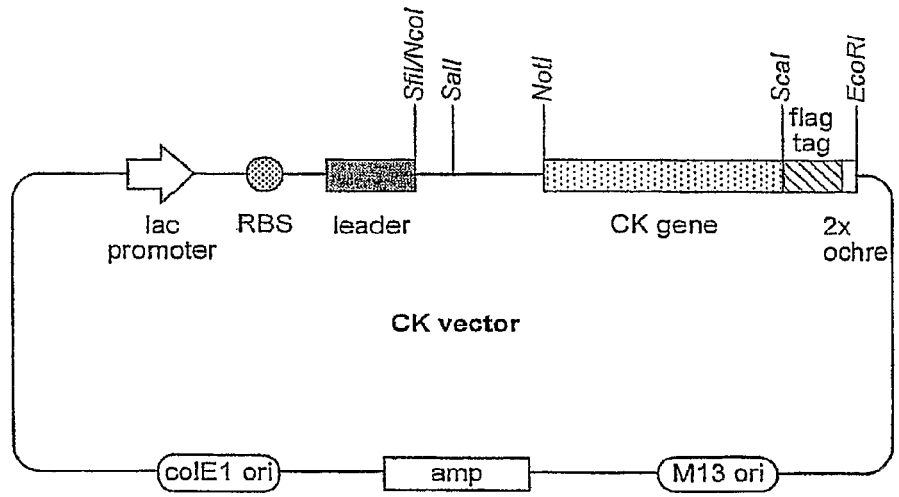

FIG. 9 is a map of the C$_K$ vector used to construct a V$_K$1/V$_K$2 multispecific ligand.

Figure 10:
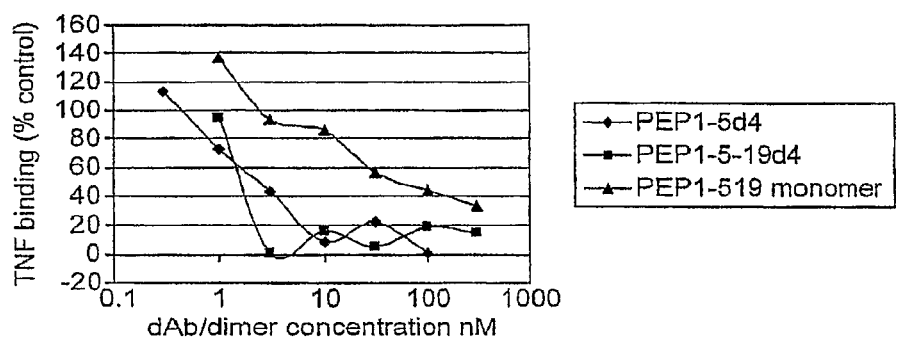

FIG. 10 shows a TNF receptor assay comparing TAR1-5 dimer 4, TAR1-5-19 dimer 4 and TAR1-5-19 monomer.

Figure 11:
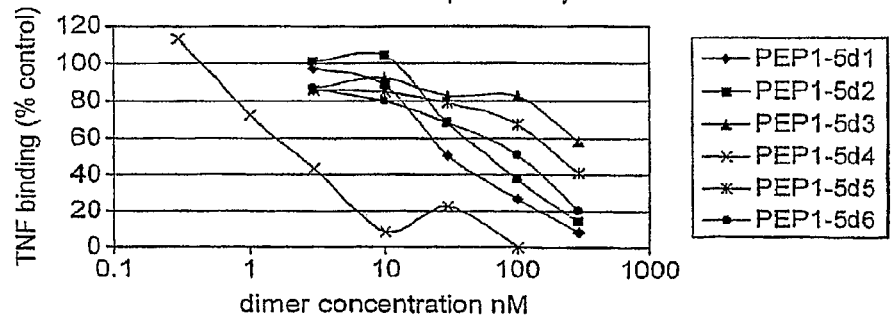

FIG. 11 shows a TNF receptor assay comparing TAR1-5 dimers 1-6. All dimers have been FPLC purified and the results for the optimal dimeric species are shown.

Figure 12:
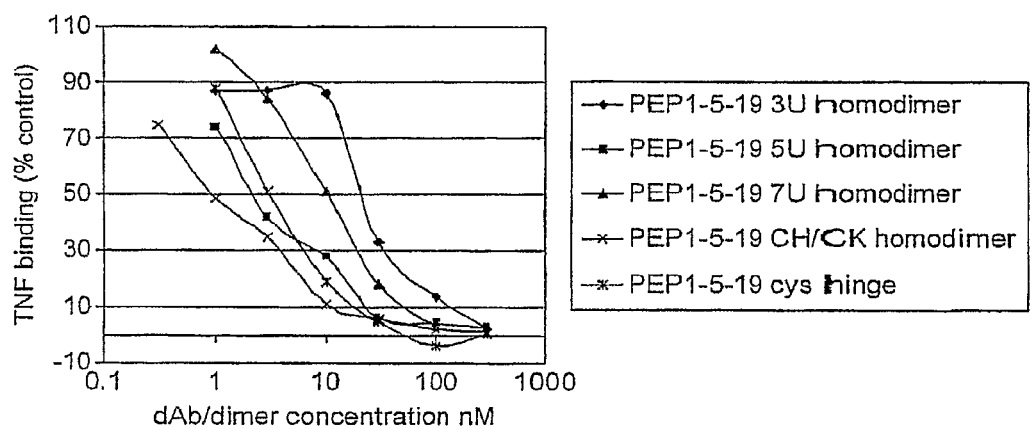

FIG. 12 shows a TNF receptor assay of TAR1-5 19 homodimers in different formats: dAb-linker-dAb format with 3U, 5U or 7U linker, Fab format and cysteine hinge linker format.

FIG. 13 shows Dummy VH sequence for library 1. (amino acid sequence ((SEQ ID NO:5; nucleotide sequences: coding strand (SEQ ID NO:20), noncoding strand (SEQ ID NO:21) The sequence of the VH framework based on germline sequence DP47-JH4b. Positions where NNK randomisation (N=A or T or C or G nucleotides; K=G or T nucleotides) has been incorporated into library 1 are indicated in bold underlined text.

FIG. 14 shows Dummy VH sequence for library 2. (amino acid sequence ((SEQ ID NO:22; nucleotide sequences: coding strand (SEQ ID NO:23), noncoding strand (SEQ ID NO:24) The sequence of the VH framework based on germline sequence DP47-JH4b. Positions where NNK randomisation (N=A or T or C or G nucleotides; K=G or T nucleotides) has been incorporated into library 2 are indicated in bold underlined text.

FIG. 15 shows Dummy V$_K$ sequence for library 3. (amino acid sequence ((SEQ ID NO:16; nucleotide sequences: coding strand (SEQ ID NO:25), noncoding strand (SEQ ID NO:26) The sequence of the V$_K$ framework based on germline sequence DP$_K$9-J$_K$1. Positions where NNK randomisation (N=A or T or C or G nucleotides; K=G or T nucleotides) has been incorporated into library 3 are indicated in bold underlined text.

FIG. 16 shows nucleotide and amino acid sequence of anti MSA dAbs MSA 16 (nucleotide sequence (SEQ ID NO:27), amino acid sequence (SEQ ID NO:28) and MSA 26 (nucleotide sequence (SEQ ID NO:29), amino acid sequence (SEQ ID NO:30).

Figure 17:
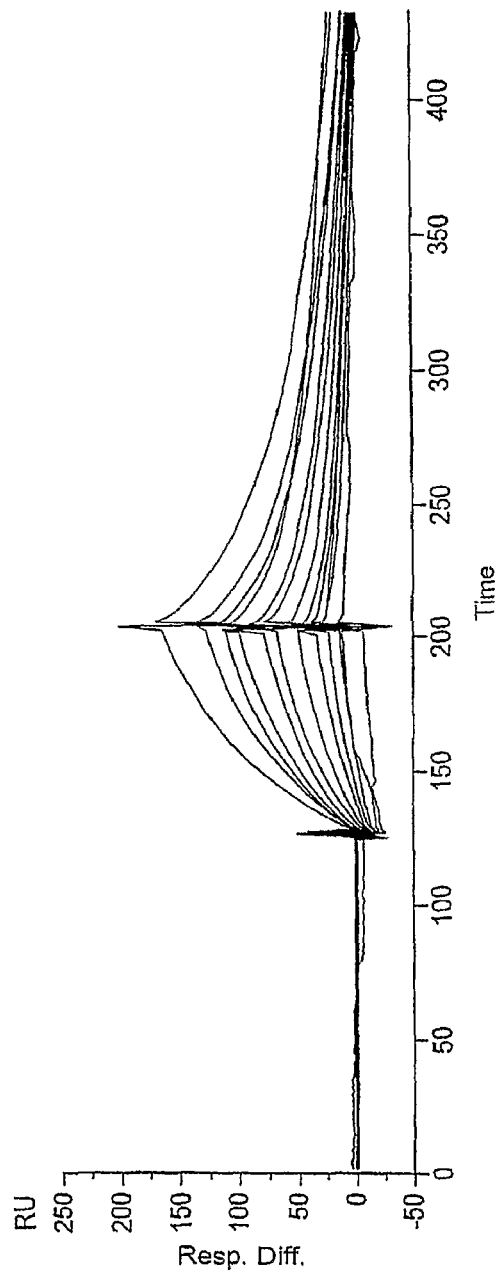

FIG. 17 shows inhibition biacore of MSA 16 and 26. Purified dAbs MSA16 and MSA26 were analysed by inhibition biacore to determine K$_d$. Briefly, the dAbs were tested to determine the concentration of dAb required to achieve 200 RUs of response on a biacore CM5 chip coated with a high density of MSA. Once the required concentrations of dAb had been determined, MSA antigen at a range of concentrations around the expected K$_d$ was premixed with the dAb and incubated overnight. Binding to the MSA coated biacore chip of dAb in each of the premixes was then measured at a high flow-rate of 30 μl/minute.

Figure 18:
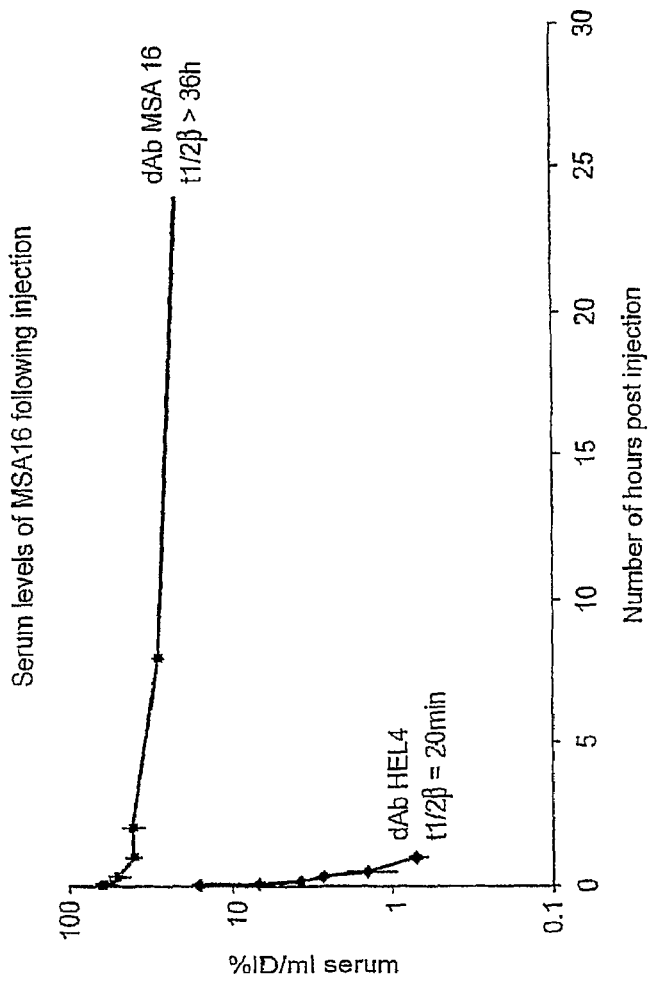

FIG. 18 shows serum levels of MSA16 following injection. Serum half life of the dAb MSA16 was determined in mouse. MSA16 was dosed as single i.v. injections at approx 1.5 mg/kg into CD1 mice. Modelling with a 2 compartment model showed MSA16 had a t1/2α of 0.98 hr, a t1/2β of 36.5 hr and an AUC of 913 hr.mg/ml. MSA16 had a considerably lengthened half life compared with HEL4 (an anti-hen egg white lysozyme dAb) which had a t1/2α of 0.06 hr and a t1/2β of 0.34 hr.

FIGS. 19a-19c shows an ELISA (FIG. 19a) and TNF receptor assay (FIGS. 19b, 19c) showing inhibition of TNF binding with a Fab-like fragment comprising MSA26Ck and TAR1-5-19CH. Addition of MSA with the Fab-like fragment reduces the level of inhibition. An ELISA plate coated with 1 μg/ml TNFα was probed with dual specific V$_K$ C$_H$ and V$_K$ Ck Fab like fragment and also with a control TNFα binding dAb at a concentration calculated to give a similar signal on the ELISA. Both the dual specific and control dAb were used to probe the ELISA plate in the presence and in the absence of 2 mg/ml MSA. The signal in the dual specific well was reduced by more than 50% but the signal in the dAb well was not reduced at all (see FIG. 19a). The same dual specific protein was also put into the receptor assay with and without MSA and competition by MSA was also shown (see FIG. 19c). This demonstrates that binding of MSA to the dual specific is competitive with binding to TNFα.

Figure 20:
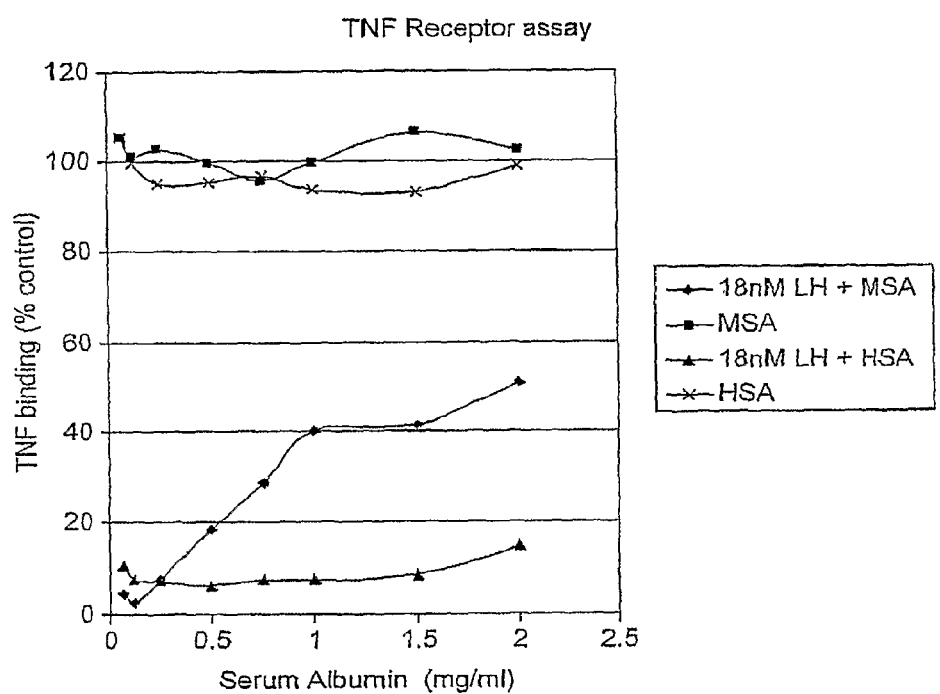

FIG. 20 shows a TNF receptor assay showing inhibition of TNF binding with a disulphide bonded heterodimer of TAR1-5-19 dAb and MSA16 dAb. Addition of MSA with the dimer reduces the level of inhibition in a dose dependant manner. The TNF receptor assay (FIG. 19 (b)) was conducted in the presence of a constant concentration of heterodimer (18 nM)

and a dilution series of MSA and HSA. The presence of HSA at a range of concentrations (up to 2 mg/ml) did not cause a reduction in the ability of the dimer to inhibit TNFα. However, the addition of MSA caused a dose dependant reduction in the ability of the dimer to inhibit TNFα (FIG. 19a). This demonstrates that MSA and TNFα compete for binding to the cys bonded TAR1-5-19, MSA16 dimer. MSA and HSA alone did not have an effect on the TNF binding level in the assay.

FIG. 21A-21M shows the amino acid sequences (SEQ ID NOS:31-98 and SEQ ID NOS:373-401 and 431) of several human immunoglobulin variable domains that have binding specificity for human TNFR1. The presented amino acid sequences are continuous with no gaps; the symbol ~ has been inserted into the sequences to indicate the locations of the complementarity determining regions (CDRs). CDR1 is flanked by ~, CDR2 is flanked by ~~, and CDR3 is flanked by ~~~.

FIG. 22A-22T shows the nucleotide sequences (SEQ ID NOS:99-166 and SEQ ID NOS:402-430 and 432) of several nucleic acids that encode the human immunoglobulin variable domains presented in FIG. 21A-21M. The presented nucleotide sequences are continuous with no gaps; the symbol ~ has been inserted into the sequences to indicate the location of the sequences encoding the CDRs. The sequences encoding CDR1 are flanked by the sequences encoding CDR2 are flanked by ~~, and the sequences encoding CDR3 are flanked by ~~~.

FIG. 23A-23B shows the amino acid sequences (SEQ ID NOS:167-179) of several human immunoglobulin variable domains that have binding specificity for mouse TNFR1. The presented amino acid sequences are continuous with no gaps. In some of the sequences the symbol ~ has been inserted to indicate the location of the complementarity determining regions (CDRs). CDR1 is flanked by ~, CDR2 is flanked by ~~, and CDR3 is flanked by ~~~.

FIG. 24A-24C shows the nucleotide sequences (SEQ ID NOS:180-192 and 626) of several nucleic acids that encode the human immunoglobulin variable domains presented in FIG. 23A-23B. SEQ ID NO:186 and SEQ ID NO:626 both encode the amino acid sequence of SEQ ID NO:173. The sequences of SEQ ID NO:626 encoding CDR1 are flanked by ~, the sequences encoding CDR2 are flanked by ~~, and the sequences encoding CDR3 are flanked by ~~~.

Figure 25F:
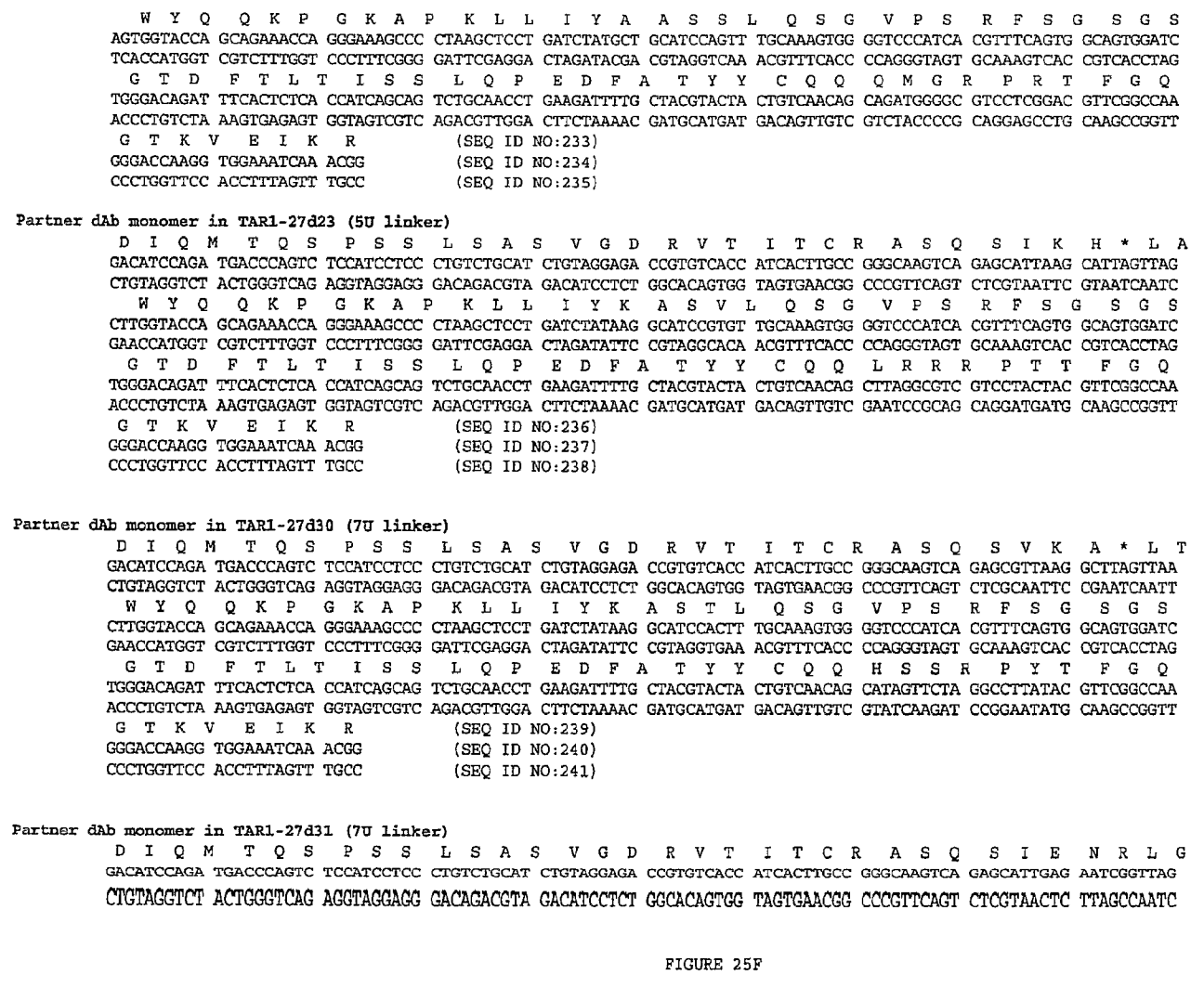

FIG. 25A-25L shows the nucleotide sequences encoding several human immunoglobulin variable domains and the amino acid sequences of the encoded human immunoglobulin variable domains (SEQ ID NOS:193-198 and 200-295).

Figure 26:
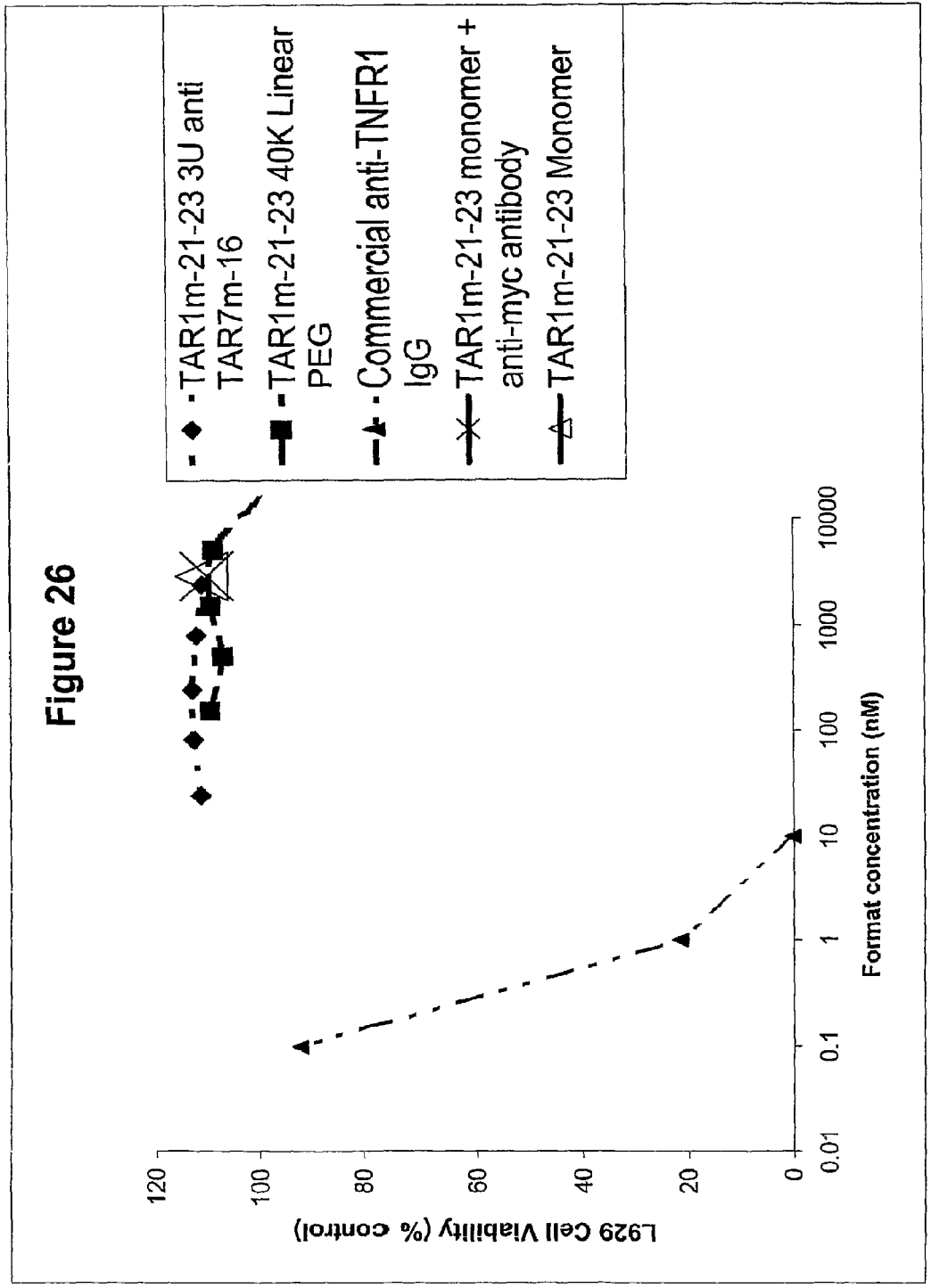

FIG. 26 is a graph showing that anti-TNFR1 dAb formats do not substantially agonize TNFR1 in an L929 assay. L929 cells were cultured in media that contained a range of concentrations of anti-TNFR1 dAb monomer (TAR2m-21-23), TAR2m-21-23 monomer cross-linked by a commercially available anti-myc antibody (9E10), dual specific anti-TNFR1 dAb/anti-SA dAb (TAR2m-21-23 3U TAR7m-16), or pegylated anti-TNFR1 dAb monomer (TAR2m-21-23 40K PEG). In the case of TAR2m-21-23 monomer cross-linked by the anti-myc antibody, the dAb and antibody were mixed in a 2:1 ratio and pre-incubated for one hour at room-temperature to simulate the effects of in vivo immune cross-linking prior to culture. (The TAR2m-21-23 monomer includes a myc epitope.) TAR2m-21-23 monomer was incubated with the L929 cells at a concentration of 3,000 nM. TAR2m-21-23 monomer and anti-Myc antibody were incubated at a dAb concentration of 3,000 nM. TAR2m-21-23 3U TAR7m-16 was incubated with the cells at 25 nM, 83.3 nM, 250 nM, 833 nM and 2,500 nM concentrations. TAR2m-21-23 40K PEG was incubated with the cells at 158.25 nM, 527.5 nM, 1582.5 nM, 5,275 nM and 15,825 nM concentrations. After incubation overnight, cell viability was assessed. The results revealed that incubation of L929 cells with 10 nM, 1 nM or 0.1 nM of a commercially-available anti-TNFR1 IgG antibody that crosslinks and agonizes TNFR1 (Catalog No. AF-425-PB; R&D Systems, Minneapolis, Minn.) resulted in a dose-dependent increase in non-viable cells, thereby demonstrating the sensitivity of these cells to agonists of TNFR1. In contrast, incubation with various amounts of anti-TNFR1 formats did not antagonize TNFR1 and did not result in an increase in the number of non-viable cells in the cultures, even when used at more than 1000 times the concentration of the commercially-available anti-TNFR1 IgG antibody.

FIG. 27A-27I shows the amino acid sequences (SEQ ID NOS:433-517 and 627) of several human immunoglobulin variable domains that have binding specificity for human TNFR1. The presented amino acid sequences are continuous with no gaps; the symbol ~ has been inserted into the sequences to indicate the locations of the complementarity determining regions (CDRs). CDR1 is flanked by ~, CDR2 is flanked by ~~, and CDR3 is flanked by ~~~.

FIG. 28A-28O shows the nucleotide sequences (SEQ ID NOS:518-602 and 628) of several nucleic acids that encode the human immunoglobulin variable domains presented in FIG. 27A-27H. The presented nucleotide sequences are continuous with no gaps; the symbol ~ has been inserted into the sequences to indicate the location of the sequences encoding the CDRs. The sequences encoding CDR1 are flanked by ~, the sequences encoding CDR2 are flanked by ~~, and the sequences encoding CDR3 are flanked by ~~~.

DETAILED DESCRIPTION OF THE INVENTION

Within this specification embodiments have been described in a way which enables a clear and concise specification to be written, but it is intended and will be appreciated that embodiments may be variously combined or separated without parting from the invention.

Definitions

"Complementary" Two immunoglobulin domains are "complementary" where they belong to families of structures which form cognate pairs or groups or are derived from such families and retain this feature. For example, a $V_H$ domain and a $V_L$ domain of an antibody are complementary; two $V_H$ domains are not complementary, and two $V_L$ domains are not complementary. Complementary domains may be found in other members of the immunoglobulin superfamily, such as the $V_α$ and $V_β$ (or γ and δ) domains of the T-cell receptor. In the context of the second configuration of the present invention, non-complementary domains do not bind a target molecule cooperatively, but act independently on different target epitopes which may be on the same or different molecules. Domains which are artificial, such as domains based on protein scaffolds which do not bind epitopes unless engineered to do so, are non-complementary. Likewise, two domains based on (for example) an immunoglobulin domain and a fibronectin domain are not complementary.

"Immunoglobulin" This refers to a family of polypeptides which retain the immunoglobulin fold characteristic of antibody molecules, which contains two β sheets and, usually, a conserved disulphide bond. Members of the immunoglobulin superfamily are involved in many aspects of cellular and non-cellular interactions in vivo, including widespread roles in the immune system (for example, antibodies, T-cell receptor molecules and the like), involvement in cell adhesion (for example the ICAM molecules) and intracellular signalling (for example, receptor molecules, such as the PDGF receptor). The present invention is applicable to all immunoglobulin superfamily molecules which possess binding domains. Preferably, the present invention relates to antibodies.

"Combining" Variable domains according to the invention are combined to form a group of domains; for example, complementary domains may be combined, such as $V_L$ domains being combined with $V_H$ domains. Non-complementary domains may also be combined. Domains may be combined in a number of ways, involving linkage of the domains by covalent or non-covalent means.

"Domain" A domain is a folded protein structure which retains its tertiary structure independently of the rest of the protein. Generally, domains are responsible for discrete functional properties of proteins, and in many cases may be added, removed or transferred to other proteins without loss of function of the remainder of the protein and/or of the domain. By single antibody variable domain is meant a folded polypeptide domain comprising sequences characteristic of antibody variable domains. It therefore includes complete antibody variable domains and modified variable domains, for example in which one or more loops have been replaced by sequences which are not characteristic of antibody variable domains, or antibody variable domains which have been truncated or comprise N- or C-terminal extensions, as well as folded fragments of variable domains which retain at least in part the binding activity and specificity of the full-length domain.

"Repertoire" A collection of diverse variants, for example polypeptide variants which differ in their primary sequence. A library used in the present invention will encompass a repertoire of polypeptides comprising at least 1000 members.

"Library" The term library refers to a mixture of heterogeneous polypeptides or nucleic acids. The library is composed of members, each of which have a single polypeptide or nucleic acid sequence. To this extent, library is synonymous with repertoire. Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. Preferably, each individual organism or cell contains only one or a limited number of library members. Advantageously, the nucleic acids are incorporated into expression vectors, in order to allow expression of the polypeptides encoded by the nucleic acids. In a preferred aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of genetically diverse polypeptide variants.

A "closed conformation multi-specific ligand" describes a multi-specific ligand as herein defined comprising at least two epitope binding domains as herein defined. The term 'closed conformation' (multi-specific ligand) means that the epitope binding domains of the ligand are arranged such that epitope binding by one epitope binding domain competes with epitope binding by another epitope binding domain. That is, cognate epitopes may be bound by each epitope binding domain individually but not simultaneously. The closed conformation of the ligand can be achieved using methods herein described.

"Antibody" An antibody (for example IgG, IgM, IgA, IgD or IgE) or fragment (such as a Fab, F(ab')$_2$, Fv, disulphide linked Fv, scFv, closed conformation multispecific antibody, disulphide-linked scFv, diabody) whether derived from any species naturally producing an antibody, or created by recombinant DNA technology; whether isolated from serum, B-cells, hybridomas, transfectomas, yeast or bacteria).

"Dual-specific ligand" A ligand comprising a first immunoglobulin single variable domain and a second immunoglobulin single variable domain as herein defined, wherein the variable regions are capable of binding to two different antigens or two epitopes on the same antigen which are not normally bound by a monospecific immunoglobulin. For example, the two epitopes may be on the same hapten, but are not the same epitope or sufficiently adjacent to be bound by a monospecific ligand. The dual specific ligands according to the invention are composed of variable domains which have different specificities, and do not contain mutually complementary variable domain pairs which have the same specificity.

"Antigen" A molecule that is bound by a ligand according to the present invention. Typically, antigens are bound by antibody ligands and are capable of raising an antibody response in vivo. It may be a polypeptide, protein, nucleic acid or other molecule. Generally, the dual specific ligands according to the invention are selected for target specificity against a particular antigen. In the case of conventional antibodies and fragments thereof, the antibody binding site defined by the variable loops (L1, L2, L3 and H1, H2, H3) is capable of binding to the antigen. "Epitope" A unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation.

"Generic ligand" A ligand that binds to all members of a repertoire. Generally, not bound through the antigen binding site as defined above. Non-limiting examples include protein A, protein L and protein G.

"Selecting" Derived by screening, or derived by a Darwinian selection process, in which binding interactions are made between a domain and the antigen or epitope or between an antibody and an antigen or epitope. Thus a first variable domain may be selected for binding to an antigen or epitope in the presence or in the absence of a complementary variable domain.

"Universal framework" A single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. The invention provides for the use of a single framework, or a set of such frameworks, which has been found to permit the derivation of virtually any binding specificity though variation in the hypervariable regions alone.

"Half-life" The time taken for the serum concentration of the ligand to reduce by 50%, in vivo, for example due to degradation of the ligand and/or clearance or sequestration of the ligand by natural mechanisms. The ligands of the invention are stabilised in vivo and their half-life increased by binding to molecules which resist degradation and/or clearance or sequestration. Typically, such molecules are naturally occurring proteins which themselves have a long half-life in vivo. The half-life of a ligand is increased if its functional activity persists, in vivo, for a longer period than a similar ligand which is not specific for the half-life increasing molecule. Thus, a ligand specific for HSA and a target molecule is compared with the same ligand wherein the specificity for HSA is not present, that it does not bind HSA but binds another molecule. For example, it may bind a second epitope on the target molecule. Typically, the half life is increased by 10%, 20%, 30%, 40%, 50% or more. Increases in the range of 2×, 3×, 4×, 5×, 10×, 20×, 30×, 40×, 50× or more of the half life are possible. Alternatively, or in addition, increases in the range of up to 30×, 40×, 50×, 60×, 70×, 80×, 90×, 100×, 150× of the half life are possible.

"Homogeneous immunoassay" An immunoassay in which analyte is detected without need for a step of separating bound and un-bound reagents.

"Substantially identical (or "substantially homologous")" A first amino acid or nucleotide sequence that contains a sufficient number of identical or equivalent (e.g., with a similar side chain, e.g., conserved amino acid substitutions) amino acid residues or nucleotides to a second amino acid or nucleotide sequence such that the first and second amino acid or nucleotide sequences have similar activities. In the case of antibodies, the second antibody has the same binding specificity and has at least 50% of the affinity of the same.

As used herein, the terms "low stringency," "medium stringency," "high stringency," or "very high stringency conditions" describe conditions for nucleic acid hybridization and washing. Guidance for performing hybridization reactions can be found in *Current Protocols in Molecular Biology*, John Wiley & Sons, N.Y. (1989), 6.3.1-6.3.6, which is incorporated herein by reference in its entirety. Aqueous and non-aqueous methods are described in that reference and either can be used. Specific hybridization conditions referred to herein are as follows: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and preferably (4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

As herein defined the term "closed conformation" (multi-specific ligand) means that the epitope binding domains of the ligand are attached to or associated with each other, optionally by means of a protein skeleton, such that epitope binding by one epitope binding domain competes with epitope binding by another epitope binding domain. That is, cognate epitopes may be bound by each epitope binding domain individually but not simultaneously. The closed conformation of the ligand can be achieved using methods herein described.

"Open conformation" means that the epitope binding domains of the ligand are attached to or associated with each other, optionally by means of a protein skeleton, such that epitope binding by one epitope binding domain does not compete with epitope binding by another epitope binding domain.

As referred to herein, the term "competes" means that the binding of a first epitope to its cognate epitope binding domain is inhibited when a second epitope is bound to its cognate epitope binding domain. For example, binding may be inhibited sterically, for example by physical blocking of a binding domain or by alteration of the structure or environment of a binding domain such that its affinity or avidity for an epitope is reduced.

The phrase "immunoglobulin single variable domain" refers to an antibody variable region ($V_H$, $V_{HH}$, $V_L$) that specifically binds an antigen or epitope independently of other V regions or domains; however, as the term is used herein, an immunoglobulin single variable domain can be present in a format (e.g., homo- or hetero-multimer) with other variable regions or variable domains where the other regions or domains are not required for antigen binding by the single immunoglobulin variable domain (i.e., where the immunoglobulin single variable domain binds antigen independently of the additional variable domains). "Immunoglobulin single variable domain" encompasses not only an isolated antibody single variable domain polypeptide, but also larger polypeptides that comprise one or more monomers of an antibody single variable domain polypeptide sequence. A "domain antibody" or "dAb" is the same as an "immunoglobulin single variable domain" polypeptide as the term is used herein. An immunoglobulin single variable domain polypeptide, as used herein refers to a mammalian immunoglobulin single variable domain polypeptide, preferably human, but also includes rodent (for example, as disclosed in WO 00/29004, the contents of which are incorporated herein by reference in their entirety) or camelid $V_{HH}$ dAbs. Camelid dAbs are immunoglobulin single variable domain polypeptides which are derived from species including camel, llama, alpaca, dromedary, and guanaco, and comprise heavy chain antibodies naturally devoid of light chain: $V_{HH}$. $V_{HH}$ molecules are about ten times smaller than IgG molecules, and as single polypeptides, they are very stable, resisting extreme pH and temperature conditions.

As used herein, the term "antagonist of Tumor Necrosis Factor Receptor 1 (TNFR1)" refers to an agent (e.g., a molecule, a compound) which binds TNFR1 and can inhibit a (i.e., one or more) function of TNFR1. For example, an antagonist of TNFR1 can inhibit the binding of TNFα to TNFR1 and/or inhibit signal transduction mediated through TNFR1. Accordingly, TNFR1-mediated processes and cellular responses (e.g., TNFα-induced cell death in a standard L929 cytotoxicity assay) can be inhibited with an antagonist of TNFR1. An antagonist of TNFR1 can be, for example, a small organic molecule, natural product, protein, peptide or peptidomimetic. Antagonists of TNFR1 can be identified, for example, by screening libraries or collections of molecules, such as, the Chemical Repository of the National Cancer Institute, as described herein or using other suitable methods. Preferred antagonists of TNFR1 are antibodies, antigen-binding fragments of antibodies, ligands and dAb monomers described herein.

Sequences similar or homologous (e.g., at least about 70% sequence identity) to the sequences disclosed herein are also part of the invention. In some embodiments, the sequence identity at the amino acid level can be about 80%, 85%, 90%, 91%, 92%, 93%, 94%, 95%, 96%, 97%, 98%, 99% or higher. At the nucleic acid level, the sequence identity can be about 70%, 75%, 80%, 85%, 90%, 91%, 92%, 93%, 94%, 95%, 96%, 97%, 98%, 99% or higher. Alternatively, substantial identity exists when the nucleic acid segments will hybridize under selective hybridization conditions (e.g., very high stringency hybridization conditions), to the complement of the strand. The nucleic acids may be present in whole cells, in a cell lysate, or in a partially purified or substantially pure form.

Calculations of "homology" or "sequence identity" or "similarity" between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "homology" is equivalent to amino acid or nucleic acid "identity"). The percent identity between the two sequences is a function of the number of identical positions shared by the sequences, taking into account the number of gaps, and the length of each gap, which need to be introduced for optimal alignment of the two sequences.

Advantageously, the BLAST algorithm (version 2.0) is employed for sequence alignment, with parameters set to default values. The BLAST algorithm is described in detail at the world wide web site ("www") of the National Center for Biotechnology Information (".ncbi") of the National Institutes of Health ("nih") of the U.S. government (".gov"), in the "/Blast/" directory, in the "blast_help.html" file. The search parameters are defined as follows, and are advantageously set to the defined default parameters.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul, 1990, Proc. Natl. Acad. Sci. USA 87(6): 2264-8 (see the "blast_help.html" file, as described above) with a few enhancements. The BLAST programs were tailored for sequence similarity searching, for example to identify homologues to a query sequence. The programs are not generally useful for motif-style searching. For a discussion of basic issues in similarity searching of sequence databases, see Altschul et al. (1994).

The five BLAST programs available at the National Center for Biotechnology Information web site perform the following tasks:

"blastp" compares an amino acid query sequence against a protein sequence database;

"blastn" compares a nucleotide query sequence against a nucleotide sequence database;

"blastx" compares the six-frame conceptual translation products of a nucleotide query sequence (both strands) against a protein sequence database;

"tblastn" compares a protein query sequence against a nucleotide sequence database dynamically translated in all six reading frames (both strands).

"tblastx" compares the six-frame translations of a nucleotide query sequence against the six-frame translations of a nucleotide sequence database.

BLAST uses the following search parameters:

HISTOGRAM Display a histogram of scores for each search; default is yes. (See parameter H in the BLAST Manual).

DESCRIPTIONS Restricts the number of short descriptions of matching sequences reported to the number specified; default limit is 100 descriptions. (See parameter V in the manual page). See also EXPECT and CUTOFF.

ALIGNMENTS Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

EXPECT The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

MATRIX Specify an alternate scoring matrix for BLASTP, BLASTX, TBLASTN and TBLASTX. The default matrix is BLOSUM62 (Henikoff & Henikoff, 1992, Proc. Natl. Aacad. Sci. USA 89(22):10915-9). The valid alternative choices include: PAM40, PAM120, PAM250 and IDENTITY. No alternate scoring matrices are available for BLASTN; specifying the MATRIX directive in BLASTN requests returns an error response.

STRAND Restrict a TBLASTN search to just the top or bottom strand of the database sequences; or restrict a BLASTN, BLASTX or TBLASTX search to just reading frames on the top or bottom strand of the query sequence.

FILTER Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States, 1993, Computers and Chemistry 17:191-201, or, for BLASTN, by the DUST program of Tatusov and Lipman (see the world wide web site of the NCBI). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "N" repeated 13 times) and the letter "X" in protein sequences (e.g., "X" repeated 9 times).

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi Causes NCBI gi identifiers to be shown in the output, in addition to the accession and/or locus name.

Most preferably, sequence comparisons are conducted using the simple BLAST search algorithm provided at the NCBI world wide web site described above, in the "/BLAST" directory.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods (see generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc. which are incorporated herein by reference) and chemical methods.

TNFR1 is a transmembrane receptor containing an extracellular region that binds ligand and an intracellular domain that lacks intrinsic signal transduction activity but can associate with signal transduction molecules. The complex of TNFR1 with bound TNF contains three TNFR1 chains and three TNF chains. (Banner et al., Cell, 73(3) 431-445 (1993) The TNF ligand is present as a trimer, which is bound by three TNFR1 chains. (Id.) The three TNFR1 chains are clustered closely together in the receptor-ligand complex, and this clustering is a prerequisite to TNFR1-mediated signal transduction. In fact, multivalent agents that bind TNFR1, such as anti-TNFR1 antibodies, can induce TNFR1 clustering and signal transduction in the absence of TNF and are commonly used as TNFR1 agonists. (See, e.g., Belka et al., *EMBO*, 14(6):1156-1165 (1995); Mandik-Nayak et al., *J. Immunol*, 167:1920-1928 (2001).) Accordingly, multivalent agents that bind TNFR1, are generally not effective antagonists of TNFR1 even if they block the binding of TNFα to TNFR1.

The extracellular region of TNFR1 comprises a thirteen amino acid amino-terminal segment (amino acids 1-13 of SEQ ID NO:603 (human); amino acids 1-13 of SEQ ID NO:604 (mouse)), Domain 1 (amino acids 14-53 of SEQ ID NO:603 (human); amino acids 14-53 of SEQ ID NO:604 (mouse)), Domain 2 (amino acids 54-97 of SEQ ID NO: 603 (human); amino acids 54-97 of SEQ ID NO:604 (mouse)), Domain 3 (amino acids 98-138 of SEQ ID NO: 603 (human); amino acid 98-138 of SEQ ID NO:604 (mouse)), and Domain 4 (amino acids 139-167 of SEQ ID NO:603 (human); amino acids 139-167 of SEQ ID NO:604 (mouse)) which is followed by a membrane-proximal region (amino acids 168-182 of SEQ ID NO:603_(human); amino acids 168-183 SEQ ID NO: 604 (mouse)). (See, Banner et al., *Cell* 73(3) 431-445 (1993) and Loetscher et al., *Cell* 61(2) 351-359 (1990).) Domains 2 and 3 make contact with bound ligand (TNFβ, TNFα). (Banner et al., *Cell*, 73(3) 431-445 (1993).) The extracellular region of TNFR1 also contains a region referred to as the pre-ligand binding assembly domain or PLAD domain (amino acids 1-53 of SEQ ID NO:603_(human); amino acids 1-53 of SEQ ID NO:604 (mouse)) (The Government of the USA, WO 01/58953; Deng et al., *Nature Medicine, doi:* 10.1038/nm1304 (2005)).

TNFR1 is shed from the surface of cells in vivo through a process that includes proteolysis of TNFR1 in Domain 4 or in the membrane-proximal region (amino acids 168-182 of SEQ ID NO:603; amino acids 168-183 of SEQ ID NO:604), to produce a soluble form of TNFR1. Soluble TNFR1 retains the capacity to bind TNFα, and thereby functions as an endogenous inhibitor of the activity of TNFα.

The invention relates to an antibody or antigen-binding fragment thereof (e.g., dAb) or ligand that binds TNFR1 but does not compete with TNF for binding to TNFR1. For example, the antibody or antigen-binding fragment thereof (e.g., dAb) or ligand can bind Domain 1 of TNFR1 or Domain 4 of TNFR1. Such antibody or antigen-binding fragment thereof (e.g., dAb) or ligand provide advantages as diagnostic agents, and can be used to bind and detect, quantify or measure TNFR1 in a sample but will not compete with TNF in the sample for binding to TNFR1. Accordingly, an accurate determination of whether TNFR1 is present in the sample or how much TNFR1 is in the sample can be made. In some embodiments, the antibody or antigen-binding fragment thereof (e.g., dAb) or ligand that binds TNFR1 but does not compete with TNF for binding to TNFR1 is an antagonist of TNFR1 as described herein.

The invention also relates to a diagnostic kit for determine whether TNFR1 is present in a sample or how much TNFR1 is present in a sample, comprising an antibody or antigen-binding fragment thereof (e.g., dAb) or ligand that binds TNFR1 but does not compete with TNF for binding to TNFR1 and instructions for use (e.g., to determine the presence and/or quantity of TNFR1 in the sample). In some embodiments, the kit further comprises one or more ancillary reagents, such as a suitable buffer or suitable detecting reagent (e.g., a detectably labeled antibody or antigen-binding fragment thereof that binds the antibody or antigen-binding fragment thereof (e.g., dAb) or ligand that binds TNFR1 but does not compete with TNF for binding to TNFR1).

The invention also relates to a device comprising a solid surface on which an antibody or antigen-binding fragment thereof (e.g., dAb) or ligand that binds TNFR1 but does not compete with TNF for binding to TNFR1 is immobilized such that the immobilized antibody or antigen-binding fragment thereof (e.g., dAb) or ligand binds TNFR1. Any suitable solid surfaces on which an antibody or antigen-binding fragment thereof (e.g., dAb) or ligand can be immobilized can be used, for example, glass, plastics, carbohydrates (e.g., agarose beads). If desired the support can contain or be modified to contain desired functional groups to facilitate immobilizing the antibody or antigen-binding fragment thereof (e.g., dAb) or ligand. The device, and or support, can have any suitable shape, for example, a sheet, rod, strip, plate, slide, bead, pellet, disk, gel, tube, sphere, chip, plate or dish, and the like. In some embodiments, the device is a dipstick.

The invention relates to antagonists of TNFR1 (e.g., ligands described herein) that have binding specificity for Tumor Necrosis Factor Receptor 1 (TNFR1; p55; CD120a). Preferably the antagonists of the inventions do not have binding specificity for Tumor Necrosis Factor 2 (TNFR2), or do not substantially antagonize TNFR2. An antagonist of TNFR1 does not substantially antagonize TNFR2 when the antagonist (1 nM, 10 nM, 100 nM, 1 μM, 10 μM or 100 μM) results in no more than about 5% inhibition of TNFR2-mediated activity induced by TNFα (100 pg/ml) in a standard cell assay. Particularly preferred antagonists of TNFR1 are effective therapeutics for treating chronic inflammatory disease (are efficacious, have therapeutic efficacy). For example, in some embodiments, the antagonist of TNFR1 is efficacious in a model of chronic inflammatory disease, such as the mouse collagen-induced arthritis model, mouse ΔARE model of arthritis, mouse dextran sulfate sodium-induced model of inflammatory bowel disease, mouse ΔARE model of inflammatory bowel disease, mouse tobacco smoke model of chronic obstructive pulmonary disease or a suitable primate model (e.g., primate collagen-induced arthritis).

Antagonists of TNFR1 can be monovalent or multivalent. In some embodiments, the antagonist is monovalent and contains one binding site that interacts with TNFR1. Monovalent antagonists bind one TNFR1 and do not induce cross-linking or clustering of TNFR1 on the surface of cells which can lead to activation of the receptor and signal transduction. In particular embodiments, the monovalent antagonist of TNFR1 binds to Domain 1 of TNFR1. In more particular embodiments, the monovalent antagonist of TNFR1 binds to Domain 1 of TNFR1, and competes with TAR2m-21-23 for binding to mouse TNFR1 or competes with TAR2h-205 for binding to human TNFR1.

In other embodiments, the antagonist of TNFR1 is multivalent. Multivalent antagonists of TNFR1 can contain two or more copies of a particular binding site for TNFR1 or contain two or more different binding sites that bind TNFR1. For example, as described herein the antagonist of TNFR1 can be a dimer, trimer or multimer comprising two or more copies of a particular dAb that binds TNFR1, or two or more different dAbs that bind TNFR1. Preferably, a multivalent antagonist of TNFR1 does not substantially agonize TNFR1 (act as an agonist of TNFR1) in a standard cell assay (i.e., when present at a concentration of 1 nM, 10 nM, 100 nM, 1 μM, 10 μM, 100 μM, 1000 μM or 5,000 μM, results in no more than about 5% of the TNFR1-mediated activity induced by TNFα (100 pg/ml) in the assay).

In certain embodiments, the multivalent antagonist of TNFR1 contains two or more binding sites for a desired epitope or domain of TNFR1. For example, the multivalent antagonist of TNFR1 can comprise two or more binding sites that bind the same epitope in Domain 1 of TNFR1.

In other embodiments, the multivalent antagonist of TNFR1 contains two or more binding sites that bind to different epitopes or domains of TNFR1. In one example, the multivalent antagonist of TNFR1 comprises a first binding site that binds a first epitope in Domain 1 of TNFR1, and a second binding site that binds a second different epitope in Domain 1. In other examples, the multivalent antagonist of TNFR1 can comprise binding sites that bind two or more desired epitopes or domains of TNFR1. For example, the multivalent antagonists of TNFR1 can comprise binding sites for Domains 1 and 2, Domains 1 and 3, Domains 1 and 4, Domains 2 and 3, Domains 2 and 4, or Domains 3 and 4 of TNFR1. For example, the multivalent antagonists of TNFR1 can comprise binding sites for Domains 1, 2, and 3, binding sites for Domains 1, 2 and 4, or binding sites for Domains 1, 3 and 4 of TNFR1. In certain embodiments, the antagonist of TNFR1 is a dual specific ligand comprising a dAb that binds Domain 1 of TNFR1, and a dAb that binds Domain 3 of TNFR1. Preferably, such multivalent antagonists do not agonize TNFR1 when present at a concentration of about 1 nM, or about 10 nM, or about 100 nM, or about 1 μM, or about 10 μM, in a standard L929 cytotoxicity assay or a standard HeLa IL-8 assay as described herein.

Some antagonists of TNFR1 bind TNFR1 and inhibit binding of TNFα to TNFR1. In certain embodiments, such an antagonist of TNFR1 binds Domain 2 and/or Domain 3 of TNFR1. In particular embodiments, the antagonist competes with TAR2h-10-27, TAR2h-131-8, TAR2h-15-8, TAR2h-35-4, TAR2h-154-7, TAR2h-154-10 or TAR2h-185-25 for binding to TNFR1.

Other ligands (which in preferred embodiments are antagonists of TNFR1) do no inhibit binding of TNFα to TNFR1. Such ligands (and antagonists) provide advantages as diagnostic agents, because they can be used to bind and detect, quantify or measure TNFR1 in a sample and will not compete with TNF in the sample for binding to TNFR1. Accordingly, an accurate determination of whether or how much TNFR1 is in the sample can be made.

Some antagonists of TNFR1 do not inhibit binding of TNFα to TNFR1, but do inhibit signal transduction mediated through TNFR1. For example, an antagonist of TNFR1 can inhibit TNFα-induced clustering of TNFR1, which precedes signal transduction through TNFR1. Such antagonists provide several advantages. For example, in the presence of such an antagonist, TNFα can bind TNFR1 expressed on the surface of cells and be removed from the cellular environment, but TNFR1 mediated signal transduction will not be activated. Thus, TNFR1 signal-induced production of additional TNFα and other mediators of inflammation will be inhibited. Similarly, antagonists of TNFR1 that bind TNFR1 and inhibit signal transduction mediated through TNFR1, but do no inhibit binding of TNFα to TNFR1, will not inhibit the TNFα-binding and inhibiting activity of endogenously produced soluble TNFR1. Accordingly, administering such an antagonist to a mammal in need thereof can complement the endogenous regulatory pathways that inhibit the activity TNFα and the activity of TNFR1 in vivo. The invention also relates to ligands that (i) bind TNFR1 (eg, in Domain1), (ii) do not antagonize the activation of TNFR1 mediated signal transduction, and (iii) do not inhibit the binding of TNFα to TNFR1. Such a ligand binds soluble TNFR1 and do not prevent the soluble receptor from binding TNFα, and thus administering such an antagonist to a mammal in need thereof can complement the endogenous regulatory pathways that inhibit the activity TNFα in vivo by increasing the half-life of the soluble receptor in the serum. These advantages are particularly relevant to ligands that have been formatted to have a larger hydrodynamic size, for example, by attachment of a PEG group, serum albumin, transferrin, transferrin receptor or at least the transferrin-binding portion thereof, an antibody Fc region, or by conjugation to an antibody domain. For example, an agent (e.g., polypeptide) that i) bind TNFR1 (eg., in Domain1), (ii) does not antagonize the activation of TNFR1 mediated signal transduction, and (iii) does not inhibit the binding of TNFα to TNFR1, such as a dAb monomer, can be formatted as a larger antigen-binding fragment of an antibody or as and antibody (e.g., formatted as a Fab, Fab', F(ab)$_2$, F(ab')$_2$, IgG, scFv). The hydrodynamine size of a ligand and its serum half-life can also be increased by conjugating or linking a TNFR1 binding agent to a binding domain (e.g., antibody or antibody fragment) that binds an antigen or epitope that increases half-live in vivo, as described herein (see, Annex 1). For example, the TNFR1 binding agent (e.g., polypeptide) can be conjugated or linked to an anti-serum albumin or anti-neonatal Fc receptor antibody or antibody fragment, eg an anti-SA or anti-neonatal Fc receptor dAb, Fab, Fab' or scFv, or to an anti-SA affibody or anti-neonatal Fc receptor affibody.

Examples of suitable albumin, albumin fragments or albumin variants for use in a TNFR1-binding ligand according to the invention are described in WO 2005/077042A2, which is incorporated herein by reference in its entirety. In particular, the following albumin, albumin fragments or albumin variants can be used in the present invention:

SEQ ID NO:1 (as disclosed in WO 2005/077042A2, this sequence being explicitly incorporated into the present disclosure by reference);

Albumin fragment or variant comprising or consisting of amino acids 1-387 of SEQ ID NO:1 in WO 2005/077042A2;

Albumin, or fragment or variant thereof, comprising an amino acid sequence selected from the group consisting of: (a) amino acids 54 to 61 of SEQ ID NO:1 in WO 2005/077042A2; (b) amino acids 76 to 89 of SEQ ID NO:1 in WO 2005/077042A2; (c) amino acids 92 to 100 of SEQ ID NO:1 in WO 2005/077042A2; (d) amino acids 170 to 176 of SEQ ID NO:1 in WO 2005/077042A2; (e) amino acids 247 to 252 of SEQ ID NO:1 in WO 2005/077042A2; (f) amino acids 266 to 277 of SEQ ID NO:1 in WO 2005/077042A2; (g) amino acids 280 to 288 of SEQ ID NO:1 in WO 2005/077042A2; (h) amino acids 362 to 368 of SEQ ID NO:1 in WO 2005/077042A2; (i) amino acids 439 to 447 of SEQ ID NO:1 in WO 2005/077042A2 (j) amino acids 462 to 475 of SEQ ID NO:1 in WO 2005/077042A2; (k) amino acids 478 to 486 of SEQ ID NO:1 in WO 2005/077042A2; and (l) amino acids 560 to 566 of SEQ ID NO:1 in WO 2005/077042A2.

Further examples of suitable albumin, fragments and analogs for use in a TNFR1-binding ligand according to the invention are described in WO 03/076567A2, which is incorporated herein by reference in its entirety. In particular, the following albumin, fragments or variants can be used in the present invention:

Human serum albumin as described in WO 03/076567A2, eg, in FIG. 3 (this sequence information being explicitly incorporated into the present disclosure by reference);

Human serum albumin (HA) consisting of a single non-glycosylated polypeptide chain of 585 amino acids with a formula molecular weight of 66,500 (See, Meloun, et al., *FEBS Letters* 58:136 (1975); Behrens, et al., *Fed. Proc.* 34:591 (1975); Lawn, et al., *Nucleic Acids Research* 9:6102-6114 (1981); Minghetti, et al., *J. Biol. Chem.* 261:6747 (1986));

A polymorphic variant or analog or fragment of albumin as described in Weitkamp, et al., *Ann. Hum. Genet.* 37:219 (1973);

An albumin fragment or variant as described in EP 322094, eg, HA(1-373., HA(1-388), HA(1-389), HA(1-369), and HA(1-419) and fragments between 1-369 and 1-419;

An albumin fragment or variant as described in EP 399666, eg, HA(1-177) and HA(1-200) and fragments between HA(1-X), where X is any number from 178 to 199.

Where a (one or more) half-life extending moiety (eg, albumin, transferrin and fragments and analogues thereof) is used in the TNFR1-binding ligands of the invention, it can be conjugated using any suitable method, such as, by direct fusion to the TNFR1-binding moiety (eg, anti-TNFR1 dAb or antibody fragment), for example by using a single nucleotide construct that encodes a fusion protein, wherein the fusion protein is encoded as a single polypeptide chain with the half-life extending moiety located N- or C-terminally to the TNFR1 binding moiety. Alternatively, conjugation can be achieved by using a peptide linker between moieties, eg, a peptide linker as described in WO 03/076567A2 or WO 2004/003019 (these linker disclosures being incorporated by reference in the present disclosure to provide examples for use in the present invention).

In more particular embodiments, the antagonist of TNFR1 that binds TNFR1 and inhibits signal transduction mediated through TNFR1, but does no inhibit binding of TNFα to TNFR1, binds Domain 1 of TNFR1 or Domain 4 of TNFR1. In certain embodiments, such an antagonist of TNFR1 is a dAb monomer or ligand that binds Domain 1 of TNFR1 or Domain 4 of TNFR1.

In a particular embodiment, the antagonist of TNFR1 (e.g., a dAb monomer or ligand) binds Domain 1 of TNFR1 and inhibits signal transduction mediated through TNFR1 upon binding of TNFα. Such an antagonist can inhibit signal transduction through TNFR1, but not inhibit TNFα binding to TNFR1 and/or shedding of TNFR1 to produce soluble TNFR1. Accordingly, administering such an antagonist to a mammal in need thereof can complement the endogenous regulatory pathways that inhibit the activity TNFα and the activity of TNFR1 in vivo.

Other antagonists of TNFR1 bind TNFR1 but do not bind in Domain 4. Such antagonists inhibit a function of TNFR1 but do not inhibit shedding of soluble TNFR1. Accordingly, administering such an antagonist to a mammal in need thereof can complement the endogenous regulatory pathways that inhibit the activity TNFα and the activity of TNFR1 in vivo.

In certain embodiments, the antagonist (e.g., chemical compound, new chemical entity, dAb monomer, ligand) binds Domain 1 of TNFR1 and competes with TAR2m-21-23 for binding to mouse TNFR1 or competes with TAR2h-205 for binding to human TNFR1. In other embodiments, the antagonist (e.g., chemical compound, new chemical entity, dAb monomer, ligand) binds Domain 2 or Domain 4 of TNFR1. In other embodiments, the antagonist (e.g., chemical compound, new chemical entity, dAb monomer, ligand) binds Domain 3 of TNFR1 and competes with TAR2h-131-8, TAR2h-15-8, TAR2h-35-4, TAR2h-154-7, TAR2h-154-10, TAR2h-185-25, or TAR2h-27-10 for binding to TNFR1 (e.g., human and/or mouse TNFR1).

Some ligands (which in preferred embodiments are antagonists of TNFR1) bind human TNFR1 and mouse TNFR1. Such ligands (e.g., antagonists, dAb monomers) provide the advantage of allowing preclinical and clinical studies using the same ligand and obviate the need to conduct preclinical studies with a suitable surrogate ligand.

In other embodiments, the antagonist or ligand is an antibody that has binding specificity for TNFR1 or an antigen-binding fragment thereof, such as an Fab fragment, Fab' fragment, F(ab')$_2$ fragment or Fv fragment (e.g., scFV). In other embodiments, the antagonist or ligand is monovalent, such as a dAb or a monovalent antigen-binding fragment of an antibody, such as an Fab fragment, Fab' fragment, or Fv fragment.

In other embodiments of the invention described throughout this disclosure, instead of the use of a "dAb" in an antagonist or ligand of the invention, it is contemplated that the skilled addressee can use a domain that comprises the CDRs of a dAb that binds TNFR1 (e.g., CDRs grafted onto a suitable protein scaffold or skeleton, eg an affibody, an SpA scaffold, an LDL receptor class A domain or an EGF domain) or can be a protein domain comprising a binding site for TNFR1, e.g., wherein the domain is selected from an affibody, an SpA domain, an LDL receptor class A domain or an EGF domain. The disclosure as a whole is to be construed accordingly to provide disclosure of antagonists, ligands and methods using such domains in place of a dAb.

Preferably, the antagonist of TNFR1 is a ligand as described herein. The ligands comprise an immunoglobulin single variable domain or domain antibody (dAb) that has binding specificity for TNFR1 or the complementarity determining regions of such a dAb in a suitable format. The ligand can be a polypeptide that consists of such a dAb, or consists essentially of such a dAb. The ligand can also be a polypeptide that comprises a dAb (or the CDRs of a dAb) in a suitable format, such as an antibody format (e.g., IgG-like format, scFv, Fab, Fab', F(ab')$_2$), a dual specific ligand that comprises a dAb that binds TNFR1 and a second dAb that binds another target protein, antigen or epitope (e.g., serum albumin), or a multispecific ligand as described herein.

Antagonists of TNFR1, including ligands according to any aspect of the present invention, as well as dAb monomers useful in constructing such ligands, may advantageously dissociate from their cognate target(s) with a $K_d$ of 300 nM to 5 pM (ie, $3\times10^{-7}$ to $5\times10^{-12}$M), preferably 50 nM to 20 pM, or 5 nM to 200 pM or 1 nM to 100 pM, $1\times10^{-7}$ M or less, $1\times10^{-8}$ M or less, $1\times10^{-9}$ M or less, $1\times10^{-10}$ M or less, $1\times10^{-11}$ M or less; and/or a $K_{off}$ rate constant of $5\times10^{-1}$ s$^{-1}$ to $1\times10^{-7}$ s$^{-1}$, preferably $1\times10^{-2}$ s$^{-1}$ to $1\times$s$^{-1}$, or $5\times10^{-3}$ s$^{1}$ to $1\times10^{-5}$ s$^{-1}$, or $5\times10^{-1}$ s$^{-1}$ or less, or $1\times10^{-2}$ s$^{-1}$ or less, or $1\times10^{-3}$ s$^{-1}$ or less, or $1\times10^{-4}$ s$^{-1}$ or less, or $1\times10^{-5}$ s$^{-1}$ or less, or $1\times10^{-6}$ s$^{-1}$ or less as determined by surface plasmon resonance. The $K_d$ rate constant is defined as $K_{off}/K_{on}$.

In other embodiments, the antagonist binds TNFR1 and inhibits a (i.e., one or more) function of TNFR1 (e.g., receptor clustering, receptor signaling or binding of TNFα to TNFR1), and also binds to another member of the TNF receptor superfamily. Preferably, this type of antagonist also inhibits a function (e.g., member clustering, signaling or binding of the member to its cognate ligand) of the other member of the TNF receptor superfamily. The TNF receptor superfamily is an art recognized group of proteins that includes TNFR1 (p55, CD120a, p60, TNF receptor superfamily member 1A, TNFRSF1A), TNFR2 (p75, p80, CD120b, TNF receptor superfamily member 1B, TNFRSF1B), CD18 (TNFRSF3, LTBR, TNFR2-RP, TNFR-RP, TNFCR, TNF-R-III), OX40 (TNFRSF4, ACT35, TXGP1L), CD40 (TNFRSF5, p50, Bp50), Fas (CD95, TNFRSF6, APO-1, APTI), DcR3 (TNFRSF6B), CD27 (TNFRSF7, Tp55, S152), CD30 (TNFRSF8, Ki-1, D1S166E), CD137 (TNFRSF9, 4-1BB, ILA), TRAILR-1 (TNFRSF10A, DR4, Apo2), TRAIL-R2 (TNFRSF10B, DR5, KILLER, TRICK2A, TRICKB), TRAILR3 (TNFRSF10C, DcR1, LIT, TRID), TRAILR4 (TNFRSF10D, DcR2, TRUNDD), RANK (TNFRSF11A), OPG (TNFRSF11B, OCIF, TR1), DR3 (TNFRSF12, TRAMP, WSL-1, LARD, WSL-LR, DDR3, TR3, APO-3), DR3L (TNFRSF12L), TAC1 (TNFRSF13B), BAFFR (TNFRSF13C), HVEM (TNFRSF14, ATAR, TR2, LIGHTR, HVEA), NGFR (TNFRSF16), BCMA (TNFRSF17, BCM), AITR (TNFRSF18, GITR), TNFRSF19, FLJ14993 (TNFRSF19L, RELT), DR6 (TNFRSF21), SOBa (TNFRSF22, Tnfrh2, 2810028K06Rik), mSOB (THFRSF23, Tnfrh1). In some embodiments, the antagonist comprises a first dAb that binds TNFR1 and inhibits a function of TNFR1 and a second dAb that binds another member of the TNF receptor superfamily, such as TNFR2 (CD120b), OX40, CD40, Fas (CD95), TRAILR-1, TRAILR-2, TAC1, BCMA and the like as listed above. In another embodiment, the antagonist comprises a dAb monomer that binds TNFR1 and inhibits a function (eg, receptor clustering, receptor signaling or binding of TNFα to TNFR1) of TNFR1 and also binds to another member of the TNF receptor superfamily, such as TNFR2 (CD120b), OX40, CD40, Fas (CD95), TRAILR-1, TRAILR-2, TAC1, BCMA and the like as listed above.

Ligands and dAb Monomers that Bind TNFR1

The invention provides ligands that comprise an anti-TNFR1 dAb monomer (e.g., dual specific ligand comprising such a dAb) that binds to TNF Receptor I with a $K_d$ of 300 nM to 5 pM (ie, $3\times10^{-7}$ to $5\times10^{-12}$M), preferably 50 nM to 20 pM, more preferably 5 nM to 200 pM and most preferably 1 nM to 100 pM, for example $1\times10^{-7}$M or less, preferably $1\times10^{-8}$M or less, more preferably $1\times10^{-9}$M or less, advantageously $1\times10^{-10}$ M or less and most preferably $1\times10^{-11}$ M or less; and/or a $K_{off}$ rate constant of $5\times10^{-1}$ s$^{-1}$ to $1\times10^{-7}$ s$^{-1}$, preferably $1\times10^{-2}$ s$^{-1}$ to $1\times10^{-6}$ s$^{-1}$, more preferably $5\times10^{-3}$ s$^{-1}$ to $1\times$s$^{-1}$, for example $5\times10^{-1}$ s$^{-1}$ or less, preferably $1\times10^{-2}$ s$^{-1}$ or less, advantageously $1\times10^{-3}$ s$^{-1}$ or less, more preferably $1\times10^{-4}$ s$^{-1}$ or less, still more preferably $1\times10^{-5}$ s$^{-1}$ or less, and most preferably $1\times10^{-6}$ s$^{-1}$ or less as determined by surface plasmon resonance.

Preferably, the ligand or dAb monomer inhibits binding of TNF alpha to TNF alpha Receptor I (p55 receptor) with an inhibitory concentration 50 (IC50) of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less. Preferably, the TNF Receptor I target is Human TNFα.

Preferably, the ligand or dAb binds human TNFR1 and inhibits binding of human TNF alpha to human TNFR1, or inhibits signaling through TNFR1 in response to TNF alpha binding. For example, in certain embodiments, a ligand or dAb monomer can bind TNFR1 and inhibit TNFR1-mediated signaling, but does not substantially inhibit binding of TNFα to TNFR1. In some embodiments, the ligand or dAb monomer inhibits TNFα-induced crosslinking or clustering of TNFR1 on the surface of a cell. Such ligands or dAbs (e.g., TAR2m-21-23 described herein) are advantageous because they can antagonize cell surface TNFR1 but do not substantially reduce the inhibitory activity of endogenous soluble TNFR1. For example, the ligand or dAb can bind TNFR1, but inhibit binding of TNFα to TNFR1 in a receptor binding assay by no more that about 10%, no more that about 5%, no more than about 4%, no more than about 3%, no more than about 2%, or no more than about 1%. Also, in these embodiments, the ligand or dAb inhibits TNFα-induced crosslinking of TNFR1 and/or TNFR1-mediated signaling in a standard cell assay by at least about 10%, at least about 20%, at least about 30%, at least about 40%, at least about 50%, at least about 60%, at least about 70%, at least about 80%, at least about 90%, at least about 95%, or at least about 99%.

The ligand can be monovalent (e.g., a dAb monomer) or multivalent (e.g., dual specific, multi-specific) as described herein. In particular embodiments, the ligand is a dAb monomer that binds Domain 1 of TNFR1. Domain antibody monomers that bind Domain 1 of TNFR1 have a small footprint, relative to other binding formats, such as a monoclonal antibody, for example. Thus, such a dAb monomer can selectively block Domain 1, but not interfere with the function of other Domains of TNFR1. For example, a dAb monomer that binds Domain 1 of TNFR1 can antagonize TNFR1 but not inhibit binding of TNFα to TNFR1 or shedding of TNFR1.

In more particular embodiments, the ligand is a dAb monomer that binds Domain 1 of TNFR1 and competes with TAR2m-21-23 for binding to mouse TNFR1 or competes with TAR2h-205 for binding to human TNFR1.

In other embodiments, the ligand is multivalent and comprises two or more dAb monomers that bind TNFR1. Multivalent ligands can contain two or more copies of a particular dAb that binds TNFR1 or contain two or more dAbs that bind TNFR1. For example, as described herein, the ligand can be a dimer, trimer or multimer comprising two or more copies of a particular dAb that binds TNFR1, or two or more different dAbs that bind TNFR1. In some examples, the ligand is a homo dimer or homo trimer that comprises two or three copies of a particular dAb that binds TNFR1, respectively. Preferably, a multivalent ligand does not substantially agonize TNFR1 (act as an agonist of TNFR1) in a standard cell assay (i.e., when present at a concentration of 1 nM, 10 nM, 100 nM, 1 μM, 10 μM, 100 μM, 1000 μM or 5,000 μM, results in no more than about 5% of the TNFR1-mediated activity induced by TNFα (100 pg/ml) in the assay).

In certain embodiments, the multivalent ligand contains two or more dAbs that bind desired epitope or domain of TNFR1. For example, the multivalent ligand can comprise two or more copies of a dAb that binds a desired epitope in Domain 1 of TNFR1.

In other embodiments, the multivalent ligand contains two or more dAbs that bind to different epitopes or domains of TNFR1. In one example, the multivalent ligand comprises a first dAb that binds a first epitope in Domain 1 of TNFR1, and a second dAb that binds a second different epitope in Domain 1 of TNFR1. In other examples, the multivalent ligand comprises dAbs that bind two or more desired epitopes or domains of TNFR1. For example, the multivalent ligand can comprise dAbs that bind Domains 1 and 2, Domains 1 and 3, Domains 1 and 4, Domains 2 and 3, Domains 2 and 4, or Domains 3 and 4 of TNFR1.

In certain embodiments, the multivalent ligand is a dual specific ligand comprising a dAb that binds Domain 1 of TNFR1, and a dAb that binds Domain 3 of TNFR1. Ligands of this type can bind TNFR1 with high aviditiy, and be more selective for binding to cells that over express TNFR1 or express TNFR1 on their surface at high density than other ligand formats, such as dAb monomers.

In other particular embodiments, the multivalent ligand comprises two or more dAbs, or two or more copies of a particular dAb, that binds Domain 1 of TNFR1. Multivalent ligands of this type can bind TNFR1 monomers with low affinity, but bind receptor multimers (e.g., trimers see in the receptor ligand complex) with high avidity. Thus, ligands of this format can be administered to effectively target receptors that have clustered or associated with each other and/or ligand (e.g., TNFα) which is required for TNFR1-mediated signal transduction.

Some ligands or dAb monomers bind TNFR1 and inhibit binding of TNFα to TNFR1. In certain embodiments, such a ligand or dAb monomer binds Domain 2 and/or Domain 3 of TNFR1. In particular embodiments, the ligand or dAb monomer binds Domain 3 of TNFR1. In more particular embodiments, the ligand or dAb monomer binds Domain 3 of TNFR1 and competes with TAR2h-10-27, TAR2h-131-8, TAR2h-15-8, TAR2h-35-4, TAR2h-154-7, TAR2h-154-10 or TAR2h-185-25 for binding to TNFR1.

Other ligands or dAb monomers do not inhibit binding of TNFα to TNFR1. Such antagonists provide advantages as diagnostic agents, because they can be used to bind and detect, quantify or measure TNFR1 in a sample and will not compete with TNF in the sample for binding to TNFR1. Accordingly, an accurate determination of whether or how much TNFR1 is in the sample can be made.

Some ligands and dAb monomers do not inhibit binding of TNFα to TNFR1, but do inhibit signal transduction mediated through TNFR1. For example, a ligand or dAb monomer can inhibit TNFα-induced clustering of TNFR1, which precedes signal transduction through TNFR1. Such ligands or dAb monomers provide several advantages, as discussed herein with respect to antagonists that have these properties. In particular embodiments, the ligand or dAb monomer of this type binds Domain 1 of TNFR1 or Domain 4 of TNFR1. In certain embodiments, the ligand is a dAb monomer that binds Domain 1 of TNFR1 or Domain 4 of TNFR1.

In a particular embodiment, the ligand or dAb monomer binds Domain 1 of TNFR1 and inhibits signal transduction mediated through TNFR1 upon binding of TNFα. Such a ligand or dAb monomer can inhibit signal transduction through TNFR1, but not inhibit TNFα binding to TNFR1 and/or shedding of TNFR1 to produce soluble TNFR1. Accordingly, administering such ligand or dAb monomer to a mammal in need thereof can complement the endogenous regulatory pathways that inhibit the activity TNFα and the activity of TNFR1 in vivo.

Other ligands or dAb monomers bind TNFR1 but do not bind in Domain 4. Such ligand or dAb monomers inhibit a function of TNFR1 but do not inhibit shedding of soluble TNFR1. Accordingly, administering such an antagonist to a mammal in need thereof can complement the endogenous regulatory pathways that inhibit the activity TNFα and the activity of TNFR1 in vivo.

Preferably, the ligand or dAb monomer neutralizes (inhibits the activity of) TNFα or TNFR1 in a standard assay (e.g., the standard L929 or standard HeLa IL-8 assays described herein) with a neutralizing dose 50 (ND50) of 500 nM to 50 pM, preferably 100 nM to 50 pM, more preferably 10 nM to 100 pM, advantageously 1 nM to 100 pM; for example 50 nM or less, preferably 5 nM or less, more preferably 500 pM or less, advantageously 200 pM or less, and most preferably 100 pM or less.

In certain embodiments, the ligand or dAb monomer specifically binds human Tumor Necrosis Factor Receptor 1 (TNFR1; p55), and dissociates from human TNFR1 with a dissociation constant ($K_d$) of 50 nM to 20 pM, and a $K_{off}$ rate constant of $5\times10^{-1}$ s$^{-1}$ to $1\times10^{-7}$ s$^{-1}$, as determined by surface plasmon resonance.

In other embodiments, the ligand or dAb monomer specifically binds TNFR1 with a $K_d$ described herein and inhibits lethality in a standard mouse LPS/D-galactosamine-induced septic shock model (i.e., prevents lethality or reduces lethality by at least about 10%, as compared with a suitable control). Preferably, the dAb monomer inhibits lethality by at least about 25%, or by at least about 50%, as compared to a suitable control in a standard mouse LPS/D-galactosamine-induced septic shock model when administered at about 5 mg/kg or more preferably about 1 mg/kg.

In other embodiments, the ligand or dAb monomer binds TNFR1 and antagonizes the activity of the TNFR1 in a standard cell assay with an ND$_{50}$ of ≤100 nM, and at a concentration of ≤10 μM the dAb agonizes the activity of the TNFR1 by ≤5% in the assay.

In particular embodiments, ligand or dAb monomer does not substantially agonize TNFR1 (act as an agonist of TNFR1) in a standard cell assay (i.e., when present at a concentration of 1 nM, 10 nM, 100 nM, 1 μM, 10 μM, 100 μM, 1000 μM or 5,000 μM, results in no more than about 5% of the TNFR1-mediated activity induced by TNFα (100 pg/ml) in the assay).

In certain embodiments, the ligand or dAb monomer is substantially resistant to aggregation. For example, in some embodiments, less than about 10%, less than about 9%, less than about 8%, less than about 7%, less than about 6%, less than about 5%, less than about 4%, less than about 3%, less than about 2% or less than about 1% of the ligand or dAb monomer aggregates when a 1-5 mg/ml, 5-10 mg/ml, 10-20 mg/ml, 20-50 mg/ml, 50-100 mg/ml, 100-200 mg/ml or 200-500 mg/ml solution of ligand or dAb in a solvent that is routinely used for drug formulation such as saline, buffered saline, citrate buffer saline, water, an emulsion, and, any of these solvents with an acceptable excipient such as those approved by the FDA, is maintained at about 22° C., 22-25° C., 25-30° C., 30-37° C., 37-40° C., 40-50° C., 50-60° C., 60-70° C., 70-80° C., 15-20° C., 10-15° C., 5-10° C., 2-5° C., 0-2° C., −10° C. to 0° C., −20° C. to −10° C., −40° C. to −20° C., −60° C. to −40° C., or −80° C. to −60° C., for a period of about time, for example, 10 minutes, 1 hour, 8 hours, 24 hours, 2 days, 3 days, 4 days, 1 week, 2 weeks, 3 weeks, 1 month, 2 months, 3 months, 4 months, 6 months, 1 year, or 2 years.

Aggregation can be assessed using any suitable method, such as, by microscopy, assessing turbidity of a solution by visual inspection or spectroscopy or any other suitable method. Preferably, aggregation is assessed by dynamic light scattering. Ligands or dAb monomers that are resistant to aggregation provide several advantages. For example, such ligands or dAb monomers can readily be produced in high yield as soluble proteins by expression using a suitable biological production system, such as *E. coli*, and can be formulated and/or stored at higher concentrations than conventional polypeptides, and with less aggregation and loss of activity.

In addition, ligands or dAb monomers that are resistant to aggregation can be produced more economically than other antigen- or epitope-binding polypeptides (e.g., conventional antibodies). For example, generally, preparation of antigen- or epitope-binding polypeptides intended for in vivo applications includes processes (e.g., gel filtration) that remove aggregated polypeptides. Failure to remove such aggregates can result in a preparation that is not suitable for in vivo applications because, for example, aggregates of an antigen-binding polypeptide that is intended to act as an antagonist can function as an agonist by inducing cross-linking or clustering of the target antigen. Protein aggregates can also reduce the efficacy of therapeutic polypeptide by inducing an immune response in the subject to which they are administered.

In contrast, the aggregation resistant ligands or dAb monomers of the invention can be prepared for in vivo applications without the need to include process steps that remove aggregates, and can be used in in vivo applications without the aforementioned disadvantages caused by polypeptide aggregates.

In some embodiments, the ligand or dAb monomer unfolds reversibly when heated to a temperature (Ts) and cooled to a temperature (Tc), wherein Ts is greater than the melting temperature (Tm) of the dAb, and Tc is lower than the melting temperature of the dAb. For example, the dAb monomer can unfold reversibly when heated to 80° C. and cooled to about room temperature. A polypeptide that unfolds reversibly loses function when unfolded but regains function upon refolding. Such polypeptides are distinguished from polypeptides that aggregate when unfolded or that improperly refold (misfolded polypeptides), i.e., do not regain function.

Polypeptide unfolding and refolding can be assessed, for example, by directly or indirectly detecting polypeptide structure using any suitable method. For example, polypeptide structure can be detected by circular dichroism (CD) (e.g., far-UV CD, near-UV CD), fluorescence (e.g., fluorescence of tryptophan side chains), susceptibility to proteolysis, nuclear magnetic resonance (NMR), or by detecting or measuring a polypeptide function that is dependent upon proper folding (e.g., binding to target ligand, binding to generic ligand). In one example, polypeptide unfolding is assessed using a functional assay in which loss of binding function (e.g., binding a generic and/or target ligand, binding a substrate) indicates that the polypeptide is unfolded.

The extent of unfolding and refolding of a ligand or dAb monomer can be determined using an unfolding or denaturation curve. An unfolding curve can be produced by plotting temperature as the ordinate and the relative concentration of folded polypeptide as the abscissa. The relative concentration of folded ligand or dAb monomer can be determined directly or indirectly using any suitable method (e.g., CD, fluorescence, binding assay). For example, a ligand or dAb monomer solution can be prepared and ellipticity of the solution determined by CD. The ellipticity value obtained represents a relative concentration of folded ligand or dAb monomer of 100%. The ligand or dAb monomer in the solution is then unfolded by incrementally raising the temperature of the solution and ellipticity is determined at suitable increments (e.g., after each increase of one degree in temperature). The ligand or dAb monomer in solution is then refolded by incrementally reducing the temperature of the solution and ellipticity is determined at suitable increments. The data can be plotted to produce an unfolding curve and a refolding curve. The unfolding and refolding curves have a characteristic sigmoidal shape that includes a portion in which the ligand or dAb monomer molecules are folded, an unfolding/refolding transition in which ligand or dAb monomer molecules are unfolded to various degrees, and a portion in which the ligand or dAb monomer molecules are unfolded. The y-axis intercept of the refolding curve is the relative amount of refolded ligand or dAb monomer recovered. A recovery of at least about 50%, or at least about 60%, or at least about 70%, or at least about 75%, or at least about 80%, or at least about 85%, or at least about 90%, or at least about 95% is indicative that the ligand or dAb monomer unfolds reversibly.

In a preferred embodiment, reversibility of unfolding of the ligand or dAb monomer is determined by preparing a ligand or dAb monomer solution and plotting heat unfolding and refolding curves. The ligand or dAb monomer solution can be prepared in any suitable solvent, such as an aqueous buffer that has a pH suitable to allow the ligand or dAb monomer to dissolve (e.g., pH that is about 3 units above or below the isoelectric point (pI)). The ligand or dAb monomer solution is concentrated enough to allow unfolding/folding to be detected. For example, the ligand or dAb monomer solution can be about 0.1 μM to about 100 μM, or preferably about 1 μM to about 10 μM.

If the melting temperature (Tm) of the ligand or dAb monomer is known, the solution can be heated to about ten degrees below the Tm (Tm-10) and folding assessed by ellipticity or fluorescence (e.g., far-UV CD scan from 200 nm to 250 nm, fixed wavelength CD at 235 nm or 225 nm; tryptophan fluorescent emission spectra at 300 to 450 nm with excitation at 298 nm) to provide 100% relative folded ligand or dAb monomer. The solution is then heated to at least ten degrees above Tm (Tm+10) in predetermined increments (e.g., increases of about 0.1 to about 1 degree), and ellipticity or fluorescence is determined at each increment. Then, the ligand or dAb monomer is refolded by cooling to at least Tm-10 in predetermined increments and ellipticity or fluorescence determined at each increment. If the melting temperature of the ligand or dAb monomer is not known, the solution can be unfolded by incrementally heating from about 25° C. to about 100° C. and then refolded by incrementally cooling to at least about 25° C., and ellipticity or fluorescence at each heating and cooling increment is determined. The data obtained can be plotted to produce an unfolding curve and a refolding curve, in which the y-axis intercept of the refolding curve is the relative amount of refolded protein recovered.

In certain embodiments, the ligands or dAb monomers of the invention are efficacious in models of chronic inflammatory diseases when an effective amount is administered. Generally an effective amount is about 1 mg/kg to about 10 mg/kg (e.g., about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg). The models of chronic inflammatory disease described herein are recognized by those skilled in the art as being predictive of therapeutic efficacy in humans. The prior art does not suggest using antagonists of TNFR1 (e.g., monovalent antagonists, ligands as described herein) in these models, or that they would be efficacious.

In particular embodiments, the ligand or dAb monomer is efficacious in the standard mouse collagen-induced arthritis model (Example 15A). For example, administering an effective amount of the ligand can reduce the average arthritic score of the summation of the four limbs in the standard mouse collagen-induced arthritis model, for example, by about 1 to about 16, about 3 to about 16, about 6 to about 16, about 9 to about 16, or about 12 to about 16, as compared to a suitable control. In another example, administering an effective amount of the ligand can delay the onset of symptoms of arthritis in the standard mouse collagen-induced arthritis model, for example, by about 1 day, about 2 days, about 3 days, about 4 days, about 5 days, about 6 days, about 7 days, about 10 days, about 14 days, about 21 days or about 28 days, as compared to a suitable control. In another example, administering an effective amount of the ligand can result in an average arthritic score of the summation of the four limbs in the standard mouse collagen-induced arthritis model of 0 to about 3, about 3 to about 5, about 5 to about 7, about 7 to about 15, about 9 to about 15, about 10 to about 15, about 12 to about 15, or about 14 to about 15.

In other embodiments, the ligand or dAb monomer is efficacious in the mouse ΔARE model of arthritis (Example 15B). For example, administering an effective amount of the ligand can reduce the average arthritic score in the mouse ΔARE model of arthritis, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the ligand can delay the onset of symptoms of arthritis in the mouse ΔARE model of arthritis by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the ligand can result in an average arthritic score in the mouse ΔARE model of arthritis of 0 to about 0.5, about 0.5 to about 1, about 1 to about 1.5, about 1.5 to about 2, or about 2 to about 2.5.

In other embodiments, the ligand or dAb monomer is efficacious in the mouse ΔARE model of inflammatory bowel disease (IBD) (Example 15B). For example, administering an effective amount of the ligand can reduce the average acute and/or chronic inflammation score in the mouse ΔARE model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the ligand can delay the onset of symptoms of IBD in the mouse ΔARE model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the ligand can result in an average acute and/or chronic inflammation score in the mouse ΔARE model of IBD of 0 to about 0.5, about 0.5 to about 1, about 1 to about 1.5, about 1.5 to about 2, or about 2 to about 2.5.

In other embodiments, the ligand or dAb monomer is efficacious in the mouse dextran sulfate sodium (DSS) induced model of IBD (Example 15C). For example, administering an effective amount of the ligand can reduce the average severity score in the mouse DSS model of IBD, for example, by about 0.1 to about 2.5, about 0.5 to about 2.5, about 1 to about 2.5, about 1.5 to about 2.5, or about 2 to about 2.5, as compared to a suitable control. In another example, administering an effective amount of the ligand can delay the onset of symptoms of IBD in the mouse DSS model of IBD by, for example, about 1 day, about 2 days, about 3 days, about 4 days, about 5 days, about 6 days, about 7 days, about 10 days, about 14 days, about 21 days or about 28 days, as compared to a suitable control. In another example, administering an effective amount of the ligand can result in an average severity score in the mouse DSS model of IBD of 0 to about 0.5, about 0.5 to about 1, about 1 to about 1.5, about 1.5 to about 2, or about 2 to about 2.5.

In particular embodiments, the ligand or dAb monomer is efficacious in the mouse tobacco smoke model of chronic obstructive pulmonary disease (COPD) (Example 15D). For example, administering an effective amount of the ligand can reduce or delay onset of the symptoms of COPD, as compared to a suitable control.

In particular embodiments, the ligand or dAb monomer specifically binds TNFR1 and comprises the amino acid sequence of TAR2-10 (SEQ ID NO:31) or a sequence that is at least 80%, at least 85%, at least 90%, at least 91%, at least 92%, at least 93%, at least 94%, at least 95%, at least 96%, at least 97%, at least 98%, or at least 99% homologous thereto.

In particular embodiments, the ligand or dAb monomer specifically binds TNFR1 and comprises the amino acid sequence of TAR2h-5 (SEQ ID NO:195) or a sequence that is at least 80%, at least 85%, at least 90%, at least 91%, at least 92%, at least 93%, at least 94%, at least 95%, at least 96%, at least 97%, at least 98%, or at least 99% homologous thereto.

In other embodiments, the ligand comprises a domain antibody (dAb) monomer that specifically binds Tumor Necrosis Factor Receptor I (TNFR1, p55, CD120a) with a Id of 300 nM to 5 pM, and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence or a dAb selected from the group consisting of TAR2h-12 (SEQ ID NO:32), TAR2h-13 (SEQ ID NO:33), TAR2h-14 (SEQ ID NO:34), TAR2h-16 (SEQ ID NO:35), TAR2h-17 (SEQ ID NO:36), TAR2h-18 (SEQ ID NO:37), TAR2h-19 (SEQ ID NO:38), TAR2h-20 (SEQ ID NO:39), TAR2h-21 (SEQ ID NO:40), TAR2h-22 (SEQ ID NO:41), TAR2h-23 (SEQ ID NO:42), TAR2h-24 (SEQ ID NO:43), TAR2h-25 (SEQ ID NO:44), TAR2h-26 (SEQ ID NO:45), TAR2h-27 (SEQ ID NO:46), TAR2h-29 (SEQ ID NO:47), TAR2h-30 (SEQ ID NO:48), TAR2h-32 (SEQ ID NO:49), TAR2h-33 (SEQ ID NO:50), TAR2h-10-1 (SEQ ID NO:51), TAR2h-10-2 (SEQ ID NO:52), TAR2h-10-3 (SEQ ID NO:53), TAR2h-10-4 (SEQ ID NO:54), TAR2h-10-5 (SEQ ID NO:55), TAR2h-10-6 (SEQ ID NO:56), TAR2h-10-7 (SEQ ID NO:57), TAR2h-10-8 (SEQ ID NO:58), TAR2h-10-9 (SEQ ID NO:59), TAR2h-10-10 (SEQ ID NO:60), TAR2h-10-11 (SEQ ID NO:61), TAR2h-10-12 (SEQ ID NO:62), TAR2h-10-13 (SEQ ID NO:63), TAR2h-10-14 (SEQ ID NO:64), TAR2h-10-15 (SEQ ID NO:65), TAR2h-10-16 (SEQ ID NO:66), TAR2h-10-17 (SEQ ID NO:67), TAR2h-10-18 (SEQ ID NO:68), TAR2h-10-19 (SEQ ID NO:69), TAR2h-10-20 (SEQ ID NO:70), TAR2h-10-21 (SEQ ID NO:71), TAR2h-10-22 (SEQ ID NO:72), TAR2h-10-27 (SEQ ID NO:73), TAR2h-10-29 (SEQ ID NO:74), TAR2h-10-31 (SEQ ID NO:75), TAR2h-10-35 (SEQ ID NO:76), TAR2h-10-36 (SEQ ID NO:77), TAR2h-10-37 (SEQ ID NO:78), TAR2h-10-38 (SEQ ID NO:79), TAR2h-10-45 (SEQ ID NO:80), TAR2h-10-47 (SEQ ID NO:81), TAR2h-10-48 (SEQ ID NO:82), TAR2h-10-57 (SEQ ID NO:83), TAR2h-10-56 (SEQ ID NO:84), TAR2h-10-58 (SEQ ID NO:85), TAR2h-10-66 (SEQ ID NO:86), TAR2h-10-64 (SEQ ID NO:87), TAR2h-10-65 (SEQ ID NO:88), TAR2h-10-68 (SEQ ID NO:89), TAR2h-10-69 (SEQ ID NO:90), TAR2h-10-67 (SEQ ID NO:91), TAR2h-10-61 (SEQ ID NO:92), TAR2h-10-62 (SEQ ID NO:93), TAR2h-10-63 (SEQ ID NO:94), TAR2h-10-60 (SEQ ID NO:95), TAR2h-10-55 (SEQ ID NO:96), TAR2h-10-59 (SEQ ID NO:97), TAR2h-10-70 (SEQ ID NO:98), TAR2h-34 (SEQ ID NO:373), TAR2h-35 (SEQ ID NO:374), TAR2h-36 (SEQ ID NO:375), TAR2h-37 (SEQ ID NO:376), TAR2h-38 (SEQ ID NO:377), TAR2h-39 (SEQ ID NO:378), TAR2h-40 (SEQ ID NO:379), TAR2h-41 (SEQ ID NO:380), TAR2h-42 (SEQ ID NO:381), TAR2h-43 (SEQ ID NO:382), TAR2h-44 (SEQ ID NO:383), TAR2h-45 (SEQ ID NO:384), TAR2h-47 (SEQ ID NO:385), TAR2h-48 (SEQ ID NO:386), TAR2h-50 (SEQ ID NO:387), TAR2h-51 (SEQ ID NO:388), TAR2h-66 (SEQ ID NO:389), TAR2h-67 (SEQ ID NO:390), TAR2h-68 (SEQ ID NO:391), TAR2h-70 (SEQ ID NO:392), TAR2h-71 (SEQ ID NO:393), TAR2h-72 (SEQ ID NO:394), TAR2h-73 (SEQ ID NO:395), TAR2h-74 (SEQ ID NO:396), TAR2h-75 (SEQ ID NO:397), TAR2h-76 (SEQ ID NO:398), TAR2h-77 (SEQ ID NO:399), TAR2h-78 (SEQ ID NO:400), TAR2h-79 (SEQ ID NO:401) and TAR2h-15 (SEQ ID NO:431).

In additional embodiments, the ligand comprises a domain antibody (dAb) monomer that specifically binds Tumor Necrosis Factor Receptor I (TNFR1, p55, CD120a) with a $K_d$ of 300 nM to 5 pM, and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence or a dAb selected from the group consisting of TAR2h-131-8 (SEQ ID NO:433), TAR2h-131-24 (SEQ ID NO:434), TAR2h-15-8 (SEQ ID NO:435), TAR2h-15-8-1 SEQ ID NO:436), TAR2h-15-8-2 (SEQ ID NO:437), TAR2h-185-23 (SEQ ID NO:438), TAR2h-154-10-5 (SEQ ID NO:439), TAR2h-14-2 (SEQ ID NO:440), TAR2h-151-8 (SEQ ID NO:441), TAR2h-152-7 (SEQ ID NO:442), TAR2h-35-4 (SEQ ID NO:443), TAR2h-154-7 (SEQ ID NO:444), TAR2h-80 (SEQ ID NO:445), TAR2h-81 (SEQ ID NO:446), TAR2h-82 (SEQ ID NO:447), TAR2h-83 (SEQ ID NO:448), TAR2h-84 (SEQ ID NO:449), TAR2h-85 (SEQ ID NO:450), TAR2h-86 (SEQ ID NO:451), TAR2h-87 (SEQ ID NO:452), TAR2h-88 (SEQ ID NO:453), TAR2h-89 (SEQ ID NO:454), TAR2h-90 (SEQ ID NO:455), TAR2h-91 (SEQ ID NO:456), TAR2h-92 (SEQ ID NO:457), TAR2h-93 (SEQ ID NO:458), TAR2h-94 (SEQ ID NO:459), TAR2h-95 (SEQ ID NO:460), TAR2h-96 (SEQ ID NO:461), TAR2h-97 (SEQ ID NO:462), TAR2h-99 (SEQ ID NO:463), TAR2h-100 (SEQ ID NO:464), TAR2h-101 (SEQ ID NO:465), TAR2h-102 (SEQ ID NO:466), TAR2h-103 (SEQ ID NO:467), TAR2h-104 (SEQ ID NO:468), TAR2h-105 (SEQ ID NO:469), TAR2h-106 (SEQ ID NO:470), TAR2h-107 (SEQ ID NO:471), TAR2h-108 (SEQ ID NO:472), TAR2h-109 (SEQ ID NO:473), TAR2h-110 (SEQ ID NO:474), TAR2h-111 (SEQ ID NO:475), TAR2h-112 (SEQ ID NO:476), TAR2h-113 (SEQ ID NO:477), TAR2h-114 (SEQ ID NO:478), TAR2h-115 (SEQ ID NO:479), TAR2h-116 (SEQ ID NO:480), TAR2h-117 (SEQ ID NO:481), TAR2h-118 (SEQ ID NO:482), TAR2h-119 (SEQ ID NO:483), TAR2h-120 (SEQ ID NO:484), TAR2h-121 (SEQ ID NO:485), TAR2h-122 (SEQ ID NO:486), TAR2h-123 (SEQ ID NO:487), TAR2h-124 (SEQ ID NO:488), TAR2h-125 (SEQ ID NO:489), TAR2h-126 (SEQ ID NO:490), TAR2h-127 (SEQ ID NO:490), TAR2h-128 (SEQ ID NO:492), TAR2h-129 (SEQ ID NO:493), TAR2h-130 (SEQ ID NO:494), TAR2h-131 (SEQ ID NO:495), TAR2h-132 (SEQ ID NO:496), TAR2h-133 (SEQ ID NO:497), TAR2h-151 (SEQ ID NO:498), TAR2h-152 (SEQ ID NO:499), TAR2h-153 (SEQ ID NO:500), TAR2h-154 (SEQ ID NO:501), TAR2h-159 (SEQ ID NO:502), TAR2h-165 (SEQ ID NO:503), TAR2h-166 (SEQ ID NO:504), TAR2h-168 (SEQ ID NO:505), TAR2h-171 (SEQ ID NO:506), TAR2h-172 (SEQ ID NO:507), TAR2h-173 (SEQ ID NO:508), TAR2h-174 (SEQ ID NO:509), TAR2h-176 (SEQ ID NO:510), TAR2h-178 (SEQ ID NO:511), TAR2h-201 (SEQ ID NO:512), TAR2h-202 (SEQ ID NO:513), TAR2h-203 (SEQ ID NO:514), TAR2h-204 (SEQ ID NO:515), TAR2h-185-25 (SEQ ID NO:516), TAR2h-154-10 (SEQ ID NO:517), and TAR2h-205 (SEQ ID NO:627).

In preferred embodiments, the ligands or dAbs comprise an amino acid sequence at least about 90%, at least about 91%, at least about 92%, at least about 93%, at least about 94%, at least about 95%, at least about 96%, at least about 97%, at least about 98%, or at least about 99% homologous to an amino acid sequence of a dAb selected from the group consisting of TAR2h-10-27 (SEQ ID NO:73), TAR2h-10-57 (SEQ ID NO:83), TAR2h-10-56 (SEQ ID NO:84), TAR2h-10-58 (SEQ ID NO:85), TAR2h-10-66 (SEQ ID NO:86), TAR2h-10-64 (SEQ ID NO:87), TAR2h-10-65 (SEQ ID NO:88), TAR2h-10-68 (SEQ ID NO:89), TAR2h-10-69 (SEQ ID NO:90), TAR2h-10-67 (SEQ ID NO:91), TAR2h-10-61 (SEQ ID NO:92), TAR2h-10-62 (SEQ ID NO:93), TAR2h-10-63 (SEQ ID NO:94), TAR2h-10-60 (SEQ ID NO:95), TAR2h-10-55 (SEQ ID NO:96), TAR2h-10-59 (SEQ ID NO:97), and TAR2h-10-70 (SEQ ID NO:98).

Particularly preferred ligands or dAbs comprise an amino acid sequence at least about 90%, at least about 91%, at least about 92%, at least about 93%, at least about 94%, at least about 95%, at least about 96%, at least about 97%, at least about 98%, or at least about 99% homologous to the amino acid sequence of SEQ ID NO:73.

In other embodiments, the ligand comprises a domain antibody (dAb) monomer that specifically binds Tumor Necrosis Factor Receptor I (TNFR1, p55, CD120a) with a $K_d$ of 300 nM to 5 pM and comprises an amino acid sequence that is at least about 80%, at least about 85%, at least about 90%, at least about 91%, at least about 92%, at least about 93%, at least about 94%, at least about 95%, at least about 96%, at least about 97%, at least about 98%, or at least about 99% homologous to the amino acid sequence or a dAb selected from the group consisting of TAR2m-14 (SEQ ID NO:167), TAR2m-15 (SEQ ID NO:168), TAR2m-19 (SEQ ID NO:169), TAR2m-20 (SEQ ID NO:170), TAR2m-21 (SEQ ID NO:171), TAR2m-24 (SEQ ID NO:172), TAR2m-21-23 (SEQ ID NO:173), TAR2m-21-07 (SEQ ID NO:174), TAR2m-21-43 (SEQ ID NO:175), TAR2m-21-48 (SEQ ID NO:176), TAR2m-21-10 (SEQ ID NO:177), TAR2m-21-06 (SEQ ID NO:178), TAR2m-21-17 (SEQ ID NO:179).

In some embodiments, the ligand comprises a dAb monomer that binds TNFR1 and competes with any of the dAbs disclosed herein for binding to TNFR1 (e.g., mouse and/or human TNFR1).

Preferably, the ligand or dAb monomer is secreted in a quantity of at least about 0.5 mg/L when expressed in *E. coli* or in *Pichia* species (e.g., *P. pastoris*). In other preferred embodiments, the dAb monomer is secreted in a quantity of at least about 0.75 mg/L, at least about 1 mg/L, at least about 4 mg/L, at least about 5 mg/L, at least about 10 mg/L, at least about 15 mg/L, at least about 20 mg/L, at least about 25 mg/L, at least about 30 mg/L, at least about 35 mg/L, at least about 40 mg/L, at least about 45 mg/L, or at least about 50 mg/L, or at least about 100 mg/L, or at least about 200 mg/L, or at least about 300 mg/L, or at least about 400 mg/L, or at least about 500 mg/L, or at least about 600 mg/L, or at least about 700 mg/L, or at least about 800 mg/L, at least about 900 mg/L, or at least about 1 g/L when expressed in *E. coli* or in *Pichia* species (e.g., *P. pastoris*). In other preferred embodiments, the dAb monomer is secreted in a quantity of at least about 1 mg/L to at least about 1 g/L, at least about 1 mg/L to at least about 750 mg/L, at least about 100 mg/L to at least about 1 g/L, at least about 200 mg/L to at least about 1 g/L, at least about 300 mg/L to at least about 1 g/L, at least about 400 mg/L to at least about 1 g/L, at least about 500 mg/L to at least about 1 g/L, at least about 600 mg/L to at least about 1 g/L, at least about 700 mg/L to at least about 1 g/L, at least about 800 mg/L to at least about 1 g/L, or at least about 900 mg/L to at least about 1 g/L when expressed in *E. coli* or in *Pichia* species (e.g., *P. pastoris*). Although, the ligands and dAb monomers described herein can be secretable when expressed in *E. coli* or in *Pichia* species (e.g., *P. pastoris*), they can be produced using any suitable method, such as synthetic chemical methods or biological production methods that do not employ *E. coli* or *Pichia* species.

The dAb monomer can comprise any suitable immunoglobulin variable domain, and preferably comprises a human variable domain or a variable domain that comprises human framework regions. In certain embodiments, the dAb monomer comprises a universal framework, as described herein.

The universal framework can be a $V_L$ framework (Vλ or $V_κ$), such as a framework that comprises the framework amino acid sequences encoded by the human germline DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 or DPK 28 immunoglobulin gene segment. If desired, the $V_L$ framework can further comprises the framework amino acid sequence encoded by the human germline $J_κ1$, $J_κ2$, $J_κ3$, $J_κ4$, or $J_κ5$ immunoglobulin gene segment.

In other embodiments the universal framework can be a $V_H$ framework, such as a framework that comprises the framework amino acid sequences encoded by the human germline DP4, DP7, DP8, DP9, DP10, DP31, DP33, DP38, DP45, DP46, DP47, DP49, DP50, DP51, DP53, DP54, DP65, DP66, DP67, DP68 or DP69 immunoglobulin gene segment. If desired, the $V_H$ framework can further comprises the framework amino acid sequence encoded by the human germline $J_H1$, $J_H2$, $J_H3$, $J_H4$, $J_H4b$, $J_H5$ and $J_H6$ immunoglobulin gene segment.

In particular embodiments, the dAb monomer ligand comprises the DPK9 $V_L$ framework, or a $V_H$ framework selected from the group consisting of DP47, DP45 and DP38.

The dAb monomer can comprises a binding site for a generic ligand, such as protein A, protein L and protein G.

In certain embodiments, the dAb monomer comprises one or more framework regions comprising an amino acid sequence that is the same as the amino acid sequence of a corresponding framework region encoded by a human germline antibody gene segment, or the amino acid sequences of one or more of said framework regions collectively comprise up to 5 amino acid differences relative to the amino acid sequence of said corresponding framework region encoded by a human germline antibody gene segment.

In other embodiments, the amino acid sequences of FW1, FW2, FW3 and FW4 of the dAb monomer are the same as the amino acid sequences of corresponding framework regions encoded by a human germline antibody gene segment, or the amino acid sequences of FW1, FW2, FW3 and FW4 collectively contain up to 10 amino acid differences relative to the amino acid sequences of corresponding framework regions encoded by said human germline antibody gene segment.

In other embodiments, the dAb monomer comprises FW1, FW2 and FW3 regions, and the amino acid sequence of said FW1, FW2 and FW3 regions are the same as the amino acid sequences of corresponding framework regions encoded by human germline antibody gene segments.

In some embodiments, the dAb monomer does not comprise a Camelid immunoglobulin variable domain, or one or more framework amino acids that are unique to immunoglobulin variable domains encoded by Camelid germline antibody gene segments.

Ligands and dAb Monomers that Bind Serum Albumin

The invention provides a ligand or dAb monomer (e.g., dual specific ligand comprising such a dAb) that binds to serum albumin (SA) with a $K_d$ of 1 nM to 500 µM (ie, ×10⁻⁹ to 5×10⁻⁴), preferably 100 nM to 10 µM. Preferably, for a dual specific ligand comprising a first anti-SA dAb and a second dAb to another target, the affinity (eg $K_d$ and/or $K_{off}$ as measured by surface plasmon resonance, eg using BiaCore) of the second dAb for its target is from 1 to 100000 times (preferably 100 to 100000, more preferably 1000 to 100000, or 10000 to 100000 times) the affinity of the first dAb for SA. For example, the first dAb binds SA with an affinity of approximately 10 µM, while the second dAb binds its target with an affinity of 100 pM. Preferably, the serum albumin is human serum albumin (HSA). In one embodiment, the first dAb (or a dAb monomer) binds SA (eg, HSA) with a $K_d$ of approximately 50, preferably 70, and more preferably 100, 150 or 200 nM.

In certain embodiments, the dAb monomer specific for SA comprises the amino acid sequence of MSA-16 (SEQ ID NO:28) or a sequence that is at least 80%, at least 85%, at least 90%, at least 91%, at least 92%, at least 93%, at least 94%, at least 95%, at least 96%, at least 97%, at least 98%, or at least 99% homologous thereto.

In other embodiments, the dAb monomer specific for SA comprises the amino acid sequence of MSA-26 (SEQ ID NO:30) or a sequence that is at least 80%, at least 85%, at least 90%, at least 91%, at least 92%, at least 93%, at least 94%, at least 95%, at least 96%, at least 97%, at least 98%, or at least 99% homologous thereto.

In certain embodiments, the dAb monomer that binds SA resists aggregation, unfolds reversibly and/or comprises a framework region as described above for dAb monomers that bind TNFR1.

Nucleic Acid Molecules, Vectors and Host Cells

The invention also provides isolated and/or recombinant nucleic acid molecules that encode the ligands and dAb monomers described herein. In certain embodiments, the isolated and/or recombinant nucleic acid comprises a nucleotide sequence that encodes a domain antibody (dAb) monomer that specifically binds Tumor Necrosis Factor Receptor I (TNFR1), wherein said nucleotide sequence is at least about 80%, at least about 85%, at least about 90%, at least about 91%, at least about 92%, at least about 93%, at least about 94%, at least about 95%, at least about 96%, at least about 97%, at least about 98%, or at least about 99% homologous to a nucleotide sequence selected from the group consisting of TAR2h-12 (SEQ ID NO:32), TAR2h-13 (SEQ ID NO:33), TAR2h-14 (SEQ ID NO:34), TAR2h-16 (SEQ ID NO:35), TAR2h-17 (SEQ ID NO:36), TAR2h-18 (SEQ ID NO:37), TAR2h-19 (SEQ ID NO:38), TAR2h-20 (SEQ ID NO:39), TAR2h-21 (SEQ ID NO:40), TAR2h-22 (SEQ ID NO:41), TAR2h-23 (SEQ ID NO:42), TAR2h-24 (SEQ ID NO:43), TAR2h-25 (SEQ ID NO:44), TAR2h-26 (SEQ ID NO:45), TAR2h-27 (SEQ ID NO:46), TAR2h-29 (SEQ ID NO:47), TAR2h-30 (SEQ ID NO:48), TAR2h-32 (SEQ ID NO:49), TAR2h-33 (SEQ ID NO:50), TAR2h-10-1 (SEQ ID NO:51), TAR2h-10-2 (SEQ ID NO:52), TAR2h-10-3 (SEQ ID NO:53), TAR2h-10-4 (SEQ ID NO:54), TAR2h-10-5 (SEQ ID NO:55), TAR2h-10-6 (SEQ ID NO:56), TAR2h-10-7 (SEQ ID NO:57), TAR2h-10-8 (SEQ ID NO:58), TAR2h-10-9 (SEQ ID NO:59), TAR2h-10-10 (SEQ ID NO:60), TAR2h-10-11 (SEQ ID NO:61), TAR2h-10-12 (SEQ ID NO:62), TAR2h-10-13 (SEQ ID NO:63), TAR2h-10-14

(SEQ ID NO:64), TAR2h-10-15 (SEQ ID NO:65), TAR2h-10-16 (SEQ ID NO:66), TAR2h-10-17 (SEQ ID NO:67), TAR2h-10-18 (SEQ ID NO:68), TAR2h-10-19 (SEQ ID NO:69), TAR2h-10-20 (SEQ ID NO:70), TAR2h-10-21 (SEQ ID NO:71), TAR2h-10-22 (SEQ ID NO:72), TAR2h-10-27 (SEQ ID NO:73), TAR2h-10-29 (SEQ ID NO:74), TAR2h-10-31 (SEQ ID NO:75), TAR2h-10-35 (SEQ ID NO:76), TAR2h-10-36 (SEQ ID NO:77), TAR2h-10-37 (SEQ ID NO:78), TAR2h-10-38 (SEQ ID NO:79), TAR2h-10-45 (SEQ ID NO:80), TAR2h-10-47 (SEQ ID NO:81), TAR2h-10-48 (SEQ ID NO:82), TAR2h-10-57 (SEQ ID NO:83), TAR2h-10-56 (SEQ ID NO:84), TAR2h-10-58 (SEQ ID NO:85), TAR2h-10-66 (SEQ ID NO:86), TAR2h-10-64 (SEQ ID NO:87), TAR2h-10-65 (SEQ ID NO:88), TAR2h-10-68 (SEQ ID NO:89), TAR2h-10-69 (SEQ ID NO:90), TAR2h-10-67 (SEQ ID NO:91), TAR2h-10-61 (SEQ ID NO:92), TAR2h-10-62 (SEQ ID NO:93), TAR2h-10-63 (SEQ ID NO:94), TAR2h-10-60 (SEQ ID NO:95), TAR2h-10-55 (SEQ ID NO:96), TAR2h-10-59 (SEQ ID NO:97), TAR2h-10-70 (SEQ ID NO:98), TAR2h-34 (SEQ ID NO:402), TAR2h-35 (SEQ ID NO:403), TAR2h-36 (SEQ ID NO:404), TAR2h-37 (SEQ ID NO:405), TAR2h-38 (SEQ ID NO:406), TAR2h-39 (SEQ ID NO:407), TAR2h-40 (SEQ ID NO:408), TAR2h-41 (SEQ ID NO:409), TAR2h-42 (SEQ ID NO:410), TAR2h-43 (SEQ ID NO:411), TAR2h-44 (SEQ ID NO:412), TAR2h-45 (SEQ ID NO:413), TAR2h-47 (SEQ ID NO:414), TAR2h-48 (SEQ ID NO:415), TAR2h-50 (SEQ ID NO:416), TAR2h-51 (SEQ ID NO:417), TAR2h-66 (SEQ ID NO:418), TAR2h-67 (SEQ ID NO:419), TAR2h-68 (SEQ ID NO:420), TAR2h-70 (SEQ ID NO:421), TAR2h-71 (SEQ ID NO:422), TAR2h-72 (SEQ ID NO:423), TAR2h-73 (SEQ ID NO:424), TAR2h-74 (SEQ ID NO:425), TAR2h-75 (SEQ ID NO:426), TAR2h-76 (SEQ ID NO:427), TAR2h-77 (SEQ ID NO:428), TAR2h-78 (SEQ ID NO:429), TAR2h-79 (SEQ ID NO:430), and TAR2h-15 (SEQ ID NO:432).

In other embodiments, the isolated and/or recombinant nucleic acid comprises a nucleotide sequence that encodes a domain antibody (dAb) monomer that specifically binds Tumor Necrosis Factor Receptor I (TNFR1), wherein said nucleotide sequence is at least about 80%, at least about 85%, at least about 90%, at least about 91%, at least about 92%, at least about 93%, at least about 94%, at least about 95%, at least about 96%, at least about 97%, at least about 98%, or at least about 99% homologous to a nucleotide sequence selected from the group consisting of TAR2h-131-8 (SEQ ID NO:518), TAR2h-131-24 (SEQ ID NO:519), TAR2h-15-8 (SEQ ID NO:520), TAR2h-15-8-1 (SEQ ID NO:521), TAR2h-15-8-2 (SEQ ID NO:522), TAR2h-185-23 (SEQ ID NO:523), TAR2h-154-10-5 (SEQ ID NO:524), TAR2h-14-2 (SEQ ID NO:525), TAR2h-151-8 (SEQ ID NO:526), TAR2h-152-7 (SEQ ID NO:527), TAR2h—35-4 (SEQ ID NO:528), TAR2h-154-7 (SEQ ID NO:529), TAR2h-80 (SEQ ID NO:530), TAR2h-81 (SEQ ID NO:531), TAR2h-82 (SEQ ID NO:532), TAR2h-83 (SEQ ID NO:533), TAR2h-84 (SEQ ID NO:534), TAR2h-85 (SEQ ID NO:535), TAR2h-86 (SEQ ID NO:536), TAR2h-87 (SEQ ID NO:537), TAR2h-88 (SEQ ID NO:538), TAR2h-89 (SEQ ID NO:539), TAR2h-90 (SEQ ID NO:540), TAR2h-91 (SEQ ID NO:541), TAR2h-92 (SEQ ID NO:542), TAR2h-93 (SEQ ID NO:543), TAR2h-94 (SEQ ID NO:544), TAR2h-95 (SEQ ID NO:545), TAR2h-96 (SEQ ID NO:546), TAR2h-97 (SEQ ID NO:547), TAR2h-99 (SEQ ID NO:548), TAR2h-100 (SEQ ID NO:549), TAR2h-101 (SEQ ID NO:550), TAR2h-102 (SEQ ID NO:551), TAR2h-103 (SEQ ID NO:552), TAR2h-104 (SEQ ID NO:553), TAR2h-105 (SEQ ID NO:554), TAR2h-106 (SEQ ID NO:555), TAR2h-107 (SEQ ID NO:556), TAR2h-108 (SEQ ID NO:557), TAR2h-109 (SEQ ID NO: δ 8), TAR2h-110 (SEQ ID NO:559), TAR2h-111 (SEQ ID NO:560), TAR2h-112 (SEQ ID NO:561), TAR2h-113 (SEQ ID NO:562), TAR2h-114 (SEQ ID NO:563), TAR2h-115 (SEQ ID NO:564), TAR2h-116 (SEQ ID NO:565), TAR2h-117 (SEQ ID NO:566), TAR2h-118 (SEQ ID NO:567), TAR2h-119 (SEQ ID NO:568), TAR2h-120 (SEQ ID NO:569), TAR2h-121 (SEQ ID NO:570), TAR2h-122 (SEQ ID NO:571), TAR2h-123 (SEQ ID NO:572), TAR2h-12 (SEQ ID NO:573), TAR2h-125 (SEQ ID NO:574), TAR2h-126 (SEQ ID NO:575), TAR2h-127 (SEQ ID NO:576), TAR2h-128 (SEQ ID NO:577), TAR2h-129 (SEQ ID NO:578), TAR2h-130 (SEQ ID NO:579), TAR2h-131 (SEQ ID NO:580), TAR2h-132 (SEQ ID NO:581), TAR2h-133 (SEQ ID NO:582), TAR2h-151 (SEQ ID NO:583), TAR2h-152 (SEQ ID NO:584), TAR2h-153 (SEQ ID NO:585), TAR2h-154 (SEQ ID NO:586), TAR2h-159 (SEQ ID NO:587), TAR2h-165 (SEQ ID NO:588), TAR2h-166 (SEQ ID NO:589), TAR2h-168 (SEQ ID NO:590), TAR2h-171 (SEQ ID NO:591), TAR2h-172 (SEQ ID NO:592), TAR2h-173 (SEQ ID NO:593), TAR2h-174 (SEQ ID NO:594), TAR2h-176 (SEQ ID NO:595), TAR2h-178 (SEQ ID NO:596), TAR2h-201 (SEQ ID NO:597), TAR2h-202 (SEQ ID NO:598), TAR2h-203 (SEQ ID NO:599), TAR2h-204 (SEQ ID NO:600), TAR2h-185-25 (SEQ ID NO:601), TAR2h-154-10 (SEQ ID NO:602), and TAR2h-205 (SEQ ID NO:628).

In a preferred embodiment, the isolated and/or recombinant nucleic acid comprise a nucleotide sequence that is at least about 90%, at least about 91%, at least about 92%, at least about 93%, at least about 94%, at least about 95%, at least about 96%, at least about 97%, at least about 98%, or at least about 99% homologous to a nucleotide sequence selected from the group consisting of TAR2h-10-27 (SEQ ID NO:141), TAR2h-10-57 (SEQ ID NO:151), TAR2h-10-56 (SEQ ID NO:152), TAR2h-10-58 (SEQ ID NO:153), TAR2h-10-66 (SEQ ID NO:154), TAR2h-10-64 SEQ ID NO:155), TAR2h-10-65 (SEQ ID NO:156), TAR2h-10-68 (SEQ ID NO:157), TAR2h-10-69 (SEQ ID NO:158), TAR2h-10-67 (SEQ ID NO:159), TAR2h-10-61 (SEQ ID NO:160), TAR2h-10-62 (SEQ ID NO:161), TAR2h-10-63 (SEQ ID NO:162), TAR2h-10-60 (SEQ ID NO:163), TAR2h-10-55 (SEQ ID NO:164), TAR2h-10-59 (SEQ ID NO:165), and TAR2h-10-70 (SEQ ID NO:166).

In other embodiments, the isolated and/or recombinant nucleic acid comprises a nucleotide sequence that encodes a domain antibody (dAb) monomer that specifically binds Tumor Necrosis Factor Receptor I (TNFR1), wherein said nucleotide sequence is at least about 80%, at least about 85%, at least about 90%, at least about 91%, at least about 92%, at least about 93%, at least about 94%, at least about 95%, at least about 96%, at least about 97%, at least about 98%, or at least about 99% homologous to a nucleotide sequence selected from the group consisting of TAR2m-14 (SEQ ID NO:180), TAR2m-15 (SEQ ID NO:181), TAR2m-19 (SEQ ID NO:182), TAR2m-20 (SEQ ID NO:183), TAR2m-21 (SEQ ID NO:184), TAR2m-24 (SEQ ID NO:185), TAR2m-21-23 (SEQ ID NO:186), TAR2m-21-07 (SEQ ID NO:187), TAR2m-21-43 (SEQ ID NO:188), TAR2m-21-48 (SEQ ID NO:189), TAR2m-21-10 (SEQ ID NO:190), TAR2m-21-06 (SEQ ID NO:191), TAR2m-21-17 (SEQ ID NO:192), and TAR2m-21-23a (SEQ ID NO:626).

The invention also provides a vector comprising a recombinant nucleic acid molecule of the invention. In certain embodiments, the vector is an expression vector comprising one or more expression control elements or sequences that are operably linked to the recombinant nucleic acid of the invention. Suitable vectors (e.g., plasmids, phagmids) and expression control elements are further described below.

The invention also provides a recombinant host cell comprising a recombinant nucleic acid molecule or vector of the invention. Suitable host cells and methods for producing the recombinant host cell of the invention are further described below.

The invention also provides a method for producing a ligand (e.g., dAb monomer, dual-specific ligand, multispecific ligand) of the invention, comprising maintaining a recombinant host cell comprising a recombinant nucleic acid of the invention under conditions suitable for expression of the recombinant nucleic acid, whereby the recombinant nucleic acid is expressed and a ligand is produced. In some embodiments, the method further comprises isolating the ligand.

Ligand Formats

Ligands according to the invention can be formatted as mono or multispecific antibodies or antibody fragments or into mono or multispecific non-immunoglobulin structures. Suitable formats include, any suitable polypeptide structure in which an antibody variable domain or the CDR thereof can be incorporated so as to confer binding specificity for antigen on the structure. A variety of suitable antibody formats are known in the art, such as, IgG-like formats, chimeric antibodies, humanized antibodies, human antibodies, single chain antibodies, bispecific antibodies, antibody heavy chains, antibody light chains, homodimers and heterodimers of antibody heavy chains and/or light chains, antigen-binding fragments of any of the foregoing (e.g., a Fv fragment (e.g., single chain Fv (scFv), a disulfide bonded Fv), a Fab fragment, a Fab' fragment, a F(ab')$_2$ fragment), a single variable domain (e.g., $V_H$, $V_L$), a dAb, and modified versions of any of the foregoing (e.g., modified by the covalent attachment of polyalkylene glycol (e.g., polyethylene glycol, polypropylene glycol, polybutylene glycol) or other suitable polymer). See, PCT/GB03/002804, filed Jun. 30, 2003, which designated the United States, (WO 2004/081026) regarding PEGylated of single variable domains and dAbs, suitable methods for preparing same, increased in vivo half life of the PEGylated single variable domains and dAb monomers and multimers, suitable PEGs, preferred hydrodynamic sizes of PEGs, and preferred hydrodynamic sizes of PEGylated single variable domains and dAb monomers and multimers. The entire teaching of PCT/GB03/002804 (WO 2004/081026), including the portions referred to above, are incorporated herein by reference.

In particular embodiments, the ligand (e.g., dAb monomer, dimer or multimer, dual specific format, multi-specific format) is PEGylated and binds Domain 1 of TNFR1 and optionally inhibits a function of TNFR1. Preferably, the PEGylated ligand inhibits signaling through TNFR1. Preferably the PEGylated ligand binds Domain 1 of TNFR1 with substantially the same affinity as the same ligand that is not PEGylated. For example, in one embodiment, the ligand is a PEGylated dAb monomer that binds Domain 1 of TNFR1 and inhibits signaling through TNFR1, wherein the PEGylated dAb monomer binds Domain 1 of TNFR1 with an affinity that differs from the affinity of dAb in unPEGylated form by no more than a factor of about 1000, preferably no more than a factor of about 100, more preferably no more than a factor of about 10, or with affinity substantially unchanged affinity relative to the unPEGylated form.

A ligand according to the invention that binds Domain 1 of membrane-bound (transmembrane) and soluble forms of TNFR1, but does not inhibit the binding of TNFα to the receptor forms, may be useful to block Domain 1 on the membrane-bound receptor (eg, to inhibit receptor clustering and/or inhibit signaling) and also to bind to the soluble form to enhance half-life, particularly when attached to PEG or as otherwise described above. In a preferred embodiment, the ligand does not bind Domain 2 of membrane-bound (transmembrane) and soluble forms of TNFR1. In another preferred embodiment, the ligand does not bind Domain 3 of membrane-bound (transmembrane) and soluble forms of TNFR1. In another preferred embodiment, the ligand does not bind Domain 2 or Domain 3 of membrane-bound (transmembrane) and soluble forms of TNFR1.

In some embodiments, the ligand is an IgG-like format. Such formats have the conventional four chain structure of an IgG molecule (2 heavy chains and two light chains), in which one or more of the variable regions ($V_H$ and or $V_L$) have been replaced with a dAb or single variable domain of a desired specificity. Preferably, each of the variable regions (2 $V_H$ regions and 2 $V_L$ regions) is replaced with a dAb or single variable domain. The dAb(s) or single variable domain(s) that are included in an IgG-like format can have the same specificity or different specificities. In some embodiments, the IgG-like format is tetravalent and can have one, two, three or four specificities. For example, the IgG-like format can be monospecific and comprises 4 dAbs that have the same specificity; bispecific and comprises 3 dAbs that have the same specificity and another dAb that has a different specificity; bispecific and comprise two dAbs that have the same specificity and two dAbs that have a common but different specificity; trispecific and comprises first and second dAbs that have the same specificity, a third dAbs with a different specificity and a fourth dAb with a different specificity from the first, second and third dAbs; or tetraspecific and comprise four dAbs that each have a different specificity. Antigen-binding fragments of IgG-like formats (e.g., Fab, $F(ab')_2$, Fab', Fv, $scF_v$) can be prepared. Preferably, the IgG-like formats or antigen-binding fragments thereof do not crosslink TNFR1.

Ligands according to the invention, including dAb monomers, dimers and trimers, can be linked to an antibody Fc region, comprising one or both of $C_H2$ and $C_H3$ domains, and optionally a hinge region. For example, vectors encoding ligands linked as a single nucleotide sequence to an Fc region may be used to prepare such polypeptides.

The invention moreover provides dimers, trimers and polymers of the aforementioned dAb monomers, in accordance with the following aspects of the present invention.

Ligands according to the invention may be combined and/or formatted into non-immunoglobulin multi-ligand structures to form multivalent complexes, which bind target molecules with the same antigen, thereby providing superior avidity. In some embodiments, at least one variable domain binds an antigen to increase the half life of the multimer. For example natural bacterial receptors such as SpA have been used as scaffolds for the grafting of CDRs to generate ligands which bind specifically to one or more epitopes. Details of this procedure are described in U.S. Pat. No. 5,831,012. Other suitable scaffolds include those based on fibronectin and affibodies. Details of suitable procedures are described in WO 98/58965. Other suitable scaffolds include lipocallin and CTLA4, as described in van den Beuken et al., J. Mol. Biol. (2001) 310, 591-601, and scaffolds such as those described in WO 00/69907 (Medical Research Council), which are based for example on the ring structure of bacterial GroEL or other chaperone polypeptides.

Protein scaffolds may be combined; for example, CDRs may be grafted on to a CTLA4 scaffold and used together with immunoglobulin $V_H$ or $V_L$ domains to form a ligand. Likewise, fibronectin, lipocallin and other scaffolds may be combined.

Dual- and Multi-Specific Ligands The inventors have described, in their copending international patent application WO 03/002609 as well as copending unpublished UK patent application 0230203.2, dual specific immunoglobulin ligands which comprise immunoglobulin single variable domains which each have different specificities. The domains may act in competition with each other or independently to bind antigens or epitopes on target molecules.

Dual-Specific ligands according to the present invention preferably comprise combinations of heavy and light chain domains. For example, the dual specific ligand may comprise a $V_H$ domain and a $V_L$ domain, which may be linked together in the form of an scFv. In addition, the ligands may comprise one or more $C_H$ or $C_L$ domains. For example, the ligands may comprise a $C_H1$ domain, $C_H2$ or $C_H3$ domain, and/or a $C_L$ domain, C□1, C□2, Cµ3 or Cµ4 domains, or any combination thereof. A hinge region domain may also be included. Such combinations of domains may, for example, mimic natural antibodies, such as IgG or IgM, or fragments thereof, such as Fv, scFv, Fab or F(ab')$_2$ molecules. Other structures, such as a single arm of an IgG molecule comprising $V_H$, $V_L$, $C_H1$ and $C_L$ domains, are envisaged.

In a preferred embodiment of the invention, the variable regions are selected from single domain V gene repertoires. Generally the repertoire of single antibody domains is displayed on the surface of filamentous bacteriophage. In a preferred embodiment each single antibody domain is selected by binding of a phage repertoire to antigen.

In a preferred embodiment of the invention each single variable domain may be selected for binding to its target antigen or epitope in the absence of a complementary variable region. In an alternative embodiment, the single variable domains may be selected for binding to its target antigen or epitope in the presence of a complementary variable region. Thus the first single variable domain may be selected in the presence of a third complementary variable domain, and the second variable domain may be selected in the presence of a fourth complementary variable domain. The complementary third or fourth variable domain may be the natural cognate variable domain having the same specificity as the single domain being tested, or a non-cognate complementary domain—such as a "dummy" variable domain.

Preferably, the dual specific ligand of the invention comprises only two variable domains although several such ligands may be incorporated together into the same protein, for example two such ligands can be incorporated into an IgG or a multimeric immunoglobulin, such as IgM. Alternatively, in another embodiment a plurality of dual specific ligands are combined to form a multimer. For example, two different dual specific ligands are combined to create a tetra-specific molecule.

It will be appreciated by one skilled in the art that the light and heavy variable regions of a dual-specific ligand produced according to the method of the present invention may be on the same polypeptide chain, or alternatively, on different polypeptide chains. In the case that the variable regions are on different polypeptide chains, then they may be linked via a linker, generally a flexible linker (such as a polypeptide chain), a chemical linking group, or any other method known in the art.

In a first configuration, the present invention provides a further improvement in dual specific ligands as developed by the present inventors, in which one specificity of the ligand is directed towards a protein or polypeptide present in vivo in an organism which can act to increase the half-life of the ligand by binding to it.

Accordingly, in a first aspect, there is provided a dual-specific ligand comprising a first immunoglobulin single variable domain having a binding specificity to a first antigen or epitope and a second complementary immunoglobulin single variable domain having a binding activity to a second antigen or epitope, wherein one or both of said antigens or epitopes acts to increase the half-life of the ligand in vivo and wherein said first and second domains lack mutually complementary domains which share the same specificity, provided that said dual specific ligand does not consist of an anti-HSA $V_H$ domain and an anti-β galactosidase $V_κ$ domain. Preferably, that neither of the first or second variable domains binds to human serum albumin (HSA).

Antigens or epitopes which increase the half-life of a ligand as described herein are advantageously present on proteins or polypeptides found in an organism in vivo. Examples include extracellular matrix proteins, blood proteins, and proteins present in various tissues in the organism. The proteins act to reduce the rate of ligand clearance from the blood, for example by acting as bulking agents, or by anchoring the ligand to a desired site of action. Examples of antigens/epitopes which increase half-life in vivo are given in Annex 1 below.

Increased half-life is useful in in vivo applications of immunoglobulins, especially antibodies and most especially antibody fragments of small size. Such fragments (Fvs, disulphide bonded Fvs, Fabs, scFvs, dAbs) suffer from rapid clearance from the body; thus, whilst they are able to reach most parts of the body rapidly, and are quick to produce and easier to handle, their in vivo applications have been limited by their only brief persistence in vivo. The invention solves this problem by providing increased half-life of the ligands in vivo and consequently longer persistence times in the body of the functional activity of the ligand.

Methods for pharmacokinetic analysis and determination of ligand half-life will be familiar to those skilled in the art. Details may be found in Kenneth, A et al: Chemical Stability of Pharmaceuticals: A Handbook for Pharmacists and in Peters et al, Pharmacokinetc analysis: A Practical Approach (1996). Reference is also made to "Pharmacokinetics", M Gibaldi & D Perron, published by Marcel Dekker, $2^{nd}$ Rev. ex edition (1982), which describes pharmacokinetic parameters such as t alpha and t beta half lives and area under the curve (AUC).

Half lives (t½ alpha and t½ beta) and AUC can be determined from a curve of serum concentration of ligand against time. The WinNonlin analysis package (available from Pharsight Corp., Mountain View, Calif. 94040, USA) can be used, for example, to model the curve. In a first phase (the alpha phase) the ligand is undergoing mainly distribution in the patient, with some elimination. A second phase (beta phase) is the terminal phase when the ligand has been distributed and the serum concentration is decreasing as the ligand is cleared from the patient. The t alpha half life is the half life of the first phase and the t beta half life is the half life of the second phase. Thus, advantageously, the present invention provides a ligand or a composition comprising a ligand according to the invention having a tα half-life in the range of 15 minutes or more. In one embodiment, the lower end of the range is 30 minutes, 45 minutes, 1 hour, 2 hours, 3 hours, 4 hours, 5 hours, 6 hours, 7 hours, 10 hours, 11 hours or 12 hours. In addition, or alternatively, a ligand or composition according to the invention will have a tα half life in the range of up to and including 12 hours. In one embodiment, the upper end of the range is 11, 10, 9, 8, 7, 6 or 5 hours. An example of a suitable range is 1 to 6 hours, 2 to 5 hours or 3 to 4 hours.

Advantageously, the present invention provides a ligand or a composition comprising a ligand according to the invention having a tβ half-life in the range of 2.5 hours or more. In one embodiment, the lower end of the range is 3 hours, 4 hours, 5 hours, 6 hours, 7 hours, 10 hours, 11 hours, or 12 hours. In addition, or alternatively, a ligand or composition according to the invention has a tβ half-life in the range of up to and including 21 days. In one embodiment, the upper end of the range is 12 hours, 24 hours, 2 days, 3 days, 5 days, 10 days, 15 days or 20 days. Advantageously a ligand or composition according to the invention will have a tβ half life in the range 12 to 60 hours. In a further embodiment, it will be in the range 12 to 48 hours. In a further embodiment still, it will be in the range 12 to 26 hours.

In addition, or alternatively to the above criteria, the present invention provides a ligand or a composition comprising a ligand according to the invention having an AUC value (area under the curve) in the range of 1 mg min/ml or more. In one embodiment, the lower end of the range is 5, 10, 15, 20, 30, 100, 200 or 300 mg.min/ml. In addition, or alternatively, a ligand or composition according to the invention has an AUC in the range of up to 600 mg.min/ml. In one embodiment, the upper end of the range is 500, 400, 300, 200, 150, 100, 75 or 50 mg.min/ml. Advantageously a ligand according to the invention will have a AUC in the range selected from the group consisting of the following: 15 to 150 mg.min/ml, 15 to 100 mg.min/ml, 15 to 75 mg.min/ml, and 15 to 50 mg.min/ml.

In a first embodiment, the dual specific ligand comprises two complementary variable domains, i.e. two variable domains that, in their natural environment, are capable of operating together as a cognate pair or group even if in the context of the present invention they bind separately to their cognate epitopes. For example, the complementary variable domains may be immunoglobulin heavy chain and light chain variable domains ($V_H$ and $V_L$). $V_H$ and $V_L$ domains are advantageously provided by scFv or Fab antibody fragments. Variable domains may be linked together to form multivalent ligands by, for example: provision of a hinge region at the C-terminus of each V domain and disulphide bonding between cysteines in the hinge regions; or provision of dAbs each with a cysteine at the C-terminus of the domain, the cysteines being disulphide bonded together; or production of V-CH & V-CL to produce a Fab format; or use of peptide linkers (for example Gly$_4$Ser linkers discussed hereinbelow) to produce dimers, trimers and further multimers.

The inventors have found that the use of complementary variable domains allows the two domain surfaces to pack together and be sequestered from the solvent. Furthermore the complementary domains are able to stabilise each other. In addition, it allows the creation of dual-specific IgG antibodies without the disadvantages of hybrid hybridomas as used in the prior art, or the need to engineer heavy or light chains at the sub-unit interfaces. The dual-specific ligands of the first aspect of the present invention have at least one $V_H/V_L$ pair. A bispecific IgG according to this invention will therefore comprise two such pairs, one pair on each arm of the Y-shaped molecule. Unlike conventional bispecific antibodies or diabodies, therefore, where the ratio of chains used is determinative in the success of the preparation thereof and leads to practical difficulties, the dual specific ligands of the invention are free from issues of chain balance. Chain imbalance in conventional bi-specific antibodies results from the association of two different $V_L$ chains with two different $V_H$ chains, where $V_L$ chain 1 together with $V_H$ chain 1 is able to bind to antigen or epitope 1 and $V_L$ chain 2 together with $V_H$ chain 2 is able to bind to antigen or epitope 2 and the two correct pairings are in some way linked to one another. Thus, only when $V_L$ chain 1 is paired with $V_H$ chain 1 and $V_L$ chain 2 is paired with $V_H$ chain 2 in a single molecule is bi-specificity created. Such bi-specific molecules can be created in two different ways. Firstly, they can be created by association of two existing $V_H/V_L$ pairings that each bind to a different antigen or epitope (for example, in a bi-specific IgG). In this case the $V_H/V_L$ pairings must come all together in a 1:1 ratio in order to create a population of molecules all of which are bi-specific. This never occurs (even when complementary CH domain is enhanced by "knobs into holes" engineering) leading to a mixture of bi-specific molecules and molecules that are only able to bind to one antigen or epitope but not the other. The second way of creating a bi-specific antibody is by the simultaneous association of two different $V_H$ chain with two different $V_L$ chains (for example in a bi-specific diabody). In this case, although there tends to be a preference for $V_L$ chain 1 to pair with $V_H$ chain 1 and $V_L$ chain 2 to pair with $V_H$ chain 2 (which can be enhanced by "knobs into holes" engineering of the $V_L$ and $V_H$ domains), this paring is never achieved in all molecules, leading to a mixed formulation whereby incorrect pairings occur that are unable to bind to either antigen or epitope.

Bi-specific antibodies constructed according to the dual-specific ligand approach according to the first aspect of the present invention overcome all of these problems because the binding to antigen or epitope 1 resides within the $V_H$ or $V_L$ domain and the binding to antigen or epitope 2 resides with the complementary $V_L$ or $V_H$ domain, respectively. Since $V_H$ and $V_L$ domains pair on a 1:1 basis all $V_H/V_L$ pairings will be bi-specific and thus all formats constructed using these $V_H/V_L$ pairings (Fv, scFvs, Fabs, minibodies, IgGs etc) will have 100% bi-specific activity.

In the context of the present invention, first and second "epitopes" are understood to be epitopes which are not the same and are not bound by a single monospecific ligand. In the first configuration of the invention, they are advantageously on different antigens, one of which acts to increase the half-life of the ligand in vivo. Likewise, the first and second antigens are advantageously not the same.

The dual specific ligands of the invention do not include ligands as described in WO 02/02773. Thus, the ligands of the present invention do not comprise complementary $V_H/V_L$ pairs which bind any one or more antigens or epitopes co-operatively. Instead, the ligands according to the first aspect of the invention comprise a $V_H/V_L$ complementary pair, wherein the V domains have different specificities. Moreover, the ligands according to the first aspect of the invention comprise $V_H/V_L$ complementary pairs having different specificities for non-structurally related epitopes or antigens. Structurally related epitopes or antigens are epitopes or antigens which possess sufficient structural similarity to be bound by a conventional $V_H/V_L$ complementary pair which acts in a co-operative manner to bind an antigen or epitope; in the case of structurally related epitopes, the epitopes are sufficiently similar in structure that they "fit" into the same binding pocket formed at the antigen binding site of the $V_H/V_L$ dimer.

In a second aspect, the present invention provides a ligand comprising a first immunoglobulin variable domain having a first antigen or epitope binding specificity and a second immunoglobulin variable domain having a second antigen or epitope binding specificity wherein one or both of said first and second variable domains bind to an antigen which increases the half-life of the ligand in vivo, and the variable domains are not complementary to one another.

In one embodiment, binding via one variable domain modulates the binding of the ligand via the second variable domain.

In this embodiment, the variable domains may be, for example, pairs of $V_H$ domains or pairs of $V_L$, domains. Binding of antigen at the first site may modulate, such as enhance or inhibit, binding of an antigen at the second site. For example, binding at the first site at least partially inhibits binding of an antigen at a second site. In such an embodiment, the ligand may for example be maintained in the body of a subject organism in vivo through binding to a protein which increases the half-life of the ligand until such a time as it becomes bound to the second target antigen and dissociates from the half-life increasing protein.

Modulation of binding in the above context is achieved as a consequence of the structural proximity of the antigen binding sites relative to one another. Such structural proximity can be achieved by the nature of the structural components linking the two or more antigen binding sites, e.g. by the provision of a ligand with a relatively rigid structure that holds the antigen binding sites in close proximity. Advantageously, the two or more antigen binding sites are in physically close proximity to one another such that one site modulates the binding of antigen at another site by a process which involves steric hindrance and/or conformational changes within the immunoglobulin molecule.

The first and the second antigen binding domains may be associated either covalently or non-covalently. In the case that the domains are covalently associated, then the association may be mediated for example by disulphide bonds or by a polypeptide linker such as $(Gly_4Ser)_n$, where n=from 1 to 8, e.g., 2, 3, 4, 5 or 7.

In the case that the variable domains are selected from V-gene repertoires selected for instance using phage display technology as herein described, then these variable domains can comprise a universal framework region, such that they may be recognised by a specific generic ligand as herein defined. The use of universal frameworks, generic ligands and the like is described in WO 99/20749. In the present invention, reference to phage display includes the use of both phage and/or phagemids.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, *Nature* 370: 389-391 (1994) and U.S. Pat. No. 6,297,053, both of which are incorporated herein by reference. Other methods of mutagenesis are well known to those of skill in the art.

In a preferred embodiment of the invention the 'dual-specific ligand' is a single chain Fv fragment. In an alternative embodiment of the invention, the 'dual-specific ligand' consists of a Fab region of an antibody. The term "Fab region" includes a Fab-like region where two VH or two VL domains are used.

The variable regions may be derived from antibodies directed against target antigens or epitopes. Alternatively they may be derived from a repertoire of single antibody domains such as those expressed on the surface of filamentous bacteriophage. Selection may be performed as described below.

In a further aspect, the present invention provides one or more nucleic acid molecules encoding at least a dual-specific ligand as herein defined. The dual specific ligand may be encoded on a single nucleic acid molecule; alternatively, each domain may be encoded by a separate nucleic acid molecule.

Where the ligand is encoded by a single nucleic acid molecule, the domains may be expressed as a fusion polypeptide, in the manner of a scFv molecule, or may be separately expressed and subsequently linked together, for example using chemical linking agents. Ligands expressed from separate nucleic acids will be linked together by appropriate means.

The nucleic acid may further encode a signal sequence for export of the polypeptides from a host cell upon expression and may be fused with a surface component of a filamentous bacteriophage particle (or other component of a selection display system) upon expression.

In a further aspect the present invention provides a vector comprising nucleic acid encoding a dual specific ligand according to the present invention.

In a yet further aspect, the present invention provides a host cell transfected with a vector encoding a dual specific ligand according to the present invention.

Expression from such a vector may be configured to produce, for example on the surface of a bacteriophage particle, variable domains for selection. This allows selection of displayed variable regions and thus selection of 'dual-specific ligands' using the method of the present invention.

The present invention further provides a kit comprising at least a dual-specific ligand according to the present invention.

In a third aspect, the invention provides a method for producing a ligand comprising a first immunoglobulin single variable domain having a first binding specificity and a second single immunoglobulin single variable domain having a second (different) binding specificity, one or both of the binding specificities being specific for an antigen which increases the half-life of the ligand in vivo, the method comprising the steps of:

a) selecting a first variable domain by its ability to bind to a first epitope,
b) selecting a second variable region by its ability to bind to a second epitope,
c) combining the variable domains; and
d) selecting the ligand by its ability to bind to said first epitope and to said second epitope.

The ligand can bind to the first and second epitopes either simultaneously or, where there is competition between the binding domains for epitope binding, the binding of one domain may preclude the binding of another domain to its cognate epitope. In one embodiment, therefore, step (d) above requires simultaneous binding to both first and second (and possibly further) epitopes; in another embodiment, the binding to the first and second epitopes is not simultaneous.

The epitopes are preferably on separate antigens.

Ligands advantageously comprise $V_H/V_L$ combinations, or $V_H/V_H$ or $V_L/V_L$ combinations of immunoglobulin variable domains, as described above. The ligands may moreover comprise camelid $V_{HH}$ domains, provided that the $V_{HH}$ domain which is specific for an antigen which increases the half-life of the ligand in vivo does not bind Hen egg white lysozyme (HEL), porcine pancreatic alpha-amylase or NmC-A; hcg, BSA-linked RR6 azo dye or *S. mutans* HG982 cells, as described in Conrath et al., (2001) JBC 276:7346-7350 and WO99/23221, neither of which describe the use of a specificity for an antigen which increases half-life to increase the half life of the ligand in vivo.

In one embodiment, said first variable domain is selected for binding to said first epitope in absence of a complementary variable domain. In a further embodiment, said first variable domain is selected for binding to said first epitope/antigen in the presence of a third variable domain in which said third variable domain is different from said second variable domain and is complementary to the first domain.

Similarly, the second domain may be selected in the absence or presence of a complementary variable domain.

The antigens or epitopes targeted by the ligands of the invention, in addition to the half-life enhancing protein, may be any antigen or epitope but advantageously is an antigen or epitope that is targeted with therapeutic benefit. The invention provides ligands, including open conformation, closed conformation and isolated dAb monomer ligands, specific for any such target, particularly those targets further identified herein. Such targets may be, or be part of, polypeptides, proteins or nucleic acids, which may be naturally occurring or synthetic. In this respect, the ligand of the invention may bind the epitope or antigen and act as an antagonist or agonist (eg, EPO receptor agonist). One skilled in the art will appreciate that the choice is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3 and HER 4. Cytokine receptors include receptors for the foregoing cytokines. It will be appreciated that this list is by no means exhaustive.

In one embodiment of the invention, the variable domains are derived from a respective antibody directed against the antigen or epitope. In a preferred embodiment the variable domains are derived from a repertoire of single variable antibody domains.

In a second configuration, the present invention provides multispecific ligands. According to the present invention the term "multi-specific ligand" refers to a ligand which possesses more than one epitope binding specificity as herein defined. Generally, the multi-specific ligand comprises two or more epitope binding domains.

Epitope binding domains according to the present invention comprise a protein scaffold and epitope interaction sites (which are advantageously on the surface of the protein scaffold). According to the present invention, advantageously, each epitope binding domain is of a different epitope binding specificity.

In the context of the present invention, first and second "epitopes" are understood to be epitopes which are not the same and are not bound by a single monospecific ligand. They may be on different antigens or on the same antigen, but separated by a sufficient distance that they do not form a single entity that could be bound by a single mono-specific $V_H/V_L$ binding pair of a conventional antibody. Experimentally, if both of the individual variable domains in single chain antibody form (domain antibodies or dAbs) are separately competed by a monospecific $V_H/V_L$ ligand against two epitopes then those two epitopes are not sufficiently far apart to be considered separate epitopes according to the present invention.

According to the present invention, advantageously, each epitope binding domain comprises an immunoglobulin variable domain. More advantageously, each immunoglobulin variable domain will be either a variable light chain domain $(V_L)$ or a variable heavy chain domain $V_H$. In the second configuration of the present invention, the immunoglobulin domains when present on a ligand according to the present invention are non-complementary, that is they do not associate to form a $V_H/V_L$ antigen binding site. Thus, multi-specific ligands as defined in the second configuration of the invention comprise immunoglobulin domains of the same sub-type, that is either variable light chain domains $(V_L)$ or variable heavy chain domains $(V_H)$. Moreover, where the ligand according to the invention is in the closed conformation, the immunoglobulin domains may be of the camelid $V_{HH}$ type.

In an alternative embodiment, the ligand(s) according to the invention do not comprise a camelid $V_{HH}$ domain. More particularly, the ligand(s) of the invention do not comprise one or more amino acid residues that are specific to camelid $V_{HH}$ domains as compared to human $V_H$ domains.

Advantageously, the single variable domains are derived from antibodies selected for binding activity against different antigens or epitopes. For example, the variable domains may be isolated at least in part by human immunisation. Alternative methods are known in the art, including isolation from human antibody libraries and synthesis of artificial antibody genes.

The variable domains advantageously bind superantigens, such as protein A or protein L. Binding to superantigens is a property of correctly folded antibody variable domains, and allows such domains to be isolated from, for example, libraries of recombinant or mutant domains.

Epitope binding domains may also be based on protein scaffolds or skeletons other than immunoglobulin domains. For example natural bacterial receptors such as SpA have been used as scaffolds for the grafting of CDRs to generate ligands which bind specifically to one or more epitopes. Details of this procedure are described in U.S. Pat. No. 5,831, 012. Other suitable scaffolds include those based on fibronectin and affibodies. Details of suitable procedures are described in WO 98/58965. Other suitable scaffolds include lipocallin and CTLA4, as described in van den Beuken et al., J. Mol. Biol. (2001) 310, 591-601, and scaffolds such as those described in WO0069907 (Medical Research Council), which are based for example on the ring structure of bacterial GroEL or other chaperone polypeptides.

Protein scaffolds may be combined; for example, CDRs may be grafted on to a CTLA4 scaffold and used together with immunoglobulin $V_H$ or $V_L$ domains to form a multivalent ligand. Likewise, fibronectin, lipocallin and other scaffolds may be combined.

In one embodiment, the multispecific ligand comprises an epitope binding domain that comprises the CDRs of a single immunoglobulin domain (dAb) that binds TNFR1 described herein grafted to a suitable protein scaffold or skeleton.

It will be appreciated by one skilled in the art that the epitope binding domains of a closed conformation multispecific ligand produced according to the method of the present invention may be on the same polypeptide chain, or alternatively, on different polypeptide chains. In the case that the variable regions are on different polypeptide chains, then they may be linked via a linker, advantageously a flexible linker (such as a polypeptide chain), a chemical linking group, or any other method known in the art.

The first and the second epitope binding domains may be associated either covalently or non-covalently. In the case that the domains are covalently associated, then the association may be mediated for example by disulphide bonds.

In certain embodiments of the second configuration of the invention, the epitopes may displace each other on binding. For example, a first epitope may be present on an antigen which, on binding to its cognate first binding domain, causes steric hindrance of a second binding domain, or a coformational change therein, which displaces the epitope bound to the second binding domain.

Advantageously, binding is reduced by 25% or more, advantageously 40%, 50%, 60%, 70%, 80%, 90% or more, and preferably up to 100% or nearly so, such that binding is completely inhibited. Binding of epitopes can be measured by conventional antigen binding assays, such as ELISA, by fluorescence based techniques, including FRET, or by techniques such as surface plasmon resonance which measure the mass of molecules.

Moreover, the invention provides a closed conformation multi-specific ligand comprising a first epitope binding domain having a first epitope binding specificity and a non-complementary second epitope binding domain having a second epitope binding specificity, wherein the first and second binding specificities compete for epitope binding such that the closed conformation multi-specific ligand may not bind both epitopes simultaneously.

The closed conformation multispecific ligands of the invention do not include ligands as described in WO 02/02773. Thus, the ligands of the present invention do not comprise complementary $V_H/V_L$ pairs which bind any one or more antigens or epitopes co-operatively. Instead, the ligands according to the invention preferably comprise non-complementary $V_H$-$V_H$ or $V_L$-$V_L$ pairs. Advantageously, each $V_H$ or $V_L$ domain in each $V_H$-$V_H$ or $V_L$-$V_L$ pair has a different epitope binding specificity, and the epitope binding sites are so arranged that the binding of an epitope at one site competes with the binding of an epitope at another site.

Advantageously, the closed conformation multispecific ligand may comprise a first domain capable of binding a target molecule, and a second domain capable of binding a molecule or group which extends the half-life of the ligand. For example, the molecule or group may be a bulky agent, such as HSA or a cell matrix protein. As used herein, the phrase "molecule or group which extends the half-life of a ligand" refers to a molecule or chemical group which, when bound by a dual-specific ligand as described herein increases the in vivo half-life of such dual specific ligand when administered to an animal, relative to a ligand that does not bind that molecule or group. Examples of molecules or groups that extend the half-life of a ligand are described hereinbelow. In a preferred embodiment, the closed conformation multispecific ligand may be capable of binding the target molecule only on displacement of the half-life enhancing molecule or group. Thus, for example, a closed conformation multispecific ligand is maintained in circulation in the bloodstream of a subject by a bulky molecule such as HSA. When a target molecule is encountered, competition between the binding domains of the closed conformation multispecific ligand results in displacement of the HSA and binding of the target.

In a preferred embodiment of the second configuration of the invention, the epitope binding domains are immunoglobulin variable regions and are selected from single domain V gene repertoires. Generally the repertoire of single antibody domains is displayed on the surface of filamentous bacteriophage. In a preferred embodiment each single antibody domain is selected by binding of a phage repertoire to antigen. In a preferred embodiment of the second configuration of the invention, the epitope binding domains are immunoglobulin variable regions and are selected from single domain V gene repertoires. Generally the repertoire of single antibody domains is displayed on the surface of filamentous bacteriophage. In a preferred embodiment each single antibody domain is selected by binding of a phage repertoire to antigen.

In one aspect, the multispecific ligand comprises at least two non-complementary variable domains. For example, the ligands may comprise a pair of $V_H$ domains or a pair of $V_L$ domains. Advantageously, the domains are of non-camelid origin; preferably they are human domains or comprise human framework regions (FWs) and one or more heterologous CDRs. CDRs and framework regions are those regions of an immunoglobulin variable domain as defined in the Kabat database of Sequences of Proteins of Immunological Interest.

Preferred human framework regions are those encoded by germline gene segments DP47 and DPK9. Advantageously, FW1, FW2 and FW3 of a $V_H$ or $V_L$ domain have the sequence of FW1, FW2 or FW3 from DP47 or DPK9. The human frameworks may optionally contain mutations, for example up to about 5 amino acid changes or up to about 10 amino acid changes collectively in the human frameworks used in the ligands of the invention.

The variable domains in the multispecific ligands according to the second configuration of the invention may be arranged in an open or a closed conformation; that is, they may be arranged such that the variable domains can bind their cognate ligands independently and simultaneously, or such that only one of the variable domains may bind its cognate ligand at any one time.

The inventors have realised that under certain structural conditions, non-complementary variable domains (for example two light chain variable domains or two heavy chain variable domains) may be present in a ligand such that binding of a first epitope to a first variable domain inhibits the binding of a second epitope to a second variable domain, even though such non-complementary domains do not operate together as a cognate pair.

Advantageously, the ligand comprises two or more pairs of variable domains; that is, it comprises at least four variable domains. Advantageously, the four variable domains comprise frameworks of human origin.

In a preferred embodiment, the human frameworks are identical to those of human germline sequences.

The present inventors consider that such antibodies will be of particular use in ligand binding assays for therapeutic and other uses.

In one embodiment of the second configuration of the invention, the variable domains are derived from an antibody directed against the first and/or second antigen or epitope. In a preferred embodiment the variable domains are derived from a repertoire of single variable antibody domains. In one example, the repertoire is a repertoire that is not created in an animal or a synthetic repertoire. In another example, the single variable domains are not isolated (at least in part) by animal immunisation. Thus, the single domains can be isolated from a naïve library.

The second configuration of the invention, in another aspect, provides a multi-specific ligand comprising a first epitope binding domain having a first epitope binding specificity and a non-complementary second epitope binding domain having a second epitope binding specificity. The first and second binding specificities may be the same or different.

In a further aspect, the present invention provides a closed conformation multi-specific ligand comprising a first epitope binding domain having a first epitope binding specificity and a non-complementary second epitope binding domain having a second epitope binding specificity wherein the first and second binding specificities are capable of competing for epitope binding such that the closed conformation multi-specific ligand cannot bind both epitopes simultaneously.

In a still further aspect, the invention provides open conformation ligands comprising non-complementary binding domains, wherein the domains are specific for a different epitope on the same target. Such ligands bind to targets with increased avidity. Similarly, the invention provides multivalent ligands comprising non-complementary binding domains specific for the same epitope and directed to targets which comprise multiple copies of said epitope, such as IL-5, PDGF-AA, PDGF-BB, TGF beta, TGF beta2, TGF beta3 and TNFα, for example human TNF Receptor 1 and human TNFα.

In a similar aspect, ligands according to the invention can be configured to bind individual epitopes with low affinity, such that binding to individual epitopes is not therapeutically significant; but the increased avidity resulting from binding to two epitopes provides a therapeutic benefit. In a particular example, epitopes may be targeted which are present individually on normal cell types, but present together only on abnormal or diseased cells, such as tumour cells. In such a situation, only the abnormal or diseased cells are effectively targeted by the bispecific ligands according to the invention.

Ligand specific for multiple copies of the same epitope, or adjacent epitopes, on the same target (known as chelating dAbs) may also be trimeric or polymeric (tertrameric or more) ligands comprising three, four or more non-complementary binding domains. For example, ligands may be constructed comprising three or four $V_H$ domains or $V_L$ domains.

Moreover, ligands are provided which bind to multisubunit targets, wherein each binding domain is specific for a subunit of said target. The ligand may be dimeric, trimeric or polymeric.

Preferably, the multi-specific ligands according to the above aspects of the invention are obtainable by the method of the first aspect of the invention.

According to the above aspect of the second configuration of the invention, advantageously the first epitope binding domain and the second epitope binding domains are non-complementary immunoglobulin variable domains, as herein defined. That is either $V_H$-$V_H$ or $V_L$-$V_L$ variable domains.

Chelating dAbs in particular may be prepared according to a preferred aspect of the invention, namely the use of anchor dAbs, in which a library of dimeric, trimeric or multimeric dAbs is constructed using a vector which comprises a constant dAb upstream or downstream of a linker sequence, with a repertoire of second, third and further dAbs being inserted on the other side of the linker. For example, the anchor or guiding dAb may be TAR1-5 ($V_\kappa$), TAR1-27($V_\kappa$), TAR2h-5 (VH) or TAR2h-6($V_\kappa$).

In alternative methodologies, the use of linkers may be avoided, for example by the use of non-covalent bonding or natural affinity between binding domains such as $V_H$ and $V_\kappa$. The invention accordingly provides a method for preparing a chelating multimeric ligand comprising the steps of:

(a) providing a vector comprising a nucleic acid sequence encoding a single binding domain specific for a first epitope on a target;

(b) providing a vector encoding a repertoire comprising second binding domains specific for a second epitope on said target, which epitope can be the same or different to the first epitope, said second epitope being adjacent to said first epitope; and (c) expressing said first and second binding domains; and (d) isolating those combinations of first and second binding domains which combine together to produce a target-binding dimer.

The first and second epitopes are adjacent such that a multimeric ligand is capable of binding to both epitopes simultaneously. This provides the ligand with the advantages of increased avidity if binding. Where the epitopes are the same, the increased avidity is obtained by the presence of multiple copies of the epitope on the target, allowing at least two copies to be simultaneously bound in order to obtain the increased avidity effect.

The binding domains may be associated by several methods, as well as the use of linkers. For example, the binding domains may comprise cys residues, avidin and streptavidin groups or other means for non-covalent attachment post-synthesis; those combinations which bind to the target efficiently will be isolated. Alternatively, a linker may be present between the first and second binding domains, which are expressed as a single polypeptide from a single vector, which comprises the first binding domain, the linker and a repertoire of second binding domains, for instance as described above.

In a preferred aspect, the first and second binding domains associate naturally when bound to antigen; for example, $V_H$ and $V_\kappa$ domains, when bound to adjacent epitopes, will naturally associate in a three-way interaction to form a stable dimer. Such associated proteins can be isolated in a target binding assay. An advantage of this procedure is that only binding domains which bind to closely adjacent epitopes, in the correct conformation, will associate and thus be isolated as a result of their increased avidity for the target.

In an alternative embodiment of the above aspect of the second configuration of the invention, at least one epitope binding domain comprises a non-immunoglobulin "protein scaffold" or "protein skeleton" as herein defined. Suitable non-immunoglobulin protein scaffolds include but are not limited to any of those selected from the group consisting of: SpA, fibronectin, GroEL and other chaperones, lipocallin, CCTLA4 and affibodies, as set forth above.

According to the above aspect of the second configuration of the invention, advantageously, the epitope binding domains are attached to a protein skeleton. Advantageously, a protein skeleton according to the invention is an immunoglobulin skeleton.

According to the present invention, the term "immunoglobulin skeleton" refers to a protein which comprises at least one immunoglobulin fold and which acts as a nucleus for one or more epitope binding domains, as defined herein.

Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

Linking of the skeleton to the epitope binding domains, as herein defined may be achieved at the polypeptide level, that is after expression of the nucleic acid encoding the skeleton and/or the epitope binding domains. Alternatively, the linking step may be performed at the nucleic acid level. Methods of linking a protein skeleton according to the present invention, to the one or more epitope binding domains include the use of protein chemistry and/or molecular biology techniques which will be familiar to those skilled in the art and are described herein.

Advantageously, the closed conformation multispecific ligand may comprise a first domain capable of binding a target molecule, and a second domain capable of binding a molecule or group which extends the half-life of the ligand. For example, the molecule or group may be a bulky agent, such as HSA or a cell matrix protein. As used herein, the phrase "molecule or group which extends the half-life of a ligand" refers to a molecule or chemical group which, when bound by a dual-specific ligand as described herein increases the in vivo half-life of such dual specific ligand when administered to an animal, relative to a ligand that does not bind that molecule or group. Examples of molecules or groups that extend the half-life of a ligand are described hereinbelow. In a preferred embodiment, the closed conformation multispecific ligand may be capable of binding the target molecule only on displacement of the half-life enhancing molecule or group. Thus, for example, a closed conformation multispecific ligand is maintained in circulation in the bloodstream of a subject by a bulky molecule such as HSA. When a target molecule is encountered, competition between the binding domains of the closed conformation multispecific ligand results in displacement of the HSA and binding of the target.

In a further aspect of the second configuration of the invention, the present invention provides one or more nucleic acid molecules encoding at least a multispecific ligand as herein defined. In one embodiment, the ligand is a closed conformation ligand. In another embodiment, it is an open conformation ligand. The multispecific ligand may be encoded on a single nucleic acid molecule; alternatively, each epitope binding domain may be encoded by a separate nucleic acid molecule. Where the ligand is encoded by a single nucleic acid molecule, the domains may be expressed as a fusion polypeptide, or may be separately expressed and subsequently linked together, for example using chemical linking agents. Ligands expressed from separate nucleic acids will be linked together by appropriate means.

The nucleic acid may further encode a signal sequence for export of the polypeptides from a host cell upon expression and may be fused with a surface component of a filamentous bacteriophage particle (or other component of a selection display system) upon expression. Leader sequences, which may be used in bacterial expression and/or phage or phagemid display, include pelB, stII, ompA, phoA, bla and pelA.

In a further aspect of the second configuration of the invention the present invention provides a vector comprising nucleic acid according to the present invention.

In a yet further aspect, the present invention provides a host cell transfected with a vector according to the present invention.

Expression from such a vector may be configured to produce, for example on the surface of a bacteriophage particle, epitope binding domains for selection. This allows selection of displayed domains and thus selection of 'multispecific ligands' using the method of the present invention.

The present invention further provides a kit comprising at least a multispecific ligand according to the present invention, which may be an open conformation or closed conformation ligand. Kits according to the invention may be, for example, diagnostic kits, therapeutic kits, kits for the detection of chemical or biological species, and the like.

The present invention provides a method for producing a multispecific ligand comprising the steps of:
a) selecting a first epitope binding domain by its ability to bind to a first epitope,
b) selecting a second epitope binding domain by its ability to bind to a second epitope,
c) combining the epitope binding domains; and
d) selecting the closed conformation multispecific ligand by its ability to bind to said first second epitope and said second epitope.

In a further aspect of the second configuration, the invention provides a method for preparing a closed conformation multi-specific ligand comprising a first epitope binding domain having a first epitope binding specificity and a non-complementary second epitope binding domain having a second epitope binding specificity, wherein the first and second binding specificities compete for epitope binding such that the closed conformation multi-specific ligand may not bind both epitopes simultaneously, said method comprising the steps of:
a) selecting a first epitope binding domain by its ability to bind to a first epitope,
b) selecting a second epitope binding domain by its ability to bind to a second epitope,
c) combining the epitope binding domains such that the domains are in a closed conformation; and
d) selecting the closed conformation multispecific ligand by its ability to bind to said first second epitope and said second epitope, but not to both said first and second epitopes simultaneously.

An alternative embodiment of the above aspect of the of the second configuration of the invention optionally comprises a further step (b1) comprising selecting a third or further epitope binding domain. In this way the multi-specific ligand produced, whether of open or closed conformation, comprises more than two epitope binding specificities. In a preferred aspect of the second configuration of the invention, where the multi-specific ligand comprises more than two epitope binding domains, at least two of said domains are in a closed conformation and compete for binding; other domains may compete for binding or may be free to associate independently with their cognate epitope(s).

In the second configuration of the invention, the first and the second epitopes are preferably different. They may be, or be part of, polypeptides, proteins or nucleic acids, which may be naturally occurring or synthetic. In this respect, the ligand of the invention may bind an epitope or antigen and act as an antagonist or agonist (eg, EPO receptor agonist). The epitope binding domains of the ligand in one embodiment have the same epitope specificity, and may for example simultaneously bind their epitope when multiple copies of the epitope are present on the same antigen. In another embodiment, these epitopes are provided on different antigens such that the ligand can bind the epitopes and bridge the antigens. One skilled in the art will appreciate that the choice of epitopes and antigens is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA-78, Eotaxin, Eotaxin-2, Exodus-2, EpoR, FGF-acidic, FGF-basic, fibroblast growth factor-10, FLT3 ligand, Fractalkine (CX3C), GDNF, G-CSF, GM-CSF, GF-β1, insulin, IFN-γ, IGF-I, IGF-II, IL-1α, IL-1β, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-β, GRO-γ, HCC1, 1-309, HER 1, HER 2, HER 3, HER 4, TACE recognition site, TNF BP-I and TNF BP-II, as well as any target disclosed in Annex 2 or Annex 3 hereto, whether in combination as set forth in the Annexes, in a different combination or individually. Cytokine receptors include receptors for the foregoing cytokines, e.g. IL-1 R1; IL-6R; IL-10R; IL-18R, as well as receptors for cytokines set forth in Annex 2 or Annex 3 and also receptors disclosed in Annex 2 and 3. It will be appreciated that this list is by no means exhaustive. Where the multispecific ligand binds to two epitopes (on the same or different antigens), the antigen(s) may be selected from this list. In particular embodiments, the ligand comprises a dAb that binds TNFR1 and a second dAb or epitope binding domain that binds any one of the these antigens. In such embodiments, the multispecific ligand can comprise any combination of immunoglobulin variable domains (e.g., $V_H V_H$, $V_H V_L$, $V_L V_L$).

Preparation of Immunoglobulin Based Multi-Specific Ligands

Dual specific ligands according to the invention, whether open or closed in conformation according to the desired configuration of the invention, may be prepared according to previously established techniques, used in the field of antibody engineering, for the preparation of scFv, "phage" antibodies and other engineered antibody molecules. Techniques for the preparation of antibodies, and in particular bispecific antibodies, are for example described in the following reviews and the references cited therein: Winter & Milstein, (1991) Nature 349:293-299; Pluckthun (1992) Immunological Reviews 130:151-188; Wright et al., (1992) Crti. Rev. Immunol. 12:125-168; Holliger, P. & Winter, G. (1993) Cuff. Op. Biotechn. 4, 446-449; Carter, et al. (1995) J. Hernatother. 4, 463-470; Chester, K. A. & Hawkins, R. E. (1995) Trends Biotechn. 13, 294-300; Hoogenboom, H. R. (1997) Nature Biotechnol. 15, 125-126; Fearon, D (1997) Nature Biotechnol. 15, 618-619; Plückthun, A. & Pack, P. (1997) Immunotechnology 3, 83-105; Carter, P. & Merchant, A. M. (1997) Cuff. Opin. Biotechnol. 8, 449-454; Holliger, P. & Winter, G. (1997) Cancer Immunol. Immun other. 45, 128-130.

The invention provides for the selection of variable domains against two different antigens or epitopes, and subsequent combination of the variable domains.

The techniques employed for selection of the variable domains employ libraries and selection procedures which are known in the art. Natural libraries (Marks et al. (1991) J. Mol. Biol., 222: 581; Vaughan et al. (1996) Nature Biotech., 14: 309) which use rearranged V genes harvested from human B cells are well known to those skilled in the art. Synthetic libraries (Hoogenboorn & Winter (1992) J. Mol. Biol., 227: 381; Barbas et al. (1992) Proc. Natl. Acad. Sci. USA, 89: 4457; Nissim et al. (1994) EMBO J., 13: 692; Griffiths et al. (1994) EMBO J., 13: 3245; De Kruif et al. (1995) J. Mol. Biol., 248: 97) are prepared by cloning immunoglobulin V genes, usually using PCR. Errors in the PCR process can lead to a high degree of randomisation. $V_H$ and/or $V_L$ libraries may be selected against target antigens or epitopes separately, in which case single domain binding is directly selected for, or together.

A preferred method for making a dual specific ligand according to the present invention comprises using a selection system in which a repertoire of variable domains is selected for binding to a first antigen or epitope and a repertoire of variable domains is selected for binding to a second antigen or epitope. The selected first and second variable domains are then combined and the dual-specific ligand selected for binding to both first and second antigen or epitope. Closed conformation ligands are selected for binding both first and second antigen or epitope in isolation but not simultaneously.

A. Library Vector Systems

A variety of selection systems are known in the art which are suitable for use in the present invention. Examples of such systems are described below.

Bacteriophage lambda expression systems may be screened directly as bacteriophage plaques or as colonies of lysogens, both as previously described (Huse et al. (1989) Science, 246: 1275; Caton and Koprowski (1990) Proc. Natl. Acad. Sci. U.S.A., 87; Mullinax et al. (1990) Proc. Natl. Acad. Sci. U.S.A., 87: 8095; Persson et al. (1991) Proc. Natl. Acad. Sci. U.S.A., 88: 2432) and are of use in the invention. Whilst such expression systems can be used to screen up to $10^6$ different members of a library, they are not really suited to screening of larger numbers (greater than $10^6$ members).

Of particular use in the construction of libraries are selection display systems, which enable a nucleic acid to be linked to the polypeptide it expresses. As used herein, a selection display system is a system that permits the selection, by suitable display means, of the individual members of the library by binding the generic and/or target ligands.

Selection protocols for isolating desired members of large libraries are known in the art, as typified by phage display techniques. Such systems, in which diverse peptide sequences are displayed on the surface of filamentous bacteriophage (Scott and Smith (1990) Science, 249: 386), have proven useful for creating libraries of antibody fragments (and the nucleotide sequences that encoding them) for the in vitro selection and amplification of specific antibody fragments that bind a target antigen (McCafferty et al., WO 92/01047). The nucleotide sequences encoding the $V_H$ and $V_L$ regions are linked to gene fragments which encode leader signals that direct them to the periplasmic space of E. coli and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encode the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) Nature, 348:

552; Kang et al. (1991) *Proc. Natl. Acad. Sci. U.S.A.,* 88: 4363; Clackson et al. (1991) *Nature,* 352: 624; Lowman et al. (1991) *Biochemistry,* 30: 10832; Burton et al. (1991) *Proc. Natl. Acad. Sci. U.S.A.,* 88: 10134; Hoogenboom et al. (1991) Nucleic Acids Res., 19: 4133; Chang et al. (1991) *J. Immunol.,* 147: 3610; Breitling et al. (1991) *Gene,* 104: 147; Marks et al. (1991) supra; Baxbas et al. (1992) supra; Hawkins and Winter (1992) *J. Immunol.,* 22: 867; Marks et al., 1992, *J. Biol. Chem.,* 267: 16007; Lerner et al. (1992) *Science,* 258: 1313, incorporated herein by reference).

One particularly advantageous approach has been the use of scFv phage-libraries (Huston et al., 1988, Proc. Natl. Acad. Sci. U.S.A., 85: 5879-5883; Chaudhary et al. (1990) Proc. Natl. Acad. Sci. U.S.A., 87: 1066-1070; McCafferty et al. (1990) supra; Clackson et al. (1991) *Nature,* 352: 624; Marks et al. (1991) *J. Mol. Biol.,* 222: 581; Chiswell et al. (1992) Trends Biotech., 10: 80; Marks et al. (1992) *J. Biol. Chem.,* 267). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys), which are incorporated herein by reference.

Other systems for generating libraries of polypeptides involve the use of cell-free enzymatic machinery for the in vitro synthesis of the library members. In one method, RNA molecules are selected by alternate rounds of selection against a target ligand and PCR amplification (Tuerk and Gold (1990) *Science,* 249: 505; Ellington and Szostak (1990) *Nature,* 346: 818). A similar technique may be used to identify DNA sequences which bind a predetermined human transcription factor (Thiesen and Bach (1990) *Nucleic Acids Res.,* 18: 3203; Beaudry and Joyce (1992) *Science,* 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection.

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

B. Library Construction

Libraries intended for selection, may be constructed using techniques known in the art, for example as set forth above, or may be purchased from commercial sources. Libraries which are useful in the present invention are described, for example, in WO99/20749. Once a vector system is chosen and one or more nucleic acid sequences encoding polypeptides of interest are cloned into the library vector, one may generate diversity within the cloned molecules by undertaking mutagenesis prior to expression; alternatively, the encoded proteins may be expressed and selected, as described above, before mutagenesis and additional rounds of selection are performed. Mutagenesis of nucleic acid sequences encoding structurally optimised polypeptides is carried out by standard molecular methods. Of particular use is the polymerase chain reaction, or PCR, (Mullis and Faloona (1987) *Methods Enzymol.,* 155: 335, herein incorporated by reference). PCR, which uses multiple cycles of DNA replication catalysed by a thermostable, DNA-dependent DNA polymerase to amplify the target sequence of interest, is well known in the art. The construction of various antibody libraries has been discussed in Winter et al. (1994) Ann. Rev. Immunology 12, 433-55, and references cited therein.

PCR is performed using template DNA (at least 1 fg; more usefully, 1-1000 ng) and at least 25 pmol of oligonucleotide primers; it may be advantageous to use a larger amount of primer when the primer pool is heavily heterogeneous, as each sequence is represented by only a small fraction of the molecules of the pool, and amounts become limiting in the later amplification cycles. A typical reaction mixture includes: 2 µl of DNA, 25 pmol of oligonucleotide primer, 2.5 µl of 10×PCR buffer 1 (Perkin-Elmer, Foster City, Calif.), 0.4 µl of 1.25 µM dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler. The length and temperature of each step of a PCR cycle, as well as the number of cycles, is adjusted in accordance to the stringency requirements in effect. Annealing temperature and timing are determined both by the efficiency with which a primer is expected to anneal to a template and the degree of mismatch that is to be tolerated; obviously, when nucleic acid molecules are simultaneously amplified and mutagenised, mismatch is required, at least in the first round of synthesis. The ability to optimise the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1-5 minutes, depending on the length of the amplified product). Final extension is generally for 4 minutes at 72° C., and may be followed by an indefinite (0-24 hour) step at 4° C.

C. Combining Single Variable Domains

Domains useful in the invention, once selected, may be combined by a variety of methods known in the art, including covalent and non-covalent methods.

Preferred methods include the use of polypeptide linkers, as described, for example, in connection with scFv molecules (Bird et al., (1988) Science 242:423-426). Discussion of suitable linkers is provided in Bird et al. Science 242, 423-426; Hudson et al, Journal Immunol Methods 231 (1999) 177-189; Hudson et al, Proc Nat Acad Sci USA 85, 5879-5883. Linkers are preferably flexible, allowing the two single domains to interact. One linker example is a $(Gly_4 Ser)_n$, linker, where n=1 to 8, eg, 2, 3, 4, 5 or 7. The linkers used in diabodies, which are less flexible, may also be employed (Holliger et al., (1993) PNAS (USA) 90:6444-6448).

In one embodiment, the linker employed is not an immunoglobulin hinge region.

Variable domains may be combined using methods other than linkers. For example, the use of disulphide bridges, provided through naturally-occurring or engineered cysteine residues, may be exploited to stabilise $V_H$-$V_H$, $V_L$-$V_L$ or $V_H$-$V_L$ dimers (Reiter et al., (1994) Protein Eng. 7:697-704) or by remodelling the interface between the variable domains to improve the "fit" and thus the stability of interaction (Ridgeway et al., (1996) Protein Eng. 7:617-621; Zhu et al., (1997) Protein Science 6:781-788).

Other techniques for joining or stabilising variable domains of immunoglobulins, and in particular antibody $V_H$ domains, may be employed as appropriate.

In accordance with the present invention, dual specific ligands can be in "closed" conformations in solution. A "closed" configuration is that in which the two domains (for example $V_H$ and $V_L$) are present in associated form, such as that of an associated $V_H$-$V_L$ pair which forms an antibody binding site. For example, scFv may be in a closed conformation, depending on the arrangement of the linker used to link the $V_H$ and $V_L$ domains. If this is sufficiently flexible to allow the domains to associate, or rigidly holds them in the associated position, it is likely that the domains will adopt a closed conformation.

Similarly, $V_H$ domain pairs and $V_L$ domain pairs may exist in a closed conformation. Generally, this will be a function of close association of the domains, such as by a rigid linker, in the ligand molecule. Ligands in a closed conformation will be unable to bind both the molecule which increases the half-life of the ligand and a second target molecule. Thus, the ligand will typically only bind the second target molecule on dissociation from the molecule which increases the half-life of the ligand.

Moreover, the construction of $V_H/V_H$, $V_L/V_L$ or $V_H/V_L$ dimers without linkers provides for competition between the domains.

Ligands according to the invention may moreover be in an open conformation. In such a conformation, the ligands will be able to simultaneously bind both the molecule which increases the half-life of the ligand and the second target molecule. Typically, variable domains in an open configuration are (in the case of $V_H$-$V_L$ pairs) held far enough apart for the domains not to interact and form an antibody binding site and not to compete for binding to their respective epitopes. In the case of $V_H/V_H$ or $V_L/V_L$ dimers, the domains are not forced together by rigid linkers. Naturally, such domain pairings will not compete for antigen binding or form an antibody binding site.

Fab fragments and whole antibodies will exist primarily in the closed conformation, although it will be appreciated that open and closed dual specific ligands are likely to exist in a variety of equilibria under different circumstances. Binding of the ligand to a target is likely to shift the balance of the equilibrium towards the open configuration. Thus, certain ligands according to the invention can exist in two conformations in solution, one of which (the open form) can bind two antigens or epitopes independently, whilst the alternative conformation (the closed form) can only bind one antigen or epitope; antigens or epitopes thus compete for binding to the ligand in this conformation.

Although the open form of the dual specific ligand may thus exist in equilibrium with the closed form in solution, it is envisaged that the equilibrium will favour the closed form; moreover, the open form can be sequestered by target binding into a closed conformation. Preferably, therefore, certain dual specific ligands of the invention are present in an equilibrium between two (open and closed) conformations.

Dual specific ligands according to the invention may be modified in order to favour an open or closed conformation. For example, stabilisation of $V_H$-$V_L$ interactions with disulphide bonds stabilises the closed conformation. Moreover, linkers used to join the domains, including $V_H$ domain and $V_L$ domain pairs, may be constructed such that the open from is favoured; for example, the linkers may sterically hinder the association of the domains, such as by incorporation of large amino acid residues in opportune locations, or the designing of a suitable rigid structure which will keep the domains physically spaced apart.

D. Characterisation of the Dual-Specific Ligand

The binding of the dual-specific ligand to its specific antigens or epitopes can be tested by methods which will be familiar to those skilled in the art and include ELISA. In a preferred embodiment of the invention binding is tested using monoclonal phage ELISA.

Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) Ann. Rev. Immunology 12, 433-55 and references cited therein.

The diversity of the selected phage monoclonal antibodies may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

E. Structure of Dual-Specific Ligands

As described above, an antibody is herein defined as an antibody (for example IgG, IgM, IgA, IgA, IgE) or fragment (Fab, Fv, disulphide linked Fv, scFv, diabody) which comprises at least one heavy and a light chain variable domain, at least two heavy chain variable domains or at least two light chain variable domains. It may be at least partly derived from any species naturally producing an antibody, or created by recombinant DNA technology; whether isolated from serum, B-cells, hybridomas, transfectomas, yeast or bacteria).

In a preferred embodiment of the invention the dual-specific ligand comprises at least one single heavy chain variable domain of an antibody and one single light chain variable domain of an antibody, or two single heavy or light chain variable domains. For example, the ligand may comprise a $V_H/V_L$ pair, a pair of $V_H$ domains or a pair of $V_L$ domains.

The first and the second variable domains of such a ligand may be on the same polypeptide chain. Alternatively they may be on separate polypeptide chains. In the case that they are on the same polypeptide chain they may be linked by a linker, which is preferentially a peptide sequence, as described above.

The first and second variable domains may be covalently or non-covalently associated. In the case that they are covalently associated, the covalent bonds may be disulphide bonds.

In the case that the variable domains are selected from V-gene repertoires selected for instance using phage display technology as herein described, then these variable domains comprise a universal framework region, such that is they may be recognised by a specific generic ligand as herein defined. The use of universal frameworks, generic ligands and the like is described in WO99/20749.

Where V-gene repertoires are used variation in polypeptide sequence is preferably located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, Nature 370: 389-391 and U.S. Pat. No. 6,297,053, both of which are incorporated herein by reference. Other methods of mutagenesis are well known to those of skill in the art.

In a preferred embodiment of the invention the 'dual-specific ligand' is a single chain Fv fragment. In an alternative embodiment of the invention, the 'dual-specific ligand' consists of a Fab format.

In a further aspect, the present invention provides nucleic acid encoding at least a 'dual-specific ligand' as herein defined.

One skilled in the art will appreciate that, depending on the aspect of the invention, both antigens or epitopes may bind simultaneously to the same antibody molecule. Alternatively, they may compete for binding to the same antibody molecule. For example, where both epitopes are bound simultaneously, both variable domains of a dual specific ligand are able to independently bind their target epitopes. Where the domains compete, the one variable domain is capable of binding its target, but not at the same time as the other variable domain binds its cognate target; or the first variable domain is capable of binding its target, but not at the same time as the second variable domain binds its cognate target.

The variable regions may be derived from antibodies directed against target antigens or epitopes. Alternatively they may be derived from a repertoire of single antibody domains such as those expressed on the surface of filamentous bacteriophage. Selection may be performed as described below.

In general, the nucleic acid molecules and vector constructs required for the performance of the present invention may be constructed and manipulated as set forth in standard laboratory manuals, such as Sambrook et al. (1989) *Molecular Cloning: A Laboratory Manual*, Cold Spring Harbor, USA.

The manipulation of nucleic acids useful in the present invention is typically carried out in recombinant vectors.

Thus in a further aspect, the present invention provides a vector comprising nucleic acid encoding at least a 'dual-specific ligand' as herein defined.

As used herein, vector refers to a discrete element that is used to introduce heterologous DNA into cells for the expression and/or replication thereof. Methods by which to select or construct and, subsequently, use such vectors are well known to one of ordinary skill in the art. Numerous vectors are publicly available, including bacterial plasmids, bacteriophage, artificial chromosomes and episomal vectors. Such vectors may be used for simple cloning and mutagenesis; alternatively gene expression vector is employed. A vector of use according to the invention may be selected to accommodate a polypeptide coding sequence of a desired size, typically from 0.25 kilobase (kb) to 40 kb or more in length A suitable host cell is transformed with the vector after in vitro cloning manipulations. Each vector contains various functional components, which generally include a cloning (or "polylinker") site, an origin of replication and at least one selectable marker gene. If given vector is an expression vector, it additionally possesses one or more of the following: enhancer element, promoter, transcription termination and signal sequences, each positioned in the vicinity of the cloning site, such that they are operatively linked to the gene encoding a ligand according to the invention.

Both cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV 40, adenovirus) are useful for cloning vectors in mammalian cells. Generally, the origin of replication is not needed for mammalian expression vectors unless these are used in mammalian cells able to replicate high levels of DNA, such as COS cells.

Advantageously, a cloning or expression vector may contain a selection gene also referred to as selectable marker. This gene encodes a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Since the replication of vectors encoding a ligand according to the present invention is most conveniently performed in *E. coli*, an *E. coli-selectable* marker, for example, the β-lactamase gene that confers resistance to the antibiotic ampicillin, is of use. These can be obtained from *E. coli* plasmids, such as pBR322 or a pUC plasmid such as pUC18 or pUC19.

Expression vectors usually contain a promoter that is recognised by the host organism and is operably linked to the coding sequence of interest. Such a promoter may be inducible or constitutive. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Promoters suitable for use with prokaryotic hosts include, for example, the β-lactamase and lactose promoter systems, alkaline phosphatase, the tryptophan (trp) promoter system and hybrid promoters such as the tac promoter. Promoters for use in bacterial systems will also generally contain a Shine-Delgarno sequence operably linked to the coding sequence.

The preferred vectors are expression vectors that enables the expression of a nucleotide sequence corresponding to a polypeptide library member. Thus, selection with the first and/or second antigen or epitope can be performed by separate propagation and expression of a single clone expressing the polypeptide library member or by use of any selection display system. As described above, the preferred selection display system is bacteriophage display. Thus, phage or phagemid vectors may be used, eg pIT1 or pIT2. Leader sequences useful in the invention include pelB, stII, ompA, phoA, bla and pelA. One example are phagemid vectors which have an *E. coli*. origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector contains a β-lactamase gene to confer selectivity on the phagemid and a lac promoter upstream of a expression cassette that consists (N to C terminal) of a pelB leader sequence (which directs the expressed polypeptide to the periplasmic space), a multiple cloning site (for cloning the nucleotide version of the library member), optionally, one or more peptide tag (for detection), optionally, one or more TAG stop codon and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or produce phage, some of which contain at least one copy of the polypeptide-pIII fusion on their surface.

Construction of vectors encoding ligands according to the invention employs conventional ligation techniques. Isolated vectors or DNA fragments are cleaved, tailored, and religated in the form desired to generate the required vector. If desired, analysis to confirm that the correct sequences are present in the constructed vector can be performed in a known fashion. Suitable methods for constructing expression vectors, preparing in vitro transcripts, introducing DNA into host cells, and performing analyses for assessing expression and function are known to those skilled in the art. The presence of a gene sequence in a sample is detected, or its amplification and/or expression quantified by conventional methods, such as Southern or Northern analysis, Western blotting, dot blotting of DNA, RNA or protein, in situ hybridisation, immunocytochemistry or sequence analysis of nucleic acid or protein molecules. Those skilled in the art will readily envisage how these methods may be modified, if desired.

Structure of Closed Conformation Multispecific Ligands

According to one aspect of the second configuration of the invention present invention, the two or more non-complementary epitope binding domains are linked so that they are in a closed conformation as herein defined. Advantageously, they may be further attached to a skeleton which may, as a alternative, or on addition to a linker described herein, facilitate the formation and/or maintenance of the closed conformation of the epitope binding sites with respect to one another.

(I) Skeletons

Skeletons may be based on immunoglobulin molecules or may be non-immunoglobulin in origin as set forth above. Preferred immunoglobulin skeletons as herein defined includes any one or more of those selected from the following: an immunoglobulin molecule comprising at least (i) the CL (kappa or lambda subclass) domain of an antibody; or (ii) the CH1 domain of an antibody heavy chain; an immunoglobulin molecule comprising the CH1 and CH2 domains of an antibody heavy chain; an immunoglobulin molecule comprising the CH1, CH2 and CH3 domains of an antibody heavy chain; or any of the subset (ii) in conjunction with the CL (kappa or lambda subclass) domain of an antibody. A hinge region domain may also be included. Such combinations of domains may, for example, mimic natural antibodies, such as IgG or IgM, or fragments thereof, such as Fv, scFv, Fab or F(ab')$_2$ molecules. Those skilled in the art will be aware that this list is not intended to be exhaustive.

(II) Protein Scaffolds

Each epitope binding domain comprises a protein scaffold and one or more CDRs which are involved in the specific interaction of the domain with one or more epitopes. Advantageously, an epitope binding domain according to the present invention comprises three CDRs. Suitable protein scaffolds include any of those selected from the group consisting of the following: those based on immunoglobulin domains, those based on fibronectin, those based on affibodies, those based on CTLA4, those based on chaperones such as GroEL, those based on lipocallin and those based on the bacterial Fe receptors SpA and SpD. Those skilled in the art will appreciate that this list is not intended to be exhaustive.

F: Scaffolds for Use in Constructing Dual Specific Ligands i. Selection of the Main-Chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1).

The dual specific ligands of the present invention are advantageously assembled from libraries of domains, such as libraries of $V_H$ domains and/or libraries of $V_L$ domains. Moreover, the dual specific ligands of the invention may themselves be provided in the form of libraries. In one aspect of the present invention, libraries of dual specific ligands and/or domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to chose residues for diversification which do not affect the canonical structure. It is known that, in the human $V_\kappa$ domain, the L1 loop can adopt one of four canonical structures, the L2 loop has a single canonical structure and that 90% of human $V_\kappa$ domains adopt one of four or five canonical structures for the L3 loop (Tomlinson et al. (1995) supra); thus, in the $V_\kappa$ domain alone, different canonical structures can combine to create a range of different main-chain conformations. Given that the $V_\lambda$ domain encodes a different range of canonical structures for the L1, L2 and L3 loops and that $V_\kappa$ and $V_\lambda$ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a preferred aspect, the dual-specific ligands of the invention possess a single known main-chain conformation.

The single main-chain conformation that is chosen is preferably commonplace among molecules of the immunoglobulin superfamily type in question. A conformation is commonplace when a significant number of naturally occurring molecules are observed to adopt it. Accordingly, in a preferred aspect of the invention, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. It is preferable that the desired combination of main-chain conformations for the different loops is created by selecting germline gene segments which encode the desired main-chain conformations. It is more preferable, that the selected germline gene segments are frequently expressed in nature, and most preferable that they are the most frequently expressed of all natural germline gene segments.

In designing dual specific ligands or libraries thereof the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS1 (79% of the expressed repertoire), H2-CS 3 (46%), L1-CS 2 of $V_\kappa$ (39%), L2-CS1 (100%), L3-CS1 of $V_\kappa$ (36%) (calculation assumes a κ:λ ratio of 70:30, Hood et al. (1967) *Cold Spring Harbor Symp. Quant. Biol.*, 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_\kappa$ segment O2/O12 (DPK9) and the $J_\kappa$ segment $J_\kappa 1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five or for all six of the antigen binding loops can be determined. Here, it is preferable that the chosen conformation is commonplace in naturally occurring antibodies and most preferable that it observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

ii. Diversification of the Canonical Sequence

Having selected several known main-chain conformations or, preferably a single known main-chain conformation, dual specific ligands according to the invention or libraries for use in the invention can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or are preferably selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.*, 226: 889), chemical mutagenesis (Deng et al. (1994) *J. Biol. Chem.*, 269: 9533) or bacterial mutator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA*, 89: 4457). Random or semi-random H3 and L3 regions have been appended to germline V gene segments to produce large libraries with unmutated framework regions (Hoogenboom & Winter (1992) *J. Mol. Biol.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; De Kruif et al. (1995) *J. Mol. Biol.*, 248: 97). Such diversification has been extended to include some or all of the other antigen binding loops (Crameri et al. (1996) *Nature Med.*, 2: 100; Riechmann et al. (1995) *Bio/Technology*, 13: 475; Morphosys, WO97/08320, supra).

Since loop randomisation has the potential to create approximately more than $10^{15}$ structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al. (1994) supra).

In a preferred embodiment, only those residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

Diversification of the Canonical Sequence as it Applies to Antibody Domains

In the case of antibody dual-specific ligands, the binding site for the target is most often the antigen binding site. Thus, in a highly preferred aspect, the invention provides libraries of or for the assembly of antibody dual-specific ligands in which only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library for use according to the invention. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.,* 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire is created where some, but not all, of the residues in the antigen binding site are diversified. As used herein in this context, the term "naive" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

The invention provides two different naive repertoires of binding domains for the construction of dual specific ligands, or a naïve library of dual specific ligands, in which some or all of the residues in the antigen binding site are varied. The "primary" library mimics the natural primary repertoire, with diversity restricted to residues at the centre of the antigen binding site that are diverse in the germline V gene segments (germline diversity) or diversified during the recombination process (junctional diversity). Those residues which are diversified include, but are not limited to, H50, H52, H52a, H53, H55, H56, H58, H95, H96, H97, H98, L50, L53, L91, L92, L93, L94 and L96. In the "somatic" library, diversity is restricted to residues that are diversified during the recombination process (junctional diversity) or are highly somatically mutated). Those residues which are diversified include, but are not limited to: H31, H33, H35, H95, H96, H97, H98, L30, L31, L32, L34 and L96. All the residues listed above as suitable for diversification in these libraries are known to make contacts in one or more antibody-antigen complexes. Since in both libraries, not all of the residues in the antigen binding site are varied, additional diversity is incorporated during selection by varying the remaining residues, if it is desired to do so. It shall be apparent to one skilled in the art that any subset of any of these residues (or additional residues which comprise the antigen binding site) can be used for the initial and/or subsequent diversification of the antigen binding site.

In the construction of libraries for use in the invention, diversification of chosen positions is typically achieved at the nucleic acid level, by altering the coding sequence which specifies the sequence of the polypeptide such that a number of possible amino acids (all 20 or a subset thereof) can be incorporated at that position. Using the IUPAC nomenclature, the most versatile codon is NNK, which encodes all amino acids as well as the TAG stop codon. The NNK codon is preferably used in order to introduce the required diversity. Other codons which achieve the same ends are also of use, including the NNN codon, which leads to the production of the additional stop codons TGA and TAA.

A feature of side-chain diversity in the antigen binding site of human antibodies is a pronounced bias which favours certain amino acid residues. If the amino acid composition of the ten most diverse positions in each of the $V_H$, $V_\kappa$ and $V_\lambda$, regions are summed, more than 76% of the side-chain diversity comes from only seven different residues, these being, serine (24%), tyrosine (14%), asparagine (11%), glycine (9%), alanine (7%), aspartate (6%) and threonine (6%). This bias towards hydrophilic residues and small residues which can provide main-chain flexibility probably reflects the evolution of surfaces which are predisposed to binding a wide range of antigens or epitopes and may help to explain the required promiscuity of antibodies in the primary repertoire.

Since it is preferable to mimic this distribution of amino acids, the distribution of amino acids at the positions to be varied preferably mimics that seen in the antigen binding site of antibodies. Such bias in the substitution of amino acids that permits selection of certain polypeptides (not just antibody polypeptides) against a range of target antigens is easily applied to any polypeptide repertoire. There are various methods for biasing the amino acid distribution at the position to be varied (including the use of tri-nucleotide mutagenesis, see WO97/08320), of which the preferred method, due to ease of synthesis, is the use of conventional degenerate codons. By comparing the amino acid profile encoded by all combinations of degenerate codons (with single, double, triple and quadruple degeneracy in equal ratios at each position) with the natural amino acid use it is possible to calculate the most representative codon. The codons (AGT)(AGC)T, (AGT)(AGC)C and (AGT)(AGC)(CT)—that is, DVT, DVC and DVY, respectively using IUPAC nomenclature—are those closest to the desired amino acid profile: they encode 22% serine and 11% tyrosine, asparagine, glycine, alanine, aspartate, threonine and cysteine. Preferably, therefore, libraries are constructed using either the DVT, DVC or DVY codon at each of the diversified positions.

G: Antigens Capable of Increasing Ligand Half-Life

The dual specific ligands according to the invention, in one configuration thereof, are capable of binding to one or more molecules which can increase the half-life of the ligand in vivo. Typically, such molecules are polypeptides which occur naturally in vivo and which resist degradation or removal by endogenous mechanisms which remove unwanted material from the organism. For example, the molecule which increases the half-life of the organism may be selected from the following:

Proteins from the extracellular matrix; for example collagen, laminins, integrins and fibronectin. Collagens are the major proteins of the extracellular matrix. About 15 types of collagen molecules are currently known, found in different parts of the body, eg type I collagen (accounting for 90% of body collagen) found in bone, skin, tendon, ligaments, cornea, internal organs or type II collagen found in cartilage, invertebral disc, notochord, vitreous humour of the eye.

Proteins found in blood, including:

Plasma proteins such as fibrin, $\alpha$-2 macroglobulin, serum albumin, fibrinogen A, fibrinogen B, serum amyloid protein A, heptaglobin, profilin, ubiquitin, uteroglobulin and $\beta$-2-microglobulin;

Enzymes and inhibitors such as plasminogen, lysozyme, cystatin C, alpha-1-antitrypsin and pancreatic trypsin inhibitor. Plasminogen is the inactive precursor of the trypsin-like serine protease plasmin. It is normally found circulating through the blood stream. When plasminogen becomes activated and is converted to plasmin, it unfolds a potent enzymatic domain that dissolves the fibrinogen fibers that entangle the blood cells in a blood clot. This is called fibrinolysis.

Immune system proteins, such as IgE, IgG, IgM.

Transport proteins such as retinol binding protein, $\alpha$-1 microglobulin.

Defensins such as beta-defensin 1, Neutrophil defensins 1,2 and 3.

Proteins found at the blood brain barrier or in neural tissues, such as melanocortin receptor, myelin, ascorbate transporter.

Transferrin receptor specific ligand-neuropharmaceutical agent fusion proteins (see U.S. Pat. No. 5,977,307);

brain capillary endothelial cell receptor, transferrin, transferrin receptor, insulin, insulin-like growth factor 1 (IGF 1) receptor, insulin-like growth factor 2 (IGF 2) receptor, insulin receptor.

Proteins localised to the kidney, such as polycystin, type IV collagen, organic anion transporter K1, Heymann's antigen.

Proteins localised to the liver, for example alcohol dehydrogenase, G250.

Blood coagulation factor X $\alpha$1 antitrypsin

HNF 1$\alpha$

Proteins localised to the lung, such as secretory component (binds IgA).

Proteins localised to the Heart, for example HSP 27. This is associated with dilated cardiomyopathy.

Proteins localised to the skin, for example keratin.

Bone specific proteins, such as bone morphogenic proteins (BMPs), which are a subset of the transforming growth factor $\beta$ superfamily that demonstrate osteogenic activity. Examples include BMP-2, -4, -5, -6, -7 (also referred to as osteogenic protein (OP-1) and -8 (OP-2).

Tumour specific proteins, including human trophoblast antigen, herceptin receptor, oestrogen receptor, cathepsins eg cathepsin B (found in liver and spleen).

Disease-specific proteins, such as antigens expressed only on activated T-cells: including LAG-3 (lymphocyte activation gene), osteoprotegerin ligand (OPGL) see Nature 402, 304-309; 1999, OX40 (a member of the TNF receptor family, expressed on activated T cells and the only costimulatory T cell molecule known to be specifically up-regulated in human T cell leukaemia virus type-I (HTLV-I)-producing cells.) See *J Immunol.* 2000 Jul. 1; 165(1):263-70; Metalloproteases (associated with arthritis/cancers), including CG6512 *Drosophila*, human paraplegin, human FtsH, human AFG3L2, murine ftsH; angiogenic growth factors, including acidic fibroblast growth factor (FGF-1), basic fibroblast growth factor (FGF-2), Vascular endothelial growth factor/vascular permeability factor (VEGF/VPF), transforming growth factor-a (TGF a), tumor necrosis factor-alpha (TNF-$\alpha$), angiogenin, interleukin-3 (IL-3), interleukin-8 (IL-8), platelet-derived endothelial growth factor (PD-ECGF), placental growth factor (PlGF), midkine platelet-derived growth factor-BB (PDGF), fractalkine.

Stress Proteins (Heat Shock Proteins)

HSPs are normally found intracellularly. When they are found extracellularly, it is an indicator that a cell has died and spilled out its contents. This unprogrammed cell death (necrosis) only occurs when as a result of trauma, disease or injury and therefore in vivo, extracellular HSPs trigger a response from the immune system that will fight infection and disease. A dual specific which binds to extracellular HSP can be localised to a disease site.

Proteins Involved in Fc Transport

Brambell receptor (also known as FcRB)

This Fc receptor has two functions, both of which are potentially useful for delivery The Functions are The transport of IgG from mother to child across the placenta the protection of IgG from degradation thereby prolonging its serum half life of IgG.

It is thought that the receptor recycles IgG from endosome.

See Holliger et al, Nat Biotechnol 1997 July; 15(7):632-6.

Ligands according to the invention may designed to be specific for the above targets without requiring any increase in or increasing half life in vivo. For example, ligands according to the invention can be specific for targets selected from the foregoing which are tissue-specific, thereby enabling tissue-specific targeting of the dual specific ligand, or a dAb monomer that binds a tissue-specific therapeutically relevant target, irrespective of any increase in half-life, although this may result. Moreover, where the ligand or dAb monomer targets kidney or liver, this may redirect the ligand or dAb monomer to an alternative clearance pathway in vivo (for example, the ligand may be directed away from liver clearance to kidney clearance).

H: Use of Multispecific Ligands According to the Second Configuration of the Invention Multispecific ligands according to the method of the second configuration of the present invention may be employed in in vivo therapeutic and prophylactic applications, in vitro and in vivo diagnostic applications, in vitro assay and reagent applications, and the like. For example antibody molecules may be used in antibody based assay techniques, such as ELISA techniques, according to methods known to those skilled in the art.

As alluded to above, the multispecific ligands according to the invention are of use in diagnostic, prophylactic and therapeutic procedures. Multispecific antibodies according to the invention are of use diagnostically in Western analysis and in situ protein detection by standard immunohistochemical procedures; for use in these applications, the ligands may be labelled in accordance with techniques known to the art. In addition, such antibody polypeptides may be used preparatively in affinity chromatography procedures, when complexed to a chromatographic support, such as a resin. All such techniques are well known to one of skill in the art.

Diagnostic uses of the closed conformation multispecific ligands according to the invention include homogenous assays for analytes which exploit the ability of closed conformation multispecific ligands to bind two targets in competition, such that two targets cannot bind simultaneously (a closed conformation), or alternatively their ability to bind two targets simultaneously (an open conformation).

In a further aspect still of the second configuration of the invention, the present invention provides a homogenous immunoassay using a ligand according to the present invention.

A true homogenous immunoassay format has been avidly sought by manufacturers of diagnostics and research assay systems used in drug discovery and development. The main diagnostics markets include human testing in hospitals, doctor's offices and clinics, commercial reference laboratories, blood banks, and the home, non-human diagnostics (for example food testing, water testing, environmental testing, bio-defence, and veterinary testing), and finally research (including drug development; basic research and academic research).

At present all these markets utilise immunoassay systems that are built around chemiluminescent, ELISA, fluorescence or in rare cases radio-immunoassay technologies. Each of these assay formats requires a separation step (separating bound from un-bound reagents). In some cases, several separation steps are required. Adding these additional steps adds reagents and automation, takes time, and affects the ultimate outcome of the assays. In human diagnostics, the separation step may be automated, which masks the problem, but does not remove it. The robotics, additional reagents, additional incubation times, and the like add considerable cost and complexity. In drug development, such as high throughput screening, where literally millions of samples are tested at once, with very low levels of test molecule, adding additional separation steps can eliminate the ability to perform a screen. However, avoiding the separation creates too much noise in the read out. Thus, there is a need for a true homogenous format that provides sensitivities at the range obtainable from present assay formats. Advantageously, an assay possesses fully quantitative read-outs with high sensitivity and a large dynamic range. Sensitivity is an important requirement, as is reducing the amount of sample required. Both of these features are features that a homogenous system offers. This is very important in point of care testing, and in drug development where samples are precious. Heterogenous systems, as currently available in the art, require large quantities of sample and expensive reagents Applications for homogenous assays include cancer testing, where the biggest assay is that for Prostate Specific Antigen, used in screening men for prostate cancer.

Other applications include fertility testing, which provides a series of tests for women attempting to conceive including beta-hcg for pregnancy. Tests for infectious diseases, including hepatitis, HIV, rubella, and other viruses and microorganisms and sexually transmitted diseases. Tests are used by blood banks, especially tests for HIV, hepatitis A, B, C, non A non B. Therapeutic drug monitoring tests include monitoring levels of prescribed drugs in patients for efficacy and to avoid toxicity, for example digoxin for arrhythmia, and phenobarbital levels in psychotic cases; theophylline for asthma. Diagnostic tests are moreover useful in abused drug testing, such as testing for cocaine, marijuana and the like. Metabolic tests are used for measuring thyroid function, anaemia and other physiological disorders and functions.

The homogenous immunoassay format is moreover useful in the manufacture of standard clinical chemistry assays. The inclusion of immunoassays and chemistry assays on the same instrument is highly advantageous in diagnostic testing. Suitable chemical assays include tests for glucose, cholesterol, potassium, and the like.

A further major application for homogenous immunoassays is drug discovery and development: high throughput screening includes testing combinatorial chemistry libraries versus targets in ultra high volume. Signal is detected, and positive groups then split into smaller groups, and eventually tested in cells and then animals. Homogenous assays may be used in all these types of test. In drug development, especially animal studies and clinical trials heavy use of immunoassays is made. Homogenous assays greatly accelerate and simplify these procedures. Other Applications include food and beverage testing: testing meat and other foods for $E.\ coli$, $salmonella$, etc; water testing, including testing at water plants for all types of contaminants including $E.\ coli$; and veterinary testing.

In a broad embodiment, the invention provides a binding assay comprising a detectable agent which is bound to a closed conformation multispcific ligand according to the invention, and whose detectable properties are altered by the binding of an analyte to said closed conformation multispecific ligand. Such an assay may be configured in several different ways, each exploiting the above properties of closed conformation multispecific ligands.

The assay relies on the direct or indirect displacement of an agent by the analyte, resulting in a change in the detectable properties of the agent. For example, where the agent is an enzyme which is capable of catalysing a reaction which has a detectable end-point, said enzyme can be bound by the ligand such as to obstruct its active site, thereby inactivating the enzyme. The analyte, which is also bound by the closed conformation multispecific ligand, displaces the enzyme, rendering it active through freeing of the active site. The enzyme is then able to react with a substrate, to give rise to a detectable event. In an alternative embodiment, the ligand may bind the enzyme outside of the active site, influencing the conformation of the enzyme and thus altering its activity. For example, the structure of the active site may be constrained by the binding of the ligand, or the binding of cofactors necessary for activity may be prevented.

The physical implementation of the assay may take any form known in the art. For example, the closed conformation multispecific ligand/enzyme complex may be provided on a test strip; the substrate may be provided in a different region of the test strip, and a solvent containing the analyte allowed to migrate through the ligand/enzyme complex, displacing the enzyme, and carrying it to the substrate region to produce a signal. Alternatively, the ligand/enzyme complex may be provided on a test stick or other solid phase, and dipped into an analyte/substrate solution, releasing enzyme into the solution in response to the presence of analyte.

Since each molecule of analyte potentially releases one enzyme molecule, the assay is quantitative, with the strength of the signal generated in a given time being dependent on the concentration of analyte in the solution.

Further configurations using the analyte in a closed conformation are possible. For example, the closed conformation multispecific ligand may be configured to bind an enzyme in an allosteric site, thereby activating the enzyme. In such an embodiment, the enzyme is active in the absence of analyte. Addition of the analyte displaces the enzyme and removes allosteric activation, thus inactivating the enzyme.

In the context of the above embodiments which employ enzyme activity as a measure of the analyte concentration, activation or inactivation of the enzyme refers to an increase or decrease in the activity of the enzyme, measured as the ability of the enzyme to catalyse a signal-generating reaction. For example, the enzyme may catalyse the conversion of an undetectable substrate to a detectable form thereof. For example, horseradish peroxidase is widely used in the art together with chromogenic or chemiluminescent substrates, which are available commercially. The level of increase or decrease of the activity of the enzyme may between 10% and 100%, such as 20%, 30%, 40%, 50%, 60%, 70%, 80% or 90%; in the case of an increase in activity, the increase may be more than 100%, i.e. 200%, 300%, 500% or more, or may not be measurable as a percentage if the baseline activity of the inhibited enzyme is undetectable.

In a further configuration, the closed conformation multispecific ligand may bind the substrate of an enzyme/substrate pair, rather than the enzyme. The substrate is therefore unavailable to the enzyme until released from the closed conformation multispecific ligand through binding of the analyte. The implementations for this configuration are as for the configurations which bind enzyme.

Moreover, the assay may be configured to bind a fluorescent molecule, such as a fluorescein or another fluorophore, in a conformation such that the fluorescence is quenched on binding to the ligand. In this case, binding of the analyte to the ligand will displace the fluorescent molecule, thus producing a signal. Alternatives to fluorescent molecules which are useful in the present invention include luminescent agents, such as luciferin/luciferase, and chromogenic agents, including agents commonly used in immunoassays such as HRP.

Therapeutic and Diagnostic Compositions and Uses

The invention provides compositions comprising an antagonist of TNFR1 (e.g. ligand) of the invention (e.g., dual-specific ligand, multi-specific ligand, dAb monomer) and a pharmaceutically acceptable carrier, diluent or excipient, and therapeutic and diagnostic methods that employ the ligands or compositions of the invention. Antagonists and ligands (e.g., dual-specific ligands, multispecific ligands, dAb monomers) according to the method of the present invention may be employed in in vivo therapeutic and prophylactic applications, in vivo diagnostic applications and the like.

Therapeutic and prophylactic uses of antagonists and ligands (e.g., multispecific ligands, dual-specific ligands, dAb monomers) of the invention involve the administration of antagonists and/or ligands according to the invention to a recipient mammal, such as a human. Dual-specific and Multi-specific ligands (e.g., dual-specific antibody formats) to bind to multimeric antigen with great avidity. Dual- or Multispecific ligands can allow the cross-linking of two antigens, for example in recruiting cytotoxic T-cells to mediate the killing of tumour cell lines.

Substantially pure ligands or binding proteins thereof, for example dAb monomers, of at least 90 to 95% homogeneity are preferred for administration to a mammal, and 98 to 99% or more homogeneity is most preferred for pharmaceutical uses, especially when the mammal is a human. Once purified, partially or to homogeneity as desired, the ligands may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

For example, the ligands or binding proteins thereof, for example dAb monomers, of the present invention will typically find use in preventing, suppressing or treating inflammatory states including acute and chronic inflammatory diseases. For example, the antagonists and/or ligands can be administered to treat, suppress or prevent a chronic inflammatory disease, allergic hypersensitivity, cancer, bacterial or viral infection, autoimmune disorders (which include, but are not limited to, Type I diabetes, asthma, multiple sclerosis, rheumatoid arthritis, juvenile rheumatoid arthritis, psoriatic arthritis, spondylarthropathy (e.g., ankylosing spondylitis), systemic lupus erythematosus, inflammatory bowel disease (e.g., Crohn's disease, ulcerative colitis), myasthenia gravis and Behcet's syndrome), psoriasis, endometriosis, and abdominal adhesions (e.g., post abdominal surgery).

Antagonists (e.g., ligands) according to the invention (e.g, dual-specific ligands, multispecific ligands, dAb monomers) which able to bind to extracellular targets involved in endocytosis (e.g. Clathrin) can be endocytosed, enabling access to intracellular targets. In addition, dual or multispecific ligands, provide a means by which a binding domain (e.g., a dAb monomer) that is specificity able to bind to an intracellular target can be delivered to an intracellular environment. This strategy requires, for example, a dual-specific ligand with physical properties that enable it to remain functional inside the cell. Alternatively, if the final destination intracellular compartment is oxidising, a well folding ligand may not need to be disulphide free.

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Advantageously, dual- or multi-specific ligands may be used to target cytokines and other molecules which cooperate synergistically in therapeutic situations in the body of an organism. The invention therefore provides a method for synergising the activity of two or more binding domains (e.g., dAbs) that bind cytokines or other molecules, comprising administering a dual- or multi-specific ligand capable of binding to said two or more molecules (e.g., cytokines). In this aspect of the invention, the dual- or multi-specific ligand may be any dual- or multi-specific ligand, including a ligand composed of complementary and/or non-complementary domains, a ligand in an open conformation, and a ligand in a closed conformation. For example, this aspect of the invention relates to combinations of $V_H$ domains and $V_L$ domains, $V_H$ domains only and $V_L$ domains only.

Synergy in a therapeutic context may be achieved in a number of ways. For example, target combinations may be therapeutically active only if both targets are targeted by the ligand, whereas targeting one target alone is not therapeutically effective. In another embodiment, one target alone may provide some low or minimal therapeutic effect, but together with a second target the combination provides a synergistic increase in therapeutic effect. Preferably, the cytokines bound by the dual- or multi-specific ligands of this aspect of the invention are selected from the list shown in Annex 2.

Moreover, dual- or multi-specific ligands may be used in oncology applications, where one specificity targets CD89, which is expressed by cytotoxic cells, and the other is tumour specific. Examples of tumour antigens which may be targeted are given in Annex 3.

Animal model systems which can be used to screen the effectiveness of the antagonists of TNFR1 (e.g, ligands, antibodies or binding proteins thereof) in protecting against or treating the disease are available. Methods for the testing of systemic lupus erythematosus (SLE) in susceptible mice are known in the art (Knight et al. (1978) *J. Exp. Med.*, 147: 1653; Reinersten et al. (1978) *New Eng. J. Med.*, 299: 515). Myasthenia Gravis (MG) is tested in SJL/J female mice by inducing the disease with soluble AchR protein from another species (Lindstrom et al. (1988) *Adv. Immunol.*, 42: 233). Arthritis is induced in a susceptible strain of mice by injection of Type II collagen (Stuart et al. (1984) *Ann. Rev. Immnol.*, 42: 233). A model by which adjuvant arthritis is induced in susceptible rats by injection of mycobacterial heat shock protein has been described (Van Eden et al. (1988) *Nature*, 331: 171). Thyroiditis is induced in mice by administration of thyroglobulin as described (Maron et al. (1980) *J. Exp. Med.*, 152: 1115). Insulin dependent diabetes mellitus (IDDM) occurs naturally or can be induced in certain strains of mice such as those described by Kanasawa et al. (1984) *Diabetologia*, 27: 113. EAE in mouse and rat serves as a model for MS in human. In this model, the demyelinating disease is induced by administration of myelin basic protein (see Paterson (1986) *Textbook of Immunopathology*, Mischer et al., eds., Grune and Stratton, N.Y., pp. 179-213; McFarlin et al. (1973) *Science*, 179: 478: and Satoh et al. (1987) *J. Immunol.*, 138: 179).

Generally, the present antagonists (e.g., ligands) will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a polypeptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) *Remington's Pharmaceutical Sciences*, 16th Edition). A variety of suitable formulations can be used, including extended release formulations.

The antagonists (e.g., ligands) of the present invention may be used as separately administered compositions or in conjunction with other agents. These can include various immunotherapeutic drugs, such as cylcosporine, methotrexate, adriamycin or cisplatinum, and immunotoxins. Pharmaceutical compositions can include "cocktails" of various cytotoxic or other agents in conjunction with the antagonists (e.g., ligands) of the present invention, or even combinations of ligands according to the present invention having different specificities, such as ligands selected using different target antigens or epitopes, whether or not they are pooled prior to administration.

The route of administration of pharmaceutical compositions according to the invention may be any of those commonly known to those of ordinary skill in the art. For therapy, including without limitation immunotherapy, the selected ligands thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician. Administration can be local (e.g., local delivery to the lung by pulmonary administration, e.g., intranasal administration) or systemic as indicated.

The ligands of this invention can be lyophilised for storage and reconstituted in a suitable carrier prior to use. This technique has been shown to be effective with conventional immunoglobulins and art-known lyophilisation and reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate.

The compositions containing the present antagonists (e.g., ligands) or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of ligand, e.g. antibody, receptor (e.g. a T-cell receptor) or binding protein thereof per kilogram of body weight, with doses of 0.05 to 2.0 mg/kg/dose being more commonly used. For prophylactic applications, compositions containing the present ligands or cocktails thereof may also be administered in similar or slightly lower dosages, to prevent, inhibit or delay onset of disease (e.g., to sustain remission or quiescence, or to prevent acute phase). The skilled clinician will be able to determine the appropriate dosing interval to treat, suppress or prevent disease. When an antagonist of TNFR1 (e.g., ligand) is administered to treat, suppress or prevent a chronic inflammatory disease, it can be administered up to four times per day, twice weekly, once weekly, once every two weeks, once a month, or once every two months, at a dose off, for example, about 10 µg/kg to about 80 mg/kg, about 100 µg/kg to about 80 mg/kg, about 1 mg/kg to about 80 mg/kg, about 1 mg/kg to about 70 mg/kg, about 1 mg/kg to about 60 mg/kg, about 1 mg/kg to about 50 mg/kg, about 1 mg/kg to about 40 mg/kg, about 1 mg/kg to about 30 mg/kg, about 1 mg/kg to about 20 mg/kg, about 1 mg/kg to about 10 mg/kg, about 10 µg/kg to about 10 mg/kg, about 10 µg/kg to about 5 mg/kg, about 10 µg/kg to about 2.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg. In particular embodiments, the antagonist of TNFR1 (e.g., ligand) is administered to treat, suppress or prevent a chronic inflammatory disease once every two weeks or once a month at a dose of about 10 µg/kg to about 10 mg/kg (e.g., about 10 µg/kg, about 100 µg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg or about 10 mg/kg.)

Treatment or therapy performed using the compositions described herein is considered "effective" if one or more symptoms are reduced (e.g., by at least 10% or at least one point on a clinical assessment scale), relative to such symptoms present before treatment, or relative to such symptoms in an individual (human or model animal) not treated with such composition or other suitable control. Symptoms will obviously vary depending upon the disease or disorder targeted, but can be measured by an ordinarily skilled clinician or technician. Such symptoms can be measured, for example, by monitoring the level of one or more biochemical indicators of the disease or disorder (e.g., levels of an enzyme or metabolite correlated with the disease, affected cell numbers, etc.), by monitoring physical manifestations (e.g., inflammation, tumor size, etc.), or by an accepted clinical assessment scale, for example, the Expanded Disability Status Scale (for multiple sclerosis), the Irvine Inflammatory Bowel Disease Questionnaire (32 point assessment evaluates quality of life with respect to bowel function, systemic symptoms, social function and emotional status—score ranges from 32 to 224, with higher scores indicating a better quality of life), the Quality of Life Rheumatoid Arthritis Scale, or other accepted clinical assessment scale as known in the field. A sustained (e.g., one day or more, preferably longer) reduction in disease or disorder symptoms by at least 10% or by one or more points on a given clinical scale is indicative of "effective" treatment. Similarly, prophylaxis performed using a composition as described herein is "effective" if the onset or severity of one or more symptoms is delayed, reduced or abolished relative to such symptoms in a similar individual (human or animal model) not treated with the composition.

A composition containing an antagonists (e.g., ligand) or cocktail thereof according to the present invention may be utilised in prophylactic and therapeutic settings to aid in the alteration, inactivation, killing or removal of a select target cell population in a mammal. In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands, e.g. antibodies, cell-surface receptors or binding proteins thereof whereby the undesired cells are killed or otherwise removed from the blood for return to the mammal in accordance with standard techniques.

A composition containing an antagonist (e.g., ligand) according to the present invention may be utilised in prophylactic and therapeutic settings to aid in the alteration, inactivation, killing or removal of a select target cell population in a mammal.

The antagonists of TNFR1 (e.g., ligands, dAb monomers) can be administered and or formulated together with one or more additional therapeutic or active agents.

When an antagonist of TNFR1 (e.g., ligand, dAb monomer) is administered with an additional therapeutic agent, the antagonist of TNFR1 can be administered before, simultaneously with or subsequent to administration of the additional agent. Generally, the antagonist of TNFR1 (e.g., ligand, dAb monomer) and additional agent are administered in a manner that provides an overlap of therapeutic effect.

In one embodiment, the invention is a method for treating, suppressing or preventing a chronic inflammatory disease, comprising administering to a mammal in need thereof a therapeutically-effective dose or amount of an antagonist of TNFR1 (e.g., a ligand that comprises a dAb monomer that binds TNFR1).

In one embodiment, the invention is a method for treating, suppressing or preventing arthritis (e.g., rheumatoid arthritis, juvenile rheumatoid arthritis, ankylosing spondylitis, psoriatic arthritis) comprising administering to a mammal in need thereof a therapeutically-effective dose or amount of an antagonist of TNFR1 (e.g., a ligand that comprises a dAb monomer that binds TNFR1).

In another embodiment, the invention is a method for treating, suppressing or preventing psoriasis comprising administering to a mammal in need thereof a therapeutically-effective dose or amount of an antagonist of TNFR1 (e.g., a ligand that comprises a dAb monomer that binds TNFR1).

In another embodiment, the invention is a method for treating, suppressing or preventing inflammatory bowel disease (e.g., Crohn's disease, ulcerative colitis) comprising administering to a mammal in need thereof a therapeutically-effective dose or amount of an antagonist of TNFR1 (e.g., a ligand that comprises a dAb monomer that binds TNFR1).

In another embodiment, the invention is a method for treating, suppressing or preventing chronic obstructive pulmonary disease (e.g., chronic bronchitis, chronic obstructive bronchitis, emphysema), comprising administering to a mammal in need thereof a therapeutically-effective dose or amount of an antagonist of TNFR1 (e.g., a ligand that comprises a dAb monomer that binds TNFR1).

In another embodiment, the invention is a method for treating, suppressing or preventing pneumonia (e.g., bacterial pneumonia, such as Staphylococcal pneumonia) comprising administering to a mammal in need thereof a therapeutically-effective dose or amount of an antagonist of TNFR1 (e.g., a ligand that comprises a dAb monomer that binds TNFR1).

The invention provides a method for treating, suppressing or preventing other pulmonary diseases in addition to chronic obstructive pulmonary disease, and pneumonia. Other pulmonary diseases that can be treated, suppressed or prevented in accordance with the invention include, for example, cystic fibrosis and asthma (e.g., steroid resistant asthma). Thus, in another embodiment, the invention is a method for treating, suppressing or preventing a pulmonary disease (e.g., cystic fibrosis, asthma) comprising administering to a mammal in need thereof a therapeutically-effective dose or amount of an antagonist of TNFR1 (e.g., a ligand that comprises a dAb monomer that binds TNFR1).

In particular embodiments, an antagonist of TNFR1 is administered via pulmonary delivery, such as by inhalation (e.g., intrabronchial, intranasal or oral inhalation, intranasal drops) or by systemic delivery (e.g., parenteral, intravenous, intramuscular, intraperitoneal, subcutaneous).

In another embodiment, the invention is a method treating, suppressing or preventing septic shock comprising administering to a mammal in need thereof a therapeutically-effective dose or amount of an antagonist of TNFR1 (e.g., a ligand that comprises a dAb monomer that binds TNFR1).

In a further aspect still of the second configuration of the invention, the present invention provides a composition comprising a closed conformation multispecific ligand, obtainable by a method of the present invention, and a pharmaceutically acceptable carrier, diluent or excipient.

Moreover, the present invention provides a method for the treatment of disease using a "closed conformation multispecific ligand" or a composition according to the present invention.

In a preferred embodiment of the invention the disease is cancer or an inflammatory disease, eg rheumatoid arthritis, asthma or Crohn's disease.

In a further aspect of the second configuration of the invention, the present invention provides a method for the diagnosis, including diagnosis of disease using a closed conformation multispecific ligand, or a composition according to the present invention. Thus in general the binding of an analyte to a closed conformation multispecific ligand may be exploited to displace an agent, which leads to the generation of a signal on displacement. For example, binding of analyte (second antigen) could displace an enzyme (first antigen) bound to the antibody providing the basis for an immunoassay, especially if the enzyme were held to the antibody through its active site.

Thus, the present invention provides a method for detecting the presence of a target molecule, comprising:

(a) providing a closed conformation multispecific ligand bound to an agent, said ligand being specific for the target molecule and the agent, wherein the agent which is bound by the ligand leads to the generation of a detectable signal on displacement from the ligand;
(b) exposing the closed conformation multispecific ligand to the target molecule; and
(c) detecting the signal generated as a result of the displacement of the agent. According to the above aspect of the second configuration of the invention, advantageously, the agent is an enzyme, which is inactive when bound by the closed conformation multi-specific ligand. Alternatively, the agent may be any one or more selected from the group consisting of the following: the substrate for an enzyme, and a fluorescent, luminescent or chromogenic molecule which is inactive or quenched when bound by the ligand.

In addition, the selected repertoires of polypeptides described herein may be used extracorporeally or in vitro selectively to kill, deplete or otherwise effectively remove a target cell population from a heterogeneous collection of cells. Blood from a mammal may be combined extracorporeally with the ligands, e.g. antibodies, cell-surface receptors or binding proteins thereof whereby the undesired cells are killed or otherwise removed from the blood for return to the mammal in accordance with standard techniques.

EXAMPLES

The invention is further described, for the purposes of illustration only, in the following examples. As used herein, for the purposes of dAb nomenclature, human TNFα is referred to as TAR1 and human TNFα receptor 1 (p55 receptor) is referred to as TAR2.

Example 1

Selection of a Dual Specific scFv Antibody (K8) Directed Against Human Serum Albumin (HSA) and β-Galactosidase (β-Gal)

This example explains a method for making a dual specific antibody directed against β-gal and HSA in which a repertoire of $V_\kappa$ variable domains linked to a germline (dummy) $V_H$ domain is selected for binding to β-gal and a repertoire of $V_H$ variable domains linked to a germline (dummy) $V_\kappa$ domain is selected for binding to HSA. The selected variable $V_H$ HSA and $V_\kappa$ β-gal domains are then combined and the antibodies selected for binding to β-gal and HSA. HSA is a half-life increasing protein found in human blood.

Four human phage antibody libraries were used in this experiment.

| Library 1 | Germline $V_\kappa$/DVT $V_H$ | $8.46 \times 10^7$ |
| Library 2 | Germline $V_\kappa$/NNK $V_H$ | $9.64 \times 10^7$ |
| Library 3 | Germline $V_H$/DVT $V_\kappa$ | $1.47 \times 10^8$ |
| Library 4 | Germline $V_H$/NNK $V_\kappa$ | $1.45 \times 10^8$ |

All libraries are based on a single human framework for $V_H$ (V3-23/DP47 and $J_H4b$) and $V_\kappa$ (O12/O2/DPK9 and $J_\kappa 1$) with side chain diversity incorporated in complementarity determining regions (CDR2 and CDR3).

Figure 1:
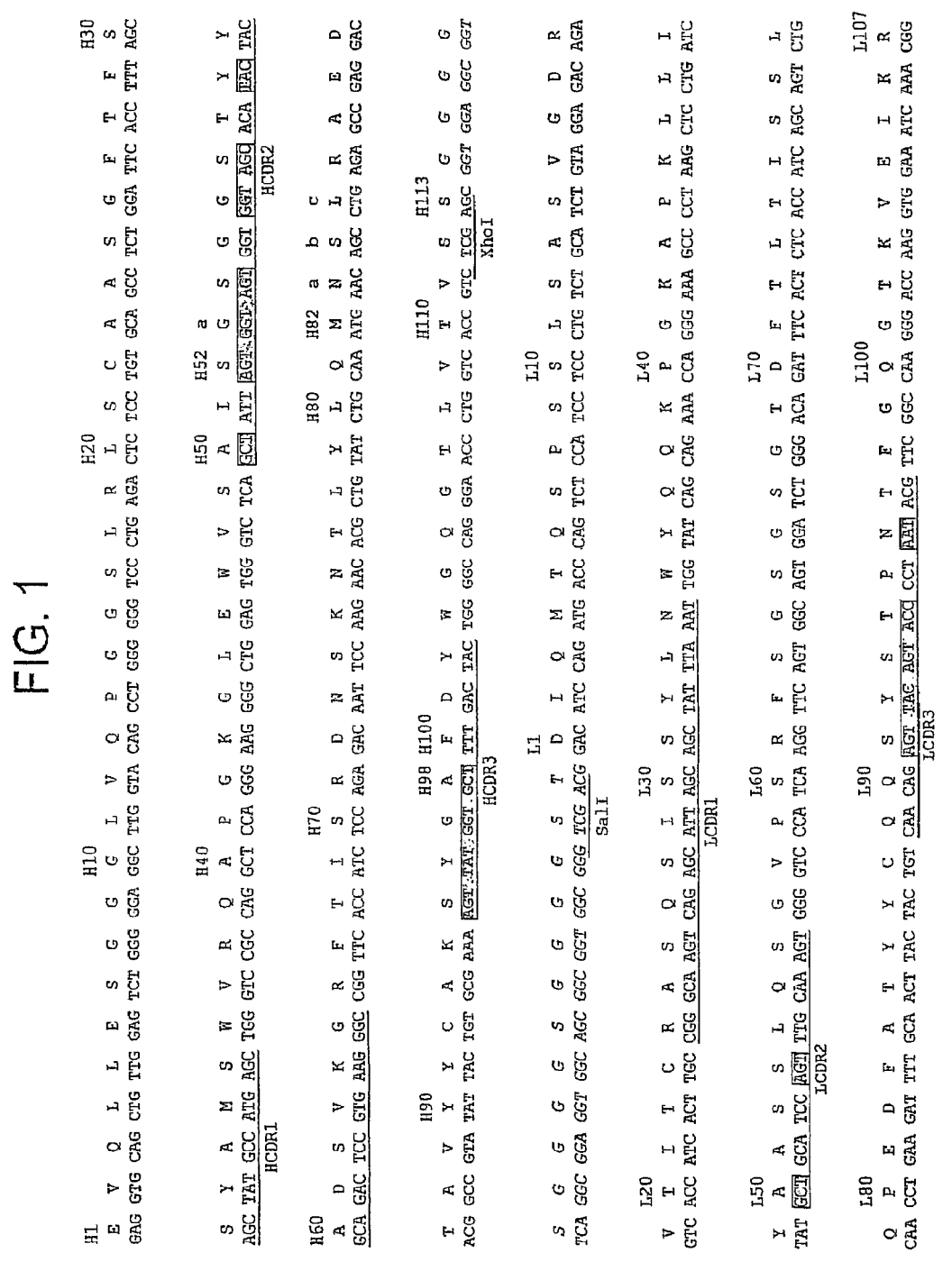

Library 1 and Library 2 contain a dummy $V_\kappa$ sequence, whereas the sequence of $V_H$ is diversified at positions H50, H52, H52a, H53, H55, H56, H58, H95, H96, H97 and H98 (DVT or NNK encoded, respectively) (FIG. 1). Library 3 and Library 4 contain a dummy $V_H$ sequence, whereas the sequence of $V_\kappa$ is diversified at positions L50, L53, L91, L92, L93, L94 and L96 (DVT or NNK encoded, respectively) (FIG. 1). The libraries are in phagemid pIT2/ScFv format (FIG. 2) and have been preselected for binding to generic ligands, Protein A and Protein L, so that the majority of clones in the unselected libraries are functional. The sizes of the libraries shown above correspond to the sizes after preselection. Library 1 and Library 2 were mixed prior to selections on antigen to yield a single $V_H$/dummy $V_\kappa$ library and Library 3 and Library 4 were mixed to form a single $V_\kappa$/dummy $V_H$ library.

Three rounds of selections were performed on β-gal using $V_\kappa$/dummy $V_H$ library and three rounds of selections were performed on HSA using $V_H$/dummy $V_\kappa$ library. In the case of β-gal the phage titres went up from $1.1 \times 10^6$ in the first round to $2.0 \times 10^8$ in the third round. In the case of HSA the phage titres went up from $2 \times 10^4$ in the first round to $1.4 \times 10^9$ in the third round. The selections were performed as described by Griffith et al., (1993), except that KM13 helper phage (which contains a pIII protein with a protease cleavage site between the D2 and D3 domains) was used and phage were eluted with 1 mg/ml trypsin in PBS. The addition of trypsin cleaves the pIII proteins derived from the helper phage (but not those from the phagemid) and elutes bound scFv-phage fusions by cleavage in the c-myc tag (FIG. 2), thereby providing a further enrichment for phages expressing functional scFvs and a corresponding reduction in background (Kristensen & Winter, Folding & Design 3: 321-328, Jul. 9, 1998). Selections were performed using immunotubes coated with either HSA or β-gal at 100 μg/ml concentration.

To check for binding, 24 colonies from the third round of each selection were screened by monoclonal phage ELISA. Phage particles were produced as described by Harrison et al., Methods Enzymol. 1996; 267:83-109. 96-well ELISA plates were coated with 100 μl of HSA or β-gal at 10 μg/ml concentration in PBS overnight at 4° C. A standard ELISA protocol was followed (Hoogenboom et al., 1991) using detection of bound phage with anti-M13-HRP conjugate. A selection of clones gave ELISA signals of greater than 1.0 with 50 μl supernatant.

Next, DNA preps were made from $V_H$/dummy $V_\kappa$ library selected on HSA and from $V_\kappa$/dummy $V_H$ library selected on β-gal using the QIAprep Spin Miniprep kit (Qiagen). To access most of the diversity, DNA preps were made from each of the three rounds of selections and then pulled together for each of the antigens. DNA preps were then digested with SalI/NotI overnight at 37° C. Following gel purification of the fragments, $V_\kappa$ chains from the $V_\kappa$/dummy $V_H$ library selected on β-gal were ligated in place of a dummy $V_\kappa$ chain of the $V_H$/dummy $V_\kappa$ library selected on HSA creating a library of $3.3 \times 10^9$ clones.

This library was then either selected on HSA (first round) and β-gal (second round), HSA/β-gal selection, or on β-gal (first round) and HSA (second round), β-gal/HSA selection. Selections were performed as described above. In each case after the second round 48 clones were tested for binding to HSA and β-gal by the monoclonal phage ELISA (as described above) and by ELISA of the soluble scFv fragments. Soluble antibody fragments were produced as described by Harrison et al., (1996), and standard ELISA protocol was followed Hoogenboom et al. (1991) Nucleic Acids Res., 19: 4133, except that 2% Tween/PBS was used as a blocking buffer and bound scFvs were detected with Protein L-HRP. Three clones (E4, E5 and E8) from the HSA/β-gal selection and two clones (K8 and K10) from the β-gal/HSA selection were able to bind both antigens. scFvs from these clones were PCR amplified and sequenced as described by Ignatovich et al., (1999) *J Mol Biol* 1999 Nov. 26; 294(2): 457-65, using the primers LMB3 and pHENseq. Sequence analysis revealed that all clones were identical. Therefore, only one clone encoding a dual specific antibody (K8) was chosen for further work (FIG. 3).

Example 2

Characterisation of the Binding Properties of the K8 Antibody

Firstly, the binding properties of the K8 antibody were characterised by the monoclonal phage ELISA. A 96-well plate was coated with 100 µl of HSA and β-gal alongside with alkaline phosphatase (APS), bovine serum albumin (BSA), peanut agglutinin, lysozyme and cytochrome c (to check for cross-reactivity) at 10 µg/ml concentration in PBS overnight at 4° C. The phagemid from K8 clone was rescued with KM13 as described by Harrison et al., (1996) and the supernatant (50 µl) containing phage assayed directly. A standard ELISA protocol was followed (Hoogenboom et al., 1991) using detection of bound phage with anti-M13-HRP conjugate. The dual specific K8 antibody was found to bind to HSA and β-gal when displayed on the surface of the phage with absorbance signals greater than 1.0 (FIG. 4). Strong binding to BSA was also observed (FIG. 4). Since HSA and BSA are 76% homologous on the amino acid level, it is not surprising that K8 antibody recognised both of these structurally related proteins. No cross-reactivity with other proteins was detected (FIG. 4).

Secondly, the binding properties of the K8 antibody were tested in a soluble scFv ELISA. Production of the soluble scFv fragment was induced by IPTG as described by Harrison et al., (1996). To determine the expression levels of K8 scFv, the soluble antibody fragments were purified from the supernatant of 50 ml inductions using Protein A-Sepharose columns as described by Harlow and Lane, Antibodies: a Laboratory Manual, (1988) Cold Spring Harbor. $OD_{280}$ was then measured and the protein concentration calculated as described by Sambrook et al., (1989). K8 scFv was produced in supernatant at 19 mg/l.

A soluble scFv ELISA was then performed using known concentrations of the K8 antibody fragment. A 96-well plate was coated with 100 µl of HSA, BSA and β-gal at 10 µg/ml and 100 µl of Protein A at 1 µg/ml concentration. 50 µl of the serial dilutions of the K8 scFv was applied and the bound antibody fragments were detected with Protein L-HRP. ELISA results confirmed the dual specific nature of the K8 antibody (FIG. 5).

To confirm that binding to β-gal is determined by the $V_\kappa$ domain and binding to HSA/BSA by the $V_H$ domain of the K8 scFv antibody, the $V_\kappa$ domain was cut out from K8 scFv DNA by SalI/NotI digestion and ligated into a SalI/NotI digested pIT2 vector containing dummy $V_H$ chain (FIGS. 1 and 2). Binding characteristics of the resulting clone K8$V_\kappa$/dummy $V_H$ were analysed by soluble scFv ELISA. Production of the soluble scFv fragments was induced by IPTG as described by Harrison et al., (1996) and the supernatant (50µ) containing scFvs assayed directly. Soluble scFv ELISA was performed as described in Example 1 and the bound scFvs were detected with Protein L-HRP. The ELISA results revealed that this clone was still able to bind β-gal, whereas binding to BSA was abolished (FIG. 6).

Example 3

Selection of Single $V_H$ Domain Antibodies Antigens A and B and Single $V_\kappa$ Domain Antibodies Directed Against Antigens C and D This example describes a method for making single $V_H$ domain antibodies directed against antigens A and B and single $V_\kappa$ domain antibodies directed against antigens C and D by selecting repertoires of virgin single antibody variable domains for binding to these antigens in the absence of the complementary variable domains.

Selections and characterisation of the binding clones is performed as described previously (see Example 5, PCT/GB 02/003014). Four clones are chosen for further work:
VH1—Anti A $V_H$
VH2—Anti B $V_H$
VK1—Anti C $V_\kappa$
VK2—Anti D $V_\kappa$ The procedures described above in Examples 1-3 may be used, in a similar manner as that described, to produce dimer molecules comprising combinations of $V_H$ domains (i.e., $V_H$-$V_H$ ligands) and combinations of $V_L$ domains ($V_L$-$V_L$ ligands).

Example 4

Creation and Characterisation of the Dual Specific ScFv Antibodies (VH1/VH2 Directed Against Antigens A and B and VK1/VK2 Directed Against Antigens C and D)

This example demonstrates that dual specific ScFv antibodies (VH1/VH2 directed against antigens A and B and VK1/VK2 directed against antigens C and D) could be created by combining $V_\kappa$ and $V_H$ single domains selected against respective antigens in a ScFv vector.

To create dual specific antibody VH1/VH2, VH1 single domain is excised from variable domain vector 1 (FIG. 7) by NcoI/XhoI digestion and ligated into NcoI/XhoI digested variable domain vector 2 (FIG. 7) to create VH1/variable domain vector 2. VH2 single domain is PCR amplified from variable domain vector 1 using primers to introduce SalI restriction site to the 5' end and NotI restriction site to the 3' end. The PCR product is then digested with SalI/NotI and ligated into SalI/NotI digested VH1/variable domain vector 2 to create VH1/VH2/variable domain vector 2.

VK1/VK2/variable domain vector 2 is created in a similar way. The dual specific nature of the produced VH1/VH2 ScFv and VK1/VK2 ScFv is tested in a soluble ScFv ELISA as described previously (see Example 6, PCT/GB 02/003014). Competition ELISA is performed as described previously (see Example 8, PCT/GB 02/003014).
Possible Outcomes:
  VH1/VH2 ScFv is able to bind antigens A and B simultaneously
  VK1/VK2 ScFv is able to bind antigens C and D simultaneously
  VH1/VH2 ScFv binding is competitive (when bound to antigen A, VH1/VH2 ScFv cannot bind to antigen B)
  VK1/VK2 ScFv binding is competitive (when bound to antigen C, VK1/VK2 ScFv cannot bind to antigen D)

Example 5

Construction of Dual Specific VH1/VH2 Fab and VK1/VK2 Fab and Analysis of their Binding Properties To create VH1/VH2 Fab, VH1 single domain is ligated into NcoI/XhoI digested CH vector (FIG. 8) to create VH1/CH and VH2 single domain is ligated into SalI/NotI digested CK vector (FIG. 9) to create VH2/CK. Plasmid DNA from VH1/

CH and VH2/CK is used to co-transform competent E. coli cells as described previously (see Example 8, PCT/GB02/003014).

The clone containing VH1/CH and VH2/CK plasmids is then induced by IPTG to produce soluble VH1/VH2 Fab as described previously (see Example 8, PCT/GB 02/003014).

VK1/VK2 Fab is produced in a similar way.

Binding properties of the produced Fabs are tested by competition ELISA as described previously (see Example 8, PCT/GB 02/003014).

Possible Outcomes:
- VH1/VH2 Fab is able to bind antigens A and B simultaneously
- VK1/VK2 Fab is able to bind antigens C and D simultaneously
- VH1/VH2 Fab binding is competitive (when bound to antigen A, VH1/VH2 Fab cannot bind to antigen B)
- VK1/VK2 Fab binding is competitive (when bound to antigen C, VK1/VK2 Fab cannot bind to antigen D)

Example 6

Chelating dAb Dimers

Summary

VH and VK homo-dimers are created in a dAb-linker-dAb format using flexible polypeptide linkers. Vectors were created in the dAb linker-dAb format containing glycine-serine linkers of different lengths 3U:$(Gly_4Ser)_3$ (SEQ ID NO:199), 5U:$(Gly_4Ser)_5$ (SEQ ID NO:629), 7U:$(Gly_4Ser)_7$ (SEQ ID NO:630) Dimer libraries were created using guiding dAbs upstream of the linker: TAR1-5 (VK), TAR1-27(VK), TAR2-5(VH) or TAR2-6(VK) and a library of corresponding second dAbs after the linker. Using this method, novel dimeric dAbs were selected. The effect of dimerisation on antigen binding was determined by ELISA and BIAcore studies and in cell neutralisation and receptor binding assays. Dimerisation of both TAR1-5 and TAR1-27 resulted in significant improvement in binding affinity and neutralisation levels.

1.0 Methods 1.1 Library Generation 1.1.1 Vectors pEDA3U, pEDA5U and pEDA7U vectors were designed to introduce different linker lengths compatible with the dAb-linker-dAb format. For pEDA3U, sense and anti-sense 73-base pair oligo linkers were annealed using a slow annealing program (95° C.-5 mins, 80° C.-10 mins, 70° C.-15 mins, 56° C.-15 mins, 42° C. until use) in buffer containing 0.1MNaCl, 10 mM Tris-HCl pH7.4 and cloned using the Xho1 and Not1 restriction sites. The linkers encompassed 3 $(Gly_4Ser)$ units and a stuffer region housed between Sal1 and Not1 cloning sites (scheme 1). In order to reduce the possibility of monomeric dAbs being selected for by phage display, the stuffer region was designed to include 3 stop codons, a Sac1 restriction site and a frame shift mutation to put the region out of frame when no second dAb was present. For pEDA5U and 7U due to the length of the linkers required, overlapping oligo-linkers were designed for each vector, annealed and elongated using Klenow. The fragment was then purified and digested using the appropriate enzymes before cloning using the Xho1 and Not1 restriction sites.

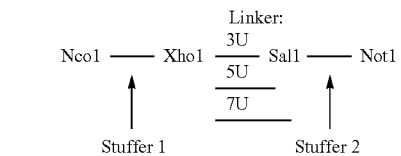

Scheme 1

1.1.2 Library Preparation

The N-terminal V gene corresponding to the guiding dAb was cloned upstream of the linker using Nco1 and Xho1 restriction sites. VH genes have existing compatible sites, however cloning VK genes required the introduction of suitable restriction sites. This was achieved by using modifying PCR primers (VK-DLIBF: 5' cggccatggcgtcaacggacat (SEQ ID NO:377); VKXho1R: 5' atgtgcgctcgagcgtttgattt 3' (SEQ ID NO:378)) in 30 cycles of PCR amplification using a 2:1 mixture of SuperTaq (HTBiotechnology Ltd) and pfu turbo (Stratagene). This maintained the Nco1 site at the 5' end while destroying the adjacent Sal1 site and introduced the Xho1 site at the 3' end. 5 guiding dAbs were cloned into each of the 3 dimer vectors: TAR1-5 (VK), TAR1-27(VK), TAR2-5(VH), TAR2-6(VK) and TAR2-7(VK). All constructs were verified by sequence analysis.

Having cloned the guiding dAbs upstream of the linker in each of the vectors (pEDA3U, 5U and 7U): TAR1-5 (VK), TAR1-27(VK), TAR2-5(VH) or TAR2-6(VK) a library of corresponding second dAbs were cloned after the linker. To achieve this, the complimentary dAb libraries were PCR amplified from phage recovered from round 1 selections of either a VK library against Human TNFα (at approximately $1 \times 10^6$ diversity after round 1) when TAR1-5 or TAR1-27 are the guiding dAbs, or a VH or VK library against human p55 TNF receptor (both at approximately $1 \times 10^5$ diversity after round 1) when TAR2-5 or TAR2-6 respectively are the guiding dAbs. For VK libraries PCR amplification was conducted using primers in 30 cycles of PCR amplification using a 2:1 mixture of SuperTaq and pfu turbo. VH libraries were PCR amplified using primers in order to introduce a Sal1 restriction site at the 5' end of the gene. The dAb library PCRs were digested with the appropriate restriction enzymes, ligated into the corresponding vectors down stream of the linker, using Sal1/Not1 restriction sites and electroporated into freshly prepared competent TG1 cells.

The titres achieved for each library are as follows:
TAR1-5: pEDA3U=$4 \times 10^8$, pEDA5U=$8 \times 10^7$, pEDA7U=$1 \times 10^8$
TAR1-27: pEDA3U=$6.2 \times 10^8$, pEDA5U=$1 \times 10^8$, pEDA7U=$1 \times 10^9$
TAR2h-5: pEDA3U=$4 \times 10^7$, pEDA5U=$2 \times 10^8$, pEDA7U=$8 \times 10^7$
TAR2h-6: pEDA3U=$7.4 \times 10^8$, pEDA5U=$1.2 \times 10^8$, pEDA7U=$2.2 \times 10^8$ 1.2 Selections 1.2.1 TNFα

Selections were conducted using human TNFα passively coated on immunotubes. Briefly, immunotubes are coated overnight with 1-4 mls of the required antigen. The immunotubes were then washed 3 times with PBS and blocked with 2% milk powder in PBS for 1-2 hrs and washed a further 3 times with PBS. The phage solution is diluted in 2% milk powder in PBS and incubated at room temperature for 2 hrs. The tubes are then washed with PBS and the phage eluted with 1 mg/ml trypsin-PBS. Three selection strategies were investigated for the TAR1-5 dimer libraries. The first round selections were carried out in immunotubes using human TNFα coated at 1 µg/ml or 20 µg/ml with 20 washes in PBS 0.1% Tween. TG1 cells are infected with the eluted phage and the titres are determined (eg, Marks et al J Mol. Biol. 1991 Dec. 5; 222(3):581-97, Richmann et al Biochemistry. 1993 Aug. 31; 32(34):8848-55).
The Titres Recovered were:
pEDA3U=2.8×10$^7$ (1 µg/ml TNF) 1.5×10$^8$ (20 µg/mlTNF), pEDA5U=1.8×10$^7$ (1 µg/ml TNF), 1.6×10$^8$ (20 µg/ml TNF) pEDA7U=8×10$^6$ (1 µg/ml TNF), 7×10$^7$ (20 µg/ml TNF).
The second round selections were carried out using 3 different methods.
1. In immunotubes, 20 washes with overnight incubation followed by a further 10 washes.
2. In immunotubes, 20 washes followed by 1 hr incubation at RT in wash buffer with (1 µg/ml TNFα) and 10 further washes.
3. Selection on streptavidin beads using 33 pmoles biotinylated human TNFα (Henderikx et al., 2002, *Selection of antibodies against biotinylated antigens*. Antibody Phage Display: Methods and protocols, Ed. O'Brien and Atkin, Humana Press). Single clones from round 2 selections were picked into 96 well plates and crude supernatant preps were made in 2 ml 96 well plate format.

TABLE 1

| | Round 1 Human TNFαimmunotube coating concentration | Round 2 selection method 1 | Round 2 selection method 2 | Round 2 selection method 3 |
|---|---|---|---|---|
| pEDA3U | 1 µg/ml | 1 × 10$^9$ | 1.8 × 10$^9$ | 2.4 × 10$^{10}$ |
| pEDA3U | 20 µg/ml | 6 × 10$^9$ | 1.8 × 10$^{10}$ | 8.5 × 10$^{10}$ |
| pEDA5U | 1 µg/ml | 9 × 10$^8$ | 1.4 × 10$^9$ | 2.8 × 10$^{10}$ |
| pEDA5U | 20 µg/ml | 9.5 × 10$^9$ | 8.5 × 10$^9$ | 2.8 × 10$^{10}$ |
| pEDA7U | 1 µg/ml | 7.8 × 10$^8$ | 1.6 × 10$^8$ | 4 × 10$^{10}$ |
| pEDA7U | 20 µg/ml | 1 × 10$^{10}$ | 8 × 10$^9$ | 1.5 × 10$^{10}$ |

For TAR1-27, selections were carried out as described previously with the following modifications. The first round selections were carried out in immunotubes using human TNFα coated at 1 µg/ml or 20 µg/ml with 20 washes in PBS 0.1% Tween. The second round selections were carried out in immunotubes using 20 washes with overnight incubation followed by a further 20 washes. Single clones from round 2 selections were picked into 96 well plates and crude supernatant preps were made in 2 ml 96 well plate format.
TAR1-27 Titres are as Follows:

TABLE 2

| | Human TNFαimmunotube coating conc | Round 1 | Round 2 |
|---|---|---|---|
| pEDA3U | 1 µg/ml | 4 × 10$^9$ | 6 × 10$^9$ |
| pEDA3U | 20 µg/ml | 5 × 10$^9$ | 4.4 × 10$^{10}$ |
| pEDA5U | 1 µg/ml | 1.5 × 10$^9$ | 1.9 × 10$^{10}$ |
| pEDA5U | 20 µg/ml | 3.4 × 10$^9$ | 3.5 × 10$^{10}$ |
| pEDA7U | 1 µg/ml | 2.6 × 10$^9$ | 5 × 10$^9$ |
| pEDA7U | 20 µg/ml | 7 × 10$^9$ | 1.4 × 10$^{10}$ |

1.2.2 TNF Receptor 1 (p55 Receptor; TAR2)
Selections were conducted as described previously for the TAR2h-5 libraries only. 3 rounds of selections were carried out in immunotubes using either 1 µg/ml human p55 TNF receptor or 10 µg/ml human p55 TNF receptor with 20 washes in PBS 0.1% Tween with overnight incubation followed by a further 20 washes. Single clones from round 2 and 3 selections were picked into 96 well plates and crude supernatant preps were made in 2 ml 96 well plate format.
TAR2h-5 Titres are as Follows:

TABLE 3

| | Round 1 human p55 TNF receptor immunotube coating concentration | Round 1 | Round 2 | Round 3 |
|---|---|---|---|---|
| pEDA3U | 1 µg/ml | 2.4 × 10$^6$ | 1.2 × 10$^7$ | 1.9 × 10$^9$ |
| pEDA3U | 10 µg/ml | 3.1 × 10$^7$ | 7 × 10$^7$ | 1 × 10$^9$ |
| pEDA5U | 1 µg/ml | 2.5 × 10$^6$ | 1.1 × 10$^7$ | 5.7 × 10$^8$ |
| pEDA5U | 10 µg/ml | 3.7 × 10$^7$ | 2.3 × 10$^8$ | 2.9 × 10$^9$ |
| pEDA7U | 1 µg/ml | 1.3 × 10$^6$ | 1.3 × 10$^7$ | 1.4 × 10$^9$ |
| pEDA7U | 10 µg/ml | 1.6 × 10$^7$ | 1.9 × 10$^7$ | 3 × 10$^{10}$ |

1.3 Screening
Single clones from round 2 or 3 selections were picked from each of the 3U, 5U and 7U libraries from the different selections methods, where appropriate. Clones were grown in 2×TY with 100 µg/ml ampicillin and 1% glucose overnight at 37° C. A 1/100 dilution of this culture was inoculated into 2 mls of 2×TY with 100 µg/ml ampicillin and 0.1% glucose in 2 ml, 96 well plate format and grown at 37° C. shaking until OD600 was approximately 0.9. The culture was then induced with 1 mM IPTG overnight at 30° C. The supernatants were clarified by centrifugation at 400 rpm for 15 mins in a sorval plate centrifuge. The supernatant preps the used for initial screening.
1.3.1 ELISA
Binding activity of dimeric recombinant proteins was compared to monomer by Protein A/L ELISA or by antigen ELISA. Briefly, a 96 well plate is coated with antigen or Protein A/L overnight at 4° C. The plate washed with 0.05% Tween-PBS, blocked for 2 hrs with 2% Tween-PBS. The sample is added to the plate incubated for 1 hr at room temperature. The plate is washed and incubated with the secondary reagent for 1 hr at room temperature. The plate is washed and developed with TMB substrate. Protein A/L-HRP or India-HRP was used as a secondary reagent. For antigen ELISAs, the antigen concentrations used were 1 µg/ml in PBS for Human TNFα and human THF receptor 1. Due to the presence of the guiding dAb in most cases dimers gave a positive ELISA signal therefore off rate determination was examined by BIAcore.
1.3.2 BIAcore
BIAcore analysys was conducted for TAR1-5 and TAR2h-5 clones. For screening, Human TNFα was coupled to a CM5 chip at high density (approximately 10000 RUs). 50 µl of Human TNFα (50 µg/nal) was coupled to the chip at 5 µl/min in acetate buffer—pH5.5. Regeneration of the chip following analysis using the standard methods is not possible due to the instability of Human TNFα, therefore after each sample was analysed, the chip was washed for 10 mins with buffer. For TAR1-5, clones supernatants from the round 2 selection were screened by BIAcore.
48 clones were screened from each of the 3U, 5U and 7U libraries obtained using the following selection methods:
R1: 1 µg/ml human TNFα immunotube, R2 1 µg/ml human TNFα immunotube, overnight wash.
R1: 20 µg/ml human TNFα immunotube, R2 20 µg/ml human TNFα immunotube, overnight wash.
R1: 1 µg/ml human TNFα immunotube, R2 33 pmoles biotinylated human TNFα on beads.
R1: 20 µg/ml human TNFα immunotube, R2 33 pmoles biotinylated human TNFα beads.

For screening, human p55 TNF receptor was coupled to a CM5 chip at high density (approximately 4000 RUs). 100 μl of human p55 TNF receptor (10 μg/ml) was coupled to the chip at 5 μl/min in acetate buffer—pH5.5. Standard regeneration conditions were examined (glycine pH2 or pH3) but in each case antigen was removed from the surface of the chip therefore as with TNFα, therefore after each sample was analysed, the chip was washed for 10 mins with buffer.

For TAR2-5, clones supernatants from the round 2 selection were screened. 48 clones were screened from each of the 3U, 5U and 7U libraries, using the following selection methods:

R1: 1 μg/ml human p55 TNF receptor immunotube, R2 1 μg/ml human p55 TNF receptor immunotube, overnight wash.

R1: 10 μg/ml human p55 TNF receptor immunotube, R2 10 μg/ml human p55 TNF receptor immunotube, overnight wash.

1.3.3 Receptor and Cell Assays

The ability of the dimers to neutralise in the receptor assay was conducted as follows:

Receptor Binding

Anti-TNF dAbs were tested for the ability to inhibit the binding of TNF to recombinant TNF receptor 1 (p55). Briefly, Maxisorp plates were incubated overnight with 30 mg/ml anti-human Fc mouse monoclonal antibody (Zymed, San Francisco, USA). The wells were washed with phosphate buffered saline (PBS) containing 0.05% Tween-20 and then blocked with 1% BSA in PBS before being incubated with 100 ng/ml TNF receptor 1 Fc fusion protein (R&D Systems, Minneapolis, USA). Anti-TNF dAb was mixed with TNF which was added to the washed wells at a final concentration of 10 ng/ml. TNF binding was detected with 0.2 mg/ml biotinylated anti-TNF antibody (HyCult biotechnology, Uben, Netherlands) followed by 1 in 500 dilution of horse radish peroxidase labelled streptavidin (Amersham Biosciences, UK) and then incubation with TMB substrate (KPL, Gaithersburg, USA). The reaction was stopped by the addition of HCl and the absorbance was read at 450 nm. Anti-TNF dAb activity lead to a decrease in TNF binding and therefore a decrease in absorbance compared with the TNF only control.

L929 Cytotoxicity Assay

Anti-TNF dAbs were also tested for the ability to neutralise the cytotoxic activity of TNF on mouse L929 fibroblasts (Evans, T. (2000) Molecular Biotechnology 15, 243-248). Briefly, L929 cells plated in microtitre plates were incubated overnight with anti-TNF dAb, 100 pg/ml TNF and 1 mg/ml actinomycin D (Sigma, Poole, UK). Cell viability was measured by reading absorbance at 490 nm following an incubation with [3-(4,5-dimethylthiazol-2-yl)-5-(3-carboxymethoxyphenyl)-2-(4-sulfophenyl)-2H-tetrazolium (Promega, Madison, USA). Anti-TNF dAb activity lead to a decrease in TNF cytotoxicity and therefore an increase in absorbance compared with the TNF only control.

In the initial screen, supernatants prepared for BIAcore analysis, described above, were also used in the receptor assay. Further analysis of selected dimers was also conducted in the receptor and cell assays using purified proteins.

HeLa IL-8 Assay

Anti-TNFR1 or anti-TNF alpha dAbs were tested for the ability to neutralise the induction of IL-8 secretion by TNF in HeLa cells (method adapted from that of Akeson, L. et al (1996) Journal of Biological Chemistry 271, 30517-30523, describing the induction of IL-8 by IL-1 in HUVEC; here we look at induction by human TNF alpha and we use HeLa cells instead of the HUVEC cell line). Briefly, HeLa cells plated in microtitre plates were incubated overnight with dAb and 300 pg/ml TNF. Post incubation the supernatant was aspirated off the cells and IL-8 concentration measured via a sandwich ELISA (R&D Systems). Anti-TNFR1 dAb activity lead to a decrease in IL-8 secretion into the supernatant compared with the TNF only control.

The L929 assay is used throughout the following experiments; however, the use of the HeLa IL-8 assay is preferred to measure anti-TNF receptor 1 (p55) ligands; the presence of mouse p55 in the L929 assay poses certain limitations in its use.

1.4 Sequence Analysis

Dimers that proved to have interesting properties in the BIAcore and the receptor assay screens were sequenced. Sequences are detailed in the sequence listing.

1.5 Formatting 1.5.1 TAR1-5-19 Dimers

The TAR1-5 dimers that were shown to have good neutralisation properties were re-formatted and analysed in the cell and receptor assays. The TAR1-5 guiding dab was substituted with the affinity matured clone TAR1-5-19. To achieve this TAR1-5 was cloned out of the individual dimer pair and substituted with TAR1-5-19 that had been amplified by PCR. In addition, TAR1-5-19 homodimers were also constructed in the 3U, 5U and 7U vectors. The N terminal copy of the gene was amplified by PCR and cloned as described above and the C-terminal gene fragment was cloned using existing Sal1 and Not1 restriction sites.

1.5.2 Mutagenesis

The amber stop codon present in dAb2, one of the C-terminal dAbs in the TAR1-5 dimer pairs was mutated to a glutamine by site-directed mutagenesis.

1.5.3 Fabs

The dimers containing TAR1-5 or TAR1-5-19 were reformatted into Fab expression vectors. dAbs were cloned into expression vectors containing either the CK or CH genes using Sfi1 and Not1 restriction sites and verified by sequence analysis. The CK vector is derived from a pUC based ampicillin resistant vector and the CH vector is derived from a pACYC chloramphenicol resistant vector. For Fab expression the dAb-CH and dAb-CK constructs were co-transformed into HB2151 cells and grown in 2×TY containing 0.1% glucose, 100 μg/ml ampicillin and 10 μg/ml chloramphenicol.

1.5.3 Hinge Dimerisation

Dimerisation of dAbs via cystine bond formation was examined. A short sequence of amino acids EPKSGDKTH-TCPPCP (SEQ ID NO:379) a modified form of the human IgGC1 hinge was engineered at the C terminal region on the dAb. An oligo linker encoding for this sequence was synthesised and annealed, as described previously. The linker was cloned into the pEDA vector containing TAR1-5-19 using Xho1 and Not1 restriction sites. Dimerisation occurs in situ in the periplasm.

1.6 Expression and Purification 1.6.1 Expression

Supernatants were prepared in the 2 ml, 96-well plate format for the initial screening as described previously. Following the initial screening process selected dimers were analysed further. Dimer constructs were expressed in TOP10F' or HB2151 cells as supernatants. Briefly, an individual colony from a freshly streaked plate was grown overnight at 37° C. in 2×TY with 100 μg/ml ampicillin and 1% glucose. A 1/100 dilution of this culture was inoculated into 2×TY with 100 μg/ml ampicillin and 0.1% glucose and grown at 37° C. shaking until OD600 was approximately 0.9. The culture was then induced with 1 mM IPTG overnight at 30° C.

The cells were removed by centrifugation and the supernatant purified with protein A or L agarose.

Fab and cysteine hinge dimers were expressed as periplasmic proteins in HB2152 cells. A 1/100 dilution of an overnight culture was inoculated into 2×TY with 0.1% glucose and the appropriate antibiotics and grown at 30° C. shaking until OD600 was approximately 0.9. The culture was then induced with 1 mM IPTG for 3-4 hours at 25° C. The cells were harvested by centrifugation and the pellet resuspended in periplasmic preparation buffer (30 mM Tris-HCl pH8.0, 1 mM EDTA, 20% sucrose). Following centrifugation the supernatant was retained and the pellet resuspended in 5 mM $MgSO_4$. The supernatant was harvested again by centrifugation, pooled and purified.

1.6.2 Protein A/L Purification

Optimisation of the purification of dimer proteins from Protein L agarose (Affitech, Norway) or Protein A agarose (Sigma, UK) was examined. Protein was eluted by batch or by column elution using a peristaltic pump. Three buffers were examined 0.1M Phosphate-citrate buffer pH2.6, 0.2M Glycine pH2.5 and 0.1M Glycine pH2.5. The optimal condition was determined to be under peristaltic pump conditions using 0.1M Glycine pH2.5 over 10 column volumes. Purification from protein A was conducted peristaltic pump conditions using 0.1M Glycine pH2.5.

1.6.3 FPLC Purification

Further purification was carried out by FPLC analysis on the AKTA Explorer 100 system (Amersham Biosciences Ltd). TAR1-5 and TAR1-5-19 dimers were fractionated by cation exchange chromatography (1 ml Resource S—Amersham Biosciences Ltd) eluted with a 0-1M NaCl gradient in 50 mM acetate buffer pH4. Hinge dimers were purified by ion exchange (1 ml Resource Q Amersham Biosciences Ltd) eluted with a 0-1M NaCl gradient in 25 mMTris HCl pH 8.0. Fabs were purified by size exclusion chromatography using a superose 12 (Amersham Biosciences Ltd) column run at a flow rate of 0.5 ml/min in PBS with 0.05% tween. Following purification samples were concentrated using vivaspin 5K cut off concentrators (Vivascience Ltd).

2.0 Results 2.1 TART-5 Dimers

6×96 clones were picked from the round 2 selection encompassing all the libraries and selection conditions. Supernatant preps were made and assayed by antigen and Protein L ELISA, BIAcore and in the receptor assays. In ELISAs, positive binding clones were identified from each selection method and were distributed between 3U, 5U and 7U libraries. However, as the guiding dAb is always present it was not possible to discriminate between high and low affinity binders by this method therefore BIAcore analysis was conducted.

BIAcore analysis was conducted using the 2 ml supernatants. BIAcore analysis revealed that the dimer Koff rates were vastly improved comp ared to monomeric TAR1-5. Monomer Koff rate was in the range of $10^{-1}$M compared with dimer Koff rates which were in the range of $10^{-3}$-$10^{-4}$M. 16 clones that appeared to have very slow off rates were selected, these came from the 3U, 5U and 7U libraries and were sequenced. In addition the supernatants were analysed for the ability to neutralise human TNFα in the receptor assay.

6 lead clones (d1-d6 below) that neutralised in these assays and have been sequenced. The results shows that out of the 6 clones obtained there are only 3 different second dAbs (dAb1, dAb2 and dAb3) however where the second dAb is found more than once they are linked with different length linkers.

TAR1-5d1: 3U linker $2^{nd}$ dAb=dAb1–1 µg/ml Ag immunotube overnight wash
TAR1-5d2: 3U linker $2^{nd}$ dAb=dAb2–1 µg/ml Ag immunotube overnight wash
TAR1-5d3: 5U linker $2^{nd}$ dAb=dAb2–1 µg/ml Ag immunotube overnight wash
TAR1-5d4: 5U linker $2^{nd}$ dAb=dAb3–20 µg/ml Ag immunotube overnight wash
TAR1-5d5: 5U linker $2^{nd}$ dAb=dAb1–20 µg/ml Ag immunotube overnight wash
TAR1-5d6: 7U linker $2^{nd}$ dAb=dAb1–R1:1 µg/ml Ag immunotube overnight wash, R2:beads The 6 lead clones were examined further. Protein was produced from the periplasm and supernatant, purified with protein L agarose and examined in the cell and receptor assays. The levels of neutralisation were variable (Table 1). The optimal conditions for protein preparation were determined. Protein produced from HB2151 cells as supernatants gave the highest yield (approximately 10 mgs/L of culture). The supernatants were incubated with protein L agarose for 2 hrs at room temperature or overnight at 4° C. The beads were washed with PBS/NaCl and packed onto an FPLC column using a peristaltic pump. The beads were washed with 10 column volumes of PBS/NaCl and eluted with 0.1M glycine pH2.5. In general, dimeric protein is eluted after the monomer.

TAR1-5d1-6 dimers were purified by FPLC. Three species were obtained, by FPLC purification and were identified by SDS PAGE. One species corresponds to monomer and the other two species corresponds to dimers of different sizes. The larger of the two species is possibly due to the presence of C terminal tags. These proteins were examined in the receptor assay. The data presented in table 1 represents the optimum results obtained from the two dimeric species (FIG. 11)

The three second dAbs from the dimer pairs (ie, dAb1, dAb2 and dAb3) were cloned as monomers and examined by ELISA and in the cell and receptor assay. All three dAbs bind specifically to TNF by antigen ELISA and do not cross react with plastic or BSA. As monomers, none of the dAbs neutralise in the cell or receptor assays.

2.1.2 TAR1-5-19 Dimers

TAR1-5-19 was substituted for TAR1-5 in the 6 lead clones. Analysis of all TAR1-5-19 dimers in the cell and receptor assays was conducted using total protein (protein L purified only) unless otherwise stated (Table 2). TAR1-5-19d4 and TAR1-5-19d3 have the best $ND_{50}$ (~5 nM) in the cell assay, this is consistent with the receptor assay results and is an improvement over TAR1-5-19 monomer ($ND_{50}$~30 nM). Although purified TAR1-5 dimers give variable results in the receptor and cell assays TAR1-5-19 dimers were more consistent. Variability was shown when using different elution buffers during the protein purification. Elution using 0.1M Phosphate-citrate buffer pH2.6 or 0.2M Glycine pH2.5 although removing all protein from the protein L agarose in most cases rendered it less functional.

TAR1-5-19d4 was expressed in the fermenter and purified on cation exchange FPLC to yield a completely pure dimer. As with TAR1-5d4 three species were obtained, by FPLC purification corresponding to monomer and two dimer species. This dimer was amino acid sequenced. TAR1-5-19 monomer and TAR1-5-19d4 were then examined in the receptor assay and the resulting IC50 for monomer was 30 nM and for dimer was 8 nM. The results of the receptor assay comparing TAR1-5-19 monomer, TAR1-5-19d4 and TAR1-5d4 is shown in FIG. 10.

TAR1-5-19 homodimers were made in the 3U, 5U and 7U vectors, expressed and purified on Protein L. The proteins were examined in the cell and receptor assays and the resulting $IC_{50}$s (for receptor assay) and $ND_{50}$s (for cell assay) were determined (table 3, FIG. 12).

2.2 Fabs

TAR1-5 and TAR1-5-19 dimers were also cloned into Fab format, expressed and purified on protein L agarose. Fabs were assessed in the receptor assays (Table 4). The results showed that for both TAR1-5-19 and TAR1-5 dimers the neutralisation levels were similar to the original Gly$_4$Ser linker dimers from which they were derived. A TAR1-5-19 Fab where TAR1-5-19 was displayed on both CH and CK was expressed, protein L purified and assessed in the receptor assay. The resulting IC50 was approximately 1 nM.

2.3 TAR1-27 Dimers

3×96 clones were picked from the round 2 selection encompassing all the libraries and selection conditions. 2 ml supernatant preps were made for analysis in ELISA and bioassays. Antigen ELISA gave 71 positive clones. The receptor assay of crude supernatants yielded 42 clones with inhibitory properties (TNF binding 0-60%). In the majority of cases inhibitory properties correlated with a strong ELISA signal. 42 clones were sequenced, 39 of these have unique second dAb sequences. The 12 dimers that gave the best inhibitory properties were analysed further.

The 12 neutralising clones were expressed as 200 ml supernatant preps and purified on protein L. These were assessed by protein L and antigen ELISA, BIAcore and in the receptor assay. Strong positive ELISA signals were obtained in all cases. BIAcore analysis revealed all clones to have fast on and off rates. The off rates were improved compared to monomeric TART-27, however the off rate of TAR1-27 dimers was faster (Koff is approximately in the range of $10^{-1}$ and $10^{-2}$M) than the TAR1-5 dimers examined previously (Koff is approximately in the range of $10^{-3}$-$10^{-4}$M). The stability of the purified dimers was questioned and therefore in order to improve stability, the addition on 5% glycerol, 0.5% Triton X100 or 0.5% NP40 (Sigma) was included in the purification of 2 TAR1-27 dimers (d2 and d16). Addition of NP40 or Triton X100™ improved the yield of purified product approximately 2 fold. Both dimers were assessed in the receptor assay. TAR1-27d2 gave IC50 of ~30 nM under all purification conditions. TAR1-27d16 showed no neutralisation effect when purified without the use of stabilising agents but gave an IC50 of ~50 nM when purified under stabilising conditions. No further analysis was conducted.

2.4 TAR2-5 Dimers

3×96 clones were picked from the second round selections encompassing all the libraries and selection conditions. 2 ml supernatant preps were made for analysis. Protein A and antigen ELISAs were conducted for each plate. 30 interesting clones were identified as having good off-rates by BIAcore (Koff ranges between $10^{-2}$-$10^{-3}$M). The clones were sequenced and 13 unique dimers were identified by sequence analysis.

TABLE 4

TAR1-5 dimers.

| Dimer | Cell type | Purification | Protein Fraction | Elution conditions | Receptor/ Cell assay |
| --- | --- | --- | --- | --- | --- |
| TAR1-5d1 | HB2151 | Protein L + FPLC | small dimeric species | 0.1M glycine pH 2.5 | RA~30 nM |
| TAR1-5d2 | HB2151 | Protein L + FPLC | small dimeric species | 0.1M glycine pH 2.5 | RA~50 nM |
| TAR1-5d3 | HB2151 | Protein L + FPLC | large dimeric species | 0.1M glycine pH 2.5 | RA~300 nM |
| TAR1-5d4 | HB2151 | Protein L + FPLC | small dimeric species | 0.1M glycine pH 2.5 | RA~3 nM |
| TAR1-5d5 | HB2151 | Protein L + FPLC | large dimeric species | 0.1M glycine pH 2.5 | RA~200 nM |
| TAR1-5d6 | HB2151 | Protein L + FPLC | Large dimeric species | 0.1M glycine pH 2.5 | RA~100 nM |

*note dimer 2 and dimer 3 have the same second dAb (called dAb2), however have different linker lengths (d2 = (Gly$_4$Ser)$_3$, d3 = (Gly$_4$Ser)$_3$). dAb1 is the partner dAb to dimers 1, 5 and 6. dAb3 is the partner dAb to dimer4. None of the partner dAbs neutralise alone. FPLC purification is by cation exchange unless otherwise stated. The optimal dimeric species for each dimer obtained by FPLC was determined in these assays.

TABLE 5

TAR1-5-19 dimers

| Dimer | Cell type | Purification | Protein Fraction | Elution conditions | Receptor/ Cell assay |
| --- | --- | --- | --- | --- | --- |
| TAR1-5-19 d1 | TOP10F' | Protein L | Total protein | 0.1M glycine pH 2.0 | RA~15 nM |
| TAR1-5-19 d2 (no stop codon) | TOP10F' | Protein L | Total protein | 0.1M glycine pH 2.0 + 0.05% NP40 | RA~2 nM |
| TAR1-5-19d3 (no stop codon) | TOP10F' | Protein L | Total protein | 0.1M glycine pH 2.5 + 0.05% NP40 | RA~8 nM |
| TAR1-5-19d4 | TOP10F' | Protein L + FPLC | FPLC purified fraction | 0.1M glycine pH 2.0 | RA~2-5 nM CA~12 nM |
| TAR1-5-19d5 | TOP10F' | Protein L | Total protein | 0.1M glycine pH 2.0 + NP40 | RA~8 nM CA~10 nM |
| TAR1-5-19 d6 | TOP10F' | Protein L | Total protein | 0.1M glycine pH 2.0 | RA~10 nM |

TABLE 6

TAR1-5-19 homodimers

| Dimer | Cell type | Purification | Protein Fraction | Elution conditions | Receptor/ Cell assay |
|---|---|---|---|---|---|
| TAR1-5-19 3U homodimer | HB2151 | Protein L | Total protein | 0.1M glycine pH 2.5 | RA~20 nM CA~30 nM |
| TAR1-5-19 5U homodimer | HB2151 | Protein L | Total protein | 0.1M glycine pH 2.5 | RA~2 nM CA~3 nM |
| TAR1-5-19 7U homodimer | HB2151 | Protein L | Total protein | 0.1M glycine pH 2.5 | RA~10 nM CA~15 nM |
| TAR1-5-19 cys hinge | HB2151 | Protein L + FPLC | FPLC purified dimer fraction | 0.1M glycine pH 2.5 | RA~2 nM |
| TAR1-5-19CH/ TAR1-5-19 CK | HB2151 | Protein | Total protein | 0.1M glycine pH 2.5 | RA~1 nM |

TABLE 7

TAR1-5/TAR1-5-19 Fabs

| Dimer | Cell type | Purification | Protein Fraction | Elution conditions | Receptor/ Cell assay |
|---|---|---|---|---|---|
| TAR1-5CH/ dAb1 CK | HB2151 | Protein L | Total protein | 0.1M citrate pH 2.6 | RA~90 nM |
| TAR1-5CH/ dAb2 CK | HB2151 | Protein L | Total protein | 0.1M glycine pH 2.5 | RA~30 nM CA~60 nM |
| dAb3CH/ TAR1-5CK | HB2151 | Protein L | Total protein | 0.1M citrate pH 2.6 | RA~100 nM |
| TAR1-5-19CH/ dAb1 CK | HB2151 | Protein L | Total protein | 0.1M glycine pH 2.0 | RA~6 nM |
| dAb1 CH/ TAR1-5-19CK | HB2151 | Protein L | 0.1M glycine pH 2.0 | Myc/flag | RA~6 nM |
| TAR1-5-19CH/ dAb2 CK | HB2151 | Protein L | Total protein | 0.1M glycine pH 2.0 | RA~8 nM CA~12 nM |
| TAR1-5-19CH/ dAb3CK | HB2151 | Protein L | Total protein | 0.1M glycine pH 2.0 | RA~3 nM |

Example 7 dAb Dimerisation By Terminal Cysteine Linkage

Summary

For dAb dimerisation, a free cysteine has been engineered at the C-terminus of the protein. When expressed the protein forms a dimer which can be purified by a two step purification method.

PCR Construction of TAR1-5-19CYS Dimer

See example 8 describing the dAb trimer. The trimer protocol gives rise to a mixture of monomer, dimer and trimer.

Expression and Purification of TAR1-5-19CYS Dimer

The dimer was purified from the supernatant of the culture by capture on Protein L agarose as outlined in the example 8.

Separation of TAR1-5-19CYS Monomer from the TAR1-5-19CYS Dimer

Prior to cation exchange separation, the mixed monomer/dimer sample was buffer exchanged into 50 mM sodium acetate buffer pH 4.0 using a PD-10 column (Amersham Pharmacia), following the manufacturer's guidelines. The sample was then applied to a 1 mL Resource S cation exchange column (Amersham Pharmacia), which had been pre-equilibrated with 50 mM sodium acetate pH 4.0. The monomer and dimer were separated using the following salt gradient in 50 mM sodium acetate pH 4.0:
150 to 200 mM sodium chloride over 15 column volumes
200 to 450 mM sodium chloride over 10 column volumes
450 to 1000 mM sodium chloride over 15 column volumes Fractions containing dimer only were identified using SDS-PAGE and then pooled and the pH increased to 8 by the addition of ⅕ volume of 1M Tris pH 8.0.

In Vitro Functional Binding Assay: TNF Receptor Assay and Cell Assay

The affinity of the dimer for human TNFα was determined using the TNF receptor and cell assay. IC50 in the receptor assay was approximately 0.3-0.8 nM; ND50 in the cell assay was approximately 3-8 nM.

Other Possible TAR1-5-19CYS Dimer Formats

Peg Dimers and Custom Synthetic Maleimide Dimers

Nektar (Shearwater) offer a range of bi-maleimide PEGs [mPEG2-(MAL)2 or mPEG-(MAL)2] which would allow the monomer to be formatted as a dimer, with a small linker separating the dAbs and both being linked to a PEG ranging in size from 5 to 40 kDa. It has been shown that the 5 kDa mPEG-(MAL)2 (ie, [TAR1-5-19]-Cys-maleimide-PEG×2, wherein the maleimides are linked together in the dimer) has an affinity in the TNF receptor assay of ~1-3 nM. Also the dimer can also be produced using TMEA (Tris[2-maleimidoethyl]amine) (Pierce Biotechnology) or other bi-functional linkers.

It is also possible to produce the disulphide dimer using a chemical coupling procedure using 2,2'-dithiodipyridine (Sigma Aldrich) and the reduced monomer.

Addition of a polypeptide linker or hinge to the C-terminus of the dAb. A small linker, either $(Gly_4Ser)_n$ where n=1 to 10, eg, 1, 2, 3, 4, 5, 6 or 7, an immunoglobulin (eg, IgG hinge region or random peptide sequence (eg, selected from a library of random peptide sequences) can be engineered between the dAb and the terminal cysteine residue. This can then be used to make dimers as outlined above.

Example 8 dAb Trimerisation

Summary

For dAb trimerisation, a free cysteine is required at the C-terminus of the protein. The cysteine residue, once reduced to give the free thiol, can then be used to specifically couple the protein to a trimeric maleimide molecule, for example TMEA (Tris[2-maleimidoethyl]amine).

PCR Construction of TAR1-5-19CYS

The following oligonucleotides were used to specifically PCR TAR1-5-19 with a SalI and BamHI sites for cloning and also to introduce a C-terminal cysteine residue:

```
            SalI
            ~~~~~~~~
  1 Trp Ser Ala Ser Thr Asp* Ile Gln Met Thr Gln Ser Pro Ser Ser Leu Ser Ala Ser Val
    TGG AGC GCG TCG ACG GAC ATC CAG ATG ACC CAG TCT CCA TCC TCT CTG TCT GCA TCT GTA
    ACC TCG CGC AGC TGC CTG TAG GTC TAC TGG GTC AGA GGT AGG AGA GAC AGA CGT AGA CAT

61 Gly Asp Arg Val Thr Ile Thr Cys Arg Ala Ser Gln Ser Ile Asp Ser Tyr Leu His Trp
    GGA GAC CGT GTC ACC ATC ACT TGC CGG GCA AGT CAG AGC ATT GAT AGT TAT TTA CAT TGG
    CCT CTG GCA CAG TGG TAG TGA ACG GCC CGT TCA GTC TCG TAA CTA TCA ATA AAT GTA ACC

121 Tyr Gln Gln Lys Pro Gly Lys Ala Pro Lys Leu Leu Ile Tyr Ser Ala Ser Glu Leu Gln
    TAC CAG CAG AAA CCA GGG AAA GCC CCT AAG CTC CTG ATC TAT AGT GCA TCC GAG TTG CAA
    ATG GTC GTC TTT GGT CCC TTT CGG GGA TTC GAG GAC TAG ATA TCA CGT AGG CTC AAC GTT

181 Ser Gly Val Pro Ser Arg Phe Ser Gly Ser Gly Ser Gly Thr Asp Phe Thr Leu Thr Ile
    AGT GGG GTC CCA TCA CGT TTC AGT GGC AGT GGA TCT GGG ACA GAT TTC ACT CTC ACC ATC
    TCA CCC CAG GGT AGT GCA AAG TCA CCG TCA CCT AGA CCC TGT CTA AAG TGA GAG TGG TAG

241 Ser Ser Leu Gln Pro Glu Asp Phe Ala Thr Tyr Tyr Cys Gln Gln Val Val Trp Arg Pro
    AGC AGT CTG CAA CCT GAA GAT TTT GCT ACG TAC TAC TGT CAA CAG GTT GTG TGG CGT CCT
    TCG TCA GAC GTT GGA CTT CTA AAA CGA TGC ATG ATG ACA GTT GTC CAA CAC ACC GCA GGA
                                                                          BamHI
                                                                          ~~~~~~~~

301 Phe Thr Phe Gly Gln Gly Thr Lys Val Glu Ile Lys Arg Cys * * Gly Ser Gly
    TTT ACG TTC GGC CAA GGG ACC AAG GTG GAA ATC AAA CGG TGC TAA TAA GGA TCC GGC
    AAA TGC AAG CCG GTT CCC TGG TTC CAC CTT TAG TTT GCC ACG ATT ATT CCT AGG CCG
```

(*start of TAR1-5-19CYS sequence; TAR1-5-19CYS amino acid sequence (SEQ ID NO: 293; TAR1-5-19CYS nucleotide sequences (SEQ ID NO: 294, coding strand; SEQ ID NO: 295, noncoding strand))

Forward primer (SEQ ID NO: 296)
5'-TGGAGCGCGTCGACGGACATCCAGATGACCCAGTCTCCA-3'

Reverse primer (SEQ ID NO: 297)
5'-TTAGCAGCCGGATCCTTATTAGCACCGTTTGATTTCCAC-3'

The PCR reaction (50 µL volume) was set up as follows: 200 µM dNTPs, 0.4 µM of each primer, 5 µL of 10× Pfu Turbo buffer (Stratagene), 100 ng of template plasmid (encoding TAR1-5-19), 1 µL of PfuTurbo enzyme (Stratagene) and the volume adjusted to 50 µL using sterile water. The following PCR conditions were used: initial denaturing step 94° C. for 2 mins, then 25 cycles of 94° C. for 30 secs, 64° C. for 30 sec and 72° C. for 30 sec. A final extension step was also included of 72° C. for 5 mins. The PCR product was purified and digested with SalI and BamHI and ligated into the vector which had also been cut with the same restriction enzymes. Correct clones were verified by DNA sequencing.

Expression and Purification of TAR1-5-19CYS

TAR1-5-19CYS vector was transformed into BL21 (DE3) pLysS chemically competent cells (Novagen) following the manufacturer's protocol. Cells carrying the dAb plasmid were selected for using 100 µg/mL carbenicillin and 37 µg/mL chloramphenicol. Cultures were set up in 2 L baffled flasks containing 500 mL of terrific broth (Sigma-Aldrich), 100 µg/mL carbenicillin and 37 µg/mL chloramphenicol. The cultures were grown at 30° C. at 200 rpm to an O.D. 600 of 1-1.5 and then induced with 1 mM IPTG (isopropyl-beta-D-thiogalactopyranoside, from Melford Laboratories). The expression of the dAb was allowed to continue for 12-16 hrs at 30° C. It was found that most of the dAb was present in the culture media. Therefore, the cells were separated from the media by centrifugation (8,000×g for 30 mins), and the supernatant used to purify the dAb. Per litre of supernatant, 30 mL of Protein L agarose (Affitech) was added and the dAb allowed to batch bind with stirring for 2 hours. The resin was then allowed to settle under gravity for a further hour before the supernatant was siphoned off. The agarose was then packed into a XK 50 column (Amersham Phamacia) and was washed with 10 column volumes of PBS. The bound dAb was eluted with 100 mM glycine pH 2.0 and protein containing fractions were then neutralized by the addition of ⅕ volume of 1 M Tris pH 8.0. Per litre of culture supernatant 20 mg of pure protein was isolated, which contained a 50:50 ratio of monomer to dimer.

Trimerisation of TAR1-5-19CYS 2.5 ml of 100 µM TAR1-5-19CYS was reduce with 5 mM dithiothreitol and left at room temperature for 20 minutes. The sample was then buffer exchanged using a PD-10 column (Amersham Pharmacia). The column had been pre-equilibrated with 5 mM EDTA, 50 mM sodium phosphate pH 6.5, and the sample applied and eluted following the manufactures guidelines. The sample was placed on ice until required. TMEA (Tris[2-maleimidoethyl]amine) was purchased from Pierce Biotechnology. A 20 mM stock solution of TMEA was made in 100% DMSO (dimethyl sulphoxide). It was found that a concentration of TMEA greater than 3:1 (molar ratio of dAb:TMEA) caused the rapid precipitation and cross-linking of the protein. Also the rate of precipitation and cross-linking was greater as the pH increased. Therefore using 100 µM reduced TAR1-5-19CYS, 25 µM TMEA was added to trimerise the protein and the reaction allowed to proceed at room temperature for two hours. It was found that the addition of additives such as glycerol or ethylene glycol to 20% (v/v), significantly reduced the precipitation of the trimer as the coupling reaction proceeded. After coupling, SDS-PAGE analysis showed the presence of monomer, dimer and trimer in solution.

Purification of the Trimeric TAR1-5-19CYS

40 µL of 40% glacial acetic acid was added per mL of the TMEA-TAR1-5-19cys reaction to reduce the pH to ~4. The sample was then applied to a 1 mL Resource S cation exchange column (Amersham Pharmacia), which had been pre-equilibrated with 50 mM sodium acetate pH 4.0. The dimer and trimer were partially separated using a salt gradient of 340 to 450 mM Sodium chloride, 50 mM sodium acetate pH 4.0 over 30 column volumes. Fractions containing trimer only were identified using SDS-PAGE and then pooled and the pH increased to 8 by the addition of ⅕ volume of 1M Tris pH 8.0. To prevent precipitation of the trimer during concentration steps (using 5K cut off Viva spin concentrators; Vivascience), 10% glycerol was added to the sample.

In Vitro Functional Binding Assay: TNF Receptor Assay and Cell Assay

The affinity of the trimer for human TNFα was determined using the TNF receptor and cell assay. IC50 in the receptor assay was 0.3 nM; ND50 in the cell assay was in the range of 3 to 10 nM (eg, 3 nM).

Other Possible TAR1-5-19CYS Trimer Formats

TAR1-5-19CYS may also be formatted into a trimer using the following reagents:

PEG Trimers and Custom Synthetic Maleimide Trimers

Nektar (Shearwater) offer a range of multi arm PEGs, which can be chemically modified at the terminal end of the PEG. Therefore using a PEG trimer with a maleimide functional group at the end of each arm would allow the trimerisation of the dAb in a manner similar to that outlined above using TMEA. The PEG may also have the advantage in increasing the solubility of the trimer thus preventing the problem of aggregation. Thus, one could produce a dAb trimer in which each dAb has a C-terminal cysteine that is linked to a maleimide functional group, the maleimide functional groups being linked to a PEG trimer.

Addition of a Polypeptide Linker or Hinge to the C-Terminus of the dAb

A small linker, either $(Gly_4Ser)_n$ where n=1 to 10, eg, 1, 2, 3, 4, 5, 6 or 7, an immunoglobulin (eg, IgG hinge region or random peptide sequence (eg, selected from a library of random peptide sequences) could be engineered between the dAb and the terminal cysteine residue. When used to make multimers (eg, dimers or trimers), this again would introduce a greater degree of flexibility and distance between the individual monomers, which may improve the binding characteristics to the target, eg a multisubunit target such as human TNFα.

Example 9

Selection of a Collection of Single Domain Antibodies (dAbs) Directed Against Human Serum Albumin (HSA) and Mouse Serum Albumin (MSA)

This example explains a method for making a single domain antibody (dAb) directed against serum albumin.

Selection of dAbs against both mouse serum albumin (MSA) and human serum albumin (HSA) is described. Three human phage display antibody libraries were used in this experiment, each based on a single human framework for $V_H$ (see FIG. 13: sequence of dummy $V_H$ based on V3-23/DP47 and JH4b) or $V_K$ (see FIG. 15: sequence of dummy $V_K$ based on o12/o2/DPK9 and Jk1) with side chain diversity encoded by NNK codons incorporated in complementarity determining regions (CDR1, CDR2 and CDR3).

Library 1 ($V_H$):
Diversity at positions: H30, H31, H33, H35, H50, H52, H52a, H53, H55, H56, H58, H95, H97, H98.
Library size: $6.2 \times 10^9$ Library 2 ($V_H$):
Diversity at positions: H30, H31, H33, H35, H50, H52, H52a, H53, H55, H56, H58, H95, H97, H98, H99, H100, H100a, H100b.
Library size: $4.3 \times 10^9$ Library 3 ($V_K$):
Diversity at positions: L30, L31, L32, L34, L50, L53, L91, L92, L93, L94, L96
Library size: $2 \times 10^9$ The $V_H$ and $V_K$ libraries have been preselected for binding to generic ligands protein A and protein L respectively so that the majority of clones in the unselected libraries are functional. The sizes of the libraries shown above correspond to the sizes after preselection.

Two rounds of selection were performed on serum albumin using each of the libraries separately. For each selection, antigen was coated on immunotube (nunc) in 4 ml of PBS at a concentration of 100 µg/ml. In the first round of selection, each of the three libraries was panned separately against HSA (Sigma) and MSA (Sigma). In the second round of selection, phage from each of the six first round selections was panned against (i) the same antigen again (eg $1^{st}$ round MSA, $2^{nd}$ round MSA) and (ii) against the reciprocal antigen (eg $1^{st}$ round MSA, $2^{nd}$ round HSA) resulting in a total of twelve $2^{nd}$ round selections. In each case, after the second round of selection 48 clones were tested for binding to HSA and MSA. Soluble dAb fragments were produced as described for scFv fragments by Harrison et al, Methods Enzymol. 1996; 267: 83-109 and standard ELISA protocol was followed (Hoogenboom et al. (1991) Nucleic Acids Res., 19: 4133) except that 2% tween PBS was used as a blocking buffer and bound dAbs were detected with either protein L-HRP (Sigma) (for the $V_KS$) and protein A—HRP (Amersham Pharmacia Biotech) (for the $V_Hs$).

dAbs that gave a signal above background indicating binding to MSA, HSA or both were tested in ELISA insoluble form for binding to plastic alone but all were specific for serum albumin. Clones were then sequenced (see table below) revealing that 21 unique dAb sequences had been identified. The minimum similarity (at the amino acid level) between the $V_K$ dAb clones selected was 86.25% ((69/80)×100; the result when all the diversified residues are different, eg clones 24 and 34). The minimum similarity between the $V_H$ dAb clones selected was 94% ((127/136)×100).

Next, the serum albumin binding dAbs were tested for their ability to capture biotinylated antigen from solution. ELISA protocol (as above) was followed except that ELISA plate was coated with 1 µg/ml protein L (for the $V_K$ clones) and 1 µg/ml protein A (for the $V_H$ clones). Soluble dAb was captured from solution as in the protocol and detection was with biotinylated MSA or HSA and streptavidin HRP. The biotinylated MSA and HSA had been prepared according to the manufacturer's instructions, with the aim of achieving an average of 2 biotins per serum albumin molecule. Twenty four clones were identified that captured biotinylated MSA from solution in the ELISA. Two of these (clones 2 and 38 below) also captured biotinylated HSA. Next, the dAbs were tested for their ability to bind MSA coated on a CM5 biacore chip. Eight clones were found that bound MSA on the biacore.

TABLE 8

| dAb (all capture biotinylated MSA) | H or κ | CDR1 | CDR2 | CDR3 | Binds MSA in biacore? | Captures Biotinylated HSA? |
|---|---|---|---|---|---|---|
| Vκ library 3 template (dummy) | κ | XXXLX (SEQ ID NO: 298) | XASLQS (SEQ ID NO: 299) | QQXXXXPXT (SEQ ID NO: 300) | | |
| 2, 4, 7, 41, | κ | SSYLN (SEQ ID NO: 301) | RASPLQS (SEQ ID NO: 302) | QQTYSVPPT (SEQ ID NO: 303) | | ✓ all 4 bind |
| 38, 54 | κ | SSYLN (SEQ ID NO: 304) | RASPLQS (SEQ ID NO: 305) | QQTYRIPPT (SEQ ID NO: 306) | | ✓ both bind |
| 46, 47, 52, 56 | κ | FKSLK (SEQ ID NO: 307) | NASYLQS (SEQ ED NO: 308) | QQVVYWPVT (SEQ ID NO: 309) | | |
| 13, 15 | κ | YYHLK (SEQ ID NO: 310) | KASTLQS (SEQ ID NO: 311) | QQVRKVPRT (SEQ ID NO: 312) | | |
| 30, 35 | κ | RRYLK (SEQ ID NO: 313) | QASVLQS (SEQ ID NO: 314) | QQGLYPPIT (SEQ ID NO: 315) | | |
| 19, | κ | YNWLK (SEQ ID NO: 316) | RASSLQS (SEQ ID NO: 317) | QQNVVIPRT (SEQ ID NO: 318) | | |
| 22, | κ | LWHLR (SEQ ID NO: 319) | HASLLQS (SEQ ID NO: 320) | QQSAVYPKT (SEQ ID NO: 321) | | |
| 23, | κ | FRYLA (SEQ ID NO: 322) | HASHLQS (SEQ ID NO: 323) | QQRLLYPKT (SEQ ID NO: 324) | | |
| 24, | κ | FYHLA (SEQ ID NO: 325) | PASKLQS (SEQ ID NO: 326) | QQRARWPRT (SEQ ID NO: 327) | | |
| 31, | κ | IWHLN (SEQ ID NO: 328) | RASRLQS (SEQ ID NO: 329) | QQVARVPRT (SEQ ID NO: 330) | | |
| 33, | κ | YRYLR (SEQ ID NO: 331) | KASSLQS (SEQ ID NO: 332) | QQYVGYPRT (SEQ ID NO: 333) | | |
| 34, | κ | LKYLK (SEQ ID NO: 334) | NASHLQS (SEQ ID NO: 335) | QQTTYYPIT (SEQ ID NO: 336) | | |
| 53, | κ | LRYLR (SEQ ID NO: 337) | KASWLQS (SEQ ID NO: 338) | QQVLYYPQT (SEQ ID NO: 339) | | |
| 11, | κ | LRSLK (SEQ ID NO: 340) | AASRLQS (SEQ ID NO: 341) | QQVVYWPAT (SEQ ID NO: 342) | ✓ | |
| 12, | κ | FRHLK (SEQ ID NO: 343) | AASRLQS (SEQ ID NO: 344) | QQVALYPKT (SEQ ID NO: 345) | ✓ | |
| 17, | κ | RKYLR (SEQ ID NO: 346) | TASSLQS (SEQ ID NO: 347) | QQNLFWPRT (SEQ ID NO: 348) | ✓ | |

TABLE 8-continued

| dAb (all capture biotinylated MSA) | H or κ | CDR1 | CDR2 | CDR3 | Binds MSA in biacore? | Captures Biotinylated HSA? |
|---|---|---|---|---|---|---|
| 18, | κ | RRYLN (SEQ ID NO: 349) | AASSLQS (SEQ ID NO: 350) | QQMLFYPKT (SEQ ID NO: 351) | ✓ | |
| 16, 21 | κ | IKHLK (SEQ ID NO: 352) | GASRLQS (SEQ ID NO: 353) | QQGARWPQT (SEQ ID NO: 354) | ✓ | |
| 25, 26 | κ | YYHLK (SEQ ID NO: 355) | KASTLQS (SEQ ID NO: 356) | QQVRKVPRT (SEQ ID NO: 357) | ✓ | |
| 27, | κ | YKHLK (SEQ ID NO: 358) | NASHLQS (SEQ ID NO: 359) | QQVGRYPKT (SEQ ID NO: 360) | ✓ | |
| 55, | κ | FKSLK (SEQ ID NO: 361) | NASYLQS (SEQ ID NO: 362) | QQVVYWPVT (SEQ ID NO: 363) | ✓ | |
| VH library 1 (and 2) template (dummy) | H | XXYXXX (SEQ ID NO: 364) | XIXXXGXXTXYADSVKG (SEQ ID NO: 365) | XXXX(XXXX)FDY (SEQ ID NO: 366) | | |
| 8, 10 | H | WVYQMD (SEQ ID NO: 367) | SISAFGAKTLYADSVKG (SEQ ID NO: 368) | LSGKFDY (SEQ ID NO: 369) | | |
| 36, | H | WSYQMT (SEQ ID NO: 370) | SISSFGSSTLYADSVKG (SEQ ID NO: 371) | GRDHNYSLFDY (SEQ ID NO: 372) | | |

In all cases the frameworks were identical to the frameworks in the corresponding dummy sequence, with diversity in the CDRs as indicated in the table above.

Of the eight clones that bound MSA on the biacore, two clones that are highly expressed in *E. coli* (clones MSA16 and MSA26) were chosen for further study (see example 10). Full nucleotide and amino acid sequences for MSA16 and 26 are given in FIG. 16.

Example 10

Determination of Affinity and Serum Half-Life in Mouse of MSA binding dAbs MSA16 and MSA26 dAbs MSA16 and MSA26 were expressed in the periplasm of *E. coli* and purified using batch absorbtion to protein L-agarose affinity resin (Affitech, Norway) followed by elution with glycine at pH 2.2. The purified dAbs were then analysed by inhibition biacore to determine $K_d$. Briefly, purified MSA16 and MSA26 were tested to determine the concentration of dAb required to achieve 200 RUs of response on a biacore CM5 chip coated with a high density of MSA. Once the required concentrations of dAb had been determined, MSA antigen at a range of concentrations around the expected $K_d$ was premixed with the dAb and incubated overnight. Binding to the MSA coated biacore chip of dAb in each of the premixes was then measured at a high flow-rate of 30 μl/minute. The resulting curves were used to create Klotz plots, which gave an estimated $K_d$ of 200 nM for MSA16 and 70 nM for MSA 26 (FIGS. 17 A & B).

Next, clones MSA16 and MSA26 were cloned into an expression vector with the HA tag (nucleic acid sequence: TATCCTTATGATGTTCCTGATTATGCA (SEQ ID NO: 373) and amino acid sequence: YPYDVPDYA (SEQ ID NO:374)) and 2-10 mg quantities were expressed in *E. coli* and purified from the supernatant with protein L-agarose affinity resin (Affitech, Norway) and eluted with glycine at pH2.2. Serum half life of the dAbs was determined in mouse. MSA26 and MSA16 were dosed as single i.v. injections at approx 1.5 mg/kg into CD1 mice. Analysis of serum levels was by goat anti-HA (Abeam, UK) capture and protein L-HRP (invitrogen) detection ELISA which was blocked with 4% Marvel. Washing was with 0.05% tween PBS. Standard curves of known concentrations of dAb were set up in the presence of 1xmouse serum to ensure comparability with the test samples. Modelling with a 2 compartment model showed MSA-26 had a t1/2α of 0.16 hr, a t1/2β of 14.5 hr and an area under the curve (AUC) of 465 hr.mg/ml (data not shown) and MSA-16 had a t1/2α of 0.98 hr, a t1/2β of 36.5 hr and an AUC of 913 hr.mg/ml (FIG. 18). Both anti-MSA clones had considerably lengthened half life compared with HEL4 (an anti-hen egg white lysozyme dAb) which had a t1/2α of 0.06 hr, and a t1/2β of 0.34 hr.

Example 11

Creation of $V_H$-$V_H$ and $V_κ$-$V_κ$ Dual Specific Fab like Fragments

This example describes a method for making $V_H$-$V_H$ and $V_κ$-$V_κ$ dual specifics as Fab like fragments. Before constructing each of the Fab like fragments described, dAbs that bind to targets of choice were first selected from dAb libraries similar to those described in example 9. A V$_H$ dAb, HEL4, that binds to hen egg lysozyme (Sigma) was isolated and a second V$_H$ dAb (TAR2h-5) that binds to TNFα receptor (R and D systems) was also isolated. The sequences of these are given in the sequence listing. A V$_\kappa$ dAb that binds TNFα (TAR1-5-19) was isolated by selection and affinity maturation and the sequence is also set forth in the sequence listing. A second V$_\kappa$ dAb (MSA 26) described in example 9 whose sequence is in FIG. 17B was also used in these experiments.

DNA from expression vectors containing the four dAbs described above was digested with enzymes SalI and NotI to excise the DNA coding for the dAb. A band of the expected size (300-400 bp) was purified by running the digest on an agarose gel and excising the band, followed by gel purification using the Qiagen gel purification kit (Qiagen, UK). The DNA coding for the dAbs was then inserted into either the C$_H$ or Cκ vectors (FIGS. 8 and 9) as indicated in the table below.

TABLE 9

| dAb | Target antigen | dAb V$_H$ or dAb Vκ | Inserted into vector | tag (C terminal) | Antibiotic resistance |
|---|---|---|---|---|---|
| HEL4 | Hen egg lysozyme | V$_H$ | C$_H$ | Myc | Chloramphenicol |
| TAR2-5 | TNF receptor | V$_H$ | Cκ | Flag | Ampicillin |
| TAR1-5-19 | TNF α | Vκ | C$_H$ | Myc | Chloramphenicol |
| MSA 26 | Mouse serum albumin | Vκ | Cκ | Flag | Ampicillin |

The V$_H$C$_H$ and V$_H$Cκ constructs were cotransformed into HB2151 cells. Separately, the V$_\kappa$ C$_H$ and V$_\kappa$ Cκ constructs were cotransformed into HB2151 cells. Cultures of each of the cotransformed cell lines were grown overnight (in 2×Ty containing 5% glucose, 10 μg/ml chloramphenicol and 100 μg/ml ampicillin to maintain antibiotic selection for both C$_H$ and Cκ plasmids). The overnight cultures were used to inoculate fresh media (2×Ty, 10 μg/ml chloramphenicol and 100 μg/ml ampicillin) and grown to OD 0.7-0.9 before induction by the addition of IPTG to express their C$_H$ and Cκ constructs. Expressed Fab like fragment was then purified from the periplasm by protein A purification (for the contransformed V$_H$ C$_H$ and V$_H$ CK) and MSA affinity resin purification (for the contransformed V$_\kappa$ C$_H$ and V$_\kappa$ Cκ).

V$_H$-V$_H$ Dual Specific

Expression of the V$_H$ C$_H$ and V$_H$ Cκ dual specific was tested by running the protein on a gel. The gel was blotted and a band the expected size for the Fab fragment could be detected on the Western blot via both the myc tag and the flag tag, indicating that both the V$_H$C$_H$ and V$_H$Cκ parts of the Fab like fragment were present. Next, in order to determine whether the two halves of the dual specific were present in the same Fab-like fragment, an ELISA plate was coated overnight at 4° C. with 100 μl per well of hen egg lysozyme (HEL) at 3 mg/ml in sodium bicarbonate buffer. The plate was then blocked (as described in example 1) with 2% tween PBS followed by incubation with the V$_H$ C$_H$/V$_H$ Cκ dual specific Fab like fragment. Detection of binding of the dual specific to the HEL was via the non cognate chain using 9e10 (a monoclonal antibody that binds the myc tag, Roche) and anti mouse IgG-HRP (Amersham Pharmacia Biotech). The signal for the V$_H$ C$_H$ N$_H$ Cκ dual specific Fab like fragment was 0.154 compared to a background signal of 0.069 for the V$_H$Cκ chain expressed alone. This demonstrates that the Fab like fragment has binding specificity for target antigen.

V$_\kappa$-V$_\kappa$ Dual Specific

After purifying the contransformed V$_\kappa$ C$_H$ and V$_\kappa$ Cκ dual specific Fab like fragment on an MSA affinity resin, the resulting protein was used to probe an ELISA plate coated with 1 μg/ml TNFα and an ELISA plate coated with 10 μg/ml MSA. As predicted, there was signal above background when detected with protein L-HRP on both ELISA plates (data not shown). This indicated that the fraction of protein able to bind to MSA (and therefore purified on the MSA affinity column) was also able to bind TNFα in a subsequent ELISA, confirming the dual specificity of the antibody fragment. This fraction of protein was then used for two subsequent experiments. Firstly, an ELISA plate coated with 1 μg/ml TNFα was probed with dual specific V$_\kappa$ C$_H$ and V$_\kappa$ Cκ Fab like fragment and also with a control TNFα binding dAb at a concentration calculated to give a similar signal on the ELISA. Both the dual specific and control dAb were used to probe the ELISA plate in the presence and in the absence of 2 mg/ml MSA. The signal in the dual specific well was reduced by more than 50% but the signal in the dAb well was not reduced at all (see FIG. 19a). The same protein was also put into the receptor assay with and without MSA and competition by MSA was also shown (see FIG. 19c). This demonstrates that binding of MSA to the dual specific is competitive with binding to TNFα.

Example 12

Creation of a V$_\kappa$-V$_\kappa$ Dual Specific Cys Bonded Dual Specific with Specificity for Mouse Serum Albumin and TNFα

This example describes a method for making a dual specific antibody fragment specific for both mouse serum albumin and TNFα by chemical coupling via a disulphide bond. Both MSA16 (from example 1) and TAR1-5-19 dAbs were recloned into a pET based vector with a C terminal cysteine and no tags. The two dAbs were expressed at 4-10 mg levels and purified from the supernatant using protein L-agarose affinity resin (Affitiech, Norway). The cysteine tagged dAbs were then reduced with dithiothreitol. The TAR1-5-19 dAb was then coupled with dithiodipyridine to block reformation of disulphide bonds resulting in the formation of PEP 1-5-19 homodimers. The two different dAbs were then mixed at pH 6.5 to promote disulphide bond formation and the generation of TAR1-5-19, MSA16 cys bonded heterodimers. This method for producing conjugates of two unlike proteins was originally described by King et al. (King T P, Li Y Kochoumian L Biochemistry. 1978 vol 17:1499-506 Preparation of protein conjugates via intermolecular disulfide bond formation.) Heterodimers were separated from monomeric species by cation exchange. Separation was confirmed by the presence of a band of the expected size on a SDS gel. The resulting heterodimeric species was tested in the TNF receptor assay and found to have an IC50 for neutralising TNF of approximately 18 nM. Next, the receptor assay was repeated with a constant concentration of heterodimer (18 nM) and a dilution series of MSA and HSA. The presence of HSA at a range of concentrations (up to 2 mg/ml) did not cause a reduction in the ability of the dimer to inhibit TNFα. However, the addition of MSA caused a dose dependant reduction in the ability of the dimer to inhibit TNFα (FIG. 20). This demonstrates that MSA and TNFα compete for binding to the cys bonded TART-5-19, MSA16 dimer.

Data Summary

A summary of data obtained in the experiments set forth in the foregoing examples is set forth in Annex 4.

Example 13

Activity of Anti-Mouse TNFR1 dAbs and Anti-Human TNFR1 dAbs

TABLE 10

Activity of Anti-mouse TNFR1 dAbs

| dAb | Activity (IC50) | |
|---|---|---|
| | L929 Cell Assay | Receptor Binding Assay |
| TAR2m-19 | 10 μM | 2 μM |
| TAR2m-20 | n/d | 150 nM |
| TAR2m-21 | 400 nM | n/d |
| TAR2m-24 | 1 μM | 1.3 μM |
| TAR2m-21-23 | 1 nM | n/d |
| TAR2m-21-07 | 10 nM | n/d |
| TAR2m-21-43 | 6 nM | n/d |
| TAR2m-21-48 | 6 nM | n/d |
| TAR2m-21-10 | 30 nM | n/d |
| TAR2m-21-06 | 100 nM | n/d |
| TAR2m-21-17 | 300 nM | n/d | n/d, not determined

TABLE 11

Activity of Anti-human TNFR1 dAbs

| dAb | Activity (IC50) | |
|---|---|---|
| | HeLa IL-8 Cell Assay | Receptor Binding Assay |
| TAR2h-10 | 50 nM | 30 nM |
| TAR2h-12 | 100 nM | n/d |
| TAR2h-13 | 300 nM | n/d |
| TAR2h-14 | 300 nM | 30 nM |
| TAR2h-15 | n/d | 5 nM |
| TAR2h-16 | 200 nM | 30 nM |
| TAR2h-17 | n/d | 100 nM |
| TAR2h-18 | 400 nM | n/d |
| TAR2h-22 | n/d | 200 nM |
| TAR2h-27 | 3000 nM | 30 nM |
| TAR2h-29 | 300 nM | 300 nM |
| TAR2h-32 | 100 nM | n/d |
| TAR2h-34 | n/d | 300 nM |
| TAR2h-35 | 800 nM | n/d |
| TAR2h-41 | 30 nM | 8 nM |
| TAR2h-42 | 10 nM | 15 nM |
| TAR2h-44 | 300 nM | 10 nM |
| TAR2h-47 | n/d | 8 nM |
| TAR2h-51 | n/d | 80 nM |
| TAR2h-67 | 300 nM | n/d |
| TAR2h-10-1 | n/d | 10 nM |
| TAR2h-10-2 | n/d | 11 nM |
| TAR2h-10-3 | n/d | 11 nM |
| TAR2h-10-4 | n/d | 8 nM |
| TAR2h-10-5 | n/d | 11 nM |
| TAR2h-10-7 | 30 nM | n/d |
| TAR2h-10-27 | 10 nM | 2 nM |
| TAR2h-10-55 | 20 nM | n/d | n/d, not determined

MRC-5 IL-8 Release Assay

The activities of certain dAbs that bind human TNFR1 were assessed in the following MRC-5 cell assay. The assay is based on the induction of IL-8 secretion by TNF in MRC-5 cells and is adapted from the method described in Alceson, L. et al. *Journal of Biological Chemistry* 27 1:30517-30523 (1996), describing the induction of IL-8 by IL-1 in HUVEC.

The activity of the dAbs was assayed by assessing IL-8 induction by human TNFα using MRC-5 cells instead of the HUVEC cell line. Briefly, MRC-5 cells were plated in microtitre plates and the plates were incubated overnight with dAb and human TNFα (300 pg/ml). Following incubation, the culture supernatant was aspirated and the IL-8 concentration in the supernatant was measured via a sandwich ELISA (R&D Systems). Anti-TNFR1 dAb activity resulted in a decrease in IL-8 secretion into the supernatant compared with control wells that were incubated with TNFα only.

Example 14

Mouse Septic Shock Model

The in vivo efficacy of an anti-TNFR1 dAb was assessed in a well-established experimental model for septic shock syndrome (Rothe et al., *Circulatory Shock* 44:51-56, (1995)). LPS-induced death in this model is dependent upon TNFR-1 (p55) activation. In this model mice were sensitized to the toxicity of LPS using D-galactosamine (D-GalN). The lethal LPS dose for wild-type animals in this study was about 10 ng.

LPS (*Salmonella enteritidis*, Sigma, USA) and D-Galactosamine (D-GalN, Sigma, USA) were injected intraperitoneally. D-Ga1N-sensitized (10 mg/mouse) control mice died within 18 hour following challenge with LPS (10 ng). Mortality of non-sensitized mice was recorded over a period of 1 day after challenge.

Mice were administered a dual specific ligand that binds mouse TNFR1 and mouse serum albumin (TAR2m-21-23 3U TAR7m-16; TAR7m-16 is also referred to herein as MSA16) or ENBREL® (entarecept; Immunex Corporation) by intraperitoneal injections 4 hours prior to the administration of LPS. (See, Table 12). Survival was monitored at 4-6 hour intervals over a period of 48 hours. Efficacy of anti-mouse TNFR1 dAbs was demonstrated by survival.

TABLE 12

| Treatment Group | Agent and Dose | LPS dose per mouse (ng) | Number of animals | Number of Survivors at 24 hours |
|---|---|---|---|---|
| 1 | Saline | 10 | 8 | 0/8 |
| 2 | 10 mg/kg ENBREL ® (entarecept; Immunex Corporation) | 10 | 8 | 8/8 |
| 3 | 5.4 mg/kg TAR2m-21-23 3U TAR7m-16 | 10 | 8 | 4/8 |
| 4 | 1 mg/kg TAR2m-21-23 3U TAR7m-16 | 10 | 8 | 2/8 |
| 5 | 5.4 mg/kg TAR2m-21-23 3U TAR7m-16 | 0 | 2 | 2/2 |

TAR2m-21-23 3U TAR7m-16 is a dual specific ligand that contains a dAb that binds mouse TNFR1 that is joined through a peptide linker to a dAb that binds mouse serum albumin. A nucleotide sequence encoding TAR2m-21-23 3U TAR7m-16 and the amino acid sequence of the dual specific ligand are presented below as SEQ ID NO: 375 and SEQ ID NO:376, respectively.

(SEQ ID NO: 375)
GAGGTGCAGCTGTTGGAGTCTGGGGGAGGCTTGGTACAGCCTGGGGGGTC

CCTGCGTCTCTCCTGTGCAGCCTCCGGATTCACCTTTAATAGGTATAGTA

-continued

```
TGGGGTGGCTCCGCCAGGCTCCAGGGAAGGGTCTAGAGTGGGTCTCACGG

ATTGATTCTTATGGTCGTGGTACATACTACGAAGACCCCGTGAAGGGCCG

GTTCAGCATCTCCCGCGACAATTCCAAGAACACGCTGTATCTGCAAATGA

ACAGCCTGCGTGCCGAGGACACCGCCGTATATTACTGTGCGAAAATTTCT

CAGTTTGGGTCAAATGCGTTTGACTACTGGGGTCAGGGAACCCAGGTCAC

CGTCTCGAGCGGTGGAGGCGGTTCAGGCGGAGGTGGCAGCGGCGGTGGCG

GGTCGACGGACATCCAGATGACCCAGTCTCCATCCTCCCTGTCTGCATCT

GTAGGAGACCGTGTCACCATCACTTGCCGGGCAAGTCAGAGCATTATTAA

GCATTTAAAGTGGTACCAGCAGAAACCAGGGAAAGCCCCTAAGCTCCTGA

TCTATGGTGCATCCCGGTTGCAAAGTGGGGTCCCATCACGTTTCAGTGGC

AGTGGATCTGGGACAGATTTCACTCTCACCATCAGCAGTCTGCAACCTGA

AGATTTTGCTACGTACTACTGTCAACAGGGGGCTCGGTGGCCTCAGACGT

TCGGCCAAGGGACCAAGGTGGAAATCAAACGGGCGGCCGCAGAACAAAA

CTCATCTCAGAAGAGGATCTGAAT
```

(SEQ ID NO: 376)

```
EVQLLESGGGLVQPGGSLRLSCAASGFTFNRYSMGWLRQAPGKGLEWVSR

IDSYGRGTYYEDPVKGRFSISRDNSKNTLYLQMNSLRAEDTAVYYCAKIS

QFGSNAFDYWGQGTQVTVSSGGGGSGGGGSGGGGSTDIQMTQSPSSLSAS

VGDRVTITCRASQSIIKHLKWYQQKPGKAPKLLIYGASRLQSGVPSRFSG

SGSGTDFTLTISSLQPEDFATYYCQQGARWPQTFGQGTKVEIKRAAAEQK

LISEEDLN
```

The presence of survivors in the TAR2m-21-23 3U TAR7m-16 treatment groups demonstrates that the anti-TNFR1 dAb was efficacious in inhibiting the activity of the receptor in vivo, and the results demonstrate that the effect was dose dependent. Moreover, the efficacy of the TAR2m-21-23 3U TAR7m-16 treatment compared favorably with the efficacy of ENBREL® (entarecept; Immunex Corporation). The survival of the animals which were treated with TAR2m-21-23 3U TAR7m-16 alone (Group 5, no LPS challenge) also demonstrates that TAR2m-21-23 3U TAR7m-16 was not toxic and did not agonise the receptor in vivo by receptor cross-linking.

Further studies confirmed that anti-TNFR1 dAbs do not agonise TNFR1 (act as TNFR1 agonists) in the absence of TNFα. L929 cells were cultured in media that contained a range of concentrations of either TAR2m-21-23 monomer, TAR2m-21-23 monomer cross-linked to a commercially available anti-myc antibody (9E10), TAR2m-21-23 3U TAR7m-16 or TAR2m-21-23 40K PEG. In the case of TAR2m-21-23 monomer cross-linked with the anti-myc antibody, the dAb and antibody were mixed in a 2:1 ratio and pre-incubated for one hour at room-temperature to simulate the effects of in vivo immune cross-linking prior to culture. TAR2m-21-23 monomer was incubated with the L929 cells at a concentration of 3000 nM. TAR2m-21-23 monomer and anti-Myc antibody were incubated at a dAb concentration of 3000 nM. TAR2m-21-23 3U TAR7m-16 was incubated with the cells at 25 nM, 83.3 nM, 250 nM, 833 nM and 2500 nM concentrations. TAR 2m-21-23 40K PEG was incubated with the cells at 158.25 nM, 527.5 nM, 1582.5 nM, 5275 nM and 15825 nM concentrations. After incubation overnight, cell viability was assessed as described for the L929 cell cytotoxicity assay. The results revealed that incubation with various amounts of dAbs did not result in an increase in the number of non-viable cells in the cultures. The incubation of L929 cells with 10 nM, 1 nM and 0.1 nM of a commercially-available anti-TNFR1 IgG antibody resulted in a dose-dependent increase in non-viable cells thereby demonstrating the sensitivity of these cells to TNFR1-mediated agonism. (FIG. 26).

Example 15

Models of Chronic Inflammatory Diseases

A. Mouse Collagen-Induced Arthritis Model

DBA/1 mice were injected once with an emulsion of Arthrogen-CIA adjuvant and Arthrogen-CIA collagen (MDbiosciences). At day 21, animals with high arthritic scores were removed from the study and the remainder of the animals were divided into groups of 10 with equal numbers of male and female animals. At day 21 treatments commenced with intraperitoneal injections of either saline, ENBREL® (entarecept; Immunex Corporation) or TAR2m-21-23 40 k PEG and continued for 28 days. Clinical arthritic scores on a scale of 0 to 4 were measured for each of the 4 limbs of the animals, a score of 0 was assigned for a normal limb and a score of 4 was assigned for a maximally inflamed limb with involvement of multiple joints.

A reduction of the summation of the arthritic scores of the four limbs from the maximum of 16 to (a) 14-15, (b) 12-15, (c) 10-15, (d) 9-15, (e) 7-15, (f) 5-15, (g), 3-15, or (h) 1-15 is a beneficial effect in this model. A beneficial effect can result is a summation of the arthritic scores of the four limbs of 0, 1, 2, 3, 4, 5, 6, 7, 8, 9, 10, 11, 12, 13, 14 or 15. A delay in the onset of arthritis, compared with the untreated control group, is also a beneficial effect in this model.

The clinical scores clearly demonstrated that treatment with TAR2m-21-23 40 k PEG had a very favourable impact of inhibition of the development of arthritis when compared with the saline control, and moreover the TAR2m-21-23 40 k PEG treatment compared favourably with ENBREL® (entarecept; Immunex Corporation). This is the first demonstration of inhibition of TNFR1 being efficacious in the treatment of a chronic inflammatory disease model.

B. Mouse RARE Model of IBD and Arthritis

Mice that bear a targeted deletion in the 3' AU-rich elements (AREs) of the TNF mRNA (referred to as $Tnf^{\Delta ARE}$ mice) overproduce TNF and develop an inflammatory bowel disease that is histopathologically similar to Crohn's disease. (Kontoyiannis et al., *J Exp Med* 196:1563-74 (2002).) In these mice, the Crohn's-like disease develops between 4 and 8 weeks of age, and the animals also develop clinical signs of rheumatoid arthritis.

dAbs that bind mouse TNFR-1 were assessed for efficacy in inhibiting Crohn's-like pathology and arthritis in $Tnf^{\Delta ARE}$ mice. ENBREL® (entarecept; Immunex Corporation) was used as a positive control. The agents were administered by intraperitoneal injections according to the administration and dosing regiment presented in Table 13.

The dAbs that were Studied Include:

1) TAR2m-21-23 PEGylated with one 40 kD PEG moiety;

2) dual specific TAR2m-21-23 3U TAR7m-16 which binds mouse TNFR-1 and mouse serum albumin.

TABLE 13

| Group | Treatment | Dose | Number of Doses | Number of Animals |
|---|---|---|---|---|
| 6 | ENBREL ® (entarecept; Immunex Corporation) (administered 3 times/week) | 10 mg/kg | 8 | 10 |
| 5 | TAR2m21-23 40 kD PEG (administered twice/week) | 1 mg/kg | 8 | 10 |
| 4 | TAR2m21-23 40 kD PEG (administered twice/week) | 10 mg/kg | 8 | 10 |
| 3 | TAR2m-21-23 3U TAR7m-16 (administered twice/week) | 1 mg/kg | 8 | 10 |
| 2 | TAR2m-21-23 3U TAR7m-16 (administered twice/week) | 10 mg/kg | 8 | 10 |
| 1 | Saline | NA | 8 | 10 |

At the conclusion of the dosing period, the mice were sacrificed and the terminal ileums and proximal colons were removed for analysis.

For histological analysis, the tissue samples will be sectioned and stained with hematoxylin and eosin, and acute and chronic inflammation will be scored using a semi-quantitative scoring system. The scores will be assigned as follows: acute inflammation score 0=0-1 polymorphonuclear (PMN) cell per high powered field (PMN/hpf); 1=2-10 PMN/hpf within mucosa; 2=11-20 PMN/hpf within mucosa; 3=21-30 PMN/hpf within mucosa or 11-20 PMN/hpf with extension below muscularis mucosae; 4=>30 PMN/hpf within mucosa or >20 PMN/hpf with extension below muscularis mucosae; chronic inflammation score 0=0-10 mononuclear leukocytes (ML) per hpf (ML/hpf) within mucosa; 1=11-20 mL/hpf within mucosa; 2=21-30 mL/hpf within mucosa or 11-20 mL/hpf with extension below muscularis mucosae; 3=31-40 mL/hpf within mucosa or follicular hyperplasia; and 4=>40 mL/hpf within mucosa or >30 mL/hpf with extension below muscularis mucosae or follicular hyperplasia.

The macrophenotypic signs of arthritis were scored weekly according to the following system: 0=no arthritis (normal appearance and flexion); 1=mild arthritis (joint distortion); 2=moderate arthritis (swelling, joint deformation); 3=heavy arthritis (severely impaired movement).

The TAR2m-21-23 dAb demonstrated good in vivo efficacy in the deltaARE mouse model of arthritis as both a 40 kD PEGylated monomer (TAR2m21-23 40 kD PEG) and as a dual specific anti-TNFR1/anti-SA format (TAR2m-21-23 3U TAR7m-16). At week 9 the mean arthritic scores of both the TAR2m-21-23 and the TAR2m-21-23 3U TAR7m-16 treated groups were less than 0.4. In contrast the saline control group had moderate to severe arthritis with an average arthritic score that was >1.0. The group treated with ENBREL® (entarecept; Immunex Corporation), which was administered 3 times per week as compared with TAR2m-21-23 and the TAR2m-21-23 3U TAR7m-16 which were administered twice per week, had an average score of 0.5-1.0. These results indicate that therapy with dAb formats that bind TNFR1 is a highly efficacious anti-arthritis therapy, and that both the PEGylated and dual specificity dAb formats studied are highly effective drugs for chronic inflammatory disease. Moreover these results further demonstrate that dAbs that bind TNFR1 engage the receptor only in an antagonistic manner.

C. Mouse DSS Model of IBD.

IBD will be induced in mice by administering dextran sulfate sodium (DSS) in the drinking water. (See, e.g., Okayasu I. et al., Gastroenterology 98:694-702 (1990); Podolsky K., *J. Gasteroenterol.* 38 *suppl XV*:63-66 (2003).) Adult BDF1 mice that are *H. pylori* free will be housed for 2 weeks to stabilize their circadian rhythms. All mice will be held in individually ventilated cages in a specific pathogen free (SPF) barrier unit on a 12 hour light:dark cycle. Animals will be allowed food and water ad libitum throughout.

The study will run for 7 days. The drinking water will contain 5% DSS for the duration of the study. All animals will be treated on days 1-7 in the morning (0900-1000) and evening (1600-1700). (See Table 14.) Day 1 is equivalent to a singe prophylactic dose. All animals to be weighed daily and any diarrhoea incidence will be noted. All animals will be sacrifices 24 hours following the last treatment, and will be administered a pulse of bromodeoxyuridine 40 minutes prior to sacrifice. The distal large intestines will be removed from the animals. A small sample of the distal large intestine will be placed into "RNAlater", and the remainder will be fixed in Carnoy's fixative, embedded in paraffin, sectioned (non-serial sections per slide) and stained with hematoxylin and eosin. Sections will be visually assessed for IBD severity and assigned a severity score. Histometric analyses will be performed and mean lesion area (ulcer area), mean epithelial area, and mean intramural inflammatory area will be determined.

H&E cross sections of the large intestine will be used to record a series of tissue dimensions using a Zeiss Axiohome microscope, which enables accurate quantification of areas. For each cross section, the area of epithelium plus lamina propria and the area of connective tissue will be measured. The epithelial area will then be measured separately, the difference being the area of lamina propria. In normal tissue the relative contribution of this tissue to the area is about 10%, but this increases as inflammation increases. The relative proportion of epithelium:lamina propria therefore changes.

With increasing severity the depth of this area narrows (contributing to the ulceration) and length of the colon shortens. Together these phenomena cause the cross-sectional area of the lumen to increase. This parameter can therefore also be a useful measurement of disease severity.

The tissue samples will be observed microscopically and assigned a severity score where 0=no inflammation; 1=mild inflammation around crypt base; 2=massive inflammatory infiltration, and disrupted mucosal architecture; 3=massive inflammatory infiltration, and disrupted mucosal architecture plus ulceration.

Efficacy is indicated in this model when the treatment produces a reduction of in severity score, relative to the severity score of the saline control group. For example the severity score of the treatment group can be reduced by 0.1 to about 1, 1 to about 2, or 2 to about 3. Efficacy would be indicated by a score of about 2 or less, 1 to about 2, or 1 or less.

9 groups of 6 animals will be treated as follows:

TABLE 14

| Group | |
|---|---|
| 1 | DSS in drinking water |
| 2 | DSS in drinking water + ip PEG TAR2m-21-23, 10 mg/kg 1x/d |
| 3 | DSS in drinking water + ip PEG TAR2m-21-23, 1 mg/kg 1x/d |
| 4 | DSS in drinking water + ip saline |
| 5 | DSS in drinking water + oral gavage PEG TAR2m-21-23, 0.25 mg/animal 2x/d |
| 6 | DSS in drinking water + oral gavage saline |

TABLE 14-continued

| Group | |
|---|---|
| 7 | DSS in drinking water + ip dosing +ve control e.g. steroid |
| 8 | DSS in drinking water + oral gavage +ve control e.g. 5' aminosalicylic acid or similar |
| 9 | Untreated animals |

Oral gavages will be given with ZANTAC ® (ranitidine hydrochloride; GlaxoSmithKline).

D. Mouse Model of Chronic Obstructive Pulmonary Disease (COPD)

Efficacy of anti-TNFR1 dAbs in progression of disease in a mouse sub-chronic tobacco smoke (TS) model will be assessed. (See, e.g., Wright J L and Churg A., *Chest* 122:306 S-309S (2002).) Anti-mouse TNFR1 dAbs will be administered by intraperitoneal injections every 48 hours (starting 24 hours before the first exposure to TS) and will be given as extended serum half life format (e.g., PEGylated, dual specific ligand comprising anti-SA dAb).

Alternatively the anti-TNFR1 dAb will be administered by intranasal delivery every 24 hours (starting 4 hours before the first exposure to TS) and will be given as a monomer dAb. ENBREL® (entarecept; Immunex Corporation) will be used as a positive control. TS exposure will be daily and the study will last for 1-2 weeks. (See, e.g., Vitalis et al., *Eur. Respir. J.,* 11:664-669 (1998).) Following the last TS exposure bronchoaveolar lavage will be analysed for total and differential cell counts to include neutrophils, eosinophils, macrophages and T-lymphocyte subsets. The lung lobes will be fixed in 10% buffered formalin and tissue sections analysed for enlargement of the alveoli and alveolar ducts, thickening of the small airway walls and for cell counts to include neutrophils, eosinophils, macrophages and T-lymphocyte subsets. Efficacy will be evident by a reduction in the number of neutrophils, eosinophils, macrophages and T-lymphocyte subsets that were elevated by TS exposure and a reduction in the TS-induced enlargement of the alveoli and alveolar ducts and thickening of the small airway walls.

Example 16

Construction and Expression of a Recombinant Chimeric TNFR1 Molecule

This example explains a method for the generation of a molecule made up of different murine TNFR1 domains and human TNFR1 domains (Banner D W, et al. *Cell,* 73(3):431-45 (1993).) such that the molecule contains the four defined extracellular domains of TNFR1 but that these vary in derivation between mouse and human TNFR1 proteins. The produced chimeric receptors share properties of both human TNFR1 and mouse TNFR1 according to the differing domain roles and functionality. The molecules provided a means for the assessment of the domain specificity of dAbs, antibodies and antigen-binding fragments thereof and other molecules (eg organic chemical compounds, NCE's; or protein domains such as affibodies, LDL receptor domains or EGF domains) that bind human or mouse TNFR1.

Methods

Human and mouse TNFR1 sequences were previously cloned into the *Pichia* expression vector pPicZalpha (Invitrogen) via EcoR1 and NotI restriction endonuclease sites. The template mouse TNFR1 DNA (and consequently chimeric receptor constructs ending with a murine domain 4) contained a 3' 6× Histidine tag. Human TNFR1 (and consequently chimeric receptor constructs ending with a human domain 4) contained both Myc and 6× Histidine tags in sequence at the 3' end.

Initial PCRs were performed according to standard PCR conditions using RubyTaq DNA polymerase (USB Corporation, Cleveland, Ohio), 100 ng of template DNA (comprising the relevant DNA miniprep template of either full length mTNFR1 or hTNFR1 DNA).

Typical PCR reacts were set up was as follows: 25 µl of 10× RubyTaq PCR buffer containing polymerase; 2 µl of first primer (from 10 µM stock); 2 µl of second primer (from 10 µM stock); 1 µl (100 ng) full length TNFR1 template DNA; 20 µl of dH$_2$O (to a final volume of 50 µl). The reactions were set up in thin walled tubes and placed into a thermocycler where the reaction was performed according to the following parameters.

| Initial Denaturation | 3 minutes | 94° C. |
|---|---|---|
| Denaturation | 30 seconds | 94° C. |
| Annealing (25 cycles) | 30 seconds | 55° C. |
| Extension | 1 minute | 72° C. |
| Final Extension | 10 minutes | 72° C. |

Summary of Initial PCR Reactions Used in Generation of Chimeric Constructs

| Construct* | PCR number—primers used | Template |
|---|---|---|
| MHHH | PCR 1—1 and 12 | Mouse |
| | PCR 2—2 and 3 | Human |
| HMHH | PCR 1—1 and 9 | Human |
| | PCR 2—6 and 13 | Mouse |
| | PCR 3—2 and 4 | Human |
| HHMH | PCR 1—1 and 10 | Human |
| | PCR 2—7 and 14 | Mouse |
| | PCR 3—2 and 5 | Human |
| HHHM | PCR 1—1 and 11 | Human |
| | PCR 2—2 and 8 | Mouse |
| HMMM | PCR 1—1 and 9 | Human |
| | PCR 2—2 and 6 | Mouse |

*Notation: H = human domain; M = mouse domain; eg, MHHH = mouse Domain 1, human domains 2-4.

PCR products generated these initial PCRs were cut out from a 1% agarose gel and purified using a gel purification kit (Qiagen) before elution into 50 µl dH$_2$O.

Primers Used for Chimeric TNFR1 Construct Generation

| Primer Number | Primer sequence |
|---|---|
| Primer 1 | GCCAGCATTGCTGCTAAAGAA (SEQ ID NO: 605) |
| Primer 2 | GGTCGACGGCGCTATTCAG (SEQ ID NO: 606) |
| Primer 3 | CTGCAGGGAGTGTGAGAGCGGC (SEQ ID NO: 607) |
| Primer 4 | GTGTGTGGCTGCAGGAAGAAC (SEQ ID NO: 608) |
| Primer 5 | CTGCCATGCAGGTTTCTTTC (SEQ ID NO: 609) |
| Primer 6 | CTGCAGGGAGTGTGAAAAGGG (SEQ ID NO: 610) |
| Primer 7 | GTGTGTGGCTGTAAGGAGAACC (SEQ ID NO: 611) |
| Primer 8 | CTGCCATGCAGGGTTCTTTC (SEQ ID NO: 612) |
| Primer 9 | TCACACTCCCTGCAGTCCG (SEQ ID NO: 613) |
| Primer 10 | CAGCCACACACGGTGTCCCGG (SEQ ID NO: 614) |

-continued

| Primer Number | Primer sequence |
|---|---|
| Primer 11 | CCTGCATGGCAGGTGCACACGG (SEQ ID NO: 615) |
| Primer 12 | TCACACTCCCTGCAGACTG (SEQ ID NO: 616) |
| Primer 13 | CAGCCACACACCGTGTCCTTG (SEQ ID NO: 617) |
| Primer 14 | CCTGCATGGCAGTTACACACGG (SEQ ID NO: 618) |

SOE PCR

Assembly PCR (also known as 'pull-through' or Splicing by Overlap Extension (SOE) see *Gene*, 15:77(1):61-8 (1989)) allows the primary PCR products to be brought together without digest or ligation, making use of the complementary ends of the Primary PCR products. During this process the primary products are brought together and denatured before their complementary ends are allowed to anneal together in the presence of Taq DNA polymerase and dNTPs. Several cycles of reannealing and extension result in fill-in of the complementary strands and the production of a full-length template. Primers that flank the now full-length construct cassette are added and a conventional PCR was run to amplify the assembled product. SOE PCRs were performed in order to anneal together and amplify the various TNFR1 domains derived from the initial PCRs described above. Assembly SOE PCRs were set up as follows: 40 µl 10×PCR buffer containing $MgCl_2$; ~2 µl (100 ng) cleaned product of initial PCR 1; ~2 µl (100 ng) cleaned product of initial PCR 2; 36 µl $dH_2O$ (to final volume of 80 µl). SOE primer mix was added after the assembly step as follows: 2 µl 5' flanking primer (Primer 1); 2 µl 3' flanking primer (Primer 2); 10 µl 10×PCR Buffer; 6 µl dH2O (to final volume 20 µl).

The PCR reactions were performed using the program described below. The initial assembly cycles required approximately 45 minutes after which the thermocycler was set to pause at 94° C. 20 µl of primer mix was added to each reaction and mixed.

Step 1 Assembly

| Initial Denaturation | 5 minutes | 94° C. |
|---|---|---|
| Denaturation | 1 minute | 94° C. |
| Annealing (15 cycles) | 1 minute | 55° C. |
| Extension | 1 minute | 72° C. |

Step 2 Amplification (Pause at 94° C., Primers Mix then Added)

| Denaturation | 1 minute | 94° C. |
|---|---|---|
| Annealing (25 cycles) | 1 minute | 55° C. |
| Extension | 1 minute | 72° C. |

PCR products were checked by running 3-5 µl of each reaction on a 1% agarose gel.

3) Cloning of assembled TNFR1 chimeras into the *Pichia* expression vector pPicZalpha vector (Invitrogen) was sequentially digested with EcoRI and NotI enzymes prior to Chromaspin TE-1000 gel filtration column (Clontech, Mountain View, Calif.) purification.

4) Transformation of TNFR1 Chimeric Constructs into *E. coli*

The ligated chimeric constructs were transformed into HB2151 electrocompetent *E. coli* cells and recovered for an hour in low salt LB media prior to plating on low salt LB agar with 0.25 µg/ml ZEOCIN, antibiotic formulation containing Phleomycin D (Cayla, Toulouse, France), for 24 hrs at 37° C. Individual colonies were then sequence verified to ensure the correct sequence of the chimeric construct within the expression vector and large scale Maxiprep plasmid preparations made of each chimeric construct vector.

The nucleotide sequences of prepared chimeric constructs are presented below. The chimeric constructs were named according to origin of their domains (running from Domain 1 on the left to Domain 4 on the right). For example, HMMM contains human Domain 1 and mouse Domains 2-4. Chimeric proteins that contain mouse domain 4 have only His tags and lack the spacer region between the transmembrane region and Domain 4.

HMMM (SEQ ID NO: 619)
AGTGTGTGTCCCCAAGGAAAATATATCCACCCTCAAAATAATTCGATTTGCTGTACCAAGT

GCCACAAAGGAACCTACTTGTACAATGACTGTCCAGGCCCGGGGCAGGATACGGACTGCAG

GGAGTGTGAAAAGGGCACCTTTACGGCTTCCCAGAATTACCTCAGGCAGTGCCTCAGTTGC

AAGACATGTCGGAAAGAAATGTCCCAGGTGGAGATCTCTCCTTGCCAAGCTGACAAGGACA

CGGTGTGTGGCTGTAAGGAGAACCAGTTCCAACGCTACCTGAGTGAGACACACTTCCAGTG

CGTGGACTGCAGCCCCTGCTTCAACGGCACCGTGACAATCCCCTGTAAGGAGACTCAGAAC

ACCGTGTGTAACTGCCATGCAGGGTTCTTTCTGAGAGAAAGTGAGTGCGTCCCTTGCAGCC

ACTGCAAGAAAAATGAGGAGTGTATGAAGTTGTGCCTAAGCGCTCATCATCATCATCATCA

TTAATGA

HHHM (SEQ ID NO: 620)
AGTGTGTGTCCCCAAGGAAAATATATCCACCCTCAAAATAATTCGATTTGCTGTACCAAGT

GCCACAAAGGAACCTACTTGTACAATGACTGTCCAGGCCCGGGGCAGGATACGGACTGCAG

GGAGTGTGAGAGCGGCTCCTTCACCGCTTCAGAAAACCACCTCAGACACTGCCTCAGCTGC

TCCAAATGCCGAAAGGAAATGGGTCAGGTGGAGATCTCTTCTTGCACAGTGGACCGGGACA

-continued

```
CCGTGTGTGGCTGCAGGAAGAACCAGTACCGGCATTATTGGAGTGAAAACCTTTTCCAGTG

CTTCAATTGCAGCCTCTGCCTCAATGGGACCGTGCACCTCTCCTGCCAGGAGAAACAGAAC

ACCGTGTGCACCTGCCATGCAGGGTTCTTTCTGAGAGAAAGTGAGTGCGTCCCTTGCAGCC

ACTGCAAGAAAAATGAGGAGTGTATGAAGTTGTGCCTAAGCGCTCATCATCATCATCATCA

TTAATGA
```

HHMH (SEQ ID NO: 621)
```
AGTGTGTGTCCCCAAGGAAATATATCCACCCTCAAAATAATTCGATTTGCTGTACCAAGT

GCCACAAAGGAACCTACTTGTACAATGACTGTCCAGGCCCGGGGCAGGATACGGACTGCAG

GGAGTGTGAGAGCGGCTCCTTCACCGCTTCAGAAAACCACCTCAGACACTGCCTCAGCTGC

TCCAAATGCCGAAAGGAAATGGGTCAGGTGGAGATCTCTTCTTGCACAGTGGACCGGGACA

CCGTGTGTGGCTGTAAGGAGAACCAGTTCCAACGCTACCTGAGTGAGACACACTTCCAGTG

CGTGGACTGCAGCCCCTGCTTCAACGGCACCGTGACAATCCCCTGTAAGGAGACTCAGAAC

ACCGTGTGTAACTGCCATGCAGGTTTCTTTCTAAGAGAAAACGAGTGTGTCTCCTGTAGTA

ACTGTAAGAAAAGCCTGGAGTGCACGAAGTTGTGCCTACCCCAGATTGAGAATGTTAAGGG

CACTGAGGACTCAGGCACCACAGCGGCCGCCAGCTTTCTAGAACAAAAACTCATCTCAGAA

GAGGATCTGAATAGCGCCGTCGACCATCATCATCATCATCATTGA
```

HMHH (SEQ ID NO: 622)
```
AGTGTGTGTCCCCAAGGAAATATATCCACCCTCAAAATAATTCGATTTGCTGTACCAAGT

GCCACAAAGGAACCTACTTGTACAATGACTGTCCAGGCCCGGGGCAGGATACGGACTGCAG

GGAGTGTGAAAAGGGCACCTTTACGGCTTCCCAGAATTACCTCAGGCAGTGTCTCAGTTGC

AAGACATGTCGGAAAGAAATGTCCCAGGTGGAGATCTCTCCTTGCCAAGCTGACAAGGACA

CGGTGTGTGGCTGCAGGAAGAACCAGTACCGGCATTATTGGAGTGAAAACCTTTTCCAGTG

CTTCAATTGCAGCCTCTGCCTCAATGGGACCGTGCACCTCTCCTGCCAGGAGAAACAGAAC

ACCGTGTGCACCTGCCATGCAGGTTTCTTTCTAAGAGAAAACGAGTGTGTCTCCTGTAGTA

ACTGTAAGAAAAGCCTGGAGTGCACGAAGTTGTGCCTACCCCAGATTGAGAATGTTAAGGG

CACTGAGGACTCAGGCACCACAGCGGCCGCCAGCTTTCTAGAACAAAAACTCATCTCAGAA

GAGGATCTGAATAGCGCCGTCGACCATCATCATCATCATCATTGA
```

MHHH (SEQ ID NO: 623)
```
AGCTTGTGTCCCCAAGGAAAGTATGTCCATTCTAAGAACAATTCCATCTGCTGCACCAAGT

GCCACAAAGGAACCTACTTGGTGAGTGACTGTCCGAGCCCAGGGCGGGATACAGTCTGCAG

GGAGTGTGAGAGCGGCTCCTTCACCGCTTCAGAAAACCACCTCAGACACTGCCTCAGCTGC

TCCAAATGCCGAAAGGAAATGGGTCAGGTGGAGATCTCTTCTTGCACAGTGGACCGGGACA

CCGTGTGTGGCTGCAGGAAGAACCAGTACCGGCATTATTGGAGTGAAAACCTTTTCCAGTG

CTTCAATTGCAGCCTCTGCCTCAATGGGACCGTGCACCTCTCCTGCCAGGAGAAACAGAAC

ACCGTGTGCACCTGCCATGCAGGTTTCTTTCTAAGAGAAAACGAGTGTGTCTCCTGTAGTA

ACTGTAAGAAAAGCCTGGAGTGCACGAAGTTGTGCCTACCCCAGATTGAGAATGTTAAGGG

CACTGAGGACTCAGGCACCACAGCGGCCGCCAGCTTTCTAGAACAAAAACTCATCTCAGAA

GAGGATCTGAATAGCGCCGTCGACCATCATCATCATCATCATTGA
```

5) Preparation of TNFR1 Chimeric Construct and Transformation into *Pichia pastoris*.

The plasmid DNA generated by each maxiprep was digested with the infrequent cutting restriction endonuclease PmeI in order to linearise the DNA prior to *pichia* transformation. The linearised DNA was subsequently cleaned by phenol/chloroform extraction and ethanol precipitation, before resuspension in 30 µl of dH₂O. 10 µl of the linearised DNA solution was mixed with 80 μl of electro-competent KM71H *Pichia* cells for 5 minutes prior to electroporation at 1.5 kV, 200Ω, 25 μF. Cells were immediately recovered with YPDS and incubated for 2 hours at 30° C. before plating on YPDS agar plates containing 100 μg/ml ZEOCIN, antibiotic formulation containing Phleomycin D (Cayla, Toulouse, France), for 2 days.

6) Expression of Constructs in *Pichia*

An individual transformant colony for each construct was picked into 5 ml of BMGY as a starter culture and grown for 24 hrs at 30° C. This culture was used to inoculate 500 ml of BMGY media which was grown for 24 hrs at 30° C. before cells were harvested by centrifugation at 1500-3000 g for 5 minutes at room temp. Cells were then resuspended in 100 ml of BMMY and grown for 4 days with staggered increases in methanol concentration (0.5% day 1, 1% day 2, 1.5% day 3 and 2% day 4). After expression supernatant was recovered after centrifugation of the cultures at 3300 g for 15 minutes.

7) Purification of TNFR1 Chimeric Constructs Using Nickel Resin

Culture supernatants were initially buffered through addition of 10 mM final concentration imidazole and 2×PBS. His-tagged protein was batch absorbed for 4 hours (shaking) at room temperature through addition of Nickel-NTA resin. The supernatant/resin mix was then flowed into a poly-prep column (Biorad). Resin was then washed with 10 column volumes of 2×PBS before elution using 250 mM imidazole 1×PBS. After buffer exchange the chimeric construct expression was deglycosylated using the EndoH deglycosylase before verification by SDS-PAGE.

Template DNA Sequences Used During PCR

Human (*Homo sapiens*) TNFR1 (extracellular region Genbank accession 33991418)

(SEQ ID NO: 624)
CTGGTCCCTCACCTAGGGGACAGGGAGAAGAGAGATAGTGTGTGTCCCCA

AGGAAAATATATCCACCCTCAAAATAATTCGATTTGCTGTACCAAGTGCC

ACAAAGGAACCTACTTGTACAATGACTGTCCAGGCCCGGGGCAGGATACG

GACTGCAGGGAGTGTGAGAGCGGCTCCTTCACCGCTTCAGAAAACCACCT

CAGACACTGCCTCAGCTGCTCCAAATGCCGAAAGGAAATGGGTCAGGTGG

AGATCTCTTCTTGCACAGTGGACCGGGACACCGTGTGTGGCTGCAGGAAG

AACCAGTACCGGCATTATTGGAGTGAAAACCTTTTCCAGTGCTTCAATTG

CAGCCTCTGCCTCAATGGGACCGTGCACCTCTCCTGCCAGGAGAAACAGA

ACACCGTGTGCACCTGCCATGCAGGTTTCTTTCTAAGAGAAACGAGTGT

GTCTCCTGTAGTAACTGTAAGAAAAGCCTGGAGTGCACGAAGTTGTGCCT

ACCCCAGATTGAGAATGTTAAGGGCACTGAGGACTCAGGCACCACA

The encoded extracellular region of human TNFR1 has the following amino acid sequence.

(SEQ ID NO: 603)
LVPHLGDREKRDSVCPQGKYIHPQNNSICCTKCHKGTYLYNDCPGPGQDT

DCRECESGSFTASENHLRHCLSCSKCRKEMGQVEISSCTVDRDTVCGCRK

NQYRHYWSENLFQCFNCSLCLNGTVHLSCQEKQNTVCTCHAGFFLRENEC

VSCSNCKKSLECTKLCLPQIENVKGTEDSGTT

Murine (*Mus musculus*) TNFR1 (extracellular region Genbank accession 31560798)

(SEQ ID NO: 625)
CTAGTCCCTTCTCTTGGTGACCGGGAGAAGAGGGATAGCTTGTGTCCCCA

AGGAAAGTATGTCCATTCTAAGAACAATTCCATCTGCTGCACCAAGTGCC

ACAAAGGAACCTACTTGGTGAGTGACTGTCCGAGCCCAGGGCGGGATACA

GTCTGCAGGGAGTGTGAAAAGGGCACCTTTACGGCTTCCCAGAATTACCT

CAGGCAGTGTCTCAGTTGCAAGACATGTCGGAAAGAAATGTCCCAGGTGG

ACATCTCTCCTTGCCAAGCTGACAAGGACACGGTGTGTGGCTGTAAGGAG

AACCAGTTCCAACGCTACCTGAGTGAGACACACTTCCAGTGCGTGGACTG

CAGCCCCTGCTTCAACGGCACCGTGACAATCCCCTGTAAGGAGACTCAGA

ACACCGTGTGTAACTGCCATGCAGGGTTCTTTCTGAGAGAAAGTGAGTGC

GTCCCTTGCAGCCACTGCAAGAAAAATGAGGAGTGTATGAAGTTGTGCCT

ACCTCCTCCGCTTGCAAATGTCACAAACCCCCAGGACTCAGGTACTGCG

The encoded extracellular region of murine (*Mus musculus*) TNFR1 has the following amino acid sequence.

(SEQ ID NO: 604)
LVPSLGDREKRDSLCPQGKYVHSKNNSICCTKCHKGTYLVSDCPSPGRDT

VCRECEKGTFTASQNYLRQCLSCKTCRKEMSQVEISPCQADKDTVCGCKE

NQFQRYLSETHFQCVDCSPCFNGTVTIPCKETQNTVCNCHAGFFLRESEC

VPCSHCKKNEECMKLCLPPPLANVTNPQDSGTA

Example 17

Domain Specificity of Anti-TNFR1 dAbs

This example describes a method that was used to determine the domain specificity of dAbs that bind TNFR1. The method utilised surface plasmon resonance (SPR) ('Detection of immuno-complex formation via surface plasmon resonance on gold-coated diffraction gratings.' Biosensors. 1987-88; 3(4):211-25.) to determine the ability of antibodies to bind fully human or mouse biotinylated TNFR1 that was immobilized on a SPR chip surface, after the antibodies had been incubated and equilibrated with an excess of the chimeric molecules described in Example 16. In this assay, flow of an anti-TNFR1 dAb over the TNFR1 surface generates an SPR signal indicating that amount of dAb that binds TNFR1 immoblized on the SPR chip. If the dAb is pre-incubated and equilibrated with a chimeric molecule that comprises the domain(s) of TNFR1 that the particular dAb binds, then flow of this mixture over the TNFR1 surface will produce a smaller SPR signal relative to the dAb alone. However, if the dAb is pre-incubated and equilibrated with a chimeric molecule that does not comprises the domain(s) of TNFR1 that the particular dAb binds, then flow of this mixture over the TNFR1 surface will produce a SPR signal that is about the same as the signal obtained using dAb alone.

Method

1) Generation of an SPR Chip TNFR1 Surface.

The choice of TNFR1 surface is determined by the species specificity of the anti-TNFR1 dAb to be tested. Therefore anti-human TNFR1 dAbs were evaluated using a surface coated with human TNFR1 and anti-mouse TNFR1 dAbs were evaluated using a chip coated with mouse TNFR1.

Biotinylated TNFR1 was diluted in the appropriate SPR buffer and run across a streptavidin (SA) sensor chip in a BIACORE 3000 SPR instrument (Biacore International AB, Uppsala, Sweden). A low flow-rate (5-10 pd/minute) was used in order to maximise the contact time between the biotinylated TNFR1 and the streptavidin surface. Flow continued until the streptavidin surface was saturated with biotinylated material, in order to generate a chip with maximal TNFR1 surface. The chip typically bound several hundred to several thousand SPR response units of the biotinylated material.

2) Titration of the Anti-TNFR1 Response on the SPR Chip

A successful competition experiment requires initial optimisation of the concentration of anti-TNFR1 dAb such that the minimum amount of dAb is flowed over the surface that gives a significant SPR signal. Within a certain concentration range, the dAb will bind the surface in a dose dependent manner so that the number of RUs of dAb bound reflect the concentration of dAb flowed across the chip surface.

In order to ascertain the concentration range of this dose-dependency, the anti-TNFR1 dAbs were titrated in a 10-fold dilution series of Biacore buffer ranging from a 1 in 10 dilution to a 1 in 1,000,000 dilution. The dilutions were then individually and sequentially injected across the TNFR1 chip surface, starting with the most dilute sample. The maximal number of RUs achieved at each dilution were measured. After each injection the TNFR1 surface was regenerated to remove bound anti-TNFR1 dAb where necessary using a suitable SPR regeneration buffer. Using this method the minimal concentration of anti-TNFR1 dAb required to generate a signal representing approximately 100 RU was determined.

3) Pre-Equilibration of Anti-TNFR1 dAbs/Chimerics.

Once the optimum anti-TNFR1 dAb concentration was determined, anti-TNFR1 dAb/chimeric TNFR1 mixes were set up. Mixes were set up such that the final concentration of anti-TNFR1 dAb was identical to the optimal concentration determined previously. Reactions were typically set up in 100 µl volumes containing 50 microliters of a 2× concentrate of anti-TNFR1 dAb, 40 microliters of Biacore buffer and 10 microliters of neat, purified chimeric protein. Typical concentrations for the final mix were about 10-100 µM of chimeric protein and about 10-100 nM anti-TNFR1 dAb. Mixtures were allowed to equilibrate for 30 minutes at room temperature.

4) Competition Biacore Experiment

After equilibration, each anti-TNFR1 dAb/chimeric TNFR1 mixture was sequentially run over the TNFR1 SPR surface and the number of response units measured. After each mixture was injected, the surface was regenerated to remove bound anti-TNFR1 dAb on before the next mixture was injected. The different responses generated using the different chimerics enabled determination of the TNFR1 domains bound by particular dAbs.

These studies revealed that TAR2m-21-23 binds Domain 1 of mouse TNFR1, TAR2h-205 binds Domain 1 of human TNFR1, and that TAR2h-10-27, TAR2h-131-8, TAR2h-15-8, TAR2h-35-4, TAR2h-154-7, TAR2h-154-10 and TAR2h-185-25 bind Domain 3 of human TNF'R1.

Example 18

Screening Methods

These chimeric receptor proteins described in Example 16 can be used in assays or screens to isolate agents (e.g., antibodies, dAbs, chemical compounds) that bind to particular domains within TNFR1. Briefly these methods describe the addition of chimeric proteins to crude antibody preparations prior to their screening for TNFR1 binding either by ELISA or surface plasmon resonance. Additionally they describe the use of chimeric proteins coated on a surface (e.g., ELISA plate or SPR chip) and the screening of antibodies through testing of their binding to chimeric proteins on this surface.

1) Soluble ELISA Screen

This method can be used to rapidly isolate antibodies or antibody fragments (e.g., dAbs) that bind specific domains of TNFR1 from a large repertoire of antibodies or antibody fragments of unknown specificity.

A 96 well assay plate will be coated overnight at 4° C. with 100 µl per well of chimeric TNFR1. Wells will be washed 3 times with 0.1% TPBS (Phosphate buffered saline containing Tween-20 at a concentration of 0.1%). 200 µl per well of 1% TPBS will be added to block the plate, and the plate incubated for 1-2 hours at room temperature. Wells will then be washed 3 times with PBS before addition of 50 µl of bacterial supernatant or periprep, containing the soluble antibody or antibody fragment (that contain the c-Myc epitope tag), in 50 µl 0.2% TPBS. The plate will then be incubated for 1 hour at room temperature. After this the plate will be washed 5 times with 0.1% TPBS (0.1% Tween-20 in PBS). 100 µl of a primary anti-c-Myc mouse monoclonal will then be added in 0.1% TPBS to each well and the plate will be incubated for 1 hour at room temperature. This primary antibody solution will be discarded and the plate will then be washed 5 times with 0.1% TPBS. 100 µl of prediluted anti-mouse IgG (Fc specific) HRP conjugate from goat will then be added (Sigma Cat No: A0168) and the plate will be incubated for 1 hour at room temperature. The secondary antibody will then be discarded and the plate will be washed 6 times with 0.1% TPBS followed by 2 washes with PBS. 50 µl of TMB peroxidase solution will then be added to each well and the plate will be left at room temperature for 2-60 minutes. The reaction will be stopped by the addition of 50 µl of 1M hydrochloric acid. The OD at 450 nm of the plate will be read in a 96-well plate reader within 30 minutes of acid addition. Those antibodies present in crude bacterial supernatant or peripreps that bind the domains of TNFR1 present within the chimeric protein will give a stronger ELISA signal than those that do not.

2) Competitive ELISA Screen

This method can be used to rapidly screen a diverse sets of crude antibody or antibody fragment preparations that bind TNFR1 in order to determine their domain binding specificity.

A 96 well assay plate will be coated overnight at 4° C. with 100 µl per well of murine or human TNFR1 (either human or mouse). Wells will be washed 3 times with 0.1% TPBS (Phosphate buffered saline containing Tween-20 at a concentration of 0.1%). 200 µl per well of 1% TPBS (1% Tween-20 in PBS) will be added to block the plate, and the plate incubated for 1-2 hours at room temperature. Wells will then be washed 3 times with PBS. At the same time bacterial supernatants or peripreps will be pre-equilibriated with a pre-optimised concentration of chimeric TNFR1 protein in solution. 50 µl of this crude bacterial preparation/chimeric protein mix, containing the soluble antibody or antibody fragment will then be added to the ELISA plate. The plate will be incubated for 1 hour at room temperature. Then, the plate will be washed 5 times with 0.1% TPBS (0.1% Tween-20 in PBS), and 100 µl of a primary detecting antibody (or Protein A-HRP or Protein L HRP) will be added in 0.1% TPBS, to each well and the plate will be incubated for 1 hour at room temperature. This primary antibody solution will be discarded and the plate will be washed 5 times with 0.1% TPBS. If required 100 µl of a prediluted secondary antibody/HRP conjugate from goat will then be added, and the plate will be incubated for 1 hour at room temperature. The secondary antibody will then be discarded and the plate will be washed 6 times with 0.1% TPBS followed by 2 washes with PBS. 50 µl of TMB peroxidase solution will be added to each well and the plate will be left at room temperature for 2-60 minutes. The reaction will be stopped by the addition of 50 µl of 1M hydrochloric acid. The OD at 450 nm of the plate will be read in a 96-well plate reader within 30 minutes of acid addition. A reduction in ELISA signal will be indicative of the antibody binding the chimeric TNFR1 domains rather than the full TNFR1 coated on the plate, and therefore, that the antibody binds one of the domains within the chimeric protein.

3) Competitive ELISA Screen for Antibodies and Antibody Fragments that Compete with a Reference Antibody or Antibody Fragment for Binding to TNFR1 This method can be used to rapidly screen diverse sets of crude antibody or antibody fragment preparations that bind TNFR1 for those antibodies or antibody fragments that compete with a reference antibody or antibody fragment (e.g., TAR2m-21-23) for binding to TNFR1 or bind a desired domain of TNFR1 (e.g., domain 1). The method uses a reference antibody or antibody fragment and test antibody or antibody fragment (e.g., a population of antibodies to be screened) that contain different detectable tags (epitope tags).

A 96 well assay plate will be coated overnight at 4° C. with 100 µl per well of murine or human TNFR1. Wells will be washed 3 times with 0.1% TPBS (Phosphate buffered saline containing Tween-20 at a concentration of 0.1%). 200 µl per well of 1% TPBS (1% Tween-20 in PBS) will be added to block the plate, and the plate will be incubated for 1-2 hours at room temperature. Wells will then be washed 3 times with PBS. At the same time the crude antibody preparations to be tested will be mixed with a pre-optimised concentration of reference antibody or antibody fragment (e.g., domain 1-binding antibody; TAR2m-21-23) in solution. As already stated is important that this antibody does not include the same detection tags as present in the antibodies being screened for domain binding specificity. 50 µl of this crude antibody/reference antibody mix, will be added to the ELISA plate. The plate will then be incubated for 1 hour at room temperature. After, the plate will be washed 5 times with 0.1% TPBS, 100 µl of a primary detecting antibody (that binds the tag present only on the antibody population being screened) will be added in 0.1% TPBS to each well, and the plate will be incubated for 1 hour at room temperature. This primary antibody solution will be discarded and the plate will then be washed 5 times with 0.1% TPBS. 100 µl of a prediluted secondary antibody-HRP conjugate that recognises the primary detection antibody will then be added, and the plate will be incubated for 1 hour at room temperature. The secondary antibody solution will then be discarded and the plate washed 6 times with 0.1% TPBS followed by 2 washes with PBS. 50 µl of TMB peroxidase solution will then be added to each well and the plate will be left at room temperature for 2-60 minutes. The reaction will be stopped by the addition of 50 µl of 1M hydrochloric acid. The OD at 450 nm of the plate will be read in a 96-well plate reader within 30 minutes of acid addition. A separate and parallel ELISA using this method but without addition of the reference antibody or antibody fragment should be done in parallel. A reduction in ELISA signal in the presence of the reference antibody or antibody fragment, in comparison to the ELISA signal for the same antibody preparation without competing reference antibody or antibody fragment, will be indicative that the particular antibody or antibody fragment competes with the reference antibody or antibody fragment for binding to TNFR1, and binds the same domain of TNFR1 as the reference antibody or antibody fragment.

4) SPR Screening

The ELISA methods described above can be readily adapted to a format that uses surface plasmon resonance, for example using a BIACORE 3000 SPR instrument (Biacore International AB, Uppsala, Sweden). Generally, the chimeric protein will be either immobilized on the SPR chip, or the chimeric protein will be equilibrated with crude bacterial supernatant containing anti-TNFR1 antibodies or antibody fragments, and the resultant mixture flowed over a SPR chip coated with full length human TNFR1 or murine TNFR1.

Example 19

TAR2m21-23 Dimers are High Avidity TNFR1 Antagonists

TAR2m21-23 dimers were prepared by producing a form of TAR2m21-23 that contained a cys residue at the carboxy-terminus using the methods described in Example 8. The protein (TAR2m21-23CYS) was expressed in *Pichia* and purified using Streamline Protein A. Non-reducing SDS-PAGE analysis showed that ~40-50% of the protein was present in solution as a dimer. The dimer was further purified using gel filtration chromatography.

2 mg of protein was concentrated down to about 250 µl and applied to a Superdex 75 HR gel filtration column (Amersham Bioscience) which had previously been equilibrated with PBS. The column was run at a flow rate of 0.5 ml/min and 0.5 ml fractions were collected. Elution of protein from the column was monitored at 280 nm and dimer containing fractions were identified by non-reducing SDS-PAGE. Fractions that contained dimers but no monomeric TAR2m-21-23CYS were combined. The combined fractions were concentrated and the potency of the dimeric dAb determined in the L929 TNF cell cytotoxicity assay (Example 6).

The biological potency of TAR2m21-23 dimer was compared against monomeric TAR2m-21-23 in the L929 cytotoxicity assay. In this assay, inhibition of TNF-induced cytotoxicity of mouse L929 cells by TAR2m21-23 monomer and TAR2m21-23 dimer was assessed, and results were expressed as the concentration of dAb monomer or dimer that inhibited cytotoxicity by 50% in the assay (neutralizing dose 50, ND50).

The monomeric dAb had an ND50 of about 600 pM in the assay. The ND50 of the dimerized dAb (TAR2m21-23 dimer) was about 10-fold lower (ND50 about 60-70 pM) in the assay. These results show that TAR2m21-23 dimer had a significantly improved affinity for cell surface TNFR1 in comparison to the dAb monomer. The results indicate that TAR2m21-23 dimer binds to two separate TNFR1 molecules on the cell surface simultaneously, and the resulting avidity effect upon multimerisation results in improved inhibition of TNFR1.

The dimeric format (TAR2m21-23 dimer) was then tested to see if it displayed any signs of TNFR1 agonism, i.e. the ability to cause cross-linking of TNFR1 and initiate intracellular signaling and cell death. This was achieved using a modified L929 cell cytotoxicity assay in which no TNF-α was added, but anti-TNFR1 antibodies or the dAb formats were tested to see if they agonize TNFR1 and induce cell death. Anti-TNFR1 antibody AF-425-PB (R&D Systems) which is a known agonists of TNFR1, and anti-TNFR1 antibody MAB430 (R&D Systems), a reported antagonist of TNFR1, TAR2m-21-23 and TAR2m21-23 dimer were tested in the assay.

Antibody AF-425-PB activated TNFR1 and induced cytotoxicity in the assay with a ND50 of about 100 pM. Even the reported antagonist antibody MAB430 caused receptor cross-linking and cell killing in the assay with an ND50 of about 10 nM. In contrast, TAR2m-21-23 dimer did not cause any cell death in the assay, even when present at very high concentrations (>1 µM). These results show that TAR2m21-23 dimer is not a TNFR1 agonist.

The results indicate that dialers, trimers or other multimers of dAbs that bind TNFR1 have high avidity for TNFR1 expressed on the surface of cells and are effective TNFR1 antagonists. Moreover, the results of this study show that multimers of dAbs that bind Domain 1 of TNFR1, such as TAR2m21-23 dimer, can bind two TNFR1 molecules (as can the antibodies that acted as agonists in the assay) and that binding the domain or epitope target on TNFR1 (Domain 1) prevented the close association of receptor chains that is required for the initiation of TNFR1 signaling. This property is unique for a bivalent molecule in that it is able to cross-link TNFR1 on the cell surface and yet not cause TNFR1 signaling and cell death.

Example 20

Isolation of dAbs that bind human TNFR1 and mouse TNFR1 dAbs of known sequence were expressed in *E. coli* and purified with Protein A streamline resin. After elution into Tris-Glycine, dAbs were flowed over an SPR chip to which biotinylated human TNFR1 had been immobilized (flow cell 2) and biotinylated murine TNFR1 had been immobilized (flow cell 4). (The SPR chip was coated with human TNFR1 and murine TNFR1 at similar densities.) Flow cells 1 and 3 were left blank and acted as no antigen reference surfaces for the detection and subtraction of non-specific binding.

dAb was flowed over the 4 flow cells in series (ie flow cell 1, then 2, 3 and finally 4) with the response differences between flow cells 2 and 1 measured and the response differences between flow cells 4 and 3 being also measured. The former being a measure of binding to human TNFR1 and the later binding to murine TNFR1. Specific binding curves were noted for binding to both human TNFR1 and murine TNFR1, the nature of the curves being such that a faster cm-rate for human TNFR1 than murine TNFR1 was noted. Off-rates were broadly similar. An assessment of the cross-reactivity is given by the number of response units (RU) maximally achieved by each binding event. In this example the human biotinylated TNFR1 surface comprised approximately 900 RU of TNFR1 on flow cell 2, while flow cell 4 comprised about 1400 RU of murine TNFR1. As a control, TAR2h-154-7, a human specific dAb at a concentration of 2 micromolar bound the human surface with a maximal response of 385 RU, giving a response on the mouse surface of only 4.5 RU. 2 micromolar of TAR2h-205 gave a response on the human surface of 435 RU, and a response on the mouse surface of 266 RU.

All publications mentioned in the present specification, and references cited in said publications, are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

Annex 1; Polypeptides which Enhance Half-Life In Vivo.
Alpha-1 Glycoprotein (Orosomucoid) (AAG)
Alpha-1 Antichyromotrypsin (ACT)
Alpha-1 Antitrypsin (AAT)
Alpha-1 Microglobulin (Protein HC) (AIM)
Alpha-2 Macroglobulin (A2M)
Antithrombin III (AT III)
Apolipoprotein A-1 (Apo A-1)
Apoliprotein B (Apo B)
Beta-2-microglobulin (B2M)
Ceruloplasmin (Cp)
Complement Component (C3)
Complement Component (C4)
C1 Esterase Inhibitor (C1 INH)
C-Reactive Protein (CRP)
Cystatin C (Cys C)
Ferritin (FER)
Fibrinogen (FIB)
Fibronectin (FN)
Haptoglobin (Hp)
Hemopexin (HPX)
Immunoglobulin A (IgA)
Immunoglobulin D (IgD)
Immunoglobulin E (IgE)
Immunoglobulin G (IgG)
Immunoglobulin M (IgM)
Immunoglobulin Light Chains (kapa/lambda)
Lipoprotein(a) [Lp(a)]
Mannose-bindign protein (MBP)
Myoglobin (Myo)
Plasminogen (PSM)
Prealbumin (Transthyretin) (PAL)
Retinol-binding protein (RBP)
Rheomatoid Factor (RF)
Serum Amyloid A (SAA)
Soluble Tranferrin Receptor (sTfR)
Transferrin (Tf)

| Annex 2 | |
|---|---|
| Pairing | Therapeutic relevant references. |
| TNF ALPHA/TGF-β | TGF-b and TNF when injected into the ankle joint of collagen induced arthritis model significantly enhanced joint inflammation. In non-collagen challenged mice there was no effect. |
| TNF ALPHA/IL-1 | TNF and IL-1 synergize in the pathology of uveitis. TNF and IL-1 synergize in the pathology of malaria (hypoglycaemia, NO). TNF and IL-1 synergize in the induction of polymorphonuclear (PMN) cells migration in inflammation. |

-continued

| Annex 2 | |
|---|---|
| Pairing | Therapeutic relevant references. |
| | IL-1 and TNF synergize to induce PMN infiltration into the peritoneum.<br>IL-1 and TNF synergize to induce the secretion of IL-1 by endothelial cells. Important in inflammation.<br>IL-1 or TNF alone induced some cellular infiltration into knee synovium. IL-1 induced PMNs, TNF - monocytes. Together they induced a more severe infiltration due to increased PMNs.<br>Circulating myocardial depressant substance (present in sepsis) is low levels of IL-1 and TNFacting synergistically. |
| TNF ALPHA/IL-2 | Most relating to synergisitic activation of killer T-cells. |
| TNF ALPHA/IL-3 | Synergy of interleukin 3 and tumor necrosis factor alpha in stimulating clonal growth of acute myelogenous leukemia blasts is the result of induction of secondary hematopoietic cytokines by tumor necrosis factor alpha.<br>Cancer Res. 1992 Apr. 15; 52(8): 2197-201. |
| TNF ALPHA/IL-4 | IL-4 and TNF synergize to induce VCAM expression on endothelial cells. Implied to have a role in asthma. Same for synovium - implicated in RA.<br>TNF and IL-4 synergize to induce IL-6 expression in keratinocytes.<br>Sustained elevated levels of VCAM-1 in cultured fibroblast-like synoviocytes can be achieved by TNF-alpha in combination with either IL-4 or IL-13 through increased mRNA stability. *Am J Pathol*. 1999 April; 154(4): 1149-58 |
| TNF ALPHA/IL-5 | Relationship between the tumor necrosis factor system and the serum interleukin-4, interleukin-5, interleukin-8, eosinophil cationic protein, and immunoglobulin E levels in the bronchial hyperreactivity of adults and their children. *Allergy Asthma Proc*. 2003 March-April; 24(2): 111-8. |
| TNF ALPHA/IL-6 | TNF and IL-6 are potent growth factors for OH-2, a novel human myeloma cell line. *Eur J Haematol*. 1994 July; 53(1): 31-7. |
| TNF ALPHA/IL-8 | TNF and IL-8 synergized with PMNs to activate platelets.<br>Implicated in Acute Respiratory Distress Syndrome.<br>See IL-5/TNF (asthma). Synergism between interleukin-8 and tumor necrosis factor-alpha for neutrophil-mediated platelet activation. *Eur Cytokine Netw*. 1994 September-October; 5(5): 455-60. (adult respiratory distress syndrome (ARDS)) |
| TNF ALPHA/IL-9 | |
| TNF ALPHA/IL-10 | IL-10 induces and synergizes with TNF in the induction of HIV expression in chronically infected T-cells. |
| TNF ALPHA/IL-11 | Cytokines synergistically induce osteoclast differentiation: support by immortalized or normal calvarial cells. *Am J Physiol Cell Physiol*. 2002 September; 283(3): C679-87. (Bone loss) |
| TNF ALPHA/IL-12 | |
| TNF ALPHA/IL-13 | Sustained elevated levels of VCAM-1 in cultured fibroblast-like synoviocytes can be achieved by TNF-alpha in combination with either IL-4 or IL-13 through increased mRNA stability. Am J Pathol. 1999 April; 154(4): 1149-58.<br>Interleukin-13 and tumour necrosis factor-alpha synergistically induce eotaxin production in human nasal fibroblasts. Clin Exp Allergy. 2000 March; 30(3): 348-55.<br>Interleukin-13 and tumour necrosis factor-alpha synergistically induce eotaxin production in human nasal fibroblasts. *Clin Exp Allergy*. 2000 March; 30(3): 348-55 (allergic inflammation)<br>Implications of serum TNF-beta and IL-13 in the treatment response of childhood nephrotic syndrome. *Cytokine*. 2003 Feb. 7; 21(3): 155-9. |
| TNF ALPHA/IL-14 | Effects of inhaled tumour necrosis factor alpha in subjects with mild asthma. *Thorax*. 2002 September; 57(9): 774-8. |
| TNF ALPHA/IL-15 | Effects of inhaled tumour necrosis factor alpha in subjects with mild asthma. *Thorax*. 2002 September; 57(9): 774-8. |
| TNF ALPHA/IL-16 | Tumor necrosis factor-alpha-induced synthesis of interleukin-16 in airway epithelial cells: priming for serotonin stimulation. *Am J Respir Cell Mol Biol*. 2003 March; 28(3): 354-62. (airway inflammation)<br>Correlation of circulating interleukin 16 with proinflammatory cytokines in patients with rheumatoid arthritis. *Rheumatology* (Oxford). 2001 April; 40(4): 474-5. No abstract available.<br>Interleukin 16 is up-regulated in Crohn's disease and participates in TNBS colitis in mice. *Gastroenterology*. 2000 October; 119(4): 972-82. |

Annex 2

| Pairing | Therapeutic relevant references. |
|---|---|
| TNF ALPHA/IL-17 | Inhibition of interleukin-17 prevents the development of arthritis in vaccinated mice challenged with *Borrelia burgdorferi*. *Infect Immun*. 2003 June; 71(6): 3437-42.<br>Interleukin 17 synergises with tumour necrosis factor alpha to induce cartilage destruction in vitro. *Ann Rheum Dis*. 2002 October; 61(10): 870-6.<br>A role of GM-CSF in the accumulation of neutrophils in the airways caused by IL-17 and TNF-alpha. *Eur Respir J*. 2003 March; 21(3): 387-93. (Airway inflammation)<br>Abstract Interleukin-1, tumor necrosis factor alpha, and interleukin-17 synergistically up-regulate nitric oxide and prostaglandin E2 production in explants of human osteoarthritic knee menisci. *Arthritis Rheum*. 2001 September; 44(9): 2078-83. |
| TNF ALPHA/IL-18 | Association of interleukin-18 expression with enhanced levels of both interleukin-1beta and tumor necrosis factor alpha in knee synovial tissue of patients with rheumatoid arthritis. *Arthritis Rheum*. 2003 February; 48(2): 339-47.<br>Abstract Elevated levels of interleukin-18 and tumor necrosis factor-alpha in serum of patients with type 2 diabetes mellitus: relationship with diabetic nephropathy. *Metabolism*. 2003 May; 52(5): 605-8. |
| TNF ALPHA/IL-19 | Abstract IL-19 induces production of IL-6 and TNF-alpha and results in cell apoptosis through TNF-alpha. *J Immunol*. 2002 Oct. 15; 169(8): 4288-97. |
| TNF ALPHA/IL-20 | Abstract Cytokines: IL-20—a new effector in skin inflammation. *Curr Biol*. 2001 Jul. 10; 11(13): R531-4 |
| TNF ALPHA/Complement | Inflammation and coagulation: implications for the septic patient. *Clin Infect Dis*. 2003 May 15; 36(10): 1259-65. Epub 2003 May 08. Review. |
| TNF ALPHA/IFN-γ | MHC induction in the brain.<br>Synergize in anti-viral response/IFN-β induction.<br>Neutrophil activation/respiratory burst.<br>Endothelial cell activation<br>Toxicities noted when patients treated with TNF/IFN-γ as anti-viral therapy<br>Fractalkine expression by human astrocytes.<br>Many papers on inflammatory responses—i.e. LPS, also macrophage activation.<br>Anti-TNF and anti-IFN-γ synergize to protect mice from lethal endotoxemia. |
| TGF-β/IL-1 | Prostaglndin synthesis by osteoblasts<br>IL-6 production by intestinal epithelial cells (inflammation model)<br>Stimulates IL-11 and IL-6 in lung fibroblasts (inflammation model)<br>IL-6 and IL-8 production in the retina |
| TGF-β/IL-6 | Chondrocarcoma proliferation |
| IL-1/IL-2 | B-cell activation<br>LAK cell activation<br>T-cell activation<br>IL-1 synergy with IL-2 in the generation of lymphokine activated killer cells is mediated by TNF-alpha and beta (lymphotoxin). *Cytokine*. 1992 November; 4(6): 479-87. |
| IL-1/IL-3 | |
| IL-1/IL-4 | B-cell activation<br>IL-4 induces IL-1 expression in endothelial cell activation. |
| IL-1/IL-5 | |
| IL-1/IL-6 | B cell activation<br>T cell activation (can replace accessory cells)<br>IL-1 induces IL-6 expression<br>C3 and serum amyloid expression (acute phase response)<br>HIV expression<br>Cartilage collagen breakdown. |
| IL-1/IL-7 | IL-7 is requisite for IL-1-induced thymocyte proliferation. Involvement of IL-7 in the synergistic effects of granulocyte-macrophage colony-stimulating factor or tumor necrosis factor with IL-1. *J Immunol*. 1992 Jan. 1; 148(1): 99-105. |
| IL-1/IL-8 | |
| IL-1/IL-10 | |
| IL-1/IL-11 | Cytokines synergistically induce osteoclast differentiation: support by immortalized or normal calvarial cells. *Am J Physiol Cell Physiol*. 2002 September; 283(3): C679-87. (Bone loss) |
| IL-1/IL-16 | Correlation of circulating interleukin 16 with proinflammatory cytokines in patients with rheumatoid arthritis. *Rheumatology* (Oxford). 2001 April; 40(4): 474-5. No abstract available. |

Annex 2

| Pairing | Therapeutic relevant references. |
|---|---|
| IL-1/IL-17 | Inhibition of interleukin-17 prevents the development of arthritis in vaccinated mice challenged with *Borrelia burgdorferi*. *Infect Immun*. 2003 June; 71(6): 3437-42. Contribution of interleukin 17 to human cartilage degradation and synovial inflammation in osteoarthritis. *Osteoarthritis Cartilage*. 2002 October; 10(10): 799-807. Abstract Interleukin-1, tumor necrosis factor alpha, and interleukin-17 synergistically up-regulate nitric oxide and prostaglandin E2 production in explants of human osteoarthritic knee menisci. *Arthritis Rheum*. 2001 September; 44(9): 2078-83. |
| IL-1/IL-18 | Association of interleukin-18 expression with enhanced levels of both interleukin-1beta and tumor necrosis factor alpha in knee synovial tissue of patients with rheumatoid arthritis. *Arthritis Rheum*. 2003 February; 48(2): 339-47. |
| IL-1/IFN-g | |
| IL-2/IL-3 | T-cell proliferation<br>B cell proliferation |
| IL-2/IL-4 | B-cell proliferation<br>T-cell proliferation<br>(selectively inducing activation of CD8 and NK lymphocytes)IL-2R beta agonist P1-30 acts in synergy with IL-2, IL-4, IL-9, and IL-15: biological and molecular effects. *J Immunol*. 2000 Oct. 15; 165(8): 4312-8. |
| IL-2/IL-5 | B-cell proliferation/Ig secretion<br>IL-5 induces IL-2 receptors on B-cells |
| IL-2/IL-6 | Development of cytotoxic T-cells |
| IL-2/IL-7 | |
| IL-2/IL-9 | See IL-2/IL-4 (NK-cells) |
| IL-2/IL-10 | B-cell activation |
| IL-2/IL-12 | IL-12 synergizes with IL-2 to induce lymphokine-activated cytotoxicity and perforin and granzyme gene expression in fresh human NK cells. *Cell Immunol*. 1995 Oct. 1; 165(1): 33-43. (T-cell activation) |
| IL-2/IL-15 | See IL-2/IL-4 (NK cells)<br>(T cell activation and proliferation) IL-15 and IL-2: a matter of life and death for T cells in vivo. *Nat Med*. 2001 January; 7(1): 114-8. |
| IL-2/IL-16 | Synergistic activation of CD4+ T cells by IL-16 and IL-2. *J Immunol*. 1998 Mar. 1; 160(5): 2115-20. |
| IL-2/IL-17 | Evidence for the early involvement of interleukin 17 in human and experimental renal allograft rejection. *J Pathol*. 2002 July; 197(3): 322-32. |
| IL-2/IL-18 | Interleukin 18 (IL-18) in synergy with IL-2 induces lethal lung injury in mice: a potential role for cytokines, chemokines, and natural killer cells in the pathogenesis of interstitial pneumonia. *Blood*. 2002 Feb. 15; 99(4): 1289-98. |
| IL-2/TGF-β | Control of CD4 effector fate: transforming growth factor beta 1 and interleukin 2 synergize to prevent apoptosis and promote effector expansion. *J Exp Med*. 1995 Sep. 1; 182(3): 699-709. |
| IL-2/IFN-γ | Ig secretion by B-cells<br>IL-2 induces IFN-γ expression by T-cells |
| IL-2/IFN-α/β | None |
| IL-3/IL-4 | Synergize in mast cell growth<br>Synergistic effects of IL-4 and either GM-CSF or IL-3 on the induction of CD23 expression by human monocytes: regulatory effects of IFN-alpha and IFN-gamma. *Cytokine*. 1994 July; 6(4): 407-13. |
| IL-3/IL-5 | |
| IL-3/IL-6 | |
| IL-3/IFN-γ | IL-4 and IFN-gamma synergistically increase total polymeric IgA receptor levels in human intestinal epithelial cells. Role of protein tyrosine kinases. *J Immunol*. 1996 Jun. 15; 156(12): 4807-14. |
| IL-3/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. *J Immunol*. 2003 Jun. 1; 170(11): 5359-66. (allergic inflammation) |
| IL-4/IL-2 | IL-4 synergistically enhances both IL-2- and IL-12-induced IFN-{gamma} expression in murine NK cells. *Blood*. 2003 Mar. 13 [Epub ahead of print] |
| IL-4/IL-5 | Enhanced mast cell histamine etc. secretion in response to IgE<br>A Th2-like cytokine response is involved in bullous pemphigoid. the role of IL-4 and IL-5 in the pathogenesis of |

Annex 2

| Pairing | Therapeutic relevant references. |
|---|---|
| | the disease. *Int J Immunopathol Pharmacol*. 1999 May-August; 12(2): 55-61. |
| IL-4/IL-6 | |
| IL-4/IL-10 | |
| IL-4/IL-11 | Synergistic interactions between interleukin-11 and interleukin-4 in support of proliferation of primitive hematopoietic progenitors of mice. *Blood*. 1991 Sep. 15; 78(6): 1448-51. |
| IL-4/IL-12 | Synergistic effects of IL-4 and IL-18 on IL-12-dependent IFN-gamma production by dendritic cells. *J Immunol*. 2000 Jan. 1; 164(1): 64-71. (increase Th1/Th2 differentiation) IL-4 synergistically enhances both IL-2- and IL-12-induced IFN-{gamma} expression in murine NK cells. *Blood*. 2003 Mar. 13 [Epub ahead of print] |
| IL-4/IL-13 | Abstract Interleukin-4 and interleukin-13 signaling connections maps. *Science*. 2003 Jun. 06; 300(5625): 1527-8. (allergy, asthma) Inhibition of the IL-4/IL-13 receptor system prevents allergic sensitization without affecting established allergy in a mouse model for allergic asthma. *J Allergy Clin Immunol*. 2003 June; 111(6): 1361-1369. |
| IL-4/IL-16 | (asthma) Interleukin (IL)-4/IL-9 and exogenous IL-16 induce IL-16 production by BEAS-2B cells, a bronchial epithelial cell line. *Cell Immunol*. 2001 Feb. 1; 207(2): 75-80 |
| IL-4/IL-17 | Interleukin (IL)-4 and IL-17 synergistically stimulate IL-6 secretion in human colonic myofibroblasts. *Int J Mol Med*. 2002 November; 10(5): 631-4. (Gut inflammation) |
| IL-4/IL-24 | IL-24 is expressed by rat and human macrophages. *Immunobiology*. 2002 July; 205(3): 321-34. |
| IL-4/IL-25 | Abstract New IL-17 family members promote Th1 or Th2 responses in the lung: in vivo function of the novel cytokine IL-25. *J Immunol* 2002 Jul. 1; 169(1): 443-53. (allergic inflammation) Abstract Mast cells produce interleukin-25 upon Fcepsilon RI-mediated activation. *Blood*. 2003 May 1; 101(9): 3594-6. Epub 2003 Jan. 02. (allergic inflammation) |
| IL-4/IFN-γ | Abstract Interleukin 4 induces interleukin 6 production by endothelial cells: synergy with interferon-gamma. *Eur J Immunol*. 1991 January; 21(1): 97-101. |
| IL-4/SCF | Regulation of human intestinal mast cells by stem cell factor and IL-4. *Immunol Rev*. 2001 February; 179: 57-60. Review. |
| IL-5/IL-3 | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. *J Immunol*. 2003 Jun. 1; 170(11): 5359-66. (Allergic inflammation see abstract) |
| IL-5/IL-6 | |
| IL-5/IL-13 | Inhibition of allergic airways inflammation and airway hyperresponsiveness in mice by dexamethasone: role of eosinophils, IL-5, eotaxin, and IL-13. *J Allergy Clin Immunol*. 2003 May; 111(5): 1049-61. |
| IL-5/IL-17 | Interleukin-17 orchestrates the granulocyte influx into airways after allergen inhalation in a mouse model of allergic asthma. *Am J Respir Cell Mol Biol*. 2003 January; 28(1): 42-50. |
| IL-5/IL-25 | Abstract New IL-17 family members promote Th1 or Th2 responses in the lung: in vivo function of the novel cytokine IL-25. *J Immunol*. 2002 Jul. 1; 169(1): 443-53. (allergic inflammation) Abstract Mast cells produce interleukin-25 upon Fcepsilon RI-mediated activation. *Blood*. 2003 May 1; 101(9): 3594-6. Epub 2003 Jan. 02. (allergic inflammation) |
| IL-5/IFN-γ | |
| IL-5/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. *J Immunol*. 2003 Jun. 1; 170(11): 5359-66. (Allergic inflammation) |
| IL-6/IL-10 | |
| IL-6/IL-11 | |
| IL-6/IL-16 | Interleukin-16 stimulates the expression and production of pro-inflammatory cytokines by human monocytes. *Immunology*. 2000 May; 100(1): 63-9. |

Annex 2

| Pairing | Therapeutic relevant references. |
|---|---|
| IL-6/IL-17 | Stimulation of airway mucin gene expression by interleukin (IL)-17 through IL-6 paracrine/autocrine loop. *J Biol Chem.* 2003 May 9; 278(19): 17036-43. Epub 2003 Mar. 06. (airway inflammation, asthma) |
| IL-6/IL-19 | Abstract IL-19 induces production of IL-6 and TNF-alpha and results in cell apoptosis through TNF-alpha. *J Immunol.* 2002 Oct. 15; 169(8): 4288-97. |
| IL-6/IFN-g | |
| IL-7/IL-2 | Interleukin 7 worsens graft-versus-host disease. *Blood.* 2002 Oct. 1; 100(7): 2642-9. |
| IL-7/IL-12 | Synergistic effects of IL-7 and IL-12 on human T cell activation. *J Immunol.* 1995 May 15; 154(10): 5093-102. |
| IL-7/IL-15 | Interleukin-7 and interleukin-15 regulate the expression of the bcl-2 and c-myb genes in cutaneous T-cell lymphoma cells. *Blood.* 2001 Nov. 1; 98(9): 2778-83. (growth factor) |
| IL-8/IL-11 | Abnormal production of interleukin (IL)-11 and IL-8 in polycythaemia vera. *Cytokine.* 2002 Nov. 21; 20(4): 178-83. |
| IL-8/IL-17 | The Role of IL-17 in Joint Destruction. *Drug News Perspect.* 2002 January; 15(1): 17-23. (arthritis)<br>Abstract Interleukin-17 stimulates the expression of interleukin-8, growth-related oncogene-alpha, and granulocyte-colony-stimulating factor by human airway epithelial cells. *Am J Respir Cell Mol Biol.* 2002 June; 26(6): 748-53. (airway inflammation) |
| IL-8/GSF | Interleukin-8: an autocrine/paracrine growth factor for human hematopoietic progenitors acting in synergy with colony stimulating factor-1 to promote monocyte-macrophage growth and differentiation. *Exp Hematol.* 1999 January; 27(1): 28-36. |
| IL-8/VGEF | Intracavitary VEGF, bFGF, IL-8, IL-12 levels in primary and recurrent malignant glioma. *J Neurooncol.* 2003 May; 62(3): 297-303. |
| IL-9/IL-4 | Anti-interleukin-9 antibody treatment inhibits airway inflammation and hyperreactivity in mouse asthma model. *Am J Respir Crit Care Med.* 2002 Aug. 1; 166(3): 409-16. |
| IL-9/IL-5 | Pulmonary overexpression of IL-9 induces Th2 cytokine expression, leading to immune pathology. *J Clin Invest.* 2002 January; 109(1): 29-39.<br>Th2 cytokines and asthma. Interleukin-9 as a therapeutic target for asthma. *Respir Res.* 2001; 2(2): 80-4. Epub 2001 Feb. 15. Review.<br>Abstract Interleukin-9 enhances interleukin-5 receptor expression, differentiation, and survival of human eosinophils. *Blood.* 2000 Sep. 15; 96(6): 2163-71 (asthma) |
| IL-9/IL-13 | Anti-interleukin-9 antibody treatment inhibits airway inflammation and hyperreactivity in mouse asthma model. *Am J Respir Crit Care Med.* 2002 Aug. 1; 166(3): 409-16.<br>Direct effects of interleukin-13 on epithelial cells cause airway hyperreactivity and mucus overproduction in asthma. *Nat Med.* 2002 August; 8(8): 885-9. |
| IL-9/IL-16 | See IL-4/IL-16 |
| IL-10/IL-2 | The interplay of interleukin-10 (IL-10) and interleukin-2 (IL-2) in humoral immune responses: IL-10 synergizes with IL-2 to enhance responses of human B lymphocytes in a mechanism which is different from upregulation of CD25 expression. *Cell Immunol.* 1994 September; 157(2): 478-88. |
| IL-10/IL-12 | |
| IL-10/TGF-β | IL-10 and TGF-beta cooperate in the regulatory T cell response to mucosal allergens in normal immunity and specific immunotherapy. *Eur J Immunol.* 2003 May; 33(5): 1205-14. |
| IL-10/IFN-γ | |
| IL-11/IL-6 | Interleukin-6 and interleukin-11 support human osteoclast formation by a RANKL-independent mechanism. *Bone.* 2003 January; 32(1): 1-7. (bone resorption in inflammation) |
| IL-11/IL-17 | Polarized in vivo expression, of IL-11 and IL-17 between acute and chronic skin lesions. *J Allergy Clin Immunol.* 2003 April; 111(4): 875-81. (allergic dermatitis)<br>IL-17 promotes bone erosion in murine collagen-induced arthritis through loss of the receptor activator of NF-kappa B ligand/osteoprotegerin balance. *J Immunol.* 2003 Mar. 1; 170(5): 2655-62. |
| IL-11/TGF-β | Polarized in vivo expression of IL-11 and IL-17 between acute and chronic skin lesions. *J Allergy Clin Immunol.* 2003 April; 111(4): 875-81. (allergic dermatitis) |

Annex 2

| Pairing | Therapeutic relevant references. |
|---|---|
| IL-12/IL-13 | Relationship of Interleukin-12 and Interleukin-13 imbalance with class-specific rheumatoid factors and anticardiolipin antibodies in systemic lupus erythematosus. *Clin Rheumatol.* 2003 May; 22(2): 107-11. |
| IL-12/IL-17 | Upregulation of interleukin-12 and -17 in active inflammatory bowel disease. *Scand J Gastroenterol* 2003 February; 38(2): 180-5. |
| IL-12/IL-18 | Synergistic proliferation and activation of natural killer cells by interleukin 12 and interleukin 18. *Cytokine.* 1999 November; 11(11): 822-30. Inflammatory Liver Steatosis Caused by IL-12 and IL-18. *J Interferon Cytokine Res.* 2003 March; 23(3): 155-62. |
| IL-12/IL-23 | nterleukin-23 rather than interleukin-12 is the critical cytokine for autoimmune inflammation of the brain. *Nature.* 2003 Feb. 13; 421(6924): 744-8. Abstract A unique role for IL-23 in promoting cellular immunity. *J Leukoc Biol.* 2003 January; 73(1): 49-56. Review. |
| IL-12/IL-27 | Abstract IL-27, a heterodimeric cytokine composed of EBI3 and p28 protein, induces proliferation of naive CD4(+) T cells. *Immunity.* 2002 June; 16(6): 779-90. |
| IL-12/IFN-γ | IL-12 induces IFN-γ expression by B and T-cells as part of immune stimulation. |
| IL-13/IL-5 | See IL-5/IL-13 |
| IL-13/IL-25 | Abstract New IL-17 family members promote Th1 or Th2 responses in the lung: in vivo function of the novel cytokine IL-25. *J Immunol.* 2002 Jul. 1; 169(1): 443-53. (allergic inflammation) Abstract Mast cells produce interleukin-25 upon Fcepsilon RI-mediated activation. *Blood.* 2003 May 1; 101(9): 3594-6. Epub 2003 Jan. 02. (allergic inflammation) |
| IL-15/IL-13 | Differential expression of interleukins (IL)-13 and IL-15 in ectopic and eutopic endometrium of women with endometriosis and normal fertile women. *Am J Reprod Immunol.* 2003 February; 49(2): 75-83. |
| IL-15/IL-16 | IL-15 and IL-16 overexpression in cutaneous T-cell lymphomas: stage-dependent increase in mycosis fungoides progression. *Exp Dermatol.* 2000 August; 9(4): 248-51. |
| IL-15/IL-17 | Abstract IL-17, produced by lymphocytes and neutrophils, is necessary for lipopolysaccharide-induced airway neutrophilia: IL-15 as a possible trigger. *J Immunol.* 2003 Feb. 15; 170(4): 2106-12. (airway inflammation) |
| IL-15/IL-21 | IL-21 in Synergy with IL-15 or IL-18 Enhances IFN-gamma Production in Human NK and T Cells. *J Immunol.* 2003 Jun. 1; 170(11): 5464-9. |
| IL-17/IL-23 | Interleukin-23 promotes a distinct CD4 T cell activation state characterized by the production of interleukin-17. *J Biol Chem.* 2003 Jan. 17; 278(3): 1910-4. Epub 2002 Nov. 03 |
| IL-17/TGF-β | Polarized in vivo expression of IL-11 and IL-17 between acute and chronic skin lesions. *J Allergy Clin Immunol.* 2003 April; 111(4): 875-81. (allergic dermatitis) |
| IL-18/IL-12 | Synergistic proliferation and activation of natural killer cells by interleukin 12 and interleukin 18. *Cytokine.* 1999 November; 11(11): 822-30. Abstract Inhibition of in vitro immunoglobulin production by IL-12 in murine chronic graft-vs.-host disease: synergism with IL-18. *Eur J Immunol.* 1998 June; 28(6): 2017-24. |
| IL-18/IL-21 | IL-21 in Synergy with IL-15 or IL-18 Enhances IFN-gamma Production in Human NK and T Cells. *J Immunol.* 2003 Jun. 1; 170(11): 5464-9. |
| IL-18/TGF-β | Interleukin 18 and transforming growth factor beta1 in the serum of patients with Graves' ophthalmopathy treated with corticosteroids. *Int Immunopharmacol.* 2003 April; 3(4): 549-52. |
| IL-18/IFN-γ | |
| Anti-TNF ALPHA/anti-CD4 | Synergistic therapeutic effect in DBA/1 arthritic mice. |

Annex 3
Oncology combinations

| Target | Disease | Pair with |
|---|---|---|
| CD89* | Use as cytotoxic cell recruiter | All |
| CD19 | B cell lymphomas | HLA-DR<br>CD5 |
| HLA-DR | B cell lymphomas | CD89<br>CD19<br>CD5 |
| CD38 | Multiple myeloma | CD138<br>CD56<br>HLA-DR |
| CD138 | Multiple myeloma | CD38<br>CD56<br>HLA-DR |
| CD138 | Lung cancer | CD56<br>CEA |
| CD33 | Acute myelod lymphoma | CD34<br>HLA-DR |
| CD56 | Lung cancer | CD138<br>CEA |
| CEA | Pan carcinoma | MET receptor |
| VEGF | Pan carcinoma | MET receptor |
| VEGF receptor | Pan carcinoma | MET receptor |
| IL-13 | Asthma/pulmonary inflammation | IL-4<br>IL-5<br>Eotaxin(s)<br>MDC<br>TARC<br>TNFα<br>IL-9<br>EGFR<br>CD40L<br>IL-25<br>MCP-1<br>TGFβ |
| IL-4 | Asthma | IL-13<br>IL-5<br>Eotaxin(s)<br>MDC<br>TARC<br>TNFα<br>IL-9<br>EGFR<br>CD40L<br>IL-25<br>MCP-1<br>TGFβ |
| Eotaxin | Asthma | IL-5<br>Eotaxin-2<br>Eotaxin-3 |
| EGFR | cancer | HER2/neu<br>HER3<br>HER4 |
| HER2 | cancer | HER3<br>HER4 |
| TNFR1 | RA/Crohn's disease | IL-1R<br>IL-6R<br>IL-18R |
| TNFα | RA/Crohn's disease | IL-1α/β<br>IL-6<br>IL-18<br>ICAM-1<br>IL-15<br>IL-17 |
| IL-1R | RA/Crohn's disease | IL-6R<br>IL-18R |
| IL-18R | RA/Crohn's disease | IL-6R |

Annex 4
Data Summary

| TARGET | dAb | Equilibrium dissocation constant (Kd = Koff/Kon) | Koff | IC50 for ligand assay | ND50 for cell based neutralisn assay |
|---|---|---|---|---|---|
| TAR1 | TAR1 monomers | 300 nM to 5 pM (ie, $3 \times 10^{-7}$ to $5 \times 10^{-12}$), preferably 50 nM to 20 pM | $5 \times 10^{-1}$ to $1 \times 10^{-7}$ | 500 nM to 100 pM | 500 nM to 50 pM |
|  | TAR1 dimers | As TAR1 monomer | As TAR1 monomer | AsTAR1 monomer | As TAR1 monomer |
|  | TAR1 trimers | As TAR1 monomer | As TAR1 monomer | As TAR1 monomer | As TAR1 monomer |
|  | TAR1-5 TAR1-27 |  |  |  |  |
|  | TAR1-5-19 monomer | 30 nM |  |  |  |
|  | TAR1-5-19 homodimer |  |  | With $(Gly_4Ser)_3$ linker = 20 nm<br>With $(Gly_4Ser)_5$ linker = 2 nm<br>With $(Gly_4Ser)_7$ linker = 10 nm<br>In Fab format = 1 nM | =30 nM<br>=3 nM<br>=15 nM |
|  | TAR1-5-19 heterodimers |  |  | With $(Gly_4Ser)_n$ linker<br>TAR1-5-19 d2 = 2 nM<br>TAR1-5-19 d3 = 8 nM<br>TAR1-5-19 d4 = 2-5 nM<br>TAR1-5-19 d5 = 8 nM | =12 nM<br>=10 nM<br>=12 nM |

Annex 4
Data Summary

| TARGET | dAb | Equilibrium dissocation constant (Kd = Koff/Kon) | Koff | IC50 for ligand assay | ND50 for cell based neutralisn assay |
|---|---|---|---|---|---|
| | TAR1-5 heterodimers | | | In Fab format<br>TAR1-5-19CH<br>d1CK = 6 nM<br>TAR1-5-19CK<br>d1CH = 6 nM<br>TAR1-5-19CH<br>d2CK = 8 nM<br>TAR1-5-19CH<br>d3CK = 3 nM<br>With (Gly$_4$Ser)$_n$ linker<br>TAR1-5d1 = 30 nM<br>TAR1-5d2 = 50 nM<br>TAR1-5d3 = 300 nM<br>TAR1-5d4 = 3 nM<br>TAR1-5d5 = 200 nM<br>TAR1-5d6 = 100 nM<br>In Fab format<br>TAR1-5CH<br>d2CK = 30 nM<br>TAR1-5CK<br>d3CH = 100 nM | =60 nM |
| | TAR1-5-19 homotrimer | | | 0.3 nM | 3-10 nM (eg, 3 nM) |
| TAR2 | TAR2 monomers TAR2-10 TAR2-5 | As TAR1 monomer | As TAR1 monomer | 500 nM to 100 pM | 500 nM to 50 pM |
| Serum Albumin | Anti-SA monomers | 1 nM to 500 µM, preferably 100 nM to 10 µM<br>In Dual Specific format, target affinity is 1 to 100,000 x affinity of SA dAb affinity, eg 100 pM (target) and 10 µM SA affinity. | | 1 nM to 500 µM, preferably 100 nM to 10 µM<br>In Dual Specific format, target affinity is 1 to 100,000 x affinity of SA dAb affinity, eg 100 pM (target) and 10 µM SA affinity. | |
| | MSA-16 | 200 nM | | | |
| | MSA-26 | 70 nM | | | |

What is claimed is:

1. An antagonist of Tumor Necrosis Factor I (TNFR1) that binds TNFR1 and inhibits signal transduction through TNFR1, (i) wherein said antagonist does not inhibit binding of TNFα to membrane-bound TNFR1, and (ii) wherein said antagonist competes with TAR2h205 (SEQ ID NO: 627 in FIG. 271) for binding to human TNFR1.

2. The antagonist of claim 1, wherein said antagonist inhibits TNFα induced cell death in a standard L929 cytotoxicity assay or TNFαinduced secretion of IL8 in a standard HeLa IL8 assay.

3. The antagonist of claim 1, wherein said antagonist is a domain antibody (dAb).

4. A ligand comprising a domain antibody (dAb) as defined in claim 3.

5. The ligand of claim 4, wherein the ligand comprises said TNFR1binding dAb and a halflife extending moiety.

6. The ligand of claim 5, wherein the half-life extending moiety is a polyethylene glycol moiety, serum albumin or a fragment thereof, transferrin receptor or a transferring binding portion thereof, or an antibody or antibody fragment comprising a binding site for a polypeptide that enhances halflife in vivo.

7. The ligand of claim 6, wherein the half-life extending moiety is an antibody or antibody fragment comprising a binding site for serum albumin or neonatal Fc receptor.

8. An isolated nucleic acid encoding a dAb as defined in claim 3.

9. A vector comprising a recombinant nucleic acid encoding a dAb as defined in claim 3.

10. A host cell comprising a vector of claim 9 or a nucleic acid of claim 8.

11. A method for producing a polypeptide comprising maintaining a host cell of claim 10 under conditions suitable for expression of the recombinant nucleic acid or vector, whereby a polypeptide is produced.

12. A pharmaceutical composition comprising a dAb of claim 3, or a ligand of claim 4 and a pharmacologically acceptable carrier.

* * * * *